United States Patent
Brace et al.

(10) Patent No.: US 11,052,076 B2
(45) Date of Patent: Jul. 6, 2021

(54) SPIROCYCLIC INDOLINES AS IL-17 MODULATORS

(71) Applicant: UCB BIOPHARMA SRL, Brussels (BE)

(72) Inventors: Gareth Neil Brace, Abingdon (GB); Rose Elizabeth Chappell, Abingdon (GB); Hervé Jean Claude Deboves, Abingdon (GB); Anne Marie Foley, Slough (GB); Gregory Foulkes, Abingdon (GB); Elizabeth Pearl Jones, Bracknell (GB); Fabien Claude Lecomte, Slough (GB); Joanna Rachel Quincey, Slough (GB); Monika-Sarah Elisabeth Dorothea Schulze, Slough (GB); Matthew Duncan Selby, Slough (GB); Adam Peter Smalley, Slough (GB); Richard David Taylor, Slough (GB); Robert James Townsend, Abingdon (GB); Zhaoning Zhu, Slough (GB)

(73) Assignee: UCB Biopharma SRL, Brussels (BE)

(*) Notice: Subject to any disclaimer, the term of this patent is extended or adjusted under 35 U.S.C. 154(b) by 0 days.

(21) Appl. No.: 16/619,573

(22) PCT Filed: Jun. 12, 2018

(86) PCT No.: PCT/EP2018/065558
§ 371 (c)(1),
(2) Date: Dec. 5, 2019

(87) PCT Pub. No.: WO2018/229079
PCT Pub. Date: Dec. 20, 2018

(65) Prior Publication Data
US 2020/0138797 A1 May 7, 2020

(30) Foreign Application Priority Data
Jun. 14, 2017 (GB) ...................................... 1709456

(51) Int. Cl.
| | | |
|---|---|---|
| *C07D 471/10* | (2006.01) | |
| *C07D 487/10* | (2006.01) | |
| *C07D 495/10* | (2006.01) | |
| *C07D 491/20* | (2006.01) | |
| *A61K 31/4439* | (2006.01) | |
| *A61K 31/407* | (2006.01) | |
| *A61K 31/4155* | (2006.01) | |
| *A61K 31/4192* | (2006.01) | |
| *A61K 31/4196* | (2006.01) | |
| *A61K 31/422* | (2006.01) | |
| *A61K 31/427* | (2006.01) | |
| *A61K 31/433* | (2006.01) | |
| *A61K 31/437* | (2006.01) | |
| *A61K 31/501* | (2006.01) | |

(Continued)

(52) U.S. Cl.
CPC ........ *A61K 31/4439* (2013.01); *A61K 31/407* (2013.01); *A61K 31/4155* (2013.01); *A61K 31/4192* (2013.01); *A61K 31/4196* (2013.01); *A61K 31/422* (2013.01); *A61K 31/427* (2013.01); *A61K 31/433* (2013.01); *A61K 31/437* (2013.01); *A61K 31/501* (2013.01); *A61K 31/502* (2013.01); *A61K 31/506* (2013.01); *C07D 471/10* (2013.01); *C07D 487/10* (2013.01); *C07D 491/107* (2013.01); *C07D 491/20* (2013.01); *C07D 495/10* (2013.01); *C07D 519/00* (2013.01)

(58) Field of Classification Search
CPC .. C07D 471/10; C07D 487/10; C07D 495/10; C07D 491/20
See application file for complete search history.

(56) References Cited

U.S. PATENT DOCUMENTS

| 4,666,923 A | 5/1987 | Hoelck et al. |
| 4,810,801 A | 3/1989 | Mertens et al. |

(Continued)

FOREIGN PATENT DOCUMENTS

| JP | S57102863 | 6/1982 |
| WO | WO 2005/000232 | 1/2005 |

(Continued)

OTHER PUBLICATIONS

Brunner, et al. Document No. 2014:451044, retrieved from STN; entered in STN on Mar. 20, 2014.*

(Continued)

*Primary Examiner* — Shawquia Jackson
(74) *Attorney, Agent, or Firm* — McDonnell Boehnen Hulbert & Berghoff LLP

(57) ABSTRACT

A series of substituted spirocyclic 2-oxoindoline derivatives, and analogues thereof, being potent modulators of human IL-17 activity, are accordingly of benefit in the treatment and/or prevention of various human ailments, including inflammatory and autoimmune disorders.

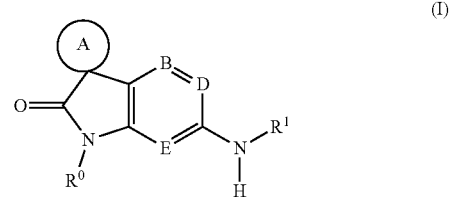

14 Claims, No Drawings

(51) Int. Cl.
*A61K 31/502* (2006.01)
*A61K 31/506* (2006.01)
*C07D 491/107* (2006.01)
*C07D 519/00* (2006.01)

(56) References Cited

U.S. PATENT DOCUMENTS 4,835,280 A 5/1989 Martens et al.
4,985,448 A 1/1991 Zilch et al.

FOREIGN PATENT DOCUMENTS

| WO | WO 2013/124026 | 8/2013 |
| WO | WO 2014/040969 | 3/2014 |
| WO | WO 2015/004533 | 1/2015 |
| WO | WO 2015/015378 | 2/2015 |
| WO | WO 2016/120849 | 8/2016 |
| WO | WO 2016/120850 | 8/2016 |
| WO | WO 2017/069224 | 4/2017 |

OTHER PUBLICATIONS

Sun, et al. Document No. 143:229720, retrieved from STN; entered in STN on Jun. 16, 2005.*
Chen, Guoqing P. Document No. 142:74456, retrieved from STN; entered in STN on Dec. 24, 2004.*
Baldwin, et al. Document No. 116:20938, retrieved from STN; entered in STN on Jan. 24, 1992.*
Zilch, et al. Document No. 112:76970, retrieved from STN; entered in STN on Mar. 3, 1990.*
Martens, et al. Document No. 112:20899, retrieved from STN; entered in STN on Jan. 21, 1980.*
Mertens, et al. Document No. 107:115534, retrieved from STN; entered in STN on Oct. 1987.*
Takeda Chemical. Document No. 97:182208, retrieved from STN; entered in STN on May 12, 1984.*
Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
Haidle, Andrew M. et al., "MARK inhibitors: Declaring a No-Go decision on a chemical series based on extensive DMPK experimentation", Bioorganic & Medicinal Chemistry Letters, Pergamon, Amsterdam, NL, vol. 27, No. 1, Aug. 25, 2016, pp. 109-113.
Database Registry (Online) Chemical Abstracts Service, Columbus, Ohio, US, Sep. 16, 2009.
International Search Report dated Aug. 10, 2018 of PCT/EP2018/065558, 6 pages.

* cited by examiner

SPIROCYCLIC INDOLINES AS IL-17 MODULATORS

CROSS-REFERENCE TO RELATED APPLICATIONS

This application is a U.S. national phase of International Application No. PCT/EP2018/065558, filed Jun. 12, 2018, which claims priority from Great Britain Application no. 1709456.6, filed Jun. 14, 2017, the disclosure of each of which is incorporated herein by reference in its entirety.

The present invention relates to heterocyclic compounds, and to their use in therapy. More particularly, this invention is concerned with pharmacologically active spirocyclic oxoindoline derivatives, and analogues thereof. These compounds act as modulators of IL-17 activity, and are accordingly of benefit as pharmaceutical agents for the treatment and/or prevention of pathological conditions, including adverse inflammatory and autoimmune disorders.

IL-17A (originally named CTLA-8 and also known as IL-17) is a pro-inflammatory cytokine and the founder member of the IL-17 family (Rouvier et al., *J. Immunol.*, 1993, 150, 5445-5456). Subsequently, five additional members of the family (IL-17B to IL-17F) have been identified, including the most closely related, IL-17F (ML-1), which shares approximately 55% amino acid sequence homology with IL-17A (Moseley et al., *Cytokine Growth Factor Rev.*, 2003, 14, 155-174). IL-17A and IL-17F are expressed by the recently defined autoimmune related subset of T helper cells, Th17, that also express IL-21 and IL-22 signature cytokines (Korn et al., *Ann. Rev. Immunol.*, 2009, 27, 485-517). IL-17A and IL-17F are expressed as homodimers, but may also be expressed as the IL-17A/F heterodimer (Wright et al., *J. Immunol.*, 2008, 181, 2799-2805). IL-17A and F signal through the receptors IL-17R, IL-17RC or an IL-17RA/RC receptor complex (Gaffen, *Cytokine*, 2008, 43, 402-407). Both IL-17A and IL-17F have been associated with a number of autoimmune diseases.

The compounds in accordance with the present invention, being potent modulators of human IL-17 activity, are therefore beneficial in the treatment and/or prevention of various human ailments, including inflammatory and autoimmune disorders.

Furthermore, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/116682 and WO 2014/066726 relate to separate classes of chemical compounds that are stated to modulate the activity of IL-17 and to be useful in the treatment of medical conditions, including inflammatory diseases.

None of the prior art available to date, however, discloses or suggests the precise structural class of spirocyclic oxoindoline derivatives, and analogues thereof, as provided by the present invention.

The present invention provides a compound of formula (I), or a pharmaceutically acceptable salt thereof:

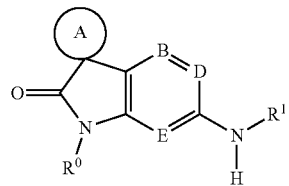

(I)

wherein
ring A represents $C_{3-9}$ cycloalkyl, $C_{3-7}$ heterocycloalkyl or $C_{4-9}$ heterobicycloalkyl, any of which groups may be optionally substituted by one or more substituents;
B represents C—$R^2$ or N;
D represents C—$R^3$ or N;
E represents C—$R^4$ or N;
$R^0$ represents hydrogen or $C_{1-6}$ alkyl;
$R^1$ represents —$COR^a$ or —$SO_2R^b$; or $R^1$ represents $C_{1-6}$ alkyl, $C_{3-9}$ cycloalkyl, $C_{3-9}$ cycloalkyl($C_{1-6}$)alkyl, $C_{5-9}$ spirocycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;
$R^2$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;
$R^3$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;
$R^4$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;
$R^a$ represents hydrogen; or $R^a$ represents $C_{1-6}$ alkyl, $C_{2-7}$ alkenyl, $C_{3-9}$ cycloalkyl, $C_{3-9}$ cycloalkyl($C_{1-6}$)alkyl, $C_{3-9}$ cycloalkylidenyl($C_{1-6}$)alkyl, $C_{4-9}$ bicycloalkyl($C_{1-6}$)alkyl, $C_{4-9}$ bicycloalkylidenyl($C_{1-6}$)alkyl, $C_{5-6}$ spirocycloalkyl($C_{1-6}$)alkyl, $C_{9-11}$ tricycloalkyl-($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkylidenyl($C_{1-6}$)alkyl, heteroaryl or heteroaryl($C_{1-6}$)alkyl, any of which groups may be optionally substituted by one or more substituents; and
$R^b$ represents $C_{1-6}$ alkyl, $C_{2-7}$ alkenyl, $C_{3-9}$ cycloalkyl, $C_{3-9}$ cycloalkyl($C_{1-6}$)alkyl, $C_{3-9}$ cycloalkylidenyl($C_{1-6}$)alkyl, $C_{4-9}$ bicycloalkyl($C_{1-6}$)alkyl, $C_{4-9}$ bicycloalkylidenyl-($C_{1-6}$)alkyl, $C_{5-9}$ spirocycloalkyl($C_{1-6}$)alkyl, $C_{9-11}$ tricycloalkyl ($C_{1-6}$)alkyl, aryl, aryl($C_{1-6}$)-alkyl, $C_{3-7}$ heterocycloalkyl, $C_{3-7}$ heterocycloalkyl($C_{1-6}$)alkyl, $C_{3-7}$ heterocycloalkylidenyl-($C_{1-6}$)alkyl, heteroaryl or heteroaryl($C_{1-6}$)alkyl, any of which groups may be optionally substituted by one or more substituents.

The present invention also provides a compound of formula (I) as depicted above, or a pharmaceutically acceptable salt thereof, for use in therapy.

The present invention also provides a compound of formula (I) as depicted above, or a pharmaceutically acceptable salt thereof, for use in the treatment and/or prevention of disorders for which the administration of a modulator of IL-17 function is indicated.

The present invention also provides the use of a compound of formula (I) as depicted above, or a pharmaceutically acceptable salt thereof, for the manufacture of a medicament for the treatment and/or prevention of disorders for which the administration of a modulator of IL-17 function is indicated.

The present invention also provides a method for the treatment and/or prevention of disorders for which the administration of a modulator of IL-17 function is indicated which comprises administering to a patient in need of such treatment an effective amount of a compound of formula (I) as depicted above, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one, two or three substituents. Suitably, such groups will be unsubstituted, or substituted by one or two substituents.

For use in medicine, the salts of the compounds of formula (I) will be pharmaceutically acceptable salts. Other salts may, however, be useful in the preparation of the compounds of formula (I) or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of formula (I) include acid addition salts which may, for example, be formed by mixing a solution of a compound of formula (I) with a solution of a pharmaceutically acceptable acid.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable alkenyl groups which may be present on the compounds of use in the invention include straight-chained and branched $C_{2-7}$ alkenyl groups, for example $C_{2-4}$ alkenyl groups. Typical examples include vinyl, allyl and buten-1-yl.

The term "$C_{3-9}$ cycloalkyl" as used herein refers to monovalent groups of 3 to 9 carbon atoms derived from a saturated monocyclic hydrocarbon, and may comprise benzo-fused analogues thereof. Suitable $C_{3-9}$ cycloalkyl groups include cyclopropyl, cyclobutyl, benzocyclobutenyl, cyclopentyl, indanyl, cyclohexyl, tetrahydronaphthalenyl, cycloheptyl, benzocycloheptenyl, cyclooctyl and cyclononanyl.

The term "$C_{3-9}$ cycloalkylidenyl" as used herein refers to monovalent groups of 3 to 9 carbon atoms derived from a saturated monocyclic hydrocarbon, optionally comprising benzo-fused analogues thereof, attached to the remainder of the molecule via a C=C double bond. Typically, such groups include cyclobutylidenyl, cyclopentylidenyl, cyclohexylidenyl, cycloheptylidenyl, cyclooctylidenyl and cyclononanylidenyl.

The term "$C_{4-9}$ bicycloalkyl" as used herein refers to monovalent groups of 4 to 9 carbon atoms derived from a saturated bicyclic hydrocarbon. Typical bicycloalkyl groups include bicyclo[1.1.1]pentanyl, bicyclo[3.1.0]hexanyl, bicyclo[4.1.0]heptanyl, bicyclo-[2.2.1]heptanyl, bicyclo[2.2.2]octanyl, bicyclo[3.3.0]octanyl and bicyclo[3.2.1]octanyl.

The term "$C_{4-9}$ bicycloalkylidenyl" as used herein refers to monovalent groups of 4 to 9 carbon atoms derived from a saturated bicyclic hydrocarbon, attached to the remainder of the molecule via a C=C double bond. Typically, such groups include bicyclo[3.1.0]hexanylidenyl, bicyclo[2.2.1]heptanylidenyl and bicyclo[3.2.1]octanyliden-yl.

The term "$C_{5-9}$ spirocycloalkyl" as used herein refers to saturated bicyclic ring systems containing 5 to 9 carbon atoms, in which the two rings are linked by a common atom. Suitable spirocycloalkyl groups include spiro[2.3]hexanyl, spiro[2.4]heptanyl, spiro[3.3]heptanyl, spiro[3.4]octanyl, spiro[3.5]nonanyl and spiro[4.4]nonanyl.

The term "$C_{9-11}$ tricycloalkyl" as used herein refers to monovalent groups of 9 to 11 carbon atoms derived from a saturated tricyclic hydrocarbon. Typical tricycloalkyl groups include adamantanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzofuranyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkylidenyl" as used herein refers to saturated monocyclic rings containing 3 to 7 carbon atoms and at least one heteroatom selected from oxygen, sulphur and nitrogen, attached to the remainder of the molecule via a C=C double bond. Typically, such groups include tetrahydropyranylidenyl and piperidinylidenyl.

The term "$C_{4-9}$ heterobicycloalkyl" as used herein corresponds to $C_4$-9 bicycloalkyl wherein one or more of the carbon atoms have been replaced by one or more heteroatoms selected from oxygen, sulphur and nitrogen. Typical heterobicycloalkyl groups include 6-oxabicyclo[3.1.0]hexanyl, 3-azabicyclo[3.1.0]hexanyl, 2-oxa-5-azabicyclo[2.2.1]heptanyl, 6-azabicyclo[3.2.0]heptanyl, 6-oxabicyclo[3.1.1]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo-[2.2.2]octanyl, 8-oxabicyclo[3.2.1]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,7-dioxa-9-azabicyclo-[3.3.1]nonanyl and 3,9-diazabicyclo[4.2.1]nonanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, pyrazolo[1,5-a]pyrazinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo-[2,1-b]thiazolyl, imidazo[1,2-a]pyridinyl, imidazo[4,5-b]pyridinyl, imidazo[1,2-b]-pyridazinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In a first embodiment, ring A represents optionally substituted $C_{3-9}$ cycloalkyl. In one aspect of that embodiment, ring A represents optionally substituted $C_{4-7}$ cycloalkyl.

In a second embodiment, ring A represents optionally substituted $C_{3-7}$ heterocycloalkyl. In one aspect of that embodiment, ring A represents optionally substituted $C_{4-6}$ heterocycloalkyl.

In a third embodiment, ring A represents optionally substituted $C_{4-9}$ heterobicycloalkyl. In one aspect of that embodiment, ring A represents optionally substituted $C_{5-7}$ heterobicycloalkyl.

Typically, ring A represents cyclopropyl, cyclobutyl, cyclopentyl, cyclohexyl, cycloheptyl, cyclooctyl, cyclononanyl, oxetanyl, azetidinyl, tetrahydrofuranyl, pyrrolidinyl, oxazolidinyl, thiazolidinyl, isothiazolidinyl, imidazolidinyl, tetrahydro-pyranyl, tetrahydrothiopyranyl, piperidinyl, piperazinyl, homopiperazinyl, morpholinyl, thiomorpholinyl, azepanyl, oxazepanyl, diazepanyl, thiadiazepanyl, azocanyl, 6-oxa-bicyclo[3.1.0]hexanyl, 6-oxabicyclo[3.1.1]heptanyl or 8-oxabicyclo[3.2.1]octanyl, any of which groups may be optionally substituted by one or more substituents.

Appositely, ring A represents pyrrolidinyl, tetrahydropyranyl, tetrahydrothio-pyranyl or piperidinyl, any of which groups may be optionally substituted by one or more substituents.

Suitably, ring A represents tetrahydropyranyl, tetrahydrothiopyranyl or piperidinyl, any of which groups may be optionally substituted by one or more substituents.

In a particular embodiment, ring A represents tetrahydropyranyl, which group may be optionally substituted by one or more substituents.

Typical examples of optional substituents on ring A include one, two or three substituents independently selected from $C_{1-6}$ alkyl, halogen, cyano, trifluoro-methyl, hydroxy, oxo, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, imino, $C_{1-6}$ alkylamino and di($C_{1-6}$)alkylamino.

Suitable examples of optional substituents on ring A include one, two or three substituents independently selected from $C_{1-6}$ alkyl, oxo and imino.

Typical examples of particular substituents on ring A include one, two or three substituents independently selected from methyl, fluoro, chloro, bromo, cyano, trifluoro-methyl, hydroxy, oxo, methoxy, methylthio, methylsulphinyl, methylsulphonyl, acetyl, amino, imino, methylamino and dimethylamino.

Suitable examples of particular substituents on ring A include one, two or three substituents independently selected from methyl, oxo and imino.

Selected values of ring A include pyrrolidinyl, tetrahydropyranyl, (methyl)-tetrahydropyranyl, tetrahydrothiopyranyl, (oxo)tetrahydrothiopyranyl, (dioxo)tetrahydro-thiopyranyl, (imino)(oxo)tetrahydrothiopyranyl and piperidinyl.

Typical values of ring A include tetrahydropyranyl, tetrahydrothiopyranyl and piperidinyl.

A particular value of ring A is tetrahydropyranyl.

In one embodiment, B represents C—$R^2$. In another embodiment, B represents N.

In one embodiment, D represents C—$R^3$. In another embodiment, D represents N.

In one embodiment, E represents C—$R^4$. In another embodiment, E represents N.

In a first embodiment, B represents C—$R^2$, D represents C—$R^3$ and E represents C—$R^4$.

In a second embodiment, B represents C—$R^2$, D represents C—$R^3$ and E represents N.

In a third embodiment, B represents C—$R^2$, D represents N and E represents C—$R^4$.

In a fourth embodiment, B represents C—$R^2$, D represents N and E represents N.

In a fifth embodiment, B represents N, D represents C—$R^3$ and E represents C—$R^4$.

In a sixth embodiment, B represents N, D represents C—$R^3$ and E represents N.

In a seventh embodiment, B represents N, D represents N and E represents C—$R^4$.

In an eighth embodiment, B represents N, D represents N and E represents N.

Suitably, the present invention provides a compound of formula (I-1), (I-2), (I-3), (I-4) or (I-5), or a pharmaceutically acceptable salt thereof:

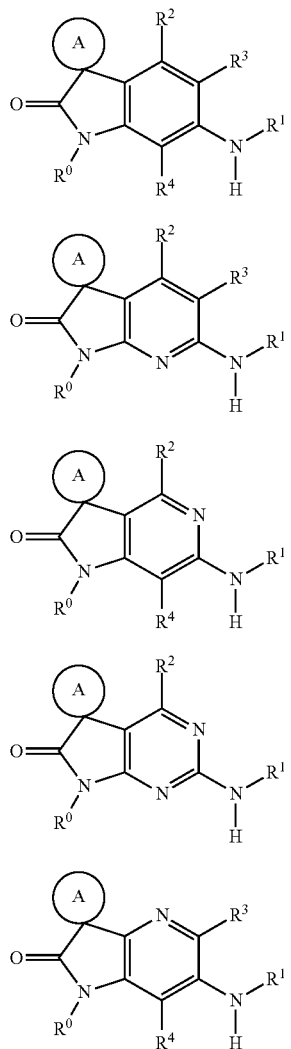

wherein A, $R^0$, $R^1$, $R^2$, $R^3$ and $R^4$ are as defined above.

In a first embodiment, $R^0$ represents hydrogen. In a second embodiment, $R^0$ represents $C_{1-6}$ alkyl, especially methyl.

Suitably, $R^0$ represents hydrogen or methyl.

Typical examples of optional substituents on $R^1$ include one, two or three substituents independently selected from $C_{1-6}$ alkyl, halogen, cyano, trifluoromethyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino and di($C_{1-6}$)alkylamino.

Typical examples of particular substituents on $R^1$ include one, two or three substituents independently selected from methyl, fluoro, chloro, bromo, cyano, trifluoro-methyl, hydroxy, oxo, methoxy, methylthio, methylsulphinyl, methylsulphonyl, acetyl, amino, methylamino and dimethylamino.

Suitably, $R^1$ represents —$COR^a$.

Typically, $R^2$ represents hydrogen or halogen.

In a first embodiment, $R^2$ represents hydrogen. In a second embodiment, $R^2$ represents halogen. In a first aspect of that embodiment, $R^2$ represents fluoro. In a second aspect of that embodiment, $R^2$ represents chloro. In a third embodiment, $R^2$ represents cyano. In a fourth embodiment, $R^2$ represents $C_{1-6}$ alkyl, especially methyl. In a fifth embodiment, $R^2$ represents fluoromethyl. In a sixth embodiment, $R^2$ represents difluoromethyl. In a seventh embodiment, $R^2$ represents trifluoromethyl. In an eighth embodiment, $R^2$ represents hydroxy. In a ninth embodiment, $R^2$ represents $C_{1-6}$ alkoxy, especially methoxy. In a tenth embodiment, $R^2$ represents difluoromethoxy. In an eleventh embodiment, $R^2$ represents trifluoromethoxy. In a twelfth embodiment, $R^2$ represents $C_{1-6}$ alkylsulphinyl, especially methylsulphinyl. In a thirteenth embodiment, $R^2$ represents $C_{1-6}$ alkylsulphonyl, especially methylsulphonyl.

Suitably, $R^2$ represents hydrogen or fluoro.

Typically, $R^3$ represents hydrogen or halogen.

In a first embodiment, $R^3$ represents hydrogen. In a second embodiment, $R^3$ represents halogen. In a first aspect of that embodiment, $R^3$ represents fluoro. In a second aspect of that embodiment, $R^3$ represents chloro. In a third embodiment, $R^3$ represents cyano. In a fourth embodiment, $R^3$ represents $C_{1-6}$ alkyl, especially methyl. In a fifth embodiment, $R^3$ represents fluoromethyl. In a sixth embodiment, $R^3$ represents difluoromethyl. In a seventh embodiment, $R^3$ represents trifluoromethyl. In an eighth embodiment, $R^3$ represents hydroxy. In a ninth embodiment, $R^3$ represents $C_{1-6}$ alkoxy, especially methoxy. In a tenth embodiment, $R^3$ represents difluoromethoxy. In an eleventh embodiment, $R^3$ represents trifluoromethoxy. In a twelfth embodiment, $R^3$ represents $C_{1-6}$ alkylsulphinyl, especially methylsulphinyl. In a thirteenth embodiment, $R^3$ represents $C_{1-6}$ alkylsulphonyl, especially methylsulphonyl.

Appositely, $R^3$ represents hydrogen, fluoro or chloro.

Suitably, $R^3$ represents hydrogen or fluoro.

In a first embodiment, $R^4$ represents hydrogen. In a second embodiment, $R^4$ represents halogen. In a first aspect of that embodiment, $R^4$ represents fluoro. In a second aspect of that embodiment, $R^4$ represents chloro. In a third embodiment, $R^4$ represents cyano. In a fourth embodiment, $R^4$ represents $C_{1-6}$ alkyl, especially methyl. In a fifth embodiment, $R^4$ represents fluoromethyl. In a sixth embodiment, $R^4$ represents difluoromethyl. In a seventh embodiment, $R^4$ represents trifluoromethyl. In an eighth embodiment, $R^4$ represents hydroxy. In a ninth embodiment, $R^4$ represents $C_{1-6}$ alkoxy, especially methoxy. In a tenth embodiment, $R^4$ represents difluoromethoxy. In an eleventh embodiment, $R^4$ represents trifluoromethoxy. In a twelfth embodiment, $R^4$ represents $C_{1-6}$ alkylsulphinyl, especially methylsulphinyl. In a thirteenth embodiment, $R^4$ represents $C_{1-6}$ alkylsulphonyl, especially methylsulphonyl.

Generally, $R^a$ represents hydrogen; or $R^a$ represents $C_{1-6}$ alkyl, $C_{3-9}$ cycloalkyl, $C_{3-9}$ cycloalkyl($C_{1-6}$)alkyl, $C_{3-9}$ cycloalkylidenyl($C_{1-6}$)alkyl, $C_{4-9}$ bicycloalkyl($C_{1-6}$)alkyl, $C_{5-9}$ spirocycloalkyl($C_{1-6}$)alkyl, $C_{9-11}$ tricycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkylidenyl($C_{1-6}$)alkyl, heteroaryl or heteroaryl($C_{1-6}$)alkyl, any of which groups may be optionally substituted by one or more substituents.

Typically, $R^a$ represents $C_{1-6}$ alkyl, $C_{3-9}$ cycloalkyl, $C_{3-9}$ cycloalkyl($C_{1-6}$)alkyl, $C_{3-9}$ cycloalkylidenyl($C_{1-6}$)alkyl, $C_{4-9}$ bicycloalkyl($C_{1-6}$)alkyl, $C_{5-9}$ spirocycloalkyl($C_{1-6}$)alkyl, $C_{9-11}$ tricycloalkyl($C_{1-6}$)alkyl, aryl, aryl($C_{1-6}$)alkyl, $C_{3-7}$ heterocycloalkyl, $C_{3-7}$ hetero-cycloalkyl($C_{1-6}$)alkyl, $C_{3-7}$ heterocycloalkylidenyl($C_{1-6}$)alkyl, heteroaryl or heteroaryl-($C_{1-6}$)alkyl, any of which groups may be optionally substituted by one or more substituents.

Suitably, $R^a$ represents $C_{1-6}$ alkyl, $C_{3-9}$ cycloalkyl($C_{1-6}$) alkyl, $C_{5-9}$ spirocycloalkyl-($C_{1-6}$)alkyl or aryl($C_{1-6}$)alkyl, any of which groups may be optionally substituted by one or more substituents.

In a particular embodiment, $R^a$ is other than hydrogen.

Typical values of $R^a$ include methyl, ethyl, 2-methylpropyl, 2-methylbutyl, 3-methylbutyl, cyclopropylmethyl, cyclopentylmethyl, indanylmethyl, cyclohexylmethyl, cyclohexylethyl, cyclooctylmethyl, cyclopentylidenylmethyl, cyclohexylidenylmethyl, cycloheptylidenylmethyl, cyclooctylidenylmethyl, spiro[3.3]heptanylmethyl, adamantanyl-methyl, adamantanylethyl, phenyl, benzyl, phenylethyl, phenylpropyl, naphthylmethyl, naphthylethyl, tetrahydropyranylidenylmethyl, thienylmethyl, thienylethyl, indolylmethyl, indolylethyl, pyridinylmethyl and pyridinylethyl, any of which groups may be optionally substituted by one or more substituents.

Suitable values of $R^a$ include methyl, cyclohexylmethyl, cyclooctylmethyl, spiro[3.3]heptanylmethyl and phenylethyl, any of which groups may be optionally substituted by one or more substituents.

Typical examples of optional substituents on $R^a$ include one, two or three substituents independently selected from halogen, cyano, nitro, $C_{1-6}$ alkyl, trifluoro-methyl, phenyl, hydroxy, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, ($C_{1-6}$)alkylheteroarylcarbonylamino, heteroaryl($C_{1-6}$)-alkylcarbonylamino, aminoheteroaryl($C_{1-6}$)alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminocarbonyl-amino, $C_{1-6}$ alkylaminocarbonylamino, di($C_{1-6}$)alkylaminocarbonylamino, aminosulfonyl, $C_{1-6}$ alkylaminosulfonyl and di($C_{1-6}$)alkylaminosulfonyl.

Suitable examples of optional substituents on $R^a$ include one, two or three substituents independently selected from halogen, cyano, $C_{1-6}$ alkyl, trifluoromethyl, phenyl, hydroxy, $C_{1-6}$ alkoxy, amino, $C_{2-6}$ alkylcarbonylamino, ($C_{1-6}$)alkylheteroaryl-carbonylamino, heteroaryl($C_{1-6}$)alkylcarbonylamino, aminoheteroaryl($C_{1-6}$)alkylcarbonyl-amino and aminocarbonyl.

Apposite examples of optional substituents on $R^a$ include one, two or three substituents independently selected from halogen, amino, $C_{2-6}$ alkylcarbonylamino, ($C_{1-6}$)alkylheteroarylcarbonylamino, heteroaryl($C_{1-6}$)alkylcarbonylamino and aminoheteroaryl($C_{1-6}$)alkylcarbonylamino.

Favoured examples of optional substituents on $R^a$ include one, two or three substituents independently selected from halogen, cyano, nitro, $C_{1-6}$ alkyl, trifluoro-methyl, trifluoroethyl, phenyl, hydroxy, oxo, $C_{1-6}$ alkoxy, difluoromethoxy, trifluoro-methoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkyl-sulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylamino-sulfonyl, di($C_{1-6}$)alkylaminosulfonyl, —$R^{5a}$, —NHCOR$^6$, NHS(O)$_2$R$^6$, —R$^7$, —NHR$^7$ and —CONHR$^7$, wherein $R^{5a}$, $R^6$ and $R^7$ are as defined below.

Selected examples of optional substituents on $R^a$ include one, two or three substituents independently selected from halogen, $C_{1-6}$ alkyl, trifluoromethyl, trifluoro-ethyl, phenyl, $C_{1-6}$ alkoxy, —$R^{5a}$, —NHCOR$^6$, NHS(O)$_2$R$^6$, —R$^7$, —NHR$^7$ and —CONHR$^7$, wherein $R^{5a}$, $R^6$ and $R^7$ are as defined below.

Typical examples of specific substituents on $R^a$ include one, two or three substituents independently selected from fluoro, chloro, bromo, cyano, nitro, methyl, ethyl, isopropyl, tert-butyl, trifluoromethyl, phenyl, hydroxy, oxo, methoxy, tert-butoxy, difluoromethoxy, trifluoromethoxy, methylthio, methylsulfinyl, methylsulfonyl, amino, methylamino, tert-butylamino, dimethylamino, acetylamino, methylpyrazolylcarbonyl-amino, pyridinylmethylcarbonylamino, aminopyridinylmethylcarbonylamino, methoxy-carbonylamino, methylsulfonylamino, formyl, acetyl, carboxy, methoxycarbonyl, ethoxycarbonyl, tert-butoxycarbonyl, aminocarbonyl, methylaminocarbonyl, dimethyl-aminocarbonyl, aminocarbonylamino, methylaminocarbonylamino, dimethylamino-carbonylamino, aminosulfonyl, methylaminosulfonyl and dimethylaminosulfonyl.

Suitable examples of specific substituents on $R^a$ include one, two or three substituents independently selected from fluoro, chloro, bromo, cyano, methyl, trifluoromethyl, phenyl, hydroxy, methoxy, tert-butoxy, amino, acetylamino, methyl-pyrazolylcarbonylamino, pyridinylmethylcarbonylamino, aminopyridinylmethylcarbonyl-amino and aminocarbonyl.

Apposite examples of specific substituents on $R^a$ include one, two or three substituents independently selected from chloro, amino, acetylamino, methylpyrazolyl-carbonylamino, pyridinylmethylcarbonylamino and aminopyridinylmethylcarbonylamino.

Favoured examples of specific substituents on $R^a$ include one, two or three substituents independently selected from fluoro, chloro, bromo, cyano, nitro, methyl, ethyl, isopropyl, tert-butyl, trifluoromethyl, trifluoroethyl, phenyl, hydroxy, oxo, methoxy, isopropoxy, tert-butoxy, difluoromethoxy, trifluoromethoxy, methylthio, methylsulfinyl, methylsulfonyl, amino, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylamino-carbonyl, dimethylaminocarbonyl, aminosulfonyl, methylaminosulfonyl, dimethylamino-sulfonyl, —$R^{5a}$, —NHCOR$^6$, NHS(O)$_2$R$^6$, —R$^7$, —NHR$^7$ and —CONHR$^7$, wherein $R^{5a}$, $R^6$ and $R^7$ are as defined below.

Selected examples of specific substituents on $R^a$ include one, two or three substituents independently selected from fluoro, chloro, bromo, methyl, trifluoromethyl, trifluoroethyl, phenyl, isopropoxy, tert-butoxy, —$R^{5a}$, —NHCOR$^6$, NHS(O)$_2$R$^6$, —R$^7$, —NHR$^7$ and —CONHR$^7$, wherein $R^{5a}$, $R^6$ and $R^7$ are as defined below.

Illustrative values of $R^a$ include methyl, methylpyrazolylcarbonylaminomethyl, ethyl, 2-methylpropyl, 2-methylbutyl, 3-methylbutyl, cyclopropylmethyl, cyclopentylmethyl, indanylmethyl, cyclohexylmethyl, (cyclohexyl)(pyridinylmethylcarbonylamino)-methyl, cyclohexylethyl, cyclooctylmethyl, (amino)(cyclooctyl)methyl, (acetylamino)-(cyclooctyl)methyl, (cyclooctyl)(methylpyrazolylcarbonylamino)methyl, (cyclooctyl)-(pyridinylmethylcarbonylamino)methyl, (aminopyridinylmethylcarbonylamino)-(cyclooctyl)methyl, (methylpyrazolylcarbonylamino)(spiro[3.3]heptanyl)
methyl, phenyl, chlorophenyl, benzyl, fluorobenzyl, chlorobenzyl, phenylethyl, fluorophenylethyl, chlorophenylethyl, (chloro)(fluoro)phenylethyl, dichlorophenylethyl, bromophenylethyl, cyanophenylethyl, methylphenylethyl, trifluoromethylphenylethyl, biphenylethyl, hydroxyphenylethyl, methoxyphenylethyl, tert-butoxyphenylethyl, (chloro)(pyridinyl-methylcarbonylamino)phenylethyl, aminocarbonylphenylethyl, phenylpropyl, chloro-phenylpropyl, naphthylmethyl, naphthylethyl, (methylpyrazolylcarbonylamino)-(tetrahydropyranylidenyl)methyl, thienylmethyl, thienylethyl, indolylmethyl, indolylethyl, pyridinylmethyl and pyridinylethyl.

Representative values of $R^a$ include methylpyrazolylcarbonylaminomethyl, (cyclohexyl)(pyridinylmethylcarbonylamino)methyl, (amino)(cyclooctyl)methyl, (acetylamino)(cyclooctyl)methyl, (cyclooctyl)(methylpyrazolylcarbonylamino)methyl, (cyclooctyl)(pyridinylmethylcarbonylamino)methyl, (aminopyridinylmethylcarbonyl-amino)(cyclooctyl)methyl, (methylpyrazolylcarbonylamino)(spiro[3.3]heptanyl)methyl and (chloro)(pyridinylmethylcarbonylamino)phenylethyl.

Generally, $R^b$ represents $C_{1-6}$ alkyl, $C_{3-9}$ cycloalkyl, $C_{3-9}$ cycloalkyl($C_{1-6}$)alkyl, $C_{3-9}$ cycloalkylidenyl($C_{1-6}$)alkyl, $C_{4-9}$ bicycloalkyl($C_{1-6}$)alkyl, $C_{5-9}$ spirocycloalkyl($C_{1-6}$)alkyl, $C_{9-11}$ tricycloalkyl($C_{1-6}$)alkyl, aryl, aryl($C_{1-6}$)alkyl, $C_{3-7}$ heterocycloalkyl, $C_{3-7}$ heterocyclo-alkyl($C_{1-6}$)alkyl, $C_{3-7}$ heterocycloalkylidenyl($C_{1-6}$)alkyl, heteroaryl or heteroaryl ($C_{1-6}$)-alkyl, any of which groups may be optionally substituted by one or more substituents.

Suitably, $R^b$ represents $C_{1-6}$ alkyl, $C_{3-9}$ cycloalkyl($C_{1-6}$) alkyl, $C_{5-9}$ spirocycloalkyl-($C_{1-6}$)alkyl or aryl($C_{1-6}$)alkyl, any of which groups may be optionally substituted by one or more substituents.

Typical values of $R^b$ include methyl, ethyl, 2-methylpropyl, 2-methylbutyl, 3-methylbutyl, cyclopropylmethyl, cyclopentylmethyl, indanylmethyl, cyclohexylmethyl, cyclohexylethyl, cyclooctylmethyl, cyclopentylidenylmethyl, cyclohexylidenylmethyl, cycloheptylidenylmethyl, cyclooctylidenylmethyl, spiro[3.3]heptanylmethyl, adamantanyl-methyl, adamantanylethyl, phenyl, benzyl, phenylethyl, phenylpropyl, naphthylmethyl, naphthylethyl, tetrahydropyranylidenylmethyl, thienylmethyl, thienylethyl, indolylmethyl, indolylethyl, pyridinylmethyl and pyridinylethyl, any of which groups may be optionally substituted by one or more substituents.

Suitable values of $R^b$ include methyl, cyclohexylmethyl, cyclooctylmethyl, spiro[3.3]heptanylmethyl and phenylethyl, any of which groups may be optionally substituted by one or more substituents.

Typical examples of optional substituents on $R^b$ include one, two or three substituents independently selected from halogen, cyano, nitro, $C_{1-6}$ alkyl, trifluoro-methyl, phenyl, hydroxy, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, ($C_{1-6}$)alkylheteroarylcarbonylamino, heteroaryl($C_{1-6}$)-alkylcarbonylamino, aminoheteroaryl($C_{1-6}$)alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminocarbonyl-amino, $C_{1-6}$ alkylaminocarbonylamino, di($C_{1-6}$)alkylaminocarbonylamino, aminosulfonyl, $C_{1-6}$ alkylaminosulfonyl and di($C_{1-6}$)alkylaminosulfonyl.

Suitable examples of optional substituents on $R^b$ include one, two or three substituents independently selected from halogen, cyano, $C_{1-6}$ alkyl, trifluoromethyl, phenyl, hydroxy, $C_{1-6}$ alkoxy, amino, $C_{2-6}$ alkylcarbonylamino, ($C_{1-6}$)alkylheteroaryl-carbonylamino, heteroaryl($C_{1-6}$)alkylcarbonylamino, aminoheteroaryl($C_{1-6}$)alkylcarbonyl-amino and aminocarbonyl.

Apposite examples of optional substituents on $R^b$ include one, two or three substituents independently selected from halogen, amino, $C_{2-6}$ alkylcarbonylamino, ($C_{1-6}$)alkylheteroarylcarbonylamino, heteroaryl($C_{1-6}$)alkylcarbonylamino and aminoheteroaryl($C_{1-6}$)alkylcarbonylamino.

Favoured examples of optional substituents on $R^b$ include one, two or three substituents independently selected from halogen, cyano, nitro, $C_{1-6}$ alkyl, trifluoro-methyl, trifluoroethyl, phenyl, hydroxy, oxo, $C_{1-6}$ alkoxy, difluoromethoxy, trifluoro-methoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkyl-sulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylamino-sulfonyl, di($C_{1-6}$)alkylaminosulfonyl, —$R^{5a}$, —NHCOR$^6$, NHS(O)$_2$R$^6$, —R$^7$, —NHR$^7$ and —CONHR$^7$, wherein $R^{5a}$, $R^6$ and $R^7$ are as defined below.

Selected examples of optional substituents on $R^b$ include one, two or three substituents independently selected from halogen, $C_{1-6}$ alkyl, trifluoromethyl, trifluoro-ethyl, phenyl, $C_{1-6}$ alkoxy, —$R^{5a}$, —NHCOR$^6$, NHS(O)$_2$R$^6$, —R$^7$, —NHR$^7$ and —CONHR$^7$, wherein $R^{5a}$, $R^6$ and $R^7$ are as defined below.

Typical examples of specific substituents on $R^b$ include one, two or three substituents independently selected from fluoro, chloro, bromo, cyano, nitro, methyl, ethyl, isopropyl, tert-butyl, trifluoromethyl, phenyl, hydroxy, oxo, methoxy, tert-butoxy, difluoromethoxy, trifluoromethoxy, methylthio, methylsulfinyl, methylsulfonyl, amino, methylamino, tert-butylamino, dimethylamino, acetylamino, methylpyrazolylcarbonyl-amino, pyridinylmethylcarbonylamino, aminopyridinylmethylcarbonylamino, methoxy-carbonylamino, methylsulfonylamino, formyl, acetyl, carboxy, methoxycarbonyl, ethoxycarbonyl, tert-butoxycarbonyl, aminocarbonyl, methylaminocarbonyl, dimethyl-aminocarbonyl, aminocarbonylamino, methylaminocarbonylamino, dimethylamino-carbonylamino, aminosulfonyl, methylaminosulfonyl and dimethylaminosulfonyl.

Suitable examples of specific substituents on $R^b$ include one, two or three substituents independently selected from fluoro, chloro, bromo, cyano, methyl, trifluoromethyl, phenyl, hydroxy, methoxy, tert-butoxy, amino, acetylamino, methyl-pyrazolylcarbonylamino, pyridinylmethylcarbonylamino, aminopyridinylmethylcarbonyl-amino and aminocarbonyl.

Apposite examples of specific substituents on $R^b$ include one, two or three substituents independently selected from chloro, amino, acetylamino, methylpyrazolyl-carbonylamino, pyridinylmethylcarbonylamino and aminopyridinylmethylcarbonylamino.

Favoured examples of specific substituents on $R^b$ include one, two or three substituents independently selected from fluoro, chloro, bromo, cyano, nitro, methyl, ethyl, isopropyl, tert-butyl, trifluoromethyl, trifluoroethyl, phenyl, hydroxy, oxo, methoxy, isopropoxy, tert-butoxy, difluoromethoxy, trifluoromethoxy, methylthio, methylsulfinyl, methylsulfonyl, amino, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylamino-carbonyl, dimethylaminocarbonyl, aminosulfonyl, methylaminosulfonyl, dimethylamino-sulfonyl, —$R^{5a}$, —NHCOR$^6$, NHS(O)$_2$R$^6$, —R$^7$, —NHR$^7$ and —CONHR$^7$, wherein $R^{5a}$, $R^6$ and $R^7$ are as defined below.

Selected examples of specific substituents on $R^b$ include one, two or three substituents independently selected from fluoro, chloro, bromo, methyl, trifluoromethyl, trifluoro-ethyl, phenyl, isopropoxy, tert-butoxy, —$R^{5a}$, —NHCOR$^6$, NHS(O)$_2$R$^6$, —R$^7$, —NHR$^7$ and —CONHR$^7$, wherein $R^{5a}$, $R^6$ and $R^7$ are as defined below.

Illustrative values of $R^b$ include methyl, methylpyrazolylcarbonylaminomethyl, ethyl, 2-methylpropyl, 2-methylbutyl, 3-methylbutyl, cyclopropylmethyl, cyclopentylmethyl, indanylmethyl, cyclohexylmethyl, (cyclohexyl) (pyridinylmethylcarbonylamino)-methyl, cyclohexylethyl, cyclooctylmethyl, (amino)(cyclooctyl)methyl, (acetylamino)-(cyclooctyl)methyl, (cyclooctyl)(methylpyrazolylcarbonylamino)methyl, (cyclooctyl)-(pyridinylmethylcarbonylamino)methyl, (aminopyridinylmethylcarbonylamino)-(cyclooctyl)methyl, (methylpyrazolylcarbonylamino)(spiro[3.3]heptanyl) methyl, phenyl, chlorophenyl, benzyl, fluorobenzyl, chlorobenzyl, phenylethyl, fluorophenylethyl, chlorophenylethyl, (chloro)(fluoro)phenylethyl, dichlorophenylethyl, bromophenylethyl, cyanophenylethyl, methylphenylethyl, trifluoromethylphenylethyl, biphenylethyl, hydroxyphenylethyl, methoxyphenylethyl, tert-butoxyphenylethyl, (chloro) (pyridinyl-methylcarbonylamino)phenylethyl, aminocarbonylphenylethyl, phenylpropyl, chloro-phenylpropyl, naphthylmethyl, naphthylethyl, (methylpyrazolylcarbonylamino)-(tetrahydropyranylidenyl)methyl, thienylmethyl, thienylethyl, indolylmethyl, indolylethyl, pyridinylmethyl and pyridinylethyl.

Representative values of $R^b$ include methylpyrazolylcarbonylaminomethyl, (cyclohexyl)(pyridinylmethylcarbonylamino)methyl, (amino)(cyclooctyl)methyl, (acetylamino)(cyclooctyl)methyl, (cyclooctyl) (methylpyrazolylcarbonylamino)methyl, (cyclooctyl) (pyridinylmethylcarbonylamino)methyl, (aminopyridinylmethylcarbonyl-amino)(cyclooctyl)methyl, (methylpyrazolylcarbonylamino)(spiro[3.3]heptanyl) methyl and (chloro)(pyridinylmethylcarbonylamino)phenylethyl.

A particular sub-class of compounds according to the invention is represented by the compounds of formula (IA), and pharmaceutically acceptable salts thereof:

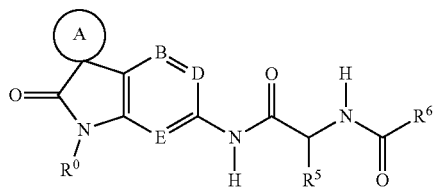

(IA)

wherein

A, B, D, E and $R^0$ are as defined above;

$R^5$ represents hydrogen; or $R^5$ represents $C_{1-5}$ alkyl, $C_{3-9}$ cycloalkyl, $C_{3-9}$ cyclo-alkyl($C_{1-5}$)alkyl, $C_{4-9}$ bicycloalkyl, $C_{4-9}$ bicycloalkyl($C_{1-5}$)alkyl, $C_{5-9}$ spirocycloalkyl, $C_{5-9}$ spirocycloalkyl($C_{1-5}$)alkyl, $C_{9-11}$ tricycloalkyl, $C_{9-11}$ tricycloalkyl($C_{1-5}$)alkyl, aryl, aryl-($C_{1-5}$)alkyl, $C_{3-7}$ heterocycloalkyl, $C_{3-7}$ heterocycloalkyl($C_{1-5}$)alkyl, heteroaryl or heteroaryl($C_{1-5}$)alkyl, any of which groups may be optionally substituted by one or more substituents;

$R^6$ represents —$NR^{6a}R^{6b}$ or —$OR^{6c}$; or $R^6$ represents $C_{1-9}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl, heteroaryl($C_{1-6}$)alkyl or spiro [($C_{3-7}$)heterocycloalkyl][heteroaryl], any of which groups may be optionally substituted by one or more substituents;

$R^{6a}$ represents hydrogen; or $R^{6a}$ represents $C_{1-6}$ alkyl, $C_{3-7}$ cycloalkyl, $C_{3-7}$ cyclo-alkyl($C_{1-6}$)alkyl, aryl, aryl($C_{1-6}$)alkyl, $C_{3-7}$ heterocycloalkyl, $C_{3-7}$ heterocycloalkyl($C_{1-6}$)-alkyl, heteroaryl, heteroaryl($C_{1-6}$)alkyl or spiro[($C_{3-7}$)heterocycloalkyl][heteroaryl], any of which groups may be optionally substituted by one or more substituents.

$R^{6b}$ represents hydrogen or $C_{1-6}$ alkyl; and $R^{6c}$ represents $C_{1-6}$ alkyl, $C_{3-7}$ cycloalkyl, $C_{3-7}$ cycloalkyl ($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

A second sub-class of compounds according to the invention is represented by the compounds of formula (IB), and pharmaceutically acceptable salts thereof:

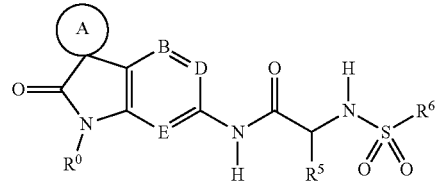

(IB)

wherein

A, B, D, E, $R^0$, $R^5$ and $R^6$ are as defined above.

A third sub-class of compounds according to the invention is represented by the compounds of formula (IC), and pharmaceutically acceptable salts thereof:

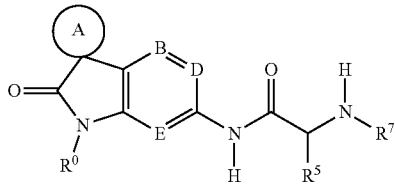

(IC)

wherein

A, B, D, E, $R^0$ and $R^5$ are as defined above; and $R^7$ represents aryl, heteroaryl or spiro[($C_{3-7}$)heterocycloalkyl][heteroaryl], any of which groups may be optionally substituted by one or more substituents.

A fourth sub-class of compounds according to the invention is represented by the compounds of formula (ID), and pharmaceutically acceptable salts thereof:

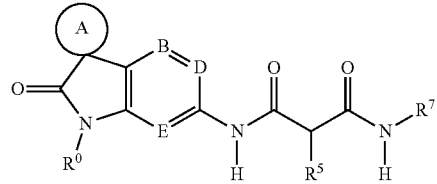

(ID)

wherein

A, B, D, E, $R^0$, $R^5$ and $R^7$ are as defined above.

A fifth sub-class of compounds according to the invention is represented by the compounds of formula (IE), and pharmaceutically acceptable salts thereof:

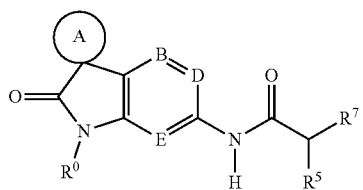

(IE)

wherein

A, B, D, E, $R^0$, $R^5$ and $R^7$ are as defined above.

A sixth sub-class of compounds according to the invention is represented by the compounds of formula (IF), and pharmaceutically acceptable salts thereof:

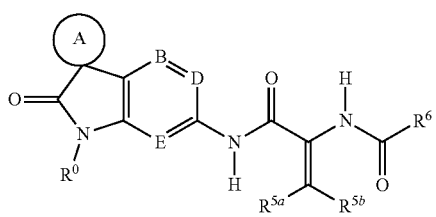

(IF)

wherein

A, B, D, E, $R^0$ and $R^6$ are as defined above;

$R^{5a}$ represents $C_{3-7}$ cycloalkyl, $C_{4-9}$ bicycloalkyl, aryl, $C_{3-7}$ heterocycloalkyl or heteroaryl, any of which groups may be optionally substituted by one or more substituents; and $R^{5b}$ represents hydrogen or $C_{1-6}$ alkyl; or $R^{5a}$ and $R^{5b}$, when taken together with the carbon atom to which they are both attached, represent $C_{3-7}$ cycloalkyl, $C_{4-9}$ bicycloalkyl or $C_{3-7}$ heterocycloalkyl, any of which groups may be optionally substituted by one or more substituents.

Generally, $R^5$ represents hydrogen; or $R^5$ represents $C_{1-5}$ alkyl, $C_{3-9}$ cycloalkyl, $C_{3-9}$ cycloalkyl($C_{1-5}$)alkyl, $C_{4-9}$ bicycloalkyl, $C_{5-9}$ spirocycloalkyl, $C_{5-9}$ spirocycloalkyl-($C_{1-5}$)alkyl, $C_{9-11}$ tricycloalkyl, $C_{9-11}$ tricycloalkyl($C_{1-5}$)alkyl, aryl, aryl($C_{1-5}$)alkyl, $C_{3-7}$ heterocycloalkyl, $C_{3-7}$ heterocycloalkyl($C_{1-5}$)alkyl, heteroaryl or heteroaryl($C_{1-5}$)alkyl, any of which groups may be optionally substituted by one or more substituents.

Favourably, $R^5$ represents hydrogen; or $R^5$ represents $C_{1-5}$ alkyl, $C_{3-9}$ cycloalkyl, $C_{3-9}$ cycloalkyl($C_{1-5}$)alkyl, $C_{4-9}$ bicycloalkyl, $C_{4-9}$ bicycloalkyl($C_{1-5}$)alkyl, $C_{5-9}$ spiro-cycloalkyl, $C_{9-11}$ tricycloalkyl, $C_{9-11}$ tricycloalkyl($C_{1-5}$)alkyl, aryl, aryl($C_{1-5}$)alkyl, $C_{3-7}$ heterocycloalkyl, $C_{3-7}$ heterocycloalkyl($C_{1-5}$)alkyl or heteroaryl($C_{1-5}$)alkyl, any of which groups may be optionally substituted by one or more substituents.

Typically, $R^5$ represents $C_{1-5}$ alkyl, $C_{3-9}$ cycloalkyl, $C_{3-9}$ cycloalkyl($C_{1-5}$)alkyl, $C_{4-9}$ bicycloalkyl, $C_{5-9}$ spirocycloalkyl, $C_{5-9}$ spirocycloalkyl($C_{1-5}$)alkyl, $C_{9-11}$ tricycloalkyl, $C_{9-11}$ tricycloalkyl($C_{1-5}$)alkyl, aryl, aryl($C_{1-5}$)alkyl, $C_{3-7}$ heterocycloalkyl, $C_{3-7}$ heterocyclo-alkyl($C_{1-5}$)alkyl, heteroaryl or heteroaryl($C_{1-5}$)alkyl, any of which groups may be optionally substituted by one or more substituents. Additionally, $R^5$ may represent $C_{4-9}$ bicycloalkyl($C_{1-5}$)alkyl, which group may be optionally substituted by one or more substituents.

Suitably, $R^5$ represents hydrogen; or $R^5$ represents $C_{1-5}$ alkyl, $C_{3-9}$ cycloalkyl, $C_{3-9}$ cycloalkyl(C is)alkyl, $C_{4-9}$ bicycloalkyl, $C_{5-9}$ spirocycloalkyl, $C_{5-9}$ spirocycloalkyl($C_{1-5}$)- alkyl, $C_{9-11}$ tricycloalkyl, $C_{9-11}$ tricycloalkyl($C_{1-5}$)alkyl, aryl, aryl($C_{1-5}$)alkyl or heteroaryl-($C_{1-5}$)alkyl, any of which groups may be optionally substituted by one or more substituents.

Appositely, $R^5$ represents hydrogen; or $R^5$ represents $C_{3-9}$ cycloalkyl, $C_{5-9}$ spiro-cycloalkyl or aryl($C_{1-5}$)alkyl, any of which groups may be optionally substituted by one or more substituents.

In a first embodiment, $R^5$ represents hydrogen. In a second embodiment, $R^5$ represents optionally substituted $C_{1-5}$ alkyl. In a third embodiment, $R^5$ represents optionally substituted $C_{3-9}$ cycloalkyl. In a fourth embodiment, $R^5$ represents optionally substituted $C_{3-9}$ cycloalkyl($C_{1-5}$)alkyl. In a fifth embodiment, $R^5$ represents optionally substituted $C_{4-9}$ bicycloalkyl. In a sixth embodiment, $R^5$ represents optionally substituted $C_{4-9}$ bicycloalkyl($C_{1-5}$)alkyl. In a seventh embodiment, $R^5$ represents optionally substituted $C_{5-9}$ spirocycloalkyl. In an eighth embodiment, $R^5$ represents optionally substituted $C_{5-9}$ spirocycloalkyl($C_{1-5}$)alkyl. In a ninth embodiment, $R^5$ represents optionally substituted $C_{9-11}$ tricycloalkyl. In a tenth embodiment, $R^5$ represents optionally substituted $C_{9-11}$ tricycloalkyl($C_{1-5}$)alkyl. In an eleventh embodiment, $R^5$ represents optionally substituted aryl. In a twelfth embodiment, $R^5$ represents optionally substituted aryl($C_{1-5}$)alkyl. In a thirteenth embodiment, $R^5$ represents optionally substituted $C_{3-7}$ heterocycloalkyl. In a fourteenth embodiment, $R^5$ represents optionally substituted $C_{3-7}$ heterocycloalkyl($C_{1-5}$)alkyl. In a fifteenth embodiment, $R^5$ represents optionally substituted heteroaryl. In a sixteenth embodiment, $R^5$ represents optionally substituted heteroaryl($C_{1-5}$)alkyl.

In a particular embodiment, $R^5$ is other than hydrogen.

Typical values of $R^5$ include methyl, isopropyl, 1-methylpropyl, 2-methylpropyl, cyclopropyl, cyclopentyl, indanyl, cyclohexyl, cyclooctyl, cyclohexylmethyl, spiro[3.3]-heptanyl, spiro[3.3]heptanylmethyl, adamantanyl, adamantanylmethyl, phenyl, benzyl, phenylethyl, naphthylmethyl, thienyl, indolyl, pyridinyl, thienylmethyl, indolylmethyl and pyridinylmethyl, any of which groups may be optionally substituted by one or more substituents. Additional values include cyclobutyl, benzocyclobutenyl, tetrahydro-naphthalenyl, cycloheptyl, benzocycloheptenyl, cyclononanyl, cyclobutylmethyl, cyclobutylethyl, bicyclo[3.1.0]hexanyl, bicyclo[2.2.1]heptanyl, bicyclo[3.3.0]octanyl, bicyclo[3.2.1]octanyl, bicyclo[1.1.1]pentanylmethyl, phenylpropyl, tetrahydropyranyl, azocanyl, dihydrobenzofuranylmethyl and pyrrolylethyl, any of which groups may be optionally substituted by one or more substituents.

Selected values of $R^5$ include methyl, cyclobutyl, benzocyclobutenyl, cyclopentyl, indanyl, cyclohexyl, tetrahydronaphthalenyl, cycloheptyl, benzocycloheptenyl, cyclooctyl, cyclononanyl, cyclobutylmethyl, cyclobutylethyl, bicyclo[3.1.0]hexanyl, bicyclo[2.2.1]-heptanyl, bicyclo[3.3.0]octanyl, bicyclo[3.2.1]octanyl, bicyclo[1.1.1]pentanylmethyl, spiro[3.3]heptanyl, adamantanyl, adamantanylmethyl, phenyl, benzyl, phenylethyl, phenylpropyl, tetrahydropyranyl, azocanyl, dihydrobenzofuranylmethyl and pyrrolylethyl, any of which groups may be optionally substituted by one or more substituents.

Suitable values of $R^5$ include cyclohexyl, cyclooctyl, spiro[3.3]heptanyl and benzyl, any of which groups may be optionally substituted by one or more substituents.

Typical examples of optional substituents on $R^5$ include one, two or three substituents independently selected from halogen, cyano, nitro, $C_{1-6}$ alkyl, trifluoro-methyl, phenyl, hydroxy, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkyl-aminocarbonyl, di($C_{1-6}$)alkylaminocarbonyl, aminosulfonyl, $C_{1-6}$ alkylaminosulfonyl and di($C_{1-6}$)alkylaminosulfonyl. Additional examples include trifluoroethyl.

Suitable examples of optional substituents on $R^5$ include one, two or three substituents independently selected from halogen, cyano, $C_{1-6}$ alkyl, trifluoromethyl, phenyl, hydroxy, $C_{1-6}$ alkoxy and aminocarbonyl, especially halogen.

Favoured examples of optional substituents on $R^5$ include one, two or three substituents independently selected from halogen, $C_{1-6}$ alkyl, trifluoromethyl, phenyl and $C_{1-6}$ alkoxy, especially halogen.

Typical examples of specific substituents on $R^5$ include one, two or three substituents independently selected from fluoro, chloro, bromo, cyano, nitro, methyl, ethyl, isopropyl, tert-butyl, trifluoromethyl, phenyl, hydroxy, oxo, methoxy, tert-butoxy, difluoromethoxy, trifluoromethoxy, methylthio, methylsulfinyl, methylsulfonyl, amino, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, amino-sulfonyl, methylaminosulfonyl and dimethylaminosulfonyl. Additional examples include trifluoroethyl and isopropoxy.

Suitable examples of specific substituents on $R^5$ include one, two or three substituents independently selected from fluoro, chloro, bromo, cyano, methyl, trifluoro-methyl, phenyl, hydroxy, methoxy, tert-butoxy and aminocarbonyl, especially chloro. Additional examples include isopropoxy.

Favoured examples of specific substituents on $R^5$ include one, two or three substituents independently selected from fluoro, chloro, bromo, methyl, trifluoromethyl, phenyl, isopropoxy and tert-butoxy, especially chloro.

Illustrative values of $R^5$ include hydrogen, methyl, isopropyl, 1-methylpropyl, 2-methylpropyl, cyclopropyl, cyclopentyl, indanyl, cyclohexyl, cyclooctyl, cyclohexylmethyl, spiro[3.3]heptanyl, phenyl, chlorophenyl, benzyl, fluorobenzyl, chlorobenzyl, (chloro)(fluoro)benzyl, dichlorobenzyl, bromobenzyl, cyanobenzyl, methylbenzyl, trifluoromethylbenzyl, phenylbenzyl, hydroxybenzyl, methoxybenzyl, tert-butoxybenzyl, aminocarbonylbenzyl, phenylethyl, chlorophenylethyl, naphthylmethyl, thienylmethyl, indolylmethyl and pyridinylmethyl. Additional values include tert-butoxymethyl, cyclobutyl, methylcyclobutyl, dimethylcyclobutyl, phenylcyclobutyl, benzocyclobutenyl, methylcyclopentyl, difluorocyclohexyl, methylcyclohexyl, dimethylcyclohexyl, trifluoromethylcyclohexyl, tetrahydronaphthalenyl, cycloheptyl, benzocycloheptenyl, cyclononanyl, cyclobutylmethyl, difluorocyclobutylmethyl, dimethylcyclobutylmethyl, cyclobutylethyl, bicyclo[3.1.0]hexanyl, bicyclo[2.2.1]heptanyl, bicyclo[3.3.0]octanyl, bicyclo[3.2.1]octanyl, bicyclo[1.1.1]pentanylmethyl, adamantanyl, adamantanylmethyl, (chloro)(fluoro)phenyl, (fluoro)(methyl)phenyl, (bromo)(chloro)benzyl, (chloro)-(isopropoxy)benzyl, phenylpropyl, tetrahydropyranyl, tetramethyltetrahydropyranyl, azocanyl, dihydrobenzofuranylmethyl and methylpyrrolylethyl.

Selected values of $R^5$ include hydrogen, tert-butoxymethylcyclobutyl, methyl-cyclobutyl, dimethylcyclobutyl, phenylcyclobutyl, benzocyclobutenyl, cyclopentyl, methylcyclopentyl, indanyl, cyclohexyl, difluorocyclohexyl, methylcyclohexyl, dimethylcyclohexyl, trifluoromethylcyclohexyl, tetrahydronaphthalenyl, cycloheptyl, benzocycloheptenyl, cyclooctyl, cyclononanyl, cyclobutylmethyl, difluorocyclobutyl-methyl, dimethylcyclobutylmethyl, cyclobutylethyl, bicyclo[3.1.0]hexanyl, bicyclo[2.2.1]-heptanyl, bicyclo[3.3.0]octanyl, bicyclo[3.2.1]octanyl, bicyclo[1.1.1]pentanylmethyl, spiro[3.3]heptanyl, adamantanyl, adamantanylmethyl, (chloro)(fluoro)phenyl, (fluoro)-(methyl)phenyl, fluorobenzyl, chlorobenzyl, (chloro)(fluoro)benzyl, (bromo)(chloro)-benzyl, (chloro)(isopropoxy) benzyl, phenylethyl, chlorophenylethyl, phenylpropyl, tetrahydropyranyl, tetramethyltetrahydropyranyl, azocanyl, dihydrobenzofuranylmethyl and methylpyrrolylethyl.

Representative values of $R^5$ include hydrogen, cyclohexyl, cyclooctyl, spiro[3.3]-heptanyl and chlorobenzyl.

Favoured values of $R^5$ include cyclohexyl, 4-methylcyclohexyl and cyclooctyl. In a first embodiment, $R^5$ represents cyclohexyl. In a second embodiment, $R^5$ represents 4-methylcyclohexyl. In a third embodiment, $R^5$ represents cyclooctyl.

In a first embodiment, $R^{5a}$ represents optionally substituted $C_{3-7}$ cycloalkyl. In a second embodiment, $R^{5a}$ represents optionally substituted $C_{4-9}$ bicycloalkyl. In a third embodiment, $R^{5a}$ represents optionally substituted aryl. In a fourth embodiment, $R^{5a}$ represents optionally substituted $C_{3-7}$ heterocycloalkyl. In a fifth embodiment, $R^{5a}$ represents optionally substituted heteroaryl.

Typical values of $R^{5a}$ include cyclobutyl, cyclopentyl, bicyclo[1.1.1]pentanyl, phenyl, dihydrobenzofuranyl and pyrrolyl, any of which groups may be optionally substituted by one or more substituents.

Typical examples of optional substituents on $R^{5a}$ include $C_{1-6}$ alkyl, halogen, cyano, trifluoromethyl, trifluoroethyl, phenyl, hydroxy, $C_{1-6}$ alkoxy, $C_{1-6}$ alkylthio, $C_{1-6}$ alkylsulfinyl, $C_{1-6}$ alkylsulfonyl, $C_{2-6}$ alkylcarbonyl, amino, $C_{1-6}$ alkylamino and di($C_{1-6}$)alkyl-amino.

Selected examples of optional substituents on $R^{5a}$ include $C_{1-6}$ alkyl and halogen.

Typical examples of particular substituents on $R^{5a}$ include methyl, fluoro, chloro, bromo, cyano, trifluoromethyl, trifluoroethyl, phenyl, hydroxy, methoxy, methylthio, methylsulfinyl, methylsulfonyl, acetyl, amino, methylamino and dimethylamino.

Selected examples of particular substituents on $R^{5a}$ include methyl and chloro.

Selected values of $R^{5a}$ include cyclobutyl, cyclopentyl, bicyclo[1.1.1]pentanyl, phenyl, chlorophenyl, dihydrobenzofuranyl and methylpyrrolyl.

Suitably, $R^{5b}$ represents hydrogen, methyl or ethyl.

In a first embodiment, $R^{5b}$ represents hydrogen. In a second embodiment, $R^{5b}$ represents $C_{1-6}$ alkyl, especially methyl or ethyl.

Alternatively, $R^{5a}$ and $R^{5b}$, when taken together with the carbon atom to which they are both attached, may represent $C_{3-7}$ cycloalkyl, $C_{4-9}$ bicycloalkyl or $C_{3-7}$ heterocycloalkyl, any of which groups may be unsubstituted, or substituted by one or more substituents, typically by one or two substituents.

In a first embodiment, $R^{5a}$ and $R^{5b}$, when taken together with the carbon atom to which they are both attached, may suitably represent optionally substituted $C_{3-7}$ cycloalkyl. Examples include cyclobutyl, benzocyclobutenyl, cyclopentyl, indanyl, cyclohexyl, tetrahydronaphthalenyl, cycloheptanyl, benzocycloheptenyl, cyclooctanyl and cyclononanyl, any of which groups may be optionally substituted by one or more substituents.

In a second embodiment, $R^{5a}$ and $R^{5b}$, when taken together with the carbon atom to which they are both attached, may suitably represent optionally substituted $C_{4-9}$ bicycloalkyl. Examples include bicyclo[3.1.0]hexanyl, bicyclo[2.2.1]heptanyl and bicyclo[3.2.1]octanyl, any of which groups may be optionally substituted by one or more substituents.

In a third embodiment, $R^{5a}$ and $R^{5b}$, when taken together with the carbon atom to which they are both attached, may suitably represent optionally substituted $C_{3-7}$ heterocycloalkyl. Examples include tetrahydropyranyl and piperidinyl, either of which groups may be optionally substituted by one or more substituents.

Typical examples of optional substituents on such groups include $C_{1-6}$ alkyl, halogen, cyano, trifluoromethyl, trifluoroethyl, phenyl, hydroxy, $C_{1-6}$ alkoxy, $C_{1-6}$ alkyl-thio, $C_{1-6}$ alkylsulfinyl, $C_{1-6}$ alkylsulfonyl, $C_{2-6}$ alkylcarbonyl, amino, $C_{1-6}$ alkylamino and di($C_{1-6}$)alkylamino.

Selected examples of optional substituents on such groups include $C_{1-6}$ alkyl, halogen, trifluoromethyl, trifluoroethyl, phenyl and $C_{1-6}$ alkoxy.

Typical examples of particular substituents on such groups include methyl, fluoro, chloro, bromo, cyano, trifluoromethyl, trifluoroethyl, phenyl, hydroxy, methoxy, methylthio, methylsulfinyl, methylsulfonyl, acetyl, amino, methylamino and dimethylamino.

Selected examples of particular substituents on such groups include methyl, chloro, trifluoromethyl, trifluoroethyl, phenyl and methoxy.

Selected values of $R^{5a}$ and $R^{5b}$, when taken together with the carbon atom to which they are both attached, include methylcyclobutyl, dimethylcyclobutyl, phenylcyclobutyl, benzocyclobutenyl, methylbenzocyclobutenyl, chlorobenzocyclobutenyl, methoxy-benzocyclobutenyl, cyclopentyl, methylcyclopentyl, indanyl, chloroindanyl, cyclohexyl, methylcyclohexyl, dimethylcyclohexyl, trifluoromethylcyclohexyl, tetrahydro-naphthalenyl, cycloheptanyl, benzocycloheptenyl, cyclooctanyl, cyclononanyl, bicyclo[3.1.0]hexanyl, bicyclo[2.2.1]heptanyl, bicyclo[3.2.1]octanyl, tetramethyl-tetrahydropyranyl and trifluoroethylpiperidinyl.

Generally, $R^6$ represents —$NR^{6a}R^{6b}$; or $R^6$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ hetero-cycloalkyl($C_{1-6}$)alkyl, heteroaryl or heteroaryl($C_{1-6}$)alkyl, any of which groups may be optionally substituted by one or more substituents.

Favourably, $R^6$ represents —$NR^{6a}R^{6b}$ or —$OR^{6c}$; or $R^6$ represents $C_{1-9}$ alkyl, aryl, $C_{3-7}$ heterocycloalkyl, heteroaryl, heteroaryl($C_{1-6}$)alkyl or spiro[($C_{3-7}$)heterocycloalkyl]-[heteroaryl], any of which groups may be optionally substituted by one or more substituents.

Typically, $R^6$ represents —$NR^{6a}R^{6b}$; or $R^6$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents. Additionally, $R^6$ may represent —$OR^{6c}$; or $R^6$ may represent aryl, $C_{3-7}$ heterocycloalkyl or spiro[($C_{3-7}$)-heterocycloalkyl][heteroaryl], any of which groups may be optionally substituted by one or more substituents.

Suitably, $R^6$ represents $C_{1-6}$ alkyl, heteroaryl or heteroaryl($C_{1-6}$)alkyl, any of which groups may be optionally substituted by one or more substituents.

In a first embodiment, $R^6$ represents optionally substituted $C_{1-6}$ alkyl. In a second embodiment, $R^6$ represents optionally substituted $C_{3-9}$ cycloalkyl. In a third embodiment, $R^6$ represents optionally substituted $C_{3-9}$ cycloalkyl($C_{1-6}$)alkyl. In a fourth embodiment, $R^6$ represents optionally substituted aryl. In a fifth embodiment, $R^6$ represents optionally substituted aryl($C_{1-6}$)alkyl. In a sixth embodiment, $R^6$ represents optionally substituted $C_{3-7}$ heterocycloalkyl. In a seventh embodiment, $R^6$ represents optionally substituted $C_{3-7}$ heterocycloalkyl($C_{1-6}$)alkyl. In an eighth embodiment, $R^6$ represents optionally substituted heteroaryl. In a ninth embodiment, $R^6$ represents optionally substituted heteroaryl($C_{1-6}$)alkyl. In a tenth embodiment, $R^6$ represents optionally substituted spiro[($C_{3-7}$)heterocycloalkyl][heteroaryl]. In an eleventh embodiment, $R^6$ represents —$NR^{6a}R^{6b}$. In a twelfth embodiment, $R^6$ represents —$OR^{6c}$.

Typical values of $R^6$ include —$NR^{6a}R^{6b}$; and methyl, ethyl, propyl, 2-methylpropyl, butyl, cyclopropyl, cyclobutyl, cyclohexyl, cyclohexylmethyl, phenyl, benzyl, phenylethyl, pyrazolyl, pyridinyl, triazolylmethyl, benzotriazolylmethyl or pyridinylmethyl, any of which groups may be optionally substituted by one or more substituents. Additional values include —$OR^{6c}$; and tert-butyl, heptanyl, pyrrolidinyl, indolinyl, piperidinyl, morpholinyl, thiomorpholinyl, piperazinyl, pyrrolyl, pyrazolo[1,5-a]pyridinyl, 4,5,6,7-tetrahydropyrazolyl, oxazolyl, isoxazolyl, thiazolyl, isothiazolyl, imidazolyl, oxadiazolyl, thiadiazolyl, triazolyl, tetrazolyl, pyridazinyl, pyrimidinyl or spiro[tetrahydrofuran]-[indole], any of which groups may be optionally substituted by one or more substituents.

Selected values of $R^6$ include —$NR^{6a}R^{6b}$ and —$OR^{6c}$; and methyl, tert-butyl, heptanyl, phenyl, pyrrolidinyl, indolinyl, piperidinyl, morpholinyl, thiomorpholinyl, piperazinyl, pyrrolyl, pyrazolyl, pyrazolo[1,5-a]pyridinyl, 4,5,6,7-tetrahydropyrazolyl, oxazolyl, isoxazolyl, thiazolyl, isothiazolyl, imidazolyl, oxadiazolyl, thiadiazolyl, triazolyl, tetrazolyl, pyridinyl, pyridazinyl, pyrimidinyl, pyridinylmethyl or spiro[tetrahydrofuran]-[indole], any of which groups may be optionally substituted by one or more substituents.

Suitable values of $R^6$ include methyl, pyrazolyl and pyridinylmethyl, any of which groups may be optionally substituted by one or more substituents.

Typical examples of optional substituents on $R^6$ include one, two or three substituents independently selected from halogen, cyano, nitro, $C_{1-6}$ alkyl, trifluoro-methyl, phenyl, fluorophenyl, hydroxy, hydroxy($C_{1-6}$)alkyl, oxo, $C_{1-6}$ alkoxy, difluoro-methoxy, trifluoromethoxy, $C_{1-6}$ alkylthio, $C_{1-6}$ alkylsulfinyl, $C_{1-6}$ alkylsulfonyl, amino, amino($C_{1-6}$) alkyl, $C_{1-6}$ alkylamino, di($C_{1-6}$)alkylamino, pyrrolidinyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl. Additional examples include difluoromethyl, difluoroethyl, trifluoroethyl, trifluoropropyl, cyclopropyl, cyclobutyl, cyclopropylmethyl, $C_{1-6}$ alkoxy($C_{1-6}$)alkyl, di($C_{1-6}$)alkylamino-($C_{1-6}$)alkyl and tetrahydropyranyl.

Selected examples of optional substituents on $R^6$ include one, two or three substituents independently selected from halogen, $C_{1-6}$ alkyl, difluoromethyl, trifluoromethyl, difluoroethyl, trifluoroethyl, trifluoropropyl, cyclopropyl, cyclobutyl, cyclopropylmethyl, hydroxy, hydroxy($C_{1-6}$)alkyl, oxo, $C_{1-6}$ alkoxy($C_{1-6}$)alkyl, $C_{1-6}$ alkylsulfonyl, amino, amino($C_{1-6}$)alkyl, di($C_{1-6}$)alkylamino($C_{1-6}$)alkyl and tetrahydropyranyl.

Suitable examples of optional substituents on $R^6$ include one, two or three substituents independently selected from halogen, cyano, $C_{1-6}$ alkyl, trifluoromethyl, phenyl, fluorophenyl, hydroxy, hydroxy($C_{1-6}$)alkyl, oxo, $C_{1-6}$ alkoxy, trifluoromethoxy, $C_{1-6}$ alkylsulfonyl, amino, amino($C_{1-6}$)alkyl, C$_{1-6}$ alkylamino, di(C$_{1-6}$)alkylamino, pyrrolidinyl, morpholinyl, piperazinyl, C$_{2-6}$ alkylcarbonylamino(C$_{1-6}$)alkyl and carboxy.

Illustrative examples of optional substituents on R$^6$ include one, two or three substituents independently selected from C$_{1-6}$ alkyl and amino.

Typical examples of specific substituents on R$^6$ include one, two or three substituents independently selected from fluoro, chloro, bromo, cyano, nitro, methyl, ethyl, isopropyl, tert-butyl, trifluoromethyl, phenyl, fluorophenyl, hydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, morpholinyl, piperazinyl, acetyl-amino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methyl-aminocarbonyl, dimethylaminocarbonyl, aminosulfonyl, methylaminosulfonyl and dimethylaminosulfonyl. Additional examples include n-propyl, 2-methylpropyl, butan-2-yl, difluoromethyl, difluoroethyl, trifluoroethyl, trifluoropropyl, cyclopropyl, cyclobutyl, cyclopropylmethyl, hydroxyethyl, methoxymethyl, methoxyethyl, aminoisopropyl, dimethylaminoethyl, tetrahydropyranyl.

Selected examples of specific substituents on R$^6$ include one, two or three substituents independently selected from fluoro, methyl, ethyl, n-propyl, isopropyl, 2-methylpropyl, butan-2-yl, tert-butyl, difluoromethyl, trifluoromethyl, difluoroethyl, trifluoroethyl, trifluoropropyl, cyclopropyl, cyclobutyl, cyclopropylmethyl, hydroxy, hydroxyethyl, oxo, methoxymethyl, methoxyethyl, methylsulfonyl, amino, aminomethyl, aminoisopropyl, dimethylaminoethyl and tetrahydropyranyl.

Suitable examples of specific substituents on R$^6$ include one, two or three substituents independently selected from fluoro, chloro, cyano, methyl, ethyl, trifluoro-methyl, phenyl, fluorophenyl, hydroxy, hydroxymethyl, oxo, methoxy, trifluoromethoxy, methylsulfonyl, amino, aminomethyl, aminoethyl, methylamino, dimethylamino, pyrrolidinyl, morpholinyl, piperazinyl, acetylaminoethyl and carboxy.

Illustrative examples of specific substituents on R$^6$ include one, two or three substituents independently selected from methyl and amino.

Illustrative values of R$^6$ include methyl, difluoromethyl, methylsulfonylmethyl, aminomethyl, methylaminomethyl, difluoroethyl, carboxyethyl, difluoropropyl, 2-methyl-propyl, butyl, cyanocyclopropyl, methylcyclopropyl, ethylcyclopropyl, dimethyl-cyclopropyl, trifluoromethylcyclopropyl, phenylcyclopropyl, fluorophenylcyclopropyl, hydroxycyclopropyl, aminocyclopropyl, cyclobutyl, trifluoromethylcyclobutyl, cyclohexyl, cyclohexylmethyl, phenyl, fluorophenyl, chlorophenyl, cyanophenyl, methyl-phenyl, hydroxyphenyl, methylsulfonylphenyl, benzyl, fluorobenzyl, difluorobenzyl, chlorobenzyl, (chloro)(fluoro)benzyl, dichlorobenzyl, (chloro)(difluoro)benzyl, bromo-benzyl, cyanobenzyl, methylbenzyl, dimethylbenzyl, trifluoromethylbenzyl, phenylbenzyl, hydroxybenzyl, hydroxymethylbenzyl, benzoyl, methoxybenzyl, dimethoxybenzyl, trifluoromethoxybenzyl, methylsulfonylbenzyl, aminomethylbenzyl, aminoethylbenzyl, dimethylaminobenzyl, pyrrolidinylbenzyl, (dimethyl)(pyrrolidinyl)benzyl, morpholinylbenzyl, (dimethyl)(morpholinyl)benzyl, piperazinylbenzyl, acetylaminoethylbenzyl, phenylethyl, chlorophenylethyl, methylpyrazolyl, pyridinyl, triazolylmethyl, benzotriazolylmethyl, pyridinylmethyl and aminopyridinylmethyl. Additional values include —NR$^{6a}$R$^{6b}$, —OR$^{6c}$, tert-butyl, hydroxyheptanyl, pyrrolidinyl, methylpyrrolidinyl, indolinyl, piperidinyl, morpholinyl, dioxothiomorpholinyl, methylpiperazinyl, methyl-pyrrolyl, dimethylpyrazolyl, ethylpyrazolyl, (ethyl)(fluoro)pyrazolyl, (ethyl)(methyl)-pyrazolyl, n-propylpyrazolyl, isopropylpyrazolyl, 2-methylpropylpyrazolyl, butan-2-yl-pyrazolyl, difluoromethylp- yrazolyl, (difluoromethyl)(methyl)pyrazolyl, difluoroethyl-pyrazolyl, trifluoroethylpyrazolyl, trifluoropropylpyrazolyl, cyclopropylpyrazolyl, cyclobutylpyrazolyl, cyclopropylmethylpyrazolyl, hydroxyethylpyrazolyl, methoxyethyl-pyrazolyl, dimethylaminoethylpyrazolyl, tetrahydropyranylpyrazolyl, (methyl)(tetrahydro-pyranyl)pyrazolyl, pyrazolo[1,5-a]pyridinyl, methyl-4,5,6,7-tetrahydropyrazolyl, oxazolyl, methyloxazolyl, ethyloxazolyl, isoxazolyl, methylisoxazolyl, dimethylisoxazolyl, ethylisoxazolyl, isopropylisoxazolyl, tert-butylisoxazolyl, trifluoromethylisoxazolyl, cyclopropylisoxazolyl, cyclobutylisoxazolyl, methoxymethyli- soxazolyl, aminomethylisoxazolyl, aminoisopropylisoxazolyl, thiazolyl, methylthiazolyl, dimethylthiazolyl, isothiazolyl, methylisothiazolyl, methylimidazolyl, methyloxadiazolyl, methylthiadiazolyl, methyltriazolyl, dimethyltriazolyl, ethyltriazolyl, methyltetrazolyl, methylpyridinyl, pyridazinyl, pyrimidinyl, methylpyrimidinyl and spiro[tetrahydrofuran][oxoindole].

Selected values of R$^6$ include —NR$^{6a}$R$^{6b}$, —OR$^{6c}$, methyl, tert-butyl, hydroxyheptanyl, phenyl, fluorophenyl, methylsulfonylphenyl, pyrrolidinyl, methyl-pyrrolidinyl, indolinyl, piperidinyl, morpholinyl, dioxothiomorpholinyl, methyl-piperazinyl, methylpyrrolyl, methylpyrazolyl, dimethylpyrazolyl, ethylpyrazolyl, (ethyl)-(fluoro)pyrazolyl, (ethyl)(methyl)pyrazolyl, n-propylpyrazolyl, isopropylpyrazolyl, 2-methylpropylpyrazolyl, butan-2-ylpyrazolyl, difluoromethylpyrazolyl, (difluoromethyl)-(methyl)pyrazolyl, difluoroethylpyrazolyl, trifluoroethylpyrazolyl, trifluoropropyl-pyrazolyl, cyclopropylpyrazolyl, cyclobutylpyrazolyl, cyclopropylmethylpyrazolyl, hydroxyethylpyrazolyl, methoxyethylpyrazolyl, dimethylaminoethylpyrazolyl, tetrahydropyranylpyrazolyl, (methyl)(tetrahydropyranyl)pyrazolyl, pyrazolo[1,5-a]-pyridinyl, methyl-4,5,6,7-tetrahydropyrazolyl, oxazolyl, methyloxazolyl, ethyloxazolyl, isoxazolyl, methylisoxazolyl, dimethylisoxazolyl, ethylisoxazolyl, isopropylisoxazolyl, tert-butylisoxazolyl, trifluoromethylisoxazolyl, cyclopropylisoxazolyl, cyclobutylisoxazolyl, methoxymethylisoxazolyl, aminomethylisoxazolyl, aminoisopropylisoxazolyl, thiazolyl, methylthiazolyl, dimethylthiazolyl, isothiazolyl, methylisothiazolyl, methyl-imidazolyl, methyloxadiazolyl, methylthiadiazolyl, methyltriazolyl, dimethyltriazolyl, ethyltriazolyl, methyltetrazolyl, pyridinyl, methylpyridinyl, pyridazinyl, pyrimidinyl, methylpyrimidinyl, pyridinylmethyl, aminopyridinylmethyl and spiro[tetrahydrofuran]-[oxoindole].

Representative values of R$^6$ include methyl, methylpyrazolyl, pyridinylmethyl and aminopyridinylmethyl.

Generally, R$^{6a}$ represents hydrogen or C$_{1-6}$ alkyl.

Favourably, R$^{6a}$ represents C$_{1-6}$ alkyl, C$_{3-7}$ cycloalkyl, aryl(C$_{1-6}$)alkyl, C$_{3-7}$ heterocycloalkyl or spiro[(C$_{3-7}$)heterocycloalkyl][heteroaryl], any of which groups may be optionally substituted by one or more substituents.

Typically, R$^{6a}$ represents hydrogen or methyl.

In a first embodiment, R$^{6a}$ represents hydrogen. In a second embodiment, R$^{6a}$ represents optionally substituted C$_{1-6}$ alkyl. In a first aspect of that embodiment, R$^{6a}$ represents unsubstituted C$_{1-6}$ alkyl, especially methyl. In a second aspect of that embodiment, R$^{6a}$ represents monosubstituted, disubstituted or trisubstituted C$_{1-6}$ alkyl. In a third embodiment, R$^{6a}$ represents optionally substituted C$_{3-7}$ cycloalkyl.

In a fourth embodiment, $R^{6a}$ represents optionally substituted $C_{3-7}$ cycloalkyl($C_{1-6}$)alkyl. In a fifth embodiment, $R^{6a}$ represents optionally substituted aryl. In a sixth embodiment, $R^{6a}$ represents optionally substituted aryl($C_{1-6}$)alkyl. In a seventh embodiment, $R^{6a}$ represents optionally substituted $C_{3-7}$ heterocycloalkyl. In an eighth embodiment, $R^{6a}$ represents optionally substituted $C_{3-7}$ heterocycloalkyl ($C_{1-6}$)alkyl. In a ninth embodiment, $R^{6a}$ represents optionally substituted heteroaryl. In a tenth embodiment, $R^{6a}$ represents optionally substituted heteroaryl($C_{1-6}$)alkyl. In an eleventh embodiment, $R^{6a}$ represents optionally substituted spiro[($C_{3-7}$)heterocycloalkyl][heteroaryl].

Typical values of $R^{6a}$ include methyl, ethyl, n-propyl, isopropyl, 2,2-dimethyl-propyl, cyclohexyl, benzyl, tetrahydrofuranyl, tetrahydropyranyl, tetrahydrothiopyranyl and spiro[tetrahydrofuran][indole], any of which groups may be optionally substituted by one or more substituents.

Typical examples of optional substituents on $R^{6a}$ include one, two or three substituents independently selected from halogen, cyano, nitro, $C_{1-6}$ alkyl, trifluoro-methyl, phenyl, fluorophenyl, hydroxy, hydroxy($C_{1-6}$)alkyl, oxo, $C_{1-6}$ alkoxy, difluoro-methoxy, trifluoromethoxy, $C_{1-6}$ alkylthio, $C_{1-6}$ alkylsulfinyl, $C_{1-6}$ alkylsulfonyl, amino, amino($C_{1-6}$) alkyl, $C_{1-6}$ alkylamino, di($C_{1-6}$)alkylamino, pyrrolidinyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Selected examples of optional substituents on $R^{6a}$ include one, two or three substituents independently selected from trifluoromethyl, oxo and $C_{1-6}$ alkoxy.

Typical examples of specific substituents on $R^{6a}$ include one, two or three substituents independently selected from fluoro, chloro, bromo, cyano, nitro, methyl, ethyl, isopropyl, tert-butyl, trifluoromethyl, phenyl, fluorophenyl, hydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, morpholinyl, piperazinyl, acetyl-amino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methyl-aminocarbonyl, dimethylaminocarbonyl, aminosulfonyl, methylaminosulfonyl and dimethylaminosulfonyl.

Selected examples of specific substituents on $R^{6a}$ include one, two or three substituents independently selected from trifluoromethyl, oxo and methoxy.

Selected values of $R^{6a}$ include methyl, ethyl, trifluoroethyl, methoxyethyl, n-propyl, isopropyl, 2,2-dimethylpropyl, cyclohexyl, benzyl, tetrahydrofuranyl, tetrahydropyranyl, oxotetrahydrothiopyranyl and spiro[tetrahydrofuran][oxoindole].

Suitably, $R^{6b}$ represents hydrogen, methyl, ethyl, n-propyl or isopropyl.

Typically, $R^{6b}$ represents hydrogen or methyl.

In a first embodiment, $R^{6b}$ represents hydrogen. In a second embodiment, $R^{6b}$ represents $C_{1-6}$ alkyl. In a particular aspect of that embodiment, $R^{6b}$ represents methyl, ethyl, n-propyl or isopropyl, especially methyl.

Favourably, $R^{6c}$ represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl or heteroaryl($C_{1-6}$)alkyl, any of which groups may be optionally substituted by one or more substituents.

In a first embodiment, $R^{6c}$ represents optionally substituted $C_{1-6}$ alkyl. In a second embodiment, $R^{6c}$ represents optionally substituted $C_{3-7}$ cycloalkyl. In a third embodiment, $R^{6c}$ represents optionally substituted $C_{3-7}$ cycloalkyl ($C_{1-6}$)alkyl. In a fourth embodiment, $R^{6c}$ represents optionally substituted aryl. In a fifth embodiment, $R^{6c}$ represents optionally substituted aryl($C_{1-6}$)alkyl. In a sixth embodiment, $R^{6c}$ represents optionally substituted $C_{3-7}$ heterocycloalkyl. In a seventh embodiment, $R^{6c}$ represents optionally substituted $C_{3-7}$ heterocycloalkyl($C_{1-6}$)alkyl. In an eighth embodiment, $R^{6c}$ represents optionally substituted heteroaryl. In a ninth embodiment, $R^{6c}$ represents optionally substituted heteroaryl($C_{1-6}$)alkyl.

Typical values of $R^{6c}$ include methyl, ethyl, isopropyl, 2-methylpropyl, tert-butyl, 2,2-dimethylpropyl, cyclobutyl, cyclopentyl, cyclohexyl, cyclopropylmethyl, cyclohexylmethyl, oxetanyl, azetidinyl, tetrahydrofuranyl, tetrahydropyranyl, tetrahydropyranyl-methyl, pyrazolylmethyl, oxazolylmethyl, isoxazolylmethyl, imidazolylmethyl and pyrazinylmethyl, any of which groups may be optionally substituted by one or more substituents.

Typical examples of optional substituents on $R^{6c}$ include one, two or three substituents independently selected from halogen, cyano, nitro, $C_{1-6}$ alkyl, trifluoro-methyl, phenyl, fluorophenyl, hydroxy, hydroxy($C_{1-6}$)alkyl, oxo, $C_{1-6}$ alkoxy, difluoro-methoxy, trifluoromethoxy, $C_{1-6}$ alkylthio, $C_{1-6}$ alkylsulfinyl, $C_{1-6}$ alkylsulfonyl, amino, amino($C_{1-6}$) alkyl, $C_{1-6}$ alkylamino, di($C_{1-6}$)alkylamino, pyrrolidinyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Selected examples of optional substituents on $R^{6c}$ include one, two or three substituents independently selected from $C_{1-6}$ alkyl, trifluoromethyl, $C_{1-6}$ alkoxy and $C_{2-6}$ alkoxycarbonyl.

Typical examples of specific substituents on $R^{6c}$ include one, two or three substituents independently selected from fluoro, chloro, bromo, cyano, nitro, methyl, ethyl, isopropyl, tert-butyl, trifluoromethyl, phenyl, fluorophenyl, hydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, morpholinyl, piperazinyl, acetyl-amino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methyl-aminocarbonyl, dimethylaminocarbonyl, aminosulfonyl, methylaminosulfonyl and dimethylaminosulfonyl.

Selected examples of specific substituents on $R^{6c}$ include one, two or three substituents independently selected from methyl, trifluoromethyl, methoxy and tert-butoxycarbonyl.

Selected values of $R^{6c}$ include methyl, trifluoroethyl, methoxyethyl, isopropyl, 2-methylpropyl, tert-butyl, 2,2-dimethylpropyl, cyclobutyl, cyclopentyl, cyclohexyl, cyclopropylmethyl, cyclohexylmethyl, oxetanyl, methyloxetanyl, azetidinyl, tert-butoxycarbonylazetidinyl, tetrahydrofuranyl, tetrahydropyranyl, tetrahydropyranylmethyl, methylpyrazolylmethyl, oxazolylmethyl, isoxazolylmethyl, methylimidazolylmethyl and pyrazinylmethyl.

In a first embodiment, $R^7$ represents aryl, which group may be optionally substituted by one or more substituents. In a second embodiment, $R^7$ represents heteroaryl, which group may be optionally substituted by one or more substituents. In a third embodiment, $R^7$ represents spiro[$(C_{3-7})$ heterocycloalkyl][heteroaryl], which group may be optionally substituted by one or more substituents.

Typical values of $R^7$ include phenyl, pyrazolo[1,5-a]pyrazinyl, benzoxazolyl, benzothiazolyl, benzimidazolyl, imidazo[1,2-b]pyridazinyl, purinyl, pyridinyl, pyridazinyl, cinnolinyl, pyrimidinyl, pyrazinyl and spiro[tetrahydropyranyl][indole], any of which groups may be optionally substituted by one or more substituents.

Typical examples of optional substituents on $R^7$ include one, two or three substituents independently selected from halogen, cyano, nitro, $C_{1-6}$ alkyl, difluoromethyl, trifluoromethyl, phenyl, fluorophenyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, pyrrolidinyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Selected examples of optional substituents on $R^7$ include one, two or three substituents independently selected from halogen, cyano, $C_{1-6}$ alkyl, difluoromethyl, trifluoromethyl, oxo, $C_{1-6}$ alkoxy, difluoromethoxy and di($C_{1-6}$)alkylamino.

Typical examples of specific substituents on $R^7$ include one, two or three substituents independently selected from fluoro, chloro, bromo, cyano, nitro, methyl, ethyl, isopropyl, tert-butyl, difluoromethyl, trifluoromethyl, phenyl, fluorophenyl, hydroxy, hydroxymethyl, oxo, methoxy, isopropoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, morpholinyl, piperazinyl, acetylamino, acetylaminoethyl, methoxycarbonylamino, methylsulfonyl-amino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl.

Selected examples of specific substituents on $R^7$ include one, two or three substituents independently selected from fluoro, chloro, cyano, methyl, ethyl, isopropyl, difluoromethyl, trifluoromethyl, oxo, methoxy, isopropoxy, difluoromethoxy and dimethylamino.

Selected values of $R^7$ include phenyl, pyrazolo[1,5-a]pyrazinyl, benzoxazolyl, fluorobenzoxazolyl, methylbenzoxazolyl, benzothiazolyl, benzimidazolyl, fluoro-benzimidazolyl, imidazo[1,2-b]pyridazinyl, purinyl, pyridinyl, cyanopyridinyl, methyl-pyridinyl, methoxypyridinyl, pyridazinyl, chloropyridazinyl, cyanopyridazinyl, methylpyridazinyl, ethylpyridazinyl, isopropylpyridazinyl, difluoromethylpyridazinyl, trifluoro-methylpyridazinyl, methoxypyridazinyl, isopropoxypyridazinyl, difluoromethoxypyridazinyl, dimethylaminopyridazinyl, cinnolinyl, pyrimidinyl, pyrazinyl, methyl-pyrazinyl and spiro[tetrahydropyranyl][oxoindole].

One sub-class of the compounds of formula (IA) above is represented by the compounds of formula (IIA), and pharmaceutically acceptable salts thereof:

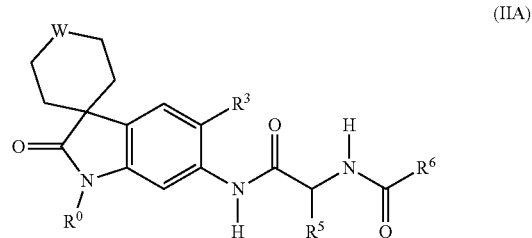

(IIA)

wherein
W represents O, S, S(O), S(O)$_2$, S(O)(NH) or N—$R^{17}$;
$R^{17}$ represents hydrogen or $C_{1-6}$ alkyl; and
$R^0$, $R^3$, $R^5$ and $R^6$ are as defined above.
Typically, W represents O, S, S(O), S(O)$_2$ or N—$R^{17}$.
Suitably, W represents O, S or N—$R^{17}$.
In a first embodiment, W represents O. In a second embodiment, W represents S. In a third embodiment, W represents S(O). In a fourth embodiment, W represents S(O)$_2$. In a fifth embodiment, W represents S(O)(NH). In a sixth embodiment, W represents N—$R^{17}$.
Suitably, $R^{17}$ represents hydrogen or methyl.
In a first embodiment, $R^{17}$ represents hydrogen. In a second embodiment, $R^{17}$ represents $C_{1-6}$ alkyl. In a first aspect of that embodiment, $R^{17}$ represents methyl.

Another sub-class of the compounds of formula (IA) above is represented by the compounds of formula (IIB), and pharmaceutically acceptable salts thereof:

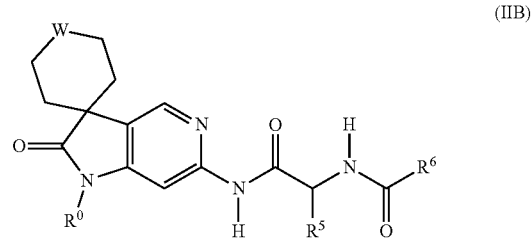

(IIB)

wherein
W, $R^0$, $R^5$ and $R^6$ are as defined above.
Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments, including inflammatory and autoimmune disorders.

The compounds according to the present invention are useful in the treatment and/or prophylaxis of a pathological disorder that is mediated by a pro-inflammatory IL-17 cytokine or is associated with an increased level of a pro-inflammatory IL-17 cytokine. Generally, the pathological condition is selected from the group consisting of infections (viral, bacterial, fungal and parasitic), endotoxic shock associated with infection, arthritis, rheumatoid arthritis, psoriatic arthritis, systemic onset juvenile idiopathic arthritis (JIA), systemic lupus erythematosus (SLE), asthma, chronic obstructive airways disease (COAD), chronic obstructive pulmonary disease (COPD), acute lung injury, pelvic inflammatory disease, Alzheimer's Disease, Crohn's disease, inflammatory bowel disease, irritable bowel syndrome, ulcerative colitis, Castleman's disease, ankylosing spondylitis and other spondyloarthropathies, dermatomyositis, myocarditis, uveitis, exophthalmos, autoimmune thyroiditis, Peyronie's Disease, coeliac disease, gall bladder disease, Pilonidal disease, peritonitis, psoriasis, atopic dermatitis, vasculitis, surgical adhesions, stroke, autoimmune diabetes, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, fibrosing disorders including pulmonary fibrosis, liver fibrosis, renal fibrosis, scleroderma or systemic sclerosis, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, chronic lymphatic leukemia, gastric cancer and colon cancer), heart disease including ischaemic diseases such as myocardial infarction as well as atherosclerosis, intravascular coagulation, bone resorption, osteoporosis, periodontitis, hypochlorhydia and pain (particularly pain associated with inflammation).

WO 2009/089036 reveals that modulators of IL-17 activity may be administered to inhibit or reduce the severity of ocular inflammatory disorders, in particular ocular surface inflammatory disorders including Dry Eye Syndrome (DES). Consequently, the compounds in accordance with the present invention are useful in the treatment and/or prevention of an IL-17-mediated ocular inflammatory disorder, in particular an IL-17-mediated ocular surface inflammatory disorder including Dry Eye Syndrome. Ocular surface inflammatory disorders include Dry Eye Syndrome, penetrating keratoplasty, corneal transplantation, lamellar or partial thickness transplantation, selective endothelial transplantation, corneal neovascularization, keratoprosthesis surgery, corneal ocular surface inflammatory conditions, conjunctival scarring disorders, ocular autoimmune conditions, Pemphigoid syndrome, Stevens-Johnson syndrome, ocular allergy, severe allergic (atopic) eye disease, conjunctivitis and microbial keratitis. Particular categories of Dry Eye Syndrome include keratoconjunctivitis sicca (KCS), Sjögren syndrome, Sjögren syndrome-associated keratoconjunctivitis sicca, non-Sjögren syndrome-associated keratoconjunctivitis sicca, keratitis sicca, sicca syndrome, xerophthalmia, tear film disorder, decreased tear production, aqueous tear deficiency (ATD), meibomian gland dysfunction and evaporative loss.

Illustratively, the compounds of the present invention may be useful in the treatment and/or prophylaxis of a pathological disorder selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, scleroderma, systemic sclerosis, lung fibrosis, inflammatory bowel diseases (including Crohn's disease and ulcerative colitis), ankylosing spondylitis and other spondylo-arthropathies, cancer and pain (particularly pain associated with inflammation).

Suitably, the compounds of the present invention are useful in the treatment and/or prophylaxis of psoriasis, psoriatic arthritis or ankylosing spondylitis.

The present invention also provides a pharmaceutical composition which comprises a compound in accordance with the invention as described above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds according to the present invention may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds according to the present invention may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration the compounds according to the present invention may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound according to the present invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above wherein $R^1$ represents —$COR^a$ may be prepared by a process which comprises reacting a carboxylic acid of formula $R^aCO_2H$, or a salt thereof, e.g. a lithium salt thereof, with a compound of formula (III):

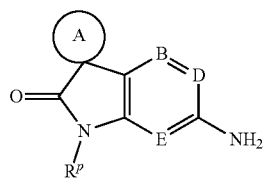

(III)

wherein A, B, D, E and $R^a$ are as defined above, and $R^p$ corresponds to the group $R^0$ as defined above, or $R^p$ represents a N-protecting group; followed, as necessary, by removal of the N-protecting group $R^p$.

The N-protecting group $R^p$ will suitably be tert-butoxycarbonyl (BOC), benzyl, or 2-(trimethylsilyl)ethoxymethyl (SEM).

The reaction is conveniently accomplished in the presence of a coupling agent. Suitable coupling agents include 2-(7-aza-1H-benzotriazol-1-yl)-1,1,3,3-tetramethyl-uronium hexafluorophosphate (HATU).

Where compound (III) is reacted with a carboxylic acid of formula $R^aCO_2H$, the reaction is generally carried out in the presence of a base. Suitable bases include organic amines, e.g. a trialkylamine such as N,N-diisopropylethylamine. The reaction is conveniently performed at ambient temperature in a suitable solvent, e.g. a cyclic ether such as tetrahydrofuran, or a dipolar aprotic solvent such as N,N-dimethylformamide, or a chlorinated solvent such as dichloromethane.

Where compound (III) is reacted with the lithium salt of a carboxylic acid of formula $R^aCO_2H$, the reaction is generally carried out at ambient temperature in a suitable solvent, e.g. a dipolar aprotic solvent such as N,N-dimethylformamide.

Where the N-protecting group $R^p$ is BOC, the subsequent removal thereof may conveniently be effected by treatment with an acid, e.g. a mineral acid such as hydrochloric acid, or an organic acid such as trifluoroacetic acid.

Where the N-protecting group $R^p$ is benzyl, the subsequent removal thereof may conveniently be effected by catalytic hydrogenation, typically by treatment with gaseous hydrogen in the presence of a hydrogenation catalyst, e.g. palladium on charcoal.

Where the N-protecting group $R^p$ is SEM, the subsequent removal thereof may conveniently be effected by treatment with a fluoride salt, e.g. tetra-n-butylammonium fluoride; or by treatment with an acid, e.g. a mineral acid such as hydrochloric acid, or an organic acid such as trifluoroacetic acid.

Where $R^a$ represents —$CH(R^5)N(H)C(O)R^6$, the intermediates of formula $R^aCO_2H$ may be prepared by a two-step procedure which comprises: (i) reacting a carboxylic acid of formula $R^6$—$CO_2H$ with a compound of formula (IV):

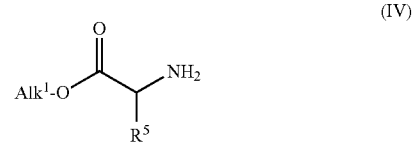

(IV)

wherein $Alk^1$ represents $C_{1-4}$ alkyl, e.g. methyl, and $R^5$ and $R^6$ are as defined above; under conditions analogous to those described above for the reaction between compound (III) and a carboxylic acid of formula $R^aCO_2H$; and (ii) saponification of the resulting material by treatment with a base.

As for the reaction between compound (III) and a carboxylic acid of formula $R^aCO_2H$, the coupling agent employed in step (i) may suitably be HATU.

Alternatively, the coupling agent may be 2,4,6-tripropyl-1,3,5,2,4,6-trioxa-triphosphorinane 2,4,6-trioxide, in which case the reaction may generally be carried out in the presence of a base which may suitably include organic amines, e.g. a trialkylamine such as N,N-diisopropylethylamine, or an aromatic base such as pyridine. The reaction is conveniently performed at ambient temperature in a suitable solvent, e.g. an organic ester such as ethyl acetate and/or a cyclic ether such as tetrahydrofuran.

Alternatively, the coupling agent may be a mixture of N-(3-dimethylaminopropyl)-N'-ethylcarbodiimide hydrochloride and 1-hydroxybenzotriazole, in which case the reaction may generally be carried out in the presence of a base, e.g. an organic amine such as N,N-diisopropylethylamine. The reaction is conveniently performed at ambient temperature in a suitable solvent, e.g. a dipolar aprotic solvent such as N,N-dimethyl-formamide.

The saponification reaction in step (ii) will generally be effected by treatment with a base. Suitable bases include inorganic hydroxides, e.g. an alkali metal hydroxide such as lithium hydroxide. Where lithium hydroxide is employed in step (ii) of the above procedure, the product may be the lithium salt of the carboxylic acid of formula R$^a$CO$_2$H.

Step (ii) is conveniently effected at ambient temperature in water and a suitable organic solvent, e.g. a cyclic ether such as tetrahydrofuran, optionally in admixture with a C$_{1-4}$ alkanol such as methanol.

In another procedure, the compounds of formula (I) above wherein R$^1$ represents —SO$_2$R$^b$ may be prepared by a process which comprises reacting a compound of formula R$^b$SO$_2$C$_1$ with a compound of formula (III) as defined above.

The reaction is conveniently accomplished at ambient temperature in the presence of a base, e.g. an organic base such as triethylamine, in a suitable solvent, e.g. a chlorinated hydrocarbon solvent such as dichloromethane.

In another procedure, the compounds of formula (I) above wherein R$^1$ represents —COR$^a$ may be prepared by a process which comprises reacting an amide of formula R$^a$CONH$_2$ with a compound of formula (V):

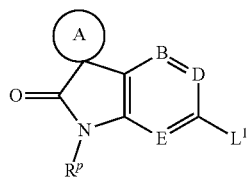

(V)

wherein A, B, D, E, R$^a$ and R$^p$ are as defined above, and L$^1$ represents a suitable leaving group; in the presence of a transition metal catalyst; followed, as necessary, by removal of the N-protecting group R$^p$.

The leaving group L$^1$ is suitably a halogen atom, e.g. chloro or bromo.

The transition metal catalyst is suitably [(2-di-tert-butylphosphino-3,6-dimethoxy-2',4',6'-triisopropyl-1,1'-biphenyl)-2-(2'-amino-1,1'-biphenyl)]palladium(II) methanesulfonate (tBuBrettPhos Pd G3), in which case the reaction will generally be performed in the presence of 2-(di-tert-butylphosphino)-2',4',6'-triisopropyl-3,6-dimethoxy-1,1'-biphenyl (tBuBrettPhos). The reaction is conveniently carried out at an elevated temperature in the presence of a base, e.g. an inorganic base such as potassium carbonate, in a suitable solvent, e.g. a lower alkanol such as tert-butanol.

Alternatively, the transition metal catalyst may suitably be tris(dibenzylidene-acetone)dipalladium(0), in which case the reaction will generally be performed in the presence of 2-dicyclohexylphosphino-2',4',6'-triisopropylbiphenyl (XPhos) or 4,5-bis(diphenylphosphino)-9,9-dimethylxanthene (Xantphos). The reaction is conveniently carried out at an elevated temperature in the presence of a base, e.g. a carbonate salt such as potassium carbonate or cesium carbonate, in a suitable solvent, e.g. a cyclic ether such as 1,4-dioxane, or a C$_{1-6}$ alkanol such as tert-butanol.

In another procedure, the compounds of formula (I) above wherein R$^1$ is an aryl or heteroaryl moiety may be prepared by a process which comprises reacting a compound of formula R$^1$—NH$_2$ with a compound of formula (V) as defined above in the presence of a transition metal catalyst; followed, as necessary, by removal of the N-protecting group R$^p$.

The transition metal catalyst is suitably tris(dibenzylideneacetone)dipalladium(0), in which case the reaction will generally be performed in the presence of 2-(di-tert-butyl)-phosphino-2',4',6'-triisopropylbiphenyl (tert-BuXPhos). The reaction is conveniently carried out at an elevated temperature in the presence of a base, e.g. a tert-butoxide salt such as sodium tert-butoxide, in a suitable solvent, e.g. a cyclic ether such as 1,4-dioxane.

The intermediates of formula (V) above may be prepared by reacting the appropriate α,ω-dihaloalkane with a compound of formula (VI):

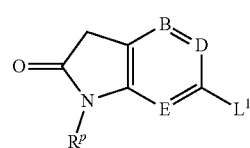

(VI)

wherein B, D, E, L$^1$ and R$^p$ are as defined above.

The reaction is generally performed in the presence of a base, e.g. an inorganic base such as cesium carbonate. The reaction will conveniently be carried out at ambient or elevated temperature, as appropriate, in a suitable solvent, e.g. a dipolar aprotic solvent such as N,N-dimethylformamide, or a carbonyl solvent such as acetone, or a sulfoxide solvent such as dimethyl sulfoxide.

The intermediates of formula (VI) above may be prepared by a two-step procedure from a compound of formula (VII):

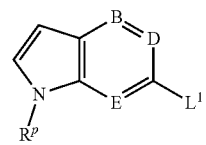

(VII)

wherein B, D, E, L$^1$ and R$^p$ are as defined above; which procedure comprises the following steps:

(i) treatment of compound (VII) with pyridinium tribromide or N-bromo-succinimide; and (ii) treatment of the 3,3-dibromo-2-oxoindoline derivative thereby obtained with metallic zinc.

Step (i) is conveniently carried out at ambient temperature in a suitable solvent, e.g. a cyclic ether such as 1,4-dioxane, or a C$_{1-4}$ alkanol such as tert-butanol, typically in admixture with water.

Step (ii) is conveniently carried out in the presence of ammonium chloride at an elevated temperature in a suitable solvent, e.g. a dipolar aprotic solvent such as N,N-dimethylformamide, or a cyclic ether such as tetrahydrofuran. Alternatively, step (ii) may be accomplished in acetic acid at ambient temperature in a suitable solvent, e.g. a cyclic ether such as tetrahydrofuran.

Similarly, the intermediates of formula (III) above may be prepared by reacting the appropriate α,ω-dihaloalkane with a compound of formula (VI-A):

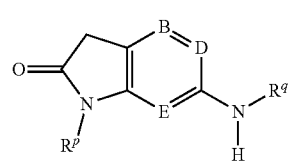

(VI-A)

wherein B, D, E and $R^p$ are as defined above, and $R^q$ represents hydrogen or an N-protecting group; under conditions analogous to those described above for the reaction of an α,ω-dihaloalkane with a compound of formula (VI); followed, as appropriate, by removal of the N-protecting group(s) $R^p$ and/or $R^q$.

The N-protecting group $R^q$ will suitably be tert-butoxycarbonyl (BOC).

Where the N-protecting group $R^q$ is BOC, the subsequent removal thereof may conveniently be effected by treatment with an acid, e.g. a mineral acid such as hydrochloric acid, or an organic acid such as trifluoroacetic acid.

In another procedure, the compounds of formula (IA) above may be prepared by a process which comprises reacting a compound of formula (III) as defined above with a compound of formula (VIII):

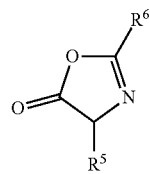

(VIII)

wherein $R^5$ and $R^6$ are as defined above; followed, as necessary, by removal of the N-protecting group $R^p$.

The reaction between compounds (III) and (VIII) will generally be performed in the presence of acetic acid. The reaction is conveniently carried out at an elevated temperature in a suitable solvent, e.g. a cyclic ether such as tetrahydrofuran.

Similarly, the compounds of formula (IF) above may be prepared by a process which comprises reacting a compound of formula (III) as defined above with a compound of formula (IX):

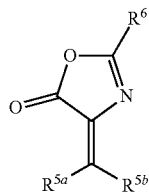

(IX)

wherein $R^{5a}$, $R^{5b}$ and $R^6$ are as defined above; under conditions analogous to those described above for the reaction between compounds (III) and (VIII); followed, as necessary, by removal of the N-protecting group $R^p$.

Where the respective values of $R^5$, $R^{5a}$ and $R^{5b}$ permit, an intermediate of formula (VIII) may be obtained from the corresponding intermediate of formula (IX) by conventional catalytic hydrogenation.

The intermediates of formula (IX) above may be prepared by reacting a compound of formula $R^{5a}C(O)R^{5b}$ with a compound of formula (VIII) as defined above wherein $R^5$ represents hydrogen.

The reaction is conveniently effected by treating the reagents with titanium tetrachloride; followed by treatment of the resulting material with pyridine.

In another procedure, the compounds of formula (IA) above may be prepared by a process which comprises reacting a carboxylic acid of formula $R^6$—$CO_2H$ with a compound of formula (X):

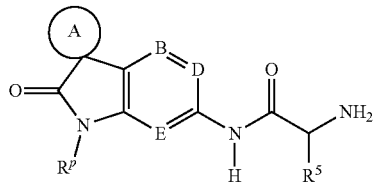

(X)

wherein A, B, D, E, $R^p$, $R^5$ and $R^6$ are as defined above; under conditions analogous to those described above for the reaction between compound (III) and a carboxylic acid of formula $R^aCO_2H$; followed, as necessary, by removal of the N-protecting group $R^p$.

Similarly, the compounds of formula (IA) above wherein $R^6$ represents —$NR^{6a}R^{6b}$ may be prepared by a process which comprises reacting a carbamate derivative of formula $L^2$-C(O)$NR^{6a}R^{6b}$, wherein $L^2$ represents a suitable leaving group, with a compound of formula (X) as defined above; followed, as necessary, by removal of the N-protecting group $R^p$.

The leaving group $L^2$ is suitably a halogen atom, e.g. chloro; or $L^2$ is suitably phenoxy.

Where $L^2$ is a halogen atom, the reaction is conveniently carried out at ambient temperature in the presence of a base, e.g. an organic amine such as triethylamine, in a suitable solvent, e.g. a chlorinated solvent such as dichloromethane.

Where $L^2$ is phenoxy, the reaction is conveniently carried out at an elevated temperature in the presence of 4-(dimethylamino)pyridine, in a suitable solvent, e.g. a nitrile solvent such as acetonitrile.

Similarly, the compounds of formula (IA) above wherein $R^6$ represents —$OR^{6c}$ may be prepared by a process which comprises reacting a compound of formula $L^3$-C(O)$OR^{6c}$, wherein $L^3$ represents a suitable leaving group, with a compound of formula (X) as defined above; followed, as necessary, by removal of the N-protecting group $R^p$.

The leaving group $L^3$ is suitably a halogen atom, e.g. chloro.

The reaction is conveniently carried out at ambient temperature in the presence of a base, e.g. an organic amine such as triethylamine, typically in admixture with pyridine, in a suitable solvent, e.g. a cyclic ether such as tetrahydrofuran.

In another procedure, the compounds of formula (IB) above may be prepared by a process which comprises reacting a compound of formula (X) as defined above with a compound of formula $L^4$-S(O)$_2R^6$, wherein $R^6$ is as defined above, and $L^4$ represents a suitable leaving group; followed, as necessary, by removal of the N-protecting group $R^p$.

The leaving group $L^4$ is suitably a halogen atom, e.g. chloro.

The reaction is conveniently carried out at ambient temperature in the presence of a base, e.g. an organic amine such as N,N-diisopropylethylamine, in a suitable solvent, e.g. a chlorinated solvent such as dichloromethane.

In another procedure, the compounds of formula (IC) above may be prepared by a process which comprises reacting a compound of formula (X) as defined above with a compound of formula $L^5$-$R^7$, wherein $R^7$ is as defined above, and $L^5$ represents a suitable leaving group; followed, as necessary, by removal of the N-protecting group $R^p$.

The leaving group $L^5$ is suitably a halogen atom, e.g. chloro or bromo.

The reaction is conveniently carried out in the presence of a base. Suitable bases include organic amines, e.g. a trialkylamine such as N,N-diisopropylethylamine. The reaction is typically performed at an elevated temperature in a suitable solvent, e.g. a cyclic ether such as 1,4-dioxane.

Alternatively, the reaction may be performed in the presence of a transition metal catalyst. Suitable transition metal catalysts of use in this procedure include [(2-di-tert-butylphosphino-3,6-dimethoxy-2',4',6'-triisopropyl-1,1'-biphenyl)-2-(2'-amino-1,1'-biphenyl)]palladium(II) methanesulfonate (tBuBrettPhos Pd G3). The reaction is conveniently carried out at an elevated temperature in the presence of a base, e.g. an inorganic base such as potassium tert-butoxide, in a suitable solvent or solvent mixture. The solvent or solvents may suitably be selected from a cyclic ether such as 1,4-dioxane, and a sulfoxide solvent such as dimethyl sulfoxide.

The intermediates of formula (X) above may be prepared by reacting a compound of formula (III) as defined above with a compound of formula (XI), or a salt thereof, e.g. a lithium salt thereof:

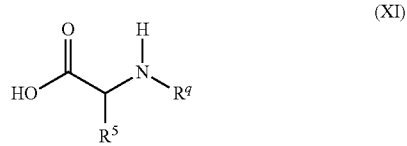

(XI)

wherein $R^5$ and $R^q$ are as defined above; under conditions analogous to those described above for the reaction between compound (III) and a carboxylic acid of formula $R^aCO_2H$; followed, as necessary, by removal of the N-protecting group $R^q$.

In another procedure, the compounds of formula (ID) above may be prepared by a process which comprises reacting a compound of formula $R^7$—$NH_2$ with a compound of formula (XII):

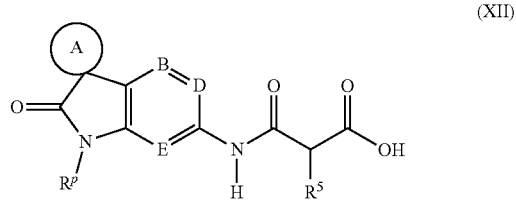

(XII)

wherein A, B, D, E, $R^p$, $R^5$ and $R^7$ are as defined above; under conditions analogous to those described above for the reaction between compound (III) and a carboxylic acid of formula $R^aCO_2H$; followed, as necessary, by removal of the N-protecting group $R^p$.

The intermediates of formula (XII) above may be prepared by a two-step procedure which comprises: (i) reacting a compound of formula (III) as defined above with a compound of formula (XIII), or a salt thereof, e.g. a lithium salt thereof:

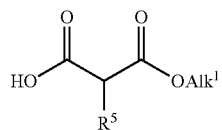

(XIII)

wherein $R^5$ and $Alk^1$ are as defined above; under conditions analogous to those described above for the reaction between compound (III) and a carboxylic acid of formula $R^aCO_2H$; and (ii) saponification of the resulting material by treatment with a base.

The saponification reaction in step (ii) will generally be effected by treatment with a base. Suitable bases include inorganic hydroxides, e.g. an alkali metal hydroxide such as lithium hydroxide. Where lithium hydroxide is employed in step (ii) of the above procedure, the product may be the lithium salt of the carboxylic acid of formula (XII).

Step (ii) is conveniently effected at ambient temperature in water and a suitable organic solvent, e.g. a $C_{1-4}$ alkanol such as ethanol.

Where they are not commercially available, the starting materials of formula (IV), (VI-A), (VII), (XI) and (XIII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) comprising a N—BOC moiety (wherein BOC is an abbreviation for tert-butoxycarbonyl) may be converted into the corresponding compound comprising a N—H moiety by treatment with an acid, e.g. a mineral acid such as hydrochloric acid, or an organic acid such as trifluoroacetic acid.

A compound of formula (I) comprising an amino (—$NH_2$) moiety may be acylated, e.g. acetylated, by treatment with a suitable acyl halide, e.g. acetyl chloride, typically in the presence of a base, e.g. an organic base such as N,N-diisopropylethylamine.

A compound which contains an N—H moiety may be alkylated, e.g. methylated, by treatment with the appropriate alkyl halide, e.g. iodomethane, typically at ambient temperature in the presence of a base, e.g. sodium hydride, in a suitable solvent, e.g. a dipolar aprotic solvent such as N,N-dimethylformamide.

A compound of formula (I) wherein $R^3$ is hydrogen may be converted into the corresponding compound wherein $R^3$ is fluoro by treatment with Selectfluor™.

A compound of formula (I) wherein $R^3$ is hydrogen may be converted into the corresponding compound wherein $R^3$ is chloro by treatment with N-chlorosuccinimide, typically in the presence of acetic acid.

Where the respective values of $R^5$, $R^{5a}$ and $R^{5b}$ permit, a compound of formula (IA) may be obtained from the corresponding compound of formula (IF) by conventional catalytic hydrogenation, e.g. by treatment with gaseous hydrogen in the presence of a hydrogenation catalyst such as palladium on charcoal.

A compound containing the moiety —S— may be converted into the corresponding compound containing the moiety —S(O)— by treatment with 3-chloroperoxybenzoic acid. Likewise, a compound containing the moiety —S— or —S(O)— may be converted into the corresponding compound containing the moiety —S(O)$_2$— by treatment with 3-chloroperoxy-benzoic acid.

A compound containing the moiety —S— may be converted into the corresponding compound containing the moiety —S(O)(NH)— by treatment with ammonium carbamate and (diacetoxyiodo)benzene.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in Greene's Protective Groups in Organic Synthesis, ed. P. G. M. Wuts, John Wiley & Sons, 5$^{th}$ edition, 2014. The protecting groups may be removed at any convenient subsequent stage utilising methods known from the art.

The compounds in accordance with this invention potently inhibit the ability of IL-17A to bind to IL-17RA. When tested in the IL-17 FRET assay described below, compounds of the present invention exhibit an IC$_{50}$ value of 10 μM or less, generally of 5 μM or less, usually of 1 μM or less, typically of 500 nM or less, suitably of 100 nM or less, ideally of 50 nM or less, and preferably of 25 nM or less (the skilled person will appreciate that a lower IC$_{50}$ figure denotes a more active compound).

Moreover, certain compounds in accordance with this invention potently inhibit IL-17 induced IL-6 release from human dermal fibroblasts. Indeed, when tested in the HDF cell line assay described below, compounds of the present invention exhibit an IC$_{50}$ value of 10 μM or less, generally of 5 μM or less, usually of 1 μM or less, typically of 500 nM or less, suitably of 100 nM or less, ideally of 50 nM or less, and preferably of 25 nM or less (as before, the skilled person will appreciate that a lower IC$_{50}$ figure denotes a more active compound).

IL-7 FRET Assay

The purpose of this assay is to test the ability of compounds to disrupt the interaction between IL-17A and soluble IL-17 Receptor A (IL-17RA). The ability of a compound to inhibit IL-17A binding to IL-17RA is measured in this assay.

An IL-17AA-TEV-Human Fc construct was expressed in a CHO SXE cell system and purified by protein A chromatography and size exclusion. The protein was labelled with an amine reactive AlexaFluor 647 dye (Thermo Fisher # A20006), as per manufacturer's instruction.

Soluble IL-17RA (33-317)-HKH-TEV-Fc was expressed in an Expi HEK293 cell system and purified by protein A chromatography and size exclusion. The Fc tag was cleaved by TEV, producing IL-17RA (33-317)-HKH, and the protein was labelled with amine reactive terbium (Thermo Fisher # PV3581).

In assay buffer [Dulbecco's PBS (Sigma #14190-094), 0.05% P20 (Thermo Scientific #28320), 1 mg/mL BSA (Sigma # A2153-500G)] the following solutions were prepared:
For IL-17A assay
   IL-17A-Fc-AF647 at 5 nM
   IL-17RA-HKH-Tb at 5 nM
Compounds were serially diluted in DMSO before receiving an aqueous dilution into a 384 well dilution plate (Greiner #781281), to give a 25% DMSO solution.

IL-17A (10 μL) was added to a black low volume assay plate (Costar #4511) and diluted compound (5 μL) was transferred from the aqueous dilution plate. The cytokine and compound were allowed to incubate for 1 h, then IL-17RA (10 μL) was added. The plates were wrapped in foil and incubated at room temperature for 18-20 h with gentle shaking (<400 rpm) before being read on a Perkin Elmer Envision plate reader (Excitation: 330 nm; Emission 615/645 nm).

The final assay concentrations were IL-17A-AF647 2 nM and IL-17RA-Tb 2 nM, 5% DMSO.

When tested in the IL-17 FRET assay, the compounds of the accompanying Examples were all found to exhibit IC$_{50}$ values of 10 μM or better.

When tested in the IL-17 FRET assay, compounds of the accompanying Examples exhibit IC$_{50}$ values generally in the range of about 0.01 nM to about 10 μM, usually in the range of about 0.01 nM to about 5 μM, typically in the range of about 0.01 nM to about 1 μM, suitably in the range of about 0.01 nM to about 500 nM, appositely in the range of about 0.01 nM to about 100 nM, ideally in the range of about 0.01 nM to about 50 nM, and preferably in the range of about 0.01 nM to about 25 nM.

Inhibition of IL-17A Induced IL-6 Release from Dermal Fibroblast Cell Line

The purpose of this assay is to test the neutralising ability to IL-17 proteins, in a human primary cell system. Stimulation of normal human dermal fibroblasts (HDF) with IL-17 alone produces only a very weak signal but in combination with certain other cytokines, such as TNFα, a synergistic effect can be seen in the production of inflammatory cytokines, i.e. IL-6.

HDFs were stimulated with IL-17A (50 pM) in combination with TNF-α (25 pM). The resultant IL-6 response was then measured using a homogenous time-resolved FRET kit from Cisbio. The kit utilises two monoclonal antibodies, one labelled with Eu-Cryptate (Donor) and the second with d2 or XL665 (Acceptor). The intensity of the signal is proportional to the concentration of IL-6 present in the sample (Ratio is calculated by 665/620×104).

The ability of a compound to inhibit IL-17 induced IL-6 release from human dermal fibroblasts is measured in this assay.

HDF cells (Sigma #106-05n) were cultured in complete media (DMEM+10% FCS+2 mM L-glutamine) and maintained in a tissue culture flask using standard techniques. Cells were harvested from the tissue culture flask on the morning of the assay using TrypLE (Invitrogen #12605036). The TrypLE was neutralised using complete medium (45 mL) and the cells were centrifuged at 300×g for 3 minutes. The cells were re-suspended in complete media (5 mL) counted and adjusted to a concentration of $3.125 \times 10^4$ cells/mL before being added to the 384 well assay plate (Corning #3701) at 40 μL per well. The cells were left for a minimum of three hours, at 37° C./5% $CO_2$, to adhere to the plate.

Compounds were serially diluted in DMSO before receiving an aqueous dilution into a 384 well dilution plate (Greiner #781281), where 5 μL from the titration plate was transferred to 45 μL of complete media and mixed to give a solution containing 10% DMSO.

Mixtures of TNFα and IL-17 cytokine were prepared in complete media to final concentrations of TNFα 25 pM/IL-17A 50 pM, then 30 μL of the solution was added to a 384 well reagent plate (Greiner #781281).

10 μL from the aqueous dilution plate was transferred to the reagent plate containing 30 μL of the diluted cytokines, to give a 2.5% DMSO solution. The compounds were incubated with the cytokine mixtures for one hour at 37° C. After the incubation, 10 μL was transferred to the assay plate, to give a 0.5% DMSO solution, then incubated for 18-20 h at 37° C./5% $CO_2$.

From the Cisbio IL-6 FRET kit (Cisbio #62IL6PEB) europium cryptate and Alexa 665 were diluted in reconstitution buffer and mixed 1:1, as per kit insert. To a white low volume 384 well plate (Greiner #784075) were added FRET reagents (10 μL), then supernatant (10 μL) was transferred from the assay plate to Greiner reagent plate. The mixture was incubated at room temperature for 3 h with gentle shaking (<400 rpm) before being read on a Synergy Neo 2 plate reader (Excitation: 330 nm; Emission: 615/645 nm).

When tested in the above assay, compounds of the accompanying Examples were found to exhibit $IC_{50}$ values of 10 μM or better.

When tested in the above assay, compounds of the accompanying Examples exhibit $IC_{50}$ values generally in the range of about 0.01 nM to about 10 μM, usually in the range of about 0.01 nM to about 5 μM, typically in the range of about 0.01 nM to about 1 μM, suitably in the range of about 0.01 nM to about 500 nM, appositely in the range of about 0.01 nM to about 100 nM, ideally in the range of about 0.01 nM to about 50 nM, and preferably in the range of about 0.01 nM to about 25 nM.

The following Examples illustrate the preparation of compounds according to the invention.

EXAMPLES

Abbreviations

DCM: dichloromethane
MeOH: methanol
DMF: N,N-dimethylformamide
THF: tetrahydrofuran
DMSO: dimethyl sulfoxide
EtOH: ethanol
NBS: N-bromosuccinimide
TFA: trifluoroacetic acid
SEM-Cl: 2-(trimethylsilyl)ethoxymethyl chloride
EDCI•HCl: N-(3-dimethylaminopropyl)-N'-ethylcarbodiimide hydrochloride
HATU: 2-(7-aza-1H-benzotriazol-1-yl)-1,1,3,3-tetramethyluronium hexafluorophosphate Selectfluor™: 1-chloromethyl-4-fluoro-1,4-diazoniabicyclo[2.2.2]octane bis(tetrafluoro-borate)
$Pd_2(dba)_3$: tris(dibenzylideneacetone)dipalladium(0)
XPhos: 2-dicyclohexylphosphino-2',4',6'-triisopropylbiphenyl
Xantphos: 4,5-bis(diphenylphosphino)-9,9-dimethylxanthene
tBuBrettPhos Pd G3: [(2-di-tert-butylphosphino-3,6-dimethoxy-2',4',6'-triisopropyl-1,1'-biphenyl)-2-(2'-amino-1,1'-biphenyl)] palladium(II) methanesulfonate
DIPEA: N,N-diisopropylethylamine
EtOAc: ethyl acetate
NCS: N-chlorosuccinimide
HOBt: 1-hydroxybenzotriazole
h: hour
M: mass
HPLC: High Performance Liquid Chromatography
LCMS: Liquid Chromatography Mass Spectrometry
ES+: Electrospray Positive Ionisation
r.t.: room temperature
RT: retention time Analytical Conditions Compounds were named with the aid of ACD/Name Batch (Network) version 11.01, and/or Accelrys Draw 4.2, and/or Elemental, Dotmatics, and/or Chemaxon.

All reactions involving air-or moisture-sensitive reagents were performed under a nitrogen atmosphere using dried solvents and glassware.

NMR spectra were recorded on a Bruker Avance III HD 500 MHz, 400 MHz, 300 MHz or 250 MHz spectrometer.

Specific Optical Rotations were measured using a Rudolph Research Analytical Autopol 1 polarimeter, S2 Serial 32026.

uPLC-MS was performed on a Waters Acquity UPLC system coupled to a Waters Acquity PDA detector, an ELS detector and an MSD (Scan Positive: 150-850).

Method 1
Phenomenex Kinetex-XB, C18 2.1×100 mm, 1.7 μm column
Mobile Phase A: 0.1% formic acid in water
Mobile Phase B: 0.1% formic acid in acetonitrile
Gradient program: Flow rate 0.6 mL/minute; column temperature 40° C.

| Time | A % | B % |
| --- | --- | --- |
| 0.00 | 95.00 | 5.00 |
| 5.30 | 0.00 | 100.0 |
| 5.80 | 0.00 | 100.0 |
| 5.82 | 95.00 | 5.00 |

Method 2
Waters UPLC® CSH™ C18, 2.1 mm×100 mm, 1.7 μm column
Mobile Phase A: 2 mM ammonium bicarbonate adjusted to pH 10 with ammonium hydroxide
Mobile Phase B: acetonitrile
Gradient program: Flow rate 0.6 mL/minute; column temperature 40° C.

| Time | A % | B % |
| --- | --- | --- |
| 0.00 | 95.00 | 5.00 |
| 5.30 | 0.00 | 100.0 |
| 5.80 | 0.00 | 100.0 |
| 5.82 | 95.00 | 5.00 |

HPLC-MS
1. Performed on a Shimadzu LCMS-2010EV system coupled to SPD-M20A PDA and PL 2100 detectors.

Method 3
Phenomenex Kinetex Core-Shell C8 50×2.1 mm, 5 μm column, protected by
Phenomenex 'Security Guard' column
Mobile Phase A: 0.1% formic acid in water
Mobile Phase B: 0.1% formic acid in acetonitrile
Gradient program: Flow rate 1.2 mL/minute; column temperature 400° C.

| Time | A % | B % |
|---|---|---|
| 0.00 | 95.00 | 5.00 |
| 1.20 | 0.00 | 100.0 |
| 1.30 | 0.00 | 100.0 |
| 1.31 | 95.00 | 5.00 |

Method 4
Waters Atlantis dC18 (2.1×100 mm, 3 μm) column
Mobile Phase A: 0.1% formic acid in water
Mobile Phase B: 0.1% formic acid in acetonitrile
Gradient program: Flow rate 0.6 mL/minute; column temperature 40° C.

| Time | A % | B % |
|---|---|---|
| 0.00 | 95.00 | 5.00 |
| 5.00 | 0.00 | 100.0 |
| 5.40 | 0.00 | 100.0 |
| 5.42 | 95.00 | 5.00 |

2. Performed on an Agilent 1200-6120 LC-MS system coupled to Detection (230 to 400 nm and 215 nm) and Mass Spec Detection Agilent 6120 Mass Spectrometer (ES) m/z 120 to 800.

Method 5
X-Bridge C18 Waters 2.1×20 mm, 2.5 μm column
Mobile Phase A: 10 mM ammonium formate in water+0.1% formic acid
Mobile Phase B: acetonitrile+5% water+0.1% formic acid
Gradient program: Flow rate 1 mL/minute

| Time | A % | B % |
|---|---|---|
| 0.00 | 94.00 | 6.00 |
| 1.50 | 5.00 | 95.00 |
| 2.25 | 5.00 | 95.00 |
| 2.50 | 94.00 | 6.00 |

Method 6
X-Bridge C18 Waters 2.1×20 mm, 2.5 μm column
Mobile Phase A: 10 nM ammonium formate in water+0.1% ammonia solution
Mobile Phase B: acetonitrile+5% water+0.1% ammonia solution
Gradient program: Flow rate 1 mL/minute

| Time | A % | B % |
|---|---|---|
| 0.00 | 96.00 | 4.00 |
| 4.00 | 5.00 | 95.00 |
| 5.00 | 5.00 | 95.00 |
| 5.10 | 96.00 | 4.00 |

Method 7
X-Bridge C18 Waters 2.1×20 mm, 2.5 μm column
Mobile Phase A: 10 mM ammonium formate in water+0.1% ammonia solution
Mobile Phase B: acetonitrile+5% water+0.1% ammonia solution
Gradient program: Flow rate 1 mL/minute

| Time | A % | B % |
|---|---|---|
| 0.00 | 96.00 | 4.00 |
| 1.50 | 5.00 | 95.00 |
| 2.25 | 5.00 | 95.00 |
| 2.50 | 96.00 | 4.00 |

Automated Preparative Reverse Phase HPLC Purification
1. Performed using a Gilson system with a Gilson 306 pump, a Gilson 215 autoinjector, a Gilson 215 fraction collector and a Gilson 156 UV detector.

Method 8
X-Bridge C18 Waters 30×100 mm, 5 μm column
Mobile Phase A: water+0.2% ammonia solution
Mobile Phase B: acetonitrile+0.2% ammonia solution
Gradient program: Flow rate 40 mL/minute

| Time | A % | B % |
|---|---|---|
| 0.00 | 95 | 5 |
| 2.00 | 95 | 5 |
| 2.50 | 75 | 25 |
| 16.50 | 35 | 65 |
| 17.00 | 0 | 100 |
| 19.00 | 0 | 100 |
| 19.50 | 95 | 5 |

2. Performed using A Gilson system with a Gilson 331&332 pump, a Gilson GX281 autoinjector, a Gilson GX281 fraction collector and a Gilson 159 UV detector.

Method 9
X-Bridge C18 Waters 30×100 mm, 10 μm column
Mobile Phase A: water+0.2% ammonia solution
Mobile Phase B: acetonitrile+0.2% ammonia solution
Gradient program: Flow rate 40 mL/minute

| Time | A % | B % |
|---|---|---|
| 0.00 | 70 | 30 |
| 0.55 | 70 | 30 |
| 11.00 | 5 | 95 |
| 13.10 | 5 | 95 |
| 13.31 | 70 | 30 |

Method 10
X-Bridge C18 Waters 30×100 mm, 10 μm column
Mobile Phase A: water+0.2% ammonia solution
Mobile Phase B: acetonitrile+0.2% ammonia solution
Gradient program: Flow rate 40 mL/minute

| Time | A % | B % |
|---|---|---|
| 0.00 | 90 | 10 |
| 0.55 | 90 | 10 |
| 14.44 | 5 | 95 |
| 16.55 | 5 | 95 |
| 16.75 | 90 | 10 |

Method 11
Sunfire C18 Waters 30×100 mm, 10 μm column
Mobile Phase A: water+0.1% formic acid
Mobile Phase B: acetonitrile+0.1% formic acid
Gradient program: Flow rate 40 mL/minute

| Time  | A % | B % |
|-------|-----|-----|
| 0.00  | 70  | 30  |
| 0.55  | 70  | 30  |
| 11.00 | 5   | 95  |
| 13.10 | 5   | 95  |
| 13.31 | 70  | 30  |

Column chromatography separations were performed using a Biotage® Isolera 4 system with Biotage® SNAP KP-Sil pre-packed silica gel columns.
Chiral SFC Analysis
Method 12
Waters Thar 3100 SFC system connected to a Waters 2998 PDA detector
Method 13
Waters UPC2-SQD2 system
Chiral SFC Separation
Method 14
Waters Thar SFC system with a Waters Thar FDM pump, a Waters Thar Alias autoinjector, a Waters Thar fraction collector and a Waters 2998 PDA detector
Method 15
Waters Prep 100-SQD2
HPLC-MS was performed on a Waters ZQ system coupled to Waters 2996 PDA and Waters 2420 detectors.
Method 16
Phenomenex Gemini-NX C18 2.0 mm×50 mm, 3 μm column
Mobile Phase A: 2 mM $NH_4HCO_3$ modified to pH 10 with $NH_4OH$
Mobile Phase B: acetonitrile
Gradient program: Flow rate 1 mL/minute; column temperature 40° C.

| Time | A %   | B %    |
|------|-------|--------|
| 0.00 | 99.00 | 1.00   |
| 1.80 | 0.00  | 100.00 |
| 2.10 | 0.00  | 100.00 |
| 2.30 | 99.00 | 1.00   |
| 3.50 | 99.00 | 1.00   |

Method 17
Waters Atlantis dC18 4.6×50 mm, 3 μm column
Mobile Phase A: 0.1% formic acid in water
Mobile Phase B: 0.1% formic acid in acetonitrile
Gradient program: Flow rate 0.8 mL/minute; column temperature 40° C.

| Time | A %   | B %   |
|------|-------|-------|
| 0.00 | 30.00 | 70.00 |
| 3.00 | 90.00 | 10.0  |
| 6.00 | 90.00 | 10.0  |

Method 18
Waters Atlantis dC18 4.6×50 mm, 3 μm column
Mobile Phase A: 0.1% formic acid in water
Mobile Phase B: 0.1% formic acid in acetonitrile
Gradient program: Flow rate 0.6 mL/minute; column temperature 40° C.

| Time | A %   | B %   |
|------|-------|-------|
| 0.00 | 50.00 | 50.00 |
| 3.00 | 95.00 | 5.00  |
| 6.00 | 95.00 | 5.00  |

HPLC-MS was performed on an Agilent 1200-6120 LC-MS system coupled to Detection (230 to 400 nm and 215 nm) and Mass Spec Detection Agilent 6120 Mass Spectrometer (ES) m/z 15 120 to 800.
Method 19
X-Bridge C18 Waters 2.1×20 mm, 2.5 Lm column
Mobile Phase A: 10 mM ammonium formate in water+0.1% formic acid
Mobile Phase B: acetonitrile+5% water+0.1% formic acid
Gradient program: Flow rate 1 mL/minute

| Time | A %   | B %   |
|------|-------|-------|
| 0.00 | 95.00 | 5.00  |
| 4.00 | 5.00  | 95.00 |
| 5.00 | 5.00  | 95.00 |
| 5.10 | 95.00 | 5.00  |

Automated preparative reverse phase HPLC purification was performed using a Gilson system with a Gilson 331 & 332 pump, a Gilson GX281 autoinjector, a Gilson GX281 fraction collector and a Gilson 159 UV detector.
Method 20
Sunfire C18 Waters 30×100 mm, 10 μm column
Mobile Phase A: water+0.1% formic acid
Mobile Phase B: acetonitrile+0.1% formic acid
Gradient program: Flow rate 40 mL/minute

| Time  | A %   | B %   |
|-------|-------|-------|
| 0.00  | 90.00 | 10.00 |
| 0.55  | 90.00 | 10.00 |
| 14.44 | 5.00  | 95.00 |
| 16.55 | 5.00  | 95.00 |
| 16.75 | 90.00 | 10.00 |

HPLC-MS was performed on an Agilent 1200RR-6140 LC-MS system coupled to a DAD SL detector.
Method 21
XBridge C18 2.1×20 mm, 2.5 μm column
Mobile Phase A: 10 mM ammonium formate in water+0.1% formic acid
Mobile Phase B: acetonitrile+5% water+0.1% formic acid
Gradient program: Flow rate 1 mL/minute; column temperature 40° C.

| Time | A %   | B %   |
|------|-------|-------|
| 0.00 | 95.00 | 5.00  |
| 4.00 | 5.00  | 95.00 |
| 5.00 | 5.00  | 95.00 |
| 5.10 | 95.00 | 5.00  |

Automated preparative reverse phase HPLC purification was performed using a Waters FractionLynx Prep system coupled to a SQD2 mass spectrometer and a Waters 2998 PDA detector.

Method 22

Waters XBridge Prep C18 19×100 mm, 5 μm column

Mobile Phase A: 10 mM ammonium bicarbonate in water+0.1% ammonia solution

Mobile Phase B: acetonitrile+5% solvent A+0.1% ammonia solution

Gradient program: Flow rate 20 mL/minute

| Time  | A %   | B %   |
|-------|-------|-------|
| 0.00  | 65.00 | 35.00 |
| 2.50  | 65.00 | 35.00 |
| 11.00 | 50.00 | 50.00 |
| 11.50 | 5.00  | 95.00 |
| 12.50 | 5.00  | 95.00 |
| 13.00 | 65.00 | 35.00 | uPLC-MS was performed on a Waters Classic Acquity-QDa LC-MS system coupled to a Waters Acquity PDA detector.

Method 23

Waters Acquity UPLC BEH, C18 2.1×50 mm, 1.7 μm column

Mobile Phase A: 10 mM ammonium formate in water+0.1% ammonia solution

Mobile Phase B: acetonitrile+5% water+0.1% ammonia solution

Gradient program: Flow rate 0.7 mL/minute; column temperature 40° C.

| Time | A %   | B %   |
|------|-------|-------|
| 0.00 | 98.00 | 2.00  |
| 4.00 | 5.00  | 95.00 |
| 5.00 | 5.00  | 95.00 |
| 5.10 | 98.00 | 2.00  |

Automated preparative reverse phase HPLC purification was performed using a Waters FractionLynx Prep system coupled to a SQD2 mass spectrometer and a Waters 2998 PDA detector.

Method 24

Waters XBridge Prep Phenyl 19×150 mm, 5 μm column

Mobile Phase A: 10 mM ammonium bicarbonate in water+0.1% ammonia solution

Mobile Phase B: acetonitrile+5% solvent A+0.1% ammonia solution

Gradient program: Flow rate 20 mL/minute

| Time  | A %   | B %   |
|-------|-------|-------|
| 0.00  | 70.00 | 30.00 |
| 2.50  | 70.00 | 30.00 |
| 11.00 | 55.00 | 45.00 |
| 11.50 | 5.00  | 95.00 |
| 12.50 | 5.00  | 95.00 |
| 13.00 | 70.00 | 30.00 |

Method 25

Waters XBridge Prep Phenyl 19×150 mm, 5 μm column

Mobile Phase A: 10 mM ammonium bicarbonate in water+0.1% ammonia solution

Mobile Phase B: acetonitrile+5% solvent A+0.1% ammonia solution

Gradient program: Flow rate 20 mL/minute

| Time  | A %   | B %   |
|-------|-------|-------|
| 0.00  | 65.00 | 35.00 |
| 2.50  | 65.00 | 35.00 |
| 11.00 | 50.00 | 50.00 |
| 11.50 | 5.00  | 95.00 |
| 12.50 | 5.00  | 95.00 |
| 13.00 | 65.00 | 35.00 |

Method 26

Waters XBridge Prep C18 19×100 mm, 5 μm column

Mobile Phase A: 10 mM ammonium bicarbonate in water+0.1% ammonia solution

Mobile Phase B: acetonitrile+5% solvent A+0.1% ammonia solution

Gradient program: Flow rate 20 mL/minute

| Time  | A %   | B %   |
|-------|-------|-------|
| 0.00  | 65.00 | 35.00 |
| 2.00  | 65.00 | 35.00 |
| 12.00 | 50.00 | 50.00 |
| 16.00 | 5.00  | 95.00 |
| 18.00 | 65.00 | 35.00 | uPLC-MS was performed on a Waters Classic Acquity-QDa LC-MS system coupled to a Waters Acquity PDA detector.

Method 27

Waters Acquity UPLC BEH, C18 2.1×50 mm, 2.5 μm column

Mobile Phase A: 10 mM ammonium formate in water+0.1% ammonia solution

Mobile Phase B: acetonitrile+5% water+0.1% ammonia solution

Gradient program: Flow rate 1.0 mL/minute; column temperature 45° C.

| Time | A %   | B %   |
|------|-------|-------|
| 0.00 | 95.00 | 5.00  |
| 2.10 | 5.00  | 95.00 |
| 2.3  | 5.00  | 95.00 |
| 5.35 | 95.00 | 5.00  |

Method 28

Waters Acquity UPLC BEH, C18 2.1×30 mm, 1.7 μm column

Mobile Phase A: water/acetonitrile/formic acid (95/5/750 μL)

Mobile Phase B: water/acetonitrile/formic acid (5/95/500 μL)

Gradient program: Flow rate 0.8 mL/minute; column temperature 45° C.

| Time | A %   | B %   |
|------|-------|-------|
| 0.00 | 95.00 | 5.00  |
| 1.80 | 5.00  | 95.00 |
| 2.4  | 5.00  | 95.00 |
| 2.5  | 95.00 | 5.00  |

HPLC-MS was performed on a Shimadzu LCMS-2010EV system coupled to SPD-M20A PDA and PL 2100 detectors.

Method 29
Phenomenex Kinetex Core-Shell C8 50×2.1 mm, 2.6 µm column protected by
Phenomenex 'Security Guard' column
Mobile Phase A: water+0.1% formic acid
Mobile Phase B: acetonitrile+0.1% formic acid
Gradient program: Flow rate 0.6 mL/minute; column temperature 40° C.

| Time | A % | B % |
|---|---|---|
| 0.00 | 95 | 5 |
| 4.40 | 0 | 100 |
| 5.40 | 0 | 100 |
| 5.42 | 5 | 95 |
| 6.00 | 5 | 95 |

Automated preparative reverse phase HPLC purification was performed using a Gilson system with a Gilson 306 pump, a Gilson 215 autoinjector, a Gilson 215 fraction collector and a Gilson 156 UV detector.
Method 30
Sunfire C18 Waters 19×100 mm, 5 µm column
Mobile Phase A: water+0.1% formic acid
Mobile Phase B: acetonitrile+0.1% formic acid
Gradient program: Flow rate 20 mL/minute

| Time | A % | B % |
|---|---|---|
| 0.00 | 95 | 5 |
| 1.90 | 95 | 5 |
| 2.00 | 68 | 32 |
| 16.00 | 58 | 42 |
| 16.10 | 5 | 95 |
| 18.00 | 5 | 95 |
| 18.10 | 95 | 5 |

Method 31
Sunfire C18 Waters 19×100 mm, 5 µm column
Mobile Phase A: water+0.1% formic acid
Mobile Phase B: acetonitrile+0.1% formic acid
Gradient program: Flow rate 20 mL/minute

| Time | A % | B % |
|---|---|---|
| 0.00 | 95 | 5 |
| 2.00 | 95 | 5 |
| 2.50 | 55 | 45 |
| 22.50 | 55 | 45 |
| 23.00 | 100 | 0 |
| 25.00 | 100 | 0 |
| 25.50 | 95 | 5 |

Chiral HPLC Separation
Method 32
Gilson system with a Gilson 321/322 pump, a Gilson GX241 autoinjector, a Gilson PREP FC fraction collector and a Gilson 171/172 UV detector.
HPLC-MS
1. Performed on a Shimadzu LC-20AB & MS 2010.
Method 33
Luna-C18(2) 2.0×30 mm, 3 µm column
Mobile Phase A: water+0.037% (v/v) TFA
Mobile Phase B: acetonitrile+0.018% (v/v) TFA
Gradient program: Flow rate 0.8 mL/minute; column temperature 40° C.

| Time | A % | B % |
|---|---|---|
| 0.00 | 100.0 | 0.0 |
| 1.60 | 40.0 | 60.0 |
| 1.66 | 0.0 | 100.0 |
| 2.20 | 0.0 | 100.0 |

2. Performed on a Shimadzu 20D & MS2020.
Method 34
Zorbax Eclipse XDB-C18 2.1×30 mm, 3.5 µm column
Mobile Phase A: water+0.037% (v/v) TFA
Mobile Phase B: acetonitrile+0.018% (v/v) TFA
Gradient program: Flow rate 0.8 mL/minute; column temperature 40° C.

| Time | A % | B % |
|---|---|---|
| 0.00 | 95.0 | 5.0 |
| 1.00 | 5.0 | 95.0 |
| 1.80 | 0.0 | 100.0 |
| 2.20 | 0.0 | 100.0 |

Chiral SFC was performed on Agilent 1100, DAD system.
Method 35
Lux Cellulose-1 4.6×150 mm, 3 µm column
Mobile Phase A: $CO_2$
Mobile Phase B: methanol (+0.1% $NH_4OH$)
Gradient program: Flow rate 3 mL/minute; column temperature 35° C.

| Time | A % | B % |
|---|---|---|
| 0.00 | 97.00 | 3.00 |
| 5.00 | 60.00 | 40.00 |
| 5.10 | 97.00 | 3.00 |

Intermediate 1

Methyl 4-(2,4-dinitrophenyl)tetrahydropyran-4-carboxylate

Sodium hydride (60% dispersion in mineral oil, 33 mg, 0.84 mmol) was added to a solution of methyl (2,4-dinitrophenyl)acetate (77 mg, 0.32 mmol) and 1-bromo-2-(2-bromoethoxy)ethane (0.046 mL, 0.321 mmol) in DMF (3 mL) at 0° C. The cooling bath was removed and the reaction mixture was stirred for 10 minutes at 20° C., then heated at 90° C. for 4 h. The reaction mixture was cooled to room temperature and saturated aqueous ammonium chloride solution (5 mL) was added. The resulting mixture was extracted with ethyl acetate (2×30 mL). The organic phase was washed with brine, dried over sodium sulfate and concentrated in vacuo. The residue was purified by flash column chromatography, using a gradient of ethyl acetate in heptane (0-100%), to afford the title compound (49 mg, 49%) as a pale orange gum. $\delta_H$ (250 MHz, $CDCl_3$) 8.62 (d, J 2.5 Hz, 1H), 8.48 (dd, J 8.8, 2.5 Hz, 1H), 7.89 (d, J 8.9 Hz, 1H), 3.97 (ddd, J 12.0, 9.5, 2.7 Hz, 2H), 3.80 (td, J 7.8, 4.1 Hz, 2H), 3.73 (s, 3H), 2.40 (d, J 13.8 Hz, 2H), 2.10 (ddd, J 13.8, 9.5, 4.3 Hz, 2H). HPLC-MS (method 3): MH+ m/z no parent ion observed, RT 1.08 minutes.

Intermediate 2

6-Aminospiro[indoline-3,4'-tetrahydropyran]-2-one

Iron powder (3.79 g, 67.8 mmol) was added to a stirred solution of Intermediate 1 (2.5 g, 4.24 mmol) in a mixture of ethanol/water/saturated aqueous ammonium chloride solution (8:1:1; 81 mL) and the suspension was stirred at 60° C. under a nitrogen atmosphere for 6.5 h. After cooling to room temperature, the mixture was diluted with water (100 mL) and ethanol (100 mL). The suspension was filtered through a kieselguhr pad, washing sequentially with ethanol (3×50 mL), methanol (3×100 mL), water (100 mL) and ethyl acetate (3×100 mL). The filtrate was concentrated in vacuo. The residue was diluted with water (100 mL) and extracted with ethyl acetate (3×100 mL), then with 1:1 isopropanol/chloroform (3×50 mL). The combined organic extracts were washed with brine (100 mL) and dried over sodium sulfate, then filtered and concentrated in vacuo. The residue was purified by flash column chromatography (KP-NH column), using a gradient of ethyl acetate in heptane (50-100%) followed by a gradient of methanol in ethyl acetate (0-10%), to afford the title compound (571 mg, 61%) as a tan powder. $\delta_H$ (500 MHz, DMSO-$d_6$) 10.09 (s, 1H), 7.11 (d, J 8.6 Hz, 1H), 6.19-6.07 (m, 2H), 5.07 (s, 2H), 3.97 (ddd, J 11.0, 6.9, 3.8 Hz, 2H), 3.76 (ddd, J 11.3, 7.5, 3.6 Hz, 2H), 1.70 (ddd, J 11.4, 7.5, 3.7 Hz, 2H), 1.52 (ddd, J 13.3, 6.8, 3.5 Hz, 2H). HPLC-MS (method 7): MH+m/z 219, RT 1.00 minutes.

Intermediate 3

Methyl (2S)-2-amino-3-(2-chlorophenyl)propanoate hydrochloride

Thionyl chloride (2 mL, 27.42 mmol) was added dropwise to anhydrous methanol (7.5 mL) cooled to 0° C. under nitrogen. After stirring for 5 minutes, 2-chloro-L-phenylalanine (5.0 g, 25.05 mmol) was added portionwise, followed by anhydrous methanol (7.5 mL). The suspension was heated at 50° C. for 5 h under nitrogen, then the volatiles were removed in vacuo. The residue was suspended in diethyl ether (20 mL) and concentrated again to afford the title compound (5.89 g, 94%) as a tan powder. $\delta_H$ (500 MHz, DMSO-$d_6$) 8.91 (br s, 3H), 7.49-7.39 (m, 2H), 7.35-7.30 (m, 2H), 4.12 (dd, J 9.0, 6.2 Hz, 1H), 3.59 (s, 3H), 3.39-3.32 (obs m, 1H), 3.23 (dd, J 13.8, 9.0 Hz, 1H). HPLC-MS (method 7): MH+ m/z 214, RT 1.58 minutes.

Intermediate 4

Methyl (2S)-3-(2-chlorophenyl)-2-{[2-(pyridin-4-yl)acetyl]amino}propanoate

DIPEA (12.4 mL, 75.03 mmol) was added slowly to a stirred suspension of Intermediate 3 (5.89 g, 23.53 mmol), 2-(pyridin-4-yl)acetic acid hydrochloride (4.29 g, 24.71 mmol) and HATU (9.84 g, 25.88 mmol) in anhydrous DMF (47 mL). The mixture was stirred at 20° C. under nitrogen for 16 h. The volatiles were removed in vacuo and the residue was partitioned between ethyl acetate (100 mL) and saturated aqueous sodium carbonate solution (100 mL). The aqueous layer was separated and extracted with ethyl acetate (2×100 mL). The combined organic extracts were washed with water (50 mL) and brine (2×50 mL), then dried over magnesium sulfate, filtered and concentrated in vacuo. The resulting crude dark red gum was separated by flash column chromatography, using a gradient of methanol in DCM (0-6.5%), to afford the title compound (5.95 g, 76%) as an orange viscous oil. $\delta_H$ (500 MHz, DMSO-$d_6$) 8.74 (d, J 8.2 Hz, 1H), 8.47-8.37 (m, 2H), 7.41 (dd, J 7.8, 1.3 Hz, 1H), 7.31-7.19 (m, 3H), 7.16-7.04 (m, 2H), 4.61 (ddd, J 9.9, 8.2, 5.4 Hz, 1H), 3.62 (s, 3H), 3.45 (s, 2H), 3.25 (dd, J 13.8, 5.4 Hz, 1H), 2.97 (dd, J 13.8, 9.9 Hz, 1H). HPLC-MS (method 5): MH+ m/z 333, RT 1.44 minutes. Chiral SFC (Method 12, Chiralpak AD-H 25 cm, 35% ethanol-65% carbon dioxide, 4 mL/minute): RT 2.42 minutes (100%).

Intermediate 5

(2S)-3-(2-Chlorophenyl)-2-{[2-(pyridin-4-yl)acetyl]amino}propanoic acid

A solution of lithium hydroxide monohydrate (1.20 g, 28.53 mmol) in water (18 mL) was added to a stirred solution of Intermediate 4 (5.93 g, 17.83 mmol) in THF/MeOH (1:1; 36 mL) at 0° C. The mixture was allowed to warm slowly to 20° C. and was stirred over a total of 16 h, forming a thick suspension. The volatiles were removed in vacuo. The aqueous slurry was diluted with water (150 mL) and 1M aqueous sodium hydroxide solution (50 mL). The aqueous layer was washed with tert-butyl methyl ether (50 mL). The organic phase was separated and extracted with 1M aqueous sodium hydroxide solution (50 mL). The combined aqueous layers were washed with tert-butyl methyl ether (50 mL). The pH of the aqueous phase was adjusted to 5-6 using concentrated hydrochloric acid. The material was extracted sequentially with 1:1 DCM/isopropanol (8×100 mL) and 2-methyltetrahydrofuran (12×100 mL). The organic extracts were washed with brine (50 mL), dried over magnesium sulfate and filtered, then combined and reduced in vacuo. The resulting crude yellow powder was triturated from DCM (100 mL), then the solids were collected by filtration, washed with DCM (2×50 mL) and dried in vacuo at 50° C. for 4 h, to afford the title compound (5.70 g, quantitative) as an off-white powder. $\delta_H$ (500 MHz, DMSO-$d_6$) 12.87 (br s, 1H), 8.64 (d, J 8.5 Hz, 1H), 8.41 (d, J 5.4 Hz, 2H), 7.39 (dd, J 7.9, 1.2 Hz, 1H), 7.29 (dd, J 7.4, 1.7 Hz, 1H), 7.24 (td, J 7.6, 1.8 Hz, 1H), 7.19 (td, J 7.4, 1.3 Hz, 1H), 7.10 (d, J 5.9 Hz, 2H), 4.56 (ddd, J 10.4, 8.6, 4.7 Hz, 1H), 3.43 (s, 2H), 3.28 (dd, J 13.8, 4.7 Hz, 1H), 2.91 (dd, J 13.9, 10.5 Hz, 1H). HPLC-MS (method 7): MH+ m/z 319, RT 1.26 minutes. Chiral SFC (Method 12, Chiralpak AD-H 25 cm, 25% methanol-75% carbon dioxide, 4 mL/minute): RT 2.22 minutes (100%).

Intermediate 6

[(1S)-1-Cyclohexyl-2-methoxy-2-oxoethyl]ammonium chloride

Thionyl chloride (8 mL, 110.15 mmol) was added dropwise to anhydrous methanol (60 mL) cooled to 0° C. under nitrogen. After stirring for 5 minutes, (2S)-amino-(cyclohexyl)ethanoic acid (15.72 g, 100.00 mmol) was added portionwise, then the reaction mixture was heated at 50° C. for 5 h under nitrogen. The solvent was removed in vacuo and the residue was triturated in diethyl ether (250 mL). The solids were collected by filtration to afford the title compound (16.9 g, 81%) as a white solid. $\delta_H$ (500 MHz, DMSO-$d_6$) 8.52 (s, 3H), 3.81 (d, J 5.1 Hz, 1H), 3.75 (s, 3H), 1.86-1.77 (m, 1H), 1.74-1.67 (m, 3H), 1.65-1.58 (m, 2H), 1.22-1.12 (m, 3H), 1.12-1.03 (m, 1H), 0.97 (qd, J 12.9, 12.2, 3.8 Hz, 1H). HPLC-MS (method 6): MH+ m/z 172, RT 2.32 minutes.

Intermediate 7

Methyl (2S)-2-cyclohexyl-2-{[2-(pyridin-4-yl)acetyl]amino}acetate 2,4,6-Tripropyl-1,3,5,2,4,6-trioxatriphosphorinane-2,4,6-trioxide (50 wt % solution in ethyl acetate, 39.2 mL, 66.44 mmol) was added over 30 minutes to a stirred solution of Intermediate 6 (6.90 g, 33.22 mmol), 2-(pyridin-4-yl)acetic acid hydrochloride (6.92 g, 39.87 mmol) and DIPEA (19.2 mL, 116.27 mmol) in anhydrous THF (210 mL). The mixture was stirred at 20° C. under nitrogen for 3.5 h, then diluted with water (250 mL) and washed with ethyl acetate (2×200 mL). The pH of the aqueous phase was adjusted to pH 10 by slow addition of 4M aqueous sodium hydroxide solution (21 mL), then the aqueous phase was extracted with ethyl acetate (2×300 mL). The organic extracts were combined, washed with water (250 mL) and brine (250 mL), then dried over anhydrous magnesium sulfate and filtered. The solvent was removed in vacuo. The residue was separated by flash column chromatography, using a gradient of methanol in DCM (1-8%), to afford the title compound (4.53 g, 47%) as a yellow solid. $\delta_H$ (500 MHz, DMSO-$d_6$) 8.53-8.44 (m, 3H), 7.30-7.24 (m, 2H), 4.16 (dd, J 8.7, 6.5 Hz, 1H), 3.62 (s, 3H), 3.57 (d, J 14.2 Hz, 1H), 3.54 (d, J 14.4 Hz, 1H), 1.73-1.50 (m, 6H), 1.25-1.03 (m, 4H), 0.98 (qd, J 12.5, 3.5 Hz, 1H). HPLC-MS (method 5): MH+ m/z 291, RT 1.44 minutes. Chiral SFC (Method 12, Chiralpak AD-H 25 cm, 35% ethanol-65% carbon dioxide, 4 mL/minute): RT 3.07 minutes (100%).

Intermediate 8

Lithium (2S)-2-cyclohexyl-2-{[2-(pyridin-4-yl)acetyl]amino}acetate

A solution of lithium hydroxide monohydrate (0.99 g, 23.70 mmol) in water (16 mL) was added to a stirred solution of Intermediate 7 (4.53 g, 15.80 mmol) in THF/MeOH (1:1; 32 mL) at 0° C. The mixture was allowed to warm slowly to 20° C. and stirred over a total of 16 h, forming a thick suspension. The volatiles were removed in vacuo, then the residue was diluted with water (20 mL). The solids were collected by filtration, then washed with water (20 mL) and tert-butyl methyl ether (20 mL), before drying in vacuo at 50° C. for 16 h, to afford the title compound (3.53 g, 79%) as an off-white powder. $\delta_H$ (500 MHz, D$_2$O) 8.56-8.45 (m, 2H), 7.42 (d, J 6.1 Hz, 2H), 4.13 (d, J 5.8 Hz, 1H), 3.81 (d, J 14.9 Hz, 1H), 3.72 (d, J 14.9 Hz, 1H), 1.85-1.69 (m, 3H), 1.68-1.54 (m, 3H), 1.24 (dtt, J 16.0, 12.7, 3.3 Hz, 2H), 1.16-0.91 (m, 3H). HPLC-MS (method 5): MH+ m/z 277, RT 1.15 minutes. Chiral SFC (Method 12, Chiralpak IC 25 cm, 40% isopropanol+0.2% diethylamine-60% carbon dioxide, 4 mL/minute): RT 4.40 minutes (100%).

Intermediate 9

Methyl 2-cyclooctylidene-2-formamidoacetate

A solution of potassium tert-butoxide in THF (1M, 48 mL, 48 mmol) was added dropwise to a red solution of methyl isocyanoacetate (4.0 mL, 41.8 mmol) in anhydrous THF (40 mL) at approximately −65° C. under nitrogen. After stirring for 5 minutes, a solution of cyclooctanone (5 g, 39.62 mmol) in anhydrous THF (20 mL) was added slowly at −70° C. The reaction mixture was stirred at −70° C. for 30 minutes, then the cooling bath was removed and the mixture was allowed to warm to 20° C. with stirring under nitrogen for 60 h. The resultant deep red solution was quenched with water (100 mL) and stirred at 20° C. for 1 h. The residue was extracted with ethyl acetate (3×100 mL). The combined organic extracts were washed with brine (50 mL) and dried over magnesium sulfate, then filtered and concentrated in vacuo. The resulting crude viscous orange oil was separated by flash column chromatography using a gradient of ethyl acetate in heptane (0-90%) to afford the title compound (5.37 g, 58%) as an orange viscous oil, which solidified upon standing. Major rotamer: $\delta_H$ (500 MHz, DMSO-$d_6$) 9.31 (s, 1H), 8.01 (d, J 1.5 Hz, 1H), 3.60 (s, 3H), 2.52-2.47 (m, 2H), 2.31-2.23 (m, 2H), 1.74-1.60 (m, 4H), 1.50-1.31 (m, 6H). HPLC-MS (method 5): MNa+ m/z 248, RT 1.63 minutes.

Intermediate 10

Methyl 2-cyclooctyl-2-formamidoacetate

Magnesium turnings (3.15 g, 129.60 mmol) were added carefully to a stirred solution of Intermediate 9 (2.91 g, 12.95 mmol) in anhydrous methanol (65 mL) at 0° C. under nitrogen. The suspension was stirred at 0° C. for 1 h, then allowed to warm to 20° C. over 2 h. Stirring of the turbid suspension was continued at 20° C. for 16 h. An additional portion of magnesium turnings (1 g, 41.14 mmol) was added, and the suspension was stirred at 20° C. for 3.5 h under nitrogen. The mixture was carefully concentrated in vacuo. The residue was suspended in ethyl acetate (100 mL) and water (200 mL), then cooled to 0° C. Aqueous hydrochloric acid (1M, 100 mL) was cautiously added, then concentrated hydrochloric acid was cautiously added (pH 5) to aid dissolution of the solids. The organic phase was separated, then the aqueous suspension was treated with concentrated hydrochloric acid (pH 4) and the material was extracted with ethyl acetate (100 mL). The aqueous suspension was treated with concentrated hydrochloric acid (pH 2) and the material was extracted with ethyl acetate (100 mL). The aqueous suspension was further treated with concentrated hydrochloric acid (pH 1) and the material was extracted with ethyl acetate (100 mL). The combined organic extracts were washed with brine (50 mL) and dried over magnesium sulfate, then filtered and concentrated in vacuo. The resulting crude orange viscous oil was separated by flash column chromatography, using a gradient of ethyl acetate in heptane (0-80%), to afford the title compound (1.53 g, 52%) as an orange viscous oil. Major rotamer: $\delta_H$ (500 MHz, DMSO-$d_6$) 8.46 (d, J 8.5 Hz, 1H), 8.06 (s, 1H), 4.29 (dd, J 8.6, 6.1 Hz, 1H), 3.64 (s, 3H), 2.04-1.93 (m, 1H), 1.73-1.19 (m, 14H). HPLC-MS (method 4): MH+ m/z 228, RT 3.94 minutes.

Intermediate 11

Methyl 2-amino-2-cyclooctylacetate hydrochloride

Acetyl chloride (1.9 mL, 26.72 mmol) was added cautiously at 0° C. to a stirred solution of Intermediate 10 (1.54 g, 6.77 mmol) in methanol (68 mL) under nitrogen. After stirring for 5 minutes, the solution was heated at 50° C. for 2 h, then the volatiles were concentrated in vacuo. The resulting crude orange powder was triturated from diethyl ether (40 mL) and the solids were collected by filtration, washing with diethyl ether (2×20 mL). The solids were dried in vacuo at 50° C. for 6 h to afford the title compound (1.43 g, 90%) as a tan powder. $\delta_H$ (500 MHz, DMSO-$d_6$) 8.61 (br s, 3H), 3.86 (d, J 4.4 Hz, 1H), 3.73 (s, 3H), 2.19-2.09 (m, 1H), 1.68-1.37 (m, 13H), 1.32-1.20 (m, 1H). HPLC-MS (method 3): MH+ m/z 200, RT 0.75 and 0.86 minutes.

Intermediate 12

Methyl 2-cyclooctyl-2-[(2-methylpyrazole-3-carbonyl)amino]acetate

DIPEA (1.05 mL, 6.35 mmol) was added to a stirred solution of Intermediate 11 (500 mg, 2.12 mmol), 1-methyl-1H-pyrazole-5-carboxylic acid (269 mg, 2.12 mmol) and HATU (969 mg, 2.55 mmol) in anhydrous DMF (10 mL) under a nitrogen atmosphere. The mixture was stirred at 20° C. for 18 h, then quenched with saturated aqueous sodium hydrogen carbonate solution (50 mL) and water (50 mL). The material was extracted with ethyl acetate (3×50 mL). The combined organic layers were washed with brine (2×50 mL) and dried over sodium sulfate, then filtered and concentrated in vacuo. The residue was purified by flash column chromatography, using a gradient of ethyl acetate in heptane (0-100%), to afford the title compound (618 mg, 99%) as a yellow-orange oil. $\delta_H$ (500 MHz, DMSO-$d_6$) 8.60 (d, J 8.3 Hz, 1H), 7.46 (d, J 2.1 Hz, 1H), 7.01 (d, J 2.1 Hz, 1H), 4.37 (t, J 8.1 Hz, 1H), 4.01 (s, 3H), 3.66 (s, 3H), 2.22-2.08 (m, 1H), 1.80-1.38 (m, 13H), 1.37-1.29 (m, 1H). HPLC-MS (method 5): MH+ m/z 308, RT 1.87 minutes.

Intermediate 13

Lithium 2-cyclooctyl-2-[(2-methylpyrazole-3-carbonyl)amino]acetate

To a stirred solution of Intermediate 12 (519 mg, 1.69 mmol) in THF (9 mL) and water (4.5 mL) was added lithium hydroxide monohydrate (0.106 g, 2.53 mmol). The reaction mixture was stirred at 20° C. for 22 h, then concentrated and dried in vacuo for 4 h, to afford the title compound (505 mg, quantitative) as a yellow solid. $\delta_H$ (500 MHz, DMSO-$d_6$) 7.60 (d, J 7.6 Hz, 1H), 7.42 (d, J 2.0 Hz, 1H), 6.74 (d, J 2.0 Hz, 1H), 4.01 (s, 3H), 3.88 (dd, J 7.6, 4.3 Hz, 1H), 2.11-2.01 (m, 1H), 1.74-1.22 (m, 14H). HPLC-MS (method 5): MH+ m/z 294, RT 1.71 minutes.

Intermediate 14

Methyl 2-(2-aminopyridin-4-yl)acetate

Thionyl chloride (0.3 mL, 4.14 mmol) was added dropwise to (2-aminopyridin-4-yl)acetic acid (594 mg, 3.90 mmol) in methanol (12 mL) at 0° C. The reaction mixture was allowed to warm to 20° C. and stirred for 18 h, then evaporated to dryness. The residue was partitioned between isopropanol/chloroform (1:1; 60 mL) and saturated aqueous sodium hydrogen carbonate solution (60 mL). The layers were separated, then the aqueous phase was extracted with isopropanol/chloroform (1:1; 2×60 mL). The combined organic layers were dried over sodium sulfate, filtered and concentrated in vacuo, to afford the title compound (605 mg, 93%) as a pink-red solid. $\delta_H$ (500 MHz, DMSO-$d_6$) 7.81 (d, J 5.2 Hz, 1H), 6.37 (dd, J 5.2, 1.4 Hz, 1H), 6.32 (s, 1H), 5.86 (s, 2H), 3.61 (s, 3H), 3.51 (s, 2H). HPLC-MS (method 6): MH+ m/z 167, RT 0.70 minutes.

Intermediate 15

Methyl 2-[2-(tert-butoxycarbonylamino)pyridin-4-yl]acetate

A solution of di-tert-butyl dicarbonate (433 mg, 1.98 mmol) in tert-butanol (6 mL) was added slowly to a stirred solution of Intermediate 14 (300 mg, 1.81 mmol) in tert-butanol (12 mL). The mixture was stirred at 20° C. under nitrogen for 16 h, then the volatiles were removed in vacuo. The residue was separated by flash column chromatography, using a gradient of ethyl acetate in heptane (0-100%), to afford the title compound (325 mg, 67%) as an off-white powder. $\delta_H$ (500 MHz, DMSO-$d_6$) 9.74 (br s, 1H), 8.16 (d, J 5.1 Hz, 1H), 7.74 (s, 1H), 6.93 (dd, J 5.1, 1.4 Hz, 1H), 3.72 (s, 2H), 3.63 (s, 3H), 1.47 (s, 9H). HPLC-MS (method 5): MH+ m/z 211, RT 1.67 minutes.

Intermediate 16

2-[2-(tert-Butoxycarbonylamino)pyridin-4-yl]acetic acid

A solution of lithium hydroxide monohydrate (74 mg, 1.76 mmol) in water (1.2 mL) was added to a stirred solution of Intermediate 15 (311 mg, 1.17 mmol) in MeOH/THF (1:1; 2.4 mL). The solution was stirred at 20° C. under air for 16 h, then the volatiles were removed in vacuo. The residue was diluted with water (10 mL) and washed with tert-butyl methyl ether (2×5 mL). The combined organic washings were extracted with aqueous sodium hydroxide solution (0.1M, 5 mL). The pH of the aqueous phase was adjusted to pH 5 with 3M aqueous hydrochloric acid and the material was extracted with ethyl acetate (3×20 mL). The combined organic extracts were washed with brine (20 mL) and dried over magnesium sulfate, then filtered and concentrated in vacuo, to afford the title compound (285 mg, 97%) as a white powder. $\delta_H$ (500 MHz, DMSO-$d_6$) 12.49 (br s, 1H), 9.70 (br s, 1H), 8.15 (d, J 5.1 Hz, 1H), 7.73 (s, 1H), 6.92 (dd, J 5.1, 1.4 Hz, 1H), 3.59 (s, 2H), 1.47 (s, 9H). HPLC-MS (method 5): [M+2H-tBu]+ m/z 197, RT 1.36 minutes.

Intermediate 17

Methyl 2-({2-[2-(tert-butoxycarbonylamino)pyridin-4-yl]acetyl}amino)-2-cyclooctyl-acetate DIPEA (380 µL, 2.30 mmol) was added to a stirred solution of Intermediate 11 (180 mg, 0.76 mmol), Intermediate 16 (197 mg, 0.77 mmol) and HATU (350 mg, 0.92 mmol) in anhydrous DMF (3 mL) under a nitrogen atmosphere. The mixture was stirred at 20° C. for 18 h, then quenched with saturated aqueous sodium hydrogen carbonate solution (20 mL) and water (20 mL). The material was extracted with ethyl acetate (3×20 mL). The combined organic layers were washed with brine (2×20 mL) and dried over sodium sulfate, then filtered and concentrated in vacuo. The residue was purified by flash column chromatography, using a gradient of ethyl acetate in heptane (0-100%), to afford the title compound (282 mg, 85%) as a yellow-orange oil. $\delta_H$ (500 MHz, DMSO-$d_6$) 9.65 (s, 1H), 8.48 (d, J 8.5 Hz, 1H), 8.12 (d, J 5.1 Hz, 1H), 7.75 (s, 1H), 6.91 (dd, J 5.1, 1.3 Hz, 1H), 4.22 (dd, J 8.4, 6.5 Hz, 1H), 3.62 (s, 3H), 3.57 (d, J 13.9 Hz, 1H), 3.46 (d, J 13.9 Hz, 1H), 2.03-1.93 (m, 1H), 1.69-1.22 (m, 14H), 1.45 (s, 9H). HPLC-MS (method 5): MH+ m/z 434, RT 1.97 minutes.

Intermediate 18

Lithium 2-({2-[2-(tert-butoxycarbonylamino)pyridin-4-yl]acetyl}amino)-2-cyclooctyl-acetate Lithium hydroxide monohydrate (38 mg, 0.90 mmol) was added to a stirred solution of Intermediate 17 (260 mg, 0.60 mmol) in THF (6 mL) and water (3 mL). The reaction mixture was stirred at 20° C. for 22 h, then concentrated and dried in vacuo for 4 h, to give the title compound (255 mg, quantitative) as an off-white powder. HPLC-MS (method 5): MH+ m/z 420, RT 1.82 minutes.

Intermediate 19

2-({2-[2-(tert-Butoxycarbonylamino)pyridin-4-yl]acetyl}amino)-2-cyclooctyl-N-(2-oxo-spiro[indoline-3,4'-tetrahydropyran]-6-yl)acetamide HATU (210 mg, 0.55 mmol) was added to a stirred solution of Intermediate 2 (100 mg, 0.46 mmol) and Intermediate 18 (213 mg, 0.5 mmol) in anhydrous DMF (4 mL) under a nitrogen atmosphere. The mixture was stirred at 20° C. for 15 h, then quenched with saturated aqueous sodium hydrogen carbonate solution (20 mL). Water (20 mL) and ethyl acetate (20 mL) were added, then the resultant white precipitate was filtered and washed with DCM (2×10 mL) and isopropanol/chloroform (1:1; 2×10 mL). The aqueous and organic layers were separated, then the aqueous phase was extracted with ethyl acetate (2×20 mL). The combined organic washings and extracts were dried over sodium sulfate, then filtered and concentrated in vacuo. The residue was triturated with dichloromethane. The resulting pale yellow precipitate was filtered, then washed with dichloromethane and dried in vacuo, to afford the title compound (160 mg, 56%) as a pale yellow powder. HPLC-MS (method 5): MH+ m/z 620, RT 1.89 minutes.

Intermediate 20

Methyl 2-cyclooctyl-2-{[2-(pyridin-4-yl)acetyl]amino}acetate

HATU (497 mg, 1.31 mmol) was added to a stirred solution of Intermediate 11 (257 mg, 1.09 mmol), 2-(pyridin-4-yl)acetic acid hydrochloride (190 mg, 1.09 mmol) and DIPEA (0.90 mL, 5.45 mmol) in DMF (5 mL) under nitrogen. The mixture was stirred at 20° C. under nitrogen for 16 h, then quenched with saturated aqueous sodium hydrogen carbonate solution (10 mL). The material was extracted with ethyl acetate (3×10 mL). The combined organic extracts were washed with brine (2×10 mL) and dried over sodium sulfate, then filtered and concentrated in vacuo. The residue was separated by flash column chromatography, using a gradient of ethyl acetate in heptane (20-100%) followed by a gradient of methanol in ethyl acetate (0-20%), to afford the title compound (201 mg, 58%) as a pale orange oil. $\delta_H$ (250 MHz, CDCl$_3$) 8.63-8.58 (m, 2H), 7.26 (d, J 6.0 Hz, 2H), 5.97 (d, J 8.5 Hz, 1H), 4.56 (dt, J 9.1, 4.6 Hz, 1H), 3.75 (s, 3H), 3.61 (s, 2H), 2.07 (s, 1H), 1.66-1.39 (m, 14H). HPLC-MS (method 7): MH+ m/z 319, RT 1.77 minutes.

Intermediate 21

Lithium 2-cyclooctyl-2-{[2-(pyridin-4-yl)acetyl]amino}acetate

A solution of lithium hydroxide monohydrate (56 mg, 1.33 mmol) in water (1 mL) was added slowly to a stirred solution of Intermediate 20 (281 mg, 0.88 mmol) in MeOH/THF (1:1; 2 mL) at 20° C. under air. The mixture was stirred at 20° C. for 16 h, then diluted with an additional portion of MeOH/water (1:1; 2 mL), stirring at 20° C. for a further 24 h. The solids were collected by filtration, and washed with water (2 mL) and diethyl ether/MeOH/THF (10:1:1; 12 mL), then dried in vacuo at 50° C. for 5 h, to afford the title compound (172 mg, 63%) as a white powder. $\delta_H$ (500 MHz, DMSO-d$_6$) 8.48-8.40 (m, 2H), 7.57 (d, J 8.4 Hz, 1H), 7.31-7.26 (m, 2H), 3.77 (dd, J 8.4, 4.5 Hz, 1H), 3.56 (d, J 13.9 Hz, 1H), 3.46 (d, J 13.9 Hz, 1H), 1.99-1.89 (m, 1H), 1.62-1.24 (m, 13H), 1.20-1.09 (m, 1H). HPLC-MS (method 5): MH+ m/z 305, RT 1.49 minutes.

Intermediate 22

Methyl 2-[(2-methylpyrazole-3-carbonyl)amino]acetate

DIPEA (370 µL, 2.24 mmol) was added to a stirred solution of glycine methyl ester hydrochloride (70 mg, 0.56 mmol), 1-methyl-1H-pyrazole-5-carboxylic acid (71 mg, 0.57 mmol) and HATU (255 mg, 0.67 mmol) in anhydrous DMF (1 mL) under a nitrogen atmosphere. The mixture was stirred at 20° C. for 15 h, then quenched by the addition of saturated aqueous sodium hydrogen carbonate solution (7 mL) and water (7 mL). The material was extracted sequentially with ethyl acetate (3×7 mL) and 1:1 isopropanol/chloroform (2×7 mL). The combined organic layers were washed with brine (2×7 mL) and dried over sodium sulfate, then filtered and concentrated in vacuo. The residue was purified by flash column chromatography, using a gradient of ethyl acetate in heptane (0-100%), to afford the title compound (110 mg, quantitative) as an orange-brown oil. $\delta_H$ (250 MHz, DMSO-d$_6$) 8.92 (t, J 5.6 Hz, 1H), 7.48 (d, J 2.1 Hz, 1H), 6.89 (d, J 2.1 Hz, 1H), 4.04 (s, 3H), 3.98 (d, J 5.9 Hz, 2H), 3.66 (s, 3H). HPLC-MS (method 6): MH+ m/z 198, RT 0.52 minutes.

Intermediate 23

Lithium 2-[(2-methylpyrazole-3-carbonyl)amino]acetate

Lithium hydroxide monohydrate (36 mg, 0.86 mmol) was added to a stirred solution of Intermediate 22 (140 mg, 0.71 mmol) in THF (3 mL) and water (1.5 mL). The reaction mixture was stirred at 20° C. for 64 h, then concentrated and dried in vacuo for 4 h, to afford the title compound (134 mg, quantitative) as a tan foam. HPLC-MS (method 5): MH+ m/z 184, RT 0.12-0.16 minutes.

Intermediate 24

N-(2-Bromo-5-chlorophenyl)tetrahydrothiopyran-4-carboxamide 2,4,6-Tripropyl-1,3,5,2,4,6-trioxatriphosphorinane 2,4,6-trioxide (50 wt % solution in ethyl acetate, 8.1 mL, 13.6 mmol) was added slowly to a stirred solution of 2-bromo-5-chloroaniline (1.5 g, 7.27 mmol), thiane-4-carboxylic acid (1.0 g, 6.84 mmol) and pyridine (2.7 mL, 33.4 mmol) in ethyl acetate (14 mL) at 0° C. under nitrogen. The reaction mixture was allowed to warm slowly to 20° C. and stirred for 64 h. The resultant suspension was diluted with ethyl acetate (20 mL) and quenched with water (30 mL). The solids were collected by filtration, washing sequentially with ethyl acetate (2×20 mL), water (20 mL) and diethyl ether (2×20 mL). The solids were dried at 50° C. in vacuo for 16 h, to afford the title compound (2.08 g, 86%) as a pink powder. $\delta_H$ (500 MHz, DMSO-$d_6$) 9.51 (br s, 1H), 7.71-7.65 (m, 2H), 7.21 (dd, J 8.6, 2.6 Hz, 1H), 2.71-2.62 (m, 4H), 2.57 (tt, J 11.5, 3.1 Hz, 1H), 2.19-2.08 (m, 2H), 1.78-1.63 (m, 2H). HPLC-MS (method 5): MH+ m/z 334, RT 1.90 minutes.

Intermediate 25

N-(2-Bromo-5-chlorophenyl)-N-[2-(trimethylsilyl)ethoxymethyl]tetrahydrothiopyran-4-carboxamide Sodium hydride (60% dispersion in mineral oil, 39 mg, 0.98 mmol) was added to a stirred suspension of Intermediate 24 (250 mg, 0.75 mmol) in anhydrous THF (4 mL) at 0° C. under nitrogen. The mixture was stirred at 0° C. for 30 minutes, then [2-(chloro-methoxy)ethyl](trimethyl)silane (0.2 mL, 1.13 mmol) was added at 0° C. The mixture was allowed to warm gradually to 20° C. and stirred for a total of 16 h, then quenched with water (20 mL). The material was extracted with ethyl acetate (3×30 mL). The combined organic extracts were washed with brine (20 mL) and dried over magnesium sulfate, then filtered and concentrated in vacuo. The resulting crude red viscous oil was separated by flash column chromatography, using a gradient of tert-butyl methyl ether in heptane (0-30%), to afford the title compound (299 mg, 84%) as a colourless viscous oil. Major rotamer: $\delta_H$ (500 MHz, DMSO-$d_6$) 7.85 (d, J 8.6 Hz, 1H), 7.58 (d, J 2.5 Hz, 1H), 7.49 (dd, J 8.6, 2.5 Hz, 1H), 5.30 (d, J 10.4 Hz, 1H), 4.51 (d, J 10.4 Hz, 1H), 3.64-3.51 (m, 2H), 2.59-2.47 (m, 2H), 2.46-2.38 (m, 1H), 2.34-2.26 (m, 1H), 2.09-1.88 (m, 3H), 1.84-1.65 (m, 1H), 1.62-1.49 (m, 1H), 0.93-0.79 (m, 2H), −0.02 (s, 9H). HPLC-MS (method 5): MH+ m/z 464, RT 2.26 minutes.

Intermediate 26

6-Chloro-1-[2-(trimethylsilyl)ethoxymethyl]spiro[indoline-3,4'-tetrahydrothiopran]-2-one Intermediate 25 (290 mg, 0.62 mmol) and sodium tert-butoxide (180 mg, 1.87 mmol) were dissolved in anhydrous toluene (3.1 mL). The mixture was purged with nitrogen and sonicated for 5 minutes, then charged with [1,3-bis(2,6-diisopropylphenyl)-imidazol-2-ylidene](3-chloropyridyl)palladium(II) dichloride (42.6 mg, 0.06 mmol). The mixture was purged with nitrogen and sonicated for 5 minutes, then sealed under nitrogen and heated at 110° C. for 16 h. After cooling to room temperature, the reaction mixture was partitioned with water (30 mL) and ethyl acetate (30 mL). The biphasic mixture was filtered through a kieselguhr pad, washing with water (10 mL) and ethyl acetate (2×10 mL). The organic phase was separated, then the aqueous layer was extracted with ethyl acetate (2×30 mL). The combined organic extracts were washed with brine (20 mL) and dried over magnesium sulfate, then filtered and concentrated in vacuo. The resulting crude red viscous oil was separated by flash column chromatography, using a gradient of tert-butyl methyl ether in heptane (0-20%), to afford the title compound (73 mg, 31%) as a light tan viscous oil. $\delta_H$ (500 MHz, DMSO-$d_6$) 7.52 (d, J 8.0 Hz, 1H), 7.18 (d, J 1.9 Hz, 1H), 7.13 (dd, J 8.0, 1.9 Hz, 1H), 5.11 (s, 2H), 3.52-3.45 (m, 2H), 3.13 (ddd, J 13.1, 8.6, 4.1 Hz, 2H), 2.72-2.62 (m, 2H), 1.98-1.86 (m, 4H), 0.87-0.81 (m, 2H), −0.08 (s, 9H). HPLC-MS (method 5): MNa+ m/z 406, RT 2.28 minutes.

Intermediate 27 tert-Butyl N-{2-oxo-1-[2-(trimethylsilyl)ethoxymethyl]spiro[indoline-3,4'-tetrahydro-thiopyran]-6-yl}carbamate A sealed tube was charged with Intermediate 26 (73 mg, 0.19 mmol), tert-butyl carbamate (45 mg, 0.38 mmol) and tripotassium phosphate (57 mg, 0.27 mmol). The reagents were suspended in tert-butanol (1 mL), then the mixture was purged with nitrogen and sonicated for 5 minutes. The reaction mixture was charged with [(2-di-tert-butylphosphino-3,6-dimethoxy-2',4',6'-triisopropyl-1,1'-biphenyl)-2-(2'-amino-1,1'-biphenyl)]palladium(II) methanesulfonate (4.1 mg, 0.005 mmol) and 2-(di-tert-butyl-phosphino)-2',4',6'-triisopropyl-3,6-dimethoxy-1,1'-biphenyl (2.4 mg, 0.005 mmol), then purged with nitrogen and sonicated for 5 minutes. The mixture was sealed under nitrogen and heated at 110° C. for 16 h. After cooling to room temperature, the mixture was diluted with ethyl acetate (10 mL) and filtered through a kieselguhr pad, washing with ethyl acetate (2×10 mL). The filtrate was concentrated in vacuo. The resulting crude red semi-solid was separated by flash column chromatography, using a gradient of tert-butyl methyl ether in heptane (0-50%), to afford the title compound (14 mg, 16%) as an off-white powder. $\delta_H$ (500 MHz, DMSO-$d_6$) 9.41 (s, 1H), 7.43 (s, 1H), 7.34 (d, J 8.1 Hz, 1H), 7.02 (dd, J 8.1, 1.5 Hz, 1H), 5.03 (s, 2H), 3.52-3.44 (m, 2H), 3.17-3.01 (m, 2H), 2.74-2.65 (m, 2H), 1.97-1.81 (m, 4H), 1.47 (s, 9H), 0.88-0.79 (m, 2H), −0.07 (s, 9H). HPLC-MS (method 5): MNa+ m/z 487, RT 2.23 minutes.

Intermediate 28

6-Aminospiro[indoline-3,4'-tetrahydrothiopyran]-2-one

Trifluoroacetic acid (46 μL, 0.6 mmol) was added to a stirred solution of Intermediate 27 (14 mg, 0.03 mmol) in DCM (0.5 mL). The mixture was stirred under nitrogen at 20° C. for 16 h, then diluted with DCM (2 mL). An additional portion of trifluoroacetic acid (46 μL, 0.6 mmol) was added and stirring was continued at 20° C. for 5 days under nitrogen. The mixture was diluted with DCM (2 mL) and an additional portion of trifluoroacetic acid (92 μL, 1.19 mmol) was added. Stirring was continued for 24 h at 20° C. under nitrogen, then the volatiles were removed in vacuo. The residue was azeotroped three times with dichloromethane, then dissolved in methanol (3 mL). DIPEA (50 μL, 0.3 mmol) was added, then the mixture was heated at 100° C. under nitrogen for 1.5 h. After cooling to room temperature, the mixture was diluted with DCM (20 mL) and partitioned with 0.5M aqueous hydrochloric acid (20 mL). The biphasic mixture was shaken and the phases were separated using a hydrophobic frit. The aqueous phase was washed with DCM/isopropanol (4:1; 20 mL), then adjusted to pH 5-6 with solid sodium hydrogen carbonate. The material was extracted with 4:1 DCM-isopropanol (6×20 mL). The combined organic filtrates were shaken with saturated aqueous sodium hydrogen carbonate solution (10 mL) and the organic phase was separated using a hydrophobic frit. The organic filtrate was concentrated in vacuo to afford the title compound (3.2 mg, 45%) as a tan powder. HPLC-MS (method 5): MH+ m/z 235, RT 1.29 minutes.

Intermediate 29

1'-Benzyl-6-bromospiro[indoline-3,4'-piperidine]-2-one

A suspension of 6-bromo-1,3-dihydro-2H-indol-2-one (424 mg, 2.00 mmol) in anhydrous THF (20 mL) was purged with nitrogen and sonicated for 10 minutes. The mixture was cooled to −78° C. under nitrogen and 1M sodium bis(trimethylsilyl)amide (10 mL, 10.0 mmol) was added slowly. After stirring for 60 minutes, N-benzylbis(2-chloroethyl)amine hydrochloride (590 mg, 2.20 mmol) was added in one portion and the mixture was stirred at −78° C. for 1 h. The cooling bath was removed and the mixture was allowed to warm to 20° C., then heated at 70° C. for 16 h. After cooling to room temperature, the reaction mixture was quenched with saturated aqueous ammonium chloride solution (20 mL) and diluted with water (20 mL). The material was extracted with ethyl acetate (3×100 mL). The combined organic extracts were washed with brine (50 mL) and dried over magnesium sulfate, then filtered and concentrated in vacuo. The resulting crude dark red semi-solid was dissolved in hot DCM (~20 mL) and allowed to cool to room temperature, then triturated with heptane (~60 mL). The solids were collected by filtration, washing with heptane (2×20 mL). The filtrate was concentrated in vacuo, and the process was repeated, to afford the title compound (236 mg, 32%) as a light orange powder after drying in vacuo at 50° C. for 16 h. $\delta_H$ (500 MHz, DMSO-$d_6$) 10.50 (br s, 1H), 7.42 (d, J 7.8 Hz, 1H), 7.39-7.30 (m, 4H), 7.29-7.22 (m, 1H), 7.12 (dd, J 8.0, 1.8 Hz, 1H), 6.98 (d, J 1.8 Hz, 1H), 3.61 (s, 2H), 2.91-2.70 (m, 2H), 2.62-2.48 (m, 2H), 1.87-1.74 (m, 2H), 1.72-1.56 (m, 2H). HPLC-MS (method 5): MH+ m/z 371, RT 1.56 minutes.

Intermediate 30

6-Amino-1'-benzylspiro[indoline-3,4'-piperidine]-2-one

A sealed tube was charged with Intermediate 29 (326 mg, 0.88 mmol), tert-butyl carbamate (206 mg, 1.76 mmol) and tripotassium phosphate (262 mg, 1.23 mmol). The reagents were suspended in tert-butanol (4.5 mL), then the mixture was purged with nitrogen and sonicated for 5 minutes. The reaction mixture was charged with [(2-di-tert-butylphosphino-3,6-dimethoxy-2',4',6'-triisopropyl-1,1'-biphenyl)-2-(2'-amino-1,1'-biphenyl)]palladium(II) methanesulfonate (18.7 mg, 0.02 mmol) and 2-(di-tert-butyl-phosphino)-2',4',6'-triisopropyl-3,6-dimethoxy-1,1'-biphenyl (10.8 mg, 0.02 mmol), then purged with nitrogen and sonicated for 5 minutes. The mixture was sealed under nitrogen and heated at 110° C. for 16 h. After cooling, the mixture was partitioned between ethyl acetate (30 mL) and water (30 mL), then sonicated. The solids were removed by filtration through a kieselguhr pad, washing with water (20 mL) and ethyl acetate (20 mL). The organic phase was separated, then the aqueous layer was extracted with ethyl acetate (2×30 mL) after the pH had been adjusted to pH 11 with sodium carbonate. The combined organic extracts were washed with brine (20 mL) and dried over magnesium sulfate, then filtered and reduced in vacuo. The residue was dissolved in dichloromethane (8.3 mL), then trifluoroacetic acid (0.65 mL, 8.44 mmol) was added. The solution was stirred at 20° C. under air for 18 h. The volatiles were removed in vacuo and the residue was adsorbed onto an SCX-2 cartridge. The column was washed with DCM (50 mL) and MeOH (50 mL). The material was eluted with 1M ammonia in MeOH (50 mL), then concentrated in vacuo. The resulting purple powder was separated by flash column chromatography (KP-NH column), using a gradient of ethyl acetate in heptane (0-100%) followed by a gradient of MeOH in ethyl acetate (0-10%), to afford the title compound (24 mg, 9%) as a tan viscous oil. HPLC-MS (method 5): MH+ m/z 308, RT 1.07 minutes.

Intermediate 31

N-{1-Cyclooctyl-2-[(1'-benzyl-2-oxospiro[indoline-3,4'-piperidine]-6-yl)amino]-2-oxo-ethyl}-2-methylpyrazole-3-carboxamide HATU (68 mg, 0.18 mmol) was added to a stirred suspension of Intermediate 30 (46 mg, 0.15 mmol) and Intermediate 13 (50 mg, 0.17 mmol) in anhydrous DMF (1 mL). The mixture was stirred at 20° C. under nitrogen for 64 h, then quenched with saturated aqueous sodium carbonate solution (10 mL) and stirred for 30 minutes at 20° C. The mixture was diluted with water (10 mL) and partitioned with DCM/isopropanol (4:1; 20 mL). The organic phase was separated using a hydrophobic frit, then the aqueous layer was extracted with 4:1 DCM/isopropanol (2×20 mL). The filtrate was concentrated in vacuo. The resulting crude orange gum was separated by flash column chromatography, using a gradient of ethyl acetate in heptane (0-100%) followed by a gradient of MeOH in ethyl acetate (0-20%), to afford the title compound (24 mg, 28%) as an off-white powder. $\delta_H$ (500 MHz, CD$_3$OD) 7.46 (d, J 2.1 Hz, 1H), 7.44-7.38 (m, 3H), 7.37-7.31 (m, 3H), 7.31-7.26 (m, 1H), 7.08 (dd, J 8.1, 1.9 Hz, 1H), 6.87 (d, J 2.1 Hz, 1H), 4.50 (d, J 8.7 Hz, 1H), 4.08 (s, 3H), 3.72 (s, 2H), 3.03-2.93 (m, 2H), 2.79-2.70 (m, 2H), 2.28-2.18 (m, 1H), 2.00-1.89 (m, 2H), 1.87-1.43 (m, 16H). HPLC-MS (method 5): MH+ m/z 583, RT 1.75 minutes.

Intermediate 32

Methyl 2-(tert-butoxycarbonylamino)-2-(cyclooctyl)acetate

Triethylamine (0.71 mL, 5.09 mmol) was added to a mixture of Intermediate 11 (410 mg, 1.88 mmol) and di-tert-butyl dicarbonate (444 mg, 1.89 mmol) in DCM (16 mL) and the reaction mixture was stirred at 20° C. for 64 h. The reaction mixture was washed with water (30 mL), saturated aqueous sodium hydrogen carbonate solution (30 mL) and brine (30 mL), then dried over magnesium sulfate, filtered and concentrated in vacuo. The residue was separated by flash column chromatography using a gradient of ethyl acetate in heptane (0-100%) to afford the title compound (539 mg, 96%) as a colourless free-flowing oil. $\delta_H$ (250 MHz, DMSO-$d_6$) 7.14 (d, J 8.6 Hz, 1H), 4.03-3.78 (m, 1H), 3.61 (s, 3H), 2.02-1.84 (m, 1H), 1.75-1.19 (m, 23H).

Intermediate 33

Lithium 2-(tert-butoxycarbonylamino)-2-(cyclooctyl)acetate

Lithium hydroxide monohydrate (75 mg, 1.78 mmol) was added to a stirred solution of Intermediate 32 (485 mg, 1.62 mmol) in 2:1 THF-water (12 mL). The reaction mixture was stirred at 20° C. for 15 h, then concentrated and dried in vacuo for 2 h, to afford the title compound (471 mg, quantitative) as a white solid. $\delta_H$ (500 MHz, DMSO-$d_6$) 5.78 (d, J 7.1 Hz, 1H), 3.42-3.38 (m, 1H), 1.96-1.86 (m, 1H), 1.65-1.16 (m, 23H).

Intermediate 34 tert-Butyl N-{1-cyclooctyl-2-oxo-2-[(2-oxospiro [indoline-3,4'-tetrahydropyran]-6-yl)-amino] ethyl}carbamate HATU (596 mg, 1.57 mmol) was added to a stirred solution of Intermediate 2 (285 mg, 1.31 mmol) and Intermediate 33 (403 mg, 1.39 mmol) in anhydrous DMF (6 mL) under a nitrogen atmosphere. The mixture was stirred at 20° C. for 18 h, then quenched by the addition of saturated aqueous sodium hydrogen carbonate solution (50 mL) and water (50 mL). The aqueous phase was extracted with ethyl acetate (2×50 mL) and 1:1 isopropanol-chloroform (2×50 mL). The combined organic layers were washed with brine (2×50 mL) and dried over magnesium sulfate, then filtered and concentrated in vacuo. The residue was separated by flash column chromatography using a gradient of ethyl acetate in heptane (0-100%), followed by a gradient of methanol in dichloromethane (0-100%), to afford the title compound (502 mg, 79%) as a pale yellow solid. $\delta_H$ (500 MHz, DMSO-$d_6$) 10.38 (s, 1H), 9.98 (s, 1H), 7.43 (d, J 8.1 Hz, 1H), 7.37 (d, J 1.8 Hz, 1H), 7.07 (d, J 8.0 Hz, 1H), 6.87 (d, J 8.7 Hz, 1H), 4.00 (ddd, J 11.1, 7.1, 3.5 Hz, 2H), 3.93 (t, J 8.2 Hz, 1H), 3.80 (ddd, J 11.0, 7.0, 3.6 Hz, 2H), 1.93 (s, 1H), 1.79-1.69 (m, 2H), 1.68-1.25 (m, 25H). HPLC-MS (method 6): [M+2H-tBu]+ m/z 430, RT 3.12 minutes.

Intermediate 35

2-Amino-2-cyclooctyl-N-(2-oxospiro[indoline-3,4'-tetrahydropyran]-6-yl)acetamide Trifluoroacetic acid (0.8 mL, 10.38 mmol) was added to a stirred solution of Intermediate 34 (489 mg, 1.01 mmol) in DCM (20 mL) at 20° C. under a nitrogen atmosphere. The reaction mixture was stirred at 20° C. overnight. Additional trifluoroacetic acid (0.4 mL, 5.19 mmol) was added to the reaction mixture, and stirring was continued at 20° C. for 4 h. The reaction mixture was diluted with DCM (30 mL) and quenched with saturated aqueous sodium hydrogen carbonate solution (30 mL), then extracted with 1:1 isopropanol-chloroform (3×30 mL). The combined organic layers were dried over magnesium sulfate, then filtered and concentrated in vacuo, to afford the title compound (284 mg, 73%) as a tan solid. $\delta_H$ (500 MHz, DMSO-$d_6$) 10.38 (s, 1H), 9.83 (br s, 1H), 7.47-7.37 (m, 2H), 7.06 (dd, J 8.1, 1.9 Hz, 1H), 4.01 (ddd, J 11.0, 7.1, 3.6 Hz, 2H), 3.80 (ddd, J 11.1, 7.1, 3.6 Hz, 2H), 3.09 (d, J 5.8 Hz, 1H), 2.26-1.26 (m, 21H). uPLC-MS (method 2): MH+ m/z 386, RT 3.04 minutes.

Intermediate 36

2-[(2-Methylpyrazole-3-carbonyl)amino]acetic acid

A solution of lithium hydroxide monohydrate (2.02 g, 48.10 mmol) in water (33 mL) was added to a stirred solution of Intermediate 22 (7.3 g, 37.00 mmol) in THF (67 mL). The reaction mixture was stirred at 50° C. for 2 h, then left to cool to ambient temperature. The volatiles were removed in vacuo. The aqueous residue was washed with ethyl acetate (2×100 mL), then acidified to pH 1-2 with 3M hydrochloric acid. The aqueous layer was extracted with a dichloromethane:isopropanol mixture (2:1; 3×120 mL). The organic extracts were combined, dried over anhydrous sodium sulfate and filtered. The solvent was concentrated in vacuo to afford the title compound (6.6 g, 97%) as a white solid. $\delta_H$ (250 MHz, DMSO-$d_6$) 12.66 (s, 1H), 8.81 (t, J 5.9 Hz, 1H), 7.48 (d, J 2.1 Hz, 1H), 6.89 (d, J 2.1 Hz, 1H), 4.05 (s, 3H), 3.90 (d, J 6.0 Hz, 2H). HPLC-MS: MH+ m/z 184, RT 0.174 minutes.

Intermediate 37

2-(2-Methylpyrazol-3-yl)-4H-oxazol-5-one

To stirred solution of Intermediate 36 (7.77 g, 36.06 mmol) in anhydrous DCM (72 mL) was added EDCI.HCl (8.99 g, 46.87 mmol) portionwise. The reaction mixture was stirred at ambient temperature for 1.5 h, then diluted with DCM (70 mL) and quenched with water (70 mL). The organic layer was separated, washed with water (3×70 mL) and brine (50 mL), then dried over anhydrous sodium sulfate and filtered. The solvent was concentrated in vacuo to afford the title compound (7.65 g, 77%) as a pink solid, which was utilised without further purification. $\delta_H$ (250 MHz, CDCl$_3$) 7.53 (d, J 2.0 Hz, 1H), 6.82 (d, J 2.0 Hz, 1H), 4.42 (s, 2H), 4.22 (s, 3H). HPLC-MS (method 5): [2MNa]+ m/z 353 (weak), RT 0.72 minutes.

Intermediate 38

2-(2-Methylpyrazol-3-yl)-4-(spiro[3.3]heptan-2-ylidene)oxazol-5-one

Titanium tetrachloride in DCM (1M, 4.8 mL, 4.80 mmol) was added to anhydrous THF (9 mL) at −10° C. A solution of Intermediate 37 (200 mg, 1.21 mmol) in anhydrous THF (1.5 mL) and a solution of spiro[3.3]heptan-2-one (267 mg, 2.42 mmol) in anhydrous THF (1.5 mL) were added portionwise sequentially, and the reaction mixture was stirred at 0° C. for a further 20 minutes. Anhydrous pyridine (0.784 mL, 9.69 mmol) was added at 0° C. over 30 minutes. The reaction mixture was stirred at 0° C. for a further 2 h, then at ambient temperature for 16 h. The reaction mixture was quenched by the addition of saturated aqueous ammonium chloride solution (20 mL) and stirring was continued for a further 10 minutes. The solution was extracted with ethyl acetate (2×40 mL). The organic extracts were combined and washed with brine (20 mL), then dried over anhydrous sodium sulfate and filtered. The solvent was removed in vacuo. The residue was purified using automated chromatography, using a gradient of ethyl acetate in heptane (5-40%), to afford the title compound (224 mg, 72%) as a white solid. $\delta_H$ (250 MHz, CDCl$_3$) 7.53 (d, J 2.1 Hz, 1H), 6.86 (d, J 2.1 Hz, 1H), 4.25 (s, 3H), 3.29-3.24 (m, 2H), 3.19-3.15 (m, 2H), 2.19-2.11 (m, 4H), 1.98-1.84 (m, 2H). HPLC-MS (method 5): MH+ m/z 258, RT 1.93 minutes.

Intermediate 39

2-(2-Methylpyrazol-3-yl)-4-(spiro[3.3]heptan-2-yl)-4H-oxazol-5-one

To a stirred solution of Intermediate 38 (224 mg, 0.87 mmol) in anhydrous acetonitrile (10 mL) was added 10% palladium on charcoal (50% wet, 44 mg, 20 wt %) in a single portion. The reaction mixture was placed under a hydrogen gas atmosphere and stirring was continued at ambient temperature for 20 h. A second aliquot of 10% palladium on charcoal (50% wet, 22 mg, 10 wt %) was added and the reaction mixture was stirred under hydrogen for a further 43 h. The catalyst was removed by filtration over Kieselguhr, then the filter cake was rinsed with acetonitrile (2×5 mL). The solvent was concentrated in vacuo to afford the title compound (182 mg, 81%) as a grey oil. $\delta_H$ (250 MHz, CDCl$_3$) 7.53 (d, J 2.0 Hz, 1H), 6.81 (d, J 2.0 Hz, 1H), 4.33 (d, J 6.1 Hz, 1H), 4.24 (s, 3H), 2.74 (pd, J 8.4, 6.4 Hz, 1H), 2.23-1.99 (m, 6H), 1.91-1.76 (m, 4H). HPLC-MS (method 6): (M−H)⁻ m/z 258, RT 3.08 minutes.

Intermediate 40

Methyl 2-cyclooctyl-2-(3-methylisoxazole-4-carboxamido)acetate

To a solution of 3-methylisoxazole-4-carboxylic acid (12.9 g, 66.1 mmol) in dry DMF (100 mL) at 0° C. were added with DIPEA (54.9 g, 424.6 mmol), EDCI.HCl (19.5 g, 101.9 mmol) and HOBt (13.8 g, 101.9 mmol). The reaction mixture was stirred for 15 minutes at 0° C., then Intermediate 11 (20.0 g, 84.9 mmol) was added and the reaction mixture was stirred at r.t. for 48 h. The reaction mixture was poured into ice-cold water (500 mL), and extracted with ethyl acetate (2×400 mL). The organic layer was separated, then washed with ice-cold water (2×100 mL) and 1N HCl (2×50 mL). The organic layer was dried over anhydrous Na$_2$SO$_4$, then filtered and evaporated in vacuo. The crude residue was purified by silica gel flash column chromatography, using 15% EtOAc in hexane as eluting solvent, to afford the title compound (7.9 g, 41.3%) as a pale yellow viscous oil. LC-MS (method 17): MH+ m/z 309, RT 5.5 minutes.

Intermediate 41

Lithium 2-cyclooctyl-2-(3-methylisoxazole-4-carboxamido)acetate

To a solution of Intermediate 40 (11.01 g, 35.7 mmol) in THF (90 mL) at r.t. were added water (30 mL) and lithium hydroxide monohydrate (2.248 g, 53.6 mmol). The reaction mixture was stirred for 16 h, then evaporated under vacuum. To the residue was added diethyl ether (50 mL). The mixture was stirred for 10 minutes, then filtered. The resultant solid was washed with diethyl ether (50 mL) and pentane (50 mL), then dried under vacuum, to afford the title compound (9.51 g, 91%) as an off-white solid. $\delta_H$ (400 MHz, DMSO-d$_6$) 9.69 (s, 1H), 8.21 (s, 1H), 4.11 (dd, J 8.0, 4.0 Hz, 1H), 2.35 (s, 3H), 2.05 (br s, 1H), 1.65-1.35 (m, 14H). LC-MS (method 18): MH+ m/z 295, RT 5.4 minutes.

Intermediate 42 trans-(4-Methylcyclohexyl)methanol

To a cold (−5° C. to −20° C.) solution of trans-4-methylcyclohexanecarboxylic acid (68.5 g, 0.481 mol) in THF (550 mL) was added a solution of lithium aluminum hydride (2.4M in THF, 200 mL, 0.48 mol) slowly over circa 1 h. The mixture was stirred at −20° C. for 1.5 h, then allowed to warm to ambient temperature. The mixture was re-cooled in an ice-salt bath before water (16 mL), aqueous sodium hydroxide solution (15 wt %, 16 mL), and water (40 mL) were slowly and cautiously added. The resulting viscous mixture was stirred for 10 minutes, then diethyl ether (500 mL) was added. The resulting suspension was filtered through a pad of kieselguhr. The solvents were evaporated under reduced pressure to afford the title compound (63.5 g, 100%) as a clear, colourless mobile oil. $\delta_H$ (500 MHz, CDCl$_3$) 3.44 (d, J 6.3 Hz, 2H), 1.79-1.69 (m, 4H), 1.47-1.23 (m, 3H), 1.04-0.89 (m, 4H), 0.88 (d, J 6.6 Hz, 3H).

Intermediate 43 trans-4-Methylcyclohexanecarbaldehyde

To a cold (−10° C. to −5° C.) solution of Intermediate 42 (30.31 g, 0.229 mol) in DCM (250 mL), DIPEA (122 mL, 1.15 mol) and DMSO (81.4 mL, 0.688 mol) was added solid pyridine-sulfur trioxide complex (73 g, 0.458 mol) portionwise, maintaining the internal temperature below 20° C. The reaction mixture was stirred at ambient temperature for 16 h, then washed in turn with aqueous citric acid (1M, 200 mL) and brine (200 mL). The organic layer was filtered through phase separating filter paper. The solvent was removed under reduced pressure to afford the title compound (34.9 g, 100%) as a pale yellow oil. $\delta_H$ (250 MHz, CDCl$_3$) 9.61 (d, J 1.6 Hz, 1H), 2.28-2.03 (m, 1H), 1.95 (m, 2H), 1.80 (m, 2H), 1.56-1.14 (m, 3H), 1.07-0.80 (m, 5H, including the Me signal at δ 0.90 (d, J 6.5 Hz)).

Intermediate 44

(S)-4-Methyl-N-[(1E)-(trans-4-methylcyclohexyl)methylidene]benzenesulfinamide

To a solution of Intermediate 43 (34.9 g, 229 mmol) and (S)-4-methylbenzene-sulfinamide (35.6 g, 229 mmol) in DCM (1.2 L) was added titanium(IV) ethoxide (85-90% purity, 174.5 g, 160 mL). The resulting solution was heated at reflux for 2 h. The reaction mixture was cooled to ambient temperature, then water (300 mL) was added slowly. The resulting thick paste was filtered through a pad of kieselguhr, then rinsed with DCM (300 mL) and water (300 mL). The two phases were separated. The DCM phase was dried over anhydrous sodium sulfate and filtered, then the solvent was evaporated, to give the title compound (55.7 g, 78%) as a yellow oil, which partially solidified upon standing. $\delta_H$ (250 MHz, CDCl$_3$) 8.11 (d, J 4.9 Hz, 1H), 7.70-7.49 (m, 2H), 7.29 (m, 2H), 2.40 (s, 2H), 2.38-2.24 (m, 1H), 2.06-1.66 (m, 4H), 1.53-1.16 (m, 4H), 1.07-0.91 (m, 2H), 0.89 (d, J 6.5 Hz, 3H).

Intermediate 45

N—[(S)-Cyano(trans-4-methylcyclohexyl)methyl]-(S)-4-methylbenzenesulfinamide

To a solution of diethylaluminium cyanide (1M in toluene, 103 mL, 103 mmol) in THF (400 mL) at −78° C. was added anhydrous isopropyl alcohol (5.3 mL, 69 mmol). The mixture was stirred at −78° C. for 30-60 minutes, then canulated into a solution of Intermediate 44 (90% purity, 20.2 g, 69 mmol) in THF (800 mL) at −78° C. over circa 45 minutes. The mixture was allowed to warm to room temperature, then stirred overnight. The mixture was cooled in an ice-water bath, then saturated aqueous ammonium chloride solution (300 mL) was added; some gas was evolved and the internal temperature increased to circa 30° C. After 1 h, the mixture was filtered through a pad of kieselguhr, then the pad was washed with water (300 mL) and ethyl acetate (300 mL). The organic layers were divided, and the aqueous layers were washed with more ethyl acetate. The combined organic layers were washed with brine, dried over anhydrous sodium sulfate and filtered, then the solvent was evaporated. The resulting pale yellow oil, which solidified upon standing, was taken up in hot heptane-ethyl acetate, then allowed to crystallise, to afford the title compound (7.78 g, 38%) as a white solid. The residues were evaporated and purified by automated column chromatography to give a clean mixture of the two diastereoisomers. Recrystallisation of this mixture from ethyl acetate-heptane, seeded using some of the first crop, gave a further batch of the title compound (4.05 g, 20%). $\delta_H$ (250 MHz, CDCl$_3$) 7.61 (d, J 8.3 Hz, 2H), 7.36 (d, J 8.2 Hz, 3H), 4.50 (d, J 7.8 Hz, 1H), 3.95 (dd, J 7.9, 5.8 Hz, 1H), 2.43 (s, 3H), 2.25-1.78 (m, 3H), 1.44-0.91 (m, 5H), 0.89 (d, J 6.5 Hz, 3H).

Intermediate 46

[(S)-Cyano(trans-4-methylcyclohexyl)methyl]ammonium chloride

To a stirred solution of Intermediate 45 (6.6 g, 22.73 mmol) in dry methanol (130 mL) was added about half of the volume of 4M hydrogen chloride in 1,4-dioxane (120 mL) dropwise over 2 minutes, whereupon an exotherm to 26° C. had occurred. The reaction mixture was cooled externally and the remaining half volume of 4M hydrogen chloride in 1,4-dioxane was added over 3 minutes. After 5 minutes, the flask was stoppered and the reaction mixture was stirred at ambient temperature for 2 h. The volatiles were concentrated in vacuo. Diethyl ether (100 mL) was added, then the mixture was sonicated and stirred for 15 minutes. The solids were filtered off and washed with diethyl ether (3×100 mL), then dried under a stream of nitrogen gas, to afford the title compound (4.10 g, 96%) as a white solid. $\delta_H$ (500 MHz, DMSO-d$_6$) 9.20 (s, 3H), 4.50 (d, J 5.5 Hz, 1H), 1.92-1.77 (m, 3H), 1.77-1.67 (m, 2H), 1.29 (ddp, J 11.4, 6.8, 3.4 Hz, 1H), 1.18-1.01 (m, 2H), 0.95-0.83 (m, 5H). HPLC-MS (method 1): MH$^+$ m/z 153, RT 0.46 minutes (100%). Chiral LC (method 12, Amylose-2 25 cm, 80% heptane-20% 2-propanol, 1 mL/min): RT 8.84 minutes (S, 93%).

Intermediate 47

[(S)-Carboxy(trans-4-methylcyclohexyl)methyl]ammonium chloride

A stirred solution of Intermediate 46 (4.05 g, 21.46 mmol) in a mixture of acetic acid (17 mL) and concentrated hydrochloric acid (85 mL) was heated to an external temperature of 130° C. (105° C. internal temperature). After 3 h, another portion of concentrated hydrochloric acid (25 mL) was added, followed by another portion (25 mL) after a further 2 h. The reaction mixture was heated for 1 h, then cooled. The precipitated solid was filtered and rinsed with tert-butyl methyl ether, then dried in vacuo, to afford the title compound (3.04 g, 68%) as a white solid. $\delta_H$ (500 MHz, DMSO-d$_6$) 8.35 (s, 3H), 3.69 (d, J 4.2 Hz, 1H), 1.82-1.65 (m, 4H), 1.64-1.54 (m, 1H), 1.32-1.18 (m, 2H), 1.15-1.02 (m, 1H), 0.93-0.80 (m, 5H). HPLC-MS (method 3): MH$^+$ m/z 172, RT 0.63 minutes.

Intermediate 48

(2S)-2-(tert-Butoxycarbonylamino)-2-(trans-4-methylcyclohexyl)acetic acid

To a stirred suspension of Intermediate 47 (25.1 g, 120.8 mmol) in water (350 mL) was added sodium carbonate (55 g, 0.52 mol), followed by di-tert-butyl dicarbonate (39.6 g, 181 mmol) in 1,4-dioxane (500 mL). The reaction mixture was mechanically stirred for 4 h. The volatiles were removed in vacuo, then the suspension was cooled and 1N hydrochloric acid was carefully added to achieve a pH of 1. The mixture was extracted with ethyl acetate (3×250 mL). The organic layers were combined, washed in turn with water (200 mL) and brine (200 mL), then filtered through phase separating paper. The volatiles were evaporated. The resulting solid was triturated in heptane (500 mL) and filtered, then washed with heptane (2×100 mL) and oven-dried, to give the title compound (28.8 g, 87%) as a white solid. $\delta_H$ (500 MHz, DMSO-d$_6$) 12.40 (s, 1H), 6.89 (d, J 8.5 Hz, 1H), 3.81-3.74 (m, 1H), 1.69-1.53 (m, 5H), 1.37 (s, 9H), 1.28-1.19 (m, 1H), 1.09 (dp, J 22.9, 12.6, 11.6 Hz, 2H), 0.91-0.76 (m, 5H). HPLC-MS (method 1): MH$^+$ m/z 271, RT 3.34 minutes. Chiral SFC (method 12, Chiralpak AS-H 25 cm, 10% methanol-90% CO$_2$, 4 mL/minute): RT 2.61 minutes (100%). [α]$^{20}_D$=28.3° (c 3.202, chloroform).

Intermediate 49 tert-Butyl-N-[(1S)-1-(4-methylcyclohexyl)-2-oxo-2-[(2-oxospiro[indoline-3,4'-tetrahydropyran]-6-yl)amino]ethyl]carbamate (Trans Isomer)

To a stirred solution of Intermediate 48 (503 mg, 1.85 mmol) in dry DMF (10 mL) were added Intermediate 2 (405 mg, 1.86 mmol), HATU (850 mg, 2.24 mmol) and DIPEA (0.92 mL, 5.57 mmol) at r.t. The reaction mixture was stirred for 2.5 days. With external cooling (15° C.), water (40 mL) was added. The solid which precipitated was filtered off and washed with water (2×10 mL). The filter cake was dissolved in ethyl acetate (10 mL) and passed through a sinter funnel, then rinsed through with ethyl acetate (2×5 mL). Excess water was separated off from the filtrate. The organic layer was washed with a 1:1 mixture of water and brine (20 mL), and brine (10 mL), then dried over magnesium sulphate, filtered and concentrated in vacuo. The crude residue was adsorbed onto silica gel (4.4 g) using dichloromethane and purified by automated chromatography, using a gradient of ethyl acetate in heptane (0-100%), to afford the title compound (648 mg, 70%) as a white solid. $\delta_H$ (500 MHz, DMSO-d$_6$) 10.39 (s, 1H), 9.99-9.81 (m, 1H), 7.42 (d, J 8.1 Hz, 1H), 7.38 (d, J 1.8 Hz, 1H), 7.09-7.02 (m, 1H), 6.89-6.48 (m, 1H), 4.06-3.95 (m, 2H), 3.89 (t, J 8.2 Hz, 1H), 3.84-3.66 (m, 2H), 1.79-1.69 (m, 3H), 1.69-1.44 (m, 6H), 1.40-1.28 (m, 9H), 1.28-1.20 (m, 1H), 1.21-1.06 (m, 1H), 1.06-0.93 (m, 1H), 0.90-0.75 (m, 5H). uPLC-MS (method 1): MH+ m/z 472, RT 3.52 minutes.

Intermediate 50

(2S)-2-Amino-2-(4-methylcyclohexyl)-N-(2-oxospiro[indoline-3,4'-tetrahydropyran]-6-yl)acetamide (Trans Isomer)

To a stirred solution of Intermediate 49 (606 mg, 1.29 mmol) in DCM (19 mL) was added trifluoroacetic acid (0.9 mL, 11.68 mmol). The mixture was stirred for 18 h, then heated at reflux for about 1.5 h before additional trifluoroacetic acid (0.5 mL) was added. After 1 h, the reaction mixture was cooled. With external cooling, saturated NaHCO$_3$ (30 mL) was added, followed by ethyl acetate (50 mL). The two-phase mixture was warmed to r.t., whereupon the solid dissolved. The organic layer was separated, then the aqueous layer was re-extracted with ethyl acetate (3×10 mL). The organic layers were combined and washed with a 1:1 mixture of water and brine (10 mL), and brine (10 mL), then dried over magnesium sulphate, filtered and concentrated in vacuo. More ethyl acetate (~3 mL) was added, followed by heptane (20 mL). The solid was filtered off, then washed with more heptane (4×10 mL) and dried, to afford the title compound (387 mg, 81%) as a white solid. $\delta_H$ (500 MHz, DMSO-$d_6$) 10.37 (s, 1H), 9.79 (s, 1H), 7.45-7.38 (m, 2H), 7.06 (dd, J 8.1, 1.9 Hz, 1H), 4.04-3.97 (m, 2H), 3.86-3.73 (m, 2H), 3.08 (d, J 5.8 Hz, 1H), 1.99 (s, 2H), 1.92-1.56 (m, 7H), 1.56-1.41 (m, 2H), 1.31-1.13 (m, 2H), 1.07-0.94 (m, 1H), 0.92-0.77 (m, 5H). uPLC-MS (method 3): MH+ m/z 372, RT 0.86 minutes.

Intermediate 51 tert-Butyl N-{(1S)-2-[(4-fluoro-2-oxospiro[indoline-3,4'-tetrahydropyran]-6-yl)amino]-1-(4-methylcyclohexyl)-2-oxoethyl}carbamate (Trans Isomer)

DIPEA (0.13 mL, 0.8 mmol) was added to a stirred suspension of Intermediate 74 (100 mg, 0.38 mmol), Intermediate 48 (125 mg, 0.46 mmol) and HATU (188 mg, 0.5 mmol) in anhydrous DCM (3.8 mL). The mixture was stirred at 20° C. under nitrogen for 60 h, then quenched with saturated aqueous sodium carbonate solution (10 mL) and diluted with water (10 mL). The material was extracted with DCM (3×25 mL) using a hydrophobic frit. The organic filtrate was concentrated in vacuo. The resulting viscous orange oil was separated by flash column chromatography, using a gradient of ethyl acetate in heptane (0-100%), to afford the title compound (102 mg, 52%) as an off-white powder. $\delta_H$ (500 MHz, DMSO-$d_6$) 10.58 (s, 1H), 10.14 (s, 1H), 7.09 (d, J 1.5 Hz, 1H), 7.05 (d, $^2J_{HF}$ 12.4 Hz, 1H), 6.91 (d, J 8.2 Hz, 1H), 4.11-3.98 (m, 2H), 3.86 (t, J 8.2 Hz, 1H), 3.81-3.68 (m, 2H), 2.06-1.95 (m, 2H), 1.80-1.60 (m, 5H), 1.60-1.43 (m, 2H), 1.37 (s, 9H), 1.28-1.20 (m, 1H), 1.19-0.93 (m, 2H), 0.90-0.75 (m, 5H). HPLC-MS (method 5): MH+ m/z 490, RT 2.00 minutes.

Intermediate 52

(2S)-2-Amino-N-(4-fluoro-2-oxospiro[indoline-3,4'-tetrahydropyran]-6-yl)-2-(4-methyl-cyclohexyl)acetamide (Trans Isomer)

Trifluoroacetic acid (161 μL, 2.09 mmol) was added to a stirred solution of Intermediate 51 (102 mg, 0.21 mmol) in DCM (1 mL). The mixture was stirred at 20° C. under nitrogen for 16 h, then diluted with 4:1 DCM-isopropanol (20 mL) and quenched with saturated aqueous sodium carbonate solution (10 mL) and water (10 mL). The biphasic mixture was stirred at 20° C. for 30 minutes, then the organic phase was separated using a hydrophobic frit. The aqueous layer was extracted with 4:1 DCM-isopropanol (3×10 mL). The organic filtrate was concentrated in vacuo to afford the title compound (105 mg, quantitative) as a tan powder. $\delta_H$ (500 MHz, DMSO-$d_6$) 10.58 (s, 1H), 7.14 (d, J 1.7 Hz, 1H), 7.08 (dd, $^2J_{HF}$ 12.5, J 1.6 Hz, 1H), 4.06 (t, J 10.1 Hz, 2H), 3.75 (dt, J 11.2, 3.9 Hz, 2H), 3.06 (d, J 5.8 Hz, 1H), 2.00 (ddd, J 14.3, 10.4, 4.5 Hz, 2H), 1.75-1.61 (m, 5H), 1.54-1.40 (m, 2H), 1.31-1.12 (m, 2H), 1.07-0.94 (m, 1H), 0.93-0.76 (m, 5H). HPLC-MS (method 5): MH+ m/z 390, RT 1.60 minutes.

Intermediate 53

Methyl 2-[(3-methylisoxazole-4-carbonyl)amino]acetate

To a stirred solution of 3-methylisoxazole-4-carboxylic acid (20 g, 157 mmol) in anhydrous DMF (140 mL) under a nitrogen atmosphere were added successively DIPEA (63.1 g, 488 mmol), EDCI.HCl (36.2 g, 189 mmol), HOBt (25.5 g, 189 mmol) and glycine methyl ester hydrochloride (25.5 g, 157 mmol). The mixture was stirred at 20° C. for 12 h, then quenched by the addition of saturated aqueous sodium hydrogen carbonate solution (500 mL). The material was extracted sequentially with ethyl acetate (4×1.5 L). The combined organic layers were washed with brine (2 L) and dried over sodium sulfate, then filtered and concentrated in vacuo, to afford the title compound (20 g, 64%) as a crude orange-brown oil. $\delta_H$ (400 MHz, CDCl$_3$) 8.77 (s, 1H), 6.52 (s, 1H), 4.18 (d, J 4.0 Hz, 2H), 3.81 (s, 3H), 2.51 (s, 3H). HPLC-MS (method 33): MH+ m/z 199, RT 0.86 minutes.

Intermediate 54

2-[(3-Methylisoxazole-4-carbonyl)amino]acetic acid

A solution of lithium hydroxide monohydrate (43.4 g, 1.03 mol) in methanol (930 mL) was added to a stirred solution of Intermediate 53 (186 g, 0.94 mol) in THF (1.7 L). The reaction mixture was stirred at r.t. for 3 h, then concentrated in vacuo. The aqueous residue was acidified to pH 1 with 6M aqueous hydrochloric acid solution (279 mL), then left at r.t. After 1 h, the resulting crystalline solid was filtered off, then dried in vacuo, to yield the title compound (19 g, 78%) as an off-white solid. $\delta_H$ (400 MHz, DMSO-$d_6$) 9.32 (s, 1H), 8.77 (t, J 6.0 Hz, 1H), 3.88 (s, J 8.0 Hz, 2H), 2.37 (s, 3H). LC-MS (method 34): MH+ m/z 185, RT 0.29 minutes.

Intermediate 55

2-(3-Methylisoxazol-4-yl)-4H-oxazol-5-one

To a stirred solution of Intermediate 54 (44.2 g, 240 mmol) in anhydrous DCM (440 mL) was added EDCI.HCl (59.8 g, 312 mmol) portionwise. The reaction mixture was stirred at ambient temperature for 1.5 h, then diluted with DCM (200 mL) and quenched with water (500 mL). The organic layer was separated and washed with brine (2×500 mL), then dried over anhydrous sodium sulfate and filtered. The solvent was concentrated in vacuo to afford the title compound (34 g, 86%) as a yellow solid, which was utilised without further purification. $\delta_H$ (400 MHz, CDCl$_3$) 8.83 (s, 1H), 4.37 (s, 2H), 2.56 (s, 3H). LC-MS (method 34): [M−H]⁻ m/z 167, RT 0.76 minutes.

Intermediate 56

4-{5-Methoxybicyclo[4.2.0]octa-1(6),2,4-trien-7-ylidene}-2-(3-methyl-1,2-oxazol-4-yl)-4,5-dihydro-1,3-oxazol-5-one Titanium tetrachloride in DCM (1M, 2.7 mL, 2.7 mmol) was added to anhydrous THF (4 mL) at −10° C. A solution of Intermediate 55 (0.146 g, 0.88 mmol) in anhydrous THF (1 mL) and a solution of 5-methoxybicyclo[4.2.0]octa-1,3,5-trien-7-one (0.1 g, 0.67 mmol) in anhydrous THF (1 mL) were added dropwise sequentially. The reaction mixture was stirred at 0° C. for 20 minutes, then anhydrous pyridine (0.44 mL, 14.5 mmol) was added dropwise at 0° C. over 30 minutes. The reaction mixture was stirred at 0° C. for a further 2 h, then at room temperature for 16 h. The reaction mixture was quenched by addition of saturated aqueous ammonium chloride solution (12 mL), and stirring was continued for a further 10 minutes. The solution was extracted with ethyl acetate (2×20 mL). The combined organic extracts were washed with brine (20 mL) and dried over magnesium sulfate, then filtered and concentrated in vacuo. The residue was purified by flash column chromatography, using a gradient of ethyl acetate in heptane (0-100%), to afford the title compound (188 mg, 94%) as a yellow solid. $\delta_H$ (500 MHz, DMSO-$d_6$) 9.66 (s, 1H), 7.53 (dd, J 8.5, 7.2 Hz, 1H), 7.09-6.89 (m, 2H), 3.98 (s, 2H), 3.94 (s, 3H), 2.62 (s, 3H). HPLC-MS (method 5): MH+ m/z 297, RT 1.87 minutes.

Intermediate 57

6'-Amino-1'-{[2-(trimethylsilyl)ethoxy]methyl}-1', 2'-dihydrospiro[oxane-4,3'-pyrrolo-[3,2-c]pyridine]-2'-one Lithium hexamethyldisilazane in THF (1M, 8.13 mL, 8.13 mmol) was added to a mixture of Intermediate 84 (2.5 g, 6.78 mmol), tris(dibenzylideneacetone)dipalladium(0) (0.31 g, 0.34 mmol) and (2-biphenyl)dicyclohexylphosphine (0.285 g, 0.81 mmol) in anhydrous THF (50 mL) under nitrogen. The reaction mixture was stirred at 65° C. under nitrogen for 4 h. The reaction mixture was cooled to 0° C. and 1N HCl (21 mL) was added. The reaction mixture was stirred at 0° C. for 10 minutes, then quenched with sodium carbonate (pH 11) and extracted with ethyl acetate (3×100 mL). The combined organic layers were washed with brine (100 mL) and dried over magnesium sulfate, then filtered and concentrated in vacuo. The residue was purified by flash column chromatography (KP-NH cartridge), using a gradient of heptane in ethyl acetate (0-100%), to afford the title compound (1.65 g, 69%) as a tan solid. $\delta_H$ (500 MHz, DMSO-$d_6$) 8.11 (s, 1H), 6.23 (s, 1H), 6.03 (s, 2H), 5.06 (s, 2H), 4.03 (ddd, J 10.2, 5.9, 4.0 Hz, 2H), 3.84 (ddd, J 11.7, 8.4, 3.3 Hz, 2H), 3.59-3.47 (m, 2H), 1.86 (ddd, J 12.7, 8.3, 3.9 Hz, 2H), 1.72-1.57 (m, 2H), 1.01-0.78 (m, 2H), 0.00 (s, 9H). HPLC-MS (method 3): MH+m/z 350, RT 0.97 minutes.

Intermediate 58

Methyl 2-[(2-ethylpyrazole-3-carbonyl)amino]acetate

DIPEA (35.4 mL, 214 mmol) was added to a stirred solution of methyl 2-amino-acetate hydrochloride (8.96 mL, 71.4 mmol), 2-ethylpyrazole-3-carboxylic acid (10 g, 71.4 mmol) and HATU (32.56 g, 85.6 mmol) in anhydrous DMF (90 mL) under a nitrogen atmosphere. The reaction mixture was stirred at room temperature for 16 h, then diluted with water (50 mL) and saturated aqueous sodium hydrogen carbonate solution (50 mL). The aqueous layer was extracted with tert-butyl methyl ether (3×200 mL), followed by 9:1 DCM/MeOH (2×150 mL), then 4:1 DCM/MeOH (2×150 mL). The organic extracts were combined and concentrated in vacuo. The resulting material was purified by flash column chromatography, using a gradient of ethyl acetate in heptane (0-80%), to afford the title compound (20.9 g, 78%) as a yellow oil. $\delta_H$ (250 MHz, CDCl$_3$) 7.47 (d, J 2.0 Hz, 1H), 6.58 (d, J 2.1 Hz, 1H), 6.53 (br s, 1H), 4.59 (q, J 7.2 Hz, 2H), 4.18 (d, J 5.2 Hz, 2H), 3.80 (s, 3H), 1.43 (t, J 7.2 Hz, 3H). HPLC-MS (method 5): MH+ m/z 212, RT 0.86 minutes.

Intermediate 59

2-[(2-Ethylpyrazole-3-carbonyl)amino]acetic acid

A solution of lithium hydroxide monohydrate (3.02 g, 72.0 mmol) in water (60 mL) was added to a stirred solution of Intermediate 58 (56% purity, 20.88 g, 55.36 mmol) in THF (120 mL). The reaction mixture was stirred at 50° C. for 3 h. The volatiles were removed in vacuo and the aqueous residue was extracted with ethyl acetate (2×100 mL). The aqueous phase was treated with 3M aqueous hydrochloric acid (pH 1-2) and extracted with 9:1 DCM/MeOH (2×100 mL), followed by 4:1 DCM/MeOH (2×200 mL). The organic extracts were combined and concentrated in vacuo to give the title compound (7.85 g, 37%) as a yellow oil. The aqueous phase was further extracted with 1:1 isopropanol/DCM (4×150 mL) to give a second batch of the title compound (6.27 g, 40%) as a white solid. $\delta_H$ (500 MHz, CDCl$_3$) 7.53 (d, J 2.0 Hz, 1H), 6.61 (d, J 2.0 Hz, 1H), 6.59-6.51 (m, 1H), 4.63 (q, J 7.2 Hz, 2H), 4.26 (d, J 5.2 Hz, 2H), 1.47 (t, J 7.2 Hz, 3H). HPLC-MS (method 5): MH+ m/z 198, RT 0.33 minutes.

Intermediate 60

2-(2-Ethylpyrazol-3-yl)-4H-oxazol-5-one

To stirred solution of Intermediate 59 (51% purity, 7.85 g, 20.3 mmol) in dry DCM (50 mL) was added EDCI.HCl (1:1) (5.06 g, 26.39 mmol) portionwise. The reaction mixture was stirred at ambient temperature for 2 h, then concentrated in vacuo. The resulting orange oil was diluted with water (50 mL) and extracted with tert-butyl methyl ether (3×70 mL). The organic extracts were combined, washed with water (3×50 mL) and brine (50 mL), and dried over sodium sulfate, then filtered and concentrated in vacuo, to afford the title compound (2.8 g, 66%) as an orange oil. $\delta_H$ (500 MHz, CDCl$_3$) 7.56 (d, J 2.0 Hz, 1H), 6.82 (d, J 2.0 Hz, 1H), 4.66 (q, J 7.2 Hz, 2H), 4.43 (s, 2H), 1.46 (t, J 7.2 Hz, 3H). HPLC-MS (method 3): MH+ m/z 180, RT 0.59 minutes.

Intermediate 61 (Procedure F)

4-(5-Chlorobicyclo[4.2.0]octa-1,3,5-trien-7-ylidene)-2-(1-ethyl-1H-pyrazol-5-yl)-4,5-dihydro-1,3-oxazol-5-one Titanium tetrachloride in DCM (1M, 2.62 mL, 2.62 mmol) was added to anhydrous THF (3.5 mL) at −10° C. A solution of Intermediate 60 (178 mg, 0.854 mmol) in anhydrous THF (1.5 mL) and a solution of 5-chlorobicyclo[4.2.0]octa-1,3,5-trien-7-one (100 mg, 0.66 mmol) in anhydrous THF (1.5 mL) were added portionwise sequentially. The reaction mixture was stirred at 0° C. for 20 minutes, then anhydrous pyridine (0.46 mL, 5.69 mmol) was added dropwise at 0° C. over 30 minutes. The reaction mixture was stirred at 0° C. for 2 h, and at room temperature for a further 16 h, then quenched by the addition of saturated aqueous ammonium chloride solution (7 mL). Stirring was continued for a further 10 minutes, then the solution was extracted with ethyl acetate (2×15 mL). The organic extracts were combined, washed with brine (15 mL) and dried over magnesium sulfate, then filtered and concentrated in vacuo. The residue was purified by flash column chromatography, using a gradient of ethyl acetate in heptane (0-100%), to afford the title compound (191 mg, 70%) as a yellow-orange solid. $\delta_H$ (500 MHz, DMSO-$d_6$) 7.70 (d, J 2.0 Hz, 1H), 7.61-7.52 (m, 1H), 7.48 (d, J 8.1 Hz, 1H), 7.40 (d, J 7.1 Hz, 1H), 7.01 (d, J 2.0 Hz, 1H), 4.76 (q, J 7.1 Hz, 2H), 4.07 (s, 2H), 1.40 (t, J 7.1 Hz, 3H). HPLC-MS (method 5): MH+ m/z 314 and 316, RT 2.07 minutes.

Intermediate 62

4-(1-Adamantylmethylene)-2-(2-methylpyrazol-3-yl)oxazol-5-one

Titanium tetrachloride in DCM (1M, 3.6 mL, 3.63 mmol) was added to anhydrous THF (6 mL) at −10° C. A solution of Intermediate 37 (150 mg, 0.908 mmol) in anhydrous THF (1.5 mL) and a solution of adamantane-1-carbaldehyde (298 mg, 1.82 mmol) in anhydrous DCM (2 mL) were added portionwise sequentially. The reaction mixture was stirred at 0° C. for 20 minutes, then anhydrous pyridine (0.60 mL, 7.42 mmol) was added at 0° C. over 30 minutes. The reaction mixture was stirred at 0° C. for 2 h, and at ambient temperature for a further 16 h, then quenched by the addition of saturated aqueous ammonium chloride solution (15 mL). Stirring was continued for a further 10 minutes, then the solution was extracted with ethyl acetate (2×30 mL). The organic extracts were combined and washed with brine (10 mL), then dried over anhydrous sodium sulfate and filtered. The solvent was removed in vacuo. The residue was purified using automated chromatography, using a gradient of ethyl acetate in heptane (5-40%), to afford the title compound (24 mg, 8.5%) as a beige solid. $\delta_H$ (250 MHz, CDCl$_3$) 7.55 (d, J 2.1 Hz, 1H), 6.90 (d, J 2.1 Hz, 1H), 6.49 (s, 1H), 4.30 (s, 3H), 2.10-2.03 (m, 3H), 2.03-1.97 (m, 6H), 1.80-1.73 (m, 6H). HPLC-MS (method 4): MH+ m/z 312, RT 3.20 minutes.

Intermediate 63 (Procedure G)

N-{2-(1-Adamantyl)-1-[(2-oxospiro[indoline-3,4'-tetrahydropyran]-6-yl)carbamoyl]-vinyl}-2-methylpyrazole-3-carboxamide To a stirred solution of Intermediate 2 (17 mg, 0.078 mmol) and Intermediate 62 (24 mg, 0.078 mmol) in anhydrous acetonitrile (3 mL) was added acetic acid (0.045 mL, 0.78 mmol). The reaction mixture was stirred at 60° C. for 19 h. The solvent was removed in vacuo and the residue was triturated into DCM (2 mL). The solid was collected by filtration and further dried in vacuo to afford the title compound (20 mg, 42%) as an orange solid. HPLC-MS (method 5): MH+ m/z 530, RT 1.82 minutes (87%) and RT 2.20 minutes (13%).

Intermediate 64

4-[1-(Bicyclo[1.1.1]pentan-1-yl)ethylidene]-2-(2-methylpyrazol-3-yl)oxazol-5-one Titanium tetrachloride in DCM (1M, 4.8 mL, 4.80 mmol) was added to anhydrous THF (9 mL) at −10° C. A solution of Intermediate 37 (200 mg, 1.21 mmol) in anhydrous THF (1.5 mL) and 1-(bicyclo[1.1.1]pentan-1-yl)ethan-1-one (90%, 297 mg, 2.42 mmol) in anhydrous THF (1.5 mL) were added portionwise sequentially. The reaction mixture was stirred at 0° C. for 20 minutes, then anhydrous pyridine (0.784 mL, 9.69 mmol) was added at 0° C. over 30 minutes. The reaction mixture was stirred at 0° C. for 2 h, and at ambient temperature for a further 16 h, then quenched by the addition of saturated aqueous ammonium chloride solution (20 mL). Stirring was continued for a further 10 minutes, then the solution was extracted with ethyl acetate (2×40 mL). The organic extracts were combined and washed with brine (20 mL), then dried over anhydrous sodium sulfate and filtered. The solvent was removed in vacuo. The residue was purified by automated chromatography, using a gradient of ethyl acetate in heptane (5-40%), to afford the title compound (235 mg, 73%) as a yellow solid. $\delta_H$ (250 MHz, CDCl$_3$) 7.53 (d, J 2.1 Hz, 1H), 6.85 (d, J 2.1 Hz, 1H), 4.29 (s, 3H), 2.60 (s, 1H), 2.30 (s, 3H), 2.22 (s, 6H). HPLC-MS (method 5): MH+ m/z 258, RT 2.13 minutes.

Intermediate 65

4-Cycloheptylidene-2-(2-methylpyrazol-3-yl)oxazol-5-one

Titanium tetrachloride in DCM (1M, 4.8 mL, 4.80 mmol) was added to anhydrous THF (9 mL) at −10° C. A solution of Intermediate 37 (200 mg, 1.21 mmol) in anhydrous THF (1.5 mL) and a solution of cycloheptanone (272 mg, 2.42 mmol) in anhydrous THF (1.5 mL) were added portionwise sequentially. The reaction mixture was stirred at 0° C. for 20 minutes, then anhydrous pyridine (0.784 mL, 9.69 mmol) was added at 0° C. over 30 minutes. The reaction mixture was stirred at 0° C. for 2 h, and at ambient temperature for a further 16 h, then quenched by the addition of saturated aqueous ammonium chloride solution (20 mL). Stirring was continued for a further 10 minutes, then the solution was extracted with ethyl acetate (2×40 mL). The organic extracts were combined and washed with brine (20 mL), then dried over anhydrous sodium sulfate and filtered. The solvent was removed in vacuo. The residue was purified by chromatography, using a gradient of ethyl acetate in heptane (5-40%), to afford the title compound (201 mg, 64%) as a beige solid. $\delta_H$ (250 MHz, CDCl$_3$) 7.53 (d, J 1.9 Hz, 1H), 6.86 (d, J 1.9 Hz, 1H), 4.28 (s, 3H), 3.12-3.05 (m, 2H), 3.02-2.94 (m, 2H), 1.83-1.73 (m, 4H), 1.65-1.57 (m, 4H). HPLC-MS (method 4): MH+ m/z 260, RT 3.09 minutes.

Intermediate 66 (Procedure H)

4-Cycloheptyl-2-(2-methylpyrazol-3-yl)-4H-oxazol-5-one

To a stirred solution of Intermediate 65 (120 mg, 0.52 mmol) in anhydrous THF (6 mL) was added 10% palladium on charcoal (50% wet, 12 mg, 20 wt %) as a single portion. The reaction mixture was placed under a hydrogen gas atmosphere (3 cycles of vacuum/nitrogen gas followed by 3 cycles of vacuum/hydrogen gas). Stirring was continued at ambient temperature for 5 h. Anhydrous acetonitrile (6 mL) was added and stirring under a hydrogen gas atmosphere was continued for a further 16 h. The catalyst was removed by filtration over kieselguhr, rinsing the filter cake with dry THF (2×5 mL). The solvent was concentrated in vacuo to afford the title compound (66 mg, 65%) as a pale grey oil. HPLC-MS (method 4): (M−H)⁻ m/z 260, RT 3.13 minutes.

Intermediate 67

4-(Bicyclo[3.2.1]octan-3-ylidene)-2-(2-methylpyrazol-3-yl)oxazol-5-one

Titanium tetrachloride in DCM (1M, 4.8 mL, 4.80 mmol) was added to anhydrous THF (9 mL) at −10° C. A solution of Intermediate 37 (200 mg, 1.21 mmol) in anhydrous THF (1.5 mL) and a solution of bicyclo[3.2.1]octan-3-one (301 mg, 2.42 mmol) in anhydrous THF (1.5 mL) were added portionwise sequentially. The reaction mixture was stirred at 0° C. for 20 minutes, then anhydrous pyridine (0.784 mL, 9.69 mmol) was added at 0° C. over 30 minutes. The reaction mixture was stirred at 0° C. for 2 h, and at ambient temperature for a further 16 h, then quenched by addition of saturated aqueous ammonium chloride solution (20 mL). Stirring was continued for a further 10 minutes, then the solution was extracted with ethyl acetate (2×40 mL). The organic extracts were combined and washed with brine (20 mL), then dried over anhydrous sodium sulfate and filtered. The solvent was removed in vacuo. The residue was purified by chromatography, using a gradient of ethyl acetate in heptane (5-40%), to afford the title compound (261 mg, 79%) as a yellow solid. $\delta_H$ (250 MHz, CDCl$_3$) 7.53 (d, J 2.1 Hz, 1H), 6.86 (d, J 2.1 Hz, 1H), 4.27 (s, 3H), 3.75-3.64 (m, 1H), 3.35-3.24 (m, 1H), 2.56-2.46 (m, 2H), 2.38 (t, J 16.2 Hz, 2H), 1.77 (t, J 11.4 Hz, 2H), 1.71-1.62 (m, 2H), 1.49-1.36 (m, 2H). HPLC-MS (method 4): MH+ m/z 272, RT 3.15 minutes.

Intermediate 68

4-(Bicyclo[3.2.1]octan-3-yl)-2-(2-methylpyrazol-3-yl)-4H-oxazol-5-one

To a stirred solution of Intermediate 67 (200 mg, 0.74 mmol) in anhydrous acetonitrile (10 mL) was added 10% palladium on charcoal (50% wet, 40 mg, 20 wt %) as a single portion. The reaction mixture was placed under a hydrogen gas atmosphere. Stirring was continued at ambient temperature for 6 h. The catalyst was removed by filtration over kieselguhr, rinsing the filter cake with dry acetonitrile (2×5 mL). The solvent was concentrated in vacuo to afford the title compound (200 mg, 84%) as a pale grey oil. $\delta_H$ (250 MHz, CDCl$_3$) 7.53 (d, J 2.1 Hz, 1H), 6.79 (d, J 2.0 Hz, 1H), 4.33 (d, J 6.6 Hz, 1H), 4.24 (s, 3H), 2.34-2.24 (m, 2H), 2.23-2.02 (m, 3H), 1.95-1.83 (m, 1H), 1.77-1.64 (m, 3H), 1.47-1.35 (m, 3H), 1.21-1.13 (m, 1H). HPLC-MS (method 4): (M–H)⁻ m/z 272, RT 3.13 minutes.

Intermediate 69

4-(5-Chloro-7-bicyclo[4.2.0]octa-1(6),2,4-trienylidene)-2-(2-methylpyrazol-3-yl)oxazol-5-one Titanium tetrachloride in DCM (1M, 4.8 mL, 4.80 mmol) was added to anhydrous THF (9 mL) at −10° C. A solution of Intermediate 37 (200 mg, 1.21 mmol) in anhydrous THF (1.5 mL) and a solution of 5-chlorobicyclo[4.2.0]octa-1,3,5-trien-7-one (369 mg, 2.42 mmol) in anhydrous THF (1.5 mL) were added portionwise sequentially. The reaction mixture was stirred at 0° C. for 20 minutes, then anhydrous pyridine (0.784 mL, 9.69 mmol) was added at 0° C. over 30 minutes. The reaction mixture was stirred at 0° C. for 2 h, and at ambient temperature for a further 16 h, then quenched by the addition of saturated aqueous ammonium chloride solution (20 mL). Stirring was continued for a further 10 minutes, then the solution was extracted with ethyl acetate (2×40 mL). The organic extracts were combined and washed with brine (20 mL), then dried over anhydrous sodium sulfate and filtered. The solvent was removed in vacuo. The residue was purified by automated chromatography, using a gradient of ethyl acetate in heptane (5-50%), to afford the title compound (159 mg, 44%) as a yellow solid. $\delta_H$ (250 MHz, CDCl$_3$) 7.57 (d, J 2.1 Hz, 1H), 7.39 (dd, J 8.2, 6.8 Hz, 1H), 7.33 (d, J 7.5 Hz, 1H), 7.20 (d, J 6.8 Hz, 1H), 6.92 (d, J 2.1 Hz, 1H), 4.38 (s, 3H), 4.09 (s, 2H). HPLC-MS (method 4): MH+ m/z 300, RT 3.18 minutes.

Intermediate 70

4-(2,3-Dimethylcyclobutylidene)-2-(2-methylpyrazol-3-yl)oxazol-5-one

Titanium tetrachloride in DCM (1M, 4.8 mL, 4.80 mmol) was added to anhydrous THF (9 mL) at −10° C. A solution of Intermediate 37 (200 mg, 1.21 mmol) in anhydrous THF (1.5 mL) and a solution of 2,3-dimethylcyclobutan-1-one (238 mg, 2.42 mmol) in anhydrous THF (1.5 mL) were added portionwise sequentially. The reaction mixture was stirred at 0° C. for 20 minutes, then anhydrous pyridine (0.784 mL, 9.69 mmol) was added at 0° C. over 30 minutes. The reaction mixture was stirred at 0° C. for 2 h, and at ambient temperature for a further 16 h, then quenched by the addition of saturated aqueous ammonium chloride solution (20 mL). Stirring was continued for a further 10 minutes, then the solution was extracted with ethyl acetate (2×40 mL). The organic extracts were combined and washed with brine (20 mL), then dried over anhydrous sodium sulfate and filtered. The solvent was removed in vacuo. The residue was purified by automated chromatography, using a gradient of ethyl acetate in heptane (5-40%) to afford the title compound (mixture of stereoisomers; 173 mg, 58%) as a yellow solid. HPLC-MS (method 4): MH+ m/z 246, RT 2.90 minutes (49%) and RT 2.95 minutes (51%).

Intermediate 71 tert-Butyl 6-bromo-4-fluoro-2-oxoindoline-1-carboxylate

Di-tert-butyl dicarbonate (853.88 mg, 3.91 mmol) in THF (8 mL) was added dropwise to a stirred suspension of 6-bromo-4-fluoroindolin-2-one (900 mg, 3.91 mmol) and sodium hydrogen carbonate (1.15 g, 13.69 mmol) in THF (10 mL). The reaction mixture was heated, with stirring, at 50° C. for 4.5 h, then the solid was removed by filtration and the solvent was removed in vacuo. The residue was purified by flash column chromatography, using a gradient of tert-butyl methyl ether in heptane (0-20%), to afford the title compound (1.04 g, 80%) as a yellow solid. $\delta_H$ (500 MHz, CDCl$_3$) 7.86 (s, 1H), 7.07 (dd, J 7.9, 1.5 Hz, 1H), 3.60 (s, 2H), 1.64 (s, 9H). HPLC-MS (method 5): MH+ m/z 328.2, 330.0, RT 2.05 minutes.

Intermediate 72 tert-Butyl 6-bromo-4-fluoro-2-oxospiro[indoline-3,4'-tetrahydropyran]-1-carboxylate A stirred solution of Intermediate 71 (0.8 g, 2.42 mmol) and 1-iodo-2-(2-iodo-ethoxy)ethane (0.38 mL, 2.67 mmol) in anhydrous DMF (16 mL) was cooled to −15° C. and purged with nitrogen for 5 minutes, then caesium carbonate (3.16 g, 9.69 mmol) was added. The reaction mixture was stirred for 2 h, with warming to 20° C. Water (30 mL) was added and the aqueous layer was extracted with tert-butyl methyl ether (3×30 mL). The combined organic layers were washed with water (2×30 mL) and brine (30 mL), then dried over sodium sulfate, filtered and concentrated. The resulting crude material was purified by flash column chromatography, using a gradient of tert-butyl methyl ether in heptane (0-15%), to afford the title compound (927.9 mg, 86%) as a yellow solid. $\delta_H$ (500 MHz, CDCl$_3$) 7.90 (d, J 1.3 Hz, 1H), 7.06 (dd, J 9.1, 1.6 Hz, 1H), 4.26 (t, J 11.8 Hz, 2H), 3.89 (dd, J 11.9, 3.6 Hz, 2H), 2.45-2.33 (m, 2H), 1.75-1.69 (m, 2H), 1.65 (s, 9H). HPLC-MS (method 5): [M+H-BOC]+ m/z 300.0, 302.0, RT 2.11 minutes.

Intermediate 73 tert-Butyl 6-(tert-butoxycarbonylamino)-4-fluoro-2-oxospiro[indoline-3,4'-tetrahydro-pyran]-1-carboxylate Palladium(II) acetate (17 mg, 0.08 mmol) was added to a nitrogen-degassed mixture of Intermediate 72 (476 mg, 1.19 mmol), tert-butyl carbamate (170 mg, 1.45 mmol), XPhos (30 mg, 0.06 mmol) and cesium carbonate (776 mg, 2.38 mmol) in anhydrous toluene (5 mL). The reaction mixture was heated at 90° C. for 3 h. The cooled reaction mixture was filtered through kieselguhr and rinsed with toluene (2×5 mL). The filtrate was concentrated in vacuo. The crude residue was purified by flash column chromatography, using a gradient of tert-butyl methyl ether in heptane (0-20%), to afford the title compound (533 mg, 87%) as a pale brown oil which, on standing, crystallised to an off-white solid. $\delta_H$ (250 MHz, CDCl$_3$) 7.63 (d, J 1.6 Hz, 1H), 7.11 (dd, J 11.8, 1.5 Hz, 1H), 6.56 (s, 1H), 4.25 (t, J 11.5 Hz, 2H), 3.95-3.80 (m, 2H), 2.46-2.26 (m, 2H), 1.72 (d, J 14.6 Hz, 2H), 1.64 (s, 9H), 1.51 (s, 9H). HPLC-MS (method 5): [M−H]⁻ m/z 435.0, RT 2.09 minutes.

Intermediate 74

6-Amino-4-fluorospiro[indoline-3,4'-tetrahydropyran]-2-one

Trifluoroacetic acid (2.72 mL, 33.4 mmol) was added to a solution of Intermediate 73 (86%, 339 mg, 0.67 mmol) in DCM (4.75 mL) at 20° C. The reaction mixture was stirred at 20° C. for 3 h, then quenched with saturated aqueous sodium hydrogen carbonate solution (20 mL) and extracted with DCM (3×15 mL). The organic extracts were combined, filtered through a hydrophobic frit and concentrated in vacuo. The resulting crude material was purified by flash column chromatography, using a gradient of tert-butyl methyl ether in heptane (0-100%) followed by a gradient of MeOH in tert-butyl methyl ether (0-10%). The relevant fractions were combined and concentrated in vacuo to afford the title compound (53.9 mg, 41%) as an off-white solid. $\delta_H$ (500 MHz, DMSO-d$_6$) 10.27 (s, 1H), 5.95 (d, J 1.6 Hz, 1H), 5.88 (dd, J 12.8, 1.6 Hz, 1H), 5.42 (s, 2H), 4.04 (t, J 10.1 Hz, 2H), 3.79-3.69 (m, 2H), 1.93 (ddd, J 14.2, 10.3, 4.4 Hz, 2H), 1.69-1.59 (m, 2H). uPLC-MS (method 1): MH+ m/z 237.1, RT 1.49 minutes.

Intermediate 75

4-(4-Methylcyclohexylidene)-2-(2-methylpyrazol-3-yl)oxazol-5-one

Titanium tetrachloride in DCM (1M, 48 mL, 48.0 mmol) was added to anhydrous THF (90 mL) at −10° C. A solution of Intermediate 37 (2.00 g, 12.10 mmol) in anhydrous THF (15 mL) and a solution of 4-methylcyclohexanone (2.72 g, 24.20 mmol) in anhydrous THF (15 mL) were added portionwise sequentially. The reaction mixture was stirred at 0° C. for 20 minutes, then anhydrous pyridine (7.84 mL, 96.9 mmol) was added at 0° C. over 30 minutes. The reaction mixture was stirred at 0° C. for 2 h, and at 20° C. for a further 16 h, then quenched by the addition of saturated aqueous ammonium chloride solution (200 mL). Stirring was continued for a further 10 minutes, then the solution was extracted with ethyl acetate (2×400 mL). The organic extracts were combined and washed with brine (200 mL), then dried over anhydrous sodium sulfate and filtered. The solvent was removed in vacuo. The residue was purified by flash column chromatography, using a gradient of ethyl acetate in heptane (5-40%), to afford the title compound (2.90 g, 92%) as a pale yellow solid. $\delta_H$ (500 MHz, CDCl$_3$) 7.53 (d, J 2.1 Hz, 1H), 6.86 (d, J 2.1 Hz, 1H), 4.28 (s, 3H), 3.89-3.81 (m, 1H), 3.44-3.36 (m, 1H), 2.30-2.18 (m, 2H), 2.04-1.96 (m, 2H), 1.81-1.71 (m, 1H), 1.28-1.18 (m, 2H), 0.97 (d, J 6.6 Hz, 3H). HPLC-MS (method 19): MH+ m/z 260.2, RT 3.21 minutes.

Intermediate 76

N-{2-[(4-Fluoro-2-oxospiro[indoline-3,4'-tetrahydropyran]-6-yl)amino]-1-(4-methyl-cyclohexylidene)-2-oxoethyl}-2-methylpyrazole-3-carboxamide Acetic acid (0.09 mL, 1.63 mmol) was added to a stirred solution of Intermediate 74 (73.3 mg, 0.11 mmol) and Intermediate 75 (39 μL, 0.15 mmol) in anhydrous THF (1 mL). The reaction mixture was stirred at 60° C. for 18 h under nitrogen in a sealed tube, then the solvent was removed in vacuo. The residue was purified by flash column chromatography, using a gradient of tert-butyl methyl ether in heptane (0-100%) followed by a gradient of MeOH in tert-butyl methyl ether (0-20%), to afford the title compound (73 mg, 91%) as an off-white solid. $\delta_H$ (500 MHz, CDCl$_3$) 9.33 (s, 1H), 8.56 (s, 1H), 8.18 (s, 1H), 7.72 (s, 1H), 7.44 (d, J 2.1 Hz, 1H), 6.82 (d, J 2.1 Hz, 1H), 6.54 (d, J 9.3 Hz, 1H), 4.26 (t, J 10.2 Hz, 2H), 4.16 (s, 3H), 3.94-3.87 (m, 2H), 2.83 (d, J 12.6 Hz, 1H), 2.73-2.67 (m, 1H), 2.30-2.19 (m, 2H), 2.16-2.05 (m, 1H), 2.04-1.94 (m, 1H), 1.90-1.82 (m, 2H), 1.79-1.71 (m, 2H), 1.67-1.61 (m, 1H), 1.16-1.10 (m, 2H), 0.92 (d, J 6.5 Hz, 3H). uPLC-MS (method 1): MH+ m/z 496.2, RT 1.78 minutes.

Intermediate 77 tert-Butyl N-{(1S)-1-cyclohexyl-2-oxo-2-[(2-oxospiro[indoline-3,4'-tetrahydropyran]-6-yl)amino]ethyl}carbamate DIPEA (0.15 mL, 0.92 mmol) was added to a stirred solution of Intermediate 2 (100 mg, 0.46 mmol), (2S)-[(tert-butoxycarbonyl)amino](cyclohexyl)ethanoic acid (118 mg, 0.46 mmol) and HATU (209 mg, 0.55 mmol) in anhydrous THF (2.5 mL) under a nitrogen atmosphere. The reaction mixture was stirred at 20° C. for 72 h, then water (5 mL) and saturated aqueous sodium hydrogen carbonate solution (2.5 mL) were added. Stirring was continued for a further 10 minutes. The milky reaction mixture was extracted with ethyl acetate (2×10 mL). The organic extracts were combined and washed with brine (10 mL), then dried over anhydrous sodium sulfate and filtered. The solvent was removed in vacuo. The residue was purified by flash column chromatography, using a gradient of ethyl acetate in heptane (5-100%), to afford the title compound (166 mg, 77%) as a colourless glass. $\delta_H$ (250 MHz, DMSO-d$_6$) 10.38 (s, 1H), 9.95 (s, 1H), 7.42 (d, J 8.1 Hz, 1H), 7.38 (d, J 1.8 Hz, 1H), 7.07 (dd, J 8.2, 1.7 Hz, 1H), 6.84 (d, J 8.7 Hz, 1H), 4.08-3.96 (m, 2H), 3.95-3.86 (m, 1H), 3.85-3.72 (m, 2H), 1.81-1.50

(m, 10H), 1.38 (s, 9H), 1.18-0.96 (m, 5H). HPLC-MS (method 5): MH+ m/z 458.2, RT 1.84 minutes.

Intermediate 78

(2S)-2-Amino-2-cyclohexyl-N-(2-oxospiro[indoline-3,4'-tetrahydropyran]-6-yl)acetamide Trifluoroacetic acid (0.40 mL, 5.25 mmol) was added dropwise to a stirred suspension of Intermediate 77 (165 mg, 0.35 mmol) in DCM (1.4 mL). The reaction mixture was stirred at 20° C. for 2.5 h. DCM (10 mL) and water (5 mL) were added, followed by 4M aqueous sodium hydroxide solution (1.4 mL), and stirring was continued for 5 minutes. The organic phase was collected, and the aqueous phase was extracted further with DCM-isopropanol mixture (2:1, 2×10 mL). The organic phases were combined and stirred with brine (5 mL). The organic phase was separated using a hydrophobic frit, then the solvent was concentrated in vacuo, to afford the title compound (111 mg, 79%) as a clear glassy solid. $\delta_H$ (250 MHz, DMSO-$d_6$) 10.38 (s, 1H), 9.81 (br s, 1H), 7.48-7.36 (m, 2H), 7.06 (dd, J 8.2, 1.9 Hz, 1H), 4.07-3.93 (m, 2H), 3.87-3.71 (m, 2H), 3.08 (d, J 5.7 Hz, 1H), 1.84-1.42 (m, 10H), 1.25-1.07 (m, 5H). HPLC-MS (method 5): MH+ m/z 358.2, RT 1.45 minutes.

Intermediate 79

2-Isopropyl-N-[(1S)-1-(4-methylcyclohexyl)-2-oxo-2-({2-oxo-1-[2-(trimethylsilyl)-ethoxymethyl]spiro[pyrrolo[3,2-c]pyridine-3,4'-tetrahydropyran]-6-yl}amino)ethyl]-pyrazole-3-carboxamide (Trans Isomer)

Prepared from Intermediate 107 (150 mg, 0.26 mmol) and 2-isopropylpyrazole-3-carboxylic acid (61.1 mg, 0.4 mmol) in accordance with Procedure A, and purified by flash column chromatography, using a gradient of tert-butyl methyl ether in heptane (0-100%), to give the title compound (115.4 mg, 57%) as a white powder. $\delta_H$ (500 MHz, DMSO-$d_6$) 10.74 (s, 1H), 8.60 (s, 1H), 8.53 (d, J 8.0 Hz, 1H), 8.05 (s, 1H), 7.61 (d, J 1.9 Hz, 1H), 7.04 (d, J 2.0 Hz, 1H), 5.54-5.44 (m, 1H), 5.19 (s, 2H), 4.60 (t, J 8.2 Hz, 1H), 4.15-4.08 (m, 2H), 3.96 (t, J 8.0 Hz, 2H), 3.64-3.57 (m, 2H), 1.99-1.86 (m, 4H), 1.86-1.74 (m, 4H), 1.71-1.61 (m, 1H), 1.50-1.29 (m, 9H), 1.21-1.10 (m, 1H), 1.02-0.90 (m, 6H), 0.00 (s, 9H). HPLC-MS (method 3): MH+ m/z 639.2, RT 1.45 minutes.

Intermediate 80

(2S)-2-{[6-(Difluoromethyl)pyridazin-3-yl]amino}-2-(4-methylcyclohexyl)-N-{2-oxo-1-[2-(trimethylsilyl)methoxymethyl]spiro[pyrrolo[3,2-c]pyridine-3,4'-tetrahydropyran]-6-yl}-acetamide (Trans Isomer)

Intermediate 107 (100 mg, 0.18 mmol) was dissolved in anhydrous 1,4-dioxane (0.5 mL) and DIPEA (0.09 mL, 0.53 mmol) and treated with 3-chloro-6-(difluoromethyl)-pyridazine (50 mg, 0.3 mmol). The reaction mixture was stirred at 140° C. for 18 h, then cooled to 20° C. and quenched with saturated aqueous sodium hydrogen carbonate solution (10 mL). The aqueous layer was extracted with DCM (3×20 mL). The organic extracts were combined and washed with brine (10 mL), then dried over sodium sulfate, filtered and concentrated in vacuo. The residue was purified by flash column chromatography, using a gradient of tert-butyl methyl ether in heptane (0-100%) followed by a gradient of MeOH in tert-butyl methyl ether (0-20%), to afford the title compound (113.3 mg, 33%) as an orange oil. HPLC-MS (method 5): MH+ m/z 631.0, RT 2.16 minutes.

Intermediate 81

6-Chloro-1-{[2-(trimethylsilyl)ethoxy]methyl}-1H-pyrrolo[3,2-c]pyridine

To a solution of 6-chloro-1H-pyrrolo[3,2-c]pyridine (5.00 g, 32.8 mmol) in DMF (20 mL) was added NaH (1.57 g, 39.3 mmol) at 0° C. The reaction mixture was stirred for 1 h, then SEM-Cl (6.56 g, 39.3 mmol) was added at 0° C. The reaction mixture was stirred at room temperature for 1 h, then quenched with $H_2O$ (100 mL) and extracted with DCM (3×100 mL). The organic layer was separated and washed with brine (3×100 mL), then dried over anhydrous $Na_2SO_4$ and concentrated in vacuo. The crude material was purified by column chromatography (10-15% EtOAc in hexanes) to afford the title compound (7.00 g, 75%) as a yellow oil. $\delta_H$ (400 MHz, $CD_3OD$) −0.07 (s, 9H), 0.87 (t, J 7.83 Hz, 2H), 3.52 (t, J 7.83 Hz, 2H), 5.57 (s, 2H), 6.71 (d, J 2.93 Hz, 1H), 7.50 (d, J 3.42 Hz, 1H), 7.64 (s, 1H), 8.61 (s, 1H). HPLC-MS (method 6): MH+ m/z 283.3, RT 2.12 minutes.

Intermediate 82

3,3-Dibromo-6-chloro-1-[2-(trimethylsilyl)ethoxymethyl]pyrrolo[3,2-c]pyridin-2-one To a solution of Intermediate 81 (3.50 g, 12.4 mmol) in 1,4-dioxane (50 mL) was added pyridinium tribromide (19.8 g, 61.9 mmol) portionwise at 0° C. The reaction mixture was stirred at room temperature for 1 h, then quenched with $H_2O$ (100 mL), stirred for 10 minutes and extracted with EtOAc (2×100 mL). The organic layer was separated and washed with brine (2×100 mL), then dried over anhydrous $Na_2SO_4$ and concentrated in vacuo, to afford the title compound (5.00 g, 78%) as a red oil, which was utilised without further purification. $\delta_H$ (400 MHz, $CDCl_3$) 0.00 (s, 9H), 0.92-1.00 (m, 2H), 3.59-3.65 (m, 2H), 5.31 (s, 2H), 7.33-7.37 (m, 1H), 8.75 (s, 1H). HPLC-MS (method 6): MH+ m/z 457.0, RT 2.40 minutes.

Intermediate 83

6-Chloro-1-{[2-(trimethylsilyl)ethoxy]methyl}-1,3-dihydro-2H-pyrrolo[3,2-c]pyridin-2-one To a solution of Intermediate 82 (5.00 g, 10.9 mmol) in THF (70 mL) was added Zn (7.16 g, 109 mmol) at 0° C., followed by dropwise addition of saturated $NH_4Cl$ solution (20 mL). The reaction mixture was stirred at room temperature for 3 h, then diluted with EtOAc (300 mL) and filtered through a pad of Celite. The filtrate was washed with water (2×100 mL), then dried over anhydrous $Na_2SO_4$ and concentrated in vacuo. The crude material was purified by column chromatography (25-30% EtOAc in hexanes) to afford the title compound (2.00 g, 45%) as a pale yellow oil. $\delta_H$ (400 MHz, $CD_3OD$) 0.01 (s, 9H), 0.90-0.98 (m, 2H), 3.57-3.67 (m, 2H), 3.72 (s, 2H), 5.17 (s, 2H), 7.18 (s, 1H), 8.14 (s, 1H). HPLC-MS (method 6): MH+ m/z 299.2, RT 2.08 minutes.

Intermediate 84

6'-Chloro-1'-{[2-(trimethylsilyl)ethoxy]methyl}-2,3,5,6-tetrahydrospiro[pyran-4,3'-pyrrolo[3,2-c]pyridin]-2'(1'H)-one To a solution of Intermediate 83 (2.00 g, 6.69 mmol) in acetone (30 mL) was added $Cs_2CO_3$ (6.54 g, 20.1 mmol) at 0° C. The reaction mixture was stirred at 0° C. for 10 minutes, then 1-iodo-2-(2-iodoethoxy)ethane (4.36 g, 13.4 mmol) was added at 0° C. The reaction mixture was stirred at room temperature for 6 h, then concentrated in vacuo. The residue was diluted with EtOAc (500 mL) and washed with water (2×200 mL). The organic layer was separated and washed with brine (200 mL), then dried over anhydrous $Na_2SO_4$ and concentrated in vacuo. The crude material was purified by column chromatography (15-20% EtOAc in hexanes) to afford the title compound (1.20 g, 48%) as an off-white solid. $\delta_H$ (400 MHz, DMSO-$d_6$) −0.08 (s, 9H), 0.84 (t, J 7.83 Hz, 2H), 1.74-1.85 (m, 4H), 3.50 (t, J 8.07 Hz, 2H), 3.80-3.86 (m, 2H), 3.96-4.06 (m, 2H), 5.13 (s, 2H), 7.31 (s, 1H), 8.58 (s, 1H). HPLC-MS (method 6): MH+ m/z 369.0, RT 3.18 minutes.

Intermediate 85

N-(2-Amino-1-cyclooctyl-2-oxoethyl)-2-methylpyrazole-3-carboxamide

To a solution of Intermediate 13 (0.30 g, 1.02 mmol) in DCM (15 mL) were added HATU (0.58 g, 1.53 mmol) and $NH_4Cl$ (0.22 g, 4.09 mmol). The reaction mixture was stirred at 0° C. for 10 minutes, followed by the addition of DIPEA (0.55 mL, 3.07 mmol). The reaction mixture was stirred at room temperature for 16 h, then diluted with DCM (100 mL), and washed with $H_2O$ (2×50 mL) and brine (2×25 mL). The organic layer was separated, then dried over anhydrous $Na_2SO_4$ and concentrated in vacuo. The crude material was purified by column chromatography (60-70% EtOAc in hexanes) to afford the title compound (0.23 g, 71%) as an off-white solid. $\delta_H$ (400 MHz, DMSO-$d_6$) 1.28-1.37 (m, 3H), 1.40-1.49 (m, 4H), 1.51-1.67 (m, 7H), 2.02-2.10 (m, 1H), 4.02 (s, 3H), 4.27 (t, J 8.80 Hz, 1H), 6.99 (d, J 1.96 Hz, 1H), 7.06 (br s, 1H), 7.43 (d, J 1.96 Hz, 1H), 7.50 (br s, 1H), 8.19 (d, J 9.29 Hz, 1H). HPLC-MS (method 6): MH+ m/z 293.1, RT 1.66 minutes.

Intermediate 86

N-[1-Cyclooctyl-2-oxo-2-({2-oxo-1-[2-(trimethylsilyl)ethoxymethyl]spiro[pyrrolo[3,2-c]pyridine-3,4'-tetrahydropyran]-6-yl}amino)ethyl]-2-methylpyrazole-3-carboxamide To a solution of Intermediate 85 (0.16 g, 0.54 mmol) in 1,4-dioxane (5 mL) were added Intermediate 84 (0.20 g, 0.54 mmol) and $Cs_2CO_3$ (0.53 g, 1.63 mmol). The reaction mixture was purged with argon for 10 minutes, then $Pd_2(dba)_3$ (0.05 g, 0.05 mmol) and Xantphos (0.03 g, 0.05 mmol) were added. The reaction mixture was heated at 100° C. for 16 h, then diluted with EtOAc (30 mL), filtered through a pad of Celite and washed with water (2×20 mL). The organic layer was separated, dried over anhydrous $Na_2SO_4$ and concentrated in vacuo. The crude material was purified by column chromatography (60-70% EtOAc in hexanes) to afford the title compound (0.08 g, 23%) as a light yellow solid. $\delta_H$ (400 MHz, DMSO-$d_6$) −0.11 (s, 9H), 0.80-0.90 (m, 2H), 1.38-1.59 (m, 10H), 1.62-1.77 (m, 5H), 1.78-1.87 (m, 2H), 2.16-2.19 (m, 1H), 3.49 (t, J 7.58 Hz, 2H), 3.80-3.91 (m, 3H), 3.97-4.00 (m, 1H), 4.02 (s, 4H), 4.59 (t, J 8.31 Hz, 1H), 5.07 (s, 2H), 7.02 (s, 1H), 7.46 (s, 1H), 7.93 (s, 1H), 8.42 (d, J 8.31 Hz, 1H), 8.50 (s, 1H), 10.71 (s, 1H). HPLC-MS (method 6): MH+ m/z 625.3, RT 2.37 minutes.

Intermediate 87

Diethyl 2-(5-bromo-3-nitropyridin-2-yl)malonate

To a solution of diethyl malonate (25.3 g, 158 mmol) in DMF (45 mL) was added $K_2CO_3$ (43.6 g, 316 mmol) at 0° C. The mixture was stirred for 10 minutes, then 5-bromo-2-chloro-3-nitropyridine (25.0 g, 105 mmol) was added. The reaction mixture was stirred at room temperature for 16 h, then diluted with EtOAc (250 mL) and washed with water (3×250 mL). The organic layer was separated, dried over anhydrous $Na_2SO_4$ and concentrated in vacuo. The crude material was purified by column chromatography (20% EtOAc in hexanes) to afford the title compound (26.0 g, 68%) as an off-white solid. $\delta_H$ (400 MHz, DMSO-$d_6$) 1.19 (t, J 6.85 Hz, 6H), 4.16-4.27 (m, 4H), 5.58 (s, 1H), 8.89 (s, 1H), 9.09 (s, 1H). HPLC-MS (method 6): MH+ m/z 360.9, RT 2.04 minutes.

Intermediate 88

Ethyl 2-(5-bromo-3-nitropyridin-2-yl)acetate

To a solution of Intermediate 87 (26.0 g, 72.0 mmol) in DMSO:water (1:1, 90 mL) was added lithium chloride (4.58 g, 108 mmol). The reaction mixture was heated at 100° C. for 16 h, then diluted with $H_2O$ (110 mL) and extracted with EtOAc (3×110 mL). The organic layer was separated, dried over anhydrous $Na_2SO_4$ and concentrated in vacuo. The crude residue was purified by column chromatography (10% EtOAc in hexanes) to afford the title compound (14.0 g, 67%) as a white solid. $\delta_H$ (400 MHz, DMSO-$d_6$) 1.16-1.21 (m, 3H), 4.07-4.11 (m, 2H), 4.21 (s, 2H), 8.82 (d, J 2.45 Hz, 1H), 9.04 (d, J 1.96 Hz, 1H). HPLC-MS (method 6): MH+ m/z 290.8, RT 1.90 minutes.

Intermediate 89

6-Bromo-1,3-dihydro-2H-pyrrolo[3,2-b]pyridin-2-one

To a solution of Intermediate 88 (10.0 g, 34.6 mmol) in acetic acid (200 mL) was added iron (9.51 g, 173 mmol). The reaction mixture was stirred at 60° C. for 4 h, then diluted with EtOAc (200 mL), stirred for 15 minutes, filtered through a pad of Celite, and washed with EtOAc (3×200 mL). The organic layer was separated, dried over anhydrous $Na_2SO_4$ and concentrated in vacuo. The crude residue was dissolved in 5% MeOH in EtOAc (30 mL) and adsorbed onto Fluorosil. The resulting slurry was filtered through a Celite pad and washed with 5% MeOH in EtOAc (3×200 mL). The organic layer was dried over anhydrous $Na_2SO_4$ and concentrated in vacuo, to afford the title compound (5.00 g, 68%) as a brown solid. $\delta_H$ (400 MHz, DMSO-$d_6$) 3.57 (s, 2H), 7.30 (s, 1H), 8.17 (s, 1H), 10.67 (br s, 1H). HPLC-MS (method 6): MH+ m/z 213.0, RT 1.31 minutes.

Intermediate 90

6'-Bromo-2,3,5,6-tetrahydrospiro[pyran-4,3'-pyrrolo[3,2-b]pyridin]-2'(1'H)-one To a solution of Intermediate 89 (2.00 g, 9.39 mmol) in DMSO (20 mL) was added $Cs_2CO_3$ (3.05 g, 9.39 mmol) at 0° C. The reaction mixture was stirred for 30 minutes, then 1-iodo-2-(2-iodoethoxy)ethane (3.05 g, 9.39 mmol) was added. The reaction mixture was stirred at room temperature for 5 h, then quenched with water (50 mL) and extracted with EtOAc (3×50 mL). The organic layer was separated, dried over anhydrous $Na_2SO_4$ and concentrated in vacuo. The crude residue was purified by column chromatography (20% EtOAc in hexanes) to afford the title compound (0.45 g, 17%) as a light brown liquid. $\delta_H$ (400 MHz, DMSO-$d_6$) 1.58-1.67 (m, 2H), 1.77-1.83 (m, 2H), 3.85-3.96 (m, 2H), 3.98-4.08 (m, 2H), 7.39 (d, J 1.96 Hz, 1H), 8.25 (d, J 1.96 Hz, 1H), 10.78 (s, 1H). HPLC-MS (method 6): MH+ m/z 283.1, RT 1.54 minutes.

Intermediate 91

6'-Bromo-1'-{[2-(trimethylsilyl)ethoxy]methyl}-2,3,5,6-tetrahydrospiro[pyran-4,3'-pyrrolo[3,2-b]pyridin]-2'(1'H)-one To a solution of Intermediate 90 (0.40 g, 1.41 mmol) in THF (10 mL) was added NaH (0.05 g, 2.12 mmol) at 0° C. The reaction mixture was stirred for 30 minutes, then SEM-Cl (0.35 g, 2.12 mmol) was added. The reaction mixture was stirred at room temperature for 3 h, then diluted with water (50 mL) and extracted with DCM (3×50 mL). The organic layer was separated, washed with $H_2O$ (100 mL) and brine (100 mL), then dried over anhydrous $Na_2SO_4$ and concentrated in vacuo. The crude residue was purified by column chromatography (20% EtOAc in hexanes) to afford the title compound (0.40 g, 43%) as a white solid. HPLC-MS (method 6): MH+ m/z 415.1, RT 2.34 minutes.

Intermediate 92

N-[1-Cyclooctyl-2-oxo-2-({2-oxo-1-[2-(trimethylsilyl)ethoxymethyl]spiro[pyrrolo[3,2-b]pyridine-3,4'-tetrahydropyran]-6-yl}amino)ethyl]-2-methylpyrazole-3-carboxamide To a solution of Intermediate 91 (0.30 g, 0.73 mmol) in tert-butanol (10 mL) were added Intermediate 85 (0.21 g, 0.73 mmol) and $K_2CO_3$ (0.20 g, 1.45 mmol). The reaction mixture was purged with argon for 10 minutes, then $Pd_2$(dba)$_3$ (0.07 g, 0.07 mmol) and XPhos (0.03 g, 0.07 mmol) were added. The reaction mixture was heated at 100° C. for 16 h, then diluted with EtOAc (100 mL) and filtered through a pad of Celite. The filtrate was washed with water (2×50 mL). The organic layer was separated, dried over anhydrous $Na_2SO_4$ and concentrated in vacuo. The crude residue was purified by column chromatography (50-60% EtOAc in hexanes) to afford the title compound (0.16 g, 29%) as a light yellow solid. $\delta_H$ (400 MHz, DMSO-$d_6$) -0.10 (s, 6H), 0.81-0.88 (m, 2H), 1.38-1.48 (m, 4H), 1.50-1.61 (m, 4H), 1.63-1.73 (m, 3H), 1.78-1.86 (m, 2H), 2.69 (s, 3H), 3.15-3.17 (m, 6H), 3.49 (t, J 7.78 Hz, 2H), 3.90-3.98 (m, 2H), 4.03 (s, 2H), 4.07-4.12 (m, 3H), 4.47 (t, J 8.66 Hz, 1H), 5.11 (s, 2H), 7.06 (d, J 2.01 Hz, 1H), 7.46 (d, J 2.01 Hz, 1H), 7.93 (d, J 1.76 Hz, 1H), 8.42 (d, J 1.76 Hz, 1H), 8.57 (d, J 8.28 Hz, 1H), 10.56 (s, 1H). HPLC-MS (method 6): MH+ m/z 625.3, RT 2.34 minutes.

Intermediate 93

2,4-Dichloro-7-{[2-(trimethylsilyl)ethoxy]methyl}-7H-pyrrolo[2,3-d]pyrimidine To a solution of 2,4-dichloropyrrolo[2,3-d]pyrimidine (10.0 g, 53.2 mmol) in DMF (50 mL) was added NaH (1.91 g, 79.8 mmol) at 0° C. The reaction mixture was stirred at 0° C. for 30 minutes, then SEM-Cl (9.30 mL, 79.8 mmol) was added at 0° C. The reaction mixture was stirred at room temperature for 2 h, then quenched with ice water (200 g) and extracted with diethyl ether (3×150 mL). The organic layer was separated, washed with water (100 mL) and brine (100 mL), then dried over anhydrous $Na_2SO_4$ and concentrated in vacuo. The crude residue was purified by column chromatography (0-20% EtOAc in hexanes) to afford the title compound (12.0 g, 71%) as a yellow oil. HPLC-MS (method 6): MH+ m/z 317.9, RT 2.47 minutes.

Intermediate 94

2-[(2-Chloropyrrolo[2,3-d]pyrimidin-7-yl)methoxy]ethyl(trimethyl)silane

To a solution of Intermediate 93 (1.50 g, 4.71 mmol) in EtOH (15 mL) was added 10% palladium on charcoal (0.15 g, 1.41 mmol), followed by triethylamine (3.28 mL, 23.6 mmol). The reaction mixture was stirred at room temperature for 1 h under hydrogen pressure, then filtered through a pad of Celite. The filtrate was concentrated in vacuo. The crude residue was purified by column chromatography (0-20% EtOAc in hexanes) to afford the title compound (0.36 g, 27%) as a yellow oil. $\delta_H$ (400 MHz, DMSO-$d_6$) -0.10 (s, 9H), 0.80-0.88 (m, 2H), 3.52 (t, J 8.07 Hz, 2H), 5.58 (s, 2H), 6.74 (d, J 3.42 Hz, 1H), 7.78 (d, J 3.91 Hz, 1H), 8.97 (s, 1H). HPLC-MS (method 6): MH+ m/z 283.9, RT 2.14 minutes.

Intermediate 95

5,5-Dibromo-2-chloro-7-{[2-(trimethylsilyl)ethoxy]methyl}-5,7-dihydro-6H-pyrrolo[2,3-d]pyrimidin-6-one To a solution of Intermediate 94 (1.00 g, 3.52 mmol) in tert-butanol (10 mL) and water (10 mL) was added NBS (1.88 g, 10.6 mmol) at room temperature. The reaction mixture was stirred at room temperature for 3 h, then diluted with water (50 mL), neutralised with saturated aqueous $NaHCO_3$ solution and extracted with EtOAc (3×50 mL). The organic layer was separated, washed with water (50 mL) and brine (50 mL), then dried over anhydrous $Na_2SO_4$ and concentrated in vacuo, to afford the title compound (2.00 g crude) as an off-white solid, which was utilised without further purification. $\delta_H$ (400 MHz, DMSO-$d_6$) -0.06 (s, 9H), 0.88 (t, J 7.83 Hz, 2H), 3.59-3.67 (m, 2H), 5.13 (s, 2H) 8.97 (s, 1H).

Intermediate 96

2-Chloro-7-{[2-(trimethylsilyl)ethoxy]methyl}-5,7-dihydro-6H-pyrrolo[2,3-d]pyrimidin-6-one To a solution of Intermediate 95 (2.00 g, 4.37 mmol) in THF (20 mL) and acetic acid (5 mL) was added Zn (1.43 g, 21.9 mmol) at 0° C. The reaction mixture was stirred at room temperature for 2 h, then filtered through a pad of Celite. The filtrate was diluted with water (30 mL) and extracted with EtOAc (3×50 mL). The organic layer was separated, washed with water (30 mL), and brine (30 mL), then dried over anhydrous $Na_2SO_4$ and concentrated in vacuo. The crude residue was purified by column chromatography (0-20% EtOAc in hexanes) to afford the title compound (0.93 g, 71%) as a red oil. $\delta_H$ (400 MHz, DMSO-$d_6$) −0.04 (s, 9H), 0.85-0.92 (m, 2H), 3.55-3.64 (m, 2H), 3.77 (s, 2H), 5.03 (s, 2H), 8.35 (s, 1H).

Intermediate 97

2'-Chloro-7'-{[2-(trimethylsilyl)ethoxy]methyl}-2,3,5,6-tetrahydrospiro[pyran-4,5'-pyrrolo[2,3-d]pyrimidin]-6'(7'H)-one To a solution of Intermediate 96 (0.90 g, 3.00 mmol) in DMF (10 mL) was added $Cs_2CO_3$ (2.93 g, 9.01 mmol), followed by 1-bromo-2-(2-bromoethoxy)ethane (1.04 g, 4.50 mmol). The reaction mixture was stirred at room temperature for 4 h, then poured into ice and extracted with EtOAc (3×100 mL). The organic layer was separated, washed with water (100 mL) and brine (100 mL), then dried over anhydrous $Na_2SO_4$ and concentrated in vacuo. The crude residue was purified by column chromatography (0-20% EtOAc in hexanes) to afford the title compound (0.43 g, 38%) as an orange solid. $\delta_H$ (400 MHz, DMSO-$d_6$) −0.06 (s, 9H), 0.87 (t, J 8.07 Hz, 2H), 1.70-1.78 (m, 2H), 1.82-1.95 (m, 2H), 3.55-3.63 (m, 2H), 3.77-3.86 (m, 2H), 3.93-4.00 (m, 2H), 5.05 (s, 2H), 8.85 (s, 1H). HPLC-MS (method 6): MH+ m/z 370.0, RT 2.21 minutes.

Intermediate 98

N-[1-Cyclooctyl-2-oxo-2-({6-oxo-7-[2-(trimethylsilyl)ethoxymethyl]spiro[pyrrolo[2,3-d]-pyrimidine-5,4'-tetrahydropyran]-2-yl}amino)ethyl]-2-methylpyrazole-3-carboxamide To a solution of Intermediate 97 (0.25 g, 0.68 mmol) and Intermediate 85 (0.20 g, 0.68 mmol) in 1,4-dioxane (5 mL) were added $Cs_2CO_3$ (0.44 g, 1.35 mmol), $Pd_2(dba)_3$ (0.06 g, 0.10 mmol) and Xantphos (0.04 g, 0.07 mmol). The reaction mixture was heated at 80° C. for 16 h, then filtered through a pad of Celite. The filtrate was extracted with EtOAc (3×20 mL). The organic layer was separated, washed with water (10 mL) and brine (10 mL), then dried over anhydrous $Na_2SO_4$ and concentrated in vacuo. The crude residue was purified by column chromatography (0-30% EtOAc in hexanes) to afford the title compound (0.26 g, 31%) as an orange solid. $\delta_H$ (400 MHz, DMSO-$d_6$) −0.10 (s, 9H), 0.85-0.88 (m, 2H). 1.43-1.47 (m, 8H), 1.56 (d, J 12.31 Hz, 2H), 1.60-1.74 (m, 6H), 1.85-1.94 (m, 2H), 2.15-2.23 (m, 1H), 3.61 (t, J 7.88 Hz, 2H), 3.83 (t, J 9.35 Hz, 2H), 3.95-3.97 (m, 2H), 4.03 (s, 3H), 4.69-4.74 (m, 1H), 5.07 (s, 2H), 7.03 (d, J 1.97 Hz, 1H), 7.47 (d, J 1.97 Hz, 1H), 8.41 (d, J 8.37 Hz, 1H), 8.77 (s, 1H), 10.81 (s, 1H). HPLC-MS (method 6): MH+ m/z 626.4, RT 2.26 minutes.

Intermediate 99

6-Bromo-1-methylspiro[indoline-3,4'-tetrahydropyran]-2-one

A suspension of 6-bromo-1,2-dihydrospiro[indole-3,4'-oxane]-2-one (555 mg, 1.95 mmol) in DMF (8 mL) was treated with methyl iodide (135 μL, 2.2 mmol), then cooled to 0° C. under a nitrogen atmosphere and treated with sodium hydride (60% dispersion in mineral oil, 80 mg, 2.0 mmol). The resulting mixture was allowed to warm to 20° C. over 2 h, then diluted with water (50 mL) and extracted with EtOAc (2×25 mL). The combined organic extracts were washed with water (2×25 mL) and brine (30 mL), then dried over $MgSO_4$, filtered and concentrated in vacuo, to afford the title compound (550 mg, 94%) as a white solid. $\delta_H$ (400 MHz, DMSO-$d_6$) 7.50 (d, J 7.9 Hz, 1H), 7.28 (d, J 1.8 Hz, 1H), 7.22 (dd, J 7.9, 1.8 Hz, 1H), 4.04 (ddd, J 11.6, 6.9, 4.8 Hz, 2H), 3.85-3.75 (m, 2H), 3.13 (s, 3H), 1.72 (ddd, J 5.8, 4.5, 1.9 Hz, 4H).

Intermediate 100 tert-Butyl N-(1-methyl-2-oxospiro[indoline-3,4'-tetrahydropyran]-6-yl)carbamate

A suspension of Intermediate 99 (550 mg, 1.9 mmol), cesium carbonate (1.3 g, 4 mmol), tert-butyl carbamate (250 mg, 2.1 mmol), XPhos (45 mg, 0.09 mmol) and palladium acetate (25 mg, 0.11 mmol) in toluene (10 mL) was heated at 90° C. under a nitrogen atmosphere for 18 h. The reaction mixture was cooled, then diluted with EtOAc (50 mL) and water (50 mL). The layers were separated and the aqueous layer was extracted with EtOAc (50 mL, then 20 mL). The combined organic phases were washed with brine (40 mL) and dried over $MgSO_4$, then filtered and concentrated in vacuo. The residue was purified by flash column chromatography, using a gradient of ethyl acetate in heptane (0-60%), to afford the title compound (570 mg, 92%) as a white powder. $\delta_H$ (400 MHz, DMSO-$d_6$) 9.42 (s, 1H), 7.43 (d, J 8.1 Hz, 1H), 7.29 (d, J 1.9 Hz, 1H), 6.99 (dd, J 8.1, 1.9 Hz, 1H), 4.04 (m, 2H), 3.81 (ddd, J 11.2, 6.7, 3.9 Hz, 2H), 3.09 (s, 3H), 1.77-1.58 (m, 4H), 1.49 (s, 9H). HPLC-MS (Method 6): MH+ m/z 333, RT 1.93 minutes.

Intermediate 101

6-Amino-1-methylspiro[indoline-3,4'-tetrahydropyran]-2-one

A solution of Intermediate 100 (740 mg, 2.22 mmol) in DCM (10 mL) was cooled to 0° C., then treated with TFA (5 mL). The reaction mixture was stirred under a nitrogen atmosphere for 18 h, then concentrated in vacuo. The residue was applied to an SCX2 ion-exchange cartridge and eluted with methanol, followed by $NH_3$ in methanol (3M), to give the title compound (350 mg, 68%) as a beige waxy solid. $\delta_H$ (400 MHz, DMSO-$d_6$) 7.21-7.12 (m, 1H), 6.26-6.18 (m, 2H), 5.16 (s, 2H), 4.00 (ddd, J 11.2, 7.2, 3.7 Hz, 2H), 3.78 (ddd, J 11.2, 7.2, 3.7 Hz, 2H), 3.04 (s, 3H), 1.70 (ddd, J 13.4, 7.2, 3.7 Hz, 2H), 1.56 (ddd, J 13.5, 7.3, 3.7 Hz, 2H). HPLC-MS (Method 21): MH+ m/z 233, RT 0.57 minutes.

Intermediate 102 tert-Butyl N-{1-cyclooctyl-2-[(1-methyl-2-oxospiro[indoline-3,4'-tetrahydropyran]-6-yl)amino]-2-oxoethyl}carbamate Prepared from Intermediate 101 and Intermediate 33 by a method analogous to that used to prepare Intermediate 34 to give the title compound (quantitative) as a white solid. $\delta_H$ (400 MHz, DMSO-$d_6$) 10.09 (s, 1H), 7.49 (d, J 8.1 Hz, 1H), 7.41 (d, J 1.9 Hz, 1H), 7.22 (dd, J 8.1, 1.9 Hz, 1H), 6.90 (d, J 8.8 Hz, 1H), 4.04 (ddd, J 11.2, 7.3, 3.7 Hz, 2H), 3.96 (t, J 8.4 Hz, 1H), 3.82 (ddd, J 11.1, 6.7, 4.0 Hz, 2H), 3.10 (s, 3H), 1.95 (br s, 1H), 1.77-1.25 (m, 27H). HPLC-MS (Method 6): MH+ m/z 500, RT 2.58 minutes.

Intermediate 103

2-Amino-2-cyclooctyl-N-(1-methyl-2-oxospiro[indoline-3,4'-tetrahydropyran]-6-yl)-acetamide; hydrochloride Intermediate 102 (50 mg, 0.10 mmol) was dissolved in methanol (1 mL) and HCl (4M in 1,4-dioxane, 0.25 mL, 1.00 mmol) was added. The reaction mixture was stirred at 20° C. for 48 h, then concentrated in vacuo, to afford the title compound (43 mg, quantitative) as a pink oil, which was utilised without further purification. HPLC-MS (method 7): MH+ m/z 400, RT 1.21 minutes.

Intermediate 104 tert-Butyl N-{1-(4-methylcyclohexyl)-2-oxo-2-[(2-oxospiro[indoline-3,4'-tetrahydro-pyran]-6-yl)amino]ethyl}carbamate Prepared from Intermediate 2 (2.4 g, 11.1 mmol) and 2-(tert-butoxycarbonyl-amino)-2-(4-methylcyclohexyl)acetic acid (3.6 g, 13.26 mmol) by a method analogous to that used to prepare Intermediate 49 to give the title compound (4.3 g, 69%) as a white solid. $\delta_H$ (400 MHz, DMSO-$d_6$) 10.39 (s, 1H), 10.06-9.84 (m, 1H), 7.48-7.21 (m, 2H), 7.08 (td, J 8.8, 8.2, 1.9 Hz, 1H), 6.88 (m, 1H), 4.15-3.95 (m, 2H), 3.95-3.66 (m, 3H), 1.98-1.43 (m, 9H), 1.38 (s, 14H), 1.01-0.65 (m, 3H). HPLC-MS (method 7): [M+2H-$^t$Bu]+ m/z 416, RT 2.40 minutes.

Intermediate 105

2-Amino-2-(4-methylcyclohexyl)-N-(2-oxospiro[indoline-3,4'-tetrahydropyran]-6-yl)-acetamide Prepared from Intermediate 104 (2.11 g, 4.5 mmol) by a method analogous to that used to prepare Intermediate 50 to give the title compound (1.53 g, 92%) as a white solid. HPLC-MS (Method 7): MH+ m/z 372, RT 1.11 minutes.

Intermediate 106 tert-Butyl N-[(1S)-1-(4-methylcyclohexyl)-2-oxo-2-({2-oxo-1-[2-(trimethylsilyl)ethoxy-methyl]spiro[pyrrolo[3,2-c]pyridine-3,4'-tetrahydropyran]-6-yl}amino)ethyl]carbamate (Trans Isomer)

Prepared from Intermediate 57 (2.7 g, 7.74 mmol) and Intermediate 48 (2 g, 7.37 mmol) by a method analogous to that used to prepare Intermediate 49 to give the title compound (4.2 g, 95%) as a white solid. $\delta_H$ (300 MHz, DMSO-$d_6$) 10.41 (s, 1H), 8.51 (s, 1H), 7.93 (s, 1H), 6.96 (d, J 9.2 Hz, 1H), 5.08 (s, 2H), 3.85 (t, J 8.5 Hz, 2H), 3.50 (t, J 7.8 Hz, 2H), 2.00 (s, 1H), 1.90-1.43 (m, 9H), 1.38 (m, 9H), 1.18 (m, 4H), 0.85 (m, 8H), −0.09 (s, 9H). HPLC (method 6): MH+ m/z 603, RT 1.55 minutes.

Intermediate 107

(2S)-2-Amino-2-(4-methylcyclohexyl)-N-{2-oxo-1-[2-(trimethylsilyl)ethoxymethyl]-spiro[pyrrolo[3,2-c]pyridine-3,4'-tetrahydropyran]-6-yl}acetamide; hydrochloride (Trans Isomer)

To a solution of Intermediate 106 (4.2 g, 7.0 mmol) dissolved in methanol (50 mL) was added HCl (4M in 1,4-dioxane, 17 mL, 68 mmol) at 20° C. The reaction mixture was stirred for 18 h, then concentrated in vacuo, to afford the title compound (3.74 g, 100%) as a light pink solid, which was utilised without further purification. $\delta_H$ (300 MHz, DMSO-$d_6$) 11.19 (s, 1H), 8.55 (s, 1H), 8.40 (s, 2H), 7.87 (s, 1H), 5.19-5.02 (m, 2H), 4.08-3.97 (m, 2H), 3.96-3.79 (m, 3H), 3.61-3.41 (m, 2H), 1.90-1.55 (m, 8H), 1.32-0.97 (m, 3H), 0.96-0.75 (m, 8H), −0.08 (s, 9H). HPLC-MS (method 6): MH+ m/z 503, RT 1.32 minutes.

Intermediate 108

3-Ethyl-N-[(1S)-1-(4-methylcyclohexyl)-2-oxo-2-({2-oxo-1-[2-(trimethylsilyl)ethoxy-methyl]spiro[pyrrolo[3,2-c]pyridine-3,4'-tetrahydropyran]-6-yl}amino)ethyl]isoxazole-4-carboxamide (Trans Isomer)

Prepared from Intermediate 107 (2.57 g, 4.77 mmol) and 3-ethylisoxazole-4-carboxylic acid (850 mg, 5.72 mmol) in accordance with Procedure A, and purified by flash column chromatography using a gradient of 0-100% ethyl acetate in hexanes, to give the title compound (2.70 g, 91%) as an off-white solid. $\delta_H$ (300 MHz, DMSO-$d_6$) 10.68 (s, 1H), 9.39 (s, 1H), 8.50 (d, J 0.7 Hz, 1H), 8.40 (d, J 7.9 Hz, 1H), 7.95 (s, 1H), 5.11-5.04 (m, 2H), 4.54 (m, 1H), 4.15-3.99 (m, 2H), 3.90-3.77 (m, 2H), 3.55-3.43 (m, 2H), 3.20-3.12 (m, 2H), 2.80-2.74 (m, 2H), 1.90-1.49 (m, 9H), 1.27-1.06 (m, 6H), 0.95-0.73 (m, 5H), −0.11 (s, 9H). HPLC-MS (method 7): MH+ m/z 626, RT 1.65 minutes.

Intermediate 109

2-Ethyl-N-[(1S)-1-(4-methylcyclohexyl)-2-oxo-2-({2-oxo-1-[2-(trimethylsilyl)ethoxy-methyl]spiro[pyrrolo[3,2-c]pyridine-3,4'-tetrahydropyran]-6-yl}amino)ethyl]pyrazole-3-carboxamide (Trans Isomer)

Prepared from Intermediate 107 (2.56 g, 4.75 mmol) and 1-ethyl-1H-pyrazole-5-carboxylic acid (840 mg, 5.69 mmol) in accordance with Procedure A, and purified by flash column chromatography using a gradient of 0-100% ethyl acetate in hexanes, to give the title compound (2.73 g, 92%) as an off-white solid. $\delta_H$ (300 MHz, DMSO-$d_6$) 10.66 (s, 1H), 8.54-8.40 (m, 2H), 7.94 (s, 1H), 7.49 (d, J 2.0 Hz, 1H), 7.00 (d, J 2.0 Hz, 1H), 5.08 (s, 2H), 4.50-4.38 (m, 2H), 4.06-3.94 (m, 1H), 3.90-3.79 (m, 2H), 3.49 (t, J 7.8 Hz, 2H), 1.90-1.51 (m, 10H), 1.35-1.24 (m, 5H), 0.92-0.78 (m, 9H), −0.11 (s, 9H). HPLC-MS (method 6): MH+ m/z 625, RT 1.37 minutes.

Intermediate 110

3-Cyclopropyl-N-[(1S)-1-(4-methylcyclohexyl)-2-oxo-2-({2-oxo-1-[2-(trimethylsilyl)-ethoxymethyl]spiro[pyrrolo[3,2-c]pyridine-3,4'-tetrahydropyran]-6-yl}amino)ethyl]-isoxazole-4-carboxamide (Trans Isomer)

Prepared from Intermediate 107 (100 mg, 0.19 mmol) and 3-cyclopropyl-isoxazole-4-carboxylic acid (36 mg, 0.22 mmol) in accordance with Procedure A, and purified by flash column chromatography using a gradient of 0-100% ethyl acetate in hexanes, to give the title compound (100 mg, 85%) as a clear oil, which was utilised without further purification. HPLC-MS (method 7): MH+ m/z 638, RT 1.57 minutes.

Intermediate 111 (Procedure E)

Cyclobutyl N-[(1S)-1-(4-methylcyclohexyl)-2-oxo-2-({2-oxo-1-[2-(trimethylsilyl)ethoxy-methyl]spiro [pyrrolo[3,2-c]pyridine-3,4'-tetrahydropyran]-6-yl}amino)ethyl]carbamate (Trans Isomer)

A solution of Intermediate 107 (100 mg, 0.19 mmol) in THF (5 mL) was treated with triethylamine (38 mg, 0.37 mmol) and pyridine (22 mg, 0.28 mmol), followed by the slow addition of cyclobutyl chloroformate (25 mg, 0.19 mmol). The reaction mixture was stirred at 20° C. for 18 h, then diluted with water and extracted with DCM, The combined organic layers were passed through a hydrophobic frit phase separator cartridge and concentrated in vacuo. The resulting crude yellow oil was purified by flash column chromatography, using a gradient of 0-100% ethyl acetate in hexanes, to afford the title compound (120 mg, over quant.) as a clear oil, which was utilised without further purification. HPLC-MS (method 7): MH+ m/z 601, RT 1.61 minutes.

Intermediate 112

N-[(1S)-1-(4-Methylcyclohexyl)-2-oxo-2-({2-oxo-1-[2-(trimethylsilyl)ethoxymethyl]-spiro[pyrrolo[3,2-c]pyridine-3,4'-tetrahydropyran]-6-yl}amino)ethyl]-2-(3,3,3-trifluoro-propyl)pyrazole-3-carboxamide (Trans Isomer)

Prepared from Intermediate 107 (40 mg, 0.074 mmol) and 1-(3,3,3-trifluoro-propyl)-1H-pyrazole-5-carboxylic acid (19.5 mg, 0.089 mmol) in accordance with Procedure A, and purified by flash column chromatography using a gradient of 0-100% ethyl acetate in hexanes, to give the title compound (50 mg, 97%) as a clear oil. HPLC-MS (method 6): MH+ m/z 693, RT 1.44 minutes.

Intermediate 113

3-Cyclobutyl-N-[(1S)-1-(4-methylcyclohexyl)-2-oxo-2-({2-oxo-1-[2-(trimethylsilyl)-ethoxymethyl] spiro[pyrrolo[3,2-c]pyridine-3,4'-tetrahydropyran]-6-yl}amino)ethyl]-isoxazole-4-carboxamide (Trans Isomer)

Prepared from Intermediate 107 (40 mg, 0.074 mmol) and 3-cyclobutylisoxazole-4-carboxylic acid (15 mg, 0.089 mmol) in accordance with Procedure A, and purified by flash column chromatography using a gradient of 0-100% ethyl acetate in hexanes, to give the title compound (45 mg, 93%) as a clear oil. HPLC-MS (method 7): MH+ m/z 652, RT 1.59 minutes.

Intermediate 114

2-[(6-Chloropyrrolo[2,3-b]pyridin-1-yl)methoxy] ethyl(trimethyl)silane

To a solution of 6-chloro-1H-pyrrolo[2,3-b]pyridine (10.0 g, 65.5 mmol) in DMF (100 mL) was added NaH (1.89 g, 78.6 mmol) at 0° C. SEM-Cl (13.9 mL, 78.6 mmol) was added dropwise at 0° C. The reaction mixture was stirred at room temperature for 3 h, then poured into ice and extracted with EtOAc (3×100 mL). The combined organic layers were separated, washed with water (100 mL) and brine (50 mL), then dried over anhydrous $Na_2SO_4$ and concentrated in vacuo. The crude residue was purified by column chromatography (0-5% EtOAc in hexanes) to afford the title compound (16.0 g, 86%) as a pale yellow oil. $\delta_H$ (400 MHz, DMSO-$d_6$) −0.12 (s, 9H), 0.79-0.85 (m, 2H), 3.47-3.52 (m, 2H), 5.57 (s, 2H), 6.58 (d, J 3.42 Hz, 1H), 7.18 (d, J 7.83 Hz, 1H), 7.66 (d, J 3.42 Hz, 1H), 8.04 (d, J 8.31 Hz, 1H). HPLC-MS (method 6): MH+ m/z 683.9, RT 2.44 minutes.

Intermediate 115

3,3-Dibromo-6-chloro-1-[2-(trimethylsilyl)ethoxymethyl]pyrrolo[2,3-b]pyridin-2-one To a solution of pyridinium tribromide (3.39 g, 10.6 mmol) in 1,4-dioxane (10 mL) was added Intermediate 114 (1.00 g, 3.54 mmol) solution in 1,4-dioxane (5 mL) at room temperature. The reaction mixture was stirred for 15 minutes, then diluted with water (500 mL) and extracted with EtOAc (3×250 mL). The combined organic layers were separated, washed with water (250 mL) and brine (250 mL), then dried over anhydrous $Na_2SO_4$ and concentrated in vacuo. The crude residue was purified by column chromatography (0-5% EtOAc in hexanes) to afford the title compound (1.2 g, 74%) as a red oil. $\delta_H$ (400 MHz, DMSO-$d_6$) −0.08 (s, 9H), 0.83-0.91 (m, 2H), 3.62 (t, J 8.07 Hz, 2H), 5.14 (s, 2H), 7.40 (d, J 7.83 Hz, 1H), 8.20 (d, J 8.31 Hz, 1H).

Intermediate 116

6-Chloro-1-[2-(trimethylsilyl)ethoxymethyl]-3H-pyrrolo[2,3-b]pyridin-2-one

To a solution of Intermediate 115 (15.0 g, 32.8 mmol) in THF (150 mL) and water (50 mL) was added Zn (10.7 g, 164 mmol), followed by addition of $NH_4Cl$ (8.79 g, 164 mmol) at 0° C. The reaction mixture was stirred at room temperature for 2 h, then filtered through a pad of Celite. The filtrate was diluted with water (100 mL) and extracted with EtOAc (3×100 mL). The combined organic layers were separated, washed with water (100 mL), brine (100 mL), then dried over anhydrous $Na_2SO_4$ and concentrated in vacuo. The crude residue was purified by column chromatography (0-20% EtOAc in hexanes) to afford the title compound (6.00 g, 61%) as a colourless oil. $\delta_H$ (400 MHz, DMSO-$d_6$) −0.05 (s, 9H), 0.83-0.91 (m, 2H), 3.57-3.81 (m, 2H), 3.70 (s, 2H), 5.04 (s, 2H), 7.15 (d, J 7.34 Hz, 1H), 7.69 (d, J 7.82 Hz, 1H). HPLC-MS (method 6): MH+ m/z 296.9, RT 2.23 minutes.

Intermediate 117

6-Chloro-1-[2-(trimethylsilyl)ethoxymethyl]spiro [pyrrolo[2,3-b]pyridine-3,4'-tetrahydro-pyran]-2-one To a solution of Intermediate 116 (6.00 g, 20.1 mmol) in DMF (120 mL) was added $Cs_2CO_3$ (26.2 g, 80.3 mmol), followed by addition of 1-bromo-2-(2-bromoethoxy)-ethane (6.17 mL, 40.2 mmol). The reaction mixture was stirred at room temperature for 16 h, then diluted with water (50 mL) and extracted with EtOAc (3×100 mL). The combined organic layers were separated, washed with water (100 mL)

and brine (100 mL), then dried over anhydrous Na$_2$SO$_4$ and concentrated in vacuo. The crude residue was purified by column chromatography (0-20% EtOAc in hexanes) to afford the title compound (4.00 g, 45%) as a red solid. δ$_H$ (400 MHz, DMSO-d$_6$) −0.02 (s, 9H), 0.83-0.92 (m, 2H), 1.75-1.85 (m, 4H) 3.58 (t, J 7.91 Hz, 2H) 3.75-3.87 (m, 2H), 3.96-4.06 (m, 2H), 5.06 (s, 2H), 7.19 (d, J 7.53 Hz, 1H), 8.09 (d, J 7.78 Hz, 1H). HPLC-MS (method 6): [(M−100)+H]+ m/z 269.0, RT 3.28 minutes.

Intermediate 118

N-[1-Cyclooctyl-2-oxo-2-({2-oxo-1-[2-(trimethylsilyl)ethoxymethyl]spiro[pyrrolo[2,3-b]-pyridine-3,4'-tetrahydropyran]-6-yl}amino)ethyl]-2-methylpyrazole-3-carboxamide To a solution of Intermediate 117 (0.10 g, 0.27 mmol) in tert-butanol (5 mL) were added Intermediate 85 (0.08 g, 0.27 mmol) and K$_2$CO$_3$ (0.075 g, 0.54 mmol). The reaction mixture was purged with argon for 10 minutes, then Pd$_2$(dba)$_3$ (0.02 g, 0.03 mmol) and XPhos (0.01 g, 0.03 mmol) were added. The reaction mixture was heated at 100° C. for 16 h, then diluted with EtOAc (100 mL) and filtered through a pad of Celite. The organic layer was washed with water (2×50 mL). The organic layer was separated, dried over anhydrous Na$_2$SO$_4$ and concentrated in vacuo. The crude residue was purified by column chromatography (40-50% ethyl acetate in hexane) to afford the title compound (0.11 g, 50%) as a light yellow solid. δ$_H$ (400 MHz, DMSO-d$_6$) −0.10 (s, 9H), 0.83-0.89 (m, 2H), 1.21-1.26 (m, 2H), 1.37-1.56 (m, 9H), 1.62-1.72 (m, 5H), 1.77-1.86 (m, 2H), 2.15-2.18 (m, 1H), 3.57 (t, J 8.07 Hz, 2H), 3.79-3.88 (m, 2H), 3.96-4.00 (m, 2H), 4.02 (s, 3H), 4.61-4.70 (m, 1H), 5.10 (s, 2H), 7.02 (d, J 1.96 Hz, 1H), 7.46 (d, J 2.45 Hz, 1H), 7.82 (d, J 8.31 Hz, 1H), 8.03 (d, J 7.82 Hz, 1H), 8.46 (d, J 8.80 Hz, 1H), 10.68 (s, 1H). HPLC-MS (method 6): MH+ m/z 625.8, RT 2.44 minutes.

Intermediate 119

6-Bromo-1-{[2-(trimethylsilyl)ethoxy]methyl}-1,2-dihydrospiro[indole-3,4'-oxane]-2-one To a stirred solution of 6-bromo-1,2-dihydrospiro[indole-3,4'-oxane]-2-one (10 g, 35.4 mmol) in a mixture of THF (150 mL) and DMF (150 mL), previously cooled to −5° C., was added sodium hydride (60%, 1.7 g, 42.5 mmol) portionwise. Stirring was continued at 0° C. for a further 30 minutes, then SEM-Cl (3.9 mL, 22.4 mmol) was added dropwise. The reaction mixture was allowed to warm to room temperature and stirred overnight, then poured into ice-water (600 mL) and extracted with ethyl acetate (3×300 mL). The organic extracts were combined, washed with saturated aqueous sodium hydrogen carbonate solution (300 mL) and brine (2×200 mL), then dried (Na$_2$SO$_4$), filtered and concentrated in vacuo. The residue was purified by flash column chromatography, using 0-100% EtOAc in heptane as eluent, to afford the title compound (11.84 g, 81%) as a white solid. δ$_H$ (500 MHz, DMSO-d$_6$) 7.62 (d, J 8.0 Hz, 1H), 7.39 (d, J 1.8 Hz, 1H), 7.35 (dd, J 8.0, 1.8 Hz, 1H), 5.20 (s, 2H), 4.12 (ddd, J 11.7, 8.3, 3.5 Hz, 2H), 3.99-3.81 (m, 2H), 3.61-3.54 (m, 2H), 1.87 (ddd, J 12.5, 8.3, 4.0 Hz, 2H), 1.83-1.75 (m, 2H), 0.92 (t, J 7.9 Hz, 2H), 0.00 (s, 9H). HPLC-MS (method 5): MH+ m/z 294, RT 2.17 minutes.

Intermediate 120

2-Oxo-1-[2-(trimethylsilyl)ethoxymethyl]spiro[indoline-3,4'-tetrahydropyran]-6-carboxylic acid To a stirred solution of Intermediate 119 (1.00 g, 2.425 mmol) in anhydrous THF (20 mL), previously cooled to −78° C. under nitrogen, was added 2.5M n-butyllithium (0.98 mL, 2.45 mmol) dropwise. The temperature was maintained at −78° C. for 30 minutes, then carbon dioxide (~4.0 g, as dry ice pellets) was added portionwise. Stirring was continued at −78° C. for a further 20 minutes. The reaction mixture was quenched with saturated aqueous ammonium chloride solution (2 mL) and water (1 mL), then allowed to warm to room temperature and diluted with water (20 mL) and brine (20 mL). The reaction mixture (pH 8) was extracted with ethyl acetate (30 mL), and the aqueous phase was discarded. The organic phase was extracted with 1M aqueous sodium hydroxide solution (2×20 mL). The basic aqueous extracts were combined (pH 12) and the pH was adjusted to pH 4 with 12M hydrochloric acid, then to pH 1-2 with 1M hydrochloric acid. The acidic aqueous phase was extracted with DCM (3×20 mL). The organic extracts were combined, dried over anhydrous sodium sulfate and filtered. The solvent was removed in vacuo to afford the title compound (230 mg, 24%) as a pale orange solid. δ$_H$ (250 MHz, DMSO-d$_6$) 7.71 (s, 2H), 7.59 (s, 1H), 5.16 (s, 2H), 4.06 (ddd, J 11.6, 8.1, 3.7 Hz, 2H), 3.89-3.79 (m, 2H), 3.50 (t, J 7.7 Hz, 2H), 1.87-1.67 (m, 4H), 0.84 (t, J 8.1 Hz, 2H), −0.09 (s, 9H). HPLC-MS (method 5): [M−H]− m/z 376, RT 1.90 minutes.

Intermediate 121

N-{1-Cyclooctyl-2-oxo-2-[(2-oxospiro[indoline-3,4'-tetrahydropyran]-6-yl)amino]ethyl}-2-oxo-1-[2-(trimethylsilyl)ethoxymethyl]spiro[indoline-3,4'-tetrahydropyran]-6-carboxamide Prepared from Intermediate 35 (50 mg, 0.13 mmol) and Intermediate 120 (54 mg, 0.14 mmol) in accordance with Procedure A, and purified by flash column chromatography using a gradient of methanol in dichloromethane (1-10%), to give the title compound (73 mg, 75%) as a clear glass. δ$_H$ (250 MHz, DMSO-d$_6$) 10.38 (s, 1H), 10.22 (s, 1H), 8.52 (d, J 8.6 Hz, 1H), 7.68 (s, 2H), 7.64 (s, 1H), 7.43 (d, J 8.2 Hz, 1H), 7.38 (d, J 1.8 Hz, 1H), 7.13 (dd, J 8.2, 1.8 Hz, 1H), 5.16 (s, 2H), 4.51 (t, J 9.0 Hz, 1H), 4.11-3.96 (m, 4H), 3.85 (d, J 12.0 Hz, 4H), 3.51 (t, J 7.9 Hz, 2H), 2.27-2.12 (m, 1H), 1.82-1.36 (m, 22H), 0.84 (dd, J 8.5, 7.3 Hz, 2H), −0.11 (s, 9H). HPLC-MS (method 5): [M−H]− m/z 743, RT 2.16 minutes.

Intermediate 122

2-Methyl-N-{1-(4-methylcyclohexylidene)-2-oxo-2-[(2-oxospiro[indoline-3,4'-tetrahydropyran]-6-yl)amino]ethyl}pyrazole-3-carboxamide Prepared from Intermediate 2 (70 mg, 0.3 mmol) and Intermediate 75 (78 mg, 0.3 mmol) in accordance with Procedure G, and purified by preparative chromatography (method 8), to give the title compound (21.5 mg, 15%) as a white solid. uPLC-MS (method 28): [M−H]− m/z 478, RT 1.28 minutes.

Intermediate 123

6-Amino-5-fluorospiro[indoline-3,4'-tetrahydropyran]-2-one

A suspension of Intermediate 2 (400 mg, 1.83 mmol) in THF (10 mL) was treated with 1-chloromethyl-4-fluoro-1,4-diazoniabicyclo[2.2.2]octane bis(tetrafluoroborate) (700 mg, 1.98 mmol). The reaction mixture was stirred at 20° C. under a nitrogen atmosphere for 24 h, then diluted with saturated aqueous sodium hydrogen carbonate solution (40 mL). Further solid NaHCO$_3$ was added until pH 8.5 was reached. The mixture was extracted with EtOAc (2×70 mL). The combined organic extracts were washed with brine (50 mL) and dried over MgSO$_4$, then filtered and concentrated in vacuo. The crude residue was purified by reverse phase HPLC (method 8) to afford, after freeze-drying, the title compound (22 mg, 5%) as a white solid. $\delta_H$ (250 MHz, DMSO-d$_6$) 10.13 (s, 1H), 7.19 (d, J 11.2 Hz, 1H), 6.32 (d, J 7.8 Hz, 1H), 5.12 (s, 2H), 3.98 (ddd, J 11.3, 7.3, 3.7 Hz, 2H), 3.76 (ddd, J 11.2, 7.1, 3.8 Hz, 2H), 1.69 (ddd, J 13.5, 7.1, 3.7 Hz, 2H), 1.58 (ddd, J 13.5, 7.3, 3.8 Hz, 2H). HPLC-MS (Method 6): MH+ m/z 237, RT 0.81 minutes.

Intermediate 124 tert-Butyl 7-nitro-1,3,4,9-tetrahydropyrido[3,4-b]indole-2-carboxylate

Di-tert-butyl dicarbonate (1.11 g, 5.09 mmol) was added to a stirred suspension of 7-nitro-2,3,4,9-tetrahydro-1H-beta-carboline (1 g, 4.6 mmol) in tert-butanol (46 mL) at 20° C. The mixture was stirred at 20° C. for 16 h. The volatiles were removed in vacuo, then the residue was suspended in tert-butyl methyl ether (20 mL) and sonicated. The solids were collected by filtration and washed with tert-butyl methyl ether (3×10 mL). The filtrate was concentrated, then the foregoing procedure was repeated to afford a second crop of solid. The combined solids were dried in vacuo to afford the title compound (1.37 g, 93%) as a canary yellow powder. $\delta_H$ (500 MHz, DMSO-d$_6$) 11.69 (br s, 1H), 8.27 (d, J 2.0 Hz, 1H), 7.88 (dd, J 8.8, 2.1 Hz, 1H), 7.57 (d, J 8.7 Hz, 1H), 4.65 (s, 2H), 3.68 (t, J 5.7 Hz, 2H), 2.74 (t, J 5.5 Hz, 2H), 1.44 (s, 9H). HPLC-MS (method 7): MH+ m/z 318, RT 2.01 minutes.

Intermediate 125 tert-Butyl 6-nitro-2-oxospiro[indoline-3,3'-pyrrolidine]-1'-carboxylate

1-Bromopyrrolidine-2,5-dione (400 mg, 2.25 mmol) was added portionwise over 10 minutes to a stirred suspension of Intermediate 124 (680 mg, 2.12 mmol) in 1:1:1 THF-acetic acid-water (36 mL) at 0° C. under nitrogen. The mixture was allowed to warm to approximately 20° C. over 2.5 h, then quenched with saturated aqueous sodium carbonate solution (pH 10). The resulting material was extracted with ethyl acetate (3×50 mL). The combined organic extracts were washed with saturated aqueous sodium carbonate solution (30 mL) and brine (30 mL), then dried over magnesium sulfate, filtered and concentrated in vacuo. The resultant orange gum was separated by flash column chromatography, using a gradient of ethyl acetate in heptane (0-80%), to afford the title compound (679 mg, 93%) as a pale yellow powder. $\delta_H$ (250 MHz, DMSO-d$_6$, 353K) 10.65 (br s, 1H), 7.88 (dd, J 8.2, 2.2 Hz, 1H), 7.60 (d, J 2.1 Hz, 1H), 7.48 (d, J 8.2 Hz, 1H), 3.78-3.59 (m, 2H), 3.59 (d, J 11.3 Hz, 1H), 3.53 (d, J 11.1 Hz, 1H), 2.36-2.08 (m, 2H), 1.45 (s, 9H). HPLC-MS (method 7): MNa+ m/z 356, RT 1.83 minutes.

Intermediate 126 tert-Butyl 6-amino-2-oxospiro[indoline-3,3'-pyrrolidine]-1'-carboxylate

A suspension of Intermediate 125 (679 mg, 2.04 mmol) and 10% palladium on carbon (50% water wet, 200 mg, 0.09 mmol) in ethanol (16 mL) was stirred under an atmosphere of hydrogen for 4 h. The solids were removed by filtration through a kieselguhr pad, washing with ethanol (4×20 mL), and the filtrate was concentrated in vacuo. The resulting pink-red powder was separated by flash column chromatography, using a gradient of ethyl acetate in heptane (20-100%), to afford the title compound (633 mg, 97%) as a light tan powder. $\delta_H$ (250 MHz, DMSO-d$_6$, 353K) 9.93 (br s, 1H), 6.87-6.76 (m, 1H), 6.23-6.14 (m, 2H), 4.88 (br s, 2H), 3.71-3.49 (m, 2H), 3.45 (d, J 10.8 Hz, 1H), 3.33 (d, J 10.8 Hz, 1H), 2.12 (ddd, J 12.5, 7.9, 6.5 Hz, 1H), 2.03-1.88 (m, 1H), 1.43 (s, 9H). HPLC-MS (method 7): MNa+ m/z 326, RT 1.64 minutes.

Intermediate 127 tert-Butyl 6-({2-cyclooctyl-2-[(3-methylisoxazole-4-carbonyl)amino]acetyl}amino)-2-oxospiro[indoline-3,3'-pyrrolidine]-1'-carboxylate HATU (143 mg, 0.38 mmol) was added to a mixture of Intermediate 126 (100 mg, 0.31 mmol) and Intermediate 41 (104 mg, 0.35 mmol) in anhydrous DMF (1.6 mL). The mixture was stirred at 20° C. under nitrogen for 16 h, then quenched with saturated aqueous sodium carbonate solution (20 mL). The resulting material was extracted with ethyl acetate (3×30 mL). The combined organic extracts were washed with water (20 mL) and brine (2×20 mL), then dried over magnesium sulfate, filtered and concentrated in vacuo. The resultant viscous orange oil was separated by flash column chromatography, using a gradient of ethyl acetate in heptane (0-100%), to afford, after freeze-drying, the title compound (89.8 mg, 47%) as an off-white powder. $\delta_H$ (250 MHz, DMSO-d$_6$, 353K) 10.23 (br s, 1H), 9.91 (br s, 1H), 9.34 (s, 1H), 8.07 (d, J 8.7 Hz, 1H), 7.35 (s, 1H), 7.17-7.07 (m, 2H), 4.50 (t, J 8.3 Hz, 1H), 3.73-3.54 (m, 2H), 3.50 (d, J 10.9 Hz, 1H), 3.41 (d, J 10.8 Hz, 1H), 2.39 (s, 3H), 2.20-1.96 (m, 3H), 1.79-1.35 (m, 23H). uPLC-MS (method 1): MH+ m/z 580, RT 3.74 minutes.

Intermediate 128

2-Cyclooctyl-2-[(2-methylpyrazole-3-carbonyl)amino]acetic acid

Aqueous lithium hydroxide solution (2M, 2.6 mL, 5.2 mmol) was added to a stirred solution of Intermediate 12 (1.45 g, 4.29 mmol) in 1:1 THF/MeOH (17.2 mL). The mixture was stirred at 20° C. under air for 16 h. The volatiles were removed in vacuo and the residue was diluted with water (20 mL), then washed with tert-butyl methyl ether (2×20 mL). The combined organic washings were extracted with aqueous sodium hydroxide solution (20 mL). The combined alkaline aqueous phases were treated with 3M aqueous hydrochloric acid (pH 1) and extracted with ethyl acetate (3×30 mL). The combined organic extracts were washed with brine (20 mL) and dried over magnesium sulfate, then filtered and concentrated in vacuo, to afford the title compound (1.48 g, 91%) as a white powder. $\delta_H$ (500 MHz, DMSO-d$_6$) 12.69 (br s, 1H), 8.42 (d, J 8.6 Hz, 1H), 7.45 (d, J 2.0 Hz, 1H), 7.01 (d, J 2.1 Hz, 1H), 4.33 (dd, J 8.5, 7.3 Hz, 1H), 4.02 (s, 3H), 2.19-2.06 (m, 1H), 1.75-1.27 (m, 14H). HPLC-MS (method 5): MH+ m/z 294, RT 1.71 minutes.

Intermediate 129 tert-Butyl 6-(tert-butoxycarbonylamino)-2-oxoindoline-1-carboxylate

Di-tert-butyl dicarbonate (33.5 g, 153 mmol) was added portionwise to a stirred suspension of 6-amino-1,3-dihydro-2H-indol-2-one (9.1 g, 61.4 mmol) and sodium hydrogen carbonate (18.1 g, 215 mmol) in THF (120 mL) at 20° C. under nitrogen. The mixture was heated at 70° C. for 3.5 h. An additional portion of di-tert-butyl dicarbonate (6.8 g, 31.2 mmol) was added, and heating was continued at 70° C. for 1.5 h. An additional portion of di-tert-butyl dicarbonate (6.8 g, 31.2 mmol) was added, and heating was continued at 70° C. for 5 h. After cooling to r.t., the mixture was diluted with ethyl acetate (100 mL), and the solids were removed by filtration through a kieselguhr pad, washing with ethyl acetate (2×100 mL). The filtrate was concentrated in vacuo. The resultant dark-red gum was separated by flash column chromatography, using a gradient of ethyl acetate in heptane (0-35%), then triturated with 4:1 ethyl acetate/heptane, to afford the title compound (16.23 g, 76%) as a tan powder. $\delta_H$ (500 MHz, DMSO-d$_6$) 9.42 (s, 1H), 8.03 (s, 1H), 7.17-7.08 (m, 2H), 3.64 (s, 2H), 1.57 (s, 9H), 1.47 (s, 9H). HPLC-MS (method 5): MNa+ m/z 371, RT 1.94 minutes.

Intermediate 130

Ethyl (2S)-2-(2-ethoxy-2-oxoethoxy)propanoate

Ethyl (2S)-2-hydroxypropanoate (4.8 mL, 42.0 mmol) was added to a stirred suspension of potassium carbonate (5.81 g, 42.0 mmol) in anhydrous DMF (42 mL). The suspension was stirred at 20° C. under nitrogen for 20 minutes, then ethyl bromoacetate (4.7 mL, 42.4 mmol) was added. The reaction mixture was stirred at 20° C. under nitrogen for 64 h, then diluted with tert-butyl methyl ether (50 mL). The solids were removed by filtration, and washed with tert-butyl methyl ether (2×50 mL). The filtrate was concentrated in vacuo. The resultant orange oil was separated by kugelrohr distillation (160-210° C., 18 mbar) to afford the title compound (4.57 g, 27%) as a colourless oil. $\delta_H$ (500 MHz, CDCl$_3$) 4.27 (d, J 16.5 Hz, 1H), 4.25-4.17 (m, 4H), 4.14 (q, J 6.9 Hz, 1H), 4.07 (d, J 16.5 Hz, 1H), 1.48 (d, J 6.9 Hz, 3H), 1.31-1.25 (m, 6H).

Intermediate 131

(2S)-2-(2-Hydroxyethoxy)propan-1-ol

Lithium aluminium hydride solution in diethyl ether (4M, 7.3 mL, 29.2 mmol) was added dropwise to a stirred solution of Intermediate 130 (4.57 g, 22.4 mmol) in anhydrous THF (45 mL) at 0° C. under nitrogen. The mixture was stirred at 0° C. for 1 h, then at 20° C. for 16 h. The reaction mixture was cautiously quenched by the dropwise addition of water (0.55 mL), followed by 2M aqueous sodium hydroxide solution (1.32 mL), then water (1.64 mL). The suspension was stirred at room temperature for 30 minutes, then diluted with acetone (50 mL) and filtered through a kieselguhr pad. The residues were washed with acetone (2×50 mL), and the filtrate was concentrated in vacuo. The tan oil was separated by kugelrohr distillation (90-120° C., <1 mbar) to afford the title compound (818 mg, 22%) as a colourless free-flowing oil. $\delta_H$ (500 MHz, CDCl$_3$) 3.77-3.69 (m, 3H), 3.64-3.57 (m, 2H), 3.55-3.45 (m, 2H), 3.25 (br s, 2H), 1.12 (d, J 6.2 Hz, 3H).

Intermediate 132

(2S)-1-Iodo-2-(2-iodoethoxy)propane

Iodine (8.64 g, 34.0 mmol) was added portionwise to a stirred solution of triphenylphosphine (7.14 g, 27.2 mmol) and 1H-imidazole (1.85 g, 27.2 mmol) in 3:1 diethyl ether/acetonitrile (54 mL) at 20° C. under nitrogen. After stirring at 20° C. for 30 minutes, a solution of Intermediate 131 (0.82 g, 6.81 mmol) in diethyl ether (3 mL) was added slowly, followed by a diethyl ether (2 mL) rinse. The reaction mixture was stirred at 20° C. in the dark for 22 h. The suspension was diluted with tert-butyl methyl ether (50 mL) and filtered through a kieselguhr pad, washing well with tert-butyl methyl ether (4×30 mL). The filtrate was filtered through a second kieselguhr pad, washing well with tert-butyl methyl ether (2×30 mL), then concentrated in vacuo. The resultant dark red viscous oil was separated by flash column chromatography, using a gradient of ethyl acetate in heptane (0-5%), to afford the title compound (1.44 g, 59%) as a tan free-flowing oil. $\delta_H$ (500 MHz, CDCl$_3$) 3.81-3.69 (m, 2H), 3.54-3.44 (m, 1H), 3.30-3.22 (m, 3H), 3.20 (dd, J 10.3, 5.7 Hz, 1H), 1.29 (d, J 6.1 Hz, 3H).

Intermediate 133 tert-Butyl (2'S,3S)-6-(tert-butoxycarbonylamino)-2'-methyl-2-oxospiro[indoline-3,4'-tetrahydropyran]-1-carboxylate A stirred solution of Intermediate 129 (600 mg, 1.72 mmol) and Intermediate 132 (640 mg, 1.26 mmol) in anhydrous DMF (11.5 mL) was purged with a stream of nitrogen whilst sonicating for 5 minutes. The solution was cooled to -10° C. under nitrogen, then cesium carbonate (2.24 g, 6.89 mmol) was added portionwise over 10 minutes. The suspension was allowed to warm slowly to 20° C., and stirred for a total of 16 h. The mixture was quenched by the slow addition of acetic acid (0.31 mL), and stirred at 20° C. for 5 minutes. The suspension was diluted with water (50 mL) and stirred at 20° C. for 5 minutes, then the solids were collected by filtration. The solids were washed with water (2×25 mL), then dissolved in ethyl acetate (30 mL). The organic filtrate was collected, and the residues were washed with ethyl acetate (2×20 mL). The combined organic filtrate was filtered through hydrophobic filter paper and concentrated in vacuo. The resultant orange gum was separated by sequential flash column chromatography, using a gradient of ethyl acetate in heptane (0-30%), then preparative HPLC (method 31), to afford the title compound (86.5 mg, 16%) as a white powder. $\delta_H$ (500 MHz, DMSO-d$_6$) 9.49 (s, 1H), 8.14 (d, J 1.6 Hz, 1H), 7.74 (d, J 8.4 Hz, 1H), 7.16 (dd, J 8.3, 1.8 Hz, 1H), 4.04-3.83 (m, 3H), 1.90 (td, J 13.1, 5.8 Hz, 1H), 1.62-1.54 (obs. m, 1H), 1.58 (s, 9H), 1.50-1.44 (obs. m, 1H), 1.47 (s, 9H), 1.40 (d, J 12.7 Hz, 1H), 1.10 (d, J 6.0 Hz, 3H). uPLC-MS (method 1): [M+2H-BOC]+ m/z 333, RT 4.01

Intermediate 134 tert-Butyl (2'S,3R)-6-(tert-butoxycarbonylamino)-2'-methyl-2-oxospiro[indoline-3,4'-tetrahydropyran]-1-carboxylate A stirred solution of Intermediate 129 (600 mg, 1.72 mmol) and Intermediate 132 (640 mg, 1.26 mmol) in anhydrous DMF (11.5 mL) was purged with a stream of nitrogen whilst sonicating for 5 minutes. The solution was cooled to −10° C. under nitrogen, then cesium carbonate (2.24 g, 6.89 mmol) was added portionwise over 10 minutes. The suspension was allowed to warm slowly to 20° C., and stirred for a total of 16 h. The mixture was quenched by the slow addition of acetic acid (0.31 mL), and stirred at 20° C. for 5 minutes. The suspension was diluted with water (50 mL) and stirred at 20° C. for 5 minutes, then the solids were collected by filtration. The solids were washed with water (2×25 mL), then dissolved in ethyl acetate (30 mL). The organic filtrate was collected, and the residues were washed with ethyl acetate (2×20 mL). The combined organic filtrate was filtered through hydrophobic filter paper and concentrated in vacuo. The resultant orange gum was separated by sequential flash column chromatography, using a gradient of ethyl acetate in heptane (0-30%), then preparative HPLC (method 31), to afford the title compound (166 mg, 30%) as an off-white powder. $\delta_H$ (500 MHz, DMSO-$d_6$) 9.46 (s, 1H), 8.11-7.99 (m, 1H), 7.23 (d, J 8.2 Hz, 1H), 7.15 (dd, J 8.2, 1.8 Hz, 1H), 4.17-4.00 (m, 2H), 3.77 (dd, J 11.4, 4.5 Hz, 1H), 1.86 (td, J 13.5, 5.1 Hz, 1H), 1.71 (d, J 13.6 Hz, 1H), 1.64 (d, J 13.1 Hz, 1H), 1.58 (s, 9H), 1.52 (dd, J 13.7, 11.3 Hz, 1H), 1.47 (s, 9H), 1.08 (d, J 6.2 Hz, 3H). uPLC-MS (method 1): [M+2H-BOC]+ m/z 333, RT 4.06 minutes. Chiral SFC (method 13, Lux C4 25 cm, 15% MeOH-85% carbon dioxide, 4 mL/minute): RT 2.18 minutes (98%).

Intermediate 135

(2'S,3R)-6-Amino-2'-methylspiro[indoline-3,4'-tetrahydropyran]-2-one

Trifluoroacetic acid (0.57 mL, 7.40 mmol) was added to a stirred solution of Intermediate 134 (160 mg, 0.37 mmol) in DCM (1.9 mL). The mixture was stirred under air for 4 h, then diluted with DCM (4 mL) and quenched with saturated aqueous sodium carbonate solution (3 mL) and water (3 mL). The organic phase was separated using a hydrophobic frit and the aqueous layer was extracted with DCM (2×6 mL). The organic filtrate was concentrated in vacuo to afford the title compound (99 mg, 98%) as an off-white powder. $\delta_H$ (500 MHz, DMSO-$d_6$) 9.99 (s, 1H), 6.80 (d, J 7.9 Hz, 1H), 6.13 (dd, J 8.0, 2.0 Hz, 1H), 6.09 (d, J 1.9 Hz, 1H), 5.04 (br s, 2H), 4.24-4.09 (m, 2H), 3.70 (dd, J 11.3, 4.3 Hz, 1H), 1.78 (td, J 13.3, 5.1 Hz, 1H), 1.56-1.39 (m, 3H), 1.05 (d, J 6.2 Hz, 3H). uPLC-MS (method 1): MH+ m/z 233, RT 1.00 minutes.

Intermediate 136

(2'S,3S)-6-Amino-2'-methylspiro[indoline-3,4'-tetrahydropyran]-2-one

Trifluoroacetic acid (0.29 mL, 3.76 mmol) was added to a stirred solution of Intermediate 133 (81 mg, 0.19 mmol) in DCM (1 mL). The mixture was stirred at 20° C. under air for 4 h, then diluted with DCM (5 mL) and quenched with saturated aqueous sodium carbonate solution (3 mL) and water (3 mL). The organic phase was separated using a hydrophobic frit and the aqueous layer was extracted with DCM (2×6 mL). The organic filtrate was concentrated in vacuo to afford the title compound (44.9 mg, 97%) as an off-white powder. $\delta_H$ (500 MHz, DMSO-$d_6$) 10.17 (s, 1H), 7.32 (d, J 8.1 Hz, 1H), 6.16 (d, J 2.1 Hz, 1H), 6.12 (dd, J 8.0, 2.1 Hz, 1H), 5.08 (br s, 2H), 3.96-3.81 (m, 3H), 1.84 (ddd, J 13.0, 11.2, 7.4 Hz, 1H), 1.57-1.48 (m, 1H), 1.30-1.24 (m, 1H), 1.21-1.16 (m, 1H), 1.09 (d, J 6.1 Hz, 3H). uPLC-MS (method 1): MH+ m/z 233, RT 1.00 minutes.

Intermediate 137

Ethyl (2R)-2-(2-ethoxy-2-oxoethoxy)propanoate

Ethyl (2R)-2-hydroxypropanoate (4.8 mL, 42.01 mmol) was added to a stirred suspension of potassium carbonate (5.81 g, 42.0 mmol) in anhydrous DMF (42 mL). The suspension was stirred at 20° C. under nitrogen for 20 minutes, then ethyl bromoacetate (4.7 mL, 42.38 mmol) was added. The reaction mixture was stirred at 20° C. under nitrogen for 64 h, then diluted with tert-butyl methyl ether (50 mL). The solids were removed by filtration, washing with tert-butyl methyl ether (2×50 mL). The filtrate was concentrated in vacuo. The resultant orange oil was separated by kugelrohr distillation (130-185° C., 11 mbar) to afford the title compound (4.26 g, 30%) as a colourless oil. $\delta_H$ (500 MHz, CDCl$_3$) 4.27 (d, J 16.5 Hz, 1H), 4.25-4.17 (m, 4H), 4.14 (q, J 6.9 Hz, 1H), 4.07 (d, J 16.5 Hz, 1H), 1.47 (d, J 6.9 Hz, 3H), 1.31-1.26 (m, 6H).

Intermediate 138

(2R)-2-(2-Hydroxyethoxy)propan-1-ol

Lithium aluminium hydride solution in diethyl ether (4M, 6.8 mL, 27.2 mmol) was added dropwise to a stirred solution of Intermediate 137 (4.26 g, 20.8 mmol) in anhydrous THF (45 mL) at 0° C. under nitrogen. The mixture was stirred at 0° C. for 1 h and at 20° C. for 16 h. The reaction mixture was cautiously quenched by the dropwise addition of water (0.51 mL), followed by 2M aqueous sodium hydroxide solution (1.22 mL), then water (1.53 mL). The suspension was stirred at room temperature for 30 minutes, then diluted with acetone (50 mL) and filtered through a kieselguhr pad. The residues were washed with acetone (2×50 mL) and the filtrate was concentrated in vacuo. The resultant tan oil was separated by kugelrohr distillation (100-120° C., <1 mbar) to afford the title compound (904 mg, 29%) as a colourless free-flowing oil. $\delta_H$ (500 MHz, CDCl$_3$) 3.78-3.67 (m, 3H), 3.67-3.38 (m, 6H), 1.10 (d, J 6.2 Hz, 3H).

Intermediate 139

(2R)-1-Iodo-2-(2-iodoethoxy)propane

Iodine (9.55 g, 37.63 mmol) was added portionwise to a stirred solution of triphenylphosphine (7.90 g, 30.12 mmol) and 1H-imidazole (2.06 g, 30.26 mmol) in 3:1 diethyl ether/acetonitrile (60 mL) at 20° C. under nitrogen. After stirring at 20° C. for 30 minutes, a solution of Intermediate 138 (0.90 g, 7.52 mmol) in diethyl ether (3 mL) was added slowly, followed by a diethyl ether (2 mL) rinse. The reaction mixture was stirred at 20° C. in the dark for 22 h.

The suspension was diluted with tert-butyl methyl ether (50 mL) and filtered through a kieselguhr pad, washing well with tert-butyl methyl ether (4×30 mL). The filtrate was filtered through a second kieselguhr pad, washing well with tert-butyl methyl ether (2×30 mL), then concentrated in vacuo. The resultant dark red viscous oil was separated by flash column chromatography, using a gradient of ethyl acetate in heptane (0-5%), to afford the title compound (1.32 g, 47%) as a tan free-flowing oil. $\delta_H$ (500 MHz, CDCl$_3$) 3.80-3.69 (m, 2H), 3.55-3.44 (m, 1H), 3.29-3.22 (m, 3H), 3.20 (dd, J 10.3, 5.7 Hz, 1H), 1.30 (d, J 6.1 Hz, 3H).

Intermediate 140 tert-Butyl (2'R,3S)-6-(tert-butoxycarbonylamino)-2'-methyl-2-oxospiro[indoline-3,4'-tetrahydropyran]-1-carboxylate A stirred solution of Intermediate 129 (600 mg, 1.72 mmol) and Intermediate 139 (640 mg, 1.38 mmol) in anhydrous DMF (11.5 mL) was purged with a stream of nitrogen whilst sonicating for 5 minutes. The solution was cooled to −10° C. under nitrogen and cesium carbonate (2.24 g, 6.89 mmol) was added portionwise over 10 minutes. The suspension was allowed to warm slowly to 20° C. and stirred for a total of 16 h. The mixture was quenched by the slow addition of acetic acid (0.31 mL) and stirred at 20° C. for 5 minutes. The suspension was diluted with water (50 mL) and stirred at 20° C. for 5 minutes, then the solids were collected by filtration. The solids were washed with water (2×25 mL), then dissolved in ethyl acetate (30 mL). The organic filtrate was collected, and the residues were washed with ethyl acetate (2×20 mL). The combined organic filtrate was filtered through hydrophobic filter paper and concentrated in vacuo. The resultant orange gum was separated by sequential flash column chromatography, using a gradient of ethyl acetate in heptane (0-30%), then preparative HPLC (method 31), to afford the title compound (180 mg, 30%) as a white powder. $\delta_H$ (500 MHz, DMSO-d$_6$) 9.45 (s, 1H), 8.05 (d, J 1.2 Hz, 1H), 7.23 (d, J 8.2 Hz, 1H), 7.15 (dd, J 8.2, 1.8 Hz, 1H), 4.19-4.00 (m, 2H), 3.77 (dd, J 11.5, 4.4 Hz, 1H), 1.86 (td, J 13.4, 5.0 Hz, 1H), 1.71 (d, J 13.6 Hz, 1H), 1.64 (d, J 13.2 Hz, 1H), 1.58 (s, 9H), 1.52 (dd, J 13.7, 11.3 Hz, 1H), 1.47 (s, 9H), 1.08 (d, J 6.2 Hz, 3H). uPLC-MS (method 1): [M+2H-BOC]+ m/z 333, RT 4.06 minutes. Chiral SFC (method 13, Lux C4 25 cm, 15% MeOH-85% carbon dioxide, 4 mL/minute): RT 1.96 minutes (99%).

Intermediate 141

(2'R,3S)-6-Amino-2'-methylspiro[indoline-3,4'-tetrahydropyran]-2-one

Trifluoroacetic acid (0.62 mL, 8.05 mmol) was added to a stirred solution of Intermediate 140 (175 mg, 0.41 mmol) in DCM (2 mL). The mixture was stirred at 20° C. under air for 4 h, then diluted with DCM (4 mL) and quenched with saturated aqueous sodium carbonate solution (3 mL) and water (3 mL). The organic phase was separated using a hydrophobic frit, and the aqueous layer was extracted with DCM (2×6 mL). The organic filtrate was concentrated in vacuo to afford the title compound (104 mg, quantitative) as an off-white powder. $\delta_H$ (500 MHz, DMSO-d$_6$) 9.99 (s, 1H), 6.80 (d, J 7.9 Hz, 1H), 6.13 (dd, J 7.9, 2.0 Hz, 1H), 6.09 (d, J 1.9 Hz, 1H), 5.04 (br s, 2H), 4.26-4.07 (m, 2H), 3.70 (dd, J 11.3, 4.3 Hz, 1H), 1.78 (td, J 13.3, 5.1 Hz, 1H), 1.56-1.40 (m, 3H), 1.05 (d, J 6.2 Hz, 3H). uPLC-MS (method 1): MH+ m/z 233, RT 1.00 minutes.

Intermediate 142

Ethyl 2-cyclohexyl-3-oxo-3-[(2-oxospiro[indoline-3,4'-tetrahydropyran]-6-yl)amino]-propanoate To a solution of Intermediate 2 (390 mg, 1.79 mmol) and 2-cyclohexyl-3-ethoxy-3-oxopropanoic acid lithium salt (398 mg, 1.86) in DMF (7 mL, 90.50 mmol) was added HATU (840 mg, 2.14 mmol). The reaction mixture was stirred at 20° C. for 18 h, then partitioned between EtOAc and water. The organic layers were combined, dried and concentrated under vacuum. The residue was separated by flash column chromatography, using a gradient of ethyl acetate in hexane (0-100%), to afford the title compound (623 mg, 84%). HPLC-MS (method 7): MH+ m/z 415, RT 1.24 minutes.

Intermediate 143

2-Cyclohexyl-3-oxo-3-[(2-oxospiro[indoline-3,4'-tetrahydropyran]-6-yl)amino]propanoic acid A solution of LiOH (36 mg, 1.50 mmol) in water (5 mL, 277.55 mmol) was added dropwise to a solution of Intermediate 142 (623 mg, 1.50 mmol) in ethanol (10 mL, 172.00 mmol). The reaction mixture was stirred at 20° C. for 72 h, then concentrated under vacuum, to afford the title compound (580 mg, 100%) as the lithium salt. HPLC-MS (method 7): MH+ m/z 387, RT 0.85 minutes.

Intermediate 144

N-(2-Amino-3-fluorophenyl)-2-cyclohexyl-N'-(2-oxospiro[indoline-3,4'-tetrahydro-pyran]-6-yl)propanediamide To a solution of 3-fluorobenzene-1,2-diamine (35 mg, 0.26 mmol) and Intermediate 143 (116 mg, 0.30 mmol) in DMF (2 mL, 25.90 mmol) was added HATU (124 mg, 0.32 mmol). The reaction mixture was stirred at 20° C. for 40 h, then water was added at 0° C. The resulting precipitate was collected by filtration to afford the title compound (97 mg, 75%) as a tan solid. HPLC-MS (method 7): MH+ m/z 495, RT 1.25 minutes.

Intermediate 145

N-(2-Aminophenyl)-2-cyclohexyl-N'-(2-oxospiro[indoline-3,4'-tetrahydropyran]-6-yl)-propanediamide To a solution of o-phenylenediamine (10 mg, 0.09 mmol) and Intermediate 165 (39 mg, 0.10 mmol) in DMF (1 mL, 12.90 mmol) was added HATU (45 mg, 0.12 mmol). The reaction mixture was stirred at 20° C. for 18 h, then partitioned between EtOAc and water. The organic layers were separated and washed with brine, then dried and concentrated under vacuum, to afford the title compound (40 mg, 91%). HPLC-MS (method 7): MH+ m/z 477, RT 1.18 minutes.

Intermediate 146

Diethyl 2-(azocan-1-yl)propanedioate

To a solution of heptamethyleneimine (2.25 mL, 17.70 mmol) in acetonitrile (40 mL, 763.00 mmol) was added $K_2CO_3$ (4.90 g, 35.00 mmol), followed by a solution of diethyl 2-bromopropanedioate (4.25 g, 17.80 mmol) in acetonitrile (40 mL, 763.00 mmol). The reaction mixture was stirred at 20° C. for 3 h, then concentrated under vacuum. The residue was separated by flash column chromatography, using a gradient of ethyl acetate in hexane (0-50%), to afford the title compound (3.78 g, 78%) as a colourless oil. $\delta_H$ (400 MHz, $CDCl_3$) 4.23 (q, J 7.1 Hz, 4H), 4.12 (s, 1H), 2.83 (t, J 5.4 Hz, 4H), 1.68-1.53 (m, 10H), 1.29 (t, J 7.1 Hz, 6H). LC-MS (method 7): MH+ m/z 272, RT 1.59 minutes.

Intermediate 147

2-(Azocan-1-yl)-3-ethoxy-3-oxo-propanoic acid

A solution of LiOH (22 mg, 0.92 mmol) in water (1 mL, 55.51 mmol) was added dropwise to a cooled (0° C.) solution of Intermediate 146 (250 mg, 0.92 mmol) in EtOH (4 mL, 68.70 mmol). The reaction mixture was warmed slowly to 20° C. and stirred for 4.5 h, then concentrated under vacuum, to afford the title compound (225 mg, 100%) as the lithium salt. LC-MS (method 7): MH+ m/z 244, RT 0.85 minutes.

Intermediate 148

Ethyl 2-(azocan-1-yl)-3-oxo-3-[(2-oxospiro[indoline-3,4'-tetrahydropyran]-6-yl)amino]-propanoate To a solution of Intermediate 2 (190 mg, 0.87 mmol) and Intermediate 147 (224 mg, 0.92 mmol) in DMF (4 mL, 51.70 mmol) was added HATU (410 mg, 1.05 mmol). The reaction mixture was stirred at 20° C. for 18 h, then partitioned between EtOAc and water. The organic layers were washed with brine, dried and concentrated under vacuum. The residue was separated by flash column chromatography, using a gradient of ethyl acetate in hexane (0-100%), to afford the title compound (125 mg, 32%) as a white solid. $\delta_H$ (400 MHz, $CDCl_3$) 8.97 (s, 1H), 7.63 (d, J 1.9 Hz, 1H), 7.44 (s, 1H), 7.30 (d, J 8.1 Hz, 1H), 6.87 (dd, J 8.1, 2.0 Hz, 1H), 4.38-4.17 (m, 4H), 4.10 (s, 1H), 3.92 (ddd, J 11.8, 5.5, 4.3 Hz, 2H), 2.93-2.72 (m, 4H), 2.08-1.59 (m, 14H), 1.33 (t, J 7.1 Hz, 3H). LC-MS (method 6): MH+ m/z 444, RT 2.31 minutes.

Intermediate 149

2-(Azocan-1-yl)-3-oxo-3-[(2-oxospiro[indoline-3,4'-tetrahydropyran]-6-yl)amino]-propanoic acid A solution of LiOH (12 mg, 0.50 mmol) in water (2 mL, 111.02 mmol) was added dropwise to a solution of Intermediate 148 (106 mg, 0.24 mmol) in EtOH (5 mL, 85.90 mmol). The reaction mixture was stirred at 20° C. for 18 h, then concentrated under vacuum, to afford the title compound (99 mg, 100%) as the lithium salt. LC-MS (method 7): MH+ m/z 416, RT 0.91 minutes.

Intermediate 150 tert-Butyl N-[(1S)-1-cyclohexyl-2-oxo-2-({2-oxo-1-[2-(trimethylsilyl)ethoxymethyl]-spiro[pyrrolo[3,2-c]pyridine-3,4'-tetrahydropyran]-6-yl}amino)ethyl]carbamate To a solution of (2S)-2-(tert-butoxycarbonylamino)-2-cyclohexylacetic acid (1.47 g, 5.72 mmol) and Intermediate 57 in anhydrous DCM (40 mL) were added HATU (2.69 g, 6.87 mmol) and DIPEA (1.99 mL, 11.44 mmol). The reaction mixture was stirred at 20° C. for 18 h. Additional (2S)-2-(tert-butoxycarbonylamino)-2-cyclohexylacetic acid (1.47 g, 5.72 mmol), HATU (2.69 g, 6.87 mmol) and DIPEA (1.99 mL, 11.44 mmol) were added, and the mixture was stirred for another 28 h. The reaction mixture was partitioned between DCM and water, and the aqueous phase was extracted with DCM (2×25 mL). The combined organic layers were separated through a hydrophobic frit phase separator, and concentrated in vacuo. The crude residue was purified by flash column chromatography, using a gradient of 0-100% ethyl acetate in hexanes, to afford the title compound (3.00 g, 89%) as a white solid. $\delta_H$ (300 MHz, DMSO-$d_6$) 10.41 (s, 1H), 8.60-8.34 (m, 1H), 7.93 (s, 1H), 6.94 (d, J 8.6 Hz, 1H), 5.08 (s, 2H), 4.25-3.67 (m, 2H), 3.50 (t, J 7.8 Hz, 2H), 1.94-1.45 (m, 10H), 1.38 (s, 10H), 1.24-0.93 (m, 7H), 0.93-0.74 (m, 2H), −0.09 (s, 9H). HPLC-MS (method 7): MH+ m/z 589, RT 1.69 minutes. $[\alpha]^{20}_D$=−15.53° (c 7.5, methanol).

Intermediate 151

(2S)-2-Amino-2-cyclohexyl-N-(2-oxospiro[1H-pyrrolo[3,2-c]pyridine-3,4'-tetrahydro-pyran]-6-yl)acetamide Trifluoroacetic acid (12 mL, 150 mmol) was added to a stirred solution of Intermediate 150 (3 g, 5.10 mmol) in DCM (10 mL) at 0° C. The mixture was stirred at 20° C. for 18 h, then concentrated in vacuo. The crude residue was dissolved in acetonitrile (5 mL), followed by the addition of aqueous ammonium hydroxide solution (5 mL) at 0° C. The reaction mixture was stirred at 20° C. for 20 minutes, then concentrated in vacuo. The crude residue was partitioned between EtOAc and a 2M aqueous NaOH solution, and the aqueous phase was extracted with DCM:isopropanol (10%) (3×25 mL). The combined organic layers were concentrated in vacuo to afford the title compound (1.8 g, 74%) as a solid. $\delta_H$ (300 MHz, $CDCl_3$) 9.38 (s, 1H), 8.28 (s, 1H), 8.10 (s, 1H), 4.22 (ddd, J 11.2, 6.9, 3.8 Hz, 2H), 3.93 (ddd, J 11.6, 7.6, 3.6 Hz, 2H), 3.51 (d, J 3.9 Hz, 1H), 2.05 (ddd, J 13.9, 7.7, 3.8 Hz, 4H), 1.86-1.57 (m, 8H), 1.49-1.04 (m, 6H). HPLC-MS (method 7): MH+ m/z 359, RT 0.60 minutes. $[\alpha]^{20}_D$=−77.80° (c 7.5, methanol).

Intermediate 152

Phenyl N-(2-oxospiro[indoline-3,4'-tetrahydropyran]-6-yl)carbamate

To a stirred solution of Intermediate 2 (500 mg, 2.3 mmol) and pyridine (0.222 mL, 2.74 mmol) in THF (10 mL) was added dropwise a solution of phenyl chloroformate (0.4 mL, 2.7 mmol) in THF (10 mL). The mixture was stirred for 18 h at 20° C., then diluted with EtOAc (30 mL) and washed with saturated aqueous NaHCO$_3$ solution (30 mL) followed by IN aqueous HCl solution (30 mL). The organic layer was dried over Na$_2$SO$_4$, filtered and evaporated to dryness. The residue was purified by flash chromatography on silica gel, eluting with a gradient of EtOAc in hexane (1:9 to 1:0), to yield the title compound (595 mg, 75%) as a white solid. $\delta_H$ (400 MHz, DMSO-d$_6$) 10.59-10.27 (m, 1H), 9.61-9.18 (m, 1H), 7.47-7.39 (m, 2H), 7.28-7.11 (m, 4H), 6.79-6.71 (m, 2H), 4.13-3.96 (m, 2H), 3.93-3.72 (m, 2H), 1.97-1.82 (m, 2H), 1.80-1.54 (m, 2H). HPLC-MS (Method 7): MH+ m/z 339, RT 1.12 minutes.

Intermediate 153

2-(tert-Butoxycarbonylamino)-2-(4-chloro-3-fluorophenyl)acetic acid

Di-tert-butyl dicarbonate (1.29 g, 5.89 mmol) was added to a stirred suspension of 2-amino-2-(4-chloro-3-fluorophenyl)acetic acid (1.0 g, 4.91 mmol) in THF (3.2 mL) and 1M aqueous sodium carbonate solution (9.8 mL, 9.8 mmol). The suspension was stirred at 20° C. under nitrogen for 16 h. The mixture was diluted with water (30 mL) and 1M aqueous sodium hydroxide solution (10 mL), then washed with tert-butyl methyl ether (2×50 mL). The combined organic layers were extracted with 1M aqueous sodium hydroxide solution (40 mL). The combined aqueous layers were acidified with concentrated hydrochloric acid (pH 2), and the aqueous phase was extracted with ethyl acetate (3×60 mL). The combined organic layers were washed with brine (50 mL) and dried over anhydrous magnesium sulfate, then filtered and concentrated in vacuo, to afford the title compound (1.52 g, 96%) as a white solid. $\delta_H$ (250 MHz, DMSO-d$_6$) 13.06 (br s, 1H), 7.70 (d, J 8.3 Hz, 1H), 7.58 (t, J 8.1 Hz, 1H), 7.47 (dd, J 10.5, 1.9 Hz, 1H), 7.29 (dd, J 8.2, 1.9 Hz, 1H), 5.18 (d, J 8.6 Hz, 1H), 1.39 (s, 9H). HPLC-MS (method 3): MNa+ m/z 326, RT 1.77 minutes.

Intermediate 154 tert-Butyl N-[1-(4-Chloro-3-fluorophenyl)-2-oxo-2-({2-oxo-1-[2-(trimethylsilyl)ethoxy-methyl]spiro[pyrrolo[3,2-c]pyridine-3,4'-tetrahydropyran]-6-yl}amino)ethyl]carbamate HATU (999 mg, 2.63 mmol) was added to a stirred suspension of Intermediate 57 (765 mg, 2.19 mmol), Intermediate 153 (700 mg, 2.19 mmol) and DIPEA (0.9 mL, 5.47 mmol) in DCM (25 mL). The mixture was stirred at 20° C. under nitrogen for 16 h, then partitioned between DCM (50 mL) and water (50 mL). The aqueous layer was separated and washed with DCM (2×50 mL). The combined organic layers were dried over anhydrous magnesium sulfate, filtered and concentrated in vacuo. The residue was purified by flash column chromatography, using a gradient of ethyl acetate in heptane (0-100%), to give the title compound (937 mg, 67%) as an orange solid. $\delta_H$ (500 MHz, DMSO-d$_6$) 11.01 (s, 1H), 8.61 (s, 1H), 7.95 (s, 1H), 7.84 (d, J 7.8 Hz, 1H), 7.77-7.65 (m, 2H), 7.55 (d, J 8.3 Hz, 1H), 5.67 (d, J 7.5 Hz, 1H), 5.21 (d, J 11.2 Hz, 1H), 5.19 (d, J 11.3 Hz, 1H), 4.16-4.08 (m, 2H), 4.02-3.91 (m, 2H), 3.69-3.53 (m, 2H), 2.03-1.89 (m, 2H), 1.88-1.76 (m, 2H), 1.53 (s, 9H), 1.07-0.86 (m, 2H), 0.00 (s, 9H). HPLC-MS (method 3): MH+ m/z 635, RT 2.19 minutes.

Intermediate 155

2-Amino-2-(4-chloro-3-fluorophenyl)-N-{2-oxo-1-[2-(trimethylsilyl)ethoxymethyl]spiro-[pyrrolo[3,2-c]pyridine-3,4'-tetrahydropyran]-6-yl}acetamide hydrochloride Hydrogen chloride solution in 1,4-dioxane (4M, 3.66 mL, 14.64 mmol) was added to a stirred solution of Intermediate 154 (929 mg, 1.46 mmol) in MeOH (16 mL) under nitrogen at r.t. The reaction mixture was stirred at r.t. overnight, then concentrated in vacuo, to afford the title compound (759 mg, 78%) as a yellow-orange solid. $\delta_H$ (500 MHz, DMSO-d$_6$) 11.53 (br s, 1H), 9.17 (br s, 2H), 8.64 (s, 1H), 8.01-7.84 (m, 2H), 7.81 (dd, J 10.2, 1.8 Hz, 1H), 7.64 (d, J 8.3 Hz, 1H), 5.54-5.39 (m, 1H), 5.29-5.12 (m, 2H), 4.21-4.08 (m, 2H), 4.02-3.93 (m, 2H, obs), 3.66-3.55 (m, 2H), 2.03-1.74 (m, 4H), 1.05-0.88 (m, 2H), 0.00 (s, 9H). HPLC-MS (method 3): MH+ m/z 535, RT 1.85 minutes.

Intermediate 156

N-[1-(4-Chloro-3-fluorophenyl)-2-oxo-2-({2-oxo-1-[2-(trimethylsilyl)ethoxymethyl]-spiro[pyrrolo[3,2-c]pyridine-3,4'-tetrahydropyran]-6-yl}amino)ethyl]-2-ethylpyrazole-3-carboxamide HATU (206 mg, 0.54 mmol) was added to a stirred suspension of Intermediate 155 (300 mg, 0.45 mmol), 1-ethyl-1H-pyrazole-5-carboxylic acid (63 mg, 0.45 mmol) and DIPEA (0.28 mL, 1.58 mmol) in DCM (6 mL). The mixture was stirred at 20° C. under nitrogen for 16 h, then partitioned between DCM (25 mL) and water (25 mL). The aqueous layer was separated and washed with DCM (2×25 mL). The combined organic layers were dried over anhydrous magnesium sulfate, filtered and concentrated in vacuo. The residue was purified by flash column chromatography, using a gradient of ethyl acetate in heptane (0-100%), to afford the title compound (311 mg, 89%) as an orange gum. $\delta_H$ (500 MHz, DMSO-d$_6$) 11.16 (s, 1H), 9.12 (d, J 7.0 Hz, 1H), 8.62 (s, 1H), 8.00 (s, 1H), 7.84-7.71 (m, 2H), 7.63 (d, J 2.0 Hz, 1H), 7.60 (dd, J 8.4, 1.8 Hz, 1H), 7.20 (d, J 2.1 Hz, 1H), 6.05 (d, J 7.0 Hz, 1H), 5.21 (d, J 11.2 Hz, 1H), 5.18 (d, J 11.2 Hz, 1H), 4.59 (q, J 7.2 Hz, 2H), 4.16-4.09 (m, 2H), 4.04-3.90 (m, 2H), 3.66-3.55 (m, 2H), 2.02-1.89 (m, 2H), 1.89-1.78 (m, 2H), 1.41 (t, J 7.1 Hz, 3H), 1.04-0.90 (m, 2H), 0.00 (s, 9H). HPLC-MS (method 3): MH+ m/z 657, RT 2.11 minutes.

Intermediate 157

2-(tert-Butoxycarbonylamino)-2-(4-fluoro-3-methylphenyl)acetic acid

Di-tert-butyl dicarbonate (1.43 g, 6.55 mmol) was added to a stirred suspension of 2-amino-2-(4-fluoro-3-methylphenyl)acetic acid (1.0 g, 5.46 mmol) in THF (3.6 mL) and 1M aqueous sodium carbonate solution (10.9 mL, 10.9 mmol). The suspension was stirred at 20° C. under nitrogen for 16 h. The mixture was diluted with water (30 mL) and 1M aqueous sodium hydroxide solution (10 mL), then washed with tert-butyl methyl ether (2×50 mL). The combined organic layers were extracted with 1M aqueous sodium hydroxide solution (40 mL). The combined aqueous layers were acidified with concentrated hydrochloric acid (pH 2) and extracted with ethyl acetate (3×60 mL). The combined organic layers were washed with brine (50 mL) and dried over magnesium sulfate, then filtered and concentrated in vacuo, to afford the title compound (1.26 g, 77%) as a clear orange oil. $\delta_H$ (250 MHz, DMSO-$d_6$) 12.77 (br s, 1H), 7.53 (d, J 8.0 Hz, 1H), 7.32 (dd, J 7.4, 2.1 Hz, 1H), 7.29-7.19 (m, 1H), 7.17-7.03 (m, 1H), 5.06 (d, J 8.2 Hz, 1H), 2.22 (d, J 1.7 Hz, 3H), 1.39 (s, 9H). HPLC-MS (method 3): MNa+ m/z 306, RT 1.77 minutes.

Intermediate 158 tert-Butyl N-[1-(4-fluoro-3-methylphenyl)-2-oxo-2-({2-oxo-1-[2-(trimethylsilyl)ethoxy-methyl]spiro[pyrrolo[3,2-c]pyridine-3,4'-tetrahydropyran]-6-yl}amino)ethyl]carbamate HATU (1.06 g, 2.79 mmol) was added to a stirred suspension of Intermediate 57 (812 mg, 2.32 mmol), Intermediate 157 (700 mg, 2.32 mmol) and DIPEA (0.96 mL, 5.81 mmol) in DCM (27 mL). The mixture was stirred at 20° C. under nitrogen for 16 h, then partitioned between DCM (50 mL) and water (50 mL). The aqueous layer was separated and washed with DCM (2×50 mL). The combined organic layers were dried over anhydrous magnesium sulfate, filtered and concentrated in vacuo. The residue was purified by flash column chromatography, using a gradient of ethyl acetate in heptane (0-100%), to give the title compound (1.09 g, 76%) as a yellow solid. $\delta_H$ (500 MHz, DMSO-$d_6$) 10.86 (s, 1H), 8.58 (s, 1H), 7.96 (s, 1H), 7.60 (d, J 7.7 Hz, 1H), 7.55 (dd, J 7.4, 1.8 Hz, 1H), 7.52-7.45 (m, 1H), 7.29-7.17 (m, 1H), 5.55 (d, J 7.4 Hz, 1H), 5.18 (s, 2H), 4.14-4.07 (m, 2H), 4.00-3.86 (m, 2H), 3.65-3.54 (m, 2H), 2.40-2.28 (m, 3H), 1.99-1.87 (m, 2H), 1.87-1.74 (m, 2H), 1.51 (s, 9H), 1.08-0.83 (m, 2H), 0.00 (s, 9H). HPLC-MS (method 3): MH+ m/z 615, RT 2.17 minutes.

Intermediate 159

2-Amino-2-(4-fluoro-3-methylphenyl)-N-{2-oxo-1-[2-(trimethylsilyl)ethoxymethyl]spiro-[pyrrolo[3,2-c]pyridine-3,4'-tetrahydropyran]-6-yl}acetamide hydrochloride Hydrogen chloride solution in 1,4-dioxane (4M, 4.44 mL, 17.73 mmol) was added to a stirred solution of Intermediate 158 (1.09 g, 1.73 mmol) in MeOH (19 mL) under nitrogen at r.t. The reaction was stirred at r.t. overnight, then concentrated in vacuo, to afford the title compound (1.1 g, quantitative) as a yellow-orange solid. $\delta_H$ (500 MHz, DMSO-$d_6$) 11.40 (br s, 1H), 8.99 (br d, J 4.2 Hz, 2H), 8.61 (s, 1H), 7.91 (s, 1H), 7.67-7.62 (m, 1H), 7.61-7.56 (m, 1H), 7.37 (t, J 9.1 Hz, 1H), 5.38-5.27 (m, 1H), 5.26-5.13 (m, 2H), 4.17-4.05 (m, 2H, obs.), 3.98-3.88 (m, 2H), 3.64-3.54 (m, 2H), 2.36 (s, 3H), 1.99-1.72 (m, 4H), 1.01-0.88 (m, 2H), 0.00 (s, 9H). HPLC-MS (method 3): MH+ m/z 515, RT 1.80 minutes.

Intermediate 160

2-Ethyl-N-[1-(4-fluoro-3-methylphenyl)-2-oxo-2-({2-oxo-1-[2-(trimethylsilyl)ethoxy-methyl]spiro[pyrrolo[3,2-c]pyridine-3,4'-tetrahydropyran]-6-yl}amino)ethyl]pyrazole-3-carboxamide HATU (226 mg, 0.59 mmol) was added to a stirred suspension of Intermediate 159 (300 mg, 0.50 mmol), 1-ethyl-1H-pyrazole-5-carboxylic acid (69 mg, 0.50 mmol), and DIPEA (0.30 mL, 1.73 mmol) in DCM (6 mL). The mixture was stirred at 20° C. under nitrogen for 16 h, then partitioned between DCM (25 mL) and water (25 mL). The aqueous layer was separated and washed with DCM (2×25 mL). The combined organic layers were dried over anhydrous magnesium sulfate, filtered and concentrated in vacuo. The residue was purified by flash column chromatography, using a gradient of ethyl acetate in heptane (0-100%), to give the title compound (425 mg, 78%) as an orange gum. $\delta_H$ (500 MHz, DMSO-$d_6$) 10.90 (s, 1H), 8.87 (d, J 6.9 Hz, 1H), 8.47 (s, 1H), 7.89 (s, 1H), 7.51-7.46 (m, 2H), 7.45-7.39 (m, 1H), 7.19-7.12 (m, 1H), 7.06 (d, J 2.1 Hz, 1H), 5.83 (d, J 6.8 Hz, 1H), 5.11-5.03 (m, 2H), 4.46 (q, J 7.1 Hz, 2H), 4.07-3.95 (m, 2H), 3.89-3.78 (m, 2H), 3.51-3.43 (m, 2H), 2.24 (d, J 1.4 Hz, 3H), 1.88-1.76 (m, 2H), 1.75-1.63 (m, 2H), 1.28 (t, J 7.1 Hz, 3H), 0.85-0.78 (m, 2H), -0.12 (s, 9H). HPLC-MS (method 3): MH+ m/z 637, RT 2.08 minutes.

Example 1

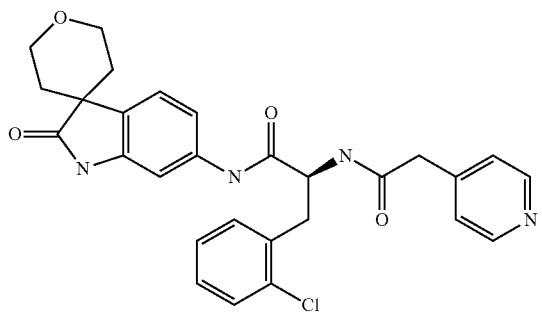 [SMILES: O=C(Cc1ccncc1)N[C@@H](Cc1ccccc1Cl)C(=O)Nc1ccc2c(c1)NC(=O)C21CCOCC1]

(2S)-3-(2-Chlorophenyl)-N-(2-oxospiro[indoline-3,4'-tetrahrahdropyran]-6-yl)-2-{[2-(pyridin-4-yl)acetyl]amino}propenamide and (2R)-3-(2-Chlorophenyl)-N-(2-oxospiro-[indoline-3,4'-tetrahydropyran]-6-yl)-2-{[2-(pyridin-4-yl)acetyl]amino}propanamide DIPEA (40 µL, 0.24 mmol) was added to a stirred suspension of Intermediate 2 (40 mg, 0.18 mmol), Intermediate 5 (61 mg, 0.19 mmol) and HATU (77 mg, 0.20 mmol) in anhydrous THF (1 mL). The mixture was stirred at 20° C. under nitrogen for 16 h, then quenched with saturated aqueous sodium carbonate solution (6 mL) and stirred for 30 minutes at 20° C. The mixture was diluted with water (6 mL) and partitioned with DCM/isopropanol (4:1; 30 mL). The organic phase was separated using a hydrophobic frit, then the aqueous layer was extracted with 4:1 DCM/isopropanol (2×20 mL). The filtrate was concentrated in vacuo. The resulting crude orange gum was separated by preparative HPLC (method 10) to afford the title compound (54 mg, 54% yield, 46% ee) as an off-white powder after freeze-drying. $\delta_H$ (500 MHz, DMSO-$d_6$) 10.39 (s, 1H), 10.09 (s, 1H), 8.63 (d, J 8.3 Hz, 1H), 8.45-8.38 (m, 2H), 7.42 (d, J 8.1 Hz, 1H), 7.39 (dd, J 7.8, 1.3 Hz, 1H), 7.33-7.27 (m, 2H), 7.23 (td, J 7.6, 1.9 Hz, 1H), 7.19 (td, J 7.4, 1.4 Hz, 1H), 7.16-7.12 (m, 2H), 7.06 (dd, J 8.1, 1.9 Hz, 1H), 4.79 (td, J 8.5, 6.1 Hz, 1H), 4.01 (ddd, J 11.1, 7.2, 3.6 Hz, 2H), 3.79 (ddd, J 11.1, 7.0, 3.7 Hz, 2H), 3.52 (d, J 14.3 Hz, 1H), 3.48 (d, J 14.3 Hz, 1H), 3.17 (dd, J 14.1, 5.9 Hz, 1H), 3.04 (dd, J 14.1, 8.7 Hz, 1H), 1.77-1.68 (m, 2H), 1.67-1.56 (m, 2H). uPLC-MS (method 2): MH+ m/z 519, RT 2.60 minutes. Chiral SFC method 12, Chiralcel OD-H 25 cm, 25% methanol-75% carbon dioxide, 4 mL/minute: RT 5.29 minutes (27%, R); RT 6.12 minutes (73%, S).

The racemate (29 mg) was separated by chiral preparative SFC method 15, Lux Cellulose-1 21.2×250 mm, 5 µm column, isocratic 25% MeOH (+0.1% NH$_4$OH), to afford the (S) enantiomer (eutomer) (3 mg) and the (R) enantiomer (5 mg) as off-white powders. Chiral SFC method 13, Lux Cellulose-1 4.6×150 mm, 3 µm column, flow rate 3.5 mL/minute, isocratic 25% MeOH+0.1% NH$_4$OH: RT 5.62 minutes (100%, R); RT 6.35 minutes (100%, S).

Example 2

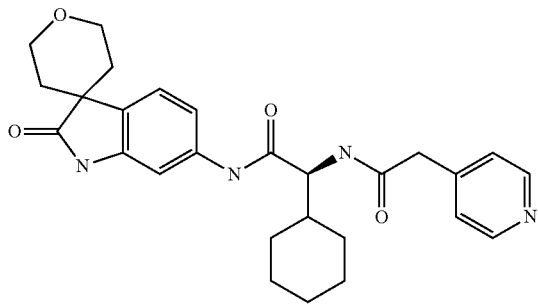 [SMILES: O=C(Cc1ccncc1)N[C@H](C(=O)Nc1ccc2c(c1)NC(=O)C21CCOCC1)C1CCCCC1]

(2S)-2-Cyclohexyl-N-(2-oxospiro[indoline-3,4'-tetrahydropyran]-6-yl)-2-{[2-(pyridin-4-yl)acetyl]amino}acetamide and (2R)-2-Cyclohexyl-N-(2-oxospiro[indoline-3,4'-tetrahydropyran]-6-yl)-2-{[2-(pyridin-4-yl)acetyl]amino}acetamide HATU (90 mg, 0.24 mmol) was added to a stirred suspension of Intermediate 8 (62 mg, 0.22 mmol) and Intermediate 2 (50 mg, 0.23 mmol) in anhydrous DMF (1.1 mL). The suspension was stirred at 20° C. for 16 h, then quenched with saturated aqueous sodium carbonate solution (3 mL) and water (3 mL) and stirred at 20° C. for 1 h. The mixture was diluted with water (6 mL), then the material was extracted with DCM (3×10 mL) and 4:1 DCM/isopropanol (3×15 mL), using a hydrophobic frit to separate the phases. The organic filtrates were combined and concentrated in vacuo. The resulting crude orange gum was separated by preparative HPLC (method 10) to afford the title compound (77 mg, 70% yield, 64% ee) as an off-white powder after freeze-drying. δ$_H$ (500 MHz, DMSO-d$_6$) 10.39 (br s, 1H), 10.12 (s, 1H), 8.50-8.45 (m, 2H), 8.42 (d, J 8.5 Hz, 1H), 7.43 (d, J 8.1 Hz, 1H), 7.36 (d, J 1.9 Hz, 1H), 7.32-7.25 (m, 2H), 7.09 (dd, J 8.1, 1.9 Hz, 1H), 4.29 (t, J 8.1 Hz, 1H), 4.01 (ddd, J 11.1, 7.2, 3.6 Hz, 2H), 3.80 (ddd, J 11.0, 7.0, 3.7 Hz, 2H), 3.61 (d, J 14.1 Hz, 1H), 3.56 (d, J 14.1 Hz, 1H), 1.79-1.49 (m, 10H), 1.23-0.92 (m, 5H). uPLC-MS (method 2): MH+ m/z 477, RT 2.61 minutes. Chiral SFC, Method 12, Chiralcel OD-H 25 cm, 30% methanol-70% carbon dioxide, 4 mL/minute: RT 2.30 minutes (18%, R); RT 2.62 minutes (82%, S).

Example 3

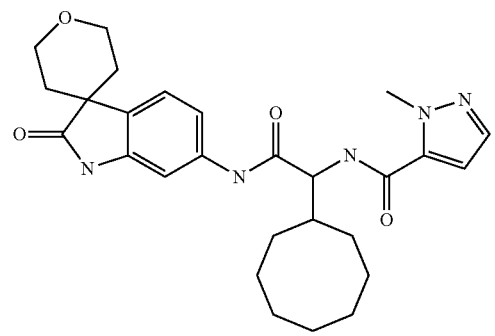 [SMILES: Cn1nccc1C(=O)NC(C(=O)Nc1ccc2c(c1)NC(=O)C21CCOCC1)C1CCCCCCC1]

N-{1-Cyclooctyl-2-oxo-2-[(2-oxospiro[indoline-3,4'-tetrahydropyran]-6-yl)amino]ethyl}-2-methylpyrazole-3-carboxamide HATU (210 mg, 0.55 mmol) was added to a stirred solution of Intermediate 2 (100 mg, 0.46 mmol) and Intermediate 13 (150 mg, 0.5 mmol) in anhydrous DMF (4 mL) under a nitrogen atmosphere. The mixture was stirred at 20° C. for 15 h, then quenched with saturated aqueous sodium hydrogen carbonate solution (20 mL) and water (20 mL). The material was extracted with ethyl acetate (3×20 mL). The combined organic layers were washed with brine (2×20 mL) and dried over sodium sulfate, then filtered and concentrated in vacuo. The residue was purified by preparative HPLC (method 10) to afford to afford the title compound (116 mg, 51%) as a white solid. δ$_H$ (500 MHz, DMSO-d$_6$) 10.39 (s, 1H), 10.22 (s, 1H), 8.52 (d, J 8.6 Hz, 1H), 7.45 (d, J 2.1 Hz, 1H), 7.43 (d, J 8.2 Hz, 1H), 7.38 (d, J 1.9 Hz, 1H), 7.12 (dd, J 8.1, 1.9 Hz, 1H), 7.05 (d, J 2.1 Hz, 1H), 4.44 (t, J 8.9 Hz, 1H), 4.05-3.96 (m, 2H), 4.03 (s, 3H), 3.80 (ddd, J 11.0, 6.9, 3.7 Hz, 2H), 2.22-2.09 (m, 1H), 1.77-1.34 (m, 18H). uPLC-MS (method 2): MH+ m/z 494, RT 3.29 minutes.

Example 4

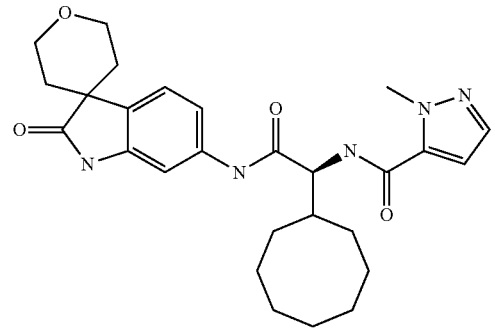 [SMILES: Cn1nccc1C(=O)N[C@H](C(=O)Nc1ccc2c(c1)NC(=O)C21CCOCC1)C1CCCCCCC1]

N-{(1S or 1R)-1-Cyclooctyl-2-oxo-2-[(2-oxospiro[indoline-3,4'-tetrahydropyran]-6-yl)-amino]ethyl}-2-methylpyrazole-3-carboxamide Example 3 (100 mg) was separated by chiral preparative SFC method 15, ChiralPak IC 20×250 mm, 5 µm column, flow rate 100 mL/minute, 25-40% MeOH (+0.1% NH₄OH) gradient, to afford the title compound (eutomer) (25 mg) as an off-white powder. Chiral SFC method 13, ChiralPak IC 4.6×150 mm, 3 μm column, flow rate 3.5 mL/minute, 25-40% MeOH (+0.1% NH₄OH) gradient: RT 3.76 minutes (100% ee, eutomer).

Example 5

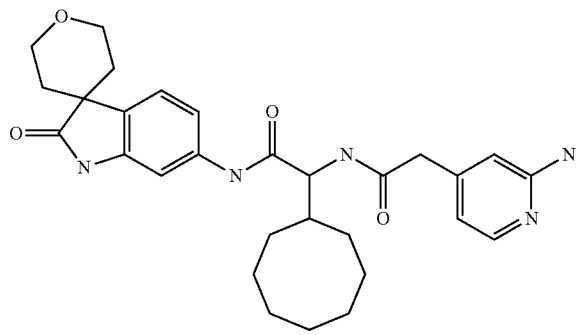 [SMILES: Nc1cc(CC(=O)NC(C(=O)Nc2ccc3c(c2)NC(=O)C32CCOCC2)C2CCCCCCC2)ccn1]

2-{[2-(2-Aminopyridin-4-yl)acetyl]amino}-2-cyclooctyl-N-(2-oxospiro[indoline-3,4'-tetrahydropyran]-6-yl)acetamide Trifluoroacetic acid (0.18 mL, 2.34 mmol) was added to a stirred solution of Intermediate 19 (142 mg, 0.23 mmol) in DCM (5 mL) at 20° C. under a nitrogen atmosphere. The reaction mixture was stirred at 20° C. overnight and diluted with dichloromethane (25 mL), then cautiously quenched with saturated aqueous sodium hydrogen carbonate solution (30 mL) and extracted with 1:1 isopropanol/chloroform (3×30 mL). The combined organic layers were dried over sodium sulfate, then filtered and concentrated in vacuo. The residue was separated by preparative HPLC (method 10) to afford the title compound (42.9 mg, 36%) as a white solid. $\delta_H$ (500 MHz, DMSO-$d_6$) 10.38 (s, 1H), 10.13 (s, 1H), 8.32 (d, J 8.9 Hz, 1H), 7.78 (d, J 5.4 Hz, 1H), 7.42 (d, J 8.1 Hz, 1H), 7.35 (d, J 1.8 Hz, 1H), 7.09 (dd, J 8.1, 1.8 Hz, 1H), 6.45-6.42 (m, 1H), 6.37 (s, 1H), 6.03 (br s, 2H), 4.30 (t, J 8.4 Hz, 1H), 4.00 (ddd, J 11.0, 7.1, 3.6 Hz, 2H), 3.79 (ddd, J 11.0, 6.9, 3.7 Hz, 2H), 3.43 (d, J 13.8 Hz, 1H), 3.37-3.24 (m, 1H, obscured by water peak), 2.01-1.92 (m, 1H), 1.77-1.70 (m, 2H), 1.68-1.26 (m, 16H). uPLC-MS (method 1): MH+ m/z 520, RT 2.04 minutes.

Example 6

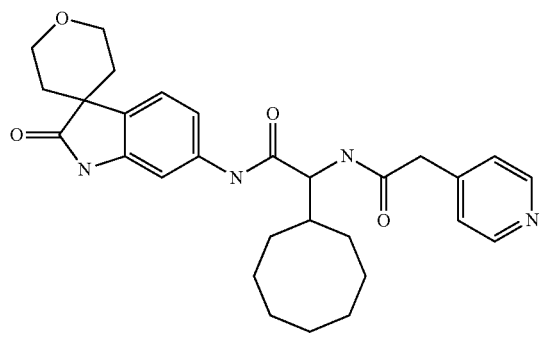 [SMILES: O=C(Cc1ccncc1)NC(C(=O)Nc1ccc2c(c1)NC(=O)C21CCOCC1)C1CCCCCCC1]

2-Cyclooctyl-N-(2-oxospiro[indoline-3,4'-tetrahydropyran]-6-yl)-2-{[2-(pyridin-4-yl)-acetyl]amino}acetamide HATU (228 mg, 0.6 mmol) was added to a stirred suspension of Intermediate 21 (171 mg, 0.55 mmol) and Intermediate 2 (126 mg, 0.58 mmol) in anhydrous DMF (2.9 mL). The mixture was stirred at 20° C. under nitrogen for 16 h, then quenched with saturated aqueous sodium carbonate solution (6 mL) and water (6 mL) and stirred at 20° C. for 30 minutes. The mixture was diluted with water (12 mL), then the material was extracted with 4:1 DCM/isopropanol (3×15 mL), using a hydrophobic frit to separate the phases. The organic filtrate was concentrated in vacuo. The resulting crude orange gum was separated by preparative HPLC (method 9) to afford the title compound (268 mg, 96%) as an off-white powder after freeze-drying. $\delta_H$ (500 MHz, DMSO-$d_6$) 10.38 (br s, 1H), 10.14 (br s, 1H), 8.52-8.39 (m, 3H), 7.42 (d, J 8.1 Hz, 1H), 7.35 (d, J 1.8 Hz, 1H), 7.30-7.25 (m, 2H), 7.08 (dd, J 8.1, 1.8 Hz, 1H), 4.31 (t, J 8.3 Hz, 1H), 4.00 (ddd, J 11.0, 7.1, 3.6 Hz, 2H), 3.79 (ddd, J 11.0, 7.0, 3.7 Hz, 2H), 3.60 (d, J 14.0 Hz, 1H), 3.53 (d, J 14.0 Hz, 1H), 2.02-1.91 (m, 1H), 1.78-1.68 (m, 2H), 1.68-1.26 (m, 16H). uPLC-MS (method 2): MH+ m/z 505, RT 2.97 minutes.

Example 7

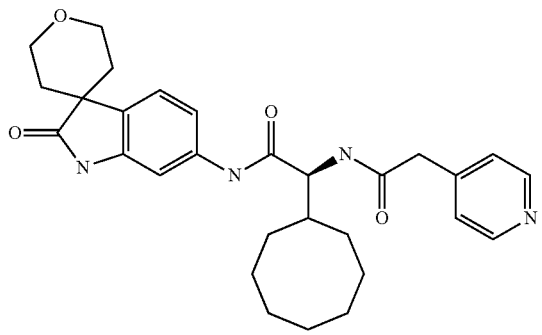 [SMILES: O=C(Cc1ccncc1)N[C@H](C(=O)Nc1ccc2c(c1)NC(=O)C21CCOCC1)C1CCCCCCC1]

(2S or 2R)-2-Cyclooctyl-N-(2-oxospiro[indoline-3,4'-tetrahydropyran]-6-yl)-2-{[2-(pyridin-4-yl)acetyl]amino}acetamide Example 6 (268 mg) was separated by chiral preparative SFC method 14 (18:82 methanol-carbon dioxide, Chiralcel OD-H 25 cm column at 15 mL/minute) to afford the title compound (eutomer) (65 mg) as an off-white powder after freeze-drying. Chiral SFC method 12, Chiralcel OD-H 25 cm, 20% methanol-80% carbon dioxide, 4 mL/minute: RT 7.97 minutes (100%).

Example 8

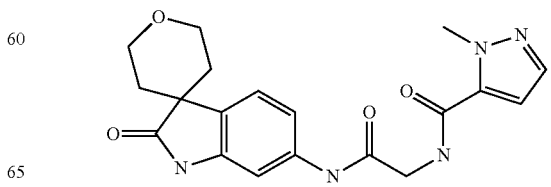

2-Methyl-N-{2-oxo-2-[(2-oxospiro[indoline-3,4'-tetrahydropyran]-6-yl)amino]ethyl}-pyrazole-3-carboxamide HATU (67 mg, 0.18 mmol) was added to a stirred solution of Intermediate 2 (32 mg, 0.15 mmol) and Intermediate 23 (30 mg, 0.16 mmol) in anhydrous DMF (1 mL) under a nitrogen atmosphere. The mixture was stirred at 20° C. for 18 h, then quenched by the addition of saturated aqueous sodium hydrogen carbonate solution (7 mL) and water (7 mL). The material was extracted with ethyl acetate (3×7 mL). The combined organic layers were washed with brine (2×7 mL) and dried over sodium sulfate, then filtered and concentrated in vacuo. The residue was separated by preparative HPLC (method 10) to afford the title compound (16 mg, 27%) as a white solid. $\delta_H$ (500 MHz, DMSO-$d_6$) 10.41 (s, 1H), 10.07 (s, 1H), 8.81 (t, J 5.9 Hz, 1H), 7.48 (d, J 2.0 Hz, 1H), 7.44 (d, J 8.1 Hz, 1H), 7.36 (d, J 1.7 Hz, 1H), 7.08 (dd, J 8.1, 1.8 Hz, 1H), 6.92 (d, J 2.0 Hz, 1H), 4.05 (s, 3H), 4.03-3.97 (m, 4H), 3.80 (ddd, J 11.1, 7.0, 3.7 Hz, 2H), 1.77-1.69 (m, 2H), 1.67-1.58 (m, 2H). uPLC-MS (method 1): MH+ m/z 384, RT 1.60 minutes.

Example 9

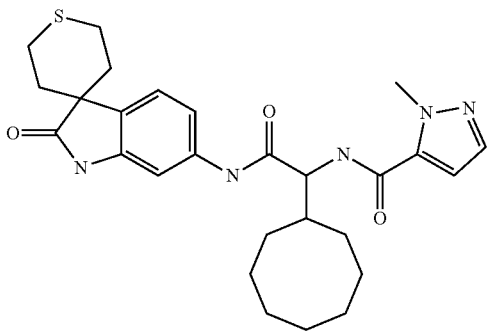 [SMILES: Cn1nccc1C(=O)NC(C(=O)Nc1ccc2c(c1)NC(=O)C21CCNCC1)C1CCCCCCC1]

N-{1-Cyclooctyl-2-oxo-2-[(2-oxospiro[indoline-3,4'-tetrahydrothiopyran]-6-yl)amino]-ethyl}-2-methylpyrazole-3-carboxamide HATU (10 mg, 0.03 mmol) was added to a stirred solution of Intermediate 28 (4.8 mg, 0.014 mmol) and Intermediate 13 (6 mg, 0.02 mmol) in anhydrous DMF (0.2 mL). The mixture was stirred at 20° C. under nitrogen for 16 h, then quenched with saturated aqueous sodium carbonate solution (10 mL) and stirred for 30 minutes at 20° C. The mixture was partitioned with 4:1 DCM/isopropanol (10 mL). The organic phase was separated using a hydrophobic frit, then the aqueous layer was extracted with 4:1 DCM/isopropanol (2×10 mL). The filtrate was concentrated in vacuo. The resulting crude tan film was separated by preparative HPLC (method 8) to afford the title compound (0.5 mg, 6%) as a white powder. $\delta_H$ (500 MHz, CDCl$_3$) 10.32 (br s, 1H), 8.36 (s, 1H), 8.17 (s, 1H), 7.91 (d, J 6.9 Hz, 1H), 7.40 (d, J 2.1 Hz, 1H), 7.22 (d, J 8.0 Hz, 1H), 6.87 (d, J 2.1 Hz, 1H), 6.67 (dd, J 8.0, 1.9 Hz, 1H), 4.41-4.30 (m, 1H), 4.13 (s, 3H), 3.32-3.16 (m, 2H), 2.78-2.65 (m, 2H), 2.35-2.24 (m, 1H), 2.13-1.99 (m, 2H), 1.98-1.82 (m, 3H), 1.77-1.11 (m, 13H). uPLC-MS (method 1): MH+ m/z 510, RT 3.54 minutes.

Example 10

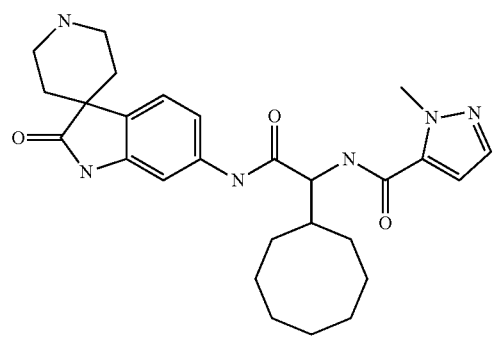

N-{1-Cyclooctyl-2-oxo-2-[(2-oxospiro[indoline-3,4'-piperidine]-6-yl)amino]ethyl}-2-methylpyrazole-3-carboxamide A suspension of Intermediate 31 (34.5 mg, 0.06 mmol) and 10% palladium on carbon (50% water wet, 25 mg, 0.012 mmol) in ethanol (4 mL) was stirred under an atmosphere of hydrogen at 20° C. for 18 h. The solids were removed by filtration through a kieselguhr pad, washing with ethanol (8×25 mL). The filtrate was concentrated in vacuo. The resulting crude tan powder was separated by preparative HPLC (method 11), then the product-containing fractions were treated with saturated aqueous sodium carbonate solution (pH 11) and extracted with 4:1 DCM/isopropanol (3×20 mL) using a hydrophobic frit. The organic filtrate was concentrated in vacuo to afford the title compound (12 mg, 39%) as a white powder after freeze-drying. $\delta_H$ (500 MHz, DMSO-$d_6$) 10.31 (s, 1H), 10.21 (s, 1H), 8.53 (d, J 8.5 Hz, 1H), 7.45 (d, J 2.0 Hz, 1H), 7.39 (d, J 8.1 Hz, 1H), 7.37 (d, J 1.7 Hz, 1H), 7.11 (dd, J 8.2, 1.9 Hz, 1H), 7.05 (d, J 2.1 Hz, 1H), 4.44 (t, J 8.9 Hz, 1H), 4.03 (s, 3H), 3.10-2.99 (m, 2H), 2.94-2.83 (m, 2H), 2.21-2.11 (m, 1H), 1.73-1.34 (m, 18H). uPLC-MS (method 1): MH+ m/z 493, RT 2.09 minutes.

Example 11

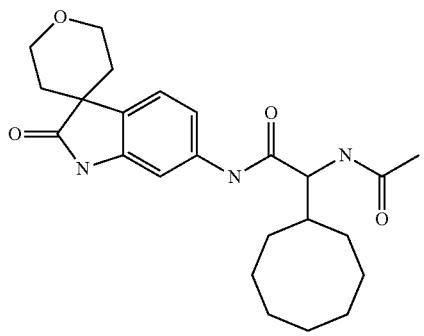 [SMILES: CC(=O)NC(C(=O)Nc1ccc2c(c1)NC(=O)C21CCOCC1)C1CCCCCCC1]

2-Acetamido-2-cyclooctyl-N-(2-oxospiro[indoline-3,4'-tetrahydropyran]-6-yl)acetamide Acetyl chloride (15 μL, 0.21 mmol) was added to a solution of Intermediate 35 (70 mg, 0.18 mmol) and DIPEA (63 µL, 0.36 mmol) in DCM (2 mL) and the solution was stirred at 20° C. for 18 h. Additional acetyl chloride (7.5 µL, 0.11 mmol) was added, and the reaction mixture was stirred at 20° C. for a further 2 h. To the reaction mixture were added saturated aqueous sodium hydrogen carbonate solution (20 mL) and 1:1 isopropanol-chloroform (20 mL). The layers were separated and the aqueous layer was extracted with 1:1 isopropanol-chloroform (2×20 mL). The combined organic layers were dried over magnesium sulfate, then filtered and concentrated in vacuo. The residue was separated by preparative HPLC (method 9) to afford the title compound (34.1 mg, 44%) as a white solid. $\delta_H$ (500 MHz, DMSO-d$_6$) 10.38 (s, 1H), 10.09 (s, 1H), 8.06 (d, J 8.8 Hz, 1H), 7.42 (d, J 8.1 Hz, 1H), 7.36 (d, J 1.8 Hz, 1H), 7.09 (dd, J 8.1, 1.9 Hz, 1H), 4.29 (t, J 8.5 Hz, 1H), 4.00 (ddd, J 11.1, 7.2, 3.6 Hz, 2H), 3.80 (ddd, J 11.1, 6.9, 3.7 Hz, 2H), 1.94 (s, 1H), 1.87 (s, 3H), 1.77-1.68 (m, 2H), 1.69-1.27 (m, 16H). uPLC-MS (method 2): MH+ m/z 428, RT 2.94 minutes.

Example 12

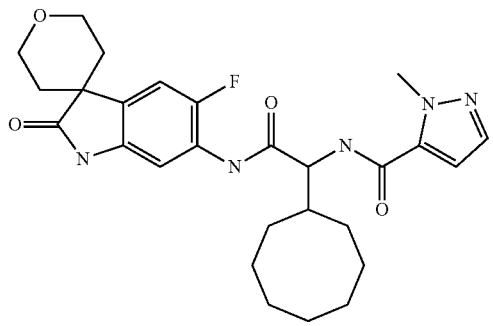 [SMILES: Cn1nccc1C(=O)NC(C(=O)Nc1cc2c(cc1F)C1(CCOCC1)C(=O)N2)C1CCCCCCC1]

N-{1-Cyclooctyl-2-[(5-fluoro-2-oxospiro[indoline-3,4'-tetrahydropyran]-6-yl)amino]-2-oxoethyl}-2-methylpyrazole-3-carboxamide Selectfluor™ (35 mg, 0.101 mmol) was added to a solution of Example 3 (50 mg, 0.101 mmol) in anhydrous DMF (1 mL). The reaction mixture was stirred at room temperature for 16 h, then saturated aqueous sodium hydrogen carbonate solution (5 mL) and 1:1 isopropanol-chloroform (20 mL) were added. The layers were separated and the aqueous layer was extracted with 1:1 isopropanol-chloroform (2×20 mL). The combined organic layers were dried over magnesium sulfate, filtered and concentrated in vacuo. The residue was separated by preparative HPLC (method 9) to afford the title compound (13.1 mg, 25%) as a white solid. $\delta_H$ (500 MHz, DMSO-d$_6$) 10.34 (s, 1H), 9.94 (s, 1H), 8.48 (s, 1H), 7.50 (d, J 10.4 Hz, 1H), 7.45 (d, J 2.0 Hz, 1H), 7.39 (d, J 6.5 Hz, 1H), 7.02 (d, J 2.0 Hz, 1H), 4.59 (d, J 8.6 Hz, 1H), 4.03 (s, 3H), 4.02-3.96 (m, 2H), 3.84-3.72 (m, 2H), 2.22-2.14 (m, 1H), 1.75-1.61 (m, 7H), 1.59-1.38 (m, 11H). $^{19}$F NMR (250 MHz, DMSO-d$_6$) δ −132.6. uPLC-MS (method 1) MH+ m/z 512, RT 3.21 minutes.

Example 13

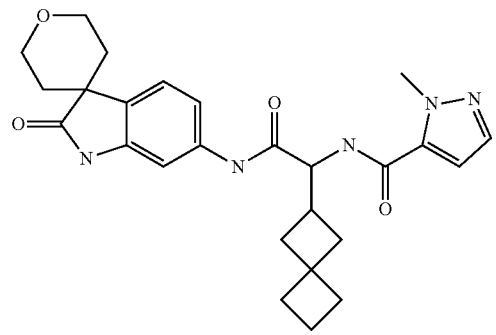 [SMILES: Cn1nccc1C(=O)NC(C(=O)Nc1ccc2c(c1)NC(=O)C21CCOCC1)C1CC2(CCC2)C1]

2-Methyl-N-{2-oxo-2-[(2-oxospiro[indoline-3,4'-tetrahydropyran]-6-yl)amino]-1-(spiro-[3.3]heptan-2-yl)ethyl}pyrazole-3-carboxamide To a stirred solution of Intermediate 2 (25 mg, 0.115 mmol) and Intermediate 39 (30 mg, 0.11 mmol) in anhydrous THF (1.1 mL) was added acetic acid (0.066 mL, 11.50 mmol). The reaction mixture was stirred at 60° C. for 3 h, then the solvent was removed in vacuo. The residue was purified by preparative HPLC (method 11) to afford the title compound (24.6 mg, 44%) as a white solid. $\delta_H$ (500 MHz, DMSO-d$_6$) 10.40 (s, 1H), 10.10 (s, 1H), 8.46 (d, J 7.6 Hz, 1H), 7.46 (d, J 2.0 Hz, 1H), 7.43 (d, J 8.1 Hz, 1H), 7.36 (d, J 1.8 Hz, 1H), 7.10 (dd, J 8.2, 1.9 Hz, 1H), 7.01 (d, J 2.1 Hz, 1H), 4.43 (dd, J 9.9, 7.6 Hz, 1H), 4.02 (s, 3H), 4.02-3.96 (m, 2H), 3.80 (ddd, J 11.0, 7.0, 3.7 Hz, 2H), 2.60-2.53 (m, 1H), 2.12 (ddd, J 11.2, 7.8, 3.7 Hz, 1H), 2.02-1.92 (m, 4H), 1.91-1.83 (m, 2H), 1.79-1.74 (m, 3H), 1.74-1.70 (m, 2H), 1.65-1.58 (m, 2H). uPLC-MS (method 1): MH+ m/z 478, RT 2.87 minutes.

Example 14

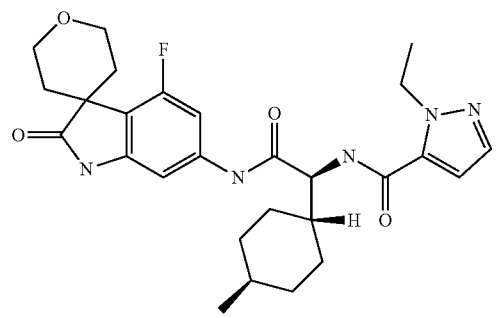 [SMILES: CCn1nccc1C(=O)N[C@H](C(=O)Nc1cc(F)c2c(c1)NC(=O)C21CCOCC1)[C@H]1CC[C@H](C)CC1]

2-Ethyl-N-{(1S)-2-[(4-fluoro-2-oxospiro[indoline-3,4'-tetrahydropyran]-6-yl)amino]-1-(4-methylcyclohexyl)-2-oxoethyl}pyrazole-3-carboxamide (Trans Isomer)

DIPEA (70 µL, 0.42 mmol) was added to a suspension of 1-ethyl-1H-pyrazole-5-carboxylic acid (40 mg, 0.29 mmol) and HATU (105 mg, 0.28 mmol) in DCM (1 mL) at 20° C. under nitrogen. The suspension was stirred at 20° C. under nitrogen for 1 h. A solution of Intermediate 52 (81.14 mg, 0.21 mmol) in DCM (1 mL) was added. The mixture was stirred at 20° C. under nitrogen for 16 h, then diluted with DCM (20 mL) and quenched with saturated aqueous sodium carbonate solution (10 mL) and water (10 mL). The biphasic mixture was stirred at 20° C. for 30 minutes, then the organic phase was separated using a hydrophobic frit. The aqueous layer was extracted with DCM (3×20 mL), and the organic filtrate was concentrated in vacuo. The resultant tan powder was separated by sequential preparative HPLC (method 10), then flash column chromatography, using a gradient of ethyl acetate in heptane (25-100%), to afford, after freeze-drying, the title compound (26.8 mg, 25%) as a white powder. $\delta_H$ (500 MHz, DMSO-$d_6$) 10.59 (s, 1H), 10.35 (s, 1H), 8.52 (d, J 7.9 Hz, 1H), 7.47 (d, J 2.0 Hz, 1H), 7.12-7.06 (m, 2H), 7.01 (d, J 2.0 Hz, 1H), 4.45 (q, J 7.2 Hz, 2H), 4.30 (t, J 8.5 Hz, 1H), 4.06 (t, J 10.2 Hz, 2H), 3.80-3.69 (m, 2H), 2.01 (ddd, J 14.3, 10.5, 4.4 Hz, 2H), 1.90-1.73 (m, 2H), 1.73-1.64 (m, 4H), 1.60-1.48 (m, 1H), 1.35-1.22 (m, 4H), 1.22-1.11 (m, 1H), 1.08-0.97 (m, 1H), 0.93-0.80 (m, 5H). uPLC-MS (method 1): MH+ m/z 512, RT 3.36 minutes.

Example 15

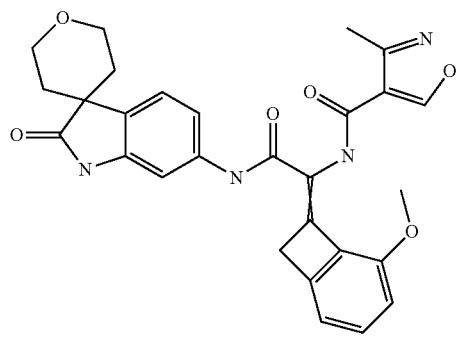 [SMILES: COc1cccc2c1C(=C(NC(=O)/C(=C/O)C(C)=N)C(=O)Nc1ccc3c(c1)NC(=O)C31CCOCC1)C2]

2-(5-Methoxybicyclo[4.2.0]octa-1,3,5-trien-7-ylidene)-2-[(3-methylisoxazol-4-yl)-formamido]-N-(2-oxo-1,2-dihydrospiro[indole-3,4'-oxane]-6-yl) acetamide (Isomer 1)

Acetic acid (0.1 mL, 1.75 mmol) was added to a solution of Intermediate 56 (50 mg, 0.17 mmol) and Intermediate 57 (89%, 42 mg, 0.17 mmol) in anhydrous THF (1.1 mL). The reaction mixture was stirred at 60° C. for 18 h, then cooled to room temperature and concentrated in vacuo. The residue was purified by preparative HPLC (method 11) to afford, after freeze-drying, the title compound (20.3 mg, 22%) as a white solid. $\delta_H$ (500 MHz, DMSO-$d_6$) 10.41 (br s, 1H), 9.80 (br s, 1H), 9.59 (br s, 1H), 9.46 (s, 1H), 7.50 (d, J 1.9 Hz, 1H), 7.45 (d, J 8.2 Hz, 1H), 7.36 (dd, J 8.4, 7.2 Hz, 1H), 7.24 (dd, J 8.2, 1.9 Hz, 1H), 6.91 (d, J 7.1 Hz, 1H), 6.87 (d, J 8.6 Hz, 1H), 4.03 (ddd, J 11.0, 7.1, 3.6 Hz, 2H), 3.91 (s, 2H), 3.82 (ddd, J 11.0, 6.9, 3.6 Hz, 2H), 3.57 (s, 3H), 2.42 (s, 3H), 1.87-1.72 (m, 2H), 1.70-1.56 (m, 2H). HPLC-MS (method 1): MH+ m/z 515, RT 2.66 minutes.

Example 16

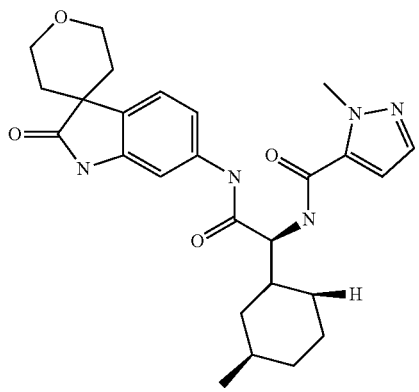

(2S)-2-[(1-Methyl-1H-pyrazol-5-yl)formamido]-N-(2-oxo-1,2-dihydrospiro[indole-3,4'-oxane]-6-yl)-2-[(1r,4S)-4-methylcyclohexyl]acetamide (Trans Isomer)

To a stirred solution of Intermediate 50 (370 mg, 1 mmol) in dry DMF (8 mL) was added 1-methyl-1H-pyrazole-5-carboxylic acid (127 mg, 1.01 mmol), then HATU (455 mg, 1.2 mmol) and DIPEA (0.5 mL, 3.03 mmol), at r.t. The reaction mixture was stirred for at least 18 hours. With external cooling, water (40 mL) was added to the reaction mixture. The precipitated solid was filtered off and washed with water (2×10 ml). The filter cake was dissolved in ethyl acetate (20 mL) and the excess water was separated. The organic layer was washed with a 1:1 mixture of water and brine (10 mL), and brine (10 mL), then dried over magnesium sulphate, filtered and concentrated in vacuo. The crude residue was adsorbed onto silica gel (3.1 g), using DCM, and purified by automated chromatography, using a gradient of ethyl acetate in heptane (0-100%), then a gradient of methanol in ethyl acetate (0-7%). The isolated material was triturated in a mixture of ethyl acetate (2 mL) and heptane (20 mL), then filtered off, washed with heptane (4×10 mL) and dried, to afford the title compound (279 mg, 58%) as a white solid. $\delta_H$ (500 MHz, DMSO-$d_6$) 10.38 (s, 1H), 10.17 (s, 1H), 8.47 (d, J 8.1 Hz, 1H), 7.45 (d, J 2.0 Hz, 1H), 7.43 (d, J 8.1 Hz, 1H), 7.39 (d, J 1.8 Hz, 1H), 7.11 (dd, J 8.2, 1.9 Hz, 1H), 7.05 (d, J 2.1 Hz, 1H), 4.34 (t, J 8.5 Hz, 1H), 4.04-3.96 (m, 5H), 3.84-3.75 (m, 2H), 1.85 (d, J 12.6 Hz, 1H), 1.81-1.65 (m, 5H), 1.65-1.52 (m, 3H), 1.34-1.12 (m, 2H), 1.09-0.97 (m, 1H), 0.93-0.79 (m, 5H). uPLC-MS (method 1): MH+ m/z 480, RT 3.01 minutes. Chiral SFC (method 12, Chiralcel OD-H 25 cm, 10% methanol-90% carbon dioxide, 4 mL/min): RT 15.31 minutes (100%).

Example 17

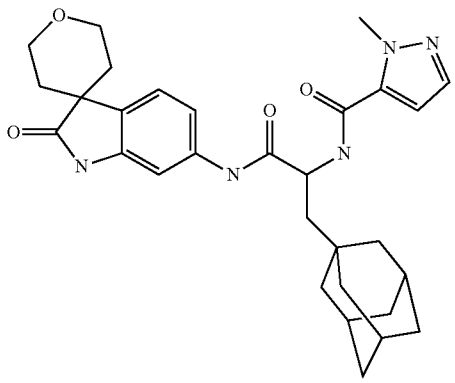 [SMILES: Cn1nccc1C(=O)NC(CC12CC3CC(CC(C3)C1)C2)C(=O)Nc1ccc2c(c1)NC(=O)C21CCOCC1]

N-{1-(1-Adamantylmethyl)-2-oxo-2-[(2-oxospiro[indoline-3,4'-tetrahydropyran]-6-yl)-amino]ethyl}-2-methylpyrazole-3-carboxamide To a stirred suspension of Intermediate 63 (20 mg, 0.038 mmol) in a mixture of THF (1 mL) and ethanol (1 mL) was added 10% palladium on charcoal (50% wet, 4 mg, 20 wt %) as a single portion. The reaction mixture was transferred to a pressure vessel and placed under a hydrogen gas atmosphere. Stirring was continued at ambient temperature for 24 h under 7 bar hydrogen pressure. A second aliquot of 10% palladium on charcoal (50% wet, 4 mg, 20 wt %) was added as a single portion and stirring was continued at ambient temperature for 30 h under 7 bar hydrogen pressure. A third aliquot of 10% palladium on charcoal (50% wet, 4 mg, 20 wt %) was added as a single portion and stirring was continued at ambient temperature for 70 h under 7 bar hydrogen pressure (total reaction time 124 h). The catalyst was removed by filtration over kieselguhr, rinsing the filter cake with THF (2×5 mL). The solvent was concentrated in vacuo to afford the title compound (9.5 mg, 42%) as a beige solid. $\delta_H$ (500 MHz, DMSO-d$_6$) 10.40 (s, 1H), 10.07 (s, 1H), 8.58 (d, J 7.9 Hz, 1H), 7.46 (d, J 2.0 Hz, 1H), 7.43 (d, J 8.2 Hz, 1H), 7.36 (d, J 1.8 Hz, 1H), 7.13 (dd, J 8.2, 1.9 Hz, 1H), 7.00 (d, J 2.1 Hz, 1H), 4.65 (td, J 8.4, 3.8 Hz, 1H), 4.03 (s, 3H), 4.04-3.97 (m, 2H), 3.80 (ddd, J 11.3, 7.2, 3.8 Hz, 2H), 1.91 (s, 3H), 1.76-1.69 (m, 3H), 1.68-1.62 (m, 6H), 1.57-1.50 (m, 7H), 1.23 (s, 2H). uPLC-MS (method 2): MH+ m/z 532, RT 3.54 minutes.

Example 18

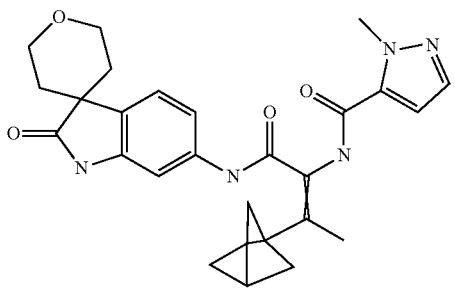 [SMILES: CC(=C(NC(=O)c1ccnn1C)C(=O)Nc1ccc2c(c1)NC(=O)C21CCOCC1)C12CC3CC31C2]

N-{2-(Bicyclo[1.1.1]pentan-1-yl)-1-[(2-oxospiro[indoline-3,4'-tetrahydropyran]-6-yl)-carbamoyl]prop-1-enyl}-2-methylpyrazole-3-carboxamide To a stirred solution of Intermediate 2 (50 mg, 0.229 mmol) and Intermediate 64 (59 mg, 0.229 mmol) in anhydrous THF (2.3 mL) was added acetic acid (0.131 mL, 2.29 mmol). The reaction mixture was stirred at 60° C. for 16 h. The solvent was removed in vacuo, and the residue was triturated in a 1:1 mixture of DCM and diethyl ether (1 mL). The solid was collected by filtration, rinsing the cake with diethyl ether (2×0.5 mL), then dried in vacuo, to afford the title compound (79.3 mg, 71%) as a beige solid. $\delta_H$ (500 MHz, DMSO-d$_6$) 10.37 (s, 1H), 10.08 (s, 1H), 9.55 (s, 1H), 7.51 (d, J 2.1 Hz, 1H), 7.49 (d, J 1.6 Hz, 1H), 7.43 (d, J 8.2 Hz, 1H), 7.16 (dd, J 8.2, 1.8 Hz, 1H), 7.07 (d, J 2.1 Hz, 1H), 4.02 (s, 3H), 4.02-3.97 (m, 2H), 3.80 (ddd, J 11.0, 7.0, 3.7 Hz, 2H), 2.45 (s, 1H), 2.02 (s, 6H), 1.81 (s, 3H), 1.74 (ddd, J 12.9, 6.8, 3.5 Hz, 2H), 1.62 (ddd, J 13.1, 7.0, 3.7 Hz, 2H). uPLC-MS (method 1): MH+ m/z 476, RT 2.69 minutes.

Example 19

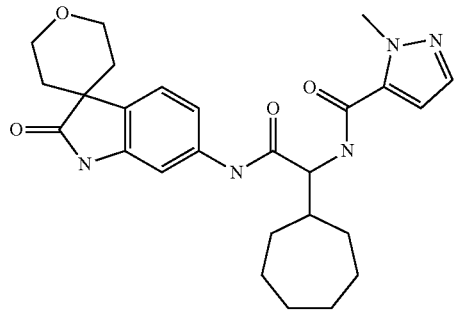 [SMILES: Cn1nccc1C(=O)NC(C(=O)Nc1ccc2c(c1)NC(=O)C21CCOCC1)C1CCCCCC1]

N-{1-Cycloheptylidene-2-oxo-2-[(2-oxospiro[indoline-3,4'-tetrahydropyran]-6-yl)amino]-ethyl}-2-methylpyrazole-3-carboxamide To a stirred solution of Intermediate 2 (50 mg, 0.229 mmol) and Intermediate 65 (60 mg, 0.229 mmol) in anhydrous THF (2.3 mL) was added acetic acid (0.131 mL, 2.29 mmol). The reaction mixture was stirred at 60° C. for 6 h. Acetic acid (0.131 mL, 2.29 mmol) was added, and heating at 60° C. was continued for a further 21 h. The solvent was removed in vacuo, and the residue was purified by low pH preparative HPLC (method 11), to afford, after freeze-drying, the title compound (35.4 mg, 32%) as a white solid. $\delta_H$ (500 MHz, DMSO-d$_6$) 10.36 (s, 1H), 9.88 (s, 1H), 9.43 (s, 1H), 7.49 (d, J 2.0 Hz, 1H), 7.46 (s, 1H), 7.41 (d, J 8.2 Hz, 1H), 7.14 (dd, J 8.2, 1.7 Hz, 1H), 7.07 (d, J 1.9 Hz, 1H), 4.01 (s, 3H), 4.04-3.98 (m, 2H), 3.80 (ddd, J 11.1, 7.0, 3.7 Hz, 2H), 2.56-2.53 (m, 2H), 2.43-2.39 (m, 2H), 1.73 (ddd, J 12.9, 6.9, 3.6 Hz, 2H), 1.66-1.58 (m, 6H), 1.52 (s, 4H). uPLC-MS (method 1): MH+ m/z 478, RT 2.74 minutes.

Example 20 (Procedure I)

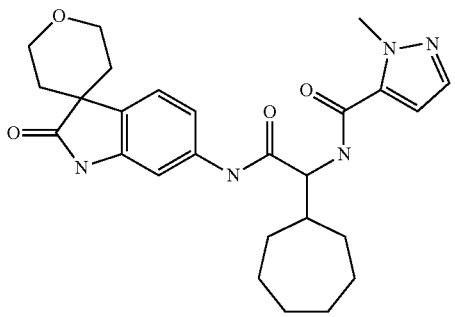 [SMILES: Cn1nccc1C(=O)NC(C(=O)Nc1ccc2c(c1)NC(=O)C21CCOCC1)C1CCCCCC1]

N-{1-Cycloheptyl-2-oxo-2-[(2-oxospiro[indoline-3,
4'-tetrahydropyran]-6-yl)amino]-ethyl}-2-methylpyrazole-3-carboxamide To a stirred solution of Intermediate 2 (30 mg, 0.137 mmol) and Intermediate 66 (60%, 60 mg, 0.137 mmol) in anhydrous THF (1.4 mL) was added acetic acid (0.131 mL, 2.29 mmol). The reaction mixture was stirred at 60° C. for 16 h. The solvent was removed in vacuo, and the residue was purified by low pH preparative HPLC (method 11), to afford, after freeze-drying, the title compound (23.8 mg, 36%) as a white solid. $\delta_H$ (500 MHz, DMSO-$d_6$) 10.39 (s, 1H), 10.19 (s, 1H), 8.48 (d, J 8.5 Hz, 1H), 7.45 (d, J 2.1 Hz, 1H), 7.43 (d, J 8.1 Hz, 1H), 7.38 (d, J 1.9 Hz, 1H), 7.12 (dd, J 8.1, 2.0 Hz, 1H), 7.05 (d, J 2.1 Hz, 1H), 4.45 (t, J 8.6 Hz, 1H), 4.02 (s, 3H), 4.00 (ddd, J 11.0, 7.1, 3.8 Hz, 2H), 3.80 (ddd, J 11.0, 7.0, 3.7 Hz, 2H), 2.11-2.03 (m, 1H), 1.73 (ddd, J 13.0, 6.8, 3.5 Hz, 3H), 1.67-1.59 (m, 5H), 1.57-1.29 (m, 8H). uPLC-MS (method 1): MH+ m/z 480, RT 2.95 minutes.

Example 21

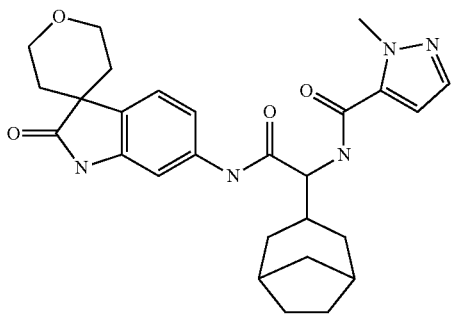 [SMILES: Cn1nccc1C(=O)NC(C(=O)Nc1ccc2c(c1)NC(=O)C21CCOCC1)C1CC2CCC(C2)C1]

N-{1-(Bicyclo[3.2.1]octan-3-yl)-2-oxo-2-[(2-oxospiro[indoline-3,4'-tetrahydropyran]-6-yl)amino]ethyl}-2-methylpyrazole-3-carboxamide (Single Isomer)

To a stirred solution of Intermediate 2 (80 mg, 0.367 mmol) and Intermediate 68 (90%, 111 mg, 0.367 mmol) in anhydrous THF (3.7 mL) was added acetic acid (0.210 mL, 3.67 mmol). The reaction mixture was stirred at 60° C. for 16 h. The solvent was removed in vacuo, and the residue was purified by low pH preparative HPLC (method 11). After freeze-drying, the resulting white solid (91.3 mg) was further separated using chiral SFC (method 14, Chiralcel OD-H 25 cm, 20% methanol-80% carbon dioxide, 15 mL/min) to afford the title compound (30 mg, 36%) as a white solid. $\delta_H$ (500 MHz, DMSO-$d_6$) 10.39 (s, 1H), 10.21 (s, 1H), 8.48 (d, J 8.6 Hz, 1H), 7.45 (d, J 2.0 Hz, 1H), 7.43 (d, J 8.2 Hz, 1H), 7.39 (d, J 1.7 Hz, 1H), 7.15 (dd, J 8.2, 1.8 Hz, 1H), 7.03 (d, J 2.0 Hz, 1H), 4.52 (dd, J 10.8, 8.8 Hz, 1H), 4.04 (s, 3H), 4.00 (ddd, J 11.0, 7.2, 3.5 Hz, 2H), 3.80 (ddd, J 11.0, 6.9, 3.7 Hz, 2H), 2.21-2.11 (m, 3H), 1.90 (dt, J 14.1, 7.2 Hz, 1H), 1.81-1.75 (m, 1H), 1.73 (ddd, J 12.6, 6.8, 3.5 Hz, 2H), 1.67-1.63 (m, 3H), 1.63-1.58 (m, 2H), 1.57-1.51 (m, 1H), 1.46 (d, J 10.9 Hz, 1H), 1.23 (dd, J 13.7, 5.8 Hz, 2H), 1.20-1.14 (m, 1H). uPLC-MS (method 1): MH+ m/z 492, RT 3.03 minutes. Chiral SFC (method 12, Chiralcel OD-H 25 cm, 20% methanol-80% carbon dioxide, 4 mL/min): RT 9.05 minutes (99%).

Example 22

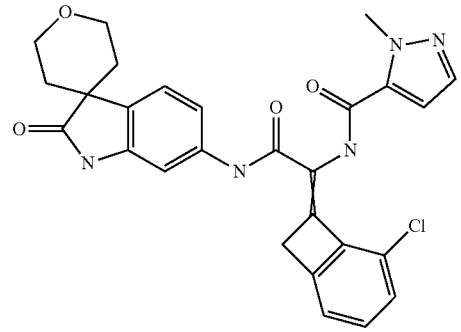 [SMILES: Cn1nccc1C(=O)NC(C(=O)Nc1ccc2c(c1)NC(=O)C21CCOCC1)=C1Cc2cccc(Cl)c21]

N-{1-(5-Chloro-7-bicyclo[4.2.0]octa-1(6),2,4-trienylidene)-2-oxo-2-[(2-oxospiro-[indoline-3,4'-tetrahydropyran]-6-yl)amino]ethyl}-2-methylpyrazole-3-carboxamide (Isomer 1)

To a stirred solution of Intermediate 2 (60 mg, 0.275 mmol) and Intermediate 69 (80 mg, 0.275 mmol) in anhydrous THF (1.8 mL) was added acetic acid (0.158 mL, 2.75 mmol). The reaction mixture was stirred at 60° C. for 16 h. The solvent was removed in vacuo, and the residue was triturated in DCM (1 mL), to afford the title compound (100 mg, 70%) as a off-white solid. $\delta_H$ (500 MHz, DMSO-$d_6$) 10.42 (s, 1H), 10.16 (s, 2H), 7.53 (d, J 2.1 Hz, 1H), 7.50 (d, J 1.9 Hz, 1H), 7.46 (d, J 8.2 Hz, 1H), 7.38 (dd, J 8.2, 7.1 Hz, 1H), 7.33-7.27 (m, 2H), 7.22 (dd, J 8.2, 1.9 Hz, 1H), 7.14 (d, J 2.1 Hz, 1H), 4.06 (s, 3H), 4.02 (ddd, J 11.0, 7.2, 3.7 Hz, 2H), 3.94 (s, 2H), 3.82 (ddd, J 11.1, 7.0, 3.8 Hz, 2H), 1.78-1.72 (m, 2H), 1.64 (ddd, J 13.1, 7.0, 3.6 Hz, 2H). uPLC-MS (method 1): MH+ m/z 518, RT 2.71 minutes.

Example 23

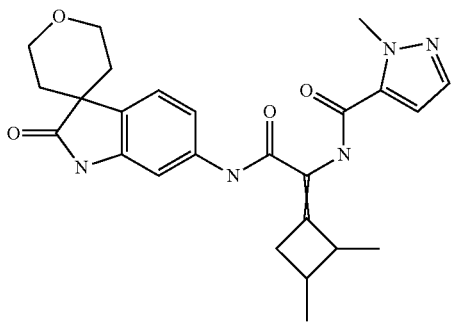 [SMILES: CC1CC(=C(NC(=O)c2ccnn2C)C(=O)Nc2ccc3c(c2)NC(=O)C32CCOCC2)C1C]

N-{1-(2,3-Dimethylcyclobutylidene)-2-oxo-2-[(2-oxospiro[indoline-3,4'-tetrahydro-pyran]-6-yl)amino]ethyl}-2-methylpyrazole-3-carboxamide (Isomer 5)

To a stirred solution of Intermediate 2 (50 mg, 0.229 mmol) and Intermediate 70 (56 mg, 0.229 mmol) in anhydrous THF (2.3 mL) was added acetic acid (0.131 mL, 2.29 mmol). The reaction mixture was stirred at 60° C. for 16 h. The solvent was removed in vacuo, and the residue was purified by low pH preparative HPLC (method 11). After freeze-drying, the resulting white solid (72.5 mg) was further separated using chiral SFC (method 14, Chiralpak IC 25 cm, 25% methanol-75% carbon dioxide, 15 mL/min) to afford the title compound (4.8 mg, 4.5%) as a white solid. $\delta_H$ (500 MHz, CD$_3$OD) 7.51 (d, J 2.1 Hz, 1H), 7.41 (d, J 8.2 Hz, 1H), 7.39 (d, J 1.9 Hz, 1H), 7.10 (dd, J 8.1, 2.0 Hz, 1H), 6.92 (d, J 2.1 Hz, 1H), 4.16 (ddd, J 11.5, 7.6, 3.7 Hz, 2H), 4.13 (s, 3H), 3.92 (ddd, J 11.2, 6.8, 3.8 Hz, 2H), 3.33 (dd, J 3.7, 2.0 Hz, 1H), 3.22 (ddd, J 17.5, 8.7, 1.5 Hz, 1H), 2.84 (d, J 17.2 Hz, 1H), 2.66-2.57 (m, 1H), 1.87 (ddd, J 13.4, 6.7, 3.8 Hz, 2H), 1.76 (ddd, J 13.7, 7.6, 3.8 Hz, 2H), 1.11 (d, J 2.9 Hz, 3H), 1.10 (d, J 2.5 Hz, 3H). uPLC-MS (method 1): MH+ m/z 464, RT 2.52 minutes. Chiral SFC (method 12, Chiralpak IC 25 cm, 25% methanol-75% carbon dioxide, 4 mL/min): RT 17.86 minutes (90%, 100% ee).

Example 24 (Procedure A)

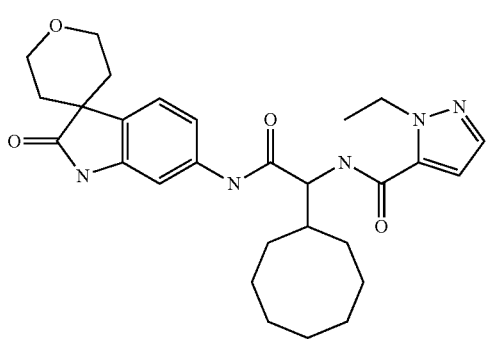 [SMILES: CCn1nccc1C(=O)NC(C(=O)Nc1ccc2c(c1)NC(=O)C21CCOCC1)C1CCCCCCC1]

N-{1-Cyclooctyl-2-oxo-2-[(2-oxospiro[indoline-3,4'-tetrahydropyran]-6-yl)amino]ethyl}-2-ethylpyrazole-3-carboxamide HATU (148 mg, 0.39 mmol) was added to a stirred suspension of Intermediate 35 (100 mg, 0.26 mmol) and 1-ethyl-1H-pyrazole-5-carboxylic acid (43.6 mg, 0.31 mmol) in anhydrous DMF (1 mL) and DIPEA (107 μL, 0.65 mmol). The suspension was stirred at 20° C. for 17 h. The reaction mixture was quenched with saturated aqueous sodium carbonate solution (5 mL) and water (5 mL), and stirred at 20° C. for 5 minutes, then extracted with tert-butyl methyl ether (2×20 mL). The combined organic extracts were washed with water (2×10 mL) and brine (10 mL), then dried over sodium sulfate, filtered and concentrated in vacuo. The resulting crude material was purified by flash column chromatography, using a gradient of tert-butyl methyl ether in heptane (0-100%) followed by a gradient of MeOH in tert-butyl methyl ether (0-10%), to afford, after freeze-drying, the title compound (85.7 mg, 59%) as a colourless solid. $\delta_H$ (500 MHz, CDCl$_3$) 10.22 (br s, 1H), 8.36 (s, 1H), 8.15 (s, 1H), 7.90 (d, J 6.6 Hz, 1H), 7.40 (d, J 2.1 Hz, 1H), 7.29-7.26 (m, 1H), 6.83 (d, J 2.0 Hz, 1H), 6.67 (dd, J 8.1, 1.9 Hz, 1H), 4.62-4.47 (m, 2H), 4.40-4.32 (m, 1H), 4.27-4.19 (m, 2H), 3.96-3.87 (m, 2H), 2.36-2.26 (m, 1H), 1.92-1.67 (m, 8H), 1.57-1.41 (m, 8H), 1.38 (t, J 7.2 Hz, 3H), 1.30-1.09 (m, 2H). uPLC-MS (method 1): MH+ m/z 508.4, RT 3.36 minutes.

Example 25

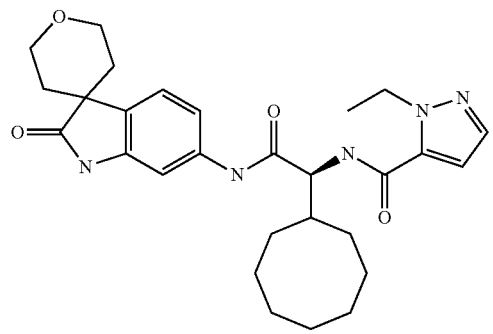 [SMILES: CCn1nccc1C(=O)N[C@H](C(=O)Nc1ccc2c(c1)NC(=O)C21CCOCC1)C1CCCCCCC1]

N-{(1S)-1-Cyclooctyl-2-oxo-2-[(2-oxospiro[indoline-3,4'-tetrahydropyran]-6-yl)amino]ethyl}-2-ethylpyrazole-3-carboxamide Example 24 (75 mg) was separated by chiral preparative SFC (method 14, Chiralpak IC 25 cm column, 70:30 carbon dioxide:MeOH, 15 mL/min) to afford the title compound (eutomer) (5 mg) as a white solid, together with the racemate (43 mg). The racemate was separated by chiral preparative SFC (method 14, Chiralpak IC 25 cm column, isocratic 70:30 carbon dioxide:MeOH, 15 mL/min) to afford more of the title compound (eutomer) (13.4 mg) as a white solid. $\delta_H$ (500 MHz, CDCl$_3$) 10.28 (s, 1H), 8.41 (s, 1H), 8.19 (s, 1H), 7.97 (d, J 7.7 Hz, 1H), 7.40 (d, J 2.0 Hz, 1H), 7.32-7.18 (m, 1H), 6.83 (d, J 2.0 Hz, 1H), 6.66 (dd, J 8.0, 1.8 Hz, 1H), 4.59-4.44 (m, 2H), 4.42-4.33 (m, 1H), 4.28-4.16 (m, 2H), 3.97-3.81 (m, 2H), 2.36 (d, J 8.7 Hz, 1H), 1.98-1.86 (m, 2H), 1.85-1.68 (m, 6H), 1.65-1.60 (m, 2H), 1.57-1.41 (m, 8H), 1.36 (t, J 7.2 Hz, 3H). uPLC-MS (method 1): MH+ m/z 508.3, RT 3.28 minutes. Chiral SFC (method 12, Chiralpak IC 25 cm column, isocratic 70:30 carbon dioxide:MeOH, 4 mL/min) RT 3.91 minutes (100%).

Example 26

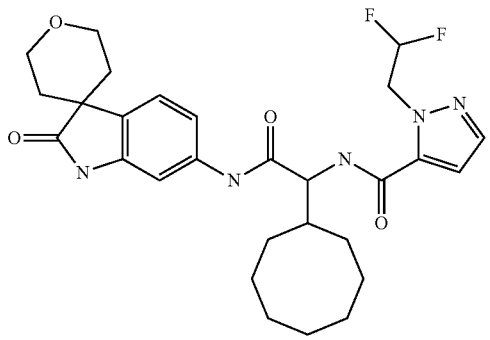 [SMILES: O=C(NC(C(=O)Nc1ccc2c(c1)NC(=O)C21CCOCC1)C1CCCCCCC1)c1ccnn1CC(F)F]

N-{1-Cyclooctyl-2-oxo-2-[(2-oxospiro[indoline-3,4'-tetrahydropyran]-6-yl)amino]ethyl}-2-(2,2-difluoroethyl)pyrazole-3-carboxamide Prepared from Intermediate 35 (46 mg, 0.12 mmol) and 2-(2,2-difluoroethyl)-pyrazole-3-carboxylic acid (25 mg, 0.14 mmol) in accordance with Procedure A, and purified by flash column chromatography using a gradient of tert-butyl methyl ether in heptane (0-100%) followed by a gradient of MeOH in tert-butyl methyl ether (0-20%), to give the title compound (20.6 mg, 29%) as a colourless solid. $\delta_H$ (500 MHz, CDCl$_3$) 10.30 (br s, 1H), 8.14-8.07 (m, 2H), 8.01 (d, J 7.2 Hz, 1H), 7.41 (d, J 2.0 Hz, 1H), 7.22 (d, J 8.0 Hz, 1H), 6.88 (d, J 2.0 Hz, 1H), 6.60 (dd, J 8.0, 1.8 Hz, 1H), 6.02 (tt, J 56.2, 4.5 Hz, 1H), 4.97-4.72 (m, 2H), 4.27 (t, J 9.0 Hz, 1H), 4.18-4.11 (m, 2H), 3.90-3.80 (m, 2H), 2.23 (d, J 9.0 Hz, 1H), 1.88-1.52 (m, 10H), 1.46-1.27 (m, 8H). uPLC-MS (method 1): MH+ m/z 544.3, RT 3.38 minutes.

Example 27

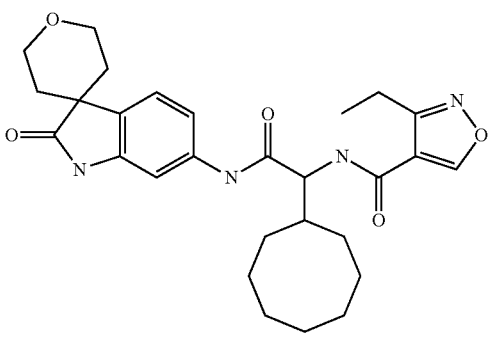 [SMILES: CCc1nocc1C(=O)NC(C(=O)Nc1ccc2c(c1)NC(=O)C21CCOCC1)C1CCCCCCC1]

N-{1-Cyclooctyl-2-oxo-2-[(2-oxospiro[indoline-3,4'-tetrahydropyran]-6-yl)amino]ethyl}-3-ethylisoxazole-4-carboxamide Prepared from Intermediate 35 (46 mg, 0.12 mmol) and 3-ethylisoxazole-4-carboxylic acid (20.2 mg, 0.14 mmol) in accordance with Procedure A, and purified by flash column chromatography using a gradient of tert-butyl methyl ether in heptane (0-100%) followed by a gradient of MeOH in tert-butyl methyl ether (0-20%), to give the title compound (14.1 mg, 21%) as a colourless solid. $\delta_H$ (500 MHz, DMSO-d$_6$) 10.31 (s, 1H), 10.14 (s, 1H), 9.32 (s, 1H), 8.41 (d, J 8.7 Hz, 1H), 7.37 (d, J 8.2 Hz, 1H), 7.31 (d, J 1.8 Hz, 1H), 7.05 (dd, J 8.1, 1.8 Hz, 1H), 4.39 (t, J 8.7 Hz, 1H), 3.98-3.89 (m, 2H), 3.79-3.67 (m, 2H), 2.77 (q, J 8.0, 7.5 Hz, 2H), 2.02 (m, 1H), 1.72-1.31 (m, 18H), 1.10 (t, J 7.5 Hz, 3H). uPLC-MS (method 1): MH+ m/z 509.3, RT 3.40 minutes.

Example 28

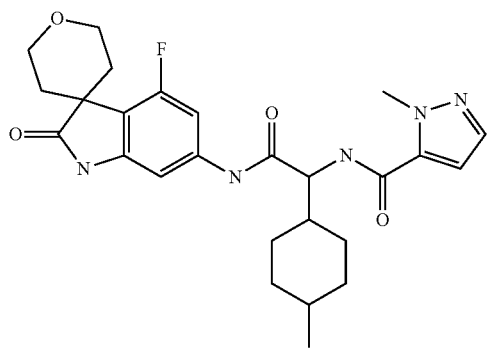 [SMILES: CC1CCC(C(NC(=O)c2ccnn2C)C(=O)Nc2cc(F)c3c(c2)NC(=O)C32CCOCC2)CC1]

N-{2-[(4-Fluoro-2-oxospiro[indoline-3,4'-tetrahydropyran]-6-yl)amino]-1-(4-methyl-cyclohexyl)-2-oxoethyl}-2-methylpyrazole-3-carboxamide 10% Palladium on charcoal (50% wet, 5.3 mg, 2.47 μmol) was added as a single portion to a stirred suspension of Intermediate 76 (73 mg, 0.1 mmol) in a mixture of THF (2.5 mL) and ethanol (2.5 mL). The reaction mixture was placed under a hydrogen gas atmosphere and stirred at 20° C. for 18 h. The catalyst was removed by filtration over kieselguhr, rinsing the filter cake with MeOH (2×15 mL). The solvent was concentrated in vacuo and the residue was dissolved in a mixture of THF (2.5 mL) and ethanol (2.5 mL). The solution was treated with 10% palladium on charcoal (50% wet, 52.52 mg, 0.02 mmol) as a single portion. The reaction mixture was placed under a hydrogen gas atmosphere and stirred at 20° C. for 4 h. The catalyst was removed by filtration over kieselguhr, rinsing the filter cake with MeOH (2×15 mL). The solvent was concentrated in vacuo. The resulting crude material was purified by preparative HPLC (method 20), then freeze-dried, to afford the title compound (7.2 mg, 14%) as a white solid. $\delta_H$ (500 MHz, CDCl$_3$) 10.38-10.10 (m, 1H), 8.70-8.41 (m, 1H), 7.94-7.74 (m, 2H), 7.43-7.37 (m, 1H), 6.91-6.81 (m, 1H), 6.48-6.39 (m, 1H), 4.63-4.31 (m, 1H), 4.28-4.22 (m, 2H), 4.15-4.09 (m, 3H), 3.97-3.88 (m, 2H), 2.29-2.16 (m, 2H), 2.11-1.96 (m, 1H), 1.95-1.83 (m, 1H), 1.80-1.68 (m, 4H), 1.37-1.25 (m, 2H), 1.21-1.06 (m, 2H), 0.99-0.84 (m, 5H). uPLC-MS (method 1): MH+ m/z 498.1, RT 3.18 minutes.

Example 29

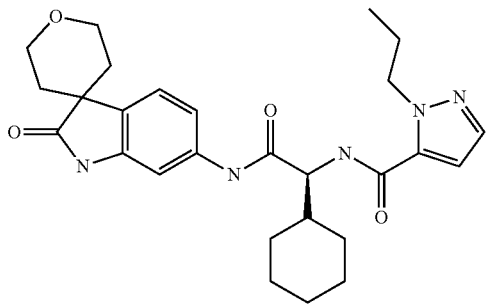 [SMILES: CCCn1nccc1C(=O)N[C@H](C(=O)Nc1ccc2c(c1)NC(=O)C21CCOCC1)C1CCCCC1]

N-{(1S)-1-Cyclohexyl-2-oxo-2-[(2-oxospiro[indoline-3,4'-tetrahydropyran]-6-yl)amino]-ethyl}-2-propylpyrazole-3-carboxamide Prepared from Intermediate 78 (50 mg, 0.14 mmol) and 2-propylpyrazole-3-carboxylic acid (25.9 mg, 0.17 mmol) in accordance with Procedure A, and purified by preparative HPLC (method 20), to give the title compound (33.5 mg, 44%) as a colourless solid. $\delta_H$ (500 MHz, DMSO-$d_6$) 10.39 (s, 1H), 10.17 (s, 1H), 8.48 (d, J 8.1 Hz, 1H), 7.48 (d, J 2.0 Hz, 1H), 7.44 (d, J 8.1 Hz, 1H), 7.39 (d, J 1.9 Hz, 1H), 7.12 (dd, J 8.2, 1.9 Hz, 1H), 7.01 (d, J 2.0 Hz, 1H), 4.41 (t, J 7.1 Hz, 2H), 4.38 (t, J 8.6 Hz, 1H), 4.06-3.97 (m, 2H), 3.89-3.75 (m, 2H), 1.92-1.78 (m, 2H), 1.78-1.66 (m, 6H), 1.66-1.53 (m, 4H), 1.26-1.09 (m, 4H), 1.08-0.97 (m, 1H), 0.77 (t, J 7.4 Hz, 3H). uPLC-MS (method 1): MH+ m/z 494.3, RT 3.04 minutes.

Example 30

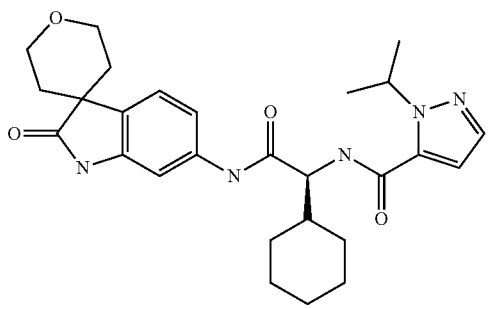 [SMILES: CC(C)n1nccc1C(=O)N[C@H](C(=O)Nc1ccc2c(c1)NC(=O)C21CCOCC1)C1CCCCC1]

N-{(1S)-1-Cyclohexyl-2-oxo-2-[(2-oxospiro[indoline-3,4'-tetrahydropyran]-6-yl)amino]-ethyl}-2-isopropylpyrazole-3-carboxamide Prepared from Intermediate 78 (50 mg, 0.14 mmol) and 2-isopropylpyrazole-3-carboxylic acid (25.9 mg, 0.17 mmol) in accordance with Procedure A, and purified by preparative HPLC (method 20), to give the title compound (35.3 mg, 49%) as a colourless solid. $\delta_H$ (500 MHz, DMSO-$d_6$) 10.39 (s, 1H), 10.17 (s, 1H), 8.45 (d, J 8.1 Hz, 1H), 7.50 (d, J 1.9 Hz, 1H), 7.44 (d, J 8.1 Hz, 1H), 7.40 (d, J 1.8 Hz, 1H), 7.12 (dd, J 8.2, 1.9 Hz, 1H), 6.95 (d, J 2.0 Hz, 1H), 5.39 (hept, J 6.5 Hz, 1H), 4.36 (t, J 8.5 Hz, 1H), 4.05-3.98 (m, 2H), 3.83-3.74 (m, 2H), 1.89-1.79 (m, 2H), 1.77-1.67 (m, 4H), 1.68-1.54 (m, 4H), 1.37 (d, J 6.6 Hz, 3H), 1.35 (d, J 6.6 Hz, 3H), 1.25-1.09 (m, 4H), 1.09-0.94 (m, 1H). uPLC-MS (method 1): MH+ m/z 494.2, RT 3.05 minutes.

Example 31

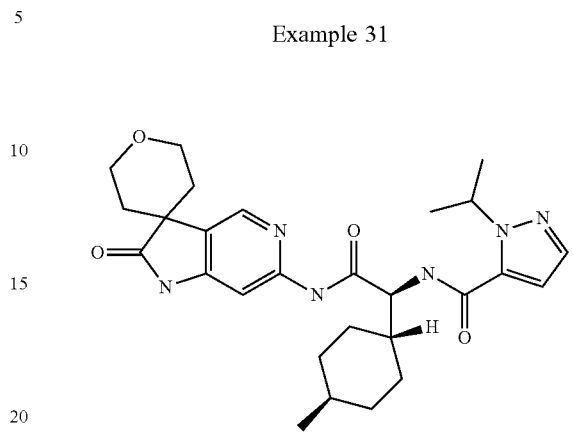

2-Isopropyl-N-{(1S)-1-(4-methylcyclohexyl)-2-oxo-2-[(2-oxospiro[1H-pyrrolo[3,2-c]-pyridine-3,4'-tetrahydropyran]-6-yl)amino]ethyl}pyrazole-3-carboxamide (Trans Isomer)

Trifluoroacetic acid (0.42 mL, 5.42 mmol) was added dropwise to a solution of Intermediate 79 (115 mg, 0.18 mmol) in DCM (1 mL) under a nitrogen atmosphere and cooled to 0° C. The reaction mixture was stirred at 20° C. for 18 h. The volatiles were removed in vacuo and the residue was dissolved in acetonitrile (1 mL) and aqueous ammonium hydroxide solution (1 mL). The reaction mixture was stirred at 20° C. for 15 minutes, then the volatiles were removed in vacuo. The residue was diluted with water (3 mL) and the aqueous phase was extracted with DCM (3×10 mL). The combined organic extracts were passed through a hydrophobic frit and dried under vacuum. The resulting crude material was purified by preparative HPLC (method 20) to afford the title compound (50.8 mg, 54%) as a white solid. $\delta_H$ (500 MHz, DMSO-$d_6$) 10.78 (s, 1H), 10.47 (s, 1H), 8.39-8.33 (m, 2H), 7.65 (s, 1H), 7.43 (d, J 1.9 Hz, 1H), 6.85 (d, J 1.9 Hz, 1H), 5.28 (h, J 6.5 Hz, 1H), 4.40 (t, J 8.3 Hz, 1H), 3.97-3.89 (m, 2H), 3.82-3.64 (m, 2H), 1.80-1.67 (m, 4H), 1.64-1.45 (m, 5H), 1.28 (dd, J 14.3, 6.6 Hz, 6H), 1.24-1.10 (m, 2H), 1.00 (q, J 12.1, 11.6 Hz, 1H), 0.88-0.70 (m, 5H). uPLC-MS (method 1): MH+ m/z 509.3, RT 2.72 minutes.

Example 32

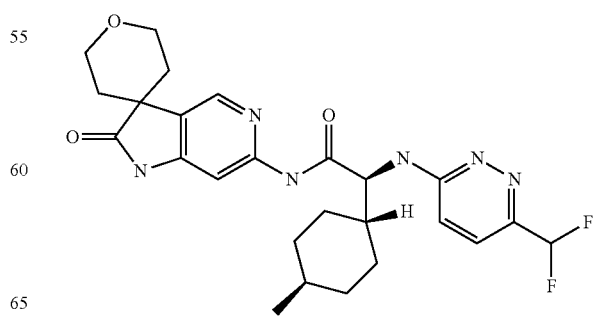

(2S)-2-{[6-(Difluoromethyl)pyridazin-3-yl]amino}-2-(4-methylcyclohexyl)-N-(2-oxo-spiro[1H-pyrrolo[3,2-c]pyridine-3,4'-tetrahydropyran]-6-yl)acetamide (Trans Isomer)

Trifluoroacetic acid (0.27 mL, 3.45 mmol) was added dropwise to a solution of Intermediate 80 (113 mg, 0.06 mmol) in DCM (0.5 mL) under a nitrogen atmosphere and cooled to 0° C. The reaction mixture was stirred at 20° C. for 18 h. The volatiles were removed in vacuo and the residue was dissolved in acetonitrile (1 mL) and aqueous ammonium hydroxide solution (1 mL). The mixture was stirred at 20° C. for 15 minutes, then the volatiles were removed in vacuo. The residue was diluted with water (3 mL) and the aqueous phase extracted with DCM (3×10 mL). The combined organic extracts were passed through a hydrophobic frit and concentrated in vacuo. The resulting crude material was purified by preparative HPLC (method 10) to afford the title compound (0.6 mg, 2%) as an off-white gum. $\delta_H$ (500 MHz, CDCl$_3$) 10.84 (s, 1H), 9.09-8.77 (m, 1H), 8.32-8.22 (m, 1H), 8.07 (s, 1H), 7.36-7.29 (m, 1H), 6.92-6.83 (m, 1H), 6.80-6.48 (m, 2H), 4.81-4.70 (m, 1H), 4.16-4.09 (m, 2H), 3.91-3.75 (m, 2H), 2.02-1.93 (m, 2H), 1.91-1.84 (m, 1H), 1.81-1.59 (m, 6H), 1.28-1.20 (m, 2H), 1.16-1.09 (m, 1H), 0.83-0.76 (m, 5H). uPLC-MS (method 1): MH+ m/z 501.2, RT 2.54 minutes.

Example 33

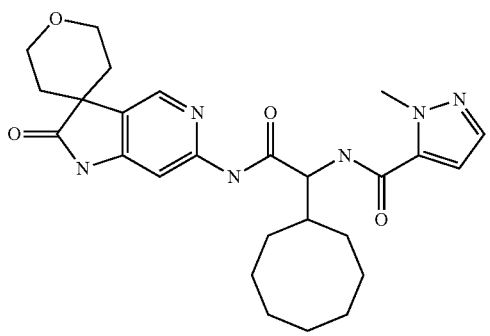 [SMILES: Cn1nccc1C(=O)NC(C(=O)Nc1cc2c(cn1)C1(CCOCC1)C(=O)N2)C1CCCCCCC1]

N-{1-Cyclooctyl-2-oxo-2-[(2-oxospiro[1H-pyrrolo[3,2-c]pyridine-3,4'-tetrahydropyran]-6-yl)amino]ethyl}-2-methylpyrazole-3-carboxamide To a solution of Intermediate 86 (0.20 g, 0.29 mmol) in DCM (5 mL) was added TFA (0.44 mL, 5.76 mmol) at 0° C. The reaction mixture was stirred at room temperature for 16 h, then concentrated in vacuo. The crude residue was dissolved in acetonitrile (3 mL) and aqueous ammonium hydroxide solution (25% in water, 3 mL) was added at 0° C. The reaction mixture was stirred at room temperature for 3 h, then concentrated in vacuo. The crude residue was purified by column chromatography (5% methanolic ammonia in DCM), followed by preparative HPLC (method 8), to afford the title compound (0.023 g, 16%) as a white solid. $\delta_H$ (400 MHz, DMSO-d$_6$) 1.34-1.73 (m, 16H), 1.77-1.89 (m, 2H), 2.15-2.18 (m, 1H), 3.78-3.84 (m, 3H), 3.95-3.98 (m, 1H), 4.01 (s, 3H), 4.57 (t, J 8.31 Hz, 1H), 7.01 (s, 1H), 7.47 (s, 1H), 7.71 (s, 1H), 8.41 (s, 1H), 8.45 (d, J 8.31 Hz, 1H), 10.63 (br s, 1H), 10.86 (br s, 1H). HPLC-MS (method 6): MH+ m/z 495.0, RT 2.44 minutes.

Example 34

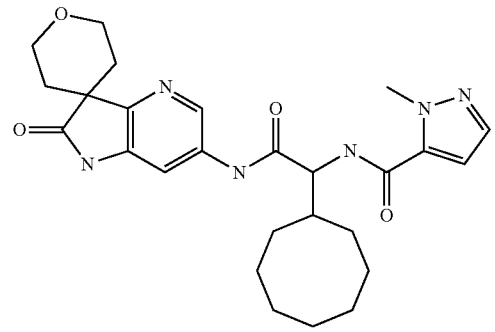 [SMILES: Cn1nccc1C(=O)NC(C(=O)Nc1cnc2c(c1)NC(=O)C21CCOCC1)C1CCCCCCC1]

N-{1-Cyclooctyl-2-oxo-2-[(2-oxospiro[1H-pyrrolo[3,2-b]pyridine-3,4'-tetrahydropyran]-6-yl)amino]ethyl}-2-methylpyrazole-3-carboxamide To a solution of Intermediate 92 (0.16 g, 0.26 mmol) in DCM (5 mL) was added TFA (0.78 mL, 10.2 mmol) at 0° C. The reaction mixture was stirred at room temperature for 16 h, then concentrated in vacuo. Acetonitrile (4 mL) and aqueous ammonium hydroxide solution (25% in water, 4 mL) were added at 0° C. The reaction mixture was stirred at room temperature for 3 h, then concentrated in vacuo. The crude residue was purified by column chromatography (6-8% MeOH in DCM) and preparative HPLC (method 8) to afford the title compound (0.021 g, 16%) as an off-white solid. $\delta_H$ (400 MHz, DMSO-d$_6$) 1.36-1.53 (m, 8H), 1.54-1.69 (m, 7H), 1.75-1.79 (m, 3H), 2.15-2.17 (m, 1H), 3.84-3.94 (m, 2H), 4.02 (s, 3H), 4.05-4.10 (m, 2H), 4.45 (t, J 8.56 Hz, 1H), 7.05 (s, 1H), 7.45 (s, 1H), 7.74 (s, 1H), 8.25 (s, 1H), 8.60 (d, J 8.31 Hz, 1H), 10.49 (br s, 1H), 10.58 (br s, 1H). HPLC-MS (method 6): MH+ m/z 495.0, RT 2.40 minutes.

Example 35

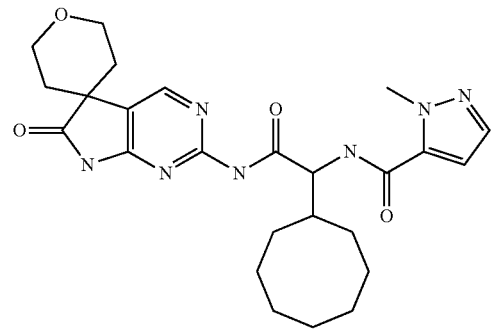 [SMILES: Cn1nccc1C(=O)NC(C(=O)Nc1ncc2c(n1)NC(=O)C21CCOCC1)C1CCCCCCC1]

N-{1-Cyclooctyl-2-oxo-2-[(6-oxospiro[7H-pyrrolo[2,3-d]pyrimidine-5,4'-tetrahydro-pyran]-2-yl)amino]ethyl}-2-methylpyrazole-3-carboxamide To a solution of Intermediate 98 (0.25 g, 0.40 mmol) in DCM (5 mL) was added TFA (1.19 mL, 16.0 mmol) at 0° C. The reaction mixture was stirred at room temperature for 16 h, then concentrated in vacuo. The residue was diluted with acetonitrile (10 mL) and aqueous ammonium hydroxide solution (10 mL) at 0° C. The reaction mixture was stirred at room temperature for 3 h, then concentrated in vacuo. The crude residue was purified by column chromatography (0-100% EtOAc in hexanes) and preparative HPLC (method 8) to afford the title compound (0.03 g, 8%) as a white solid. $\delta_H$ (400 MHz, DMSO-$d_6$) 1.36-1.51 (m, 8H), 1.55 (d, J 10.27 Hz, 2H), 1.61-1.64 (m, 6H), 1.80-1.93 (m, 2H), 2.15-2.17 (m, 1H), 3.79 (t, J 9.78 Hz, 2H), 3.92-3.99 (m, 2H), 4.02 (s, 3H), 4.61-4.64 (m, 1H), 7.01 (d, J 1.47 Hz, 1H), 7.46 (d, J 1.47 Hz, 1H), 8.42 (d, J 8.80 Hz, 1H), 8.66 (s, 1H), 10.66 (s, 1H), 11.52 (br s, 1H). HPLC-MS (method 6): MH+ m/z 496.0, RT 3.49 minutes.

Example 36

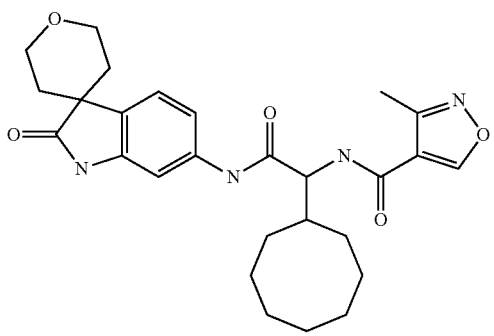 [SMILES: Cc1nocc1C(=O)NC(C(=O)Nc1ccc2c(c1)NC(=O)C21CCOCC1)C1CCCCCCC1]

N-{1-Cyclooctyl-2-oxo-2-[(2-oxospiro[indoline-3,4'-tetrahydropyran]-6-yl)amino]ethyl}-3-methylisoxazole-4-carboxamide Prepared from Intermediate 35 and 3-methyl-4-isoxazole-carboxylic acid in accordance with Procedure A to give the title compound (18%) as a white solid. $\delta_H$ (400 MHz, DMSO-$d_6$) 10.40 (s, 1H), 10.25 (s, 1H), 9.44 (s, 1H), 8.51 (d, J 8.5 Hz, 1H), 7.44 (d, J 8.1 Hz, 1H), 7.39 (d, J 1.9 Hz, 1H), 7.13 (dd, J 8.1, 2.0 Hz, 1H), 4.46 (t, J 8.7 Hz, 1H), 4.01 (ddd, J 11.1, 7.1, 3.7 Hz, 2H), 3.80 (ddd, J 11.1, 7.1, 3.8 Hz, 2H), 2.38 (s, 3H), 2.09 (br s, 1H), 1.79-1.36 (m, 18H). HPLC-MS (method 21): MH+ m/z 495, RT 2.17 minutes.

Example 37

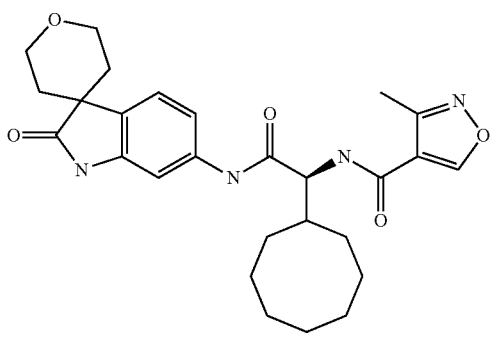 [SMILES: Cc1nocc1C(=O)N[C@H](C(=O)Nc1ccc2c(c1)NC(=O)C21CCOCC1)C1CCCCCCC1]

N-{(1S)-1-Cyclooctyl-2-oxo-2-[(2-oxospiro[indoline-3,4'-tetrahydropyran]-6-yl)amino]-ethyl}-3-methylisoxazole-4-carboxamide Example 36 was separated by chiral preparative HPLC using an Agilent 1100, DAD system on a Lux Cellulose-1 21.2×250 mm, 5 μm column, eluting with 100% MeOH (+0.1% NH$_4$OH) and a flow rate of 10 mL/min, to give the title compound (2 mg, 2%) as a white solid. HPLC-MS (Method 21): MH+ m/z 495, RT 2.11 minutes. Chiral HPLC on a Lux Cellulose-1 4.6×150 mm, 3 μm column, eluting with 100% MeOH+0.1% NH$_4$OH, 1 mL/min, 40° C., RT 2.20 minutes (100%).

Example 38

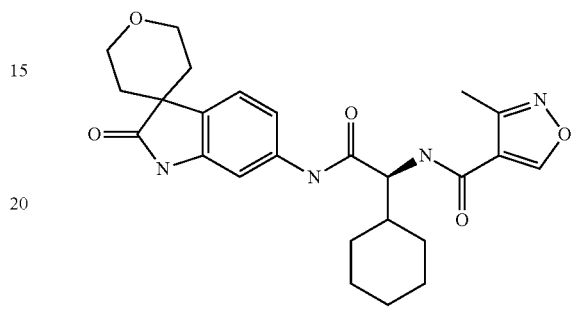

N-{(1S)-1-Cyclohexyl-2-oxo-2-[(2-oxospiro[indoline-3,4'-tetrahydropyran]-6-yl)amino]ethyl}-3-methylisoxazole-4-carboxamide Prepared from Intermediate 78 and 3-methyl-4-isoxazole-carboxylic acid in accordance with Procedure A to give the title compound (216 mg, 79%) as a white solid. $\delta_H$ (300 MHz, DMSO-$d_6$) 10.40 (s, 1H), 10.20 (s, 1H), 9.44 (s, 1H), 8.45 (d, J 8.2 Hz, 1H), 7.44 (d, J 8.1 Hz, 1H), 7.39 (d, J 1.9 Hz, 1H), 7.12 (dd, J 8.1, 2.0 Hz, 1H), 4.40 (t, J 8.4 Hz, 1H), 4.01 (ddd, J 10.9, 7.0, 3.6 Hz, 2H), 3.80 (ddd, J 11.1, 6.9, 3.8 Hz, 2H), 2.37 (s, 3H), 1.87-1.51 (m, 10H), 1.17 (m, 5H). HPLC-MS (Method 21): MH+ m/z 467, RT 1.81 minutes.

Example 39

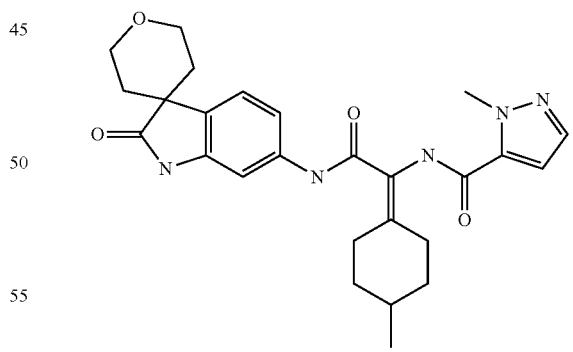

2-Methyl-N-{1-(4-methylcyclohexylidene)-2-oxo-2-[(2-oxospiro[indoline-3,4'-tetrahydropyran]-6-yl)amino]ethyl}pyrazole-3-carboxamide (Isomer 1)

Intermediate 122 was separated by chiral preparative HPLC using an Agilent 1100, DAD system on a Lux Cellulose-1 250 mm×21.2 mm, 3 μm column, eluting with 12% MeOH (+0.1% NH$_4$OH) and a flow rate of 100 mL/min, to give the title compound as a white solid. $\delta_H$ (400 MHz, DMSO-$d_6$) 10.37 (s, 1H), 10.07 (s, 1H), 9.71 (s, 1H), 7.48 (m, 2H), 7.42 (d, J 8.2 Hz, 1H), 7.16 (d, J 8.0 Hz, 1H), 7.08 (s, 1H), 4.13-3.93 (m, 5H), 3.81 (ddd, J 11.1, 7.2, 3.8 Hz, 2H), 2.80 (d, J 13.9 Hz, 1H), 2.62 (d, J 13.6 Hz, 1H), 2.06 (m, 1H), 1.89 (m, 1H), 1.86-1.54 (m, 2H), 1.28-1.05 (m, 5H), 0.93-0.81 (m 5H). HPLC-MS (Method 21): MH+ m/z 478, RT 1.79 minutes. Chiral SFC (Method 35): RT 4.5 minutes.

Example 40

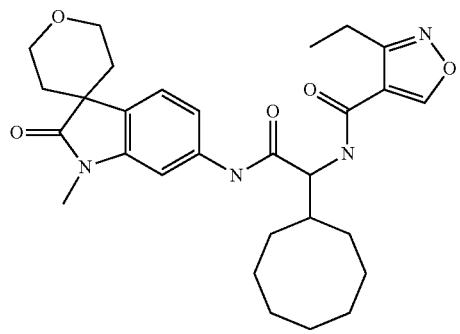 [SMILES: CCc1nocc1C(=O)NC(C(=O)Nc1ccc2c(c1)N(C)C(=O)C21CCOCC1)C1CCCCCCC1]

N-{1-Cyclooctyl-2-[(1-methyl-2-oxospiro[indoline-3,4'-tetrahydropyran]-6-yl)amino]-2-oxoethyl}-3-ethylisoxazole-4-carboxamide Prepared from Intermediate 103 (50 mg, 0.14 mmol) and 3-ethylisoxazole-4-carboxylic acid (14.2 mg, 0.10 mmol) in accordance with Procedure A, and purified by preparative HPLC (method 22), to give the title compound (7 mg, 13%) as an off-white solid. $\delta_H$ (400 MHz, DMSO-$d_6$) 10.32 (s, 1H), 9.42 (s, 1H), 8.50 (d, J 8.6 Hz, 1H), 7.53-7.39 (m, 2H), 7.26 (dd, J 8.1, 1.9 Hz, 1H), 4.49 (t, J 8.6 Hz, 1H), 4.04 (ddd, J 11.3, 7.3, 3.8 Hz, 2H), 3.82 (ddd, J 11.1, 6.5, 4.0 Hz, 2H), 3.10 (s, 3H), 2.92-2.77 (m, 2H), 2.15-2.03 (m, 1H), 1.84-1.26 (m, 18H), 1.18 (t, J 7.5 Hz, 3H). HPLC-MS (method 6): MH+m/z 523, RT 2.33 minutes.

Example 41

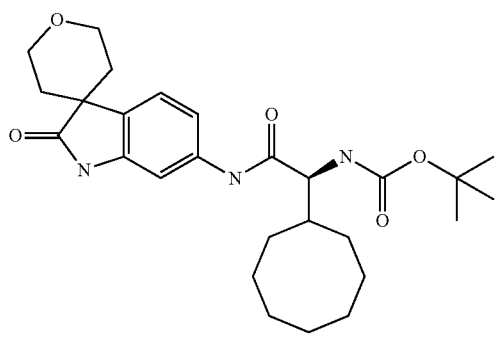 [SMILES: CC(C)(C)OC(=O)N[C@H](C(=O)Nc1ccc2c(c1)NC(=O)C21CCOCC1)C1CCCCCCC1]

tert-Butyl-N-{(1S)-1-cyclooctyl-2-oxo-2-[(2-oxospiro[indoline-3,4'-tetrahydropyran]-6-yl)amino] ethyl}carbamate Intermediate 34 (500 mg) was purified by chiral preparative SFC (method 15). The second eluting peak gave the title compound (133 mg, 27%) as an off-white solid. $\delta_H$ (400 MHz, DMSO-$d_6$) 10.38 (s, 1H), 9.99 (s, 1H), 7.43 (d, J 8.1 Hz, 1H), 7.37 (d, J 1.8 Hz, 1H), 7.08 (dd, J 8.1, 2.0 Hz, 1H), 6.89 (d, J 8.8 Hz, 1H), 4.01 (ddd, J 11.1, 7.1, 3.7 Hz, 2H), 3.94 (t, J 8.3 Hz, 1H), 3.81 (ddd, J 11.1, 7.1, 3.8 Hz, 2H), 1.94 (s, 1H), 1.79-1.69 (m, 2H), 1.68-1.25 (m, 25H). HPLC-MS (method 6): [M+2H-$^t$Bu]+ m/z 430, RT 2.40 minutes. uPLC-MS (method 23): [M+2H-$^t$Bu]+ m/z 430, RT 2.49 minutes.

Example 42 (Procedure B)

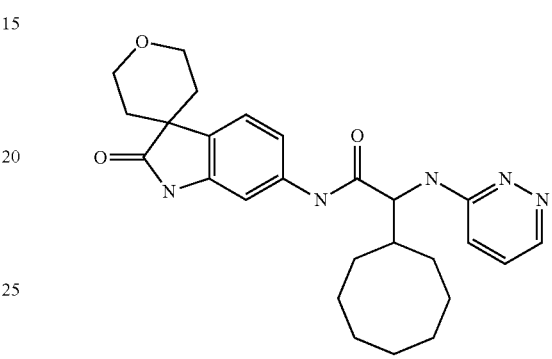

2-Cyclooctyl-N-(2-oxospiro[indoline-3,4'-tetrahydropyran]-6-yl)-2-(pyridazin-3-yl-amino)acetamide Intermediate 35 (20 mg, 0.052 mmol), 3-bromopyridazine (8.25 mg, 0.052 mmol), tBuBrettPhos Pd-G3 (4.52 mg, 0.0052 mmol) and sodium tert-butoxide (10 mg, 0.10 mmol) were added to a sealed vial and dissolved in 1,4-dioxane (0.7 mL)/DMSO (0.07 mL). The reaction mixture was stirred at 105° C. for 18 h, then filtered through celite and concentrated in vacuo. The resulting brown oil was purified by preparative HPLC (method 24) to afford, after freeze-drying, the title compound (2 mg, 8%) as an off-white solid. $\delta_H$ (400 MHz, DMSO-$d_6$) 10.37 (s, 1H), 10.23 (s, 1H), 8.42 (dd, J 4.4, 1.4 Hz, 1H), 7.46-7.36 (m, 2H), 7.23 (dd, J 9.0, 4.4 Hz, 1H), 7.11 (dd, J 8.2, 2.0 Hz, 1H), 6.99 (dt, J 8.7, 1.6 Hz, 2H), 4.66 (t, J 8.1 Hz, 1H), 4.01 (ddd, J 11.1, 7.0, 3.8 Hz, 2H), 3.80 (ddd, J 11.2, 7.1, 3.8 Hz, 2H), 1.81-1.34 (m, 19H). HPLC-MS (method 21): [M−H]+ m/z 463, RT 1.77 minutes.

Example 43

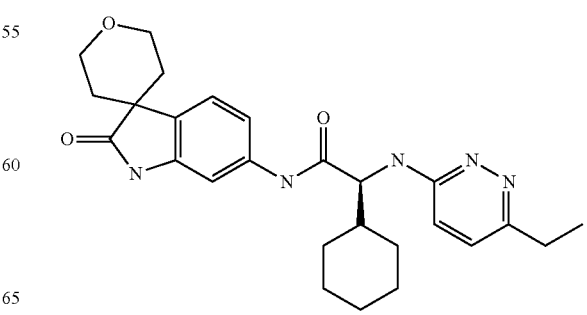

131

(2S)-2-Cyclohexyl-2-[(6-ethylpyridazin-3-yl)amino]-N-(2-oxospiro[indoline-3,4'-tetrahydropyran]-6-yl)acetamide Prepared from Intermediate 78 (50 mg, 0.14 mmol) and 3-bromo-6-ethyl-pyridazine hydrobromide (31.2 mg, 0.11 mmol) in accordance with Procedure B, and purified by preparative HPLC (method 22), to give the title compound (6 mg, 12%) as an off-white solid. $\delta_H$ (300 MHz, DMSO-$d_6$) 10.38 (s, 1H), 10.16 (s, 1H), 7.46-7.36 (m, 2H), 7.21-7.07 (m, 2H), 6.95 (d, J 9.1 Hz, 1H), 6.79 (d, J 8.3 Hz, 1H), 4.55 (t, J 7.8 Hz, 1H), 4.01 (ddd, J 11.1, 7.0, 3.7 Hz, 2H), 3.80 (td, J 7.1, 3.5 Hz, 2H), 2.67 (q, J 7.6 Hz, 2H), 1.87-1.51 (m, 9H), 1.30-1.01 (m, 9H). HPLC-MS (method 6): MH+ m/z 464, RT 1.80 minutes.

Example 44

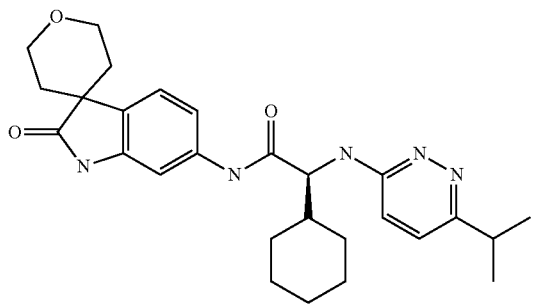 [SMILES: CC(C)c1ccc(N[C@H](C(=O)Nc2ccc3c(c2)NC(=O)C32CCOCC2)C2CCCCC2)nn1]

(2S)-2-Cyclohexyl-2-[(6-isopropylpyridazin-3-yl)amino]-N-(2-oxospiro[indoline-3,4'-tetrahydropyran]-6-yl)acetamide Prepared from Intermediate 78 (30 mg, 0.084 mmol) and 3-bromo-6-isopropyl-pyridazine (16.9 mg, 0.084 mmol) in accordance with Procedure B, and purified by preparative HPLC (method 25), to give the title compound (2 mg, 5%) as an off-white solid. $\delta_H$ (600 MHz, DMSO-$d_6$) 10.38 (s, 1H), 10.14 (s, 1H), 7.45-7.38 (m, 2H), 7.20 (d, J 9.2 Hz, 1H), 7.12 (dd, J 8.2, 2.0 Hz, 1H), 6.96 (d, J 9.2 Hz, 1H), 6.78 (d, J 8.3 Hz, 1H), 4.54 (t, J 7.9 Hz, 1H), 4.01 (ddd, J 11.2, 7.2, 3.7 Hz, 2H), 3.80 (ddd, J 11.3, 7.2, 3.7 Hz, 2H), 2.98 (m, 1H), 1.87 (m, 2H), 1.77-1.69 (m, 3H), 1.68-1.55 (s, 3H), 1.37 (m, 1H), 1.23-1.10 (m, 12H). HPLC-MS (method 6): MH+ m/z 478, RT 1.94 minutes.

Example 45

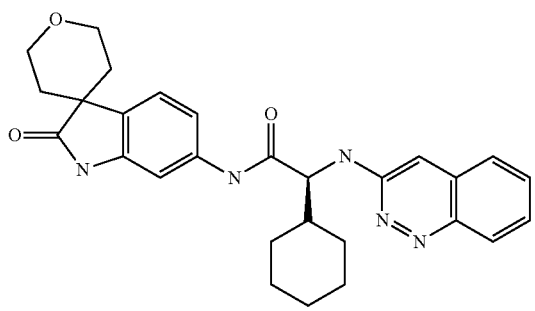 [SMILES: O=C(Nc1ccc2c(c1)NC(=O)C21CCOCC1)[C@@H](Nc1cc2ccccc2nn1)C1CCCCC1]

132

(2S)-2-(Cinnolin-3-ylamino)-2-cyclohexyl-N-(2-oxospiro[indoline-3,4'-tetrahydropyran]-6-yl)acetamide Prepared from Intermediate 78 (30 mg, 0.084 mmol) and 3-bromocinnoline (14.62 mg, 0.070 mmol) in accordance with Procedure B, and purified by preparative HPLC (method 25), to give the title compound (1.5 mg, 4%) as an off-white solid. $\delta_H$ (300 MHz, DMSO-$d_6$) 10.38 (s, 1H), 10.25 (s, 1H), 8.39 (s, 2H), 8.07 (d, J 8.6 Hz, 1H), 7.67 (d, J 8.3 Hz, 1H), 7.54 (ddd, J 8.3, 6.6, 1.3 Hz, 1H), 7.49-7.35 (m, 2H), 7.21-7.06 (m, 2H), 4.66 (t, J 8.0 Hz, 1H), 4.01 (m, 2H), 3.78 (m, 2H), 1.94 (m, 2H), 1.73-1.55 (m, 7H), 1.30-1.10 (m, 6H). HPLC-MS (method 6): MH+ m/z 486, RT 1.97 minutes.

Example 46

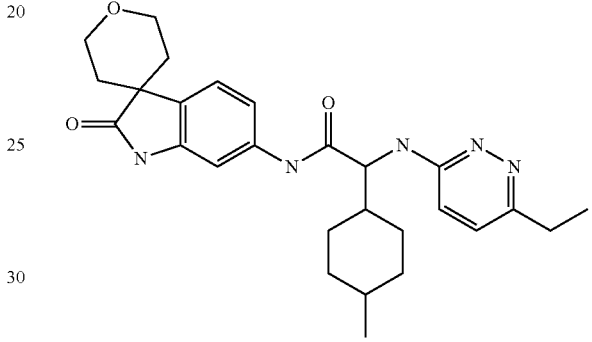

2-[(6-Ethylpyridazin-3-yl)amino]-2-(4-methylcyclohexyl)-N-(2-oxospiro[indoline-3,4'-tetrahydropyran]-6-yl)acetamide Prepared from Intermediate 105 (30 mg, 0.084 mmol) and 3-bromo-6-ethyl-pyridazine hydrobromide (38 mg, 0.135 mmol) in accordance with Procedure B, and purified by preparative HPLC (method 25), to give the title compound (3 mg, 5%) as an off-white solid. $\delta_H$ (400 MHz, DMSO-$d_6$) 10.38 (s, 1H), 10.21 (m, 1H), 7.46-7.30 (m, 2H), 7.24-7.02 (m, 2H), 6.94 (m, 1H), 6.81 (m, 1H), 4.84-4.42 (m, 1H), 4.01 (ddd, J 11.1, 7.1, 3.7 Hz, 2H), 3.79 (td, J 7.4, 3.7 Hz, 2H), 2.67 (m, 3H), 1.89 (m, 1H), 1.83-1.34 (m, 7H), 1.17 (m, 6H), 1.03-0.73 (m, 5H). HPLC-MS (method 6): MH+ m/z 478, RT 1.97 minutes.

Example 47

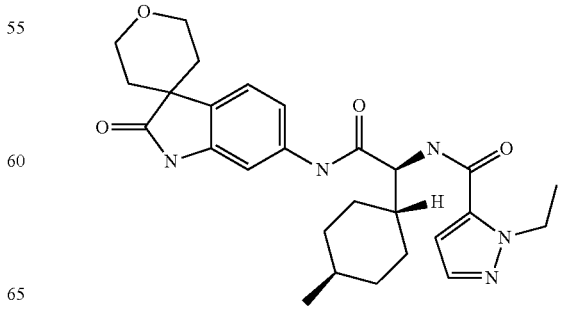

2-Ethyl-N-{(1S)-1-(4-methylcyclohexyl)-2-oxo-2-[(2-oxospiro[indoline-3,4'-tetrahydro-pyran]-6-yl)amino]ethyl}pyrazole-3-carboxamide (Trans Isomer)

Prepared from Intermediate 50 (30 mg, 0.084 mmol) and 1-ethyl-1H-pyrazole-5-carboxylic acid (49 mg, 0.35 mmol) in accordance with Procedure A, and purified by flash column chromatography using a gradient of 0-100% ethyl acetate in hexanes, to give the title compound (81 mg, 47%) as an off-white solid. $\delta_H$ (400 MHz, DMSO-d$_6$) 10.40 (s, 1H), 10.18 (s, 1H), 8.50 (d, J 8.1 Hz, 1H), 7.59-7.20 (m, 3H), 7.12 (dd, J 8.2, 2.0 Hz, 1H), 7.02 (d, J 2.1 Hz, 1H), 4.46 (q, J 7.2 Hz, 2H), 4.34 (t, J 8.5 Hz, 1H), 4.13-3.89 (m, 2H), 3.89-3.66 (m, 2H), 1.98-1.42 (m, 9H), 1.42-1.12 (m, 5H), 0.86 (d, J 6.4 Hz, 6H). HPLC-MS (method 6): MH+ m/z 494, RT 2.05 minutes. uPLC-MS (method 23): MH+ m/z 494, RT 1.62 minutes. $[\alpha]^{20}_D$=−4.30° (c 10.0, methanol).

Example 48

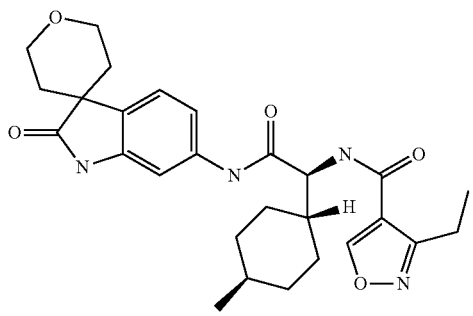 [SMILES: CCc1nocc1C(=O)N[C@H](C(=O)Nc1ccc2c(c1)NC(=O)C21CCOCC1)[C@H]1CC[C@H](C)CC1]

3-Ethyl-N-{(1S)-1-(4-methylcyclohexyl)-2-oxo-2-[(2-oxospiro[indoline-3,4'-tetrahydropyran]-6-yl)amino]ethyl}isoxazole-4-carboxamide (Trans Isomer)

Prepared from Intermediate 50 (52 mg, 0.14 mmol) and 3-ethylisoxazole-4-carboxylic acid (19.8 mg, 0.14 mmol) in accordance with Procedure A, and purified by flash column chromatography using a gradient of 0-100% ethyl acetate in hexanes, to give the title compound (51 mg, 74%) as an off-white solid. $\delta_H$ (400 MHz, DMSO-d$_6$) 10.40 (s, 1H), 10.18 (s, 1H), 9.41 (s, 1H), 8.47 (d, J 8.1 Hz, 1H), 7.56-7.25 (m, 2H), 7.11 (dd, J 8.2, 2.0 Hz, 1H), 4.37 (t, J 8.3 Hz, 1H), 4.01 (ddd, J 10.9, 6.9, 3.6 Hz, 2H), 3.89-3.70 (m, 2H), 2.84 (q, J 7.5 Hz, 2H), 1.96-1.38 (m, 9H), 1.17 (m, 5H), 0.86 (m, 6H). HPLC-MS (method 6): MH+ m/z 495, RT 2.10 minutes. uPLC-MS (method 23): MH+m/z 495, RT 1.67 minutes. $[\alpha]^{20}_D$=−0.60° (c 10.0, methanol).

Example 49

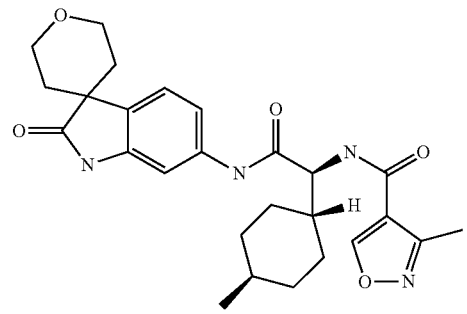 [SMILES: Cc1nocc1C(=O)N[C@H](C(=O)Nc1ccc2c(c1)NC(=O)C21CCOCC1)[C@H]1CC[C@H](C)CC1]

3-Methyl-N-{(1S)-1-(4-methylcyclohexyl)-2-oxo-2-[(2-oxospiro[indoline-3,4'-tetrahydro-pyran]-6-yl)amino]ethyl}isoxazole-4-carboxamide (Trans Isomer)

Prepared from Intermediate 50 (52 mg, 0.14 mmol) and 3-methylisoxazole-4-carboxylic acid (15.4 mg, 0.121 mmol) in accordance with Procedure A, and purified by flash column chromatography using a gradient of 0-100% ethyl acetate in hexanes, to give the title compound (51 mg, 88%) as an off-white solid. $\delta_H$ (400 MHz, DMSO-d$_6$) 10.40 (s, 1H), 10.19 (s, 1H), 9.44 (d, J 0.7 Hz, 1H), 8.46 (d, J 8.2 Hz, 1H), 7.54-7.25 (m, 2H), 7.12 (dd, J 8.2, 2.0 Hz, 1H), 4.38 (t, J 8.4 Hz, 1H), 4.01 (ddd, J 11.1, 7.1, 3.7 Hz, 2H), 3.80 (td, J 7.3, 3.6 Hz, 2H), 2.37 (s, 3H), 1.94-1.42 (m, 9H), 1.42-0.93 (m, 3H), 0.86 (d, J 6.5 Hz, 5H). HPLC-MS (method 6): MH+ m/z 481, RT 1.98 minutes. uPLC-MS (method 23): MH+ m/z 481, RT 1.58 minutes. $[\alpha]^{20}_D$=+5.65° (c 10.0, methanol).

Example 50 (Procedure C)

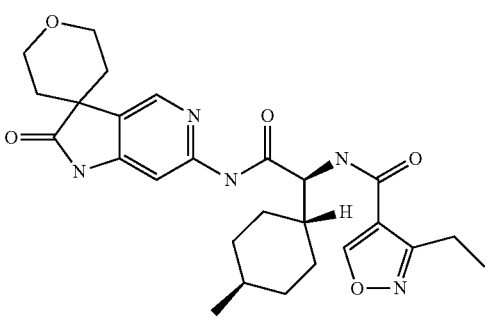 [SMILES: CCc1nocc1C(=O)N[C@H](C(=O)Nc1cc2c(cn1)C1(CCOCC1)C(=O)N2)[C@H]1CC[C@H](C)CC1]

3-Ethyl-N-{(1S)-1-(4-methylcyclohexyl)-2-oxo-2-[(2-oxospiro[1H-pyrrolo[3,2-c]-pyridine-3,4'-tetrahydropyran]-6-yl)amino]ethyl}isoxazole-4-carboxamide (Trans Isomer)

To a solution of Intermediate 108 (2.70 g, 4.32 mmol) in DCM (20 mL) at 0° C. was added dropwise trifluoroacetic acid (5 mL, 66.13 mmol). The mixture was stirred at 20° C.

for 1.5 h. Another portion of trifluoroacetic acid (5 mL, 66.13 mmol) was added at 0° C. The reaction mixture was stirred at 20° C. for a further 18 h, then concentrated in vacuo. The residue was dissolved in a mixture of acetonitrile (2 mL) and aqueous ammonium hydroxide solution (28% v/v, 2 mL). The mixture was stirred at 20° C. for 1 h. The residue was concentrated in vacuo, then partitioned between DCM and water. The aqueous phase was basified with 2M aqueous NaOH solution, then extracted with DCM:MeOH (10:1). The organic layer was concentrated in vacuo. The crude residue was purified by flash column chromatography, using a gradient of 0-100% DCM in ethyl acetate, to afford, after freeze-drying, the title compound (1.36 g, 64%) as a white solid. $\delta_H$ (300 MHz, DMSO-$d_6$) 10.86 (s, 1H), 10.57 (s, 1H), 9.40 (s, 1H), 8.45-8.36 (m, 2H), 7.71 (s, 1H), 4.52 (t, J 8.0 Hz, 1H), 4.05-3.94 (m, 2H), 3.84-3.75 (m, 2H), 2.83 (q, J 7.5 Hz, 2H), 1.80-1.57 (m, 10H), 1.32-1.06 (m, 4H), 0.94-0.77 (m, 6H). HPLC-MS (method 6): MH+ m/z 496, RT 2.17 minutes. uPLC-MS (method 23): MH+ m/z 496, RT 1.56 minutes.

Example 51

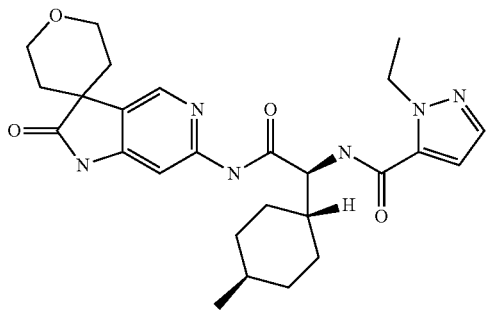 [SMILES: CCn1nccc1C(=O)N[C@H](C(=O)Nc1cc2c(cn1)C1(CCOCC1)C(=O)N2)[C@H]1CC[C@H](C)CC1]

2-Ethyl-N-{(1S)-1-(4-methylcyclohexyl)-2-oxo-2-[(2-oxospiro[1H-pyrrolo[3,2-c]-pyridine-3,4'-tetrahydropyran]-6-yl)amino]ethyl}pyrazole-3-carboxamide (Trans Isomer)

Prepared from Intermediate 109 (2.73 g, 4.36 mmol) in accordance with Procedure C, and purified by flash column chromatography using a gradient of 0-100% ethyl acetate in hexanes, to give the title compound (1.6 g, 74%) as a white solid. $\delta_H$ (400 MHz, DMSO-$d_6$) 10.87 (s, 1H), 10.57 (s, 1H), 8.49-8.39 (m, 2H), 7.72 (s, 1H), 7.49 (d, J 2.0 Hz, 1H), 6.99 (d, J 2.1 Hz, 1H), 4.53-4.40 (m, 3H), 4.06-3.94 (m, 2H), 3.88-3.76 (m, 2H), 1.88-1.50 (m, 7H), 1.33-1.17 (m, 6H), 1.14-0.99 (m, 1H), 0.95-0.78 (m, 6H). HPLC-MS (method 6): MH+ m/z 495, RT 1.92 minutes. uPLC-MS (method A): MH+m/z 495, RT 1.51 minutes. $[\alpha]^{20}_D$=−13.50° (c 10.0, methanol).

Example 52 (Procedure D)

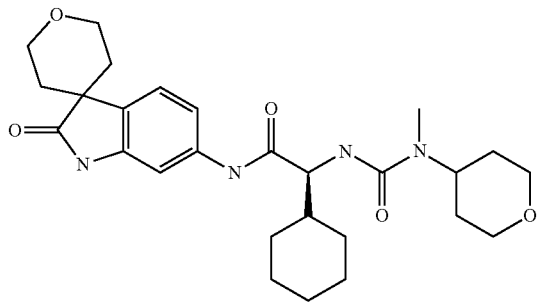 [SMILES: CN(C(=O)N[C@H](C(=O)Nc1ccc2c(c1)NC(=O)C21CCOCC1)C1CCCCC1)C1CCOCC1]

(2S)-2-Cyclohexyl-2-{[methyl(tetrahydropyran-4-yl)carbamoyl]amino}-N-(2-oxospiro-[indoline-3,4'-tetrahydropyran]-6-yl)acetamide Intermediate 78 (30 mg, 0.084 mmol) and N-methyl-N-(oxan-4-yl)carbamoyl chloride (18 mg, 0.097 mmol) were dissolved in DCM (1 mL) and triethylamine (14 μL, 10.24 mg, 0.1007 mmol) was added. The reaction mixture was stirred at 20° C. for 18 h. Additional N-methyl-N-(oxan-4-yl)carbamoyl chloride (18 mg, 0.097 mmol) and triethylamine (14 μL, 10.24 mg, 0.1007 mmol) were added. The reaction mixture was stirred at 20° C. for a further 5 h, then concentrated in vacuo. The resulting crude clear oil was purified by flash column chromatography, using a gradient of 0-100% ethyl acetate in hexanes, to afford, after freeze-drying, the title compound (15 mg, 36%) as a white solid. $\delta_H$ (400 MHz, DMSO-$d_6$) 10.38 (s, 1H), 10.01 (s, 1H), 7.46-7.36 (m, 2H), 7.09 (dd, J 8.1, 1.9 Hz, 1H), 6.05 (d, J 8.3 Hz, 1H), 4.22-3.96 (m, 4H), 3.88 (dd, J 10.6, 5.3 Hz, 2H), 3.80 (ddd, J 11.1, 7.0, 3.7 Hz, 2H), 3.41-3.31 (m, 2H, obscured by water peak at 3.31 ppm), 2.72 (s, 3H), 1.86-1.49 (m, 12H), 1.46-1.34 (m, 2H), 1.24-1.06 (m, 4H), 1.02-0.86 (m, 1H). HPLC-MS (method 6): MH+ m/z 499, RT 1.83 minutes.

Example 53

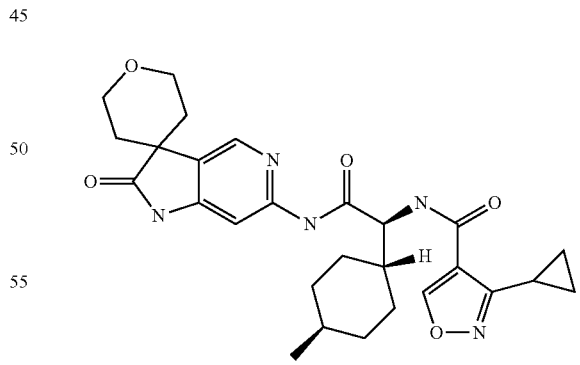

3-Cyclopropyl-N-{(1S)-1-(4-methylcyclohexyl)-2-oxo-2-[(2-oxospiro[1H-pyrrolo[3,2-c]-pyridine-3,4'-tetrahydropyran]-6-yl)amino]ethyl}isoxazole-4-carboxamide (Trans Isomer)

Prepared from Intermediate 110 (100 mg, 0.16 mmol) in accordance with Procedure C, and purified by flash column chromatography using a gradient of 0-100% ethyl acetate in hexanes, to give the title compound (56 mg, 76% yield) as a white solid. $\delta_H$ (400 MHz, DMSO-d$_6$) 10.87 (s, 1H), 10.59 (s, 1H), 9.37 (s, 1H), 8.44-8.35 (m, 2H), 7.72 (s, 1H), 4.54 (t, J 8.0 Hz, 1H), 3.99 (dt, J 11.7, 4.8 Hz, 2H), 3.88-3.76 (m, 2H), 2.43 (tt, J 8.4, 5.1 Hz, 1H), 1.88-1.52 (m, 9H), 1.36-1.14 (m, 2H), 1.14-0.9 (m, 10H). HPLC-MS (method 6): MH+ m/z 508, RT 2.29 minutes.

Example 54

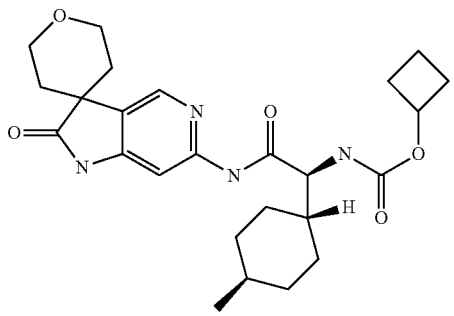 [SMILES: C[C@H]1CC[C@H]([C@H](NC(=O)OC2CCC2)C(=O)Nc2cc3c(cn2)C2(CCOCC2)C(=O)N3)CC1]

Cyclobutyl N-{(1S)-1-(4-methylcyclohexyl)-2-oxo-2-[(2-oxospiro[1H-pyrrolo[3,2-c]-pyridine-3,4'-tetrahydropyran]-6-yl)amino]ethyl}carbamate (Trans Isomer)

Prepared from Intermediate 111 (60 mg, 0.10 mmol) in accordance with Procedure C, and purified by flash column chromatography using a gradient of 0-100% ethyl acetate in hexanes followed by preparative HPLC (method 22), to give the title compound (11 mg, 23%) as a white solid. $\delta_H$ (400 MHz, DMSO-d$_6$) 10.87 (s, 1H), 10.35 (s, 1H), 8.39 (s, 1H), 7.69 (s, 1H), 7.27 (d, J 8.4 Hz, 1H), 4.80 (p, J 7.5 Hz, 1H), 4.12-3.94 (m, 3H), 3.81 (dd, J 11.5, 8.6 Hz, 2H), 2.26-2.16 (m, 2H), 2.07-1.86 (m, 2H), 1.85-1.72 (m, 2H), 1.66-1.38 (m, 7H), 1.30-0.93 (m, 4H), 0.93-0.58 (m, 6H). HPLC-MS (method 6): MH+ m/z 471, RT 2.33 minutes.

Example 55

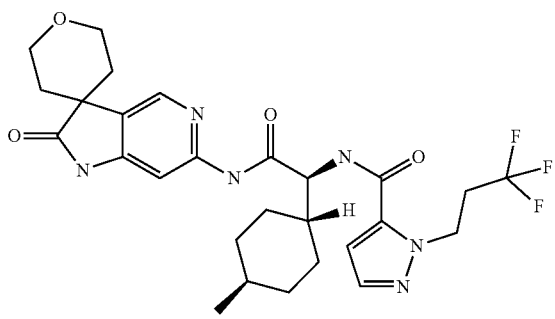 [SMILES: C[C@H]1CC[C@H]([C@H](NC(=O)c2ccnn2CCC(F)(F)F)C(=O)Nc2cc3c(cn2)C2(CCOCC2)C(=O)N3)CC1]

N-{(1S)-1-(4-Methylcyclohexyl)-2-oxo-2-[(2-oxospiro[1H-pyrrolo[3,2-c]pyridine-3,4'-tetrahydropyran]-6-yl)amino]ethyl}-2-(3,3,3-trifluoropropyl)pyrazole-3-carboxamide (Trans Isomer)

Prepared from Intermediate 112 (50 mg, 0.072 mmol) in accordance with Procedure C, and purified by flash column chromatography using a gradient of 0-100% ethyl acetate in hexanes, to give the title compound (21 mg, 52%) as a white solid. $\delta_H$ (400 MHz, DMSO-d6) 10.87 (s, 1H), 10.59 (s, 1H), 8.54 (d, J 8.1 Hz, 1H), 8.44-8.39 (m, 1H), 7.72 (d, J 0.7 Hz, 1H), 7.56 (d, J 2.0 Hz, 1H), 7.10 (d, J 2.1 Hz, 1H), 4.80-4.63 (m, 2H), 4.52 (t, J 8.3 Hz, 1H), 3.99 (dt, J 10.2, 4.6 Hz, 2H), 3.87-3.77 (m, 2H), 2.87-2.70 (m, 2H), 1.88-1.74 (m, 3H), 1.74-1.40 (m, 4H), 1.36-1.06 (m, 3H), 1.04-0.91 (m, 1H), 0.90-0.75 (m, 6H). HPLC-MS (method 6): MH+ m/z 563, RT 2.17 minutes.

Example 56

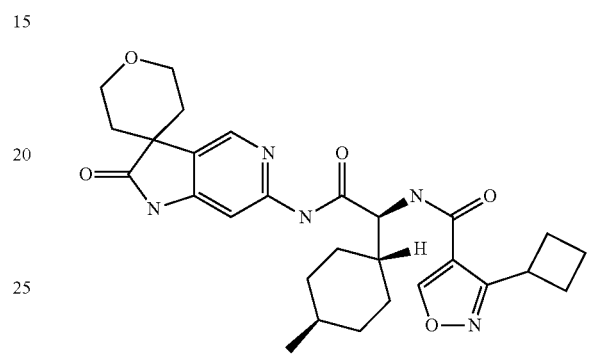

3-Cyclobutyl-N-{(1S)-1-(4-methylcyclohexyl)-2-oxo-2-[(2-oxospiro[1H-pyrrolo[3,2-c]-pyridine-3,4'-tetrahydropyran]-6-yl)amino]ethyl}isoxazole-4-carboxamide (Trans Isomer)

Prepared from Intermediate 113 (45 mg, 0.069 mmol) in accordance with Procedure C, and purified by flash column chromatography using a gradient of 0-100% ethyl acetate in hexanes followed by 0-20% methanol in ethyl acetate, to give the title compound (16 mg, 44%) as a white solid. $\delta_H$ (400 MHz, DMSO-d$_6$) 10.86 (s, 1H), 10.57 (s, 1H), 9.39 (s, 1H), 8.41 (s, 1H), 8.35 (d, J 8.0 Hz, 1H), 7.71 (s, 1H), 4.51 (t, J 8.1 Hz, 1H), 4.03-3.94 (m, 2H), 3.91-3.77 (m, 3H), 2.34-2.14 (m, 4H), 1.98-1.91 (m, 1H), 1.89-1.76 (m, 4H), 1.74-1.48 (m, 5H), 1.33-1.23 (m, 2H), 1.11-0.98 (m, 1H), 0.93-0.76 (m, 6H). HPLC-MS (method 6): MH+ m/z 522, RT 2.19 minutes.

Example 57

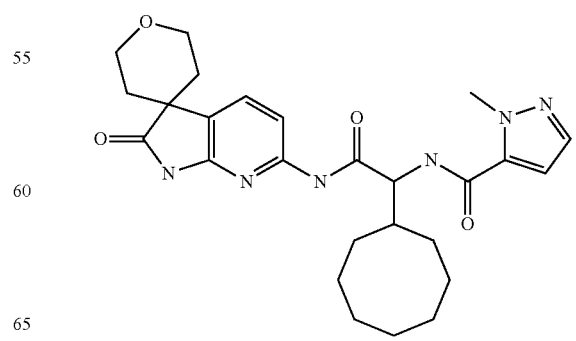

N-{1-Cyclooctyl-2-oxo-2-[(2-oxospiro[1H-pyrrolo
[2,3-b]pyridine-3,4'-tetrahydropyran]-6-yl)amino]
ethyl}-2-methylpyrazole-3-carboxamide To a solution of Intermediate 118 (0.23 g, 0.36 mmol) in
DCM (5 mL) was added TFA (0.55 mL, 7.20 mmol) at 0° C.
The reaction mixture was stirred at room temperature for 16
h, then concentrated in vacuo. Acetonitrile (3 mL) and
NH₄OH (25% solution in H₂O, 3 mL) were added at 0° C.
The reaction mixture was stirred at room temperature for 3
h, then concentrated in vacuo. The crude residue was purified by column chromatography (3-4% MeOH in DCM) to
afford the title compound (0.042 g, 22%) as an off-white
solid. $\delta_H$ (400 MHz, DMSO-d₆) 1.34-1.70 (m, 16H), 1.77-
1.87 (m, 2H), 2.14-2.17 (m, 1H), 3.80 (t, J 8.41 Hz, 2H),
3.93-4.00 (m, 2H), 4.02 (s, 3H), 4.59 (t, J 8.41 Hz, 1H), 7.02
(s, 1H), 7.46 (s, 1H), 7.69 (d, J 8.03 Hz, 1H), 7.94 (d, J 8.03
Hz, 1H), 8.45 (d, J 8.53 Hz, 1H), 10.49 (s, 1H), 11.01 (br s,
1H). HPLC-MS (method 6): MH+ m/z 495.0, RT 2.65
minutes.

Example 58

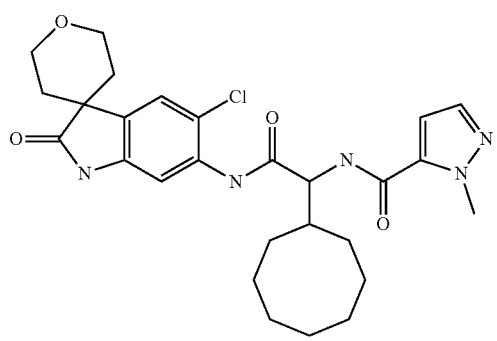 [SMILES: Cn1nccc1C(=O)NC(C(=O)Nc1cc2c(cc1Cl)C1(CCOCC1)C(=O)N2)C1CCCCCCC1]

N-{2-[(5-Chloro-2-oxospiro[indoline-3,4'-tetrahydropyran]-6-yl)amino]-1-cyclooctyl-2-oxoethyl}-2-methylpyrazole-3-carboxamide NCS (36 mg, 0.27 mmol) was added portionwise to a
solution of Example 3 (45 mg, 0.09 mmol) in acetic acid (2
mL) at 20° C. The reaction mixture was stirred at 20° C. for
10 minutes, then heated at 70° C. for 10 minutes, then
concentrated in vacuo. The residue was diluted in ethyl
acetate (50 mL), washed with saturated aqueous sodium
bicarbonate solution and brine, then dried over sodium
sulfate. The organic layers were concentrated in vacuo. The
residue was purified by preparative HPLC (method 9) to
afford the title compound (4.5 mg, 9%) as an off-white
powder. $\delta_H$ (500 MHz, CDCl₃) 10.44 (s, 1H), 8.41 (s, 1H),
8.40 (s, 1H), 7.93 (d, J 7.4 Hz, 1H), 7.38 (d, J 2.1 Hz, 1H),
7.37 (s, 1H), 6.86 (d, J 2.1 Hz, 1H), 4.45-4.37 (m, 1H),
4.27-4.18 (m, 2H), 4.13 (s, 3H), 3.95-3.85 (m, 2H), 2.35-
2.23 (m, 1H), 1.92-1.82 (m, 3H), 1.82-1.49 (m, 15H).
uPLC-MS (method 2) MH+ m/z 528 and 530, RT 3.56
minutes.

Example 59

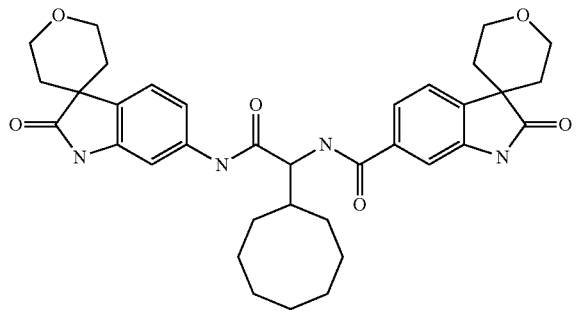 [SMILES: O=C(NC(C(=O)Nc1ccc2c(c1)NC(=O)C21CCOCC1)C1CCCCCCC1)c1ccc2c(c1)NC(=O)C21CCOCC1]

N-{1-Cyclooctyl-2-oxo-2-[(2-oxospiro[indoline-3,4'-
tetrahydropyran]-6-yl)amino]ethyl}-2-oxospiro[indoline-3,4'-tetrahydropyran]-6-carboxamide Prepared from Intermediate 121 (70 mg, 0.094 mmol) in
accordance with Procedure C, and purified by preparative
HPLC (method 11), to give the title compound (10.5 mg,
18%) as a white solid. $\delta_H$ (500 MHz, DMSO-d₆) 10.57 (s,
1H), 10.39 (s, 1H), 10.19 (s, 1H), 8.50 (d, J 8.6 Hz, 1H), 7.60
(d, J 7.8 Hz, 1H), 7.54 (dd, J 7.8, 1.5 Hz, 1H), 7.43 (d, J 8.2
Hz, 1H), 7.39 (d, J 1.9 Hz, 1H), 7.33 (d, J 1.4 Hz, 1H), 7.12
(dd, J 8.2, 1.9 Hz, 1H), 4.46 (t, J 8.8 Hz, 1H), 4.06-3.98 (m,
4H), 3.85-3.77 (m, 4H), 2.22-2.13 (m, 1H), 1.77-1.58 (m,
12H), 1.57-1.38 (m, 10H). HPLC-MS (method 1): MH+ m/z
615, RT 3.13 minutes.

Example 60

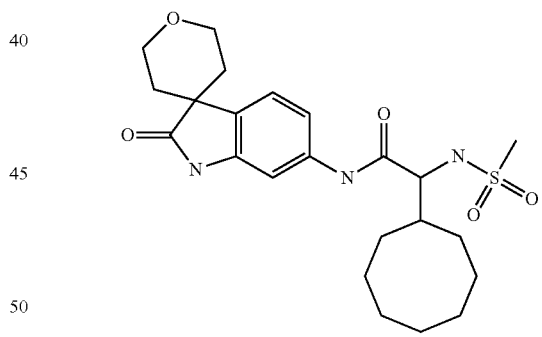

2-Cyclooctyl-2-(methanesulfonamido)-N-(2-
oxospiro[indoline-3,4'-tetrahydropyran]-6-yl)acetamide Methanesulfonyl chloride (12 μL, 0.15 mmol) was added
to a stirred solution of Intermediate 35 (50 mg, 0.12 mmol)
and DIPEA (43 μL, 0.25 mmol) in anhydrous DCM (2 mL).
The reaction mixture was stirred at 20° C. for 16 h. Additional methanesulfonyl chloride (6 μL, 0.08 mmol) was
added. The reaction mixture was stirred at 20° C. for a
further 6 h, then diluted with DCM (7 mL). The resulting
material was washed with water (7 mL) and brine (7 mL),
then dried over magnesium sulfate, filtered and concentrated
in vacuo. The residue was purified by preparative HPLC (method 10) to afford the title compound (26.7 mg, 47%) as a tan powder. δ$_H$ (500 MHz, DMSO-d$_6$) 10.40 (s, 1H), 10.18 (s, 1H), 7.53-7.46 (m, 1H), 7.44 (d, J 8.1 Hz, 1H), 7.37 (d, J 1.8 Hz, 1H), 7.09 (dd, J 8.1, 1.9 Hz, 1H), 4.01 (ddd, J 11.1, 7.1, 3.6 Hz, 2H), 3.80 (ddd, J 11.1, 7.0, 3.7 Hz, 2H), 3.77-3.69 (m, 1H), 2.81 (s, 3H), 1.98-1.87 (m, 1H), 1.80-1.30 (m, 18H). HPLC-MS (method 1): MH+ m/z 464, RT 2.90 minutes.

Example 61

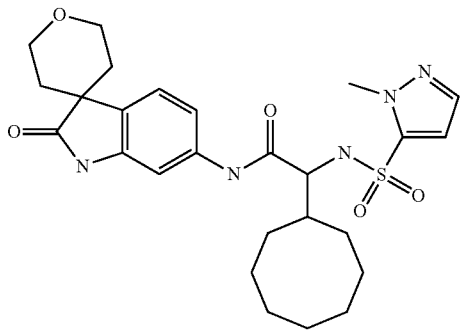 [SMILES: Cn1nccc1S(=O)(=O)NC(C(=O)Nc1ccc2c(c1)NC(=O)C21CCOCC1)C1CCCCCCC1]

2-Cyclooctyl-2-[(2-methylpyrazol-3-yl)sulfonylamino]-N-(2-oxospiro[indoline-3,4'-tetrahydropyran]-6-yl)acetamide 1-Methyl-1H-pyrazole-5-sulfonyl chloride (41 mg, 0.23 mmol) was added to a stirred solution of Intermediate 35 (100 mg, 0.15 mmol) and DIPEA (54 µL, 0.31 mmol) in anhydrous DCM (3 mL). The reaction mixture was stirred at 20° C. for 16 h, then diluted with DCM (10 mL). The resulting material was washed with water (10 mL) and brine (10 mL), then dried over magnesium sulfate, filtered and concentrated in vacuo. The residue was purified by preparative HPLC (method 10) to afford the title compound (20 mg, 24%) as an orange powder. δ$_H$ (500 MHz, DMSO-d$_6$) 10.36 (s, 1H), 9.93 (s, 1H), 8.65 (br s, 1H), 7.39 (d, J 8.1 Hz, 1H), 7.34 (d, J 1.7 Hz, 1H), 7.12 (s, 1H), 6.87 (dd, J 8.2, 1.9 Hz, 1H), 6.64 (s, 1H), 4.05-3.95 (m, 2H), 3.98 (s, 3H), 3.79 (ddd, J 10.7, 6.8, 3.6 Hz, 2H), 3.71-3.62 (m, 1H), 1.94-1.84 (m, 1H), 1.77-1.68 (m, 2H), 1.68-1.26 (m, 16H). HPLC-MS (method 1): MH+ m/z 530, RT 3.13 minutes.

Example 62

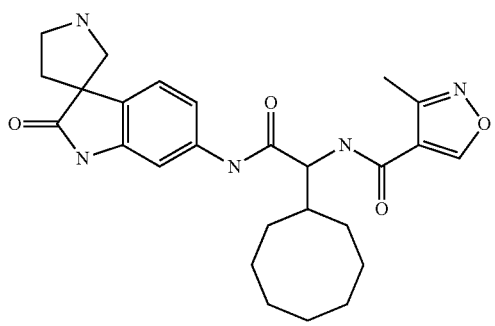 [SMILES: Cc1nocc1C(=O)NC(C(=O)Nc1ccc2c(c1)NC(=O)C21CCNC1)C1CCCCCCC1]

N-{1-Cyclooctyl-2-oxo-2-[(2-oxospiro[indoline-3,3'-pyrrolidine]-6-yl)amino]ethyl}-3-methylisoxazole-4-carboxamide (Isomer 1)

Trifluoroacetic acid (0.23 mL, 2.99 mmol) was added to a stirred suspension of Intermediate 127 (89.8 mg, 0.15 mmol) in DCM (1.2 mL). The mixture was stirred at 20° C. for 2 h, then quenched with saturated aqueous sodium carbonate solution (10 mL). The resulting material was extracted with 4:1 DCM/isopropanol (4×20 mL) using a hydrophobic frit. The organic filtrate was concentrated in vacuo. The resultant orange gum was separated by sequential preparative HPLC (method 10), chiral preparative HPLC (method 32, MeOH+0.2% diethylamine, Chiralcel OD-H 25 cm column at 9 mL/minute), and chiral preparative SFC (method 14, 25:75 MeOH+0.2% diethylamine-carbon dioxide, Chiralpak IC 25 cm column at 15 mL/minute), to afford the title compound (1.4 mg, 2%) as an off-white powder. δ$_H$ (500 MHz, CD$_3$OD) 9.12 (s, 1H), 7.43 (s, 1H), 7.27 (d, J 8.1 Hz, 1H), 7.14 (d, J 8.1 Hz, 1H), 4.49 (d, J 8.4 Hz, 1H), 3.47-3.24 (obs. m, 3H), 3.11 (d, J 10.8 Hz, 1H), 2.43 (s, 3H), 2.34-2.07 (m, 3H), 1.84-1.44 (m, 14H). uPLC-MS (method 1): MH+ m/z 480, RT 2.21 minutes. Chiral SFC (method 12, Chiralpak IC 25 cm, 35% MeOH+0.2% diethylamine-65% carbon dioxide, 4 mL/min): RT 3.89 minutes (100%).

Example 63

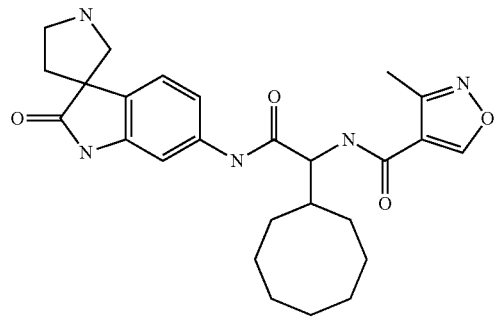 [SMILES: Cc1nocc1C(=O)NC(C(=O)Nc1ccc2c(c1)NC(=O)C21CCNC1)C1CCCCCCC1]

N-{1-Cyclooctyl-2-oxo-2-[(2-oxospiro[indoline-3,3'-pyrrolidine]-6-yl)amino]ethyl}-3-methylisoxazole-4-carboxamide (Isomer 2)

Trifluoroacetic acid (0.23 mL, 2.99 mmol) was added to a stirred suspension of Intermediate 127 (89.8 mg, 0.15 mmol) in DCM (1.2 mL). The mixture was stirred at 20° C. for 2 h, then quenched with saturated aqueous sodium carbonate solution (10 mL). The resulting material was extracted with 4:1 DCM/isopropanol (4×20 mL) using a hydrophobic frit. The organic filtrate was concentrated in vacuo. The resultant orange gum was separated by sequential preparative HPLC (method 10), chiral preparative HPLC (method 32, MeOH+0.2% diethylamine, Chiralcel OD-H 25 cm column at 9 mL/minute), and chiral preparative SFC (method 14, 25:75 MeOH+0.2% diethylamine-carbon dioxide, Chiralpak IC 25 cm column at 15 mL/minute), to afford the title compound (2.4 mg, 3%) as an off-white powder. $\delta_H$ (500 MHz, CD$_3$OD) 9.12 (s, 1H), 7.45-7.37 (m, 1H), 7.25 (d, J 8.0 Hz, 1H), 7.18-7.08 (m, 1H), 4.49 (d, J 8.3 Hz, 1H), 3.41-3.17 (obs. m, 3H), 2.99 (d, J 11.8 Hz, 1H), 2.43 (s, 3H), 2.32-2.12 (m, 2H), 2.05 (dt, J 13.5, 7.1 Hz, 1H), 1.86-1.42 (m, 14H). uPLC-MS (method 1): MH+ m/z 480, RT 2.20 minutes. Chiral SFC (method 12, Chiralpak IC 25 cm, 35% MeOH+0.2% diethylamine-65% carbon dioxide, 4 mL/min): RT 3.98 minutes (93%).

Example 64

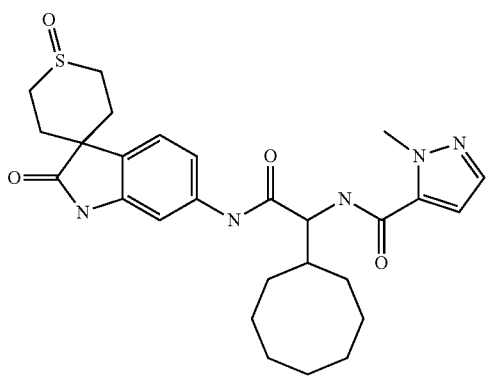 [SMILES: Cn1nccc1C(=O)NC(C(=O)Nc1ccc2c(c1)NC(=O)C21CCS(=O)CC1)C1CCCCCCC1]

N-{1-Cyclooctyl-2-[(1',2-dioxospiro[indoline-3,4'-thiane]-6-yl)amino]-2-oxoethyl}-2-methylpyrazole-3-carboxamide 3-Chloroperbenzoic acid (70%, 98 mg, 0.4 mmol) was added to a stirred suspension of Example 9 (176 mg, 0.34 mmol) in DCM (3.4 mL) at 0° C. under nitrogen. The reaction mixture was stirred at 0° C. for 3.5 h, then quenched with 1:1 10% aqueous sodium sulfite solution/saturated aqueous sodium carbonate solution (40 mL). The resulting material was extracted with 1:1 ethyl acetate/2-methyltetrahydrofuran (3×30 mL). The combined organic extracts were washed with saturated aqueous sodium carbonate solution (20 mL) and brine (20 mL), then dried over magnesium sulfate, filtered and concentrated in vacuo. The resulting crude off-white powder was separated by preparative HPLC (method 10) to afford, after freeze-drying, the title compound (23.3 mg, 13%) as a white powder. $\delta_H$ (500 MHz, DMSO-d$_6$) 10.47 (br s, 1H), 10.25 (s, 1H), 8.53 (d, J 8.5 Hz, 1H), 7.53 (d, J 8.1 Hz, 1H, minor), 7.46 (d, J 2.0 Hz, 1H), 7.41 (d, J 1.8 Hz, 1H, minor), 7.39 (d, J 1.7 Hz, 1H, major), 7.21 (d, J 8.1 Hz, 1H, major), 7.16 (dd, J 8.1, 1.8 Hz, 1H, major), 7.12 (dd, J 8.2, 1.9 Hz, 1H, minor), 7.05 (d, J 2.1 Hz, 1H), 4.44 (t, J 8.9 Hz, 1H), 4.03 (s, 3H), 3.43-3.23 (obs. m, 2H, major), 3.14-3.07 (m, 4H, minor), 2.93-2.79 (m, 2H, major), 2.56-2.43 (obs. m, 2H), 2.41-2.29 (m, 1H, minor), 2.21-2.10 (m, 1H, major), 1.75-1.33 (m, 16H). uPLC-MS (method 1): MH+ m/z 526, RT 2.75 minutes.

Example 65

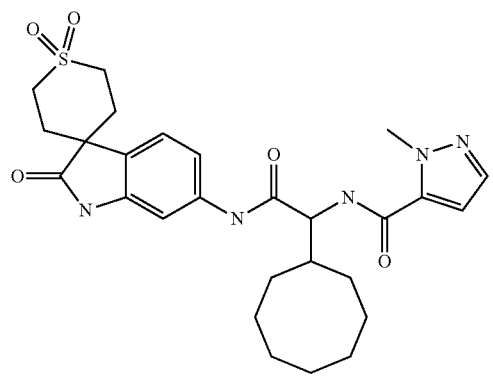 [SMILES: Cn1nccc1C(=O)NC(C(=O)Nc1ccc2c(c1)NC(=O)C21CCS(=O)(=O)CC1)C1CCCCCCC1]

N-{1-Cyclooctyl-2-oxo-2-[(1',1',2-trioxospiro[indoline-3,4'-thiane]-6-yl)amino]ethyl}-2-methylpyrazole-3-carboxamide 3-Chloroperbenzoic acid (70%, 98 mg, 0.4 mmol) was added to a stirred suspension of Example 9 (176 mg, 0.34 mmol) in DCM (3.4 mL) at 0° C. under nitrogen. The reaction mixture was stirred at 0° C. for 3.5 h, then quenched with 1:1 10% aqueous sodium sulfite solution/saturated aqueous sodium carbonate solution (40 mL). The resulting material was extracted with 1:1 ethyl acetate/2-methyltetrahydrofuran (3×30 mL). The combined organic extracts were washed with saturated aqueous sodium carbonate solution (20 mL) and brine (20 mL), then dried over magnesium sulfate, filtered and concentrated in vacuo. The resulting crude off-white powder was separated by preparative HPLC (method 10) to afford, after freeze-drying, the title compound (71.7 mg, 38%) as a white powder. $\delta_H$ (500 MHz, DMSO-d$_6$) 10.62 (br s, 1H), 10.27 (s, 1H), 8.53 (d, J 8.5 Hz, 1H), 7.45 (d, J 2.0 Hz, 1H), 7.42 (d, J 1.8 Hz, 1H), 7.31 (d, J 8.1 Hz, 1H), 7.15 (dd, J 8.2, 1.8 Hz, 1H), 7.05 (d, J 2.1 Hz, 1H), 4.43 (t, J 8.8 Hz, 1H), 4.02 (s, 3H), 3.74-3.60 (m, 2H), 3.17-3.05 (m, 2H), 2.35-2.25 (m, 2H), 2.22-2.03 (m, 3H), 1.73-1.33 (m, 14H). uPLC-MS (method 1): MH+ m/z 542, RT 3.00 minutes.

Example 66

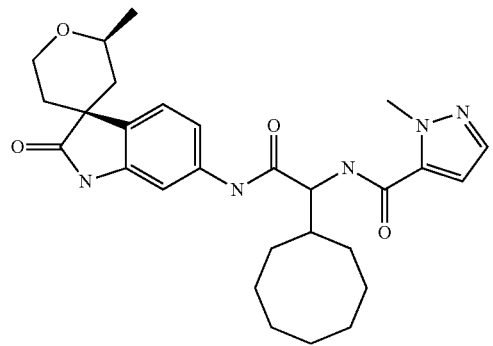 [SMILES: C[C@H]1C[C@@]2(CCO1)C(=O)Nc1cc(NC(=O)C(NC(=O)c3ccnn3C)C3CCCCCCC3)ccc12]

N-(1-Cyclooctyl-2-{[(2'S,3R)-2'-methyl-2-oxospiro [indoline-3,4'-tetrahydropyran]-6-yl]-amino}-2-oxo-ethyl)-2-methylpyrazole-3-carboxamide (Isomer 1)

DIPEA (76 µL, 0.46 mmol) was added to a stirred suspension of Intermediate 135 (96.7 mg, 0.35 mmol), Intermediate 128 (127 mg, 0.39 mmol) and HATU (161 mg, 0.42 mmol) in anhydrous THF (1.75 mL). The mixture was stirred at 20° C. under nitrogen for 16 h, then quenched with saturated aqueous sodium carbonate solution (3 mL) and water (3 mL) and stirred at 20° C. for 1 h. The mixture was extracted with 4:1 DCM/isopropanol (4×5 mL) using a hydrophobic frit, then the organic filtrate was concentrated in vacuo. The resultant tan powder was separated by chiral preparative SFC (method 14, 15:85 ethanol-carbon dioxide, Chiralpak IC 25 cm column at 15 mL/minute) to afford, after freeze-drying, the title compound (52.2 mg, 28%) as an off-white powder. $\delta_H$ (500 MHz, DMSO-$d_6$) 10.30 (s, 1H), 10.20 (s, 1H), 8.52 (d, J 8.6 Hz, 1H), 7.45 (d, J 2.0 Hz, 1H), 7.34 (d, J 1.6 Hz, 1H), 7.15 (d, J 8.1 Hz, 1H), 7.11 (dd, J 8.1, 1.7 Hz, 1H), 7.05 (d, J 2.0 Hz, 1H), 4.43 (t, J 8.9 Hz, 1H), 4.27-4.10 (m, 2H), 4.03 (s, 3H), 3.73 (dd, J 11.1, 4.6 Hz, 1H), 2.22-2.09 (m, 1H), 1.87 (td, J 13.4, 5.0 Hz, 1H), 1.74-1.33 (m, 17H), 1.07 (d, J 6.2 Hz, 3H). uPLC-MS (method 1): MH+ m/z 508, RT 3.30 minutes. Chiral SFC (method 12, Chiralpak IC 25 cm, 20% ethanol-80% carbon dioxide, 4 mL/minute): RT 5.65 minutes (98%, isomer 1).

Example 67

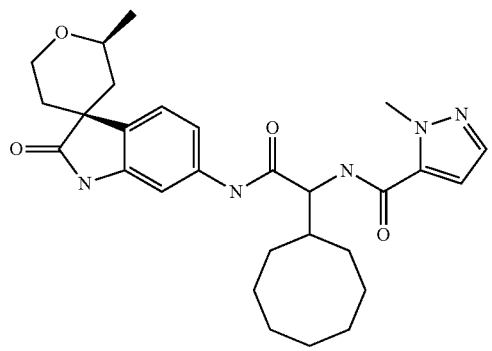 [SMILES: C[C@H]1C[C@@]2(CCO1)C(=O)Nc1cc(NC(=O)C(NC(=O)c3ccnn3C)C3CCCCCCC3)ccc12]

N-(1-Cyclooctyl-2-{[(2'S,3R)-2'-methyl-2-oxospiro [indoline-3,4'-tetrahydropyran]-6-yl]-amino}-2-oxo-ethyl)-2-methylpyrazole-3-carboxamide (Isomer 2)

DIPEA (76 µL, 0.46 mmol) was added to a stirred suspension of Intermediate 135 (96.7 mg, 0.35 mmol), Intermediate 128 (127 mg, 0.39 mmol) and HATU (161 mg, 0.42 mmol) in anhydrous THF (1.75 mL). The mixture was stirred at 20° C. under nitrogen for 16 h, then quenched with saturated aqueous sodium carbonate solution (3 mL) and water (3 mL) and stirred at 20° C. for 1 h. The mixture was extracted with 4:1 DCM/isopropanol (4×5 mL) using a hydrophobic frit, then the organic filtrate was concentrated in vacuo. The resultant tan powder was separated by chiral preparative SFC (method 14, 15:85 ethanol-carbon dioxide, Chiralpak IC 25 cm column at 15 mL/minute) to afford, after freeze-drying, the title compound (31.1 mg, 16%) as a white powder. $\delta_H$ (500 MHz, DMSO-$d_6$) 10.30 (s, 1H), 10.20 (s, 1H), 8.52 (d, J 8.6 Hz, 1H), 7.45 (d, J 2.0 Hz, 1H), 7.35 (d, J 1.6 Hz, 1H), 7.15 (d, J 8.1 Hz, 1H), 7.10 (dd, J 8.1, 1.7 Hz, 1H), 7.05 (d, J 2.0 Hz, 1H), 4.43 (t, J 8.9 Hz, 1H), 4.27-4.10 (m, 2H), 4.03 (s, 3H), 3.73 (dd, J 11.0, 4.7 Hz, 1H), 2.22-2.09 (m, 1H), 1.86 (td, J 13.3, 5.0 Hz, 1H), 1.74-1.32 (m, 17H), 1.07 (d, J 6.2 Hz, 3H). uPLC-MS (method 1): MH+ m/z 508, RT 3.29 minutes. Chiral SFC (method 12, Chiralpak IC 25 cm, 20% ethanol-80% carbon dioxide, 4 mL/minute): RT 7.23 minutes (98%, isomer 2).

Example 68

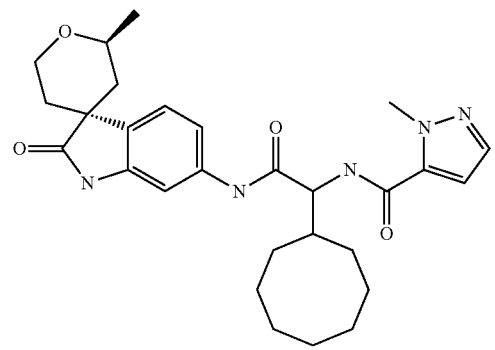 [SMILES: C[C@H]1C[C@]2(CCO1)C(=O)Nc1cc(NC(=O)C(NC(=O)c3ccnn3C)C3CCCCCCC3)ccc12]

N-(1-Cyclooctyl-2-{[(2'S,3S)-2'-methyl-2-oxospiro [indoline-3,4'-tetrahydropyran]-6-yl]-amino}-2-oxo-ethyl)-2-methylpyrazole-3-carboxamide (Isomer 3)

DIPEA (39 µL, 0.24 mmol) was added to a stirred suspension of Intermediate 136 (44.9 mg, 0.22 mmol), Intermediate 128 (65 mg, 0.2 mmol) and HATU (83 mg, 0.22 mmol) in anhydrous THF (1 mL). The mixture was stirred at 20° C. under nitrogen for 16 h, then quenched with saturated aqueous sodium carbonate solution (3 mL) and water (3 mL) and stirred at 20° C. for 1 h. The mixture was extracted with 4:1 DCM/isopropanol (4×5 mL) using a hydrophobic frit, then the organic filtrate was concentrated in vacuo. The resultant tan powder was separated by chiral preparative HPLC (method 34, 70:30 heptane-isopropanol, Chiralpak AD-H 25 cm column at 18 mL/minute) to afford, after freeze-drying, the title compound (30.6 mg, 33%) as a white powder. $\delta_H$ (500 MHz, DMSO-$d_6$) 10.48 (s, 1H), 10.24 (s, 1H), 8.52 (d, J 8.6 Hz, 1H), 7.67 (d, J 8.3 Hz, 1H), 7.46 (d, J 2.0 Hz, 1H), 7.42 (d, J 1.8 Hz, 1H), 7.12 (dd, J 8.2, 1.9 Hz, 1H), 7.05 (d, J 2.0 Hz, 1H), 4.44 (t, J 8.9 Hz, 1H), 4.03 (s, 3H), 4.01-3.81 (m, 3H), 2.23-2.04 (m, 1H), 1.87 (td, J 13.0, 6.1 Hz, 1H), 1.74-1.29 (m, 16H), 1.25 (d, J 13.4 Hz, 1H), 1.10 (d, J 6.0 Hz, 3H). uPLC-MS (method 1): MH+ m/z 508, RT 3.22 minutes. Chiral SFC (method 12, Chiralcel OD-H 25 cm, 15% MeOH-85% carbon dioxide, 4 mL/minute): RT 10.70 minutes (100%).

Example 69

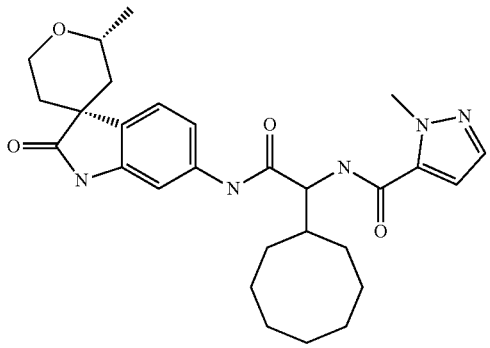 [SMILES: C[C@@H]1C[C@]2(CCO1)C(=O)Nc1cc(NC(=O)C(NC(=O)c3ccnn3C)C3CCCCCCC3)ccc12]

N-(1-Cyclooctyl-2-{[(2'R,3S)-2'-methyl-2-oxospiro[indoline-3,4'-tetrahydropyran]-6-yl]-amino}-2-oxo-ethyl)-2-methylpyrazole-3-carboxamide (Isomer 4)

DIPEA (85 µL, 0.51 mmol) was added to a stirred suspension of Intermediate 141 (102 mg, 0.4 mmol), Intermediate 128 (142 mg, 0.44 mmol) and HATU (180 mg, 0.47 mmol) in anhydrous THF (2 mL). The mixture was stirred at 20° C. under nitrogen for 16 h, then quenched with saturated aqueous sodium carbonate solution (3 mL) and water (3 mL) and stirred at 20° C. for 1 h. The mixture was extracted with 4:1 DCM/isopropanol (4×5 mL) using a hydrophobic frit, then the organic filtrate was concentrated in vacuo. The resultant tan powder was separated by chiral preparative HPLC (method 32, 50:50 heptane-isopropanol, Chiralpak AD-H 25 cm column at 18 mL/minute) to afford, after freeze-drying, the title compound (73.4 mg, 36%) as a white powder. $\delta_H$ (500 MHz, DMSO-$d_6$) 10.30 (s, 1H), 10.20 (s, 1H), 8.52 (d, J 8.6 Hz, 1H), 7.45 (d, J 2.0 Hz, 1H), 7.35 (d, J 1.6 Hz, 1H), 7.15 (d, J 8.1 Hz, 1H), 7.10 (dd, J 8.1, 1.7 Hz, 1H), 7.05 (d, J 2.0 Hz, 1H), 4.43 (t, J 8.9 Hz, 1H), 4.27-4.11 (m, 2H), 4.03 (s, 3H), 3.73 (dd, J 11.0, 4.6 Hz, 1H), 2.23-2.10 (m, 1H), 1.86 (td, J 13.4, 5.0 Hz, 1H), 1.75-1.32 (m, 17H), 1.07 (d, J 6.2 Hz, 3H). uPLC-MS (method 1): MH+ m/z 508, RT 3.29 minutes. Chiral SFC (method 12, Chiralcel OD-H 25 cm, 20% MeOH-80% carbon dioxide, 4 mL/minute): RT 5.29 minutes (99%).

Example 70

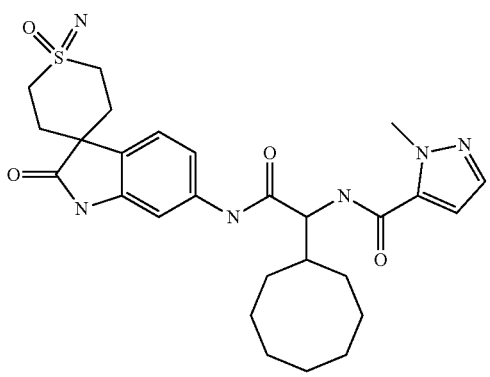 [SMILES: Cn1nccc1C(=O)NC(C(=O)Nc1ccc2c(c1)NC(=O)C21CCS(=N)(=O)CC1)C1CCCCCCC1]

N-{1-Cyclooctyl-2-[(1'-imino-1',2-dioxospiro[indoline-3,4'-thiane]-6-yl)amino]-2-oxo-ethyl}-2-methylpyrazole-3-carboxamide (Mixture of Isomers 1)

Example 9 (39 mg, 0.08 mmol), ammonium carbamate (12 mg, 0.15 mmol) and (diacetoxyiodo)benzene (62 mg, 0.19 mmol) were dissolved in MeOH (1 mL). The reaction mixture was stirred at 20° C. under nitrogen for 16 h, then the volatiles were removed in vacuo. The resultant tan powder was separated by preparative HPLC (method 10) to afford, after freeze-drying, the title compound (6.2 mg, 14%) as a white powder. $\delta_H$ (500 MHz, DMSO-$d_6$) 10.56 (br s, 1H), 10.26 (s, 1H), 8.54 (d, J 8.6 Hz, 1H), 7.45 (d, J 2.1 Hz, 1H), 7.40 (d, J 1.8 Hz, 1H), 7.21 (d, J 8.1 Hz, 1H), 7.15 (dd, J 8.2, 1.8 Hz, 1H), 7.05 (d, J 2.1 Hz, 1H), 4.43 (t, J 8.8 Hz, 1H), 4.02 (s, 3H), 3.68 (s, 1H), 3.67-3.59 (m, 2H), 3.09-2.94 (m, 2H), 2.33-2.24 (m, 2H), 2.21-2.11 (m, 1H), 2.02-1.94 (m, 2H), 1.74-1.32 (m, 14H). uPLC-MS (method 1): MH+ m/z 541, RT 2.54 minutes.

Example 71

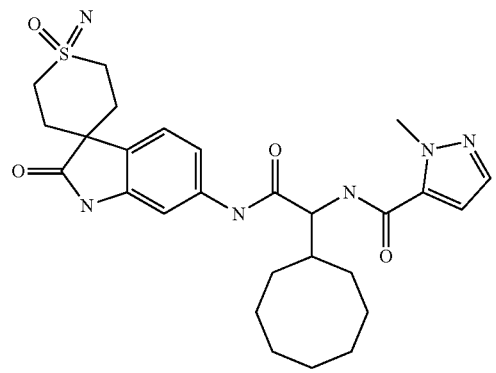 [SMILES: Cn1nccc1C(=O)NC(C(=O)Nc1ccc2c(c1)NC(=O)C21CCS(=N)(=O)CC1)C1CCCCCCC1]

N-{1-Cyclooctyl-2-[(1'-imino-1',2-dioxospiro[indoline-3,4'-thiane]-6-yl)amino]-2-oxo-ethyl}-2-methylpyrazole-3-carboxamide (Mixture of Isomers 1)

Example 9 (39 mg, 0.08 mmol), ammonium carbamate (12 mg, 0.15 mmol) and (diacetoxyiodo)benzene (62 mg, 0.19 mmol) were dissolved in MeOH (1 mL). The reaction mixture was stirred at 20° C. under nitrogen for 16 h, then the volatiles were removed in vacuo. The resultant tan powder was separated by preparative HPLC (method 10) to afford, after freeze-drying, the title compound (23.5 mg, 53%) as a white powder. $\delta_H$ (500 MHz, DMSO-$d_6$) 10.56 (br s, 1H), 10.27 (s, 1H), 8.55 (d, J 8.4 Hz, 1H), 7.45 (d, J 2.1 Hz, 1H), 7.42 (d, J 1.8 Hz, 1H), 7.28 (d, J 8.1 Hz, 1H), 7.15 (dd, J 8.2, 1.9 Hz, 1H), 7.05 (d, J 2.0 Hz, 1H), 4.43 (t, J 8.7 Hz, 1H), 4.02 (s, 3H), 3.83 (s, 1H), 3.58-3.49 (m, 2H), 3.08-2.94 (m, 2H), 2.23-2.11 (m, 3H), 2.10-2.02 (m, 2H), 1.74-1.33 (m, 14H). uPLC-MS (method 1): MH+ m/z 541, RT 2.62 minutes.

Example 72

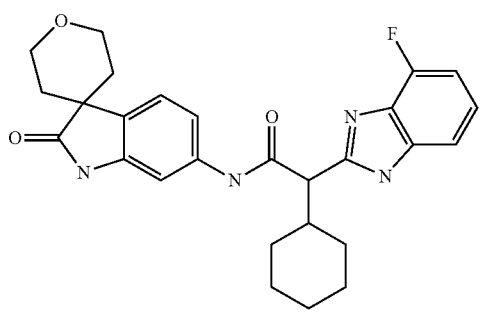 [SMILES: O=C(Nc1ccc2c(c1)NC(=O)C21CCOCC1)C(c1nc2c(F)cccc2[nH]1)C1CCCCC1]

2-Cyclohexyl-2-(4-fluoro-1H-benzimidazol-2-yl)-N-(2-oxospiro[indoline-3,4'-tetrahydro-pyran]-6-yl)acetamide Intermediate 144 (97 mg, 0.20 mmol) was dissolved in acetic acid (2 mL, 34.90 mmol). The reaction mixture was stirred at 65° C. for 18 h, then concentrated under vacuum. The crude residue was purified by preparative HPLC (method 26) to afford the title compound (2 mg, 2%) as a white solid. $\delta_H$ (300 MHz, DMSO-$d_6$) 12.59 (s, 1H), 10.44 (d, J 9.6 Hz, 2H), 7.47-7.27 (m, 3H), 7.19-7.08 (m, 2H), 6.93 (dd, J 11.0, 7.9 Hz, 1H), 4.07-3.94 (m, 2H), 3.89 (d, J 10.6 Hz, 1H), 3.85-3.72 (m, 2H), 2.35-2.20 (m, 1H), 1.79-1.57 (m, 8H), 1.31-1.12 (m, 5H), 0.99-0.87 (m, 1H). LC-MS (method 6): MH+ m/z 477, RT 2.04 minutes.

Example 73

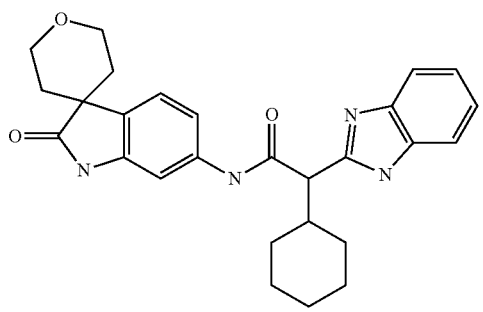 [SMILES: O=C(Nc1ccc2c(c1)NC(=O)C21CCOCC1)C(c1nc2ccccc2[nH]1)C1CCCCC1]

2-(1H-Benzimidazol-2-yl)-2-cyclohexyl-N-(2-oxospiro[indoline-3,4'-tetrahydropyran]-6-yl)acetamide Intermediate 145 (40 mg, 0.08 mmol) was dissolved in acetic acid (1 mL, 17.45 mmol). The reaction mixture was stirred at 20° C. for 2 h, then heated at 65° C. for 18 h. The reaction mixture was concentrated under vacuum, and the residue was separated by flash column chromatography, using a gradient of ethyl acetate in hexane (0-100%). The resulting crude solid was purified by preparative HPLC (method 22) to afford the title compound (3 mg, 8%) as a white solid. $\delta_H$ (300 MHz, DMSO-$d_6$) 12.28 (s, 1H), 10.48 (s, 1H), 10.42 (s, 1H), 7.63-7.45 (m, 2H), 7.43 (d, J 8.2 Hz, 1H), 7.37 (d, J 1.9 Hz, 1H), 7.21-7.05 (m, 3H), 4.00 (ddd, J 10.7, 6.7, 3.3 Hz, 2H), 3.87-3.74 (m, 3H), 2.31-2.23 (m, 1H), 1.81-1.55 (m, 8H), 1.33-1.12 (m, 5H), 0.98-0.85 (m, 1H). HPLC-MS (method 6): MH+ m/z 459, RT 2.26 minutes.

Example 74

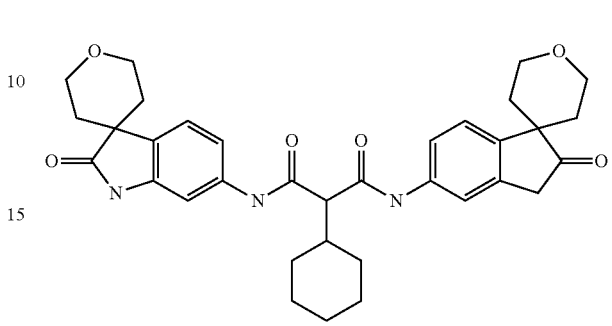

2-Cyclohexyl-N,N'-bis(2-oxospiro[indoline-3,4'-tetrahydropyran]-6-yl)propanediamide To a solution of Intermediate 2 (63 mg, 0.29 mmol) and Intermediate 143 (116 mg, 0.30 mmol) in DMF (2 mL, 25.90 mmol) was added HATU (136 mg, 0.35 mmol). The reaction mixture was stirred at 20° C. for 2 h. Water was added to the reaction mixture at 0° C. and the resulting solid was collected by filtration. The crude solid was purified by preparative HPLC (method 24) to afford the title compound (60 mg, 35%) as a white solid. $\delta_H$ (300 MHz, DMSO-$d_6$) 10.41 (s, 2H), 9.99 (s, 2H), 7.44 (d, J 8.2 Hz, 2H), 7.38 (d, J 1.9 Hz, 2H), 7.09 (dd, J 8.2, 2.0 Hz, 2H), 4.01 (ddd, J 11.0, 7.1, 3.7 Hz, 4H), 3.87-3.72 (m, 4H), 3.21 (d, J 10.5 Hz, 1H), 2.29-2.14 (m, 1H), 1.81-1.55 (m, 13H), 1.28-0.99 (m, 5H). HPLC-MS (method 23): MH+ m/z 587, RT 2.30 minutes.

Example 75

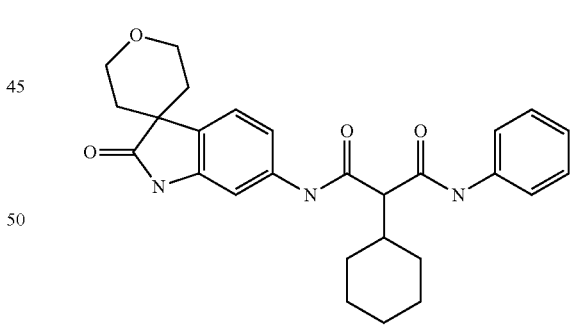

2-Cyclohexyl-N'-(2-oxospiro[indoline-3,4'-tetrahydropyran]-6-yl)-N-phenylpropane-diamide To a solution of aniline (0.02 mL, 0.2 mmol) and Intermediate 143 (50 mg, 0.13 mmol) in DMF (0.5 mL) were added HATU (65 mg, 0.17 mmol) and DIPEA (0.09 mL, 0.5 mmol). The reaction mixture was stirred at 20° C. for 1 h, then diluted in EtOAc (10 mL), washed with a 1:1 mixture of water and brine (10 mL) and dried over $Na_2SO_4$. The crude residue was purified by column chromatography (hexane to EtOAc), followed by preparative HPLC (method 24), to afford the title compound (13 mg, 22%) as a white solid. δ$_H$ (400 MHz, CD$_3$OD) 7.61-7.55 (m, 2H), 7.48-7.43 (m, 2H), 7.38-7.31 (m, 2H), 7.17-7.10 (m, 2H), 4.18 (m, 2H), 3.94 (m, 2H), 3.12 (d, J 10.1 Hz, 1H), 2.19 (q, J 10.9 Hz, 1H), 1.94-1.68 (m, 9H), 1.27 (m, 6H). HPLC-MS (method 6): MH+ m/z 462, RT 2.27 minutes.

Example 76

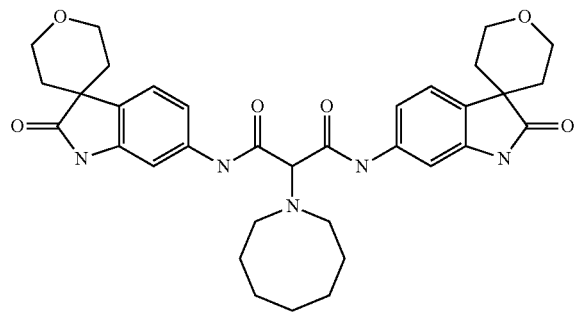 [SMILES: O=C(Nc1ccc2c(c1)NC(=O)C21CCOCC1)C(C(=O)Nc1ccc2c(c1)NC(=O)C21CCOCC1)N1CCCCCCC1]

2-(Azocan-1-yl)-N,N'-bis(2-oxospiro[indoline-3,4'-tetrahydropyran]-6-yl)propanediamide To a solution of Intermediate 2 (25 mg, 0.12 mmol) and Intermediate 149 (50 mg, 0.12 mmol) in DMF (1 mL, 12.90 mmol) was added HATU (55 mg, 0.15 mmol). The reaction mixture was stirred at 20° C. for 18 h. Water was added to the reaction mixture, and the resulting white precipitate was collected by filtration and washed with additional water. The crude residue was purified by preparative HPLC (Method 22) to afford the title compound (4 mg, 6%) as a white solid. δ$_H$ (400 MHz, DMSO-d$_6$) 10.43 (s, 2H), 9.91 (s, 2H), 7.46 (d, J 8.2 Hz, 2H), 7.40 (d, J 2.0 Hz, 2H), 7.06 (dd, J 8.2, 2.0 Hz, 2H), 4.14 (s, 1H), 4.06-3.98 (m, 4H), 3.81 (ddd, J 11.0, 6.7, 3.5 Hz, 4H), 2.82 (t, J 5.4 Hz, 4H), 1.78-1.52 (m, 18H). LC-MS (method 21): MH⁻ m/z 614, RT 1.94 minutes.

Example 77

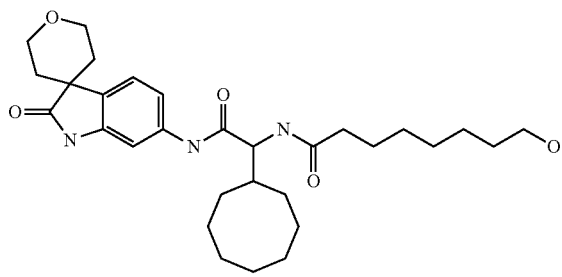 [SMILES: O=C(CCCCCCCO)NC(C(=O)Nc1ccc2c(c1)NC(=O)C21CCOCC1)C1CCCCCCC1]

N-{1-Cyclooctyl-2-oxo-2-[(2-oxospiro[indoline-3,4'-tetrahydropyran]-6-yl)amino]ethyl}-8-hydroxyoctanamide Prepared from Intermediate 35 (50 mg, 0.13 mmol) and 8-hydroxyoctanoic acid (23 mg, 0.14 mmol) in accordance with Procedure A, and purified by preparative HPLC (method 20), to give the title compound (45.2 mg, 66%) as a white powder. δ$_H$ (500 MHz, DMSO-d$_6$) 10.38 (s, 1H), 10.08 (s, 1H), 7.99 (d, J 8.8 Hz, 1H), 7.42 (d, J 8.1 Hz, 1H), 7.36 (d, J 1.8 Hz, 1H), 7.09 (dd, J 8.2, 1.8 Hz, 1H), 4.35-4.26 (m, 2H), 4.00 (ddd, J 11.0, 7.1, 3.6 Hz, 2H), 3.79 (ddd, J 11.0, 6.9, 3.6 Hz, 2H), 3.39-3.28 (obs. m, 2H), 2.23-2.06 (m, 2H), 2.00-1.89 (m, 1H), 1.79-1.69 (m, 2H), 1.69-1.28 (m, 20H), 1.27-1.18 (m, 6H). uPLC-MS (method 1): MH+ m/z 528, RT 3.06 minutes.

Example 78

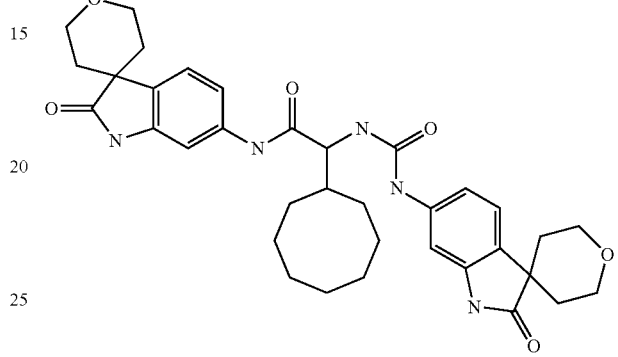

2-Cyclooctyl-N-(2-oxospiro[indoline-3,4'-tetrahydropyran]-6-yl)-2-[(2-oxospiro[indoline-3,4'-tetrahydropyran]-6-yl)carbamoylamino]acetamide A suspension of Intermediate 152 (65 mg, 0.19 mmol), Intermediate 35 (99 mg, 0.26 mmol) and 4-(dimethylamino)pyridine (60 mg, 0.49 mmol) in acetonitrile (3 mL) was heated at 60° C. under a nitrogen atmosphere for 18 h. The reaction mixture was concentrated in vacuo and triturated with water (5 mL). The resulting material was filtered and washed with a small amount of water. The resulting white solid was purified by reverse phase HPLC (method 25, with methanol as solvent A) to give, after freeze-drying, the title compound (85 mg, 74%) as a white solid. δ$_H$ (400 MHz, DMSO-d$_6$) 10.40 (s, 1H), 10.30 (s, 1H), 10.18 (s, 1H), 8.73 (s, 1H), 7.44 (d, J 8.1 Hz, 1H), 7.37 (d, J 1.9 Hz, 1H), 7.35 (d, J 8.1 Hz, 1H), 7.22 (d, J 1.9 Hz, 1H), 7.11 (dd, J 8.2, 1.9 Hz, 1H), 6.75 (dd, J 8.1, 2.0 Hz, 1H), 6.45 (d, J 8.8 Hz, 1H), 4.27 (dd, J 8.9, 6.4 Hz, 1H), 4.01 (ddt, J 11.1, 7.4, 3.7 Hz, 4H), 3.86-3.74 (m, 4H), 1.96 (d, J 8.4 Hz, 1H), 1.80-1.21 (m, 22H). HPLC-MS (Method 21): MH+ m/z 628, RT 2.16 minutes.

Examples 79 to 143

The title compounds were prepared by a three-step sequence:
Step 1: reaction of Intermediate 37 with the appropriate commercially available aldehyde or ketone in accordance with Procedure F.
Step 2: reaction of the material thereby obtained in accordance with Procedure H.
Step 3: reaction of the material thereby obtained with Intermediate 2 in accordance with Procedure I.
Chiral SFC Analysis (method 12) with the following conditions:
A: Chiralpak IC 25 cm, 15% methanol-85% carbon dioxide, 4 mL/minute B: Lux C-4 25 cm, 35% methanol-65% carbon dioxide (0.2% v/v NH$_3$), 4 mL/minute
C: Chiralcel OD-H 25 cm, 25% methanol-75% carbon dioxide, 4 mL/minute
D: Chiralpak AS-H 25 cm, 30% methanol-70% carbon dioxide, 4 mL/minute
E: Chiralpak IC 25 cm, 20% methanol-80% carbon dioxide, 15 mL/minute
F: Chiralpak IC 25 cm, 25% isopropanol-75% carbon dioxide, 4 mL/minute
G: Lux C-3 25 cm, 25% methanol-75% carbon dioxide, 4 mL/minute
H: Chiralcel OD-H 25 cm, 20% methanol-80% carbon dioxide, 4 mL/minute
I: Chiralpak AS-H 25 cm, 15% ethanol-85% carbon dioxide, 4 mL/minute

| Ex. | Structure | Product | LCMS Mass | LCMS RT (min) | LCMS Method No. |
|---|---|---|---|---|---|
| 79 | 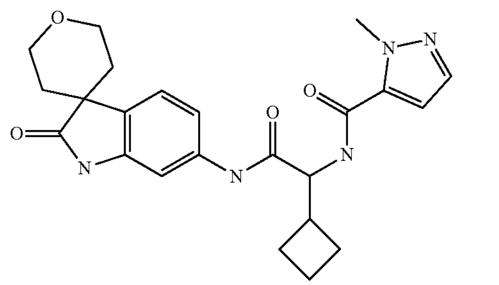 [SMILES: Cn1nccc1C(=O)NC(C(=O)Nc1ccc2c(c1)NC(=O)C21CCOCC1)C1CCC1] | N-{1-Cyclobutyl-2-oxo-2-[(2-oxospiro[1H-indole-3,4'-oxane]-6-yl)amino]ethyl}-2-methyl-pyrazole-3-carboxamide | 438.2 | 1.06 | 27 |
| 80 | 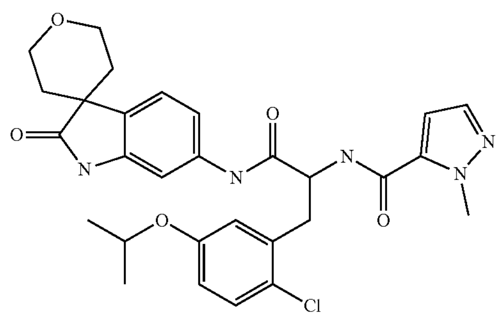 [SMILES: CC(C)Oc1ccc(Cl)c(CC(NC(=O)c2ccnn2C)C(=O)Nc2ccc3c(c2)NC(=O)C32CCOCC2)c1] | N-{3-[2-Chloro-5-(propan-2-yloxy)phenyl]-1-oxo-1-[(2-oxospiro[1H-indole-3,4'-oxane]-6-yl)amino]propan-2-yl}-2-methylpyrazole-3-carboxamide | 566.4 | 1.39 | 27 |
| 81 | 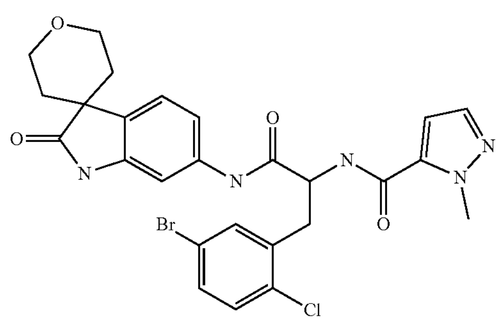 [SMILES: Cn1nccc1C(=O)NC(Cc1cc(Br)ccc1Cl)C(=O)Nc1ccc2c(c1)NC(=O)C21CCOCC1] | N-{3-(5-Bromo-2-chloro-phenyl)-1-oxo-1-[(2-oxospiro-[1H-indole-3,4'-oxane]-6-yl)-amino]propan-2-yl}-2-methyl-pyrazole-3-carboxamide | 588.1 | 1.35 | 27 |
| 82 | 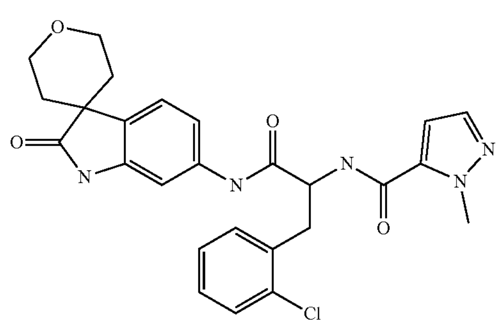 [SMILES: Cn1nccc1C(=O)NC(Cc1ccccc1Cl)C(=O)Nc1ccc2c(c1)NC(=O)C21CCOCC1] | N-[3-(2-Chlorophenyl)-1-oxo-1-[(2-oxospiro[1H-indole-3,4'-oxane]-6-yl)amino]propan-2-yl}-2-methylpyrazole-3-carboxamide | 508.4 | 1.24 | 27 |

| Ex. | Structure | Product | LCMS Mass | LCMS RT (min) | LCMS Method No. |
|---|---|---|---|---|---|
| 83 | 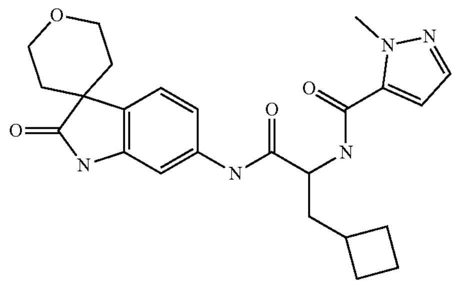 [SMILES: Cn1nccc1C(=O)NC(CC1CCC1)C(=O)Nc1ccc2c(c1)NC(=O)C21CCOCC1] | N-{3-Cyclobutyl-1-oxo-1-[(2-oxospiro[1H-indole-3,4'-oxane]-6-yl)amino]propan-2-yl}-2-methylpyrazole-3-carboxamide | 452.3 | 1.17 | 27 |
| 84 | 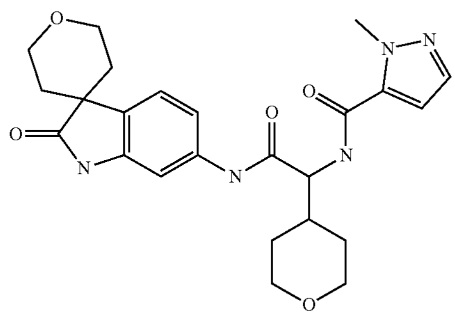 [SMILES: Cn1nccc1C(=O)NC(C(=O)Nc1ccc2c(c1)NC(=O)C21CCOCC1)C1CCOCC1] | 2-Methyl-N-[1-(oxan-4-yl)-2-oxo-2-[(2-oxospiro[1H-indole-3,4'-oxane]-6-yl)amino]ethyl}-pyrazole-3-carboxamide | 468.3 | 0.83 | 27 |
| 85 | 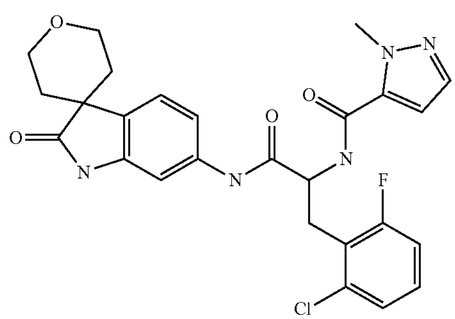 [SMILES: Cn1nccc1C(=O)NC(Cc1c(F)cccc1Cl)C(=O)Nc1ccc2c(c1)NC(=O)C21CCOCC1] | N-{3-(2-Chloro-6-fluoro-phenyl)-1-oxo-1-[(2-oxospiro-[1H-indole-3,4'-oxane]-6-yl)-amino]propan-2-yl}-2-methyl-pyrazole-3-carboxamide | 526 | 1.16 | 27 |
| 86 | 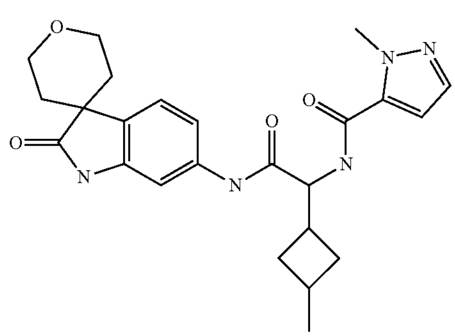 [SMILES: CC1CC(C(NC(=O)c2ccnn2C)C(=O)Nc2ccc3c(c2)NC(=O)C32CCOCC2)C1] | 2-Methyl-N-{1-(3-methyl-cyclobutyl)-2-oxo-2-[(2-oxo-spiro[1H-indole-3,4'-oxane]-6-yl)amino]ethyl}pyrazole-3-carboxamide | 452.2 | 1.11 | 27 |

-continued

| Ex. | Structure | Product | LCMS Mass | LCMS RT (min) | LCMS Method No. |
|---|---|---|---|---|---|
| 87 | 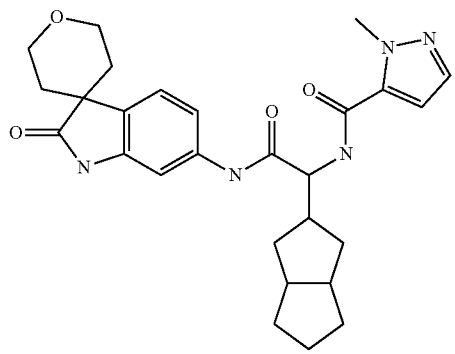 [SMILES: Cn1nccc1C(=O)NC(C(=O)Nc1ccc2c(c1)NC(=O)C21CCOCC1)C1CC2CCCC2C1] | N-{1-(1,2,3,3a,4,5,6,6a-Octahydropentalen-2-yl)-2-oxo-2-[(2-oxospiro[1H-indole-3,4'-oxane]-6-yl)amino]ethyl}-2-methylpyrazole-3-carboxamide | 492.4 | 1.36 | 27 |
| 88 | 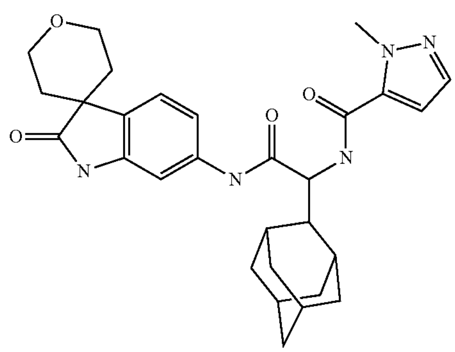 [SMILES: Cn1nccc1C(=O)NC(C(=O)Nc1ccc2c(c1)NC(=O)C21CCOCC1)C1C2CC3CC(C2)CC1C3] | N-{1-(2-Adamantyl)-2-oxo-2-[(2-oxospiro[1H-indole-3,4'-oxane]-6-yl)amino]ethyl}-2-methylpyrazole-3-carboxamide | 518.5 | 1.44 | 27 |
| 89 | 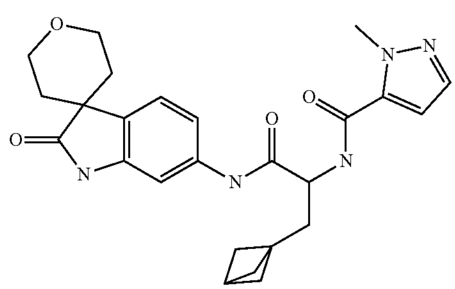 [SMILES: Cn1nccc1C(=O)NC(CC12CC(C1)C2)C(=O)Nc1ccc2c(c1)NC(=O)C21CCOCC1] | N-{3-(Bicyclo[1.1.1]pentan-1-yl)-1-oxo-1-[(2-oxospiro[1H-indole-3,4'-oxane]-6-yl)amino]-propan-2-yl}-2-methylpyrazole-3-carboxamide | 464.4 | 1.21 | 27 |
| 90 | 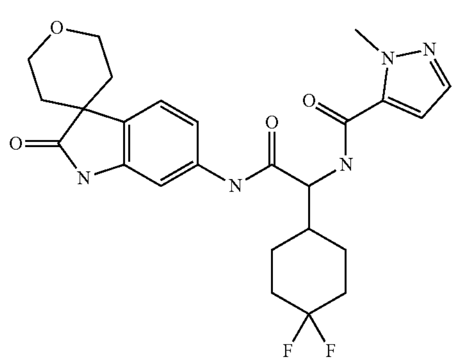 [SMILES: Cn1nccc1C(=O)NC(C(=O)Nc1ccc2c(c1)NC(=O)C21CCOCC1)C1CCC(F)(F)CC1] | N-{1-(4,4-Difluorocyclohexyl)-2-oxo-2-[(2-oxospiro[1H-indole-3,4'-oxane]-6-yl)amino]-ethyl}-2-methylpyrazole-3-carboxamide | 502.2 | 1.15 | 27 |

| Ex. | Structure | Product | LCMS Mass | LCMS RT (min) | LCMS Method No. |
|---|---|---|---|---|---|
| 91 | 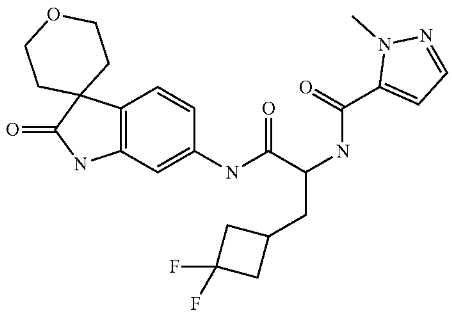 [SMILES: Cn1nccc1C(=O)NC(CC1CC(F)(F)C1)C(=O)Nc1ccc2c(c1)NC(=O)C21CCOCC1] | N-{3-(3,3-Difluorocyclobutyl)-1-oxo-1-[(2-oxospiro[1H-indole-3,4'-oxane]-6-yl)amino]-propan-2-yl}-2-methylpyrazole-3-carboxamide | 488.3 | 1.12 | 27 |
| 92 | 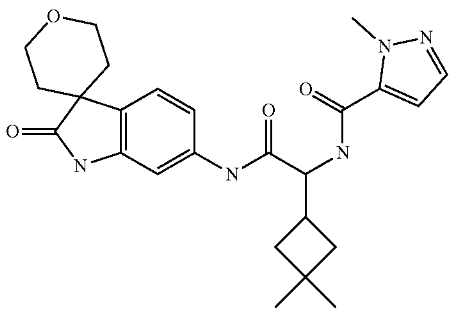 [SMILES: Cn1nccc1C(=O)NC(C(=O)Nc1ccc2c(c1)NC(=O)C21CCOCC1)C1CC(C)(C)C1] | N-{1-(3,3-Dimethylcyclobutyl)-2-oxo-2-[(2-oxospiro[1H-indole-3,4'-oxane]-6-yl)amino]-ethyl}-2-methylpyrazole-3-carboxamide | 466.3 | 1.2 | 27 |
| 93 | 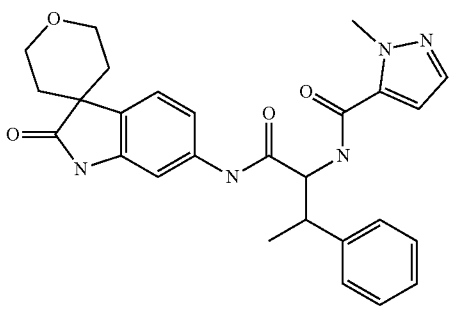 [SMILES: CC(c1ccccc1)C(NC(=O)c1ccnn1C)C(=O)Nc1ccc2c(c1)NC(=O)C21CCOCC1] | 2-Methyl-N-{1-oxo-1-[(2-oxo-spiro[1H-indole-3,4'-oxane]-6-yl)amino]-3-phenylbutan-2-yl}-pyrazole-3-carboxamide | 488.1 | 1.12 | 27 |
| 94 | 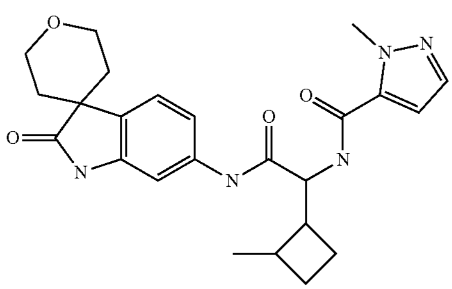 [SMILES: CC1CCC1C(NC(=O)c1ccnn1C)C(=O)Nc1ccc2c(c1)NC(=O)C21CCOCC1] | 2-Methyl-N-{1-(2-methyl-cyclobutyl)-2-oxo-2-[(2-oxo-spiro[indoline-3,4'-tetrahydro-pyran]-6-yl)amino]ethyl}-pyrazole-3-carboxamide (mixture of isomers 1 and 2) | 452.3 | 2.58 (36%) and 2.59 (58%) | 2 |
| 95 | 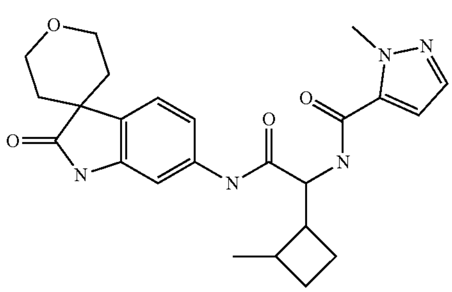 [SMILES: CC1CCC1C(NC(=O)c1ccnn1C)C(=O)Nc1ccc2c(c1)NC(=O)C21CCOCC1] | 2-Methyl-N-{1-(2-methyl-cyclobutyl)-2-oxo-2-[(2-oxo-spiro[indoline-3,4'-tetrahydro-pyran]-6-yl)amino]ethyl}-pyrazole-3-carboxamide (mixture of isomers 3 and 4) | 452.4 | 2.67 (no separation) | 2 |

-continued

| Ex. | Structure | Product | LCMS Mass | LCMS RT (min) | LCMS Method No. |
|---|---|---|---|---|---|
| 96 | 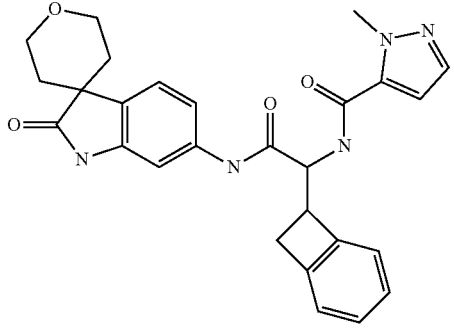 [SMILES: Cn1nccc1C(=O)NC(C(=O)Nc1ccc2c(c1)NC(=O)C21CCOCC1)C1Cc2ccccc21] | N-{1-(7-Bicyclo[4.2.0]octa-1(6),2,4-trienyl)-2-oxo-2-[(2-oxospiro[1H-indole-3,4'-oxane]-6-yl)amino]ethyl}-2-methyl-pyrazole-3-carboxamide | 486.5 | 1.14 | 27 |
| 97 | 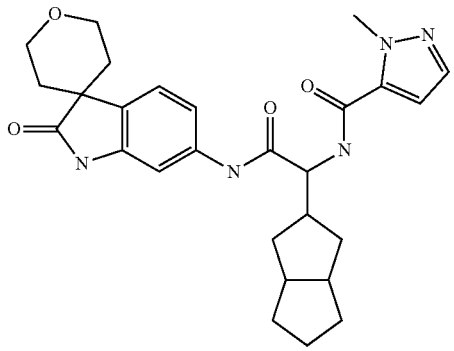 [SMILES: Cn1nccc1C(=O)NC(C(=O)Nc1ccc2c(c1)NC(=O)C21CCOCC1)C1CC2CCCC2C1] | N-{1-(1,2,3,3a,4,5,6,6a-Octahydropentalen-2-yl)-2-oxo-2-[(2-oxospiro[indoline-3,4'-tetrahydropyran]-6-yl)amino]-ethyl}-2-methylpyrazole-3-carboxamide (isomer 1) | 492.1 | 26.15 | Chiral SFC A |
| 98 | 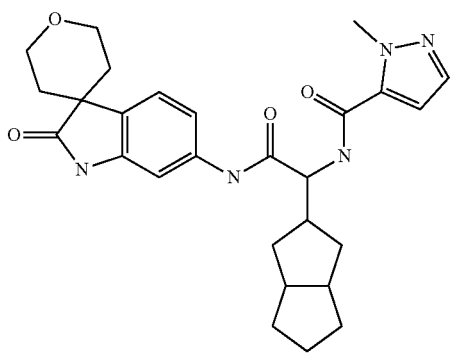 [SMILES: Cn1nccc1C(=O)NC(C(=O)Nc1ccc2c(c1)NC(=O)C21CCOCC1)C1CC2CCCC2C1] | N-{1-(1,2,3,3a,4,5,6,6a-Octahydropentalen-2-yl)-2-oxo-2-[(2-oxospiro[indoline-3,4'-tetrahydropyran]-6-yl)amino]-ethyl}-2-methylpyrazole-3-carboxamide (isomer 2) | 492.1 | 28.62 | Chiral SFC A |
| 99 | 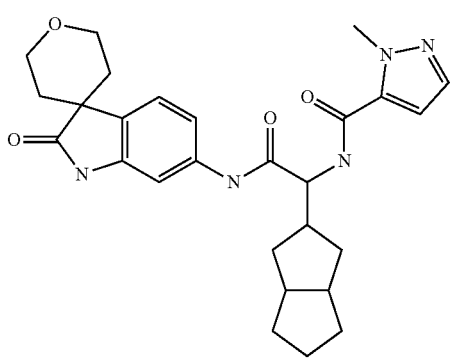 [SMILES: Cn1nccc1C(=O)NC(C(=O)Nc1ccc2c(c1)NC(=O)C21CCOCC1)C1CC2CCCC2C1] | N-{1-(1,2,3,3a,4,5,6,6a-Octahydropentalen-2-yl)-2-oxo-2-[(2-oxospiro[indoline-3,4'-tetrahydropyran]-6-yl)amino]-ethyl}-2-methylpyrazole-3-carboxamide (isomer 3) | 492.1 | 34.24 | Chiral SFC A |

-continued

| Ex. | Structure | Product | LCMS Mass | LCMS RT (min) | LCMS Method No. |
|---|---|---|---|---|---|
| 100 | 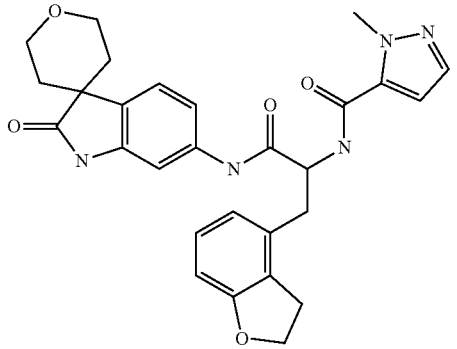 [SMILES: Cn1nccc1C(=O)NC(Cc1cccc2c1CCO2)C(=O)Nc1ccc2c(c1)NC(=O)C21CCOCC1] | N-{3-(2,3-Dihydro-1-benzofuran-4-yl)-1-oxo-1-[(2-oxospiro[1H-indole-3,4'-oxane]-6-yl)amino]propan-2-yl}-2-methylpyrazole-3-carboxamide | 516.4 | 1.14 | 27 |
| 101 | 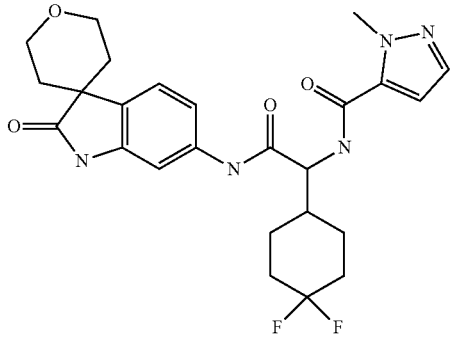 [SMILES: Cn1nccc1C(=O)NC(C(=O)Nc1ccc2c(c1)NC(=O)C21CCOCC1)C1CCC(F)(F)CC1] | N-{1-(4,4-Difluorocyclohexyl)-2-oxo-2-[(2-oxospiro[indoline-3,4'-tetrahydropyran]-6-yl)-amino]ethyl}-2-methylpyrazole-3-carboxamide (isomer 1) | 502.2 | 1.79 | Chiral SFC B |
| 102 | 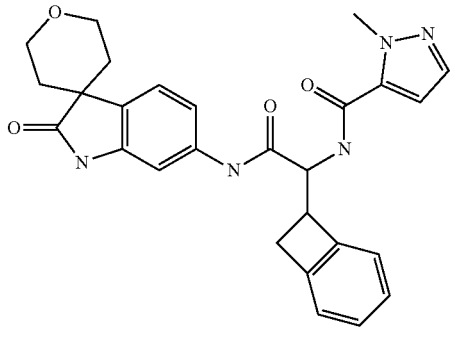 [SMILES: Cn1nccc1C(=O)NC(C(=O)Nc1ccc2c(c1)NC(=O)C21CCOCC1)C1Cc2ccccc21] | N-{1-(7-Bicyclo[4.2.0]octa-1(6),2,4-trienyl)-2-oxo-2-[(2-oxospiro[indoline-3,4'-tetrahydropyran]-6-yl)amino]-ethyl}-2-methylpyrazole-3-carboxamide (isomer 1) | 486.1 | 7.39 | Chiral SFC C |
| 103 | 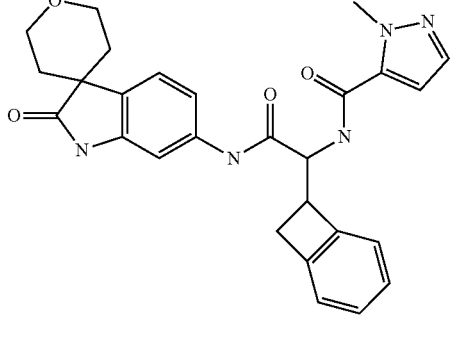 | N-{1-(7-Bicyclo[4.2.0]octa-1(6),2,4-trienyl)-2-oxo-2-[(2-oxospiro[indoline-3,4'-tetrahydropyran]-6-yl)amino]-ethyl}-2-methylpyrazole-3-carboxamide (isomer 2) | 486.1 | 5.82 | Chiral SFC C |

-continued

| Ex. | Structure | Product | LCMS Mass | LCMS RT (min) | LCMS Method No. |
|---|---|---|---|---|---|
| 104 | 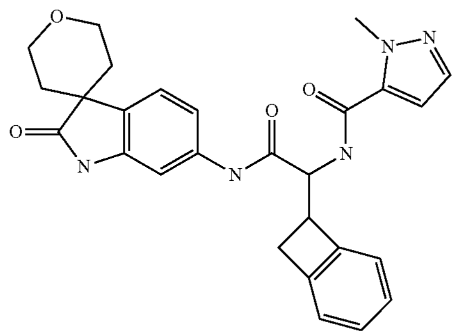 [SMILES: Cn1nccc1C(=O)NC(C(=O)Nc1ccc2c(c1)NC(=O)C21CCOCC1)C1Cc2ccccc21] | N-{1-(7-Bicyclo[4.2.0]octa-1(6),2,4-trienyl)-2-oxo-2-[(2-oxospiro[indoline-3,4'-tetrahydropyran]-6-yl)amino]-ethyl}-2-methylpyrazole-3-carboxamide (isomer 3) | 486.1 | 3.92 | Chiral SFC C |
| 105 | 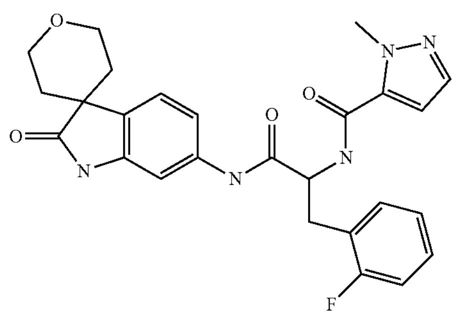 [SMILES: Cn1nccc1C(=O)NC(Cc1ccccc1F)C(=O)Nc1ccc2c(c1)NC(=O)C21CCOCC1] | N-{3-(2-Fluorophenyl)-1-oxo-1-[(2-oxospiro[1H-indole-3,4'-oxane]-6-yl)amino]propan-2-yl}-2-methylpyrazole-3-carboxamide | 492.4 | 1.16 | 27 |
| 106 | 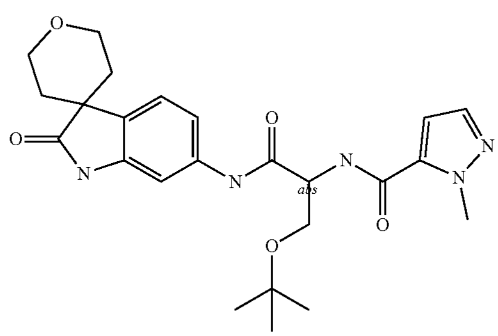 [SMILES: Cn1nccc1C(=O)NC(COC(C)(C)C)C(=O)Nc1ccc2c(c1)NC(=O)C21CCOCC1] | 2-Methyl-N-{(2S)-3-[(2-methyl-propan-2-yl)oxy]-1-oxo-1-[(2-oxospiro[1H-indole-3,4'-oxane]-6-yl)amino]propan-2-yl}-pyrazole-3-carboxamide | 470.5 | 2.75 | Chiral SFC D |
| 107 | 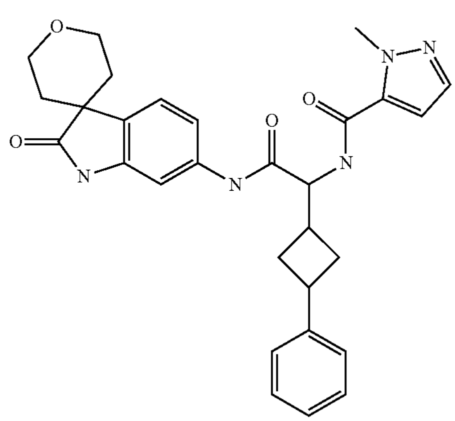 [SMILES: Cn1nccc1C(=O)NC(C(=O)Nc1ccc2c(c1)NC(=O)C21CCOCC1)C1CC(c2ccccc2)C1] | 2-Methyl-N-{2-oxo-2-[(2-oxo-spiro[1H-indole-3,4'-oxane]-6-yl)amino]-1-(3-phenyl-cyclobutyl)ethyl}pyrazole-3-carboxamide | 514.5 | 1.34 | 27 |

-continued

| Ex. | Structure | Product | LCMS Mass | LCMS RT (min) | LCMS Method No. |
|---|---|---|---|---|---|
| 108 | 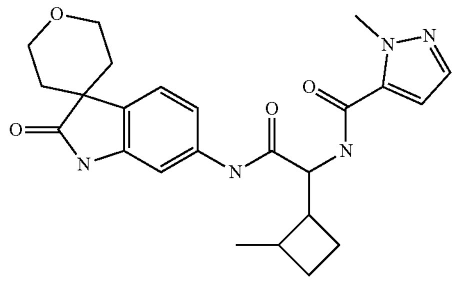 [SMILES: CC1CCC1C(NC(=O)c1ccnn1C)C(=O)Nc1ccc2c(c1)NC(=O)C21CCOCC1] | 2-Methyl-N-{1-(2-methyl-cyclobutyl)-2-oxo-2-[(2-oxo-spiro[indoline-3,4'-tetrahydro-pyran]-6-yl)amino]ethy}-pyrazole-3-carboxamide (isomer 5) | 452.1 | 8.73 | Chiral SFC E |
| 109 | 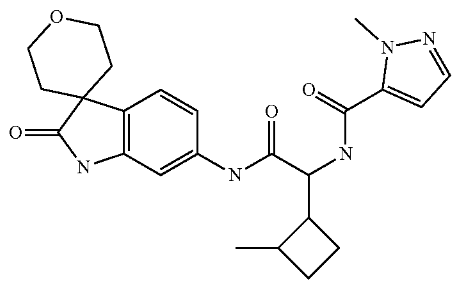 [SMILES: CC1CCC1C(NC(=O)c1ccnn1C)C(=O)Nc1ccc2c(c1)NC(=O)C21CCOCC1] | 2-Methyl-N-{1-(2-methyl-cyclobutyl)-2-oxo-2-[(2-oxo-spiro[indoline-3,4'-tetrahydro-pyran]-6-yl)amino]ethy}-pyrazole-3-carboxamide (isomer 6) | 452.1 | 10.74 | Chiral SFC E |
| 110 | 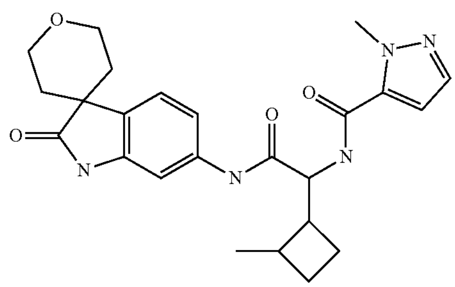 [SMILES: CC1CCC1C(NC(=O)c1ccnn1C)C(=O)Nc1ccc2c(c1)NC(=O)C21CCOCC1] | 2-Methyl-N-{1-(2-methyl-cyclobutyl)-2-oxo-2-[(2-oxo-spiro[indoline-3,4'-tetrahydro-pyran]-6-yl)amino]ethy}-pyrazole-3-carboxamide (isomer 7) | 452.1 | 7.22 | Chiral SFC F |
| 111 | 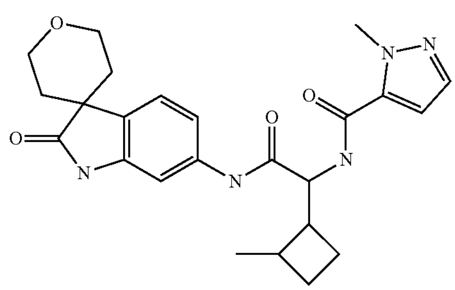 [SMILES: CC1CCC1C(NC(=O)c1ccnn1C)C(=O)Nc1ccc2c(c1)NC(=O)C21CCOCC1] | 2-Methyl-N-{1-(2-methyl-cyclobutyl)-2-oxo-2-[(2-oxo-spiro[indoline-3,4'-tetrahydro-pyran]-6-yl)amino]ethy}-pyrazole-3-carboxamide (isomer 8) | 452.1 | 10.14 | Chiral SFC F |
| 112 | 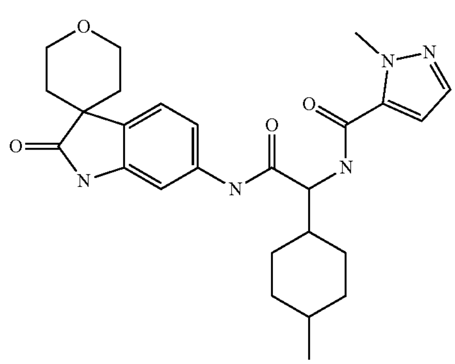 [SMILES: CC1CCC(C(NC(=O)c2ccnn2C)C(=O)Nc2ccc3c(c2)NC(=O)C32CCOCC2)CC1] | 2-Methyl-N-{1-(4-methyl-cyclohexyl)-2-oxo-2-[(2-oxo-spiro[1H-indole-3,4'-oxane]-6-yl)amino]ethyl}pyrazole-3-carboxamide | 480.5 | 1.33 | 27 |

| Ex. | Structure | Product | LCMS Mass | LCMS RT (min) | LCMS Method No. |
|---|---|---|---|---|---|
| 113 | 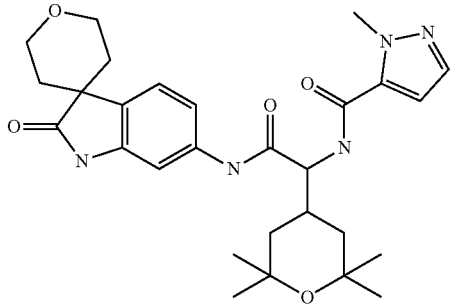 [SMILES: Cn1nccc1C(=O)NC(C(=O)Nc1ccc2c(c1)NC(=O)C21CCOCC1)C1CC(C)(C)OC(C)(C)C1] | 2-Methyl-N-{2-oxo-2-[(2-oxo-spiro[1H-indole-3,4'-oxane]-6-yl)amino]-1-(2,2,6,6-tetramethyloxan-4-yl)ethyl}-pyrazole-3-carboxamide | 524.5 | 1.17 | 27 |
| 114 | 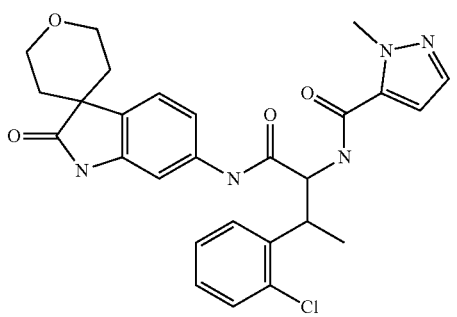 [SMILES: CC(c1ccccc1Cl)C(NC(=O)c1ccnn1C)C(=O)Nc1ccc2c(c1)NC(=O)C21CCOCC1] | N-{2-(2-Chlorophenyl)-1-[(2-oxospiro[indoline-3,4'-tetra-hydropyran]-6-yl)carbamoyl]-propyl}-2-methylpyrazole-3-carboxamide (isomer 1) | 522.2 | 2.80 | 1 |
| 115 | 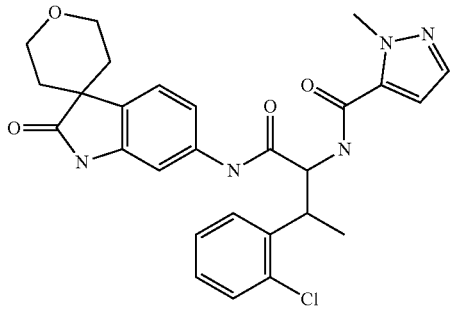 [SMILES: CC(c1ccccc1Cl)C(NC(=O)c1ccnn1C)C(=O)Nc1ccc2c(c1)NC(=O)C21CCOCC1] | N-{2-(2-Chlorophenyl)-1-[(2-oxospiro[indoline-3,4'-tetra-hydropyran]-6-yl)carbamoyl]-propyl}-2-methylpyrazole-3-carboxamide (isomer 2) | 522.2 | 2.88 | 1 |
| 116 | 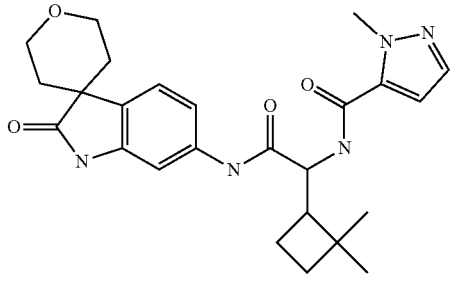 [SMILES: Cn1nccc1C(=O)NC(C(=O)Nc1ccc2c(c1)NC(=O)C21CCOCC1)C1CCC1(C)C] | N-[1-(2,2-Dimethylcyclobutyl)-2-oxo-2-[(2-oxospiro[1H-indole-3,4'-oxane]-6-yl)amino]-ethyl}-2-methylpyrazole-3-carboxamide | 466.5 | 1.25 | 27 |
| 117 | 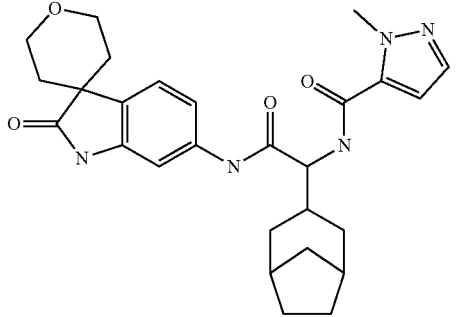 [SMILES: Cn1nccc1C(=O)NC(C(=O)Nc1ccc2c(c1)NC(=O)C21CCOCC1)C1CC2CCC(C2)C1] | N-{1-(Bicyclo[3.2.1]octan-3-yl)-2-oxo-2-[(2-oxospiro[1H-indole-3,4'-oxane]-6-yl)amino]-ethyl}-2-methylpyrazole-3-carboxamide | 492.5 | 1.36 | 27 |

-continued

| Ex. | Structure | Product | LCMS Mass | LCMS RT (min) | LCMS Method No. |
|---|---|---|---|---|---|
| 118 | 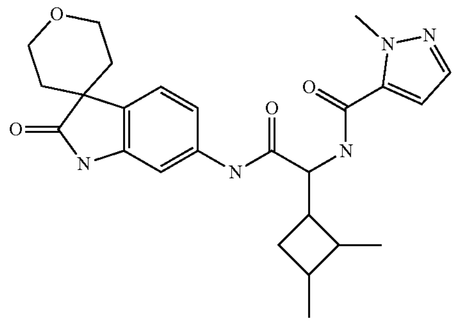 [SMILES: CC1CC(C(NC(=O)c2ccnn2C)C(=O)Nc2ccc3c(c2)NC(=O)C32CCOCC2)C1C] | N-{1-(2,3-Dimethylcyclobutyl)-2-oxo-2-[(2-oxospiro[1H-indole-3,4'-oxane]-6-yl)amino]-ethyl}-2-methylpyrazole-3-carboxamide | 466.5 | 1.26 | 27 |
| 119 | 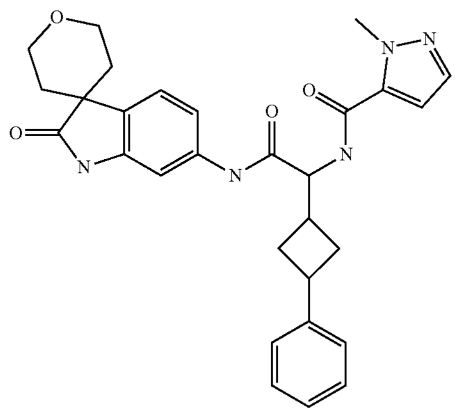 [SMILES: Cn1nccc1C(=O)NC(C(=O)Nc1ccc2c(c1)NC(=O)C21CCOCC1)C1CC(c2ccccc2)C1] | 2-Methyl-N-[2-oxo-2-[(2-oxo-spiro[indoline-3,4'-tetrahydro-pyran]-6-yl)amino]-1-(3-phenyl-cyclobutyl)ethyl}pyrazole-3-carboxamide (isomer 1) | 514.2 | 4.65 | Chiral SFC G |
| 120 | 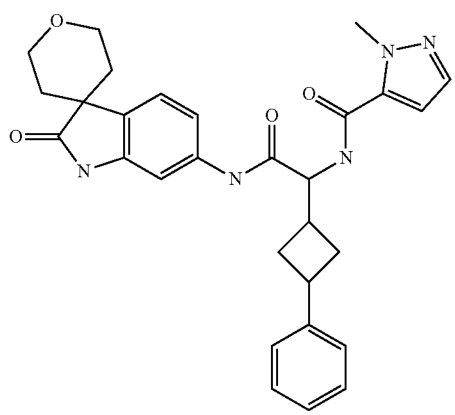 [SMILES: Cn1nccc1C(=O)NC(C(=O)Nc1ccc2c(c1)NC(=O)C21CCOCC1)C1CC(c2ccccc2)C1] | 2-Methyl-N-[2-oxo-2-[(2-oxo-spiro[indoline-3,4'-tetrahydro-pyran]-6-yl)amino]-1-(3-phenyl-cyclobutyl)ethyl}pyrazole-3-carboxamide (isomer 2) | 514.1 | 6.79 | Chiral SFC G |
| 121 | 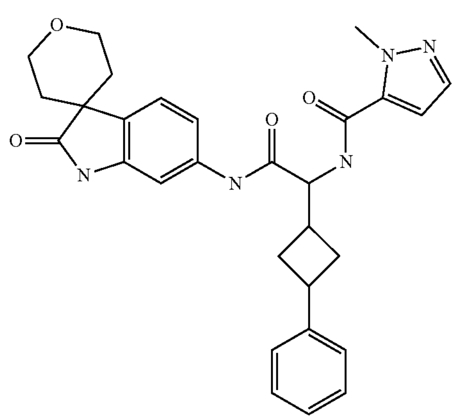 [SMILES: Cn1nccc1C(=O)NC(C(=O)Nc1ccc2c(c1)NC(=O)C21CCOCC1)C1CC(c2ccccc2)C1] | 2-Methyl-N-[2-oxo-2-[(2-oxo-spiro[indoline-3,4'-tetrahydro-pyran]-6-yl)amino]-1-(3-phenyl-cyclobutyl)ethyl}pyrazole-3-carboxamide (isomer 3) | 514.2 | 5.39 | Chiral SFC G |

| Ex. | Structure | Product | LCMS Mass | LCMS RT (min) | LCMS Method No. |
|---|---|---|---|---|---|
| 122 | 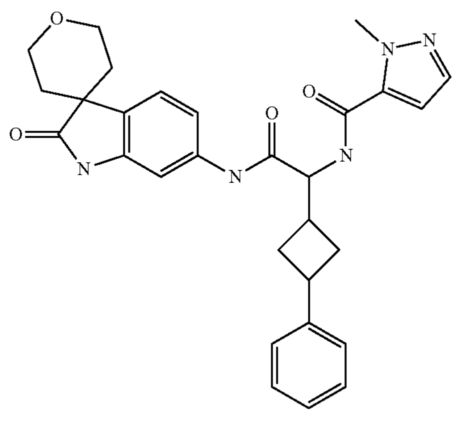 [SMILES: Cn1nccc1C(=O)NC(C(=O)Nc1ccc2c(c1)NC(=O)C21CCOCC1)C1CC(c2ccccc2)C1] | 2-Methyl-N-[2-oxo-2-[(2-oxo-spiro[indoline-3,4'-tetrahydro-pyran]-6-yl)amino]-1-(3-phenyl-cyclobutyl)ethyl}pyrazole-3-carboxamide (isomer 4) | 514.1 | 2.97 | Chiral SFC G |
| 123 | 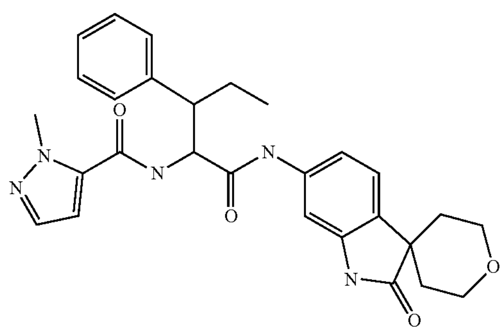 [SMILES: CCC(c1ccccc1)C(NC(=O)c1ccnn1C)C(=O)Nc1ccc2c(c1)NC(=O)C21CCOCC1] | 2-Methyl-N-{1-oxo-1-[(2-oxo-spiro[1H-indole-3,41-oxane]-6-yl)amino]-3-phenylpentan-2-yl}pyrazole-3-carboxamide | 502.5 | 1.26 | 27 |
| 124 | 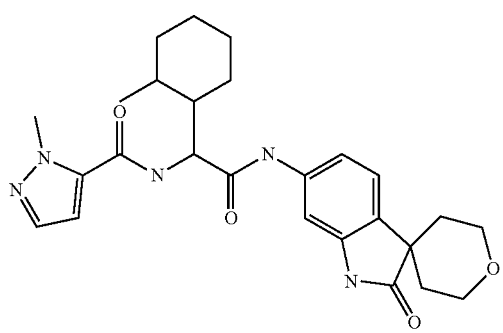 [SMILES: CC1CCCCC1C(NC(=O)c1ccnn1C)C(=O)Nc1ccc2c(c1)NC(=O)C21CCOCC1] | 2-Methyl-N-{1-(2-methyl-cyclohexyl)-2-oxo-2-[(2-oxo-spiro[1H-indole-3,4'-oxane]-6-yl)amino]ethyl}pyrazole-3-carboxamide | 480.5 | 1.31 | 27 |
| 125 | 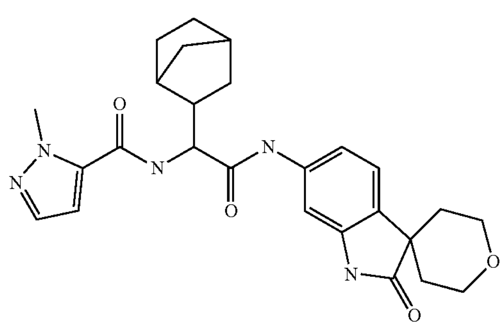 [SMILES: Cn1nccc1C(=O)NC(C(=O)Nc1ccc2c(c1)NC(=O)C21CCOCC1)C1CC2CCC1C2] | 2-Methyl-N-{2-oxo-2-[(2-oxo-spiro[1H-indole-3,4'-oxane]-6-yl)amino]-1-[rac-(1R,4S)-bicyclo[2.2.1]heptan-2-yl]-ethyl}pyrazole-3-carboxamide (isomer 1) | 478.5 | 1.26 | 27 |

| Ex. | Structure | Product | LCMS Mass | LCMS RT (min) | LCMS Method No. |
|---|---|---|---|---|---|
| 126 | 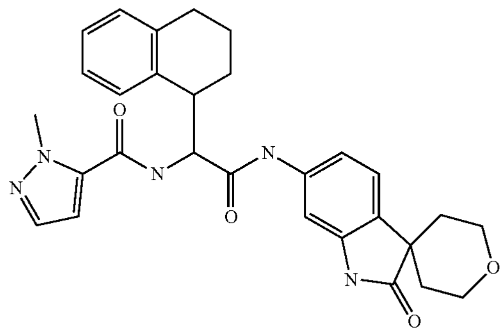 [SMILES: Cn1nccc1C(=O)NC(C(=O)Nc1ccc2c(c1)NC(=O)C21CCOCC1)C1CCCc2ccccc21] | 2-Methyl-N-{2-oxo-2-[(2-oxo-spiro[1H-indole-3,4'-oxane]-6-yl)amino]-1-(1,2,3,4-tetrahydro-naphthalen-1-yl)ethyl}pyrazole-3-carboxamide | 514.5 | 1.28 | 27 |
| 127 | 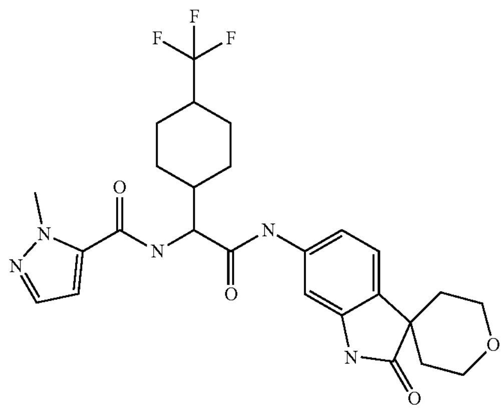 [SMILES: Cn1nccc1C(=O)NC(C(=O)Nc1ccc2c(c1)NC(=O)C21CCOCC1)C1CCC(C(F)(F)F)CC1] | 2-Methyl-N-{2-oxo-2-[(2-oxo-spiro[1H-indole-3,4'-oxane]-6-yl)amino]-1-[4-(trifluoro-methyl)cyclohexyl]ethyl}-pyrazole-3-carboxamide | 534.5 | 1.31 | 27 |
| 128 | 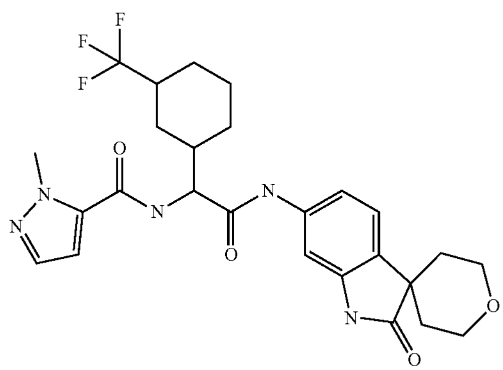 [SMILES: Cn1nccc1C(=O)NC(C(=O)Nc1ccc2c(c1)NC(=O)C21CCOCC1)C1CCCC(C(F)(F)F)C1] | 2-Methyl-N-{2-oxo-2-[(2-oxo-spiro[1H-indole-3,4'-oxane]-6-yl)amino]-1-[3-(trifluoro-methyl)cyclohexyl]ethyl}-pyrazole-3-carboxamide | 534.5 | 1.32 | 27 |
| 129 | 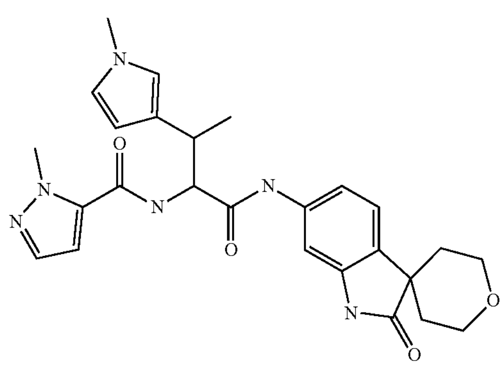 [SMILES: CC(c1ccn(C)c1)C(NC(=O)c1ccnn1C)C(=O)Nc1ccc2c(c1)NC(=O)C21CCOCC1] | 2-Methyl-N-{3-(1-methylpyrrol-3-yl)-1-oxo-1-[(2-oxospiro[1H-indole-3,4'-oxane]-6-yl)amino]-butan-2-yl}pyrazole-3-carboxamide | 491.5 | 1.09 | 27 |

-continued

| Ex. | Structure | Product | LCMS Mass | LCMS RT (min) | LCMS Method No. |
|---|---|---|---|---|---|
| 130 | 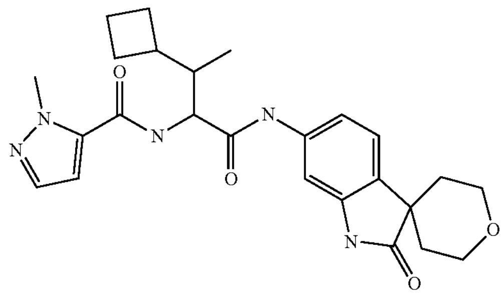 [SMILES: CC(C1CCC1)C(NC(=O)c1ccnn1C)C(=O)Nc1ccc2c(c1)NC(=O)C21CCOCC1] | N-{3-Cyclobutyl-1-oxo-1-[(2-oxospiro[1H-indole-3,4'-oxane]-6-yl)amino]butan-2-yl}-2-methylpyrazole-3-carboxamide | 466.5 | 1.25 | 27 |
| 131 | 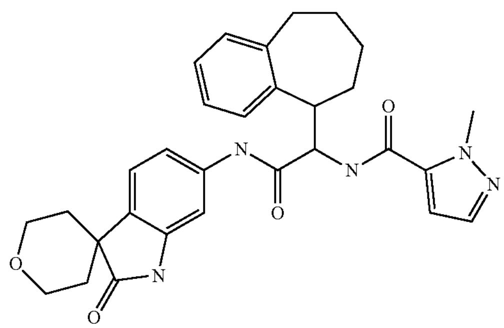 [SMILES: Cn1nccc1C(=O)NC(C(=O)Nc1ccc2c(c1)NC(=O)C21CCOCC1)C1CCCCc2ccccc21] | 2-Methyl-N-{2-oxo-2-[(2-oxo-spiro[1H-indole-3,4'-oxane]-6-yl)amino]-1-(6,7,8,9-tetrahydro-5H-benzo[7]annulen-5-yl)-ethyl}pyrazole-3-carboxamide | 528.5 | 1.35 | 27 |
| 132 | 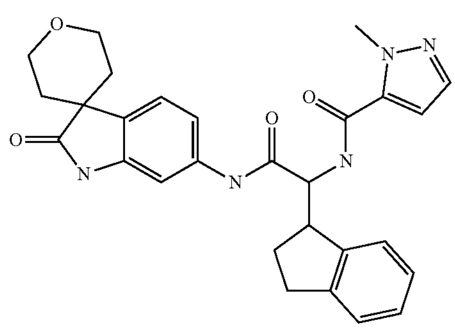 [SMILES: Cn1nccc1C(=O)NC(C(=O)Nc1ccc2c(c1)NC(=O)C21CCOCC1)C1CCc2ccccc21] | N-{1-(2,3-Dihydro-1H-inden-1-yl)-2-oxo-2-[(2-oxospiro[1H-indole-3,4'-oxane]-6-yl)amino]-ethyl}-2-methylpyrazole-3-carboxamide | 500.5 | 1.24 | 27 |
| 133 | 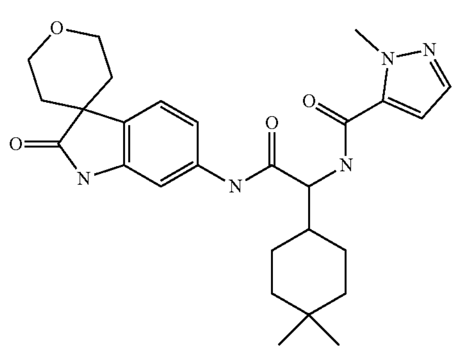 [SMILES: Cn1nccc1C(=O)NC(C(=O)Nc1ccc2c(c1)NC(=O)C21CCOCC1)C1CCC(C)(C)CC1] | N-{1-(4,4-Dimethylcyclohexyl)-2-oxo-2-[(2-oxospiro[1H-indole-3,4'-oxane]-6-yl)amino]-ethyl}-2-methylpyrazole-3-carboxamide | 494.5 | 1.41 | 27 |

-continued

| Ex. | Structure | Product | LCMS Mass | LCMS RT (min) | LCMS Method No. |
|---|---|---|---|---|---|
| 134 | 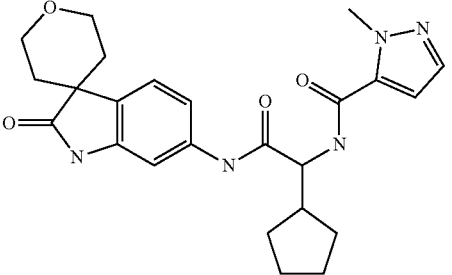 [SMILES: Cn1nccc1C(=O)NC(C(=O)Nc1ccc2c(c1)NC(=O)C21CCOCC1)C1CCCC1] | N-{1-Cyclopentyl-2-oxo-2-[(2-oxospiro[1H-indole-3,4'-oxane]-6-yl)amino]ethyl}-2-methyl-pyrazole-3-carboxamide | 452.5 | 1.15 | 27 |
| 135 | 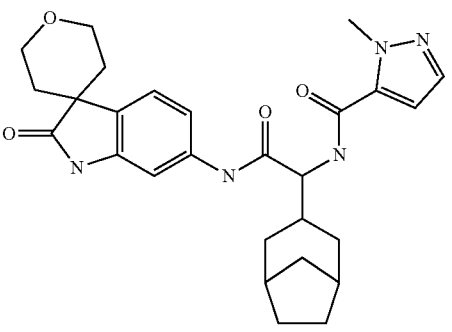 [SMILES: Cn1nccc1C(=O)NC(C(=O)Nc1ccc2c(c1)NC(=O)C21CCOCC1)C1CC2CCC(C2)C1] | N-{1-(Bicyclo[3.2.1]octan-3-yl)-2-oxo-2-[(2-oxospiro-[indoline-3,4'-tetrahydropyran]-6-yl)amino]ethyl}-2-methyl-pyrazole-3-carboxamide (isomer 1) | 492.2 | 4.95 | Chiral SFC H |
| 136 | 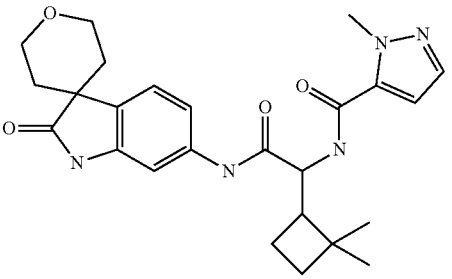 [SMILES: Cn1nccc1C(=O)NC(C(=O)Nc1ccc2c(c1)NC(=O)C21CCOCC1)C1CCC1(C)C] | N-{1-(2,2-Dimethylcyclobutyl)-2-oxo-2-[(2-oxospiro[indoline-3,4'-tetrahydropyran]-6-yl)-amino]ethyl}-2-methylpyrazole-3-carboxamide (isomer 1) | 466.1 | 36.04 | Chiral SFC I |
| 137 | 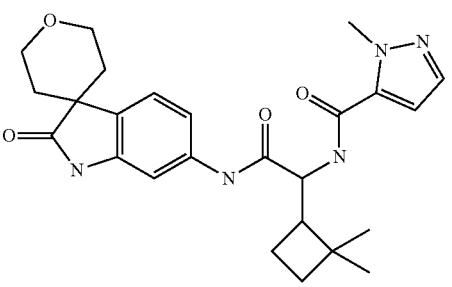 [SMILES: Cn1nccc1C(=O)NC(C(=O)Nc1ccc2c(c1)NC(=O)C21CCOCC1)C1CCC1(C)C] | N-{1-(2,2-Dimethylcyclobutyl)-2-oxo-2-[(2-oxospiro[indoline-3,4'-tetrahydropyran]-6-yl)-amino]ethyl}-2-methylpyrazole-3-carboxamide (isomer 2) | 466.1 | 9.78 | Chiral SFC I |
| 138 | 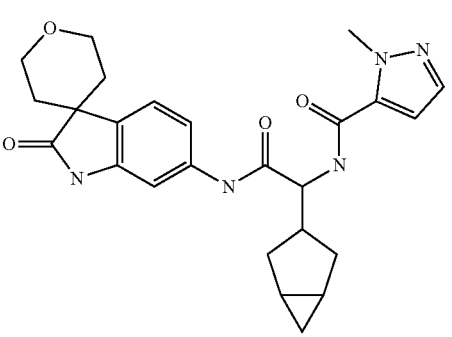 [SMILES: Cn1nccc1C(=O)NC(C(=O)Nc1ccc2c(c1)NC(=O)C21CCOCC1)C1CC2CC2C1] | N-{1-(Bicyclo[3.1.0]hexan-3-yl)-2-oxo-2-[(2-oxospiro[1H-indole-3,4'-oxane]-6-yl)amino]-ethyl}-2-methylpyrazole-3-carboxamide | 464.5 | 1.19 | 27 |

-continued

| Ex. | Structure | Product | LCMS Mass | LCMS RT (min) | LCMS Method No. |
|---|---|---|---|---|---|
| 139 | 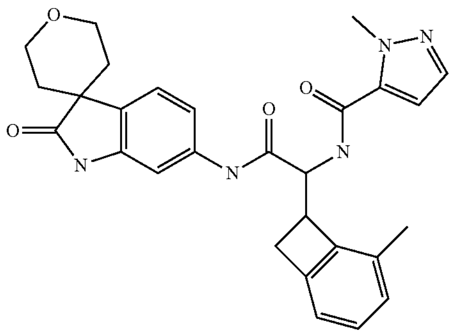 [SMILES: Cc1cccc2c1C(C(NC(=O)c1ccnn1C)C(=O)Nc1ccc3c(c1)NC(=O)C31CCOCC1)C2] | N-{1-(5-Chloro-7-bicyclo-[4.2.0]octa-1(6),2,4-trienyl)-2-oxo-2-[(2-oxospiro[indoline-3,4'-tetrahydropyran]-6-yl)-amino]ethyl}-2-methylpyrazole-3-carboxamide (isomer 1) | 520.2 | 2.77 | 1 |
| 140 | 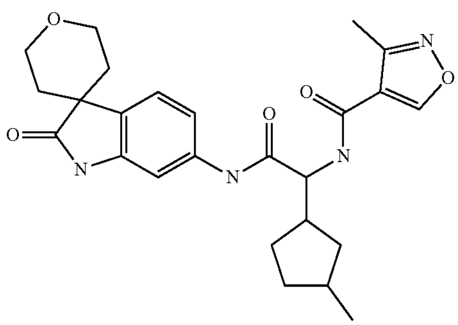 [SMILES: Cc1nocc1C(=O)NC(C(=O)Nc1ccc2c(c1)NC(=O)C21CCOCC1)C1CCC(C)C1] | 3-Methyl-N-{1-(3-methyl-cyclopentyl)-2-oxo-2-[(2-oxo-spiro[1H-indole-3,4'-oxane]-6-yl)amino]ethyl}-1,2-oxazole-4-carboxamide | 467.5 | 1.29 | 27 |
| 141 | 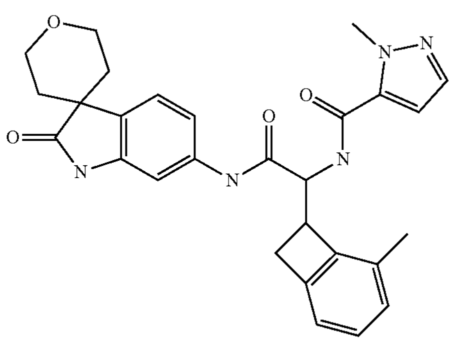 [SMILES: Cc1cccc2c1C(C(NC(=O)c1ccnn1C)C(=O)Nc1ccc3c(c1)NC(=O)C31CCOCC1)C2] | N-{1-(5-Chloro-7-bicyclo-[4.2.0]octa-1(6),2,4-trienyl)-2-oxo-2-[(2-oxospiro[indoline-3,4'-tetrahydropyran]-6-yl)-amino]ethyl}-2-methylpyrazole-3-carboxamide (isomer 2) | 520.2 | 2.83 | 1 |
| 142 | 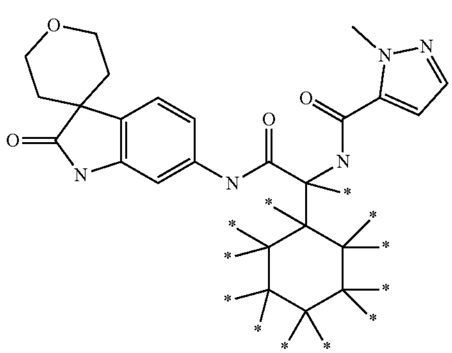 [SMILES: *C(NC(=O)c1ccnn1C)(C(=O)Nc1ccc2c(c1)NC(=O)C21CCOCC1)C1(*)C(*)(*)C(*)(*)C(*)(*)C(*)(*)C1(*)*] | N-{1-Deuterio-2-oxo-2-[(2-oxo-spiro[1H-indole-3,4'-oxane]-6-yl)amino]-1-(1,2,2,3,3,4,4,5,5,6,6-undecadeuteriocyclohexyl)-ethyl}-2-methylpyrazole-3-carboxamide | 478.5 | 1.23 | 27 |

| Ex. | Structure | Product | LCMS Mass | LCMS RT (min) | LCMS Method No. |
|---|---|---|---|---|---|
| 143 | 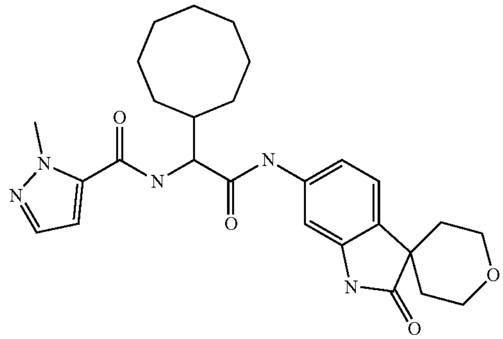 [SMILES: Cn1nccc1C(=O)NC(C(=O)Nc1ccc2c(c1)NC(=O)C21CCOCC1)C1CCCCCCC1] | N-{1-Cyclononyl-2-oxo-2-[(2-oxospiro[1H-indole-3,4'-oxane]-6-yl)amino]ethyl}-2-methyl-pyrazole-3-carboxamide | 508.3 | 1.51 | 28 |

Selected ¹H NMR Data:

| Ex. | ¹H NMR Data |
|---|---|
| 94 | Major isomer 1: δ$_H$ (500 MHz, DMSO-d$_6$) 10.39 (s, 1H), 10.21 (s, 1H), 8.46 (d, J 7.5 Hz, 1H), 7.45 (t, J 2.2 Hz, 1H), 7.43 (d, J 6.1 Hz, 1H), 7.38-7.36 (m, 1H), 7.10 (d, J 8.2 Hz, 1H), 7.02 (d, J 2.1 Hz, 1H), 4.47 (dd, J 9.9, 7.5 Hz, 1H), 4.02 (s, 3H), 4.03-3.98 (m, 2H), 3.80 (ddd, J 11.0, 6.8, 3.5 Hz, 2H), 2.32-2.24 (m, 1H), 2.15-1.99 (m, 1H), 1.99-1.92 (m, 2H), 1.77-1.69 (m, 2H), 1.66-1.55 (m, 3H), 1.47-1.35 (m, 1H), 0.87 (d, J 6.5 Hz, 3H). Minor isomer 2: δ$_H$ (500 MHz, DMSO-d$_6$) 10.39 (s, 1H), 10.17 (s, 1H), 8.52 (d, J 7.2 Hz, 1H), 7.46 (d, J 2.1 Hz, 1H), 7.45 (d, J 6.0 Hz, 1H), 7.38-7.36 (m, 1H), 7.12-7.08 (m, 1H), 6.99 (d, J 2.1 Hz, 1H), 4.55 (dd, J 11.8, 7.1 Hz, 1H), 4.02 (s, 3H), 3.99 (dd, J 7.3, 3.7 Hz, 2H), 3.80 (ddd, J 11.0, 6.8, 3.5 Hz, 2H), 2.84-2.73 (m, 1H), 2.42-2.37 (m, 1H), 2.15-1.99 (m, 1H), 1.96 (q, J 9.1 Hz, 1H), 1.77-1.69 (m, 3H), 1.66-1.60 (m, 2H), 1.47-1.35 (m, 1H), 1.05 (d, J 7 .1 Hz, 3H). |
| 95 | Major isomer 3: δ$_H$ (500 MHz, DMSO-d$_6$) 10.39 (d, J 2.4 Hz, 1H), 10.12 (s, 1H), 8.52 (d, J 8.5 Hz, 1H), 7.47 (d, J 2.1 Hz, 1H), 7.44-7.41 (m, 1H), 7.35 (d, J 1.9 Hz, 1H), 7.10 (dd, J 8.2, 1.9 Hz, 1H), 7.04 (d, J 2.1 Hz, 1H), 4.65 (t, J 8.8 Hz, 1H), 4.03 (s, 3H), 4.00 (ddd, J 10.9, 7.1, 3.7 Hz, 2H), 3.79 (ddd, J 10.5, 6.3, 3.4 Hz, 2H), 2.37-2.31 (m, 1H), 2.25-2.15 (m, 1H), 1.99-1.89 (m, 1H), 1.85-1.77 (m, 2H), 1.76-1.69 (m, 2H), 1.66-1.57 (m, 2H), 1.47-1.34 (m, 1H), 1.01 (d, J 6.6 Hz, 3H). Minor isomer 4: δ$_H$ (500 MHz, DMSO-d$_6$) 10.39 (d, J 2.4 Hz, 1H), 10.07 (s, 1H), 8.52 (d, J 8.5 Hz, 1H), 7.45 (d, J 2.1 Hz, 1H), 7.42 (d, J 6.8 Hz, 1H), 7.37 (d, J 1.9 Hz, 1H), 7.13 (dd, J 8.2, 1.9 Hz, 1H), 6.98 (d, J 2.1 Hz, 1H), 4.72 (dd, J 11.0, 8.4 Hz, 1H), 4.05 (s, 3H), 4.00 (ddd, J 10.9, 7.1, 3.7 Hz, 2H), 3.79 (ddd, J 10.5, 6.3, 3.4 Hz, 2H), 2.98-2.86 (m, 1H), 2.45-2.39 (m, 1H), 2.08-2.00 (m, 1H), 1.99-1.89 (m, 1H), 1.85-1.77 (m, 1H), 1.76-1.69 (m, 2H), 1.66-1.57 (m, 2H), 1.47-1.34 (m, 1H), 1.11 (d, J 7.2 Hz, 3H). |
| 97 | δ$_H$ (500 MHz, DMSO-d$_6$) 10.39 (s, 1H), 10.18 (s, 1H), 8.61 (d, J 7.7 Hz, 1H), 7.46 (d, J 2.0 Hz, 1H), 7.43 (d, J 8.1 Hz, 1H), 7.39 (d, J 1.8 Hz, 1H), 7.11 (dd, J 8.2, 1.9 Hz, 1H), 7.04 (d, J 2.1 Hz, 1H), 4.31 (dd, J 9.8, 7.8 Hz, 1H), 4.02 (s, 3H), 4.00 (ddd, J 11.0, 6.8, 3.6 Hz, 2H), 3.80 (ddd, J 11.0, 6.8, 3.6 Hz, 2H), 2.46-2.37 (m, 2H), 1.79-1.70 (m, 4H), 1.64-1.53 (m, 5H), 1.42 (dt, J 12.3, 9.8 Hz, 1H), 1.37-1.22 (m, 3H), 1.22-1.15 (m, 1H), 1.10-1.02 (m, 1H). |
| 98 | δ$_H$ (500 MHz, DMSO-d$_6$) 10.39 (s, 1H), 10.13 (s, 1H), 8.59 (d, J 7.7 Hz, 1H), 7.46 (d, J 2.1 Hz, 1H), 7.43 (d, J 8.1 Hz, 1H), 7.37 (d, J 1.9 Hz, 1H), 7.10 (dd, J 8.2, 1.9 Hz, 1H), 7.04 (d, J 2.1 Hz, 1H), 4.35 (dd, J 9.3, 7.9 Hz, 1H), 4.02 (s, 3H), 4.00 (dt, J 11.0, 6.9, 3.7 Hz, 2H), 3.80 (ddd, J 11.0, 6.9, 3.7 Hz, 2H), 2.43-2.36 (m, 2H), 2.24-2.16 (m, 1H), 2.16-2.10 (m, 1H), 1.80-1.70 (m, 3H), 1.65-1.58 (m, 2H), 1.55-1.42 (m, 4H), 1.39-1.30 (m, 2H), 1.07 (td, J 12.0, 9.1 Hz, 1H), 0.88-0.81 (m, 1H). |
| 99 | δ$_H$ (500 MHz, DMSO-d$_6$) 10.39 (s, 1H), 10.18 (s, 1H), 8.61 (d, J 7.7 Hz, 1H), 7.46 (d, J 2.1 Hz, 1H), 7.43 (d, J 8.2 Hz, 1H), 7.39 (d, J 1.9 Hz, 1H), 7.11 (dd, J 8.2, 1.9 Hz, 1H), 7.04 (d, J 2.1 Hz, 1H), 4.31 (dd, J 9.9, 7.8 Hz, 1H), 4.02 (s, 3H), 4.00 (ddd, J 11.0, 6.9, 3.6 Hz, 2H), 3.80 (ddd, J 11.0, 6.9, 3.6 Hz, 2H), 2.47-2.37 (m, 2H), 1.80-1.70 (m, 4H), 1.65-1.52 (m, 5H), 1.48-1.37 (m, 1H), 1.35-1.15 (m, 4H), 1.12-1.01 (m, 1H). |
| 101 | δ$_H$ (500 MHz, DMSO-d$_6$) 10.41 (s, 1H), 10.26 (s, 1H), 8.62 (d, J 8.1 Hz, 1H), 7.47 (d, J 2.1 Hz, 1H), 7.44 (d, J 8.1 Hz, 1H), 7.38 (d, J 1.8 Hz, 1H), 7.12 (dd, J 8.1, 1.9 Hz, 1H), 7.05 (d, J 2.1 Hz, 1H), 4.46 (t, J 8.6 Hz, 1H), 4.03 (s, 3H), 4.02-3.98 (m, 2H), 3.80 (ddd, J 11.0, 6.9, 3.7 Hz, 2H), 2.07-1.94 (m, 3H), 1.91 (d, J 12.8 Hz, 1H), 1.86-1.77 (m, 1H), 1.77-1.69 (m, 3H), 1.69-1.58 (m, 3H), 1.49-1.39 (m, 1H), 1.36-1.27 (m, 1H). |
| 102 | δ$_H$ (500 MHz, DMSO-d$_6$) 10.42 (s, 1H), 10.24 (s, 1H), 8.85 (d, J 7.7 Hz, 1H), 7.50-7.44 (m, 2H), 7.42 (d, J 1.9 Hz, 1H), 7.23 (t, J 7.5 Hz, 1H), 7.18-7.12 (m, 3H), 7.01 (d, J 2.1 Hz, 1H), 6.87 (d, J 7.3 Hz, 1H), 4.71 (dd, J 10.2, 7.7 Hz, 1H), 4.05-3.99 (m, 2H), 4.01 (s, 3H), 3.93 (ddd, J 10.0, 5.0, 2.3 Hz, 1H), 3.81 (ddd, J 10.6, 5.9, 3.2 Hz, 2H), 3.39-3.34 (m, 1H), 3.01 (dd, J 14.4, 2.0 Hz, 1H), 1.79-1.72 (m, 2H), 1.68-1.61 (m, 2H). |

| Ex. | ¹H NMR Data |
|---|---|
| 103 | δ$_H$ (500 MHz, DMSO-d$_6$) 10.42 (s, 1H), 10.30 (s, 1H), 9.13 (d, J 7.8 Hz, 1H), 7.52 (d, J 2.1 Hz, 1H), 7.45 (d, J 8.1 Hz, 1H), 7.42 (d, J 1.9 Hz, 1H), 7.22 (t, J 7.5 Hz, 1H), 7.18-7.12 (m, 4H), 7.09 (d, J 7.2 Hz, 1H), 4.65 (dd, J 10.9, 7.8 Hz, 1H), 4.02 (s, 3H), 3.99 (d, J 3.7 Hz, 2H), 3.92 (ddd, J 10.9, 5.0, 2.4 Hz, 1H), 3.80 (ddd, J 11.1, 6.9, 3.7 Hz, 2H), 3.31-3.27 (m, 1H), 3.21 (dd, J 14.2, 2.2 Hz, 1H), 1.74 (ddd, J 12.9, 6.8, 3.7 Hz, 2H), 1.63 (ddd, J 13.1, 7.1, 3.6 Hz, 2H). |
| 104 | δ$_H$ (500 MHz, DMSO-d$_6$) 10.42 (s, 1H), 10.24 (s, 1H), 8.84 (d, J 7.7 Hz, 1H), 7.49-7.45 (m, 2H), 7.42 (d, J 1.9 Hz, 1H), 7.23 (t, J 7.5 Hz, 1H), 7.18-7.12 (m, 3H), 7.01 (d, J 2.1 Hz, 1H), 6.87 (d, J 7.2 Hz, 1H), 4.71 (dd, J 10.3, 7.7 Hz, 1H), 4.05-4.01 (m, 2H), 4.01 (s, 3H), 3.93 (ddd, J 10.4, 5.0, 2.4 Hz, 1H), 3.85-3.78 (m, 2H), 3.39-3.35 (m, 1H), 3.01 (dd, J 14.4, 2.0 Hz, 1H), 1.79-1.72 (m, 2H), 1.64 (ddd, J 13.8, 7.0, 3.4 Hz, 2H). |
| 106 | δ$_H$ (500 MHz, CD3OD) 7.51-7.40 (m, 3H), 7.10 (dd, J 8.1, 1.9 Hz, 1H), 6.89 (dd, J 4.7, 2.1 Hz, 1H), 4.75 (t, J 5.8 Hz, 1H), 4.20-4.12 (m, 2H), 4.11 (s, 3H), 3.96-3.88 (m, 2H), 3.81-3.74 (m, 2H), 1.92-1.83 (m, 2H), 1.82-1.71 (m, 2H), 1.21 (s, 9H). 3 × NH not observed; ca. 85:15 rotamers. |
| 108 | δ$_H$ (500 MHz, DMSO-d$_6$) 10.39 (s, 1H), 10.22 (s, 1H), 8.47 (d, J 7.5 Hz, 1H), 7.45 (d, J 2.0 Hz, 1H), 7.44 (d, J 8.1 Hz, 1H), 7.37 (d, J 1.8 Hz, 1H), 7.10 (dd, J 8.2, 1.9 Hz, 1H), 7.02 (d, J 2.1 Hz, 1H), 4.47 (dd, J 9.9, 7.5 Hz, 1H), 4.02 (s, 3H), 4.01-3.97 (m, 2H), 3.80 (ddd, J 11.1, 6.9, 3.7 Hz, 2H), 2.41-2.34 (m, 1H), 2.28 (p, J 9.1 Hz, 1H), 1.97 (p, J 8.1 Hz, 2H), 1.77-1.71 (m, 2H), 1.65-1.55 (m, 3H), 1.41 (p, J 9.8, 9.3 Hz, 1H), 0.87 (d, J 6.5 Hz, 3H). |
| 109 | δ$_H$ (500 MHz, DMSO-d$_6$) 10.39 (s, 1H), 10.18 (s, 1H), 8.53 (d, J 7.1 Hz, 1H), 7.46 (d, J 2.0 Hz, 1H), 7.43 (d, J 8.1 Hz, 1H), 7.38 (d, J 1.9 Hz, 1H), 7.10 (dd, J 8.2, 1.8 Hz, 1H), 6.99 (d, J 2.1 Hz, 1H), 4.54 (dd, J 11.7, 7.1 Hz, 1H), 4.02 (s, 3H), 4.01-3.98 (m, 2H), 3.84-3.75 (m, 2H), 2.84-2.73 (m, 1H), 2.14-1.95 (m, 2H), 1.79-1.68 (m, 3H), 1.65-1.58 (m, 2H), 1.44-1.34 (m, 1H), 1.29-1.16 (m, 1H), 1.05 (d, J 7.1 Hz, 3H). |
| 110 | δ$_H$ (500 MHz, DMSO-d$_6$) 10.39 (s, 1H), 10.12 (s, 1H), 8.51 (d, J 8.5 Hz, 1H), 7.47 (d, J 2.0 Hz, 1H), 7.43 (d, J 8.2 Hz, 1H), 7.35 (d, J 1.9 Hz, 1H), 7.10 (dd, J 8.2, 1.9 Hz, 1H), 7.04 (d, J 2.1 Hz, 1H), 4.65 (t, J 8.7 Hz, 1H), 4.03 (s, 3H), 4.02-3.97 (m, 2H), 3.79 (ddd, J 11.1, 7.0, 3.9 Hz, 2H), 2.36-2.30 (m, 1H), 2.21 (dt, J 15.6, 8.2 Hz, 1H), 1.93 (dd, J 10.1, 7.6 Hz, 2H), 1.82-1.79 (m, 1H), 1.75-1.70 (m, 2H), 1.65-1.59 (m, 2H), 1.42-1.37 (m, 1H), 1.01 (d, J 6.6 Hz, 3H). |
| 111 | δ$_H$ (500 MHz, DMSO-d$_6$) 10.39 (s, 1H), 10.08 (s, 1H), 8.52 (d, J 8.3 Hz, 1H), 7.45 (d, J 2.0 Hz, 1H), 7.42 (d, J 8.2 Hz, 1H), 7.37 (d, J 1.9 Hz, 1H), 7.13 (dd, J 8.2, 1.9 Hz, 1H), 6.98 (d, J 2.1 Hz, 1H), 4.72 (dd, J 10.9, 8.4 Hz, 1H), 4.05 (s, 3H), 4.00 (ddd, J 11.1, 7.2, 3.6 Hz, 2H), 3.79 (ddd, J 11.0, 7.0, 3.7 Hz, 2H), 2.97-2.88 (m, 1H), 2.46-2.39 (m, 1H), 2.08-2.00 (m, 1H), 1.97-1.91 (m, 1H), 1.84-1.78 (m, 1H), 1.75-1.70 (m, 2H), 1.64-1.57 (m, 2H), 1.45-1.40 (m, 1H), 1.11 (d, J 7.2 Hz, 3H). |
| 114 | δ$_H$ (500 MHz, DMSO-d$_6$) 10.33 (s, 1H), 9.99 (s, 1H), 8.93 (d, J 8.7 Hz, 1H), 7.63 (dd, J 7.9, 1.4 Hz, 1H), 7.49 (d, J 2.1 Hz, 1H), 7.36 (d, J 8.0 Hz, 2H), 7.29 (td, J 7.6, 1.1 Hz, 1H), 7.19 (td, J 7.7, 1.4 Hz, 1H), 7.16 (d, J 1.8 Hz, 1H), 7.12 (d, J 2.1 Hz, 1H), 6.92 (dd, J 8.2, 1.9 Hz, 1H), 5.01 (dd, J 10.3, 8.8 Hz, 1H), 4.05 (s, 3H), 3.98 (ddd, J 10.3, 6.8, 3.4 Hz, 2H), 3.97-3.92 (m, 1H), 3.77 (ddd, J 11.0, 7.0, 3.7 Hz, 2H), 1.69 (ddd, J 12.8, 6.6, 3.5 Hz, 2H), 1.58 (ddd, J 12.8, 6.6, 3.5 Hz, 2H), 1.24 (d, J 6.9 Hz, 3H). |
| 115 | δ$_H$ (500 MHz, DMSO-d$_6$) 10.49 (s, 1H), 10.44 (s, 1H), 8.63 (d, J 8.8 Hz, 1H), 7.47 (d, J 8.2 Hz, 1H), 7.42-7.38 (m, 3H), 7.35 (d, J 2.0 Hz, 1H), 7.30 (td, J 7.4, 0.9 Hz, 1H), 7.21 (td, J 7.8, 1.6 Hz, 1H), 7.17 (dd, J 8.1, 1.9 Hz, 1H), 6.72 (d, J 2.1 Hz, 1H), 5.12 (dd, J 10.4, 9.1 Hz, 1H), 4.01 (ddd, J 11.0, 7.2, 3.7 Hz, 2H), 3.89 (s, 3H), 3.83-3.75 (m, 3H), 1.74 (ddd, J 13.2, 7.1, 3.7 Hz, 2H), 1.63 (ddd, J 13.2, 7.1, 3.7 Hz, 2H), 1.19 (d, J 7.0 Hz, 3H). |
| 119 | δ$_H$ (500 MHz, DMSO-d$_6$) 10.40 (s, 1H), 10.16 (s, 1H), 8.60 (d, J 7.5 Hz, 1H), 7.47 (d, J 2.0 Hz, 1H), 7.43 (d, J 8.2 Hz, 1H), 7.37 (d, J 1.8 Hz, 1H), 7.30 (t, J 7.5 Hz, 2H), 7.24 (d, J 7.1 Hz, 2H), 7.19-7.16 (m, 1H), 7.10 (dd, J 8.2, 1.9 Hz, 1H), 7.04 (d, J 2.1 Hz, 1H), 4.55 (dd, J 9.4, 7.7 Hz, 1H), 4.02 (s, 3H), 4.02-3.97 (m, 2H), 3.82-3.77 (m, 2H), 3.40-3.35 (m, 1H), 2.72 (h, J 17.6, 8.7 Hz, 1H), 2.55-2.52 (m, 1H), 2.35-2.28 (m, 1H), 2.17 (q, J 10.3 Hz, 1H), 1.89 (q, J 10.1 Hz, 1H), 1.73 (ddd, J 12.8, 6.8, 3.5 Hz, 2H), 1.65-1.59 (m, 2H). |
| 120 | δ$_H$ (500 MHz, DMSO-d$_6$) 10.40 (s, 1H), 10.31 (s, 1H), 8.63-8.58 (m, 1H), 7.47 (d, J 2.0 Hz, 1H), 7.44 (d, J 8.1 Hz, 1H), 7.40 (d, J 1.8 Hz, 1H), 7.34-7.26 (m, 4H), 7.20-7.16 (m, 1H), 7.14 (dd, J 8.2, 1.9 Hz, 1H), 7.04 (d, J 2.0 Hz, 1H), 4.76 (dd, J 10.5, 7.5 Hz, 1H), 4.05 (s, 3H), 4.03-3.98 (m, 2H), 3.83-3.77 (m, 2H), 3.68-3.60 (m, 1H), 2.81-2.70 (m, 1H), 2.44-2.37 (m, 1H), 2.26 (t, J 7.5 Hz, 2H), 2.22-2.15 (m, 1H), 1.77-1.69 (m, 2H), 1.66-1.58 (m, 2H). |
| 121 | δ$_H$ (500 MHz, DMSO-d$_6$) 10.40 (s, 1H), 10.16 (s, 1H), 8.60 (d, J 7.5 Hz, 1H), 7.47 (d, J 2.0 Hz, 1H), 7.43 (d, J 8.2 Hz, 1H), 7.37 (d, J 1.9 Hz, 1H), 7.32-7.28 (m, 2H), 7.24 (d, J 7.1 Hz, 2H), 7.18 (t, J 7.2 Hz, 1H), 7.10 (dd, J 8.1, 1.9 Hz, 1H), 7.04 (d, J 2.1 Hz, 1H), 4.55 (dd, J 9.5, 7.7 Hz, 1H), 4.02 (s, 3H), 4.02-3.97 (m, 2H), 3.82-3.77 (m, 2H), 3.40-3.35 (m, 1H), 2.77-2.68 (m, 1H), 2.49-2.48 (m, 1H), 2.35-2.28 (m, 1H), 2.17 (q, J 10.3 Hz, 1H), 1.89 (q, J 10.2 Hz, 1H), 1.76-1.70 (m, 2H), 1.65-1.59 (m, 2H). |
| 122 | δ$_H$ (500 MHz, DMSO-d$_6$) 10.41 (s, 1H), 10.34 (s, 1H), 8.67 (d, J 7.1 Hz, 1H), 7.46 (d, J 2.0 Hz, 1H), 7.44 (d, J 8.1 Hz, 1H), 7.40 (d, J 1.8 Hz, 1H), 7.33-7.26 (m, 4H), 7.18 (t, J 7.0 Hz, 1H), 7.14 (dd, J 8.1, 1.9 Hz, 1H), 7.05 (d, J 2.0 Hz, 1H), 4.76 (dd, J 10.5, 7.5 Hz, 1H), 4.05 (s, 3H), 4.03-3.98 (m, 2H), 3.80 (ddd, J 10.6, 6.8, 3.3 Hz, 2H), 3.64 (p, J 8.0 Hz, 1H), 2.83-2.74 (m, 1H), 2.43-2.37 (m, 1H), 2.26 (t, J 7.5 Hz, 2H), 2.21-2.15 (m, 1H), 1.75-1.70 (m, 2H), 1.64-1.59 (m, 2H). |
| 135 | δ$_H$ (500 MHz, DMSO-d$_6$) 10.39 (s, 1H), 10.20 (s, 1H), 8.48 (d, J 8.6 Hz, 1H), 7.45 (d, J 2.1 Hz, 1H), 7.43 (d, J 8.2 Hz, 1H), 7.39 (d, J 1.8 Hz, 1H), 7.15 (dd, J 8.2, 1.9 Hz, 1H), |

| Ex. | ¹H NMR Data |
|---|---|
| | 7.03 (d, J 2.1 Hz, 1H), 4.52 (dd, J 10.9, 8.7 Hz, 1H), 4.04 (s, 3H), 4.01 (ddd, J 11.0, 6.7, 3.2 Hz, 2H), 3.79 (ddd, J 11.1, 7.0, 3.7 Hz, 2H), 2.21-2.11 (m, 3H), 1.90 (dt, J 14.0, 7.1 Hz, 1H), 1.81-1.76 (m, 1H), 1.73 (ddd, J 12.9, 6.9, 3.6 Hz, 2H), 1.66-1.63 (m, 3H), 1.63-1.57 (m, 2H), 1.57-1.52 (m, 1H), 1.46 (d, J 10.8 Hz, 1H), 1.27-1.20 (m, 2H), 1.20-1.14 (m, 1H). |
| 136 | $\delta_H$ (500 MHz, DMSO-$d_6$) 10.40 (s, 1H), 10.20 (s, 1H), 8.64 (d, J 8.4 Hz, 1H), 7.46 (d, J 2.1 Hz, 1H), 7.43 (d, J 8.2 Hz, 1H), 7.36 (d, J 1.9 Hz, 1H), 7.11 (dd, J 8.2, 1.9 Hz, 1H), 6.99 (d, J 2.1 Hz, 1H), 4.63 (dd, J 11.5, 8.5 Hz, 1H), 4.03 (s, 3H), 4.02-3.98 (m, 2H), 3.79 (ddd, J 10.8, 6.4, 3.3 Hz, 2H), 1.98-1.90 (m, 1H), 1.75-1.71 (m, 2H), 1.68-1.57 (m, 5H), 1.52-1.47 (m, 1H), 1.09 (s, 3H), 1.05 (s, 3H). |
| 137 | $\delta_H$ (500 MHz, DMSO-$d_6$) 10.38 (s, 1H), 10.14 (s, 1H), 8.48 (d, J 8.0 Hz, 1H), 7.45 (d, J 2.1 Hz, 1H), 7.43 (d, J 8.2 Hz, 1H), 7.38 (d, J 1.9 Hz, 1H), 7.13 (dd, J 8.2, 1.9 Hz, 1H), 6.99 (d, J 2.1 Hz, 1H), 4.55 (dd, J 11.1, 8.1 Hz, 1H), 4.03 (s, 3H), 4.00 (ddd, J 11.0, 7.1, 3.5 Hz, 2H), 3.79 (ddd, J 11.2, 7.1, 3.7 Hz, 2H), 2.57 (q, J 10.1, 9.7 Hz, 1H), 1.96-1.88 (m, 1H), 1.76-1.70 (m, 2H), 1.69-1.58 (m, 4H), 1.56-1.47 (m, 1H), 1.17 (s, 3H), 0.97 (s, 3H). |
| 139 | $\delta_H$ (500 MHz, DMSO-$d_6$) 10.40 (s, 1H), 10.36 (s, 1H), 8.72 (d, J 8.3 Hz, 1H), 7.45-7.42 (m, 2H), 7.40 (d, J 1.9 Hz, 1H), 7.25 (d, J 7.6 Hz, 1H), 7.17 (d, J 8.2 Hz, 1H), 7.15-7.10 (m, 2H), 6.89 (d, J 2.1 Hz, 1H), 4.95 (t, J 8.6 Hz, 1H), 4.09 (ddd, J 8.2, 5.3, 2.4 Hz, 1H), 4.00 (dt, J 6.6, 4.1 Hz, 2H), 3.97 (s, 3H), 3.80 (ddd, J 11.0, 6.9, 3.9 Hz, 2H), 3.31-3.28 (m, 1H), 3.07 (dd, J 14.4, 2.1 Hz, 1H), 1.77-1.71 (m, 2H), 1.66-1.59 (m, 2H). |
| 141 | $\delta_H$ (500 MHz, DMSO-$d_6$) 10.42 (s, 1H), 10.26 (s, 1H), 9.06 (d, J 8.5 Hz, 1H), 7.48 (d, J 2.1 Hz, 1H), 7.45 (d, J 8.1 Hz, 1H), 7.38 (d, J 1.9 Hz, 1H), 7.26 (t, J 6.8, 6.4 Hz, 1H), 7.17 (d, J 8.1 Hz, 1H), 7.15-7.11 (m, 2H), 7.08 (d, J 2.1 Hz, 1H), 4.85 (dd, J 10.7, 8.5 Hz, 1H), 4.11 (ddd, J 10.6, 5.3, 2.5 Hz, 1H), 4.03 (s, 3H), 4.03-3.97 (m, 2H), 3.80 (ddd, J 11.0, 6.9, 3.7 Hz, 2H), 3.31-3.27 (m, 1H), 3.12 (dd, J 14.5, 2.3 Hz, 1H), 1.73 (ddd, J 12.9, 6.8, 3.5 Hz, 2H), 1.63 (ddd, J 13.3, 7.0, 3.7 Hz, 2H). |

Examples 144 & 145

The title compounds were prepared by a three-step sequence:

Step 1: reaction of Intermediate 37 with the appropriate commercially available aldehyde or ketone in accordance with Procedure F.

Step 2: reaction of the material thereby obtained in accordance with Procedure H.

Step 3: reaction of the material thereby obtained with Intermediate 123 in accordance with Procedure I.

| Ex. | Structure | Product | LCMS Mass | LCMS RT (min) | LCMS Method No. |
|---|---|---|---|---|---|
| 144 | 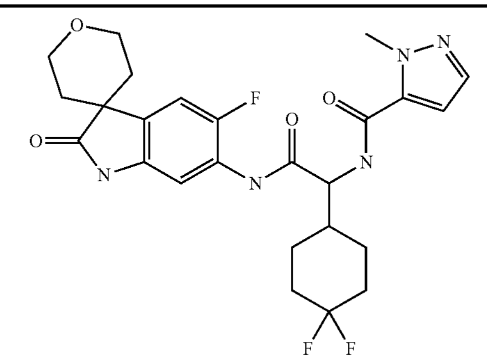 | N-{1-(4,4-Difluorocyclohexyl)-2-[(5-fluoro-2-oxospiro[1H-indole-3,4'-oxane]-6-yl)amino]-2-oxoethyl}-2-methylpyrazole-3-carboxamide | 520.5 | 1.20 | 27 |
| 145 | 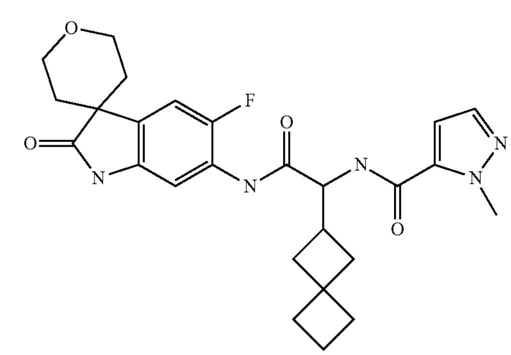 [SMILES: Cn1nccc1C(=O)NC(C(=O)Nc1cc2c(cc1F)C1(CCOCC1)C(=O)N2)C1CC2(CCC2)C1] | N-{2-[(5-Fluoro-2-oxospiro[1H-indole-3,4'-oxane]-6-yl)amino]-2-oxo-1-(spiro[3.3]heptan-2-yl)-ethyl}-2-methylpyrazole-3-carboxamide | 496.5 | 1.37 | 27 |

Examples 146 to 183

The title compounds were prepared by a two-step sequence:

Step 1: reaction of Intermediate 37 with the appropriate commercially available aldehyde or ketone in accordance with Procedure F.

Step 2: reaction of the material thereby obtained with Intermediate 2 in accordance with Procedure G.

| Ex. | Structure | Product | LCMS Mass | LCMS RT (min) | LCMS Method No. |
|---|---|---|---|---|---|
| 146 | 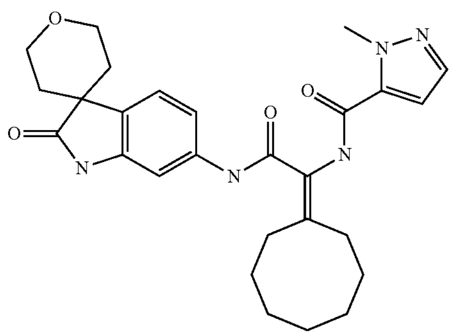 [SMILES: Cn1nccc1C(=O)NC(C(=O)Nc1ccc2c(c1)NC(=O)C21CCOCC1)=C1CCCCCCC1] | N-{1-Cyclooctylidene-2-oxo-2-[(2-oxospiro[1H-indole-3,4'-oxane]-6-yl)amino]ethyl}-2-methylpyrazole-3-carboxamide | 492.5 | 1.34 | 27 |
| 147 | 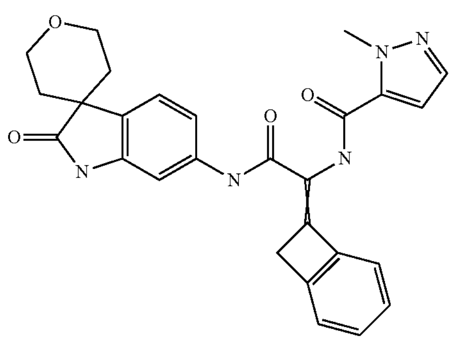 [SMILES: Cn1nccc1C(=O)NC(C(=O)Nc1ccc2c(c1)NC(=O)C21CCOCC1)=C1Cc2ccccc21] | N-{1-(7-Bicyclo[4.2.0]octa-1(6),2,4-trienylidene)-2-oxo-2-[(2-oxospiro[1H-indole-3,4'-oxane]-6-yl)amino]ethyl}-2-methylpyrazole-3-carboxamide | 484 | 1.1 | 27 |
| 148 | 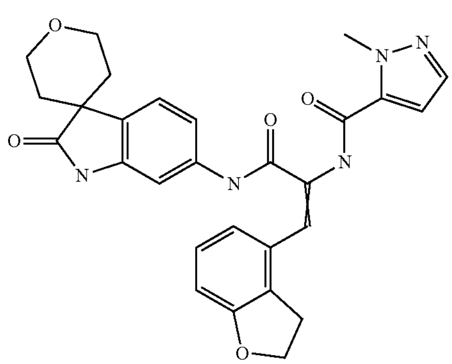 [SMILES: Cn1nccc1C(=O)NC(=Cc1cccc2c1CCO2)C(=O)Nc1ccc2c(c1)NC(=O)C21CCOCC1] | N-{1-(2,3-Dihydro-1-benzofuran-4-yl)-3-oxo-3-[(2-oxospiro[1H-indole-3,4'-oxane]-6-yl)amino]prop-1-en-2-yl}-2-methylpyrazole-3-carboxamide | 514.4 | 1.14 | 27 |

| Ex. | Structure | Product | LCMS Mass | LCMS RT (min) | LCMS Method No. |
|---|---|---|---|---|---|
| 149 | 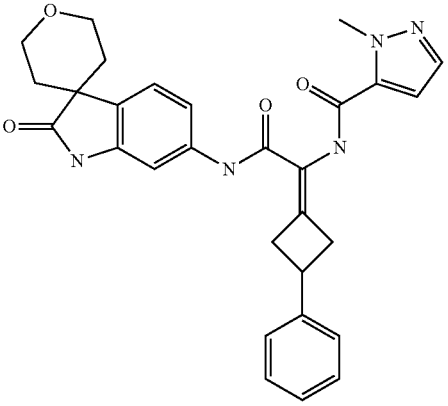 [SMILES: Cn1nccc1C(=O)NC(C(=O)Nc1ccc2c(c1)NC(=O)C21CCOCC1)=C1CC(c2ccccc2)C1] | 2-Methyl-N-[2-oxo-2-[(2-oxo-spiro[1H-indole-3,4'-oxane]-6-yl)amino]-1-(3-phenylcyclo-butylidene)ethyl}pyrazole-3-carboxamide | 512.5 | 1.3 | 27 |
| 150 | 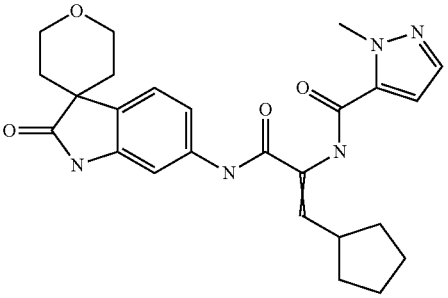 [SMILES: Cn1nccc1C(=O)NC(=CC1CCCC1)C(=O)Nc1ccc2c(c1)NC(=O)C21CCOCC1] | N-{1-Cyclopentyl-3-oxo-3-[(2-oxospiro[1H-indole-3,4'-oxane]-6-yl)amino]prop-1-en-2-yl}-2-methylpyrazole-3-carboxamide | 464.5 | 1.2 | 27 |
| 151 | 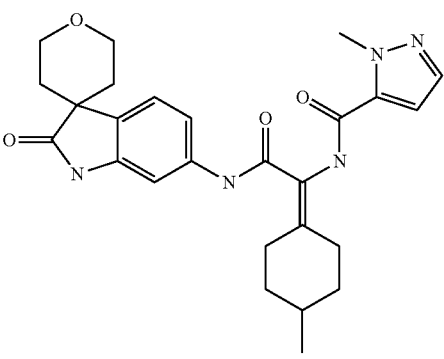 [SMILES: CC1CCC(=C(NC(=O)c2ccnn2C)C(=O)Nc2ccc3c(c2)NC(=O)C32CCOCC2)CC1] | 2-Methyl-N-{1-(4-methyl-cyclohexylidene)-2-oxo-2-[(2-oxospiro[1H-indole-3,4'-oxane]-6-yl)amino]ethyl}pyrazole-3-carboxamide | 478.0 | 1.26 | 28 |
| 152 | 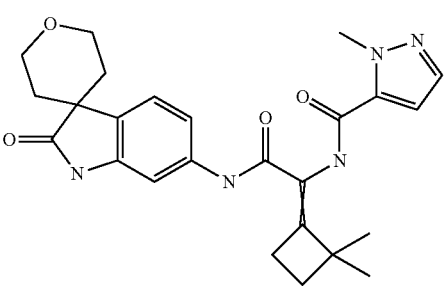 [SMILES: Cn1nccc1C(=O)NC(C(=O)Nc1ccc2c(c1)NC(=O)C21CCOCC1)=C1CCC1(C)C] | N-{1-(2,2-Dimethylcyclo-butylidene)-2-oxo-2-[(2-oxo-spiro[1H-indole-3,4'-oxane]-6-yl)amino]ethyl}-2-methyl-pyrazole-3-carboxamide | 464.5 | 1.16 | 27 |

| Ex. | Structure | Product | LCMS Mass | LCMS RT (min) | LCMS Method No. |
|---|---|---|---|---|---|
| 153 | 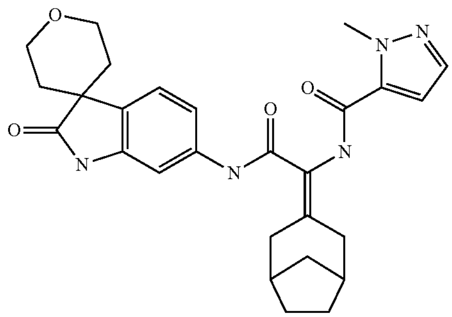 [SMILES: Cn1nccc1C(=O)NC(C(=O)Nc1ccc2c(c1)NC(=O)C21CCOCC1)=C1CC2CCC(C1)C2] | N-{1-(Bicyclo[3.2.1]octan-3-ylidene)-2-oxo-2-[(2-oxospiro-[1H-indole-3,4'-oxane]-6-yl)-amino]ethyl}-2-methylpyrazole-3-carboxamide | 490.5 | 1.27 | 27 |
| 154 | 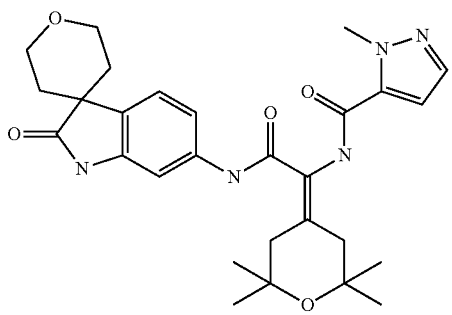 [SMILES: Cn1nccc1C(=O)NC(C(=O)Nc1ccc2c(c1)NC(=O)C21CCOCC1)=C1CC(C)(C)OC(C)(C)C1] | 2-Methyl-N-{2-oxo-2-[(2-oxo-spiro[1H-indole-3,4'-oxane]-6-yl)amino]-1-(2,2,6,6-tetra-methyloxan-4-ylidene)ethyl}-pyrazole-3-carboxamide | 522.5 | 1.15 | 27 |
| 155 | 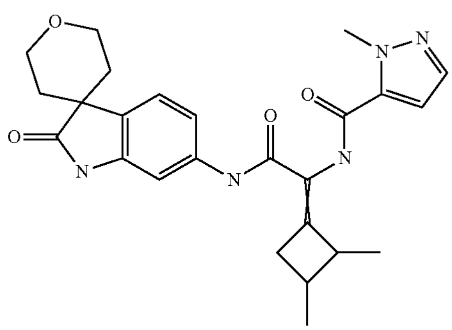 [SMILES: CC1CC(=C(NC(=O)c2ccnn2C)C(=O)Nc2ccc3c(c2)NC(=O)C32CCOCC2)C1C] | N-{1-(2,3-Dimethylcyclo-butylidene)-2-oxo-2-[(2-oxo-spiro[1H-indole-3,4'-oxane]-6-yl)amino]ethyl}-2-methyl-pyrazole-3-carboxamide | 464.4 | 1.17 | 27 |
| 156 | 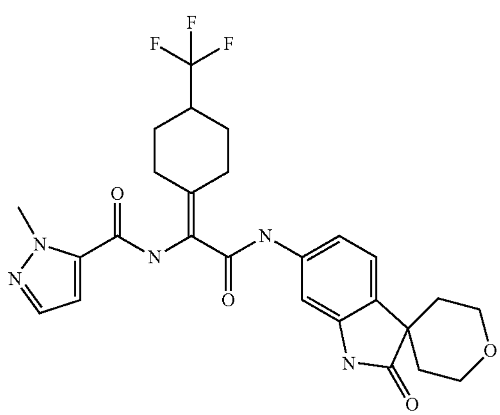 [SMILES: Cn1nccc1C(=O)NC(C(=O)Nc1ccc2c(c1)NC(=O)C21CCOCC1)=C1CCC(C(F)(F)F)CC1] | 2-Methyl-N-{2-oxo-2-[(2-oxo-spiro[1H-indole-3,4'-oxane]-6-yl)amino]-1-[4-(trifluoro-methyl)cyclohexylidene]ethyl}-pyrazole-3-carboxamide | 532.4 | 1.25 | 27 |

-continued

| Ex. | Structure | Product | LCMS Mass | LCMS RT (min) | LCMS Method No. |
|---|---|---|---|---|---|
| 157 | 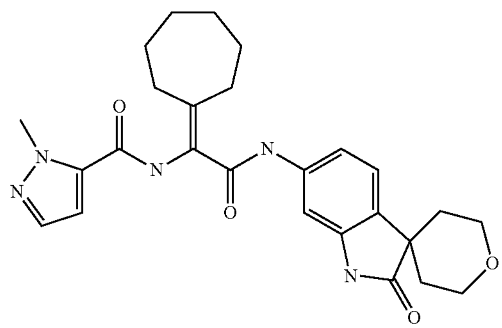 [SMILES: Cn1nccc1C(=O)NC(C(=O)Nc1ccc2c(c1)NC(=O)C21CCOCC1)=C1CCCCCC1] | N-{1-Cycloheptylidene-2-oxo-2-[(2-oxospiro[1H-indole-3,4'-oxane]-6-yl)amino]ethyl}-2-methylpyrazole-3-carboxamide | 478.5 | 1.24 | 27 |
| 158 | 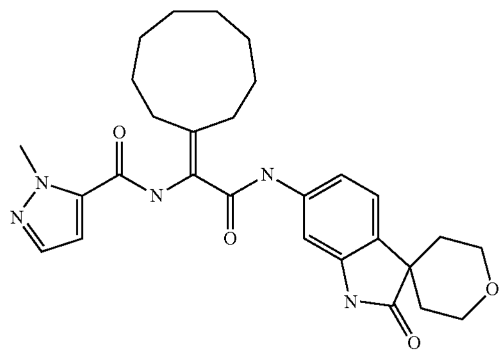 [SMILES: Cn1nccc1C(=O)NC(C(=O)Nc1ccc2c(c1)NC(=O)C21CCOCC1)=C1CCCCCCCC1] | N-{1-Cyclononylidene-2-oxo-2-[(2-oxospiro[1H-indole-3,4'-oxane]-6-yl)amino]ethyl}-2-methylpyrazole-3-carboxamide | 506.5 | 1.41 | 27 |
| 159 | 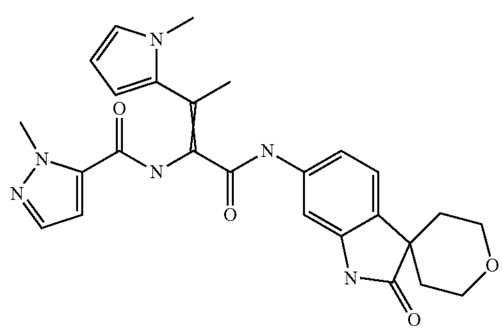 [SMILES: CC(=C(NC(=O)c1ccnn1C)C(=O)Nc1ccc2c(c1)NC(=O)C21CCOCC1)c1cccn1C] | 2-Methyl-N-{3-(1-methylpyrrol-2-yl)-1-oxo-1-[(2-oxospiro[1H-indole-3,4'-oxane]-6-yl)amino]-but-2-en-2-yl}pyrazole-3-carboxamide | 489.4 | 1.09 | 27 |
| 160 | 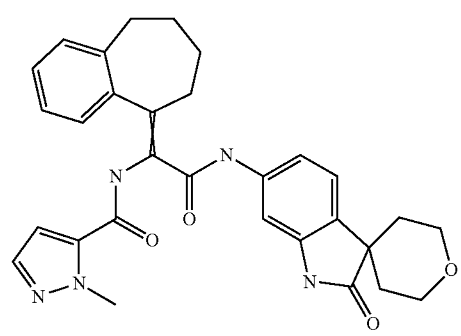 [SMILES: Cn1nccc1C(=O)NC(C(=O)Nc1ccc2c(c1)NC(=O)C21CCOCC1)=C1CCCCc2ccccc21] | 2-Methyl-N-{2-oxo-2-[(2-oxospiro[1H-indole-3,4'-oxane]-6-yl)amino]-1-(6,7,8,9-tetrahydro-benzo[7]annulen-5-ylidene)-ethyl}pyrazole-3-carboxamide | 526.2 | 1.20 | 28 |

-continued

| Ex. | Structure | Product | LCMS Mass | LCMS RT (min) | LCMS Method No. |
|---|---|---|---|---|---|
| 161 | 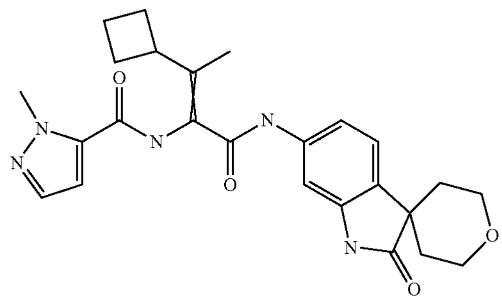 [SMILES: CC(=C(NC(=O)c1ccnn1C)C(=O)Nc1ccc2c(c1)NC(=O)C21CCOCC1)C1CCC1] | N-{3-Cyclobutyl-1-oxo-1-[(2-oxospiro[1H-indole-3,4'-oxane]-6-yl)amino]but-2-en-2-yl}-2-methylpyrazole-3-carboxamide | 464.2 | 1.17 | 28 |
| 162 | 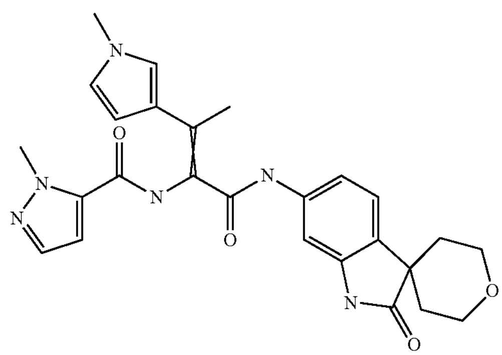 [SMILES: CC(=C(NC(=O)c1ccnn1C)C(=O)Nc1ccc2c(c1)NC(=O)C21CCOCC1)c1ccn(C)c1] | 2-Methyl-N-{3-(1-methylpyrrol-3-yl)-1-oxo-1-[(2-oxospiro[1H-indole-3,4'-oxane]-6-yl)amino]-but-2-en-2-yl}pyrazole-3-carboxamide | 489.5 | 1.04 | 27 |
| 163 | 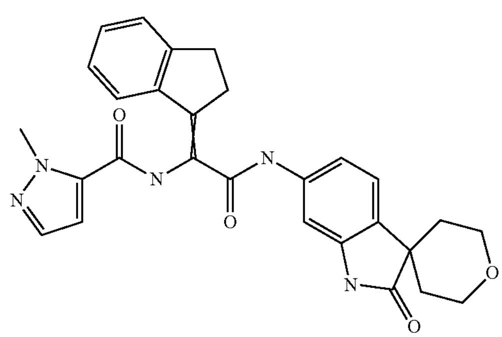 [SMILES: Cn1nccc1C(=O)NC(C(=O)Nc1ccc2c(c1)NC(=O)C21CCOCC1)=C1CCc2ccccc21] | N-{1-(2,3-Dihydroinden-1-ylidene)-2-oxo-2-[(2-oxospiro-[1H-indole-3,4'-oxane]-6-yl)-amino]ethyl}-2-methylpyrazole-3-carboxamide | 498 | 2.62 | 1 |
| 164 | 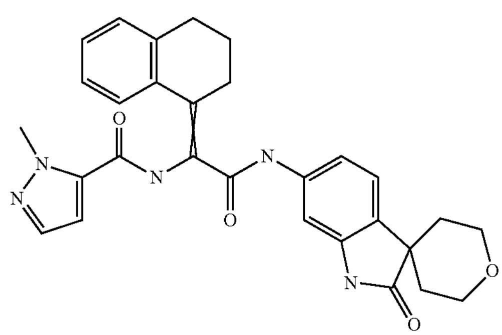 [SMILES: Cn1nccc1C(=O)NC(C(=O)Nc1ccc2c(c1)NC(=O)C21CCOCC1)=C1CCCc2ccccc21] | N-{1-(3,4-Dihydro-2H-naphthalen-1-ylidene)-2-oxo-2-[(2-oxospiro[1H-indole-3,4'-oxane]-6-yl)amino]ethyl}-2-methylpyrazole-3-carboxamide | 512.2 | 1.27 | 28 |

-continued

| Ex. | Structure | Product | LCMS Mass | LCMS RT (min) | LCMS Method No. |
|---|---|---|---|---|---|
| 165 | 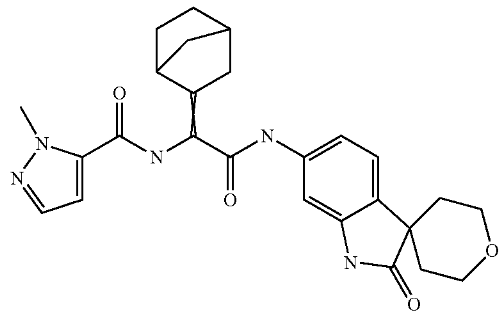 [SMILES: Cn1nccc1C(=O)NC(C(=O)Nc1ccc2c(c1)NC(=O)C21CCOCC1)=C1CC2CCC1C2] | 2-Methyl-N-{2-oxo-2-[(2-oxo-spiro[1H-indole-3,4'-oxane]-6-yl)amino]-1-[rac-(1R,4S)-bicyclo[2.2.1]heptan-2-ylidene]-ethyl}pyrazole-3-carboxamide | 476.2 | 1.20 | 28 |
| 166 | 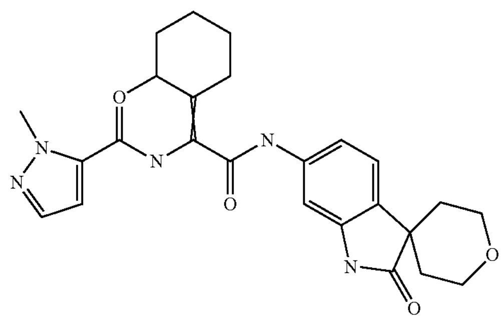 | 2-Methyl-N-{1-(2-methylcyclo-hexylidene)-2-oxo-2-[(2-oxo-spiro[1H-indole-3,4'-oxane]-6-yl)amino]ethyl}pyrazole-3-carboxamide | 478.5 | 1.24 | 27 |
| 167 | 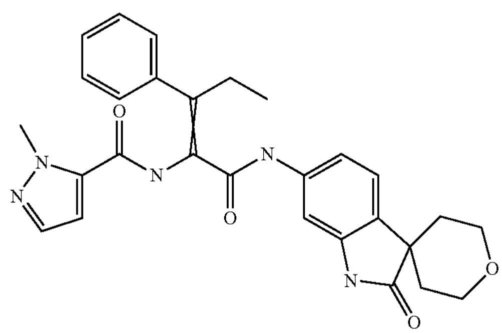 [SMILES: CCC(=C(NC(=O)c1ccnn1C)C(=O)Nc1ccc2c(c1)NC(=O)C21CCOCC1)c1ccccc1] | 2-Methyl-N-{1-oxo-1-[(2-oxo-spiro[1H-indole-3,4'-oxane]-6-yl)amino]-3-phenylpent-2-en-2-yl}pyrazole-3-carboxamide | 500.2 | 1.29 | 28 |
| 168 | 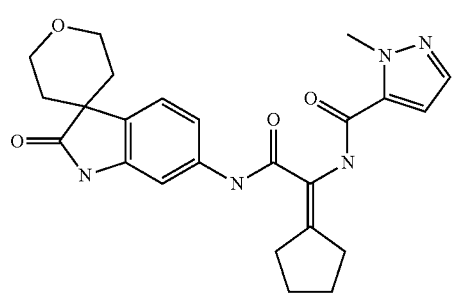 [SMILES: Cn1nccc1C(=O)NC(C(=O)Nc1ccc2c(c1)NC(=O)C21CCOCC1)=C1CCCC1] | N-{1-Cyclopentylidene-2-oxo-2-[(2-oxospiro[1H-indole-3,4'-oxane]-6-yl)amino]ethyl}-2-methylpyrazole-3-carboxamide | 450 | 2.34 | 1 |
| 169 | 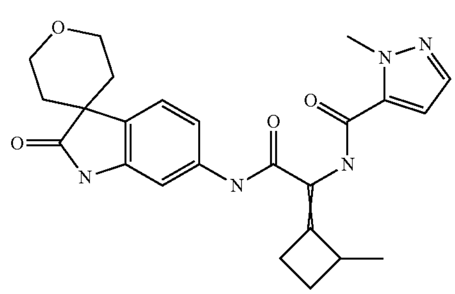 [SMILES: CC1CCC1=C(NC(=O)c1ccnn1C)C(=O)Nc1ccc2c(c1)NC(=O)C21CCOCC1] | 2-Methyl-N-{1-(2-methylcyclo-butylidene)-2-oxo-2-[(2-oxo-spiro[1H-indole-3,4'-oxane]-6-yl)amino]ethyl}pyrazole-3-carboxamide | 450.4 | 1.07 | 27 |

-continued

| Ex. | Structure | Product | LCMS Mass | LCMS RT (min) | LCMS Method No. |
|---|---|---|---|---|---|
| 170 | 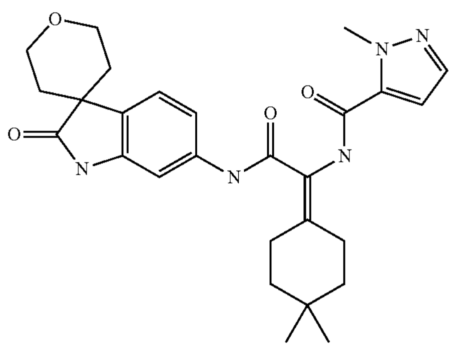 [SMILES: Cn1nccc1C(=O)NC(C(=O)Nc1ccc2c(c1)NC(=O)C21CCOCC1)=C1CCC(C)(C)CC1] | N-{1-(4,4-Dimethylcyclo-hexylidene)-2-oxo-2-[(2-oxo-spiro[1H-indole-3,4'-oxane]-6-yl)amino]ethyl}-2-methyl-pyrazole-3-carboxamide | 492.5 | 1.32 | 27 |
| 171 | 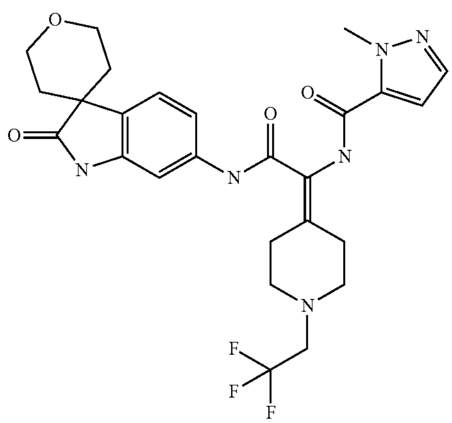 [SMILES: Cn1nccc1C(=O)NC(C(=O)Nc1ccc2c(c1)NC(=O)C21CCOCC1)=C1CCN(CC(F)(F)F)CC1] | 2-Methyl-N-{2-oxo-2-[(2-oxo-spiro[1H-indole-3,4'-oxane]-6-yl)amino]-1-[1-(2,2,2-trifluoro-ethyl)piperidin-4-ylidene]-ethyl}pyrazole-3-carboxamide | 547.4, | 1.12 | 27 |
| 172 | 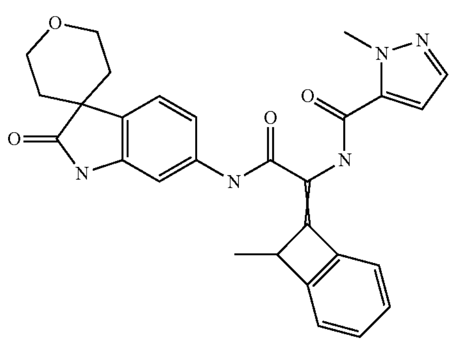 [SMILES: CC1C(=C(NC(=O)c2ccnn2C)C(=O)Nc2ccc3c(c2)NC(=O)C32CCOCC2)c2ccccc21] | 2-Methyl-N-{1-(8-methyl-7-bicyclo[4.2.0]octa-1(6),2,4-trienylidene)-2-oxo-2-[(2-oxo-spiro[1H-indole-3,4'-oxane]-6-yl)amino]ethyl}pyrazole-3-carboxamide | 498.5 | 1.25 | 27 |
| 173 | 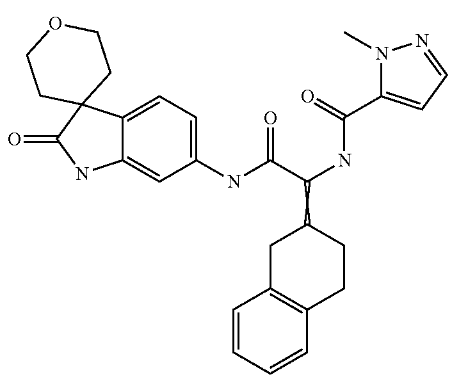 [SMILES: Cn1nccc1C(=O)NC(C(=O)Nc1ccc2c(c1)NC(=O)C21CCOCC1)=C1CCc2ccccc2C1] | N-{1-(3,4-Dihydro-1H-naphthalen-2-ylidene)-2-oxo-2-[(2-oxospiro[1H-indole-3,4'-oxane]-6-yl)amino]ethyl}-2-methylpyrazole-3-carboxamide | 512.5 | 1.24 | 27 |

-continued

| Ex. | Structure | Product | LCMS Mass | LCMS RT (min) | LCMS Method No. |
|---|---|---|---|---|---|
| 174 | 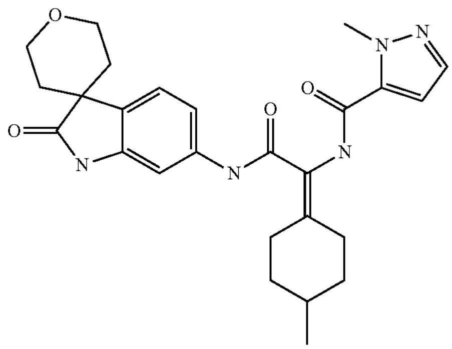 [SMILES: CC1CCC(=C(NC(=O)c2ccnn2C)C(=O)Nc2ccc3c(c2)NC(=O)C32CCOCC2)CC1] | 2-Methyl-N-{1-(4-methylcyclo-hexylidene)-2-oxo-2-[(2-oxo-spiro[1H-indole-3,4'-oxane]-6-yl)amino]ethyl}pyrazole-3-carboxamide | 478.5 | 1.25 | 27 |
| 175 | 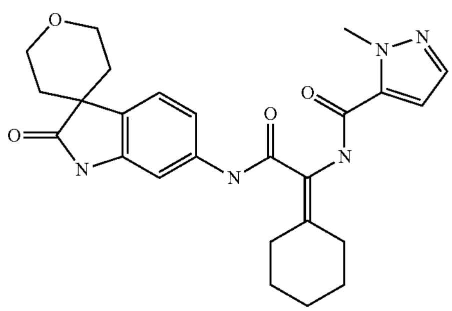 [SMILES: Cn1nccc1C(=O)NC(C(=O)Nc1ccc2c(c1)NC(=O)C21CCOCC1)=C1CCCCC1] | N-{1-Cyclohexylidene-2-oxo-2-[(2-oxospiro[1H-indole-3,4'-oxane]-6-yl)amino]ethyl}-2-methylpyrazole-3-carboxamide | 464.5 | 1.14 | 27 |
| 176 | 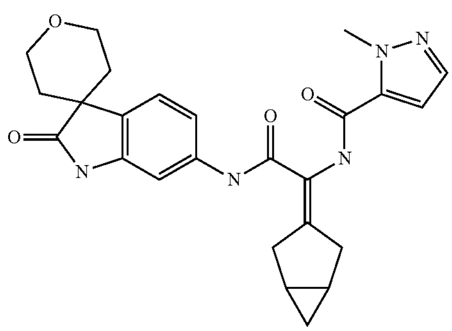 [SMILES: Cn1nccc1C(=O)NC(C(=O)Nc1ccc2c(c1)NC(=O)C21CCOCC1)=C1CC2CC2C1] | N-{1-(Bicyclo[3.1.0]hexan-3-ylidene)-2-oxo-2-[2-oxospiro-[1H-indole-3,4'-oxane]-6-yl)-amino]ethyl}-2-methylpyrazole-3-carboxamide | 462.4 | 1.11 | 27 |
| 177 | 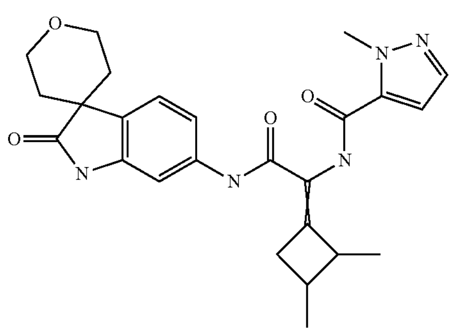 [SMILES: CC1CC(=C(NC(=O)c2ccnn2C)C(=O)Nc2ccc3c(c2)NC(=O)C32CCOCC2)C1C] | N-{1-(2,3-Dimethylcyclo-butylidene)-2-oxo-2-[2-oxo-spiro[indoline-3,4'-tetrahydro-pyran]-6-yl)amino]ethyl}-2-methylpyrazole-3-carboxamide (isomer 1) | 464.5 | 1.18 | 27 |

| Ex. | Structure | Product | LCMS Mass | LCMS RT (min) | LCMS Method No. |
|---|---|---|---|---|---|
| 178 | 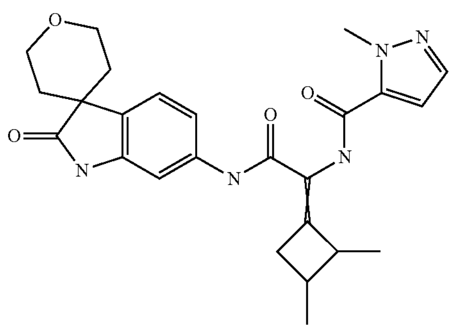 [SMILES: CC1CC(=C(NC(=O)c2ccnn2C)C(=O)Nc2ccc3c(c2)NC(=O)C32CCOCC2)C1C] | N-{1-(2,3-Dimethylcyclo-butylidene)-2-oxo-2-[(2-oxo-spiro[indoline-3,4'-tetrahydro-pyran]-6-yl)amino]ethyl}-2-methylpyrazole-3-carboxamide (isomer 2) | 464.4 | 1.21 | 27 |
| 179 | 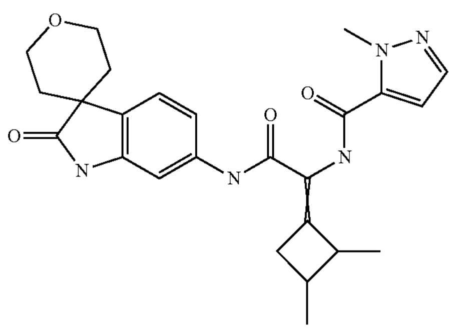 [SMILES: CC1CC(=C(NC(=O)c2ccnn2C)C(=O)Nc2ccc3c(c2)NC(=O)C32CCOCC2)C1C] | N-{1-(2,3-Dimethylcyclo-butylidene)-2-oxo-2-[2-oxo-spiro[indoline-3,4'-tetrahydro-pyran]-6-yl)amino]ethyl}-2-methylpyrazole-3-carboxamide (isomer 3) | 464.5 | 1.21 | 27 |
| 180 | 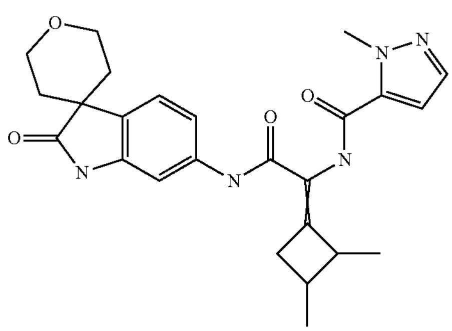 [SMILES: CC1CC(=C(NC(=O)c2ccnn2C)C(=O)Nc2ccc3c(c2)NC(=O)C32CCOCC2)C1C] | N-{1-(2,3-Dimethylcyclo-butylidene)-2-oxo-2-[(2-oxo-spiro[indoline-3,4'-tetrahydro-pyran]-6-yl)amino]ethyl}-2-methylpyrazole-3-carboxamide (isomer 4) | 464.5 | 1.21 | 27 |
| 181 | 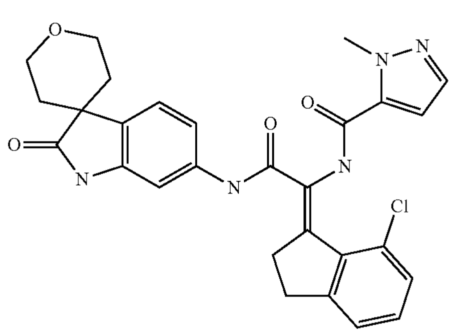 [SMILES: Cn1nccc1C(=O)N/C(C(=O)Nc1ccc2c(c1)NC(=O)C21CCOCC1)=C1/CCc2cccc(Cl)c21] | N-{(1Z)-1-(7-Chloro-2,3-dihydroinden-1-ylidene)-2-oxo-2-[(2-oxospiro[1H-indole-3,4'-oxane]-6-yl)amino]ethyl}-2-methylpyrazole-3-carboxamide | 532.4 | 1.24 | 27 |

| Ex. | Structure | Product | LCMS Mass | LCMS RT (min) | LCMS Method No. |
|---|---|---|---|---|---|
| 182 | 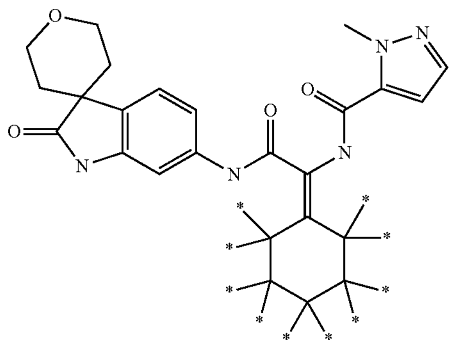 [SMILES: *C1(*)C(=C(NC(=O)c2ccnn2C)C(=O)Nc2ccc3c(c2)NC(=O)C32CCOCC2)C(*)(*)C(*)(*)C(*)(*)C1(*)*] | N-{1-(2,2,3,3,4,4,5,5,6,6-Deca-deuteriocyclohexylidene)-2-oxo-2-[(2-oxospiro[1H-indole-3,4'-oxane]-6-yl)amino]ethyl}-2-methylpyrazole-3-carboxamide | 474 | 2.55 | 1 |
| 183 | 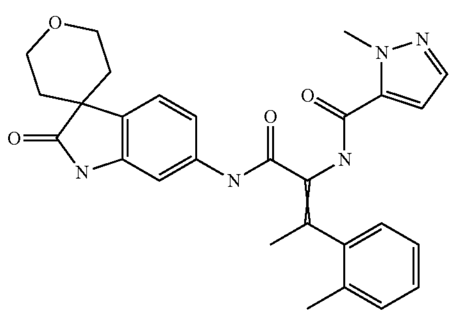 [SMILES: CC(=C(NC(=O)c1ccnn1C)C(=O)Nc1ccc2c(c1)NC(=O)C21CCOCC1)c1ccccc1C] | N-{3-(2-Chlorophenyl)-1-oxo-1-[(2-oxospiro[1H-indole-3,4'-oxane]-6-yl)amino]but-2-en-2-yl}-2-methylpyrazole-3-carboxamide | 520.2 | 1.16 | 27 |

Selected ¹H NMR Data:

| Ex. | ¹H NMR Data |
|---|---|
| 163 | $\delta_H$ (500 MHz, DMSO-d$_6$) 10.40 (s, 1H), 10.06 (s, 1H), 10.00 (s, 1H), 7.70 (d, J 7.9 Hz, 1H), 7.56 (d, J 2.0 Hz, 1H), 7.50 (d, J 1.7 Hz, 1H), 7.44 (d, J 8.1 Hz, 1H), 7.40 (d, J 7.4 Hz, 1H), 7.32 (t, J 7.7 Hz, 1H), 7.24 (t, J 7.6 Hz, 1H), 7.22 (d, J 1.9 Hz, 1H), 7.20 (d, J 1.9 Hz, 1H), 4.06 (s, 3H), 4.04-3.99 (m, 2H), 3.81 (ddd, J 10.9, 6.9, 3.6 Hz, 2H), 3.10 (dd, J 7.9, 5.0 Hz, 2H), 2.98 (dd, J 7.7, 4.8 Hz, 2H), 1.75 (ddd, J 12.8, 6.9, 3.5 Hz, 2H), 1.63 (ddd, J 13.2, 7.0, 3.7 Hz, 2H). |
| 168 | $\delta_H$ (500 MHz, DMSO-d$_6$) 10.38 (s, 1H), 9.75 (s, 1H), 9.44 (s, 1H), 7.50 (d, J 2.0 Hz, 1H), 7.46 (d, J 1.8 Hz, 1H), 7.42 (d, J 8.2 Hz, 1H), 7.17 (dd, J 8.2, 1.9 Hz, 1H), 7.05 (d, J 2.1 Hz, 1H), 4.03 (s, 3H), 4.03-3.99 (m, 2H), 3.81 (ddd, J 11.1, 7.1, 3.7 Hz, 2H), 2.68 (t, J 6.7 Hz, 2H), 2.43 (t, J 6.9 Hz, 2H), 1.75-1.59 (m, 8H). |
| 182 | $\delta_H$ (500 MHz, DMSO-d$_6$) 10.37 (s, 1H), 10.03 (s, 1H), 9.65 (s, 1H), 7.49 (d, J 2.1 Hz, 1H), 7.47 (d, J 1.4 Hz, 1H), 7.41 (d, J 8.2 Hz, 1H), 7.16 (dd, J 8.2, 1.7 Hz, 1H), 7.07 (d, J 2.0 Hz, 1H), 4.03-3.97 (m, 2H), 4.01 (s, 3H), 3.80 (ddd, J 11.1, 7.1, 3.7 Hz, 2H), 1.73 (ddd, J 13.0, 6.9, 3.6 Hz, 2H), 1.61 (ddd, J 13.1, 7.0, 3.6 Hz, 2H). |

Examples 184 & 185

The title compounds were prepared by a two-step sequence:
  Step 1: reaction of Intermediate 55 with the appropriate commercially available aldehyde or ketone in accordance with Procedure F.
  Step 2: reaction of the material thereby obtained with Intermediate 2 in accordance with Procedure G.

| Ex. | Structure | Product | LCMS Mass | LCMS RT (min) | LCMS Method No. |
|---|---|---|---|---|---|
| 184 | 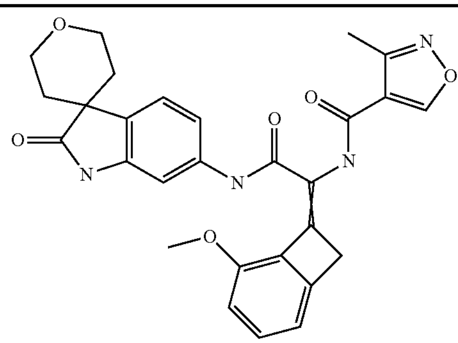 | N-{1-(5-Methoxy-7-bicyclo-[4.2.0]octa-1,3,5-trienylidene)-2-oxo-2-[(2-oxospiro[1H-indole-3,4'-oxane]-6-yl)amino]-ethyl}-3-methylisoxazole-4-carboxamide | 515.4 | 1.18 | 27 |
| 185 | 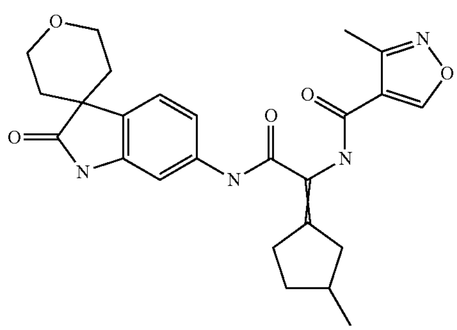 [SMILES: Cc1nocc1C(=O)NC(C(=O)Nc1ccc2c(c1)NC(=O)C21CCOCC1)=C1CCC(C)C1] | 3-Methyl-N-{1-(3-methylcyclo-pentylidene)-2-oxo-2-[(2-oxo-spiro[1H-indole-3,4'-oxane]-6-yl)amino]ethyl}isoxazole-4-carboxamide | 465.0 | 2.65 | 1 |

Selected $^1$H NMR Data:

| Ex. | $^1$H NMR Data |
|---|---|
| 185 | $\delta_H$ (500 MHz, DMSO-d$_6$) 10.38 (s, 1H), 9.70 (d, J 6.6 Hz, 1H), 9.38 (d, J 2.1 Hz, 1H), 9.37 (s, 1H), 7.46-7.43 (m, 1H), 7.41 (d, J 8.6 Hz, 1H), 7.20-7.13 (m, 1H), 4.01 (ddd, J 10.8, 7.0, 3.6 Hz, 2H), 3.80 (ddd, J 10.8, 6.9, 3.5 Hz, 2H), 2.84 (dd, J 17.3, 6.9 Hz, 0.5H), 2.76 (dd, J 18.3, 5.0 Hz, 0.5H), 2.68-2.61 (m, 0.5H), 2.60-2.54 (m, 0.5H), 2.51-2.44 (m, 1H), 2.42 (t, J 8.7 Hz, 0.5H), 2.37 (s, 3H), 2.23 (dd, J 17.4, 9.0 Hz, 0.5H), 2.06-1.97 (m, 1H), 1.89-1.80 (m, 1H), 1.79-1.71 (m, 2H), 1.65-1.58 (m, 2H), 1.31-1.19 (m, 1H), 1.07-0.95 (m, 3H). |

Examples 186 to 189

The title compounds were prepared by a three-step sequence:
Step 1: reaction of Intermediate 55 or Intermediate 60, as appropriate, with the appropriate commercially available aldehyde or ketone in accordance with Procedure F.
Step 2: reaction of the material thereby obtained with Intermediate 57 in accordance with Procedure G.
Step 3: reaction of the material thereby obtained in accordance with Procedure C.

| Ex. | Structure | Product | LCMS Mass | LCMS RT (min) | LCMS Method No. |
|---|---|---|---|---|---|
| 186 | 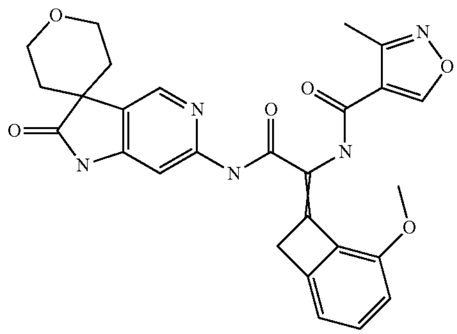 [SMILES: COc1cccc2c1C(=C(NC(=O)c1conc1C)C(=O)Nc1cc3c(cn1)C1(CCOCC1)C(=O)N3)C2] | N-{1-(5-Methoxy-7-bicyclo-[4.2.0]octa-1,3,5-trienylidene)-2-oxo-2-[(2-oxospiro[1H-pyrrolo[3,2-c]pyridine-3,4'-oxane]-6-yl)amino]ethyl}-3-methylisoxazole-4-carboxamide (isomer 1) | 516.4 | 1.15 | 27 |
| 187 | 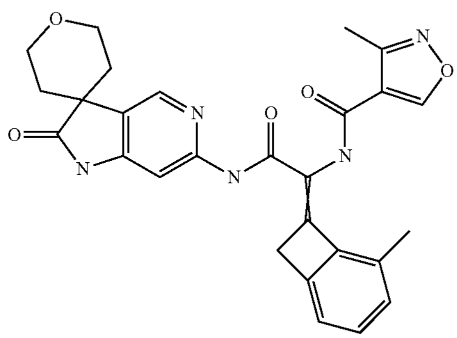 [SMILES: Cc1cccc2c1C(=C(NC(=O)c1conc1C)C(=O)Nc1cc3c(cn1)C1(CCOCC1)C(=O)N3)C2] | N-{1-(5-Chloro-7-bicyclo-[4.2.0]octa-1,3,5-trienylidene)-2-oxo-2-[(2-oxospiro[1H-pyrrolo[3,2-c]pyridine-3,4'-oxane]-6-yl)amino]ethyl}-3-methylisoxazole-4-carboxamide (isomer 1) | 520.3 | 1.19 | 27 |
| 188 | 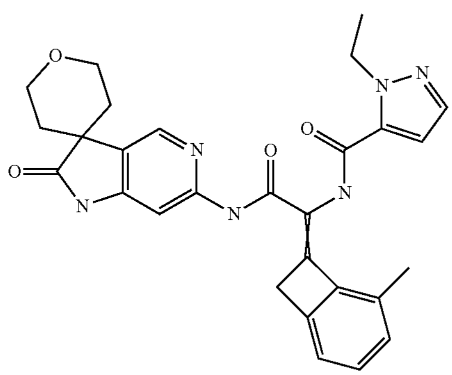 [SMILES: CCn1nccc1C(=O)NC(C(=O)Nc1cc2c(cn1)C1(CCOCC1)C(=O)N2)=C1Cc2cccc(C)c21] | N-{1-(5-Chloro-7-bicyclo-[4.2.0]octa-1,3,5-trienylidene)-2-oxo-2-[(2-oxospiro[1H-pyrrolo[3,2-c]pyridine-3,4'-oxane]-6-yl)amino]ethyl}-2-ethylpyrazole-3-carboxamide (isomer 1) | 533.4 | 1.23 | 27 |
| 189 | 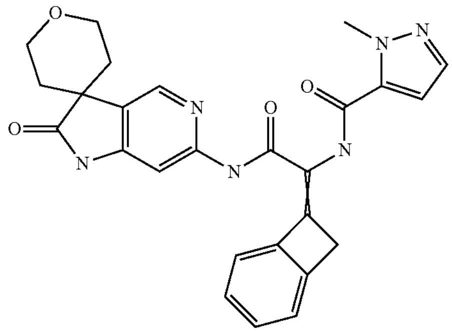 [SMILES: Cn1nccc1C(=O)NC(C(=O)Nc1cc2c(cn1)C1(CCOCC1)C(=O)N2)=C1Cc2ccccc21] | N-{1-(7-Bicyclo[4.2.0]octa-1,3,5-trienylidene)-2-oxo-2-[(2-oxospiro[1H-pyrrolo[3,2-c]-pyridine-3,4'-oxane]-6-yl)-amino]ethyl}-2-methylpyrazole-3-carboxamide (isomer 1) | 485.4 | 1.11 | 27 |

Examples 190 to 204

The title compounds were prepared in accordance with Procedure A from Intermediate 78 and the appropriate carboxylic acid.

| Ex. | Structure | Product | LCMS Mass | LCMS RT (min) | LCMS Method No. |
|---|---|---|---|---|---|
| 190 | 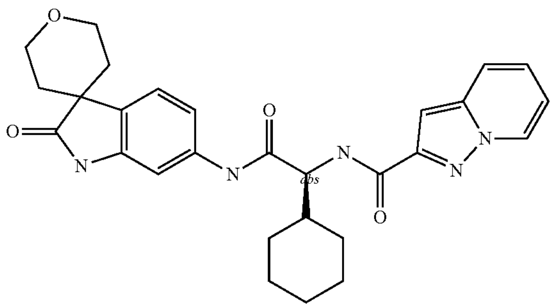 [SMILES: O=C(N[C@H](C(=O)Nc1ccc2c(c1)NC(=O)C21CCOCC1)C1CCCCC1)c1cc2ccccn2n1] | N-{(1S)-1-Cyclohexyl-2-oxo-2-[(2-oxospiro[1H-indole-3,4'-oxane]-6-yl)amino]ethyl}-pyrazolo[1,5-c]pyridine-2-carboxamide | 502.4 | 1.39 | 27 |
| 191 | 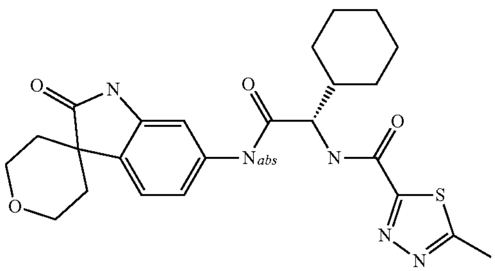 [SMILES: Cc1nnc(C(=O)N[C@H](C(=O)Nc2ccc3c(c2)NC(=O)C32CCOCC2)C2CCCCC2)s1] | N-{(1S)-1-Cyclohexyl-2-oxo-2-[(2-oxospiro[1H-indole-3,4'-oxane]-6-yl)amino]ethyl}-5-methyl-1,3,4-thiadiazole-2-carboxamide | 484.4 | 1.25 | 27 |
| 192 | 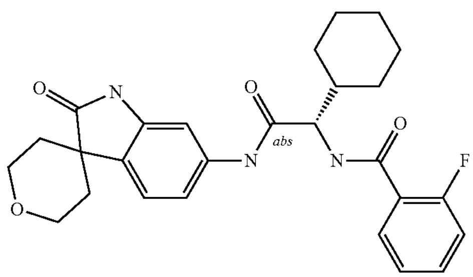 [SMILES: O=C(N[C@H](C(=O)Nc1ccc2c(c1)NC(=O)C21CCOCC1)C1CCCCC1)c1ccccc1F] | N-{(1S)-1-Cyclohexyl-2-oxo-2-[(2-oxospiro[1H-indole-3,4'-oxane]-6-yl)amino]ethyl}-2-fluorobenzamide | 480.4 | 1.42 | 27 |
| 193 | 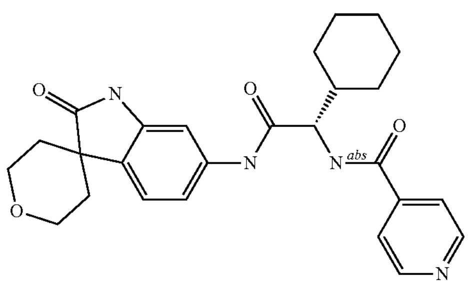 [SMILES: O=C(N[C@H](C(=O)Nc1ccc2c(c1)NC(=O)C21CCOCC1)C1CCCCC1)c1ccncc1] | N-{(1S)-1-Cyclohexyl-2-oxo-2-[(2-oxospiro[1H-indole-3,4'-oxane]-6-yl)amino]ethyl}-pyridine-4-carboxamide | 463.4 | 1.16 | 27 |
| 194 | 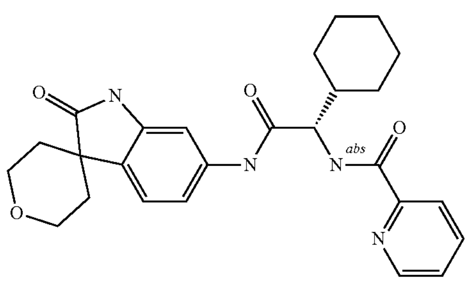 [SMILES: O=C(N[C@H](C(=O)Nc1ccc2c(c1)NC(=O)C21CCOCC1)C1CCCCC1)c1ccccn1] | N-{(1S)-1-Cyclohexyl-2-oxo-2-[(2-oxospiro[1H-indole-3,4'-oxane]-6-yl)amino]ethyl}-pyridine-2-carboxamide | 463.4 | 1.37 | 27 |

| Ex. | Structure | Product | LCMS Mass | LCMS RT (min) | LCMS Method No. |
|---|---|---|---|---|---|
| 195 | 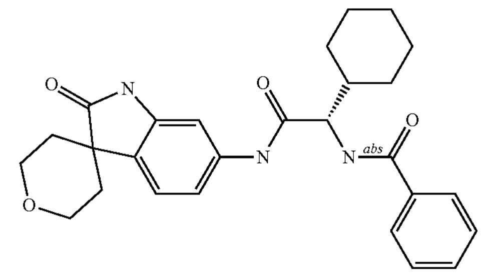 [SMILES: O=C(N[C@H](C(=O)Nc1ccc2c(c1)NC(=O)C21CCOCC1)C1CCCCC1)c1ccccc1] | N-{(1S)-1-Cyclohexyl-2-oxo-2-[(2-oxospiro[1H-indole-3,4'-oxane]-6-yl)amino]ethyl}-benzamide | 462.4 | 1.37 | 27 |
| 196 | 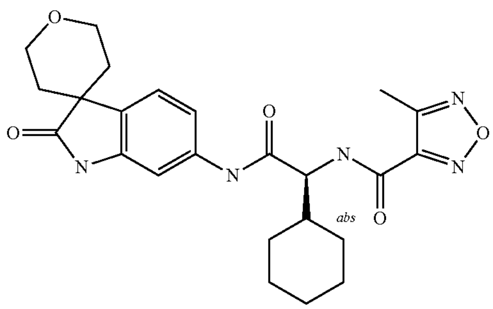 [SMILES: Cc1nonc1C(=O)N[C@H](C(=O)Nc1ccc2c(c1)NC(=O)C21CCOCC1)C1CCCCC1] | N-{(1S)-1-Cyclohexyl-2-oxo-2-[(2-oxospiro[1H-indole-3,4'-oxane]-6-yl)amino]ethyl}-4-methyl-1,2,5-oxadiazole-3-carboxamide | 468.4 | 1.4 | 27 |
| 197 | 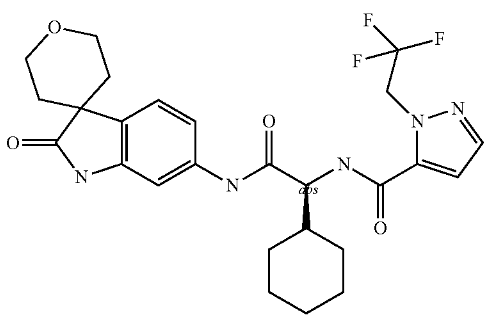 [SMILES: O=C(N[C@H](C(=O)Nc1ccc2c(c1)NC(=O)C21CCOCC1)C1CCCCC1)c1ccnn1CC(F)(F)F] | N-{(1S)-1-Cyclohexyl-2-oxo-2-[(2-oxospiro[1H-indole-3,4'-oxane]-6-yl)amino]ethyl}-2-(2,2,2-trifluoroethyl)pyrazole-3-carboxamide | 534.4 | 1.39 | 27 |
| 198 | 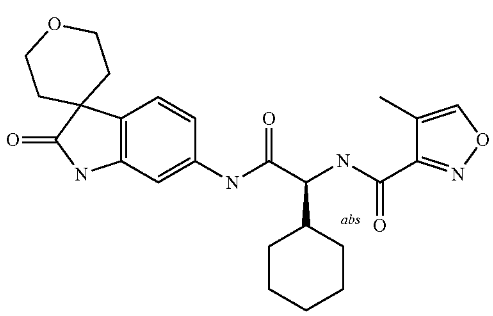 [SMILES: Cc1conc1C(=O)N[C@H](C(=O)Nc1ccc2c(c1)NC(=O)C21CCOCC1)C1CCCCC1] | N-{(1S)-1-Cyclohexyl-2-oxo-2-[(2-oxospiro[1H-indole-3,4'-oxane]-6-yl)amino]ethyl}-4-methylisoxazole-3-carboxamide | 467.4 | 1.26 | 27 |
| 199 | 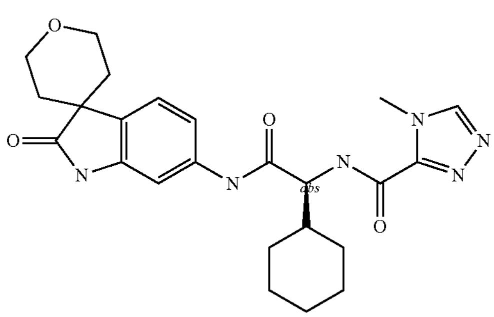 [SMILES: Cn1cnnc1C(=O)N[C@H](C(=O)Nc1ccc2c(c1)NC(=O)C21CCOCC1)C1CCCCC1] | N-{(1S)-1-Cyclohexyl-2-oxo-2-[(2-oxospiro[1H-indole-3,4'-oxane]-6-yl)amino]ethyl}-4-methyl-1,2,4-triazole-3-carboxamide | 467.5 | 1.09 | 27 |

-continued

| Ex. | Structure | Product | LCMS Mass | LCMS RT (min) | LCMS Method No. |
|---|---|---|---|---|---|
| 200 | 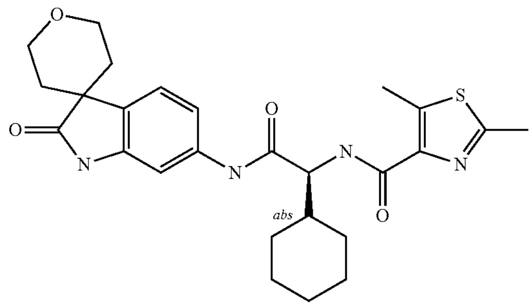 [SMILES: Cc1nc(C(=O)N[C@H](C(=O)Nc2ccc3c(c2)NC(=O)C32CCOCC2)C2CCCCC2)c(C)s1] | N-[(1S)-1-Cyclohexyl-2-oxo-2-[(2-oxospiro[1H-indole-3,4'-oxane]-6-yl)amino]ethyl]-2,5-dimethylthiazole-4-carboxamide | 497.4 | 1.27 | 27 |
| 201 | 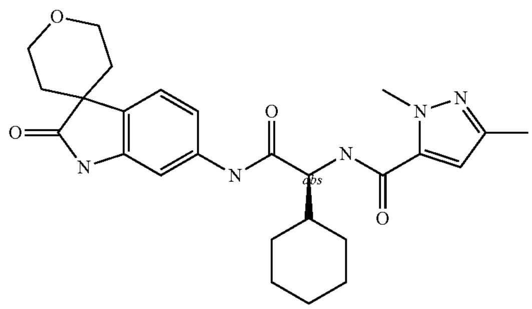 [SMILES: Cc1cc(C(=O)N[C@H](C(=O)Nc2ccc3c(c2)NC(=O)C32CCOCC2)C2CCCCC2)n(C)n1] | N-{(1S)-1-Cyclohexyl-2-oxo-2-[(2-oxospiro[1H-indole-3,4'-oxane]-6-yl)amino]ethyl}-2,5-dimethylpyrazole-3-carboxamide | 480.4 | 1.27 | 27 |
| 202 | 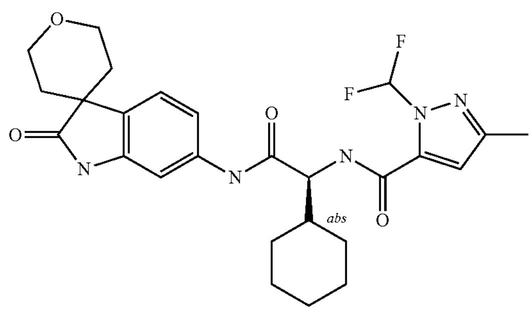 [SMILES: Cc1cc(C(=O)N[C@H](C(=O)Nc2ccc3c(c2)NC(=O)C32CCOCC2)C2CCCCC2)n(C(F)F)n1] | N-{(1S)-1-Cyclohexyl-2-oxo-2-[(2-oxospiro[1H-indole-3,4'-oxane]-6-yl)amino]ethyl}-2-(difluoromethyl)-5-methyl-pyrazole-3-carboxamide | 516.4 | 1.38 | 27 |
| 203 | 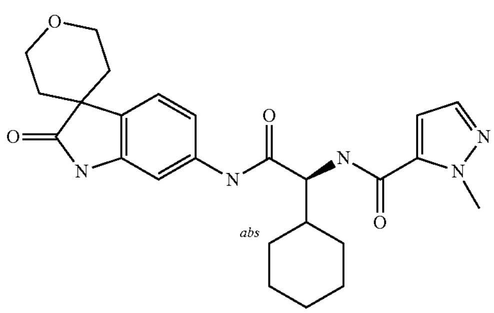 [SMILES: Cn1nccc1C(=O)N[C@H](C(=O)Nc1ccc2c(c1)NC(=O)C21CCOCC1)C1CCCCC1] | N-{(1S)-1-Cyclohexyl-2-oxo-2-[(2-oxospiro[1H-indole-3,4'-oxane]-6-yl)amino]ethyl}-2-methylpyrazole-3-carboxamide | 466.5 | 1.23 | 27 |
| 204 | 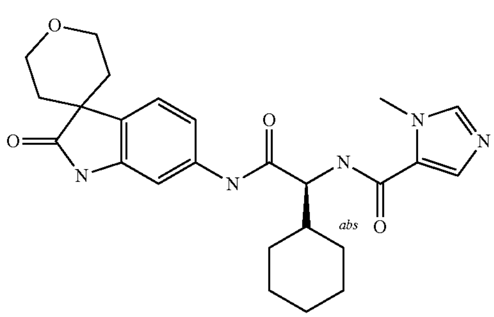 [SMILES: Cn1cncc1C(=O)N[C@H](C(=O)Nc1ccc2c(c1)NC(=O)C21CCOCC1)C1CCCCC1] | N-[(1S)-1-Cyclohexyl-2-oxo-2-[(2-oxospiro[1H-indole-3,4'-oxane]-6-yl)amino]ethyl}-3-methylimidazole-4-carboxamide | 466.4 | 1.11 | 27 |

Examples 205 to 208

The title compounds were prepared in accordance with Procedure D from Intermediate 78 and the appropriate carbamoyl chloride.

| Ex. | Structure | Product | LCMS Mass | LCMS RT (min) | LCMS Method No. |
|---|---|---|---|---|---|
| 205 | 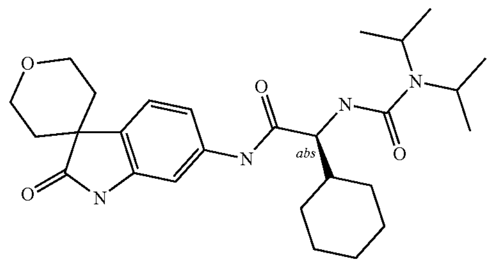 [SMILES: CC(C)N(C(=O)N[C@H](C(=O)Nc1ccc2c(c1)NC(=O)C21CCOCC1)C1CCCCC1)C(C)C] | (2S)-2-Cyclohexyl-2-[di(propan-2-yl)carbamoylamino]-N-(2-oxospiro[1H-indole-3,4'-oxane]-6-yl)acetamide | 485.6 | 1.54 | 27 |
| 206 | 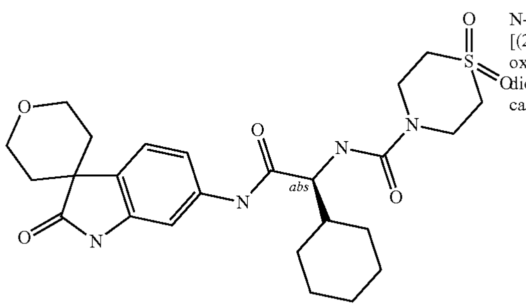 | N-{(1S)-1-Cyclohexyl-2-oxo-2-[(2-oxospiro[1H-indole-3,4'-oxane]-6-yl)amino]ethyl}-1,1-dioxo-1,4-thiazinane-4-carboxamide | 519.4 | 1.1 | 27 |
| 207 | 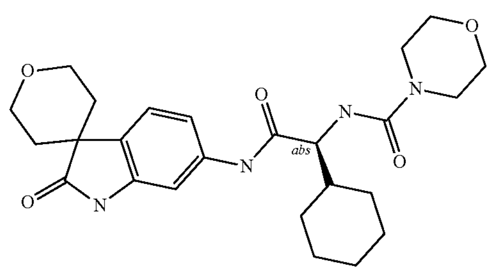 [SMILES: O=C(Nc1ccc2c(c1)NC(=O)C21CCOCC1)[C@@H](NC(=O)N1CCOCC1)C1CCCCC1] | N-{(1S)-1-Cyclohexyl-2-oxo-2-[(2-oxospiro[1H-indole-3,4'-oxane]-6-yl)amino]ethyl}-morpholine-4-carboxamide | 471.4 | 1.14 | 27 |
| 208 | 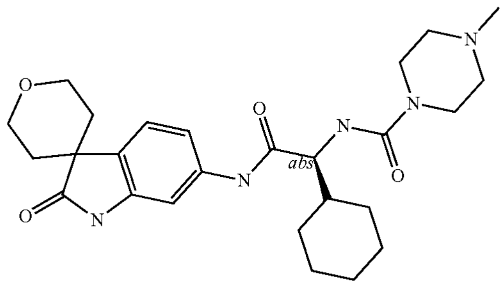 [SMILES: CN1CCN(C(=O)N[C@H](C(=O)Nc2ccc3c(c2)NC(=O)C32CCOCC2)C2CCCCC2)CC1] | N-{(1S)-1-Cyclohexyl-2-oxo-2-[(2-oxospiro[1H-indole-3,4'-oxane]-6-yl)amino]ethyl}-4-methylpiperazine-1-carboxamide | 484.5 | 1.12 | 27 |

Examples 209 to 232

The title compounds were prepared in accordance with Procedure E from Intermediate 78 and the appropriate chloroformate.

| Ex. | Structure | Product | LCMS Mass | LCMS RT (min) | LCMS Method No. |
|---|---|---|---|---|---|
| 209 | 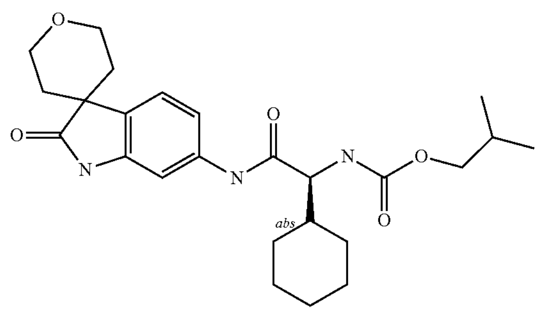 [SMILES: CC(C)COC(=O)N[C@H](C(=O)Nc1ccc2c(c1)NC(=O)C21CCOCC1)C1CCCCC1] | 2-Methylpropyl N-{(1S)-1-cyclohexyl-2-oxo-2-[(2-oxo-spiro[1H-indole-3,4'-oxane]-6-yl)amino]ethyl}carbamate | 458.5 | 1.48 | 27 |
| 210 | 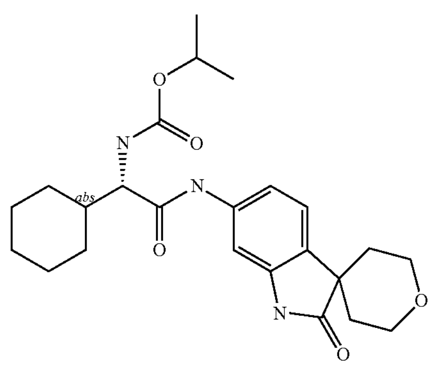 [SMILES: CC(C)OC(=O)N[C@H](C(=O)Nc1ccc2c(c1)NC(=O)C21CCOCC1)C1CCCCC1] | Propan-2-yl N-{(1S)-1-cyclohexyl-2-oxo-2-[(2-oxospiro[1H-indole-3,4'-oxane]-6-yl)amino]ethyl}carbamate | 444.5 | 1.39 | 27 |
| 211 | 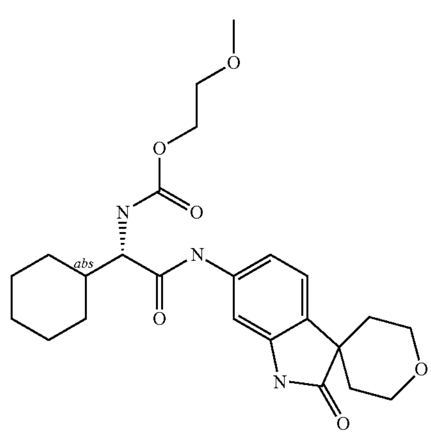 [SMILES: COCCOC(=O)N[C@H](C(=O)Nc1ccc2c(c1)NC(=O)C21CCOCC1)C1CCCCC1] | 2-Methoxyethyl N-{(1S)-1-cyclohexyl-2-oxo-2-[(2-oxo-spiro[1H-indole-3,4'-oxane]-6-yl)amino]ethyl}carbamate | 460.5 | 1.23 | 27 |

| Ex. | Structure | Product | LCMS Mass | LCMS RT (min) | LCMS Method No. |
|---|---|---|---|---|---|
| 212 | 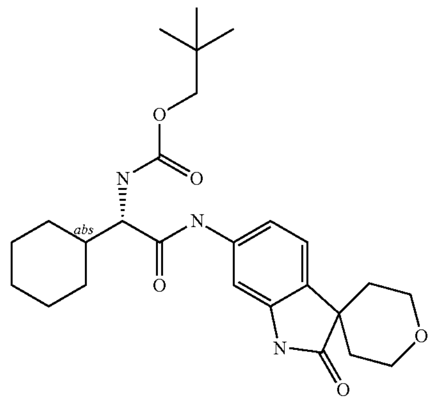 [SMILES: CC(C)(C)COC(=O)N[C@H](C(=O)Nc1ccc2c(c1)NC(=O)C21CCOCC1)C1CCCCC1] | 2,2-Dimethylpropyl N-{(1S)-1-cyclohexyl-2-oxo-2-[(2-oxo-spiro[1H-indole-3,4'-oxane]-6-yl)amino]ethyl}carbamate | 472.5 | 1.56 | 27 |
| 213 | 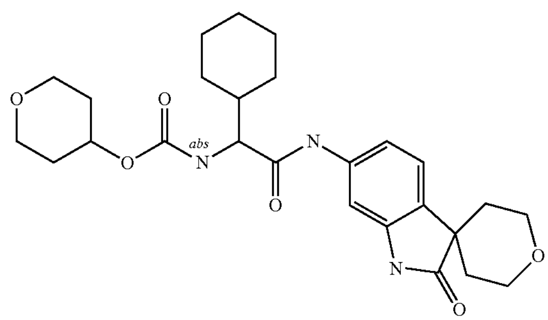 [SMILES: O=C(NC(C(=O)Nc1ccc2c(c1)NC(=O)C21CCOCC1)C1CCCCC1)OC1CCOCC1] | Oxan-4-yl N-{(1S)-1-cyclohexyl-2-oxo-2-[(2-oxospiro[1H-indole-3,4'-oxane]-6-yl)amino]-ethyl}carbamate | 486.5 | 1.26 | 27 |
| 214 | 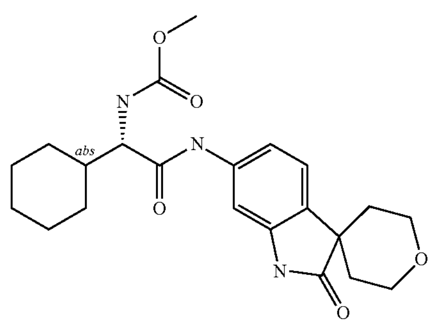 [SMILES: COC(=O)N[C@H](C(=O)Nc1ccc2c(c1)NC(=O)C21CCOCC1)C1CCCCC1] | Methyl N-{(1S)-1-cyclohexyl-2-oxo-2-[(2-oxospiro[1H-indole-3,4'-oxane]-6-yl)amino]ethyl}-carbamate | 416.4 | 1.23 | 27 |
| 215 | 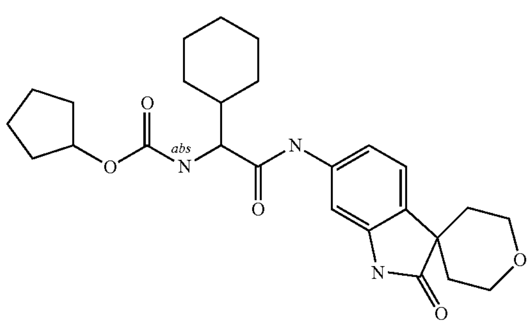 [SMILES: O=C(NC(C(=O)Nc1ccc2c(c1)NC(=O)C21CCOCC1)C1CCCCC1)OC1CCCC1] | Cyclopentyl N-{(1S)-1-cyclohexyl-2-oxo-2-[(2-oxospiro[1H-indole-3,4'-oxane]-6-yl)amino]-ethyl}carbamate | 470.5 | 1.49 | 27 |

-continued

| Ex. | Structure | Product | LCMS Mass | LCMS RT (min) | LCMS Method No. |
|---|---|---|---|---|---|
| 216 | 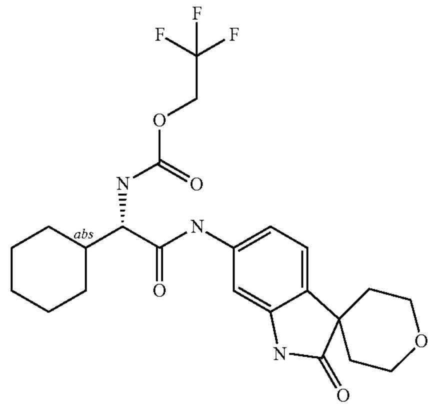 [SMILES: O=C(N[C@H](C(=O)Nc1ccc2c(c1)NC(=O)C21CCOCC1)C1CCCCC1)OCC(F)(F)F] | 2,2,2-Trifluoroethyl N-{(1S)-1-cyclohexyl-2-oxo-2-[(2-oxo-spiro[1H-indole-3,4'-oxane]-6-yl)amino]ethyl}carbamate | 484.5 | 1.43 | 27 |
| 217 | 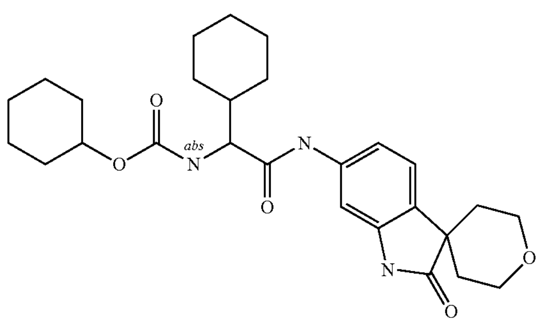 [SMILES: O=C(NC(C(=O)Nc1ccc2c(c1)NC(=O)C21CCOCC1)C1CCCCC1)OC1CCCCC1] | Cyclohexyl N-{(1S)-1-cyclo-hexyl-2-oxo-2-[(2-oxospiro[1H-indole-3,4'-oxane]-6-yl)amino]-ethyl}carbamate | 484.5 | 1.58 | 27 |
| 218 | 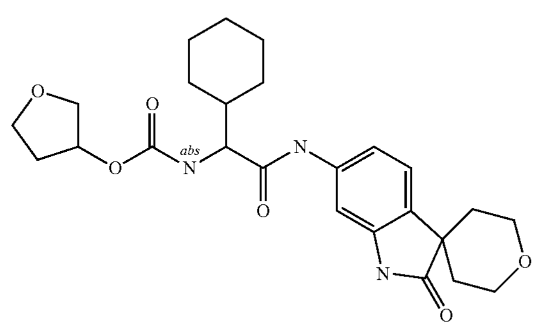 | Oxolan-3-yl N-{(1S)-1-cyclo-hexyl-2-oxo-2-[(2-oxospiro[1H-indole-3,4'-oxane]-6-yl)amino]-ethyl}carbamate | 472.5 | 1.21 | 27 |
| 219 | 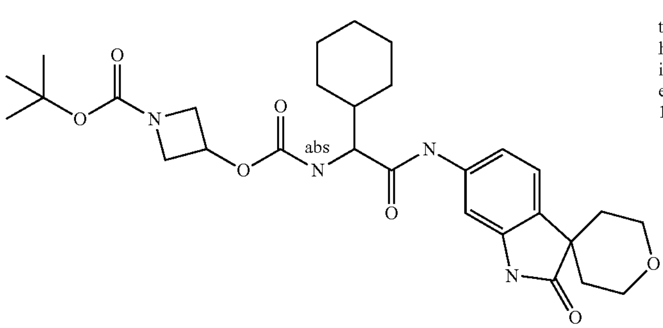 [SMILES: CC(C)(C)OC(=O)N1CC(OC(=O)NC(C(=O)Nc2ccc3c(c2)NC(=O)C32CCOCC2)C2CCCCC2)C1] | tert-Butyl 3-({(1S)-1-cyclo-hexyl-2-oxo-2-[(2-oxospiro[1H-indole-3,4'-oxane]-6-yl)amino]-ethyl}carbamoyloxy)azetidine-1-carboxylate | 557.5 | 1.49 | 27 |

-continued

| Ex. | Structure | Product | LCMS Mass | LCMS RT (min) | LCMS Method No. |
|---|---|---|---|---|---|
| 220 | 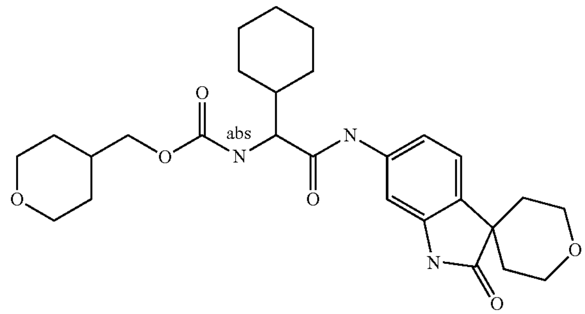 [SMILES: O=C(NC(C(=O)Nc1ccc2c(c1)NC(=O)C21CCOCC1)C1CCCCC1)OCC1CCOCC1] | Oxan-4-ylmethyl N-{(1S)-1-cyclohexyl-2-oxo-2-[(2-oxo spiro[1H-indole-3,4'-oxane]-6-yl)amino]ethyl}carbamate | 500.5 | 1.3 | 27 |
| 221 | 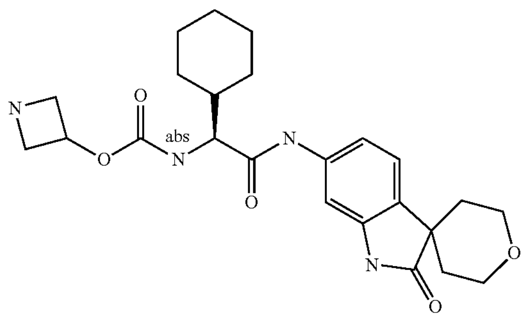 [SMILES: O=C(N[C@H](C(=O)Nc1ccc2c(c1)NC(=O)C21CCOCC1)C1CCCCC1)OC1CNC1] | Azetidin-3-yl N-{(1S)-1-cyclo-hexyl-2-oxo-2-[(2-oxospiro[1H-indole-3,4'-oxane]-6-yl)amino]-ethyl}carbamate | 457.4, | 1.11 | 27 |
| 222 | 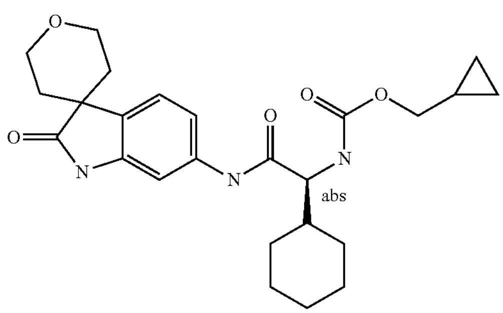 [SMILES: O=C(N[C@H](C(=O)Nc1ccc2c(c1)NC(=O)C21CCOCC1)C1CCCCC1)OCC1CC1] | Cyclopropylmethyl N-{(1S)-1-cyclohexyl-2-oxo-2-[(2-oxo-spiro[1H-indole-3,4'-oxane]-6-yl)amino]ethyl}carbamate | 456.5 | 1.42 | 27 |
| 223 | 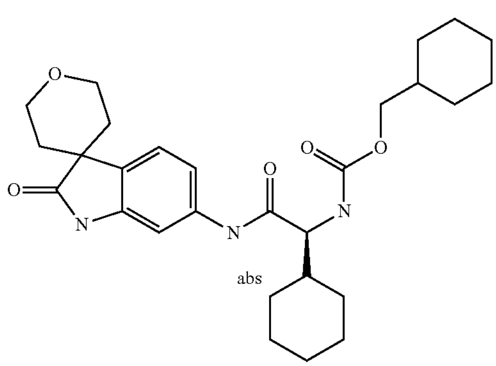 [SMILES: O=C(N[C@H](C(=O)Nc1ccc2c(c1)NC(=O)C21CCOCC1)C1CCCCC1)OCC1CCCCC1] | Cyclohexylmethyl N-{(1S)-1-cyclohexyl-2-oxo-2-[(2-oxo-spiro[1H-indole-3,4'-oxane]-6-yl)amino]ethyl}carbamate | 498.5 | 1.68 | 27 |

| Ex. | Structure | Product | LCMS Mass | LCMS RT (min) | LCMS Method No. |
|---|---|---|---|---|---|
| 224 | 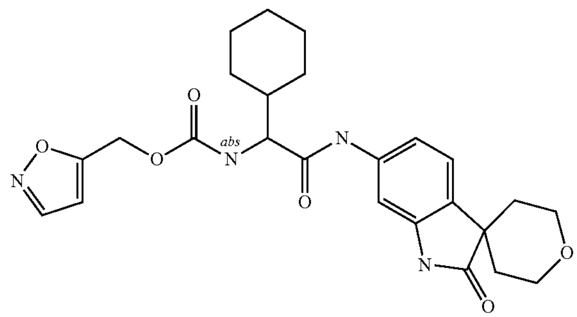 [SMILES: O=C(NC(C(=O)Nc1ccc2c(c1)NC(=O)C21CCOCC1)C1CCCCC1)OCc1ccno1] | Isoxazol-5-ylmethyl N-{(1S)-1-cyclohexyl-2-oxo-2-[(2-oxo-spiro[1H-indole-3,4'-oxane]-6-yl)amino]ethyl}carbamate | 483.5 | 1.29 | 27 |
| 225 | 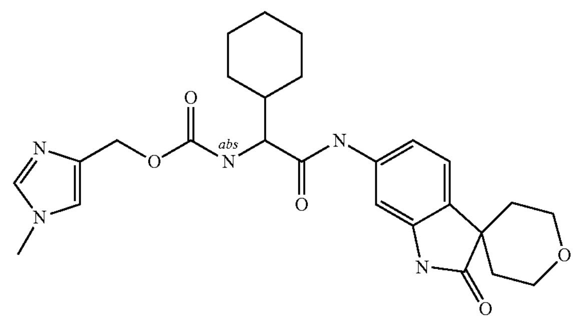 [SMILES: Cn1cnc(COC(=O)NC(C(=O)Nc2ccc3c(c2)NC(=O)C32CCOCC2)C2CCCCC2)c1] | (1-Methylimidazol-4-yl)methyl N-{(1S)-1-cyclohexyl-2-oxo-2-[(2-oxospiro[1H-indole-3,4'-oxane]-6-yl)amino]ethyl}-carbamate | 496.5 | 1.17 | 27 |
| 226 | 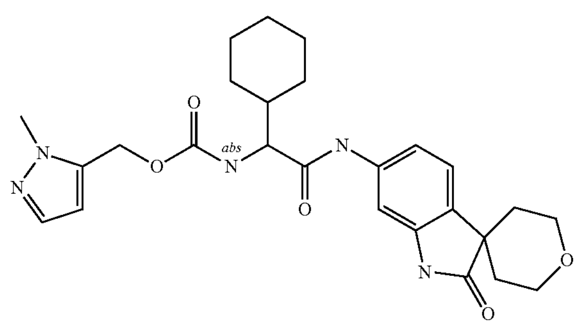 [SMILES: Cn1nccc1COC(=O)NC(C(=O)Nc1ccc2c(c1)NC(=O)C21CCOCC1)C1CCCCC1] | (2-Methylpyrazol-3-yl)methyl N-{(1S)-1-cyclohexyl-2-oxo-2-[(2-oxospiro[1H-indole-3,4'-oxane]-6-yl)amino]ethyl}-carbamate | 496.5 | 1.25 | 27 |
| 227 | 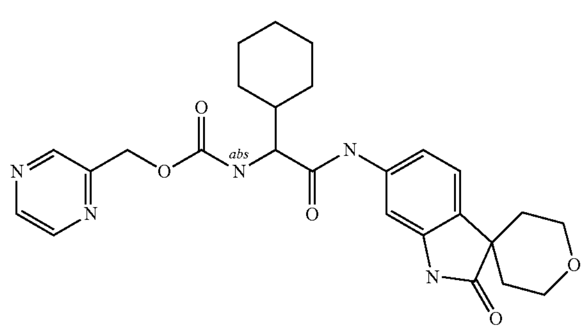 [SMILES: O=C(NC(C(=O)Nc1ccc2c(c1)NC(=O)C21CCOCC1)C1CCCCC1)OCc1cnccn1] | Pyrazin-2-ylmethyl N-{(1S)-1-cyclohexyl-2-oxo-2-[(2-oxo-spiro[1H-indole-3,4'-oxane]-6-yl)amino]ethyl}carbamate | 494.5 | 1.2 | 27 |

-continued

| Ex. | Structure | Product | LCMS Mass | LCMS RT (min) | LCMS Method No. |
|---|---|---|---|---|---|
| 228 | 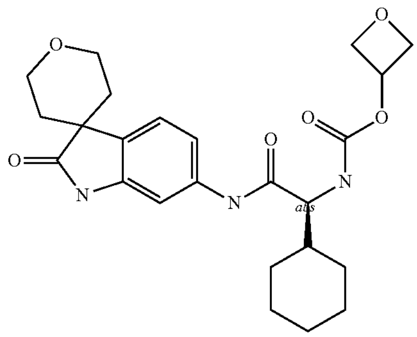 [SMILES: O=C(N[C@H](C(=O)Nc1ccc2c(c1)NC(=O)C21CCOCC1)C1CCCCC1)OC1COC1] | Oxetan-3-yl N-{(1S)-1-cyclo-hexyl-2-oxo-2-[(2-oxospiro[1H-indole-3,4'-oxane]-6-yl)amino]-ethyl}carbamate | 458.5 | 1.15 | 27 |
| 229 | 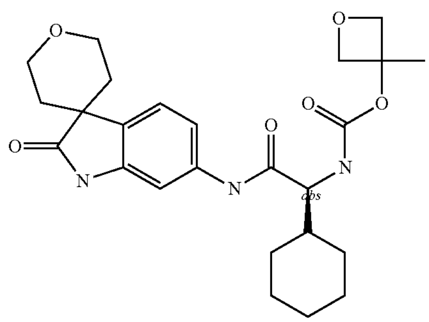 [SMILES: CC1(OC(=O)N[C@H](C(=O)Nc2ccc3c(c2)NC(=O)C32CCOCC2)C2CCCCC2)COC1] | (3-Methyloxetan-3-yl) N-{(1S)-1-cyclohexyl-2-oxo-2-[(2-oxo-spiro[1H-indole-3,4'-oxane]-6-yl)amino]ethyl}carbamate | 472.5 | 1.24 | 27 |
| 230 | 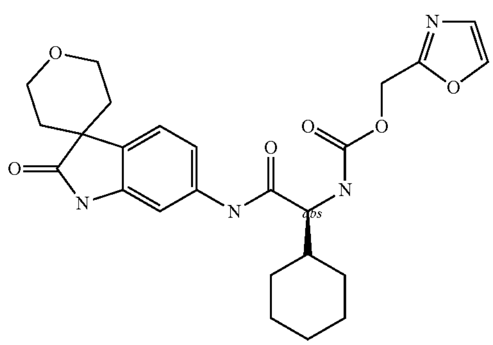 [SMILES: O=C(N[C@H](C(=O)Nc1ccc2c(c1)NC(=O)C21CCOCC1)C1CCCCC1)OCc1ncco1] | Oxazol-2-ylmethyl N-{(1S)-1-cyclohexyl-2-oxo-2-[(2-oxo-spiro[1H-indole-3,4'-oxane]-6-yl)amino]ethyl}carbamate | 483.5 | 1.19 | 27 |
| 231 | 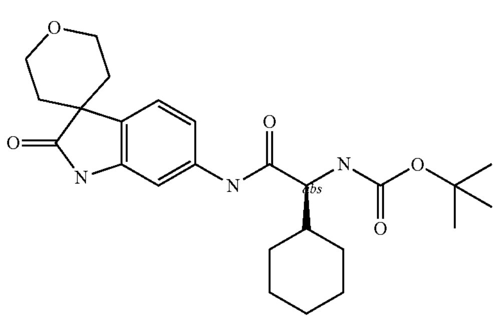 [SMILES: CC(C)(C)OC(=O)N[C@H](C(=O)Nc1ccc2c(c1)NC(=O)C21CCOCC1)C1CCCCC1] | tert-Butyl N-{(1S)-1-cyclo-hexyl-2-oxo-2-[2-oxospiro[1H-indole-3,4'-oxane]-6-yl)amino]-ethyl}carbamate | 458.5 | 1.46 | 27 |

| Ex. | Structure | Product | LCMS Mass | LCMS RT (min) | LCMS Method No. |
|---|---|---|---|---|---|
| 232 | 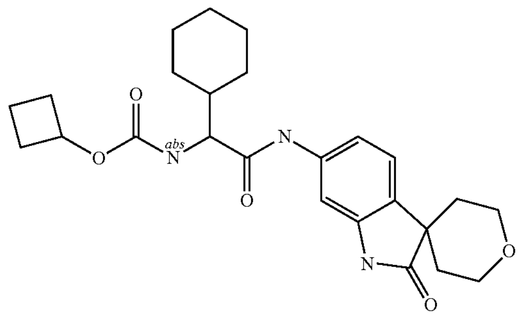 [SMILES: O=C(NC(C(=O)Nc1ccc2c(c1)NC(=O)C21CCOCC1)C1CCCCC1)OC1CCC1] | Cyclobutyl N-{(1S)-1-cyclohexyl-2-oxo-2-[(2-oxospiro[1H-indole-3,4'-oxane]-6-yl)amino]-ethyl}carbamate | 456.2 | 2.15 | 28 |

Examples 233 to 246

The title compounds were synthesized in accordance with Procedure B from Intermediate 78 and the appropriate halogeno heterocycle.

| Ex. | Structure | Product | LCMS Mass | LCMS RT (min) | LCMS Method No. |
|---|---|---|---|---|---|
| 233 | 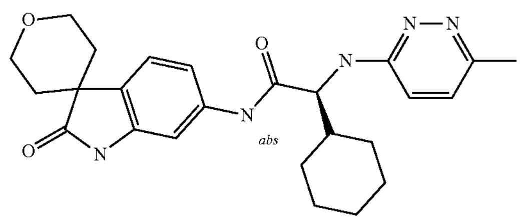 [SMILES: Cc1ccc(N[C@H](C(=O)Nc2ccc3c(c2)NC(=O)C32CCOCC2)C2CCCCC2)nn1] | (2S)-2-Cyclohexyl-2-[(6-methylpyridazin-3-yl)amino]-N-(2-oxospiro[1H-indole-3,4'-oxane]-6-yl)acetamide | 450.4 | 1.20 | 27 |
| 234 | 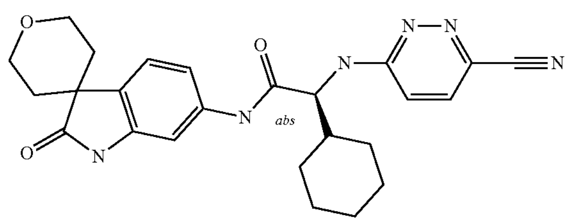 [SMILES: N#Cc1ccc(N[C@H](C(=O)Nc2ccc3c(c2)NC(=O)C32CCOCC2)C2CCCCC2)nn1] | (2S)-2-[(6-Cyanopyridazin-3-yl)amino]-2-cyclohexyl-N-(2-oxospiro[1H-indole-3,4'-oxane]-6-yl)acetamide | 461.5 | 1.29 | 27 |
| 235 | 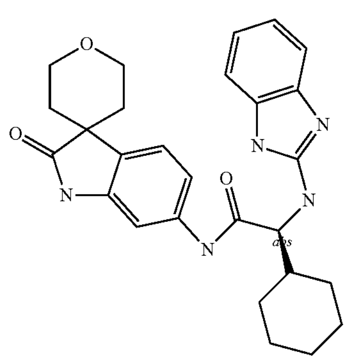 [SMILES: O=C(Nc1ccc2c(c1)NC(=O)C21CCOCC1)[C@@H](Nc1nc2ccccc2[nH]1)C1CCCCC1] | (2S)-2-(1H-Benzimidazol-2-ylamino)-2-cyclohexyl-N-(2-oxospiro[1H-indole-3,4'-oxane]-6-yl)acetamide | 474.5 | 1.31 | 27 |

-continued

| Ex. | Structure | Product | LCMS Mass | LCMS RT (min) | LCMS Method No. |
|---|---|---|---|---|---|
| 236 | 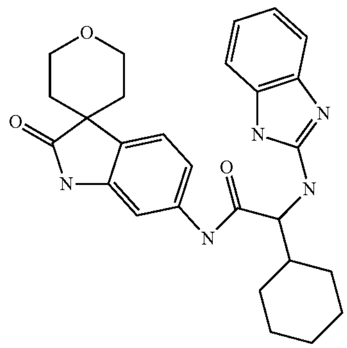 [SMILES: O=C(Nc1ccc2c(c1)NC(=O)C21CCOCC1)C(Nc1nc2ccccc2[nH]1)C1CCCCC1] | 2-(1,3-Benzoxazol-2-ylamino)-2-cyclohexyl-N-(2-oxospiro[1H-indole-3,4'-oxane]-6-yl)-acetamide | 475.5 | 1.46 | 27 |
| 237 | 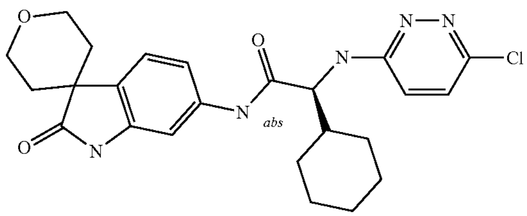 [SMILES: O=C(Nc1ccc2c(c1)NC(=O)C21CCOCC1)[C@@H](Nc1ccc(Cl)nn1)C1CCCCC1] | (2S)-2-[(6-Chloropyridazin-3-yl)amino]-2-cyclohexyl-N-(2-oxospiro[1H-indole-3,4'-oxane]-6-yl)acetamide | 470.4 | 1.34 | 27 |
| 238 | 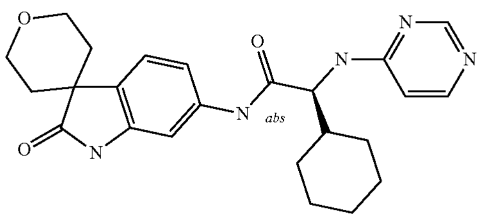 [SMILES: O=C(Nc1ccc2c(c1)NC(=O)C21CCOCC1)[C@@H](Nc1ccncn1)C1CCCCC1] | (2S)-2-Cyclohexyl-N-(2-oxo-spiro[1H-indole-3,4'-oxane]-6-yl)-2-(pyrimidin-4-ylamino)-acetamide | 436.4 | 1.17 | 27 |
| 239 | 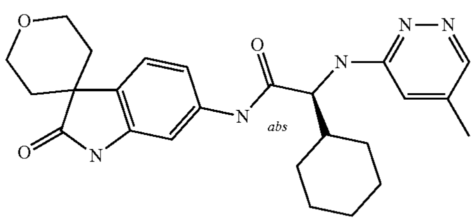 [SMILES: Cc1cnnc(N[C@H](C(=O)Nc2ccc3c(c2)NC(=O)C32CCOCC2)C2CCCCC2)c1] | (2S)-2-Cyclohexyl-2-[(5-methylpyridazin-3-yl)amino]-N-(2-oxospiro[1H-indole-3,4'-oxane]-6-yl)acetamide | 450.5 | 1.25 | 27 |
| 240 | 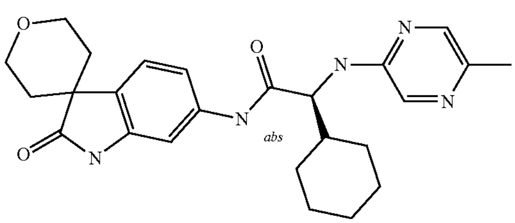 [SMILES: Cc1cnc(N[C@H](C(=O)Nc2ccc3c(c2)NC(=O)C32CCOCC2)C2CCCCC2)cn1] | (2S)-2-Cyclohexyl-2-[(5-methylpyrazin-2-yl)amino]-N-(2-oxospiro[1H-indole-3,4'-oxane]-6-yl)acetamide | 450.5 | 1.30 | 27 |
| 241 | 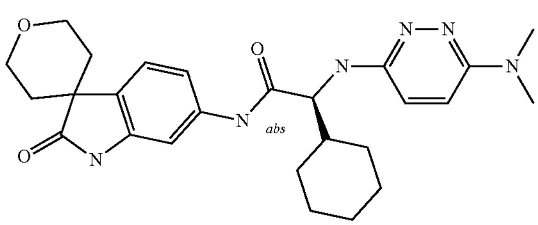 [SMILES: CN(C)c1ccc(N[C@H](C(=O)Nc2ccc3c(c2)NC(=O)C32CCOCC2)C2CCCCC2)nn1] | (2S)-2-Cyclohexyl-2-{[6-(dimethylamino)pyridazin-3-yl]amino}-N-(2-oxospiro[1H-indole-3,4'-oxane]-6-yl)-acetamide | 479.1 | 1.24 | 27 |

| Ex. | Structure | Product | LCMS Mass | LCMS RT (min) | LCMS Method No. |
|---|---|---|---|---|---|
| 242 | 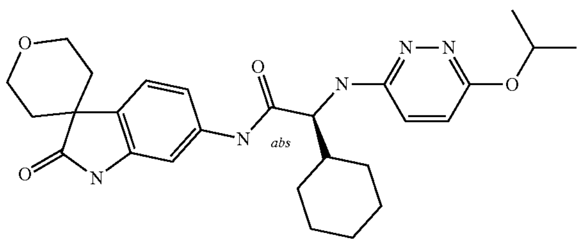 [SMILES: CC(C)Oc1ccc(N[C@H](C(=O)Nc2ccc3c(c2)NC(=O)C32CCOCC2)C2CCCCC2)nn1] | (2S)-2-Cyclohexyl-N-(2-oxo-spiro[1H-indole-3,4'-oxane]-6-yl)-2-{[6-(propan-2-yloxy)-pyridazin-3-yl]amino}acetamide | 494.0 | 2.06 | 6 |
| 243 | 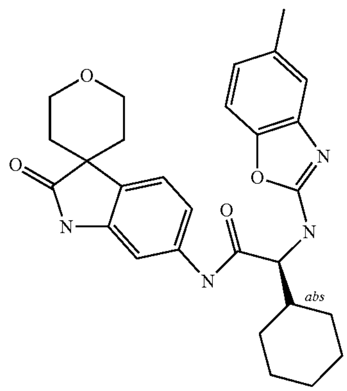 [SMILES: Cc1ccc2oc(N[C@H](C(=O)Nc3ccc4c(c3)NC(=O)C43CCOCC3)C3CCCCC3)nc2c1] | (2S)-2-Cyclohexyl-2-[(5-methyl-1,3-benzoxazol-2-yl)-amino]-N-(2-oxospiro[1H-indole-3,4'-oxane]-6-yl)-acetamide | 489.4 | 1.52 | 27 |
| 244 | 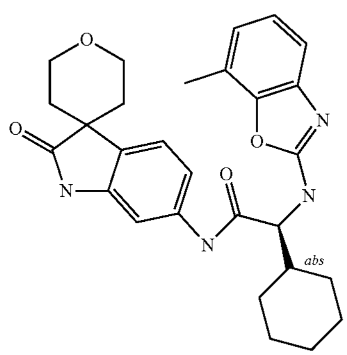 [SMILES: Cc1cccc2nc(N[C@H](C(=O)Nc3ccc4c(c3)NC(=O)C43CCOCC3)C3CCCCC3)oc12] | (2S)-2-Cyclohexyl-2-[(7-methyl-1,3-benzoxazol-2-yl)-amino]-N-(2-oxospiro[1H-indole-3,4'-oxane]-6-yl)-acetamide | 489.5 | 1.52 | 27 |
| 245 | 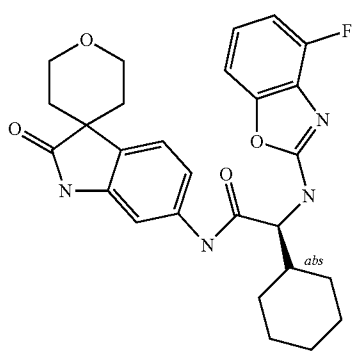 [SMILES: O=C(Nc1ccc2c(c1)NC(=O)C21CCOCC1)[C@@H](Nc1nc2c(F)cccc2o1)C1CCCCC1] | (2S)-2-Cyclohexyl-2-[(4-fluoro-1,3-benzoxazol-2-yl)amino]-N-(2-oxospiro[1H-indole-3,4'-oxane]-6-yl)acetamide | 493.4 | 1.47 | 27 |

| Ex. | Structure | Product | LCMS Mass | LCMS RT (min) | LCMS Method No. |
|---|---|---|---|---|---|
| 246 | 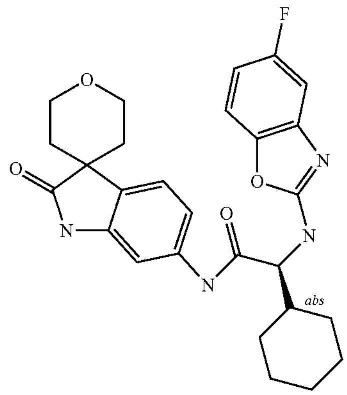 [SMILES: O=C(Nc1ccc2c(c1)NC(=O)C21CCOCC1)[C@@H](Nc1nc2cc(F)ccc2o1)C1CCCCC1] | (2S)-2-Cyclohexyl-2-[(5-fluoro-1,3-benzoxazol-2-yl)amino]-N-(2-oxospiro[1H-indole-3,4'-oxane]-6-yl)acetamide | 493.4 | 1.46 | 27 |

Selected ¹H NMR Data:

| Ex. | ¹H NMR Data |
|---|---|
| 242 | δ$_H$(400 MHz, DMSO-d$_6$) 10.38 (s, 1H), 10.10 (s, 1H), 7.45-7.38 (m, 2H), 7.16-7.01 (m, 2H), 6.82 (d, J 9.4 Hz, 1H), 6.61 (d, J 8.4 Hz, 1H), 5.21-5.07 (m, 1H), 4.43 (t, J 7.8 Hz, 1H), 4.01 (ddd, J 11.1, 7.1, 3.7 Hz, 2H), 3.80 (ddd, J 11.2, 7.0, 3.8 Hz, 2H), 1.93-1.81 (m, 1H), 1.79-1.55 (m, 9H), 1.39-1.08 (m, 11H). |

Examples 247 & 248

The title compounds were prepared in accordance with Procedure B from Intermediate 105 and the appropriate halogeno heterocycle.

| Ex. | Structure | Product | LCMS Mass | LCMS RT (min) | LCMS Method No. |
|---|---|---|---|---|---|
| 247 | 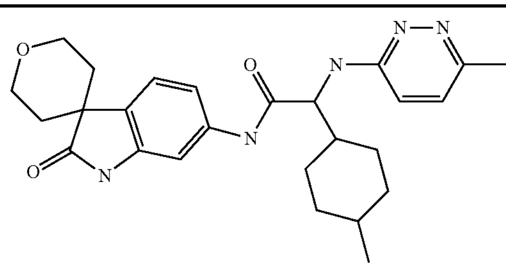 | 2-(4-Methylcyclohexyl)-2-[(6-methylpyridazin-3-yl)amino]-N-(2-oxospiro[1H-indole-3,4'-oxane]-6-yl)acetamide | 464.5 | 1.32 | 27 |
| 248 | 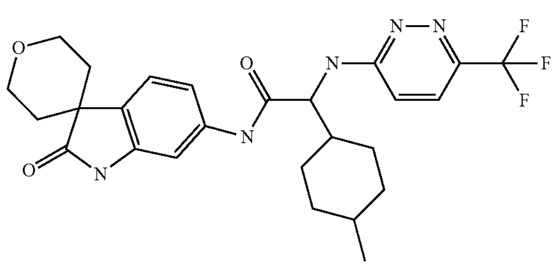 [SMILES: CC1CCC(C(Nc2ccc(C(F)(F)F)nn2)C(=O)Nc2ccc3c(c2)NC(=O)C32CCOCC2)CC1] | 2-(4-Methylcyclohexyl)-N-(2-oxospiro[1H-indole-3,4'-oxane]-6-yl)-2-{[6-(trifluoromethyl)pyridazin-3-yl]amino}acetamide | 518.5 | 1.55 | 27 |

Examples 249 to 263

The title compounds were prepared in accordance with Procedure A from Intermediate 35 and the appropriate carboxylic acid.

| Ex. | Structure | Product | LCMS Mass | LCMS RT (min) | LCMS Method No. |
|---|---|---|---|---|---|
| 249 | 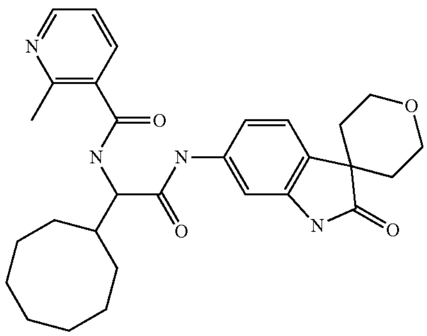 [SMILES: Cc1ncccc1C(=O)NC(C(=O)Nc1ccc2c(c1)NC(=O)C21CCOCC1)C1CCCCCCC1] | N-{1-Cyclooctyl-2-oxo-2-[(2-oxospiro[1H-indole-3,4'-oxane]-6-yl)amino]ethyl}-2-methyl-pyridine-3-carboxamide | 505.2 | 1.26 | 27 |
| 250 | 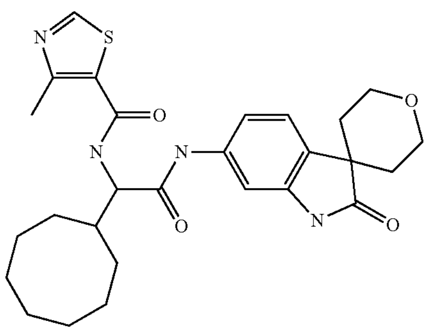 [SMILES: Cc1ncsc1C(=O)NC(C(=O)Nc1ccc2c(c1)NC(=O)C21CCOCC1)C1CCCCCCC1] | N-{1-Cyclooctyl-2-oxo-2-[(2-oxospiro[1H-indole-3,4'-oxane]-6-yl)amino]ethyl}-4-methyl-thiazole-5-carboxamide | 511.1 | 1.33 | 27 |
| 251 | 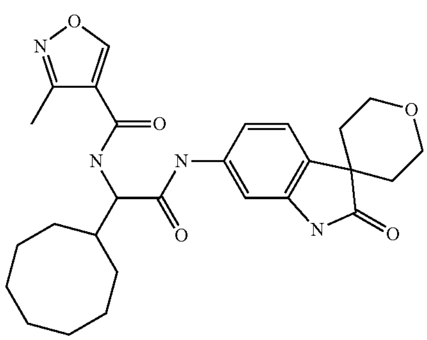 | N-{1-Cyclooctyl-2-oxo-2-[(2-oxospiro[1H-indole-3,4'-oxane]-6-yl)amino]ethyl}-3-methyl-isoxazole-4-carboxamide | 495.3 | 1.36 | 27 |
| 252 | 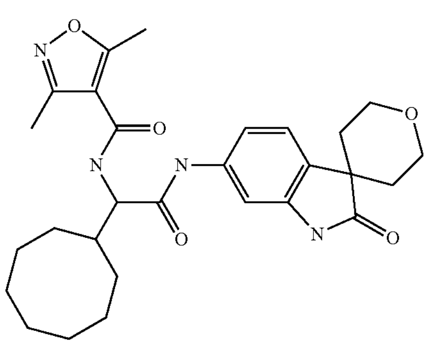 [SMILES: Cc1noc(C)c1C(=O)NC(C(=O)Nc1ccc2c(c1)NC(=O)C21CCOCC1)C1CCCCCCC1] | N-{1-Cyclooctyl-2-oxo-2-[(2-oxospiro[1H-indole-3,4'-oxane]-6-yl)amino]ethyl}-3,5-dimethyl-isoxazole-4-carboxamide | 509.2 | 1.39 | 27 |

| Ex. | Structure | Product | LCMS Mass | LCMS RT (min) | LCMS Method No. |
|---|---|---|---|---|---|
| 253 | 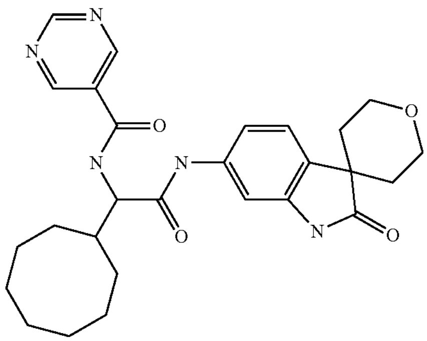 [SMILES: O=C(NC(C(=O)Nc1ccc2c(c1)NC(=O)C21CCOCC1)C1CCCCCCC1)c1cncnc1] | N-{1-Cyclooctyl-2-oxo-2-[(2-oxospiro[1H-indole-3,4'-oxane]-6-yl)amino]ethyl}pyrimidine-5-carboxamide | 492.5 | 1.29 | 27 |
| 254 | 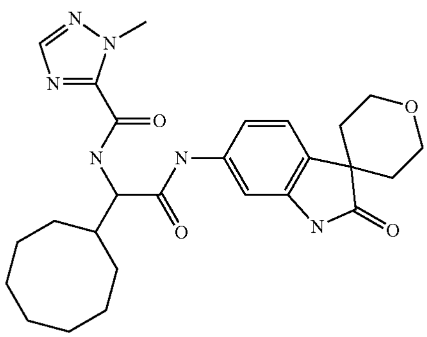 [SMILES: Cn1ncnc1C(=O)NC(C(=O)Nc1ccc2c(c1)NC(=O)C21CCOCC1)C1CCCCCCC1] | N-{1-Cyclooctyl-2-oxo-2-[(2-oxospiro[1H-indole-3,4'-oxane]-6-yl)amino]ethyl}-2-methyl-1,2,4-triazole-3-carboxamide | 495.2 | 1.38 | 27 |
| 255 | 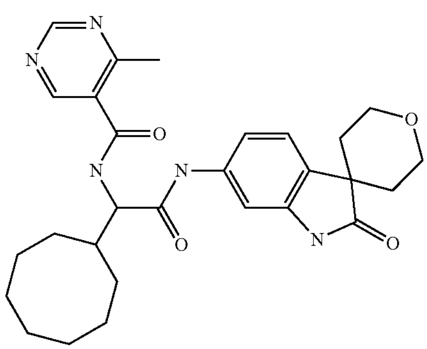 [SMILES: Cc1ncncc1C(=O)NC(C(=O)Nc1ccc2c(c1)NC(=O)C21CCOCC1)C1CCCCCCC1] | N-{1-Cyclooctyl-2-oxo-2-[(2-oxospiro[1H-indole-3,4'-oxane]-6-yl)amino]ethyl}-4-methyl-pyrimidine-5-carboxamide | 506.0 | 1.24 | 27 |
| 256 | 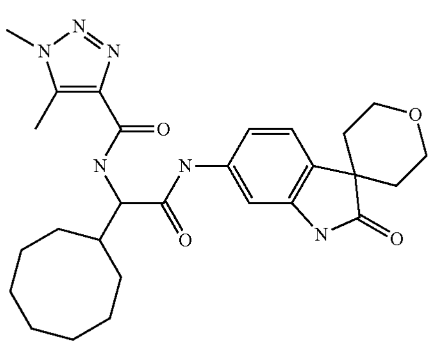 [SMILES: Cc1c(C(=O)NC(C(=O)Nc2ccc3c(c2)NC(=O)C32CCOCC2)C2CCCCCCC2)nnn1C] | N-{1-Cyclooctyl-2-oxo-2-[(2-oxospiro[1H-indole-3,4'-oxane]-6-yl)amino]ethyl}-1,5-dimethyl-1,2,3-triazole-4-carboxamide | 509.2 | 1.32 | 27 |

-continued

| Ex. | Structure | Product | LCMS Mass | LCMS RT (min) | LCMS Method No. |
|---|---|---|---|---|---|
| 257 | 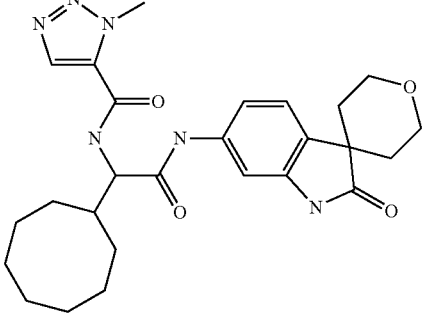 | N-{1-Cyclooctyl-2-oxo-2-[(2-oxospiro[1H-indole-3,4'-oxane]-6-yl)amino]ethyl}-3-methyl-1,2,3-triazole-4-carboxamide | 495.5 | 1.34 | 27 |
| 258 | 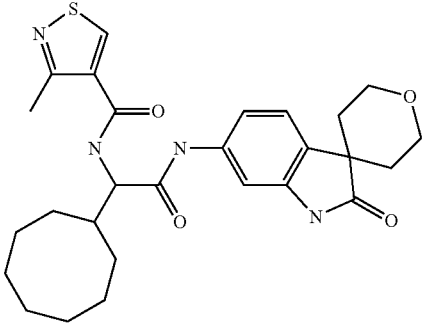 [SMILES: Cc1nscc1C(=O)NC(C(=O)Nc1ccc2c(c1)NC(=O)C21CCOCC1)C1CCCCCCC1] | N-{1-Cyclooctyl-2-oxo-2-[(2-oxospiro[1H-indole-3,4'-oxane]-6-yl)amino]ethyl}-3-methyl-isothiazole-4-carboxamide | 511.0 | 1.4 | 27 |
| 259 | 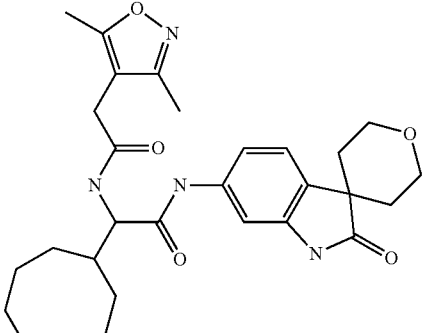 | 2-Cyclooctyl-2-{[2-(3,5-dimethylisoxazol-4-yl)acetyl]-amino}-N-(2-oxospiro[1H-indole-3,4'-oxane]-6-yl)-acetamide | 523.5 | 1.39 | 27 |
| 260 | 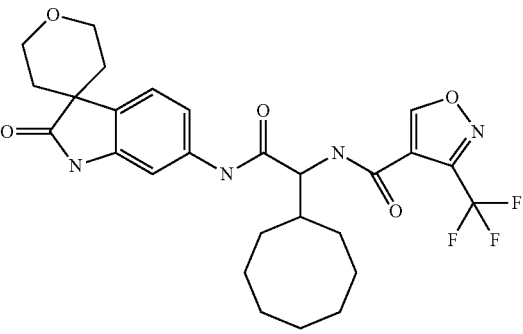 [SMILES: O=C(NC(C(=O)Nc1ccc2c(c1)NC(=O)C21CCOCC1)C1CCCCCCC1)c1conc1C(F)(F)F] | N-{1-Cyclooctyl-2-oxo-2-[(2-oxospiro[1H-indole-3,4'-oxane]-6-yl)amino]ethyl}-3-(trifluoro-methyl)isoxazole-4-carboxamide | 549.5 | 1.59 | 27 |

-continued

| Ex. | Structure | Product | LCMS Mass | LCMS RT (min) | LCMS Method No. |
|---|---|---|---|---|---|
| 261 | 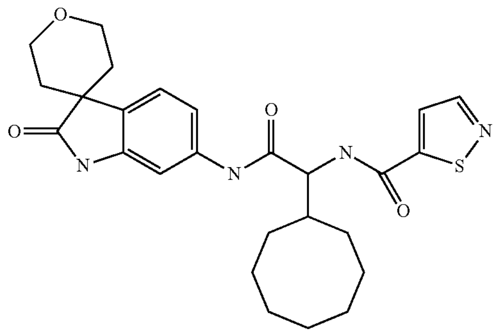 [SMILES: O=C(NC(C(=O)Nc1ccc2c(c1)NC(=O)C21CCOCC1)C1CCCCCCC1)c1ccns1] | N-{1-Cyclooctyl-2-oxo-2-[(2-oxospiro[1H-indole-3,4'-oxane]-6-yl)amino]ethyl}isothiazole-5-carboxamide | 497.5 | 1.45 | 27 |
| 262 | 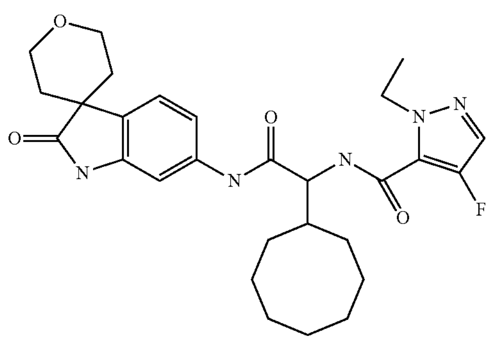 [SMILES: CCn1ncc(F)c1C(=O)NC(C(=O)Nc1ccc2c(c1)NC(=O)C21CCOCC1)C1CCCCCCC1] | N-{1-Cyclooctyl-2-oxo-2-[(2-oxospiro[1H-indole-3,4'-oxane]-6-yl)amino]ethyl}-2-ethyl-4-fluoropyrazole-3-carboxamide | 526.5 | 1.59 | 27 |
| 263 | 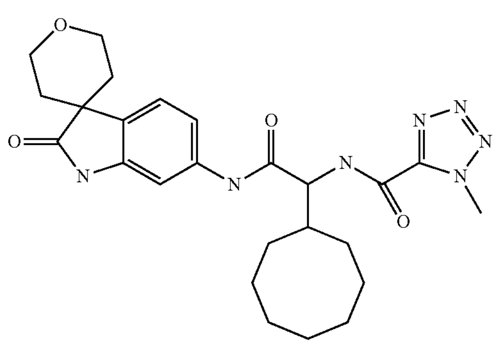 [SMILES: Cn1nnnc1C(=O)NC(C(=O)Nc1ccc2c(c1)NC(=O)C21CCOCC1)C1CCCCCCC1] | N-{1-Cyclooctyl-2-oxo-2-[(2-oxospiro[1H-indole-3,4'-oxane]-6-yl)amino]ethyl}-1-methyl-tetrazole-5-carboxamide | 496.5 | 1.43 | 27 |

Examples 264 & 265

The title compounds were prepared in accordance with Procedure D from Intermediate 35 and the appropriate carbamoyl chloride.

| Ex. | Structure | Product | LCMS Mass | LCMS RT (min) | LCMS Method No. |
|---|---|---|---|---|---|
| 264 | 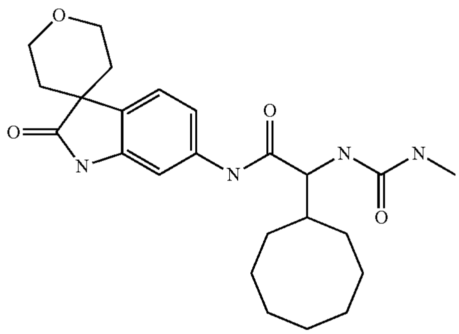 [SMILES: CNC(=O)NC(C(=O)Nc1ccc2c(c1)NC(=O)C21CCOCC1)C1CCCCCCC1] | 2-Cyclooctyl-2-(methyl-carbamoylamino)-N-(2-oxo-spiro[1H-indole-3,4'-oxane]-6-yl)acetamide | 443.3 | 1.19 | 27 |
| 265 | 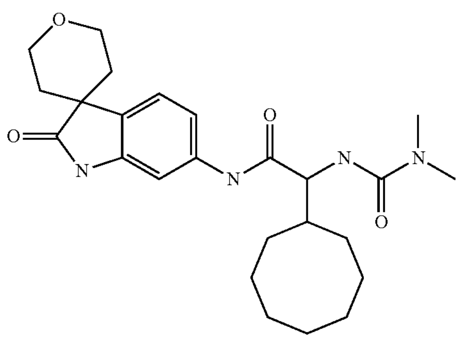 [SMILES: CN(C)C(=O)NC(C(=O)Nc1ccc2c(c1)NC(=O)C21CCOCC1)C1CCCCCCC1] | 2-Cyclooctyl-2-(dimethyl-carbamoylamino)-N-(2-oxo-spiro[1H-indole-3,4'-oxane]-6-yl)acetamide | 457.3 | 1.29 | 27 |

Examples 266 & 267

The title compounds were prepared in accordance with Procedure E from Intermediate 35 and the appropriate chloroformate.

| Ex. | Structure | Product | LCMS Mass | LCMS RT (min) | LCMS Method No. |
|---|---|---|---|---|---|
| 266 | 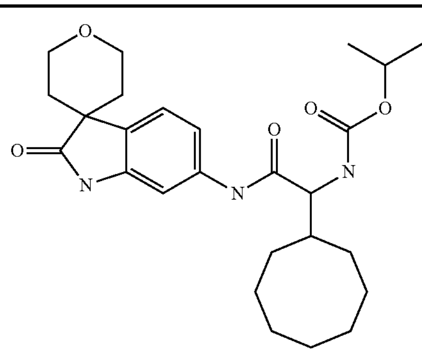 | Propan-2-yl N-{1-Cyclooctyl-2-oxo-2-[(2-oxospiro[1H-indole-3,4'-oxane]-6-yl)amino]ethyl}-carbamate | 472.5 | 1.54 | 27 |

-continued

| Ex. | Structure | Product | LCMS Mass | LCMS RT (min) | LCMS Method No. |
|---|---|---|---|---|---|
| 267 | 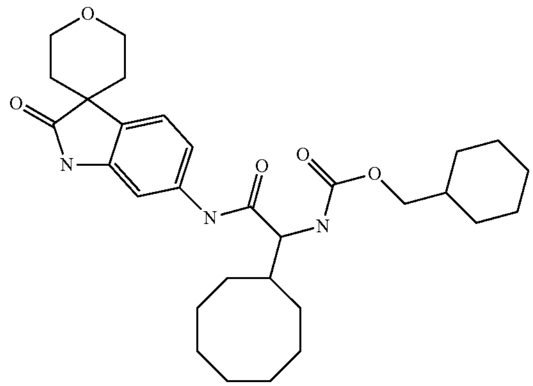 [SMILES: O=C(NC(C(=O)Nc1ccc2c(c1)NC(=O)C21CCOCC1)C1CCCCCCC1)OCC1CCCCC1] | Cyclohexylmethyl N-{1-cyclo-octyl-2-oxo-2-[(2-oxospiro[1H-indole-3,4'-oxane]-6-yl)amino]-ethyl}carbamate | 526.6 | 1.82 | 27 |

Examples 268 to 282

The title compounds were prepared in accordance with Procedure B from Intermediate 35 and the appropriate halogeno heterocycle.

| Ex. | Structure | Product | LCMS Mass | LCMS RT (min) | LCMS Method No. |
|---|---|---|---|---|---|
| 268 | 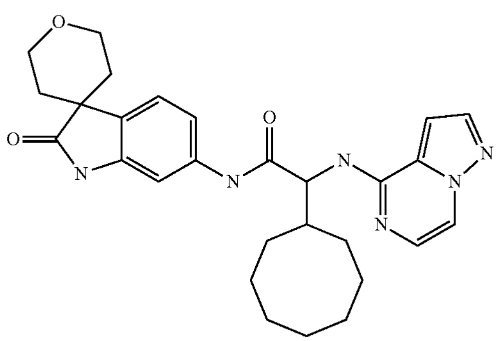 [SMILES: O=C(Nc1ccc2c(c1)NC(=O)C21CCOCC1)C(Nc1nccn2nccc12)C1CCCCCCC1] | 2-Cyclooctyl-N-(2-oxospiro[1H-indole-3,4'-oxane]-6-yl)-2-(pyrazolo[1,5-a]pyrazin-4-yl-amino)acetamide | 503.1 | 1.4 | 27 |
| 269 | 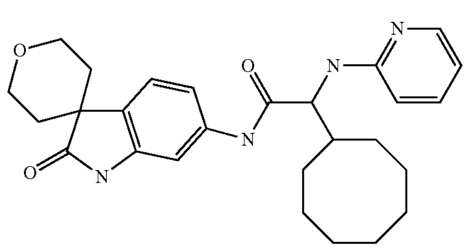 [SMILES: O=C(Nc1ccc2c(c1)NC(=O)C21CCOCC1)C(Nc1ccccn1)C1CCCCCCC1] | 2-Cyclooctyl-N-(2-oxospiro[1H-indole-3,4'-oxane]-6-yl)-2-(pyridin-2-ylamino)acetamide | 463.4 | 1.53 | 27 |

-continued

| Ex. | Structure | Product | LCMS Mass | LCMS RT (min) | LCMS Method No. |
|---|---|---|---|---|---|
| 270 | 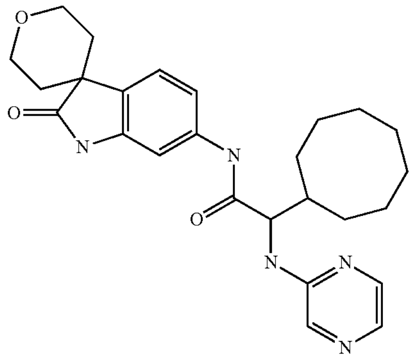 [SMILES: O=C(Nc1ccc2c(c1)NC(=O)C21CCOCC1)C(Nc1cnccn1)C1CCCCCCC1] | 2-Cyclooctyl-N-(2-oxospiro[1H-indole-3,4'-oxane]-6-yl)-2-(pyrazin-2-ylamino)acetamide | 464.5 | 1.4 | 27 |
| 271 | 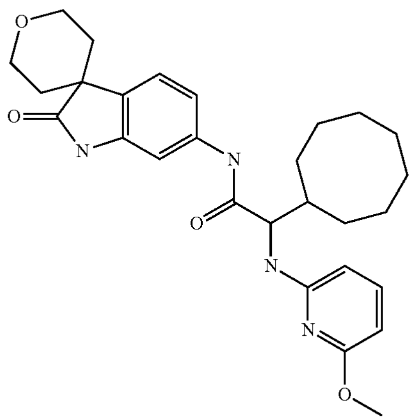 [SMILES: COc1cccc(NC(C(=O)Nc2ccc3c(c2)NC(=O)C32CCOCC2)C2CCCCCCC2)n1] | 2-Cyclooctyl-2-[(6-methoxy-pyridin-2-yl)amino]-N-(2-oxo-spiro[1H-indole-3,4'-oxane]-6-yl)acetamide | 493.5 | 1.65 | 27 |
| 272 | 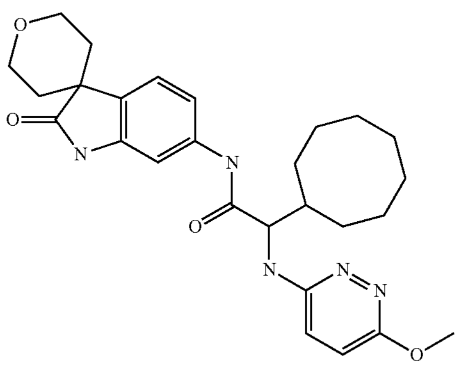 [SMILES: COc1ccc(NC(C(=O)Nc2ccc3c(c2)NC(=O)C32CCOCC2)C2CCCCCCC2)nn1] | 2-Cyclooctyl-2-[(6-methoxy-pyridazin-3-yl)amino]-N-(2-oxospiro[1H-indole-3,4'-oxane]-6-yl)acetamide | 494.5 | 1.44 | 27 |
| 273 | 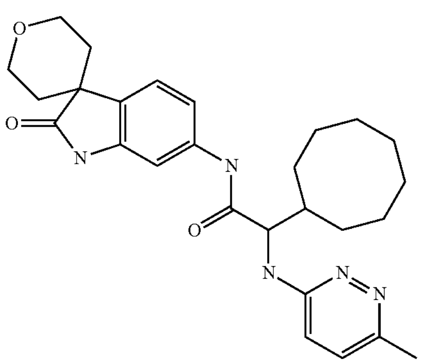 [SMILES: Cc1ccc(NC(C(=O)Nc2ccc3c(c2)NC(=O)C32CCOCC2)C2CCCCCCC2)nn1] | 2-Cyclooctyl-2-[(6-methyl-pyridazin-3-yl)amino]-N-(2-oxospiro[1H-indole-3,4'-oxane]-6-yl)acetamide | 476.0 | 1.70 | 27 |

-continued

| Ex. | Structure | Product | LCMS Mass | LCMS RT (min) | LCMS Method No. |
|---|---|---|---|---|---|
| 274 | 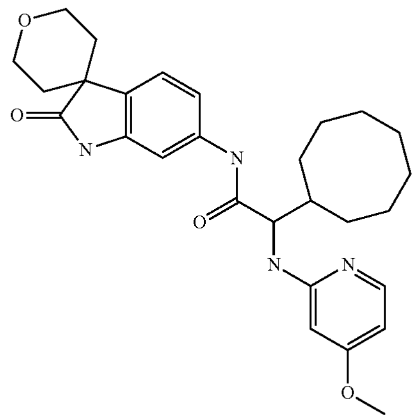 [SMILES: COc1ccnc(NC(C(=O)Nc2ccc3c(c2)NC(=O)C32CCOCC2)C2CCCCCCC2)c1] | 2-Cyclooctyl-2-[(4-methoxy-pyridin-2-yl)amino]-N-(2-oxo-spiro[1H-indole-3,4'-oxane]-6-yl)acetamide | 493.5 | 1.55 | 27 |
| 275 | 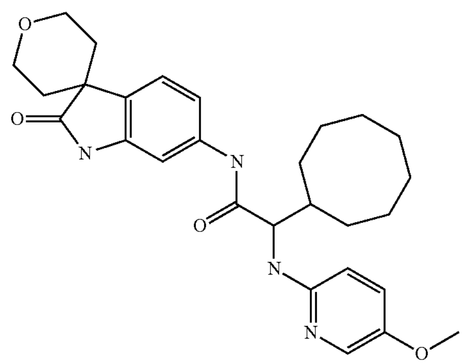 [SMILES: COc1ccc(NC(C(=O)Nc2ccc3c(c2)NC(=O)C32CCOCC2)C2CCCCCCC2)nc1] | 2-Cyclooctyl-2-[(5-methoxy-pyridin-2-yl)amino]-N-(2-oxo-spiro[1H-indole-3,4'-oxane]-6-yl)acetamide | 493.5 | 1.56 | 27 |
| 276 | 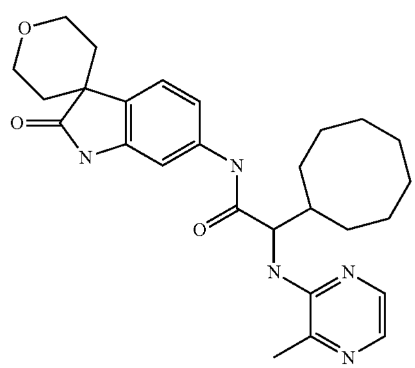 [SMILES: Cc1nccnc1NC(C(=O)Nc1ccc2c(c1)NC(=O)C21CCOCC1)C1CCCCCCC1] | 2-Cyclooctyl-2-[(3-methyl-pyrazin-2-yl)amino]-N-(2-oxo spiro[1H-indole-3,4'-oxane]-6-yl)acetamide | 478.5 | 1.49 | 27 |
| 277 | 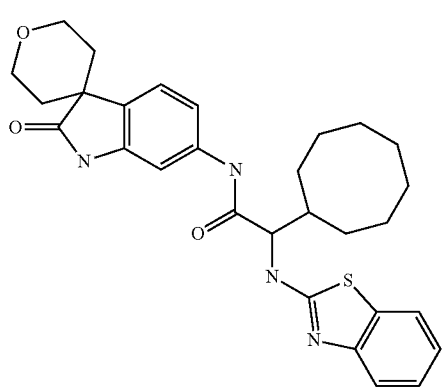 [SMILES: O=C(Nc1ccc2c(c1)NC(=O)C21CCOCC1)C(Nc1nc2ccccc2s1)C1CCCCCCC1] | 2-(1,3-Benzothiazol-2-ylamino)-2-cyclooctyl-N-(2-oxospiro[1H-indole-3,4'-oxane]-6-yl)-acetamide | 519.5 | 1.67 | 27 |

-continued

| Ex. | Structure | Product | LCMS Mass | LCMS RT (min) | LCMS Method No. |
|---|---|---|---|---|---|
| 278 | 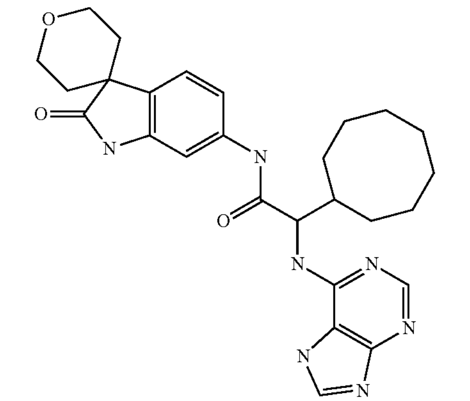 [SMILES: O=C(Nc1ccc2c(c1)NC(=O)C21CCOCC1)C(Nc1ncnc2nc[nH]c12)C1CCCCCCC1] | 2-Cyclooctyl-N-(2-oxospiro[1H-indole-3,4'-oxane]-6-yl)-2-(7H-purin-6-ylamino)acetamide | 504.5 | 1.26 | 27 |
| 279 | 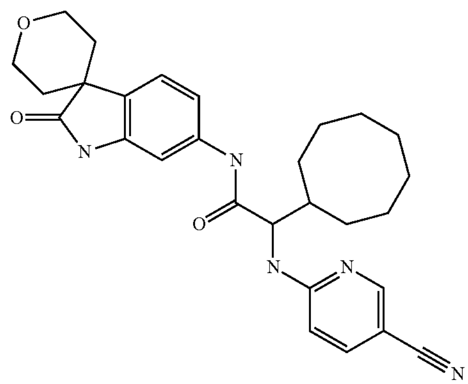 [SMILES: N#Cc1ccc(NC(C(=O)Nc2ccc3c(c2)NC(=O)C32CCOCC2)C2CCCCCCC2)nc1] | 2-[(5-Cyanopyridin-2-yl)-amino]-2-cyclooctyl-N-(2-oxo-spiro[1H-indole-3,4'-oxane]-6-yl)acetamide | 488.5 | 1.53 | 27 |
| 280 | 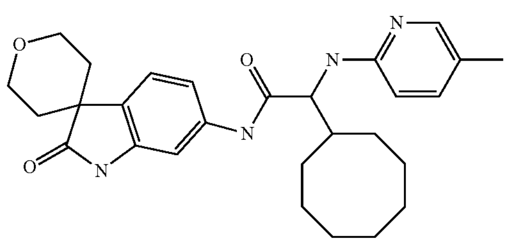 [SMILES: Cc1ccc(NC(C(=O)Nc2ccc3c(c2)NC(=O)C32CCOCC2)C2CCCCCCC2)nc1] | 2-Cyclooctyl-2-[(5-methyl-pyridin-2-yl)amino]-N-(2-oxo-spiro[1H-indole-3,4'-oxane]-6-yl)acetamide | 477.5 | 1.62 | 27 |
| 281 | 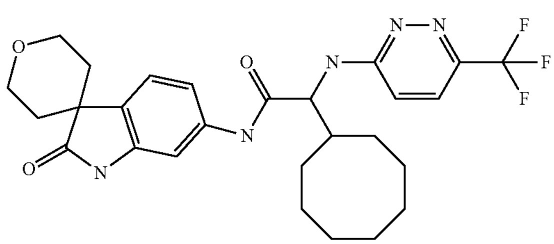 [SMILES: O=C(Nc1ccc2c(c1)NC(=O)C21CCOCC1)C(Nc1ccc(C(F)(F)F)nn1)C1CCCCCCC1] | 2-Cyclooctyl-N-(2-oxospiro[1H-indole-3,4'-oxane]-6-yl)-2-{[6-(trifluoromethyl)pyridazin-3-yl]amino}acetamide | 530.0 | 2.35 | 21 |
| 282 | 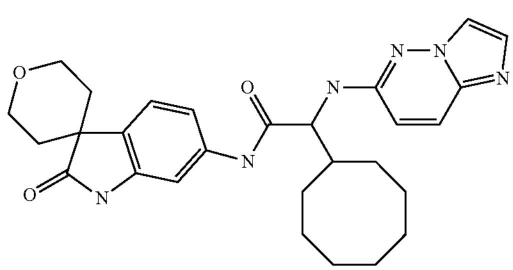 [SMILES: O=C(Nc1ccc2c(c1)NC(=O)C21CCOCC1)C(Nc1ccc2nccn2n1)C1CCCCCCC1] | 2-Cyclooctyl-2-(imidazo[1,2-b]-pyridazin-6-ylamino)-N-(2-oxo-spiro[1H-indole-3,4'-oxane]-6-yl)acetamide | 503.5 | 1.39 | 27 |

Selected ¹H NMR Data:

| Ex. | ¹H NMR Data |
|---|---|
| 273 | $\delta_H$ (400 MHz, DMSO-$d_6$) 10.37 (s, 1H), 10.18 (s, 1H), 7.45-7.35 (m, 2H), 7.16-7.07 (m, 2H), 6.93 (d, J 9.1 Hz, 1H), 6.77 (d, J 8.7 Hz, 1H), 4.64-4.55 (m, 1H), 4.01 (ddd, J 11.2, 7.2, 3.7 Hz, 2H), 3.80 (ddd, J 11.2, 7.1, 3.8 Hz, 2H), 2.35 (s, 3H), 2.07 (m, 1H), 1.80-1.29 (m, 18H). |
| 281 | $\delta_H$ (400 MHz, DMSO-$d_6$) 10.39 (s, 1H), 10.31 (s, 1H), 7.81 (d, J 8.4 Hz, 1H), 7.68 (d, J 9.4 Hz, 1H), 7.52-7.35 (m, 2H), 7.22-7.08 (m, 2H), 4.74 (s, 1H), 4.01 (ddd, J 11.0, 7.1, 3.7 Hz, 2H), 3.80 (ddd, J 11.3, 7.2, 3.8 Hz, 2H), 2.19-2.05 (m, 1H), 1.78-1.34 (m, 18H). |

Example 283

The title compound was prepared from Example 203 in accordance with a procedure analogous to that described for the preparation of Example 12.

| Ex. | Structure | Product | LCMS Mass | LCMS RT (min) | LCMS Method No. |
|---|---|---|---|---|---|
| 283 | 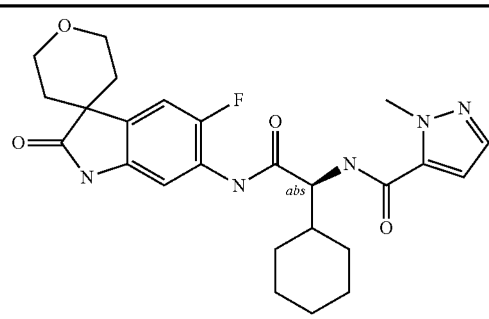 | N-{(1S)-1-Cyclohexyl-2-[(5-fluoro-2-oxospiro[1H-indole-3,4'-oxane]-6-yl)amino]-2-oxo-ethyl}-2-methylpyrazole-3-carboxamide | 484.4 | 1.25 | 27 |

Examples 284 to 286

The title compounds were prepared in accordance with Procedure A from Intermediate 151 and the appropriate carboxylic acid.

| Ex. | Structure | Product | LCMS Mass | LCMS RT (min) | LCMS Method No. |
|---|---|---|---|---|---|
| 284 | 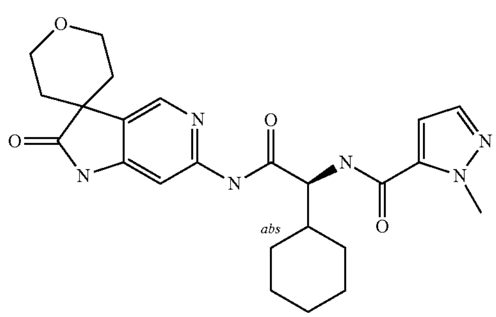 [SMILES: Cn1nccc1C(=O)N[C@H](C(=O)Nc1cc2c(cn1)C1(CCOCC1)C(=O)N2)C1CCCCC1] | N-{(1S)-1-Cyclohexyl-2-oxo-2-[(2-oxospiro[1H-pyrrolo[3,2-c]-pyridine-3,4'-oxane]-6-yl)-amino]ethyl}-2-methylpyrazole-3-carboxamide | 467.4 | 1.16 | 27 |

| Ex. | Structure | Product | LCMS Mass | LCMS RT (min) | LCMS Method No. |
|---|---|---|---|---|---|
| 285 | 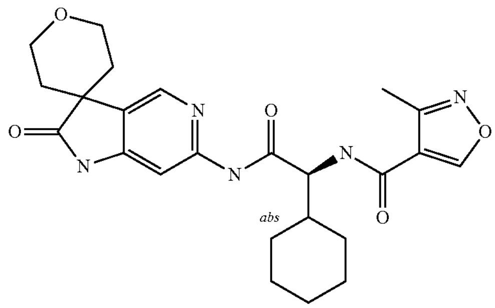 [SMILES: Cc1nocc1C(=O)N[C@H](C(=O)Nc1cc2c(cn1)C1(CCOCC1)C(=O)N2)C1CCCCC1] | N-{(1S)-1-Cyclohexyl-2-oxo-2-[(2-oxospiro[1H-pyrrolo[3,2-c]-pyridine-3,4'-oxane]-6-yl)-amino]ethyl}-3-methyl-isoxazole-4-carboxamide | 468.4 | 1.18 | 27 |
| 286 | 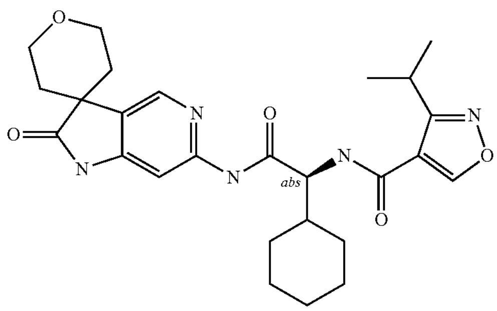 [SMILES: CC(C)c1nocc1C(=O)N[C@H](C(=O)Nc1cc2c(cn1)C1(CCOCC1)C(=O)N2)C1CCCCC1] | N-{(1S)-1-Cyclohexyl-2-oxo-2-[(2-oxospiro[1H-pyrrolo[3,2-c]-pyridine-3,4'-oxane]-6-yl)-amino]ethyl}-3-(propan-2-yl)-isoxazole-4-carboxamide | 496.4 | 1.35 | 27 |

Example 287

The title compound was prepared in accordance with Procedure D from Intermediate 151 and the appropriate carbamoyl chloride.

| Ex. | Structure | Product | LCMS Mass | LCMS RT (min) | LCMS Method No. |
|---|---|---|---|---|---|
| 287 | 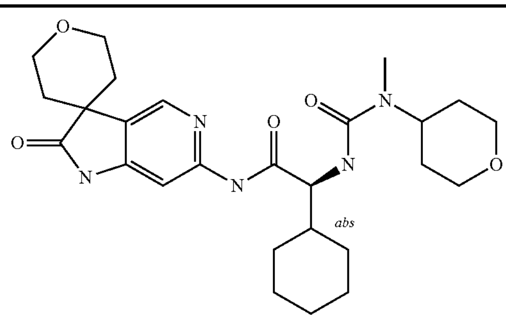 | (2S)-2-Cyclohexyl-2-{[methyl-(oxan-4-yl)carbamoyl]amino}-N-(2-oxospiro[1H-pyrrolo[3,2-c]pyridine-3,4'-oxane]-6-yl)-acetamide | 500.5 | 1.15 | 27 |

Examples 288 to 336

The title compounds were prepared by a two-step sequence:
  Step 1: reaction of Intermediate 107 with the appropriate carboxylic acid in accordance with Procedure A.
  Step 2: reaction of the material thereby obtained in accordance with Procedure C.

| Ex. | Structure | Product | LCMS Mass | LCMS RT (min) | LCMS Method No. |
|---|---|---|---|---|---|
| 288 | 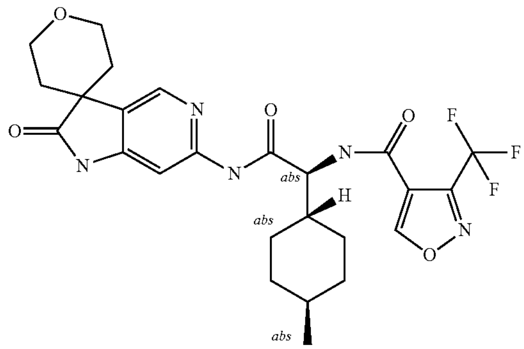 [SMILES: C[C@H]1CC[C@H]([C@H](NC(=O)c2conc2C(F)(F)F)C(=O)Nc2cc3c(cn2)C2(CCOCC2)C(=O)N3)CC1] | N-{(1S)-1-(4-Methylcyclo-hexyl)-2-oxo-2-[(2-oxospiro-[1H-pyrrolo[3,2-c]pyridine-3,4'-oxane]-6-yl)amino]ethyl}-3-(trifluoromethyl)isoxazole-4-carboxamide (trans isomer) | 536.4 | 1.46 | 27 |
| 289 | 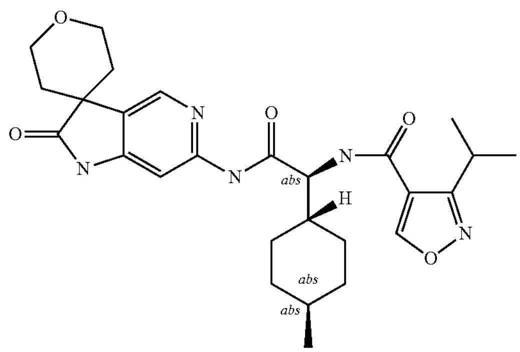 [SMILES: CC(C)c1nocc1C(=O)N[C@H](C(=O)Nc1cc2c(cn1)C1(CCOCC1)C(=O)N2)[C@H]1CC[C@H](C)CC1] | N-{(1S)-1-(4-Methylcyclo-hexyl)-2-oxo-2-[(2-oxospiro-[1H-pyrrolo[3,2-c]pyridine-3,4'-oxane]-6-yl)amino]ethyl}-3-(propan-2-yl)isoxazole-4-carboxamide (trans isomer) | 510.0 | 2.33 | 6 |
| 290 | 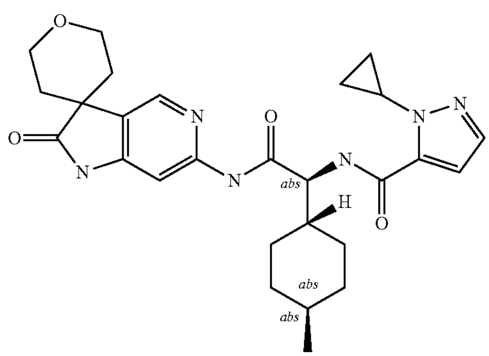 [SMILES: C[C@H]1CC[C@H]([C@H](NC(=O)c2ccnn2C2CC2)C(=O)Nc2cc3c(cn2)C2(CCOCC2)C(=O)N3)CC1] | 2-Cyclopropyl-N-{(1S)-1-(4-methylcyclohexyl)-2-oxo-2-[(2-oxospiro[1H-pyrrolo[3,2-c]-pyridine-3,4'-oxane]-6-yl)-amino]ethyl}pyrazole-3-carboxamide (trans isomer) | 507.5 | 1.38 | 27 |
| 291 | 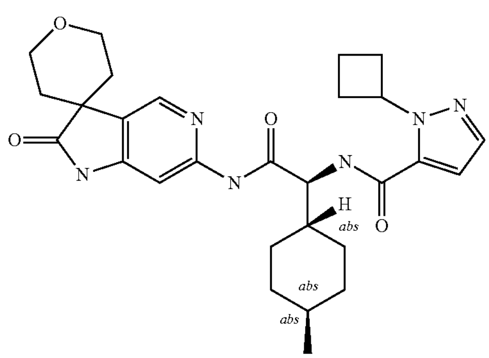 [SMILES: C[C@H]1CC[C@H]([C@H](NC(=O)c2ccnn2C2CCC2)C(=O)Nc2cc3c(cn2)C2(CCOCC2)C(=O)N3)CC1] | 2-Cyclobutyl-N-{(1S)-1-(4-methylcyclohexyl)-2-oxo-2-[(2-oxospiro[1H-pyrrolo[3,2-c]-pyridine-3,4'-oxane]-6-yl)-amino]ethyl}pyrazole-3-carboxamide (trans isomer) | 521.5 | 1.48 | 27 |

-continued

| Ex. | Structure | Product | LCMS Mass | LCMS RT (min) | LCMS Method No. |
|---|---|---|---|---|---|
| 292 | 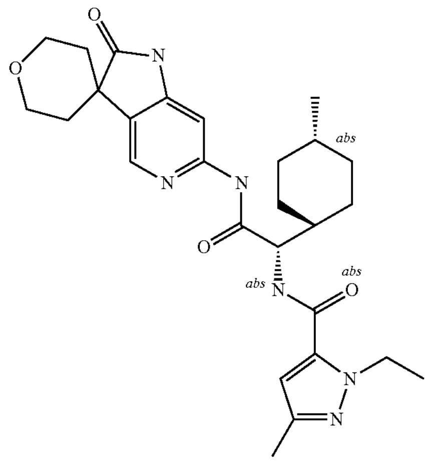 [SMILES: CCn1nc(C)cc1C(=O)N[C@H](C(=O)Nc1cc2c(cn1)C1(CCOCC1)C(=O)N2)[C@H]1CC[C@@H](C)CC1] | 2-Ethyl-5-methyl-N-{(1S)-1-(4-methylcyclohexyl)-2-oxo-2-[(2-oxospiro[1H-pyrrolo[3,2-c]-pyridine-3,4'-oxane]-6-yl)-amino]ethyl}pyrazole-3-carboxamide (trans isomer) | 509.5 | 1.39 | 27 |
| 293 | 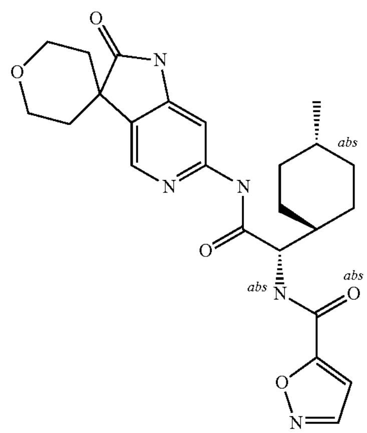 [SMILES: C[C@H]1CC[C@@H]([C@H](NC(=O)c2ccno2)C(=O)Nc2cc3c(cn2)C2(CCOCC2)C(=O)N3)CC1] | N-{(1S)-1-(4-Methylcyclohexyl)-2-oxo-2-[(2-oxospiro-[1H-pyrrolo[3,2-c]pyridine-3,4'-oxane]-6-yl)amino]ethyl}-1,2-oxazole-5-carboxamide (trans isomer) | 468.4 | 1.26 | 27 |
| 294 | 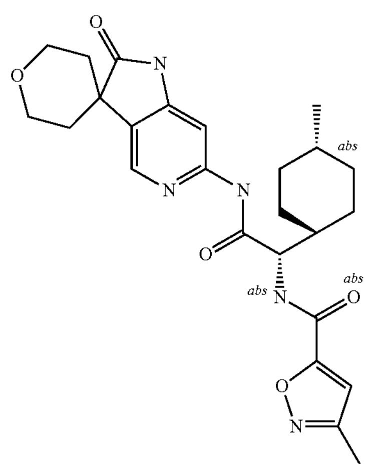 [SMILES: Cc1cc(C(=O)N[C@H](C(=O)Nc2cc3c(cn2)C2(CCOCC2)C(=O)N3)[C@H]2CC[C@@H](C)CC2)on1] | 3-Methyl-N-{(1S)-1-(4-methyl-cyclohexyl)-2-oxo-2-[(2-oxo-spiro[1H-pyrrolo[3,2-c]pyridine-3,4,-oxane]-6-yl)amino]ethyl}-isoxazole-5-carboxamide (trans isomer) | 482.4 | 1.31 | 27 |

-continued

| Ex. | Structure | Product | LCMS Mass | LCMS RT (min) | LCMS Method No. |
|---|---|---|---|---|---|
| 295 | 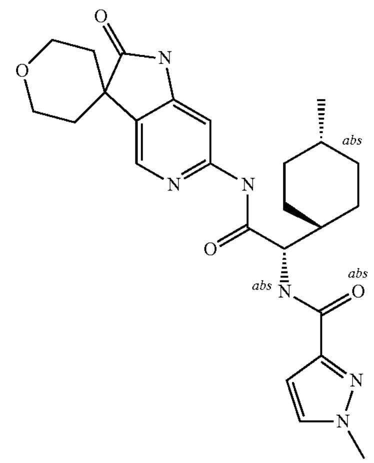 [SMILES: Cn1ccc(C(=O)N[C@H](C(=O)Nc2cc3c(cn2)C2(CCOCC2)C(=O)N3)[C@H]2CC[C@@H](C)CC2)n1] | 1-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-pyrazole-3-carboxamide (trans isomer) | 481.4 | 1.27 | 27 |
| 296 | 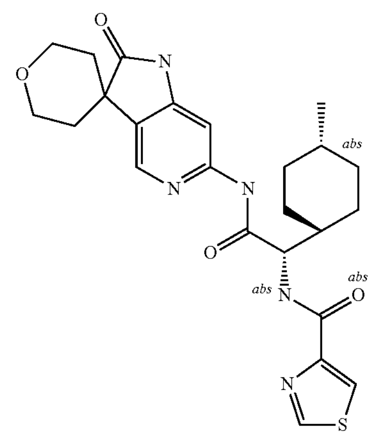 [SMILES: C[C@H]1CC[C@@H]([C@H](NC(=O)c2cscn2)C(=O)Nc2cc3c(cn2)C2(CCOCC2)C(=O)N3)CC1] | N-{(1S)-1-(4-Methylcyclo-hexyl)-2-oxo-2-[(2-oxospiro-[1H-pyrrolo[3,2-c]pyridine-3,4'-oxane]-6-yl)amino]ethyl}-thiazole-4-carboxamide (trans isomer) | 484.4 | 1.31 | 27 |
| 297 | 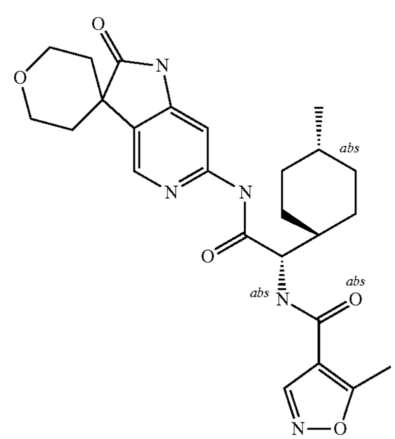 [SMILES: Cc1oncc1C(=O)N[C@H](C(=O)Nc1cc2c(cn1)C1(CCOCC1)C(=O)N2)[C@H]1CC[C@@H](C)CC1] | 5-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-isoxazole-4-carboxamide (trans isomer) | 482.4 | 1.3 | 27 |

-continued

| Ex. | Structure | Product | LCMS Mass | LCMS RT (min) | LCMS Method No. |
|---|---|---|---|---|---|
| 298 | 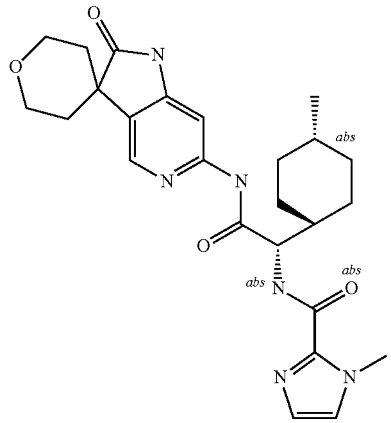 [SMILES: Cn1ccnc1C(=O)N[C@H](C(=O)Nc1cc2c(cn1)C1(CCOCC1)C(=O)N2)[C@H]1CC[C@@H](C)CC1] | 1-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-imidazole-2-carboxamide (trans isomer) | 481.4 | 1.3 | 27 |
| 299 | 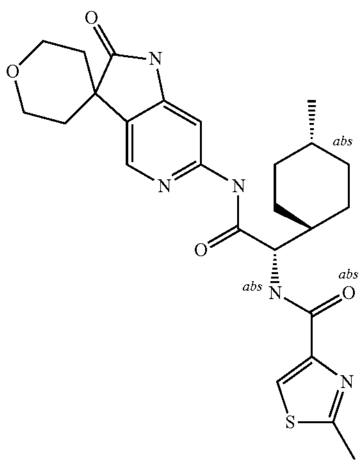 [SMILES: Cc1nc(C(=O)N[C@H](C(=O)Nc2cc3c(cn2)C2(CCOCC2)C(=O)N3)[C@H]2CC[C@@H](C)CC2)cs1] | 2-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-thiazole-4-carboxamide (trans isomer) | 498.4 | 1.41 | 27 |
| 300 | 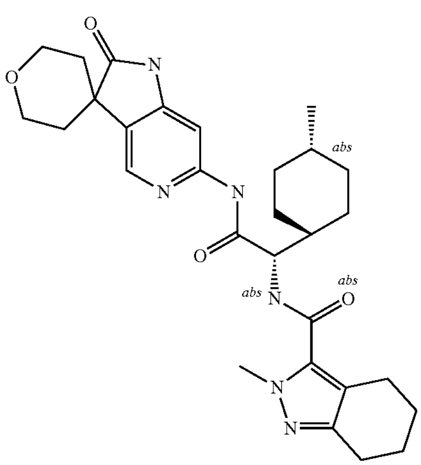 [SMILES: Cn1nc2c(c1C(=O)N[C@H](C(=O)Nc1cc3c(cn1)C1(CCOCC1)C(=O)N3)[C@H]1CC[C@@H](C)CC1)CCCC2] | 2-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-4,5,6,7-tetrahydroindazole-3-carboxamide (trans isomer) | 535.6 | 1.48 | 27 |

-continued

| Ex. | Structure | Product | LCMS Mass | LCMS RT (min) | LCMS Method No. |
|---|---|---|---|---|---|
| 301 | 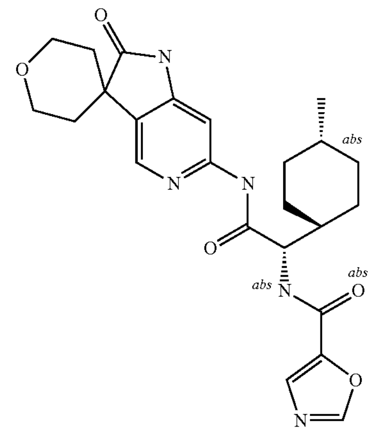 [SMILES: C[C@H]1CC[C@@H]([C@H](NC(=O)c2cnco2)C(=O)Nc2cc3c(cn2)C2(CCOCC2)C(=O)N3)CC1] | N-{(1S)-1-(4-Methylcyclohexyl)-2-oxo-2-[(2-oxospiro-[1H-pyrrolo[3,2-c]pyridine-3,4'-oxane]-6-yl)amino]ethyl}-oxazole-5-carboxamide (trans isomer) | 468.4 | 1.18 | 27 |
| 302 | 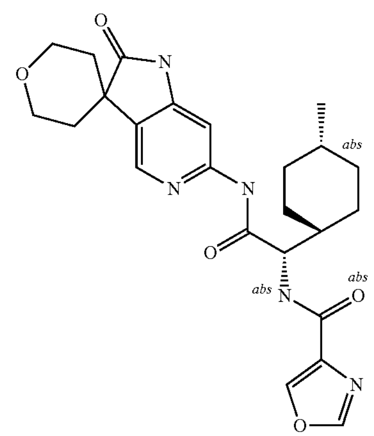 [SMILES: C[C@H]1CC[C@@H]([C@H](NC(=O)c2cocn2)C(=O)Nc2cc3c(cn2)C2(CCOCC2)C(=O)N3)CC1] | N-{(1S)-1-(4-Methylcyclohexyl)-2-oxo-2-[(2-oxospiro-[1H-pyrrolo[3,2-c]pyridine-3,4'-oxane]-6-yl)amino]ethyl}-oxazole-4-carboxamide (trans isomer) | 468.4 | 1.24 | 27 |
| 303 | 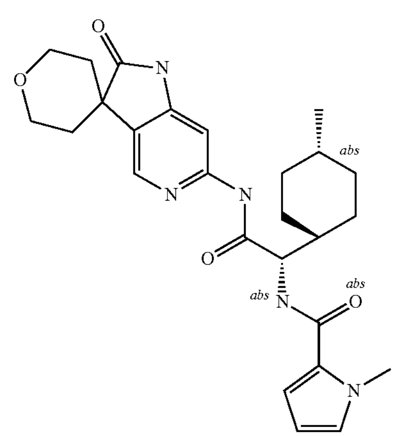 [SMILES: Cn1cccc1C(=O)N[C@H](C(=O)Nc1cc2c(cn1)C1(CCOCC1)C(=O)N2)[C@H]1CC[C@@H](C)CC1] | 1-Methyl-N-{(1S)-1-(4-methylcyclohexyl)-2-oxo-2-[(2-oxospiro[1H-pyrrolo[3,2-c]pyridine-3,4'-oxane]-6-yl)amino]ethyl}-pyrrole-2-carboxamide (trans isomer) | 480.4 | 1.41 | 27 |

-continued

| Ex. | Structure | Product | LCMS Mass | LCMS RT (min) | LCMS Method No. |
|---|---|---|---|---|---|
| 304 | 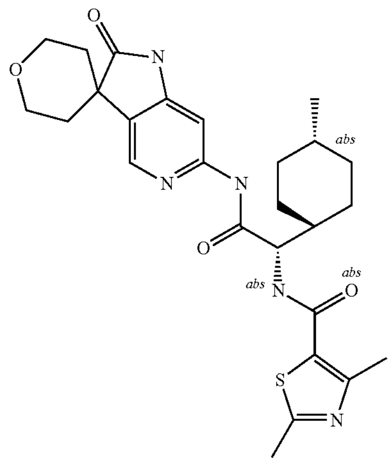 [SMILES: Cc1nc(C)c(C(=O)N[C@H](C(=O)Nc2cc3c(cn2)C2(CCOCC2)C(=O)N3)[C@H]2CC[C@@H](C)CC2)s1] | 2,4-Dimethyl-N-{(1S)-1-(4-methylcyclohexyl)-2-oxo-2-[(2-oxospiro[1H-pyrrolo[3,2-c]-pyridine-3,4'-oxane]-6-yl)-amino]ethyl}thiazole-5-carboxamide (trans isomer) | 512.4 | 1.32 | 27 |
| 305 | 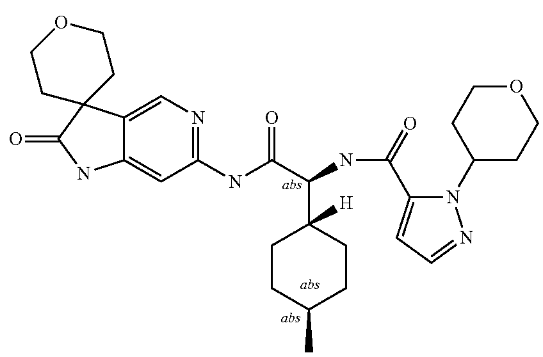 [SMILES: C[C@H]1CC[C@H]([C@H](NC(=O)c2ccnn2C2CCOCC2)C(=O)Nc2cc3c(cn2)C2(CCOCC2)C(=O)N3)CC1] | N-{(1S)-1-(4-Methylcyclohexyl)-2-oxo-2-[(2-oxospiro-[1H-pyrrolo[3,2-c]pyridine-3,4'-oxane]-6-yl)amino]ethyl}-2-(oxan-4-yl)pyrazole-3-carboxamide (trans isomer) | 551.5 | 1.34 | 27 |
| 306 | 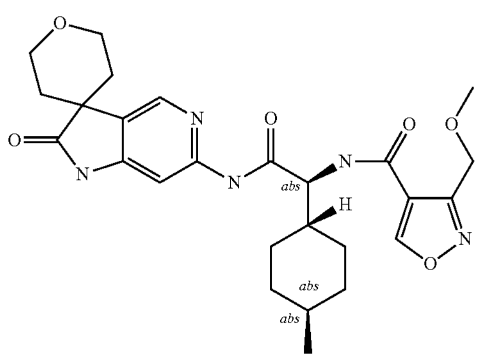 [SMILES: COCc1nocc1C(=O)N[C@H](C(=O)Nc1cc2c(cn1)C1(CCOCC1)C(=O)N2)[C@H]1CC[C@H](C)CC1] | 3-(Methoxymethyl)-N-{(1S)-1-(4-methylcyclohexyl)-2-oxo-2-[(2-oxospiro[1H-pyrrolo[3,2-c]-pyridine-3,4'-oxane]-6-yl)-amino]ethyl}-1,2-oxazole-4-carboxamide (trans isomer) | 512.4 | 1.35 | 27 |
| 307 | 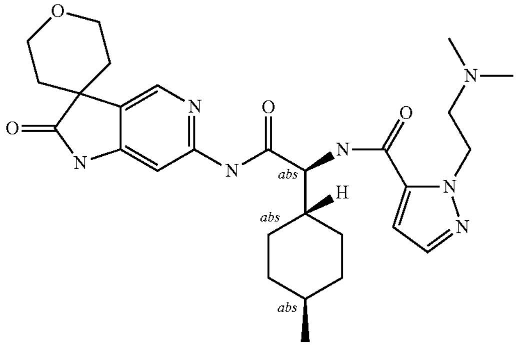 [SMILES: CN(C)CCn1nccc1C(=O)N[C@H](C(=O)Nc1cc2c(cn1)C1(CCOCC1)C(=O)N2)[C@H]1CC[C@H](C)CC1] | 2-[2-(Dimethylamino)ethyl]-N-{(1S)-1-(4-methylcyclohexyl)-2-oxo-2-[(2-oxospiro[1H-pyrrolo-[3,2-c]pyridine-3,4'-oxane]-6-yl)amino]ethyl}pyrazole-3-carboxamide (trans isomer) | 538.5 | 1.27 | 27 |

-continued

| Ex. | Structure | Product | LCMS Mass | LCMS RT (min) | LCMS Method No. |
|---|---|---|---|---|---|
| 308 | 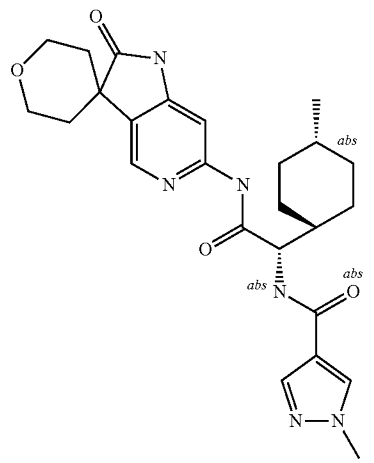 [SMILES: Cn1cc(C(=O)N[C@H](C(=O)Nc2cc3c(cn2)C2(CCOCC2)C(=O)N3)[C@H]2CC[C@@H](C)CC2)cn1] | 1-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-pyrazole-4-carboxamide (trans isomer) | 481.4 | 1.19 | 27 |
| 309 | 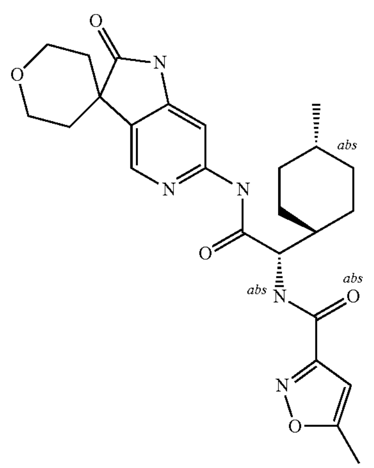 [SMILES: Cc1cc(C(=O)N[C@H](C(=O)Nc2cc3c(cn2)C2(CCOCC2)C(=O)N3)[C@H]2CC[C@@H](C)CC2)no1] | 5-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-isoxazole-3-carboxamide (trans isomer) | 482.4 | 1.41 | 27 |
| 310 | 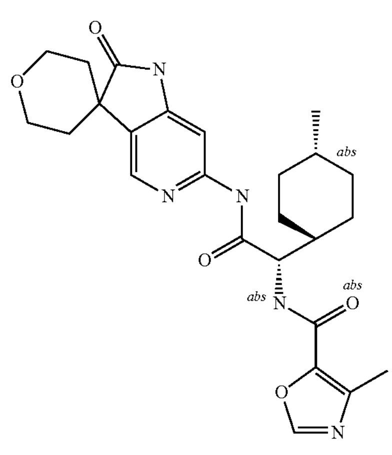 [SMILES: Cc1ncoc1C(=O)N[C@H](C(=O)Nc1cc2c(cn1)C1(CCOCC1)C(=O)N2)[C@H]1CC[C@@H](C)CC1] | 4-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-oxazole-5-carboxamide (trans isomer) | 482.4 | 1.27 | 27 |

-continued

| Ex. | Structure | Product | LCMS Mass | LCMS RT (min) | LCMS Method No. |
|---|---|---|---|---|---|
| 311 | 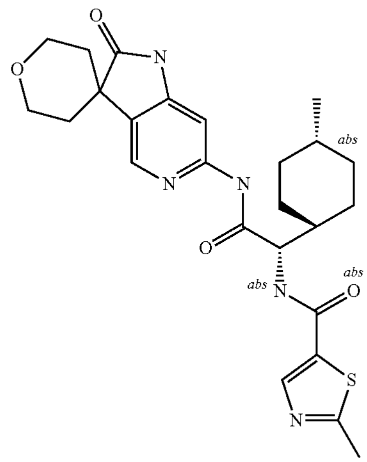 [SMILES: Cc1ncc(C(=O)N[C@H](C(=O)Nc2cc3c(cn2)C2(CCOCC2)C(=O)N3)[C@H]2CC[C@@H](C)CC2)s1] | 2-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-thiazole-5-carboxamide (trans isomer) | 498.4 | 1.29 | 27 |
| 312 | 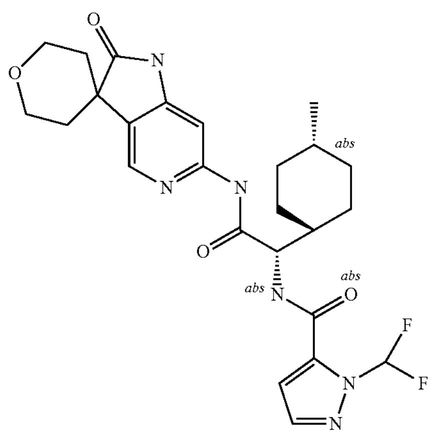 [SMILES: C[C@H]1CC[C@@H]([C@H](NC(=O)c2ccnn2C(F)F)C(=O)Nc2cc3c(cn2)C2(CCOCC2)C(=O)N3)CC1] | 2-(Difluoromethyl)-N-{(1S)-1-(4-methylcyclohexyl)-2-oxo-2-[(2-oxospiro[1H-pyrrolo[3,2-c]-pyridine-3,4'-oxane]-6-yl)-amino]ethyl}pyrazole-3-carboxamide (trans isomer) | 517.5 | 1.4 | 27 |
| 313 | 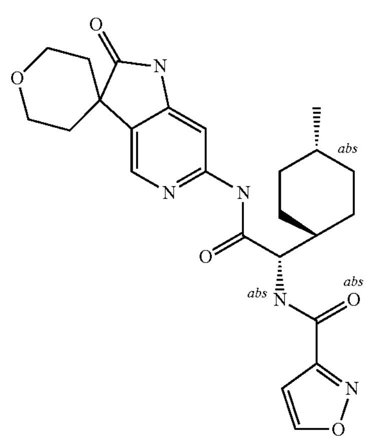 [SMILES: C[C@H]1CC[C@@H]([C@H](NC(=O)c2ccon2)C(=O)Nc2cc3c(cn2)C2(CCOCC2)C(=O)N3)CC1] | N-{(1S)-1-(4-Methylcyclo-hexyl)-2-oxo-2-[(2-oxospiro-[1H-pyrrolo[3,2-c]pyridine-3,4'-oxane]-6-yl)amino]ethyl}-isoxazole-3-carboxamide (trans isomer) | 468.4 | 1.33 | 27 |

-continued

| Ex. | Structure | Product | LCMS Mass | LCMS RT (min) | LCMS Method No. |
|---|---|---|---|---|---|
| 314 | 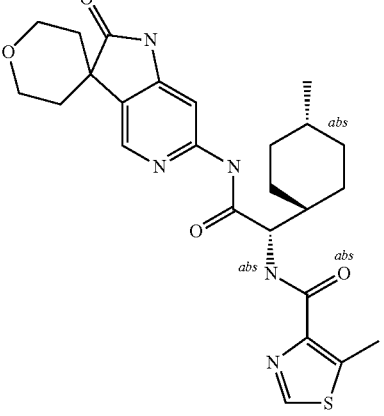 | 5-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-thiazole-4-carboxamide (trans isomer) | 498.5 | 1.47 | 27 |
| 315 | 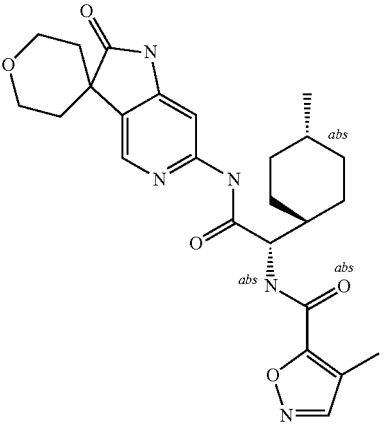 [SMILES: Cc1cnoc1C(=O)N[C@H](C(=O)Nc1cc2c(cn1)C1(CCOCC1)C(=O)N2)[C@H]1CC[C@@H](C)CC1] | 4-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-isoxazole-5-carboxamide (trans isomer) | 482.4 | 1.39 | 27 |
| 316 | 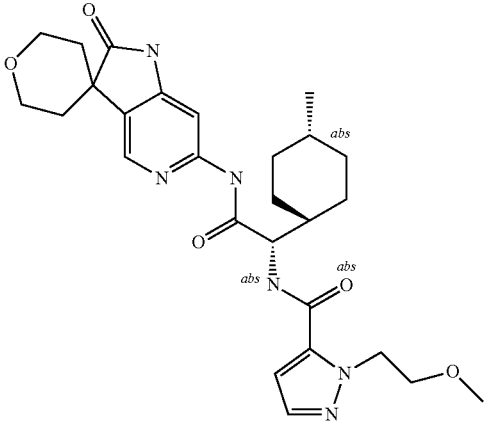 [SMILES: COCCn1nccc1C(=O)N[C@H](C(=O)Nc1cc2c(cn1)C1(CCOCC1)C(=O)N2)[C@H]1CC[C@@H](C)CC1] | 2-(2-Methoxyethyl)-N-{(1S)-1-(4-methylcyclohexyl)-2-oxo-2-[(2-oxospiro[1H-pyrrolo[3,2-c]-pyridine-3,4'-oxane]-6-yl)-amino]ethyl}pyrazole-3-carboxamide (trans isomer) | 525.5 | 1.32 | 27 |

-continued

| Ex. | Structure | Product | LCMS Mass | LCMS RT (min) | LCMS Method No. |
|---|---|---|---|---|---|
| 317 | 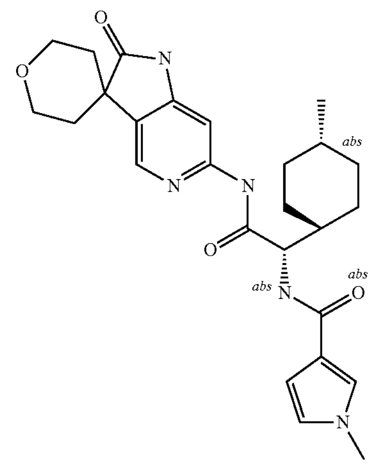 | 1-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-pyrrole-3-carboxamide (trans isomer) | 480.4 | 1.31 | 27 |
| 318 | 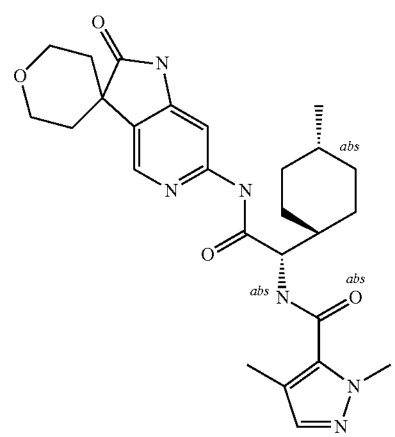 [SMILES: Cc1cnn(C)c1C(=O)N[C@H](C(=O)Nc1cc2c(cn1)C1(CCOCC1)C(=O)N2)[C@H]1CC[C@@H](C)CC1] | 2,4-Dimethyl-N-{(1S)-1-(4-methylcyclohexyl)-2-oxo-2-[(2-oxospiro[1H-pyrrolo[3,2-c]-pyridine-3,4'-oxane]-6-yl)-amino]ethyl}pyrazole-3-carboxamide (trans isomer) | 495.5 | 1.33 | 27 |
| 319 | 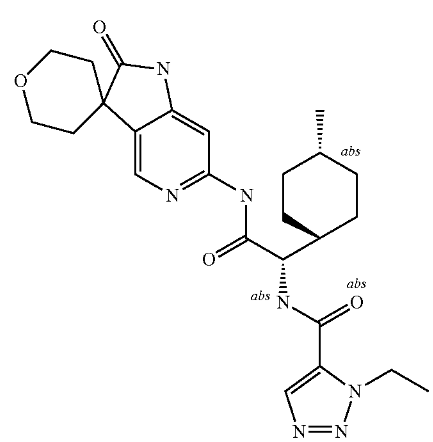 [SMILES: CCn1nncc1C(=O)N[C@H](C(=O)Nc1cc2c(cn1)C1(CCOCC1)C(=O)N2)[C@H]1CC[C@@H](C)CC1] | 3-Ethyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-1,2,3-triazole-4-carboxamide (trans isomer) | 496.4 | 1.29 | 27 |

| Ex. | Structure | Product | LCMS Mass | LCMS RT (min) | LCMS Method No. |
|---|---|---|---|---|---|
| 320 | 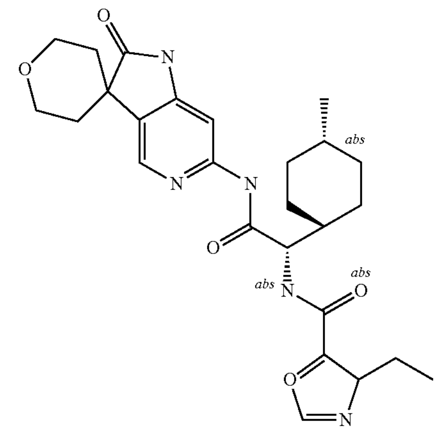 | 4-Ethyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-oxazole-5-carboxamide (trans isomer) | 496.4 | 1.35 | 27 |
| 321 | 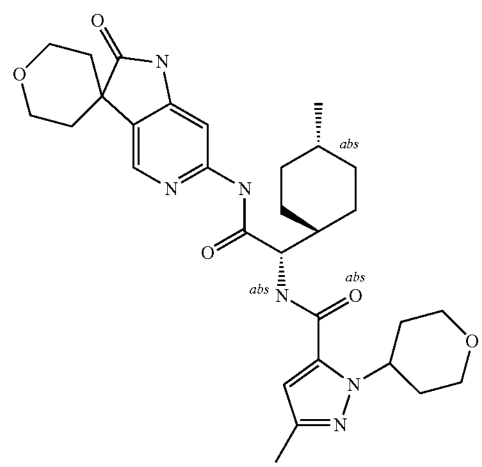 [SMILES: Cc1cc(C(=O)N[C@H](C(=O)Nc2cc3c(cn2)C2(CCOCC2)C(=O)N3)[C@H]2CC[C@@H](C)CC2)n(C2CCOCC2)n1] | 5-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-2-(oxan-4-yl)pyrazole-3-carboxamide (trans isomer) | 565.5 | 1.40 | 27 |
| 322 | 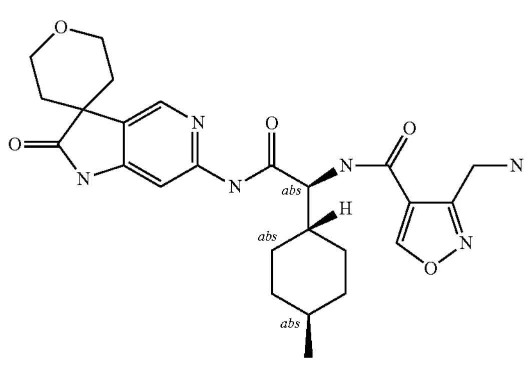 [SMILES: C[C@H]1CC[C@H]([C@H](NC(=O)c2conc2CN)C(=O)Nc2cc3c(cn2)C2(CCOCC2)C(=O)N3)CC1] | 3-(Aminomethyl)-N-{(1S)-1-(4-methylcyclohexyl)-2-oxo-2-[(2-oxospiro[1H-pyrrolo[3,2-c]-pyridine-3,4'-oxane]-6-yl)-amino]ethyl}-oxazole-4-carboxamide (trans isomer) | 497.5 | 1.21 | 27 |

-continued

| Ex. | Structure | Product | LCMS Mass | LCMS RT (min) | LCMS Method No. |
|---|---|---|---|---|---|
| 323 | 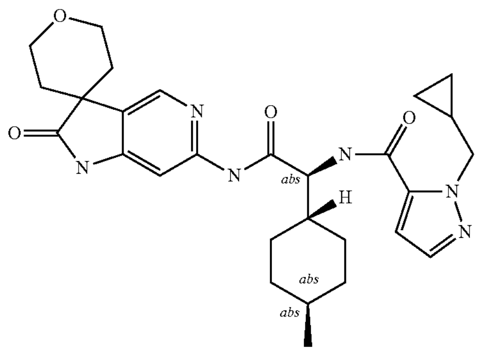 [SMILES: C[C@H]1CC[C@H]([C@H](NC(=O)c2ccnn2CC2CC2)C(=O)Nc2cc3c(cn2)C2(CCOCC2)C(=O)N3)CC1] | 2-(Cyclopropylmethyl)-N-{(1S)-1-(4-methylcyclohexyl)-2-oxo-2-[(2-oxospiro[1H-pyrrolo[3,2-c]pyridine-3,4'-oxane]-6-yl)-amino]ethyl}pyrazole-3-carboxamide (trans isomer) | 521.0 | 2.07 | 6 |
| 324 | 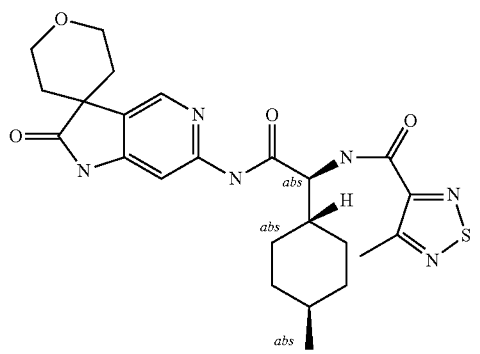 [SMILES: Cc1nsnc1C(=O)N[C@H](C(=O)Nc1cc2c(cn1)C1(CCOCC1)C(=O)N2)[C@H]1CC[C@H](C)CC1] | 4-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-1,2,5-thiadiazole-3-carboxamide (trans isomer) | 499.3 | 1.49 | 27 |
| 325 | 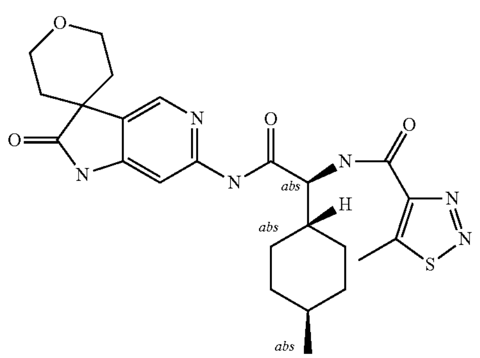 [SMILES: Cc1snnc1C(=O)N[C@H](C(=O)Nc1cc2c(cn1)C1(CCOCC1)C(=O)N2)[C@H]1CC[C@H](C)CC1] | 5-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-1,2,3-thiadiazole-4-carboxamide (trans isomer) | 499.4 | 1.44 | 27 |
| 326 | 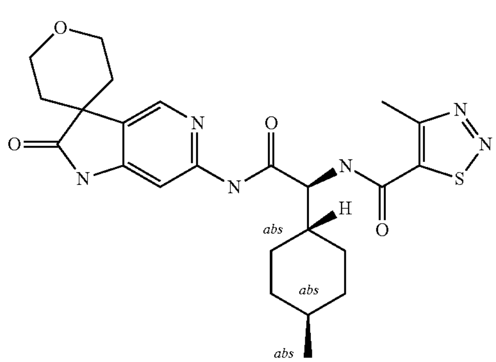 [SMILES: Cc1nnsc1C(=O)N[C@H](C(=O)Nc1cc2c(cn1)C1(CCOCC1)C(=O)N2)[C@H]1CC[C@H](C)CC1] | 4-Methyl-N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-1,2,3-thiadiazole-5-carboxamide (trans isomer) | 499.4 | 1.34 | 27 |

| Ex. | Structure | Product | LCMS Mass | LCMS RT (min) | LCMS Method No. |
|---|---|---|---|---|---|
| 327 | 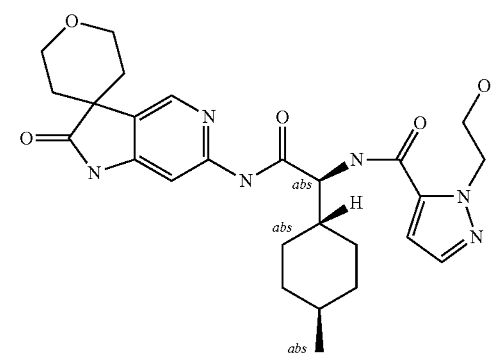 [SMILES: C[C@H]1CC[C@H]([C@H](NC(=O)c2ccnn2CCO)C(=O)Nc2cc3c(cn2)C2(CCOCC2)C(=O)N3)CC1] | 2-(2-Hydroxyethyl)-N-{(1S)-1-(4-methylcyclohexyl)-2-oxo-2-[(2-oxospiro[1H-pyrrolo[3,2-c]-pyridine-3,4'-oxane]-6-yl)-amino]ethyl}pyrazole-3-carboxamide (trans isomer) | 511.4 | 1.19 | 27 |
| 328 | 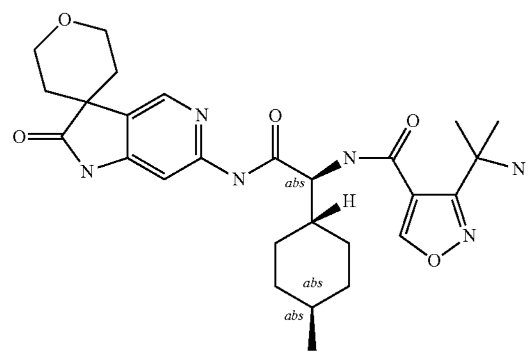 [SMILES: CC(C)(N)c1nocc1C(=O)N[C@H](C(=O)Nc1cc2c(cn1)C1(CCOCC1)C(=O)N2)[C@H]1CC[C@H](C)CC1] | 3-(2-Aminopropan-2-yl)-N-{(1S)-1-(4-methylcyclohexyl)-2-oxo-2-[(2-oxospiro[1H-pyrrolo-[3,2-c]pyridine-3,4'-oxane]-6-yl)amino]ethyl}-isoxazole-4-carboxamide (trans isomer) | 525.4 | 1.35 | 27 |
| 329 | 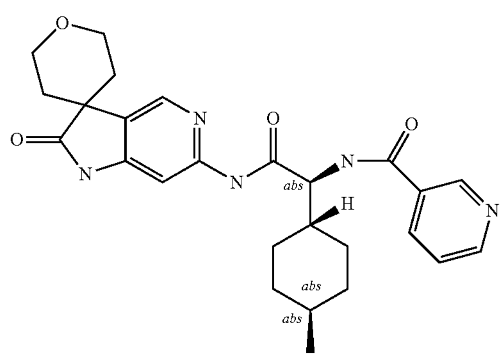 [SMILES: C[C@H]1CC[C@H]([C@H](NC(=O)c2cccnc2)C(=O)Nc2cc3c(cn2)C2(CCOCC2)C(=O)N3)CC1] | N-{(1S)-1-(4-Methylcyclo-hexyl)-2-oxo-2-[(2-oxospiro-[1H-pyrrolo[3,2-c]pyridine-3,4'-tetrahydropyran]-6-yl)amino]-ethyl}pyridine-3-carboxamide (trans isomer) | 478.4 | 1.29 | 27 |
| 330 | 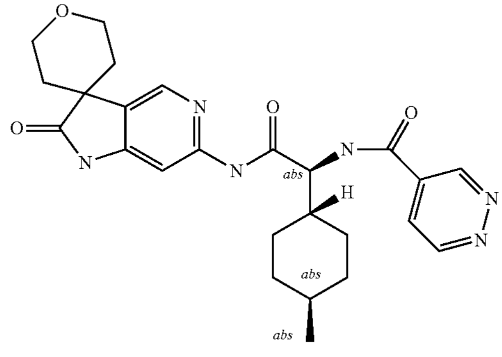 [SMILES: C[C@H]1CC[C@H]([C@H](NC(=O)c2ccnnc2)C(=O)Nc2cc3c(cn2)C2(CCOCC2)C(=O)N3)CC1] | N-{(1S)-1-(4-Methylcyclo-hexyl)-2-oxo-2-[(2-oxospiro-[1H-pyrrolo[3,2-c]pyridine-3,4'-tetrahydropyran]-6-yl)amino]-ethyl}pyridazine-4-carboxamide (trans isomer) | 479.5 | 1.15 | 27 |

-continued

| Ex. | Structure | Product | LCMS Mass | LCMS RT (min) | LCMS Method No. |
|---|---|---|---|---|---|
| 331 | 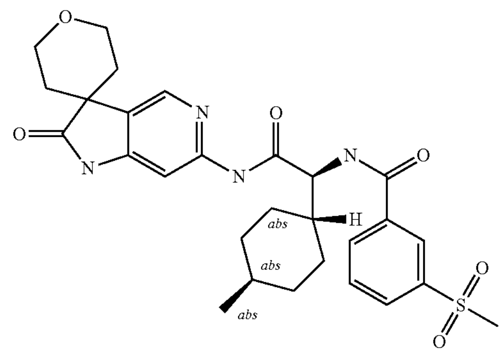 [SMILES: CS(=O)(=O)c1cccc(C(=O)N[C@H](C(=O)Nc2cc3c(cn2)C2(CCOCC2)C(=O)N3)[C@H]2CC[C@H](C)CC2)c1] | N-{(1S)-1-(4-Methylcyclo-hexyl)-2-oxo-2-[(2-oxospiro-[1H-pyrrolo[3,2-c]pyridine-3,4'-tetrahydropyran]-6-yl)amino]-ethyl}-3-(methylsulfonyl)-benzamide (trans isomer) | 555.4 | 1.33 | 27 |
| 332 | 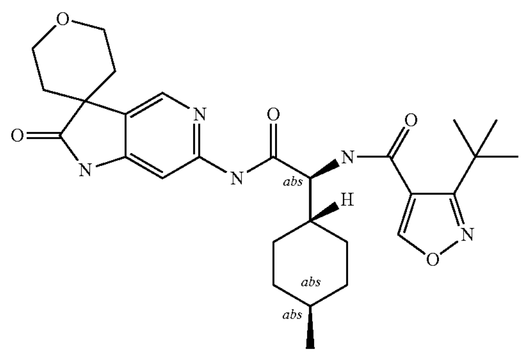 [SMILES: CC(C)(C)c1nocc1C(=O)N[C@H](C(=O)Nc1cc2c(cn1)C1(CCOCC1)C(=O)N2)[C@H]1CC[C@H](C)CC1] | 3-tert-Butyl-N-{(1S)-1-(4-methylcyclohexyl)-2-oxo-2-[(2-oxospiro[1H-pyrrolo[3,2-c]-pyridine-3,4'-tetrahydropyran]-6-yl)amino]ethyl}isoxazole-4-carboxamide (trans isomer) | 524.4 | 1.52 | 27 |
| 333 | 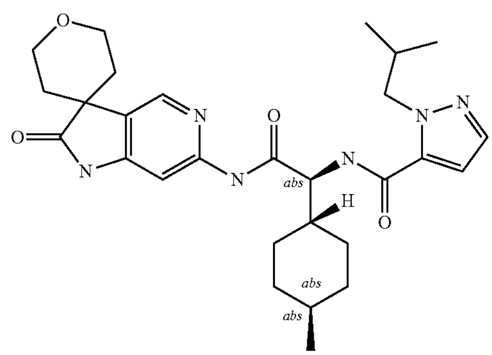 [SMILES: CC(C)Cn1nccc1C(=O)N[C@H](C(=O)Nc1cc2c(cn1)C1(CCOCC1)C(=O)N2)[C@H]1CC[C@H](C)CC1] | N-{(1S)-1-(4-Methylcyclo-hexyl)-2-oxo-2-[(2-oxospiro-[1H-pyrrolo[3,2-c]pyridine-3,4'-oxane]-6-yl)amino]ethyl}-2-(2-methylpropyl)pyrazole-3-carboxamide (trans isomer) | 523.5 | 1.5 | 27 |
| 334 | 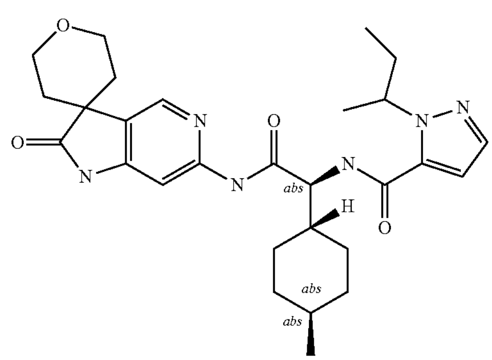 [SMILES: CCC(C)n1nccc1C(=O)N[C@H](C(=O)Nc1cc2c(cn1)C1(CCOCC1)C(=O)N2)[C@H]1CC[C@H](C)CC1] | 2-(Butan-2-yl)-N-{(1S)-1-(4-methylcyclohexyl)-2-oxo-2-[(2-oxospiro[1H-pyrrolo[3,2-c]-pyridine-3,4'-oxane]-6-yl)-amino]ethyl}pyrazole-3-carboxamide (trans isomers) | 523.3 | Isomer 1: 2.89 Isomer 2: 2.92 | 1 |

-continued

| Ex. | Structure | Product | LCMS Mass | LCMS RT (min) | LCMS Method No. |
|---|---|---|---|---|---|
| 335 | 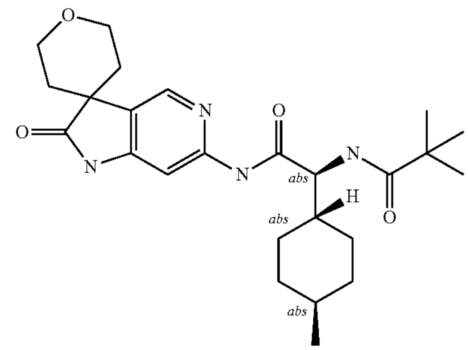 [SMILES: CC(C)(C)C(=O)N[C@H](C(=O)Nc1cc2c(cn1)C1(CCOCC1)C(=O)N2)[C@H]1CC[C@H](C)CC1] | 2,2-Dimethyl-N-{(1S)-1-(4-methylcyclohexyl)-2-oxo-2-[(2-oxospiro[1H-pyrrolo[3,2-c]-pyridine-3,4'-oxane]-6-yl)-amino]ethyl}propanamide (trans isomer) | 457.4 | 1.42 | 27 |
| 336 | 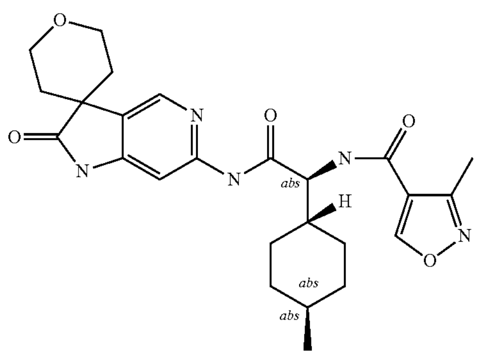 [SMILES: Cc1nocc1C(=O)N[C@H](C(=O)Nc1cc2c(cn1)C1(CCOCC1)C(=O)N2)[C@H]1CC[C@H](C)CC1] | 3-Methyl-N-[(1S)-1-(4-methyl-cyclohexyl)-2-oxo-2-[(2-oxo-spiro[1H-pyrrolo[3,2-c]pyridine-3,4'-oxane]-6-yl)amino]ethyl}-isoxazole-4-carboxamide (trans isomer) | 482.0 | 1.51 | 23 |

Selected $^1$H NMR Data:

| Ex. | $^1$H NMR Data |
|---|---|
| 289 | $\delta_H$ (400 MHz, DMSO-d$_6$) 10.86 (s, 1H), 10.57 (s, 1H), 9.35 (s, 1H), 8.51-8.24 (m, 2H), 7.71 (d, J 0.7 Hz, 1H), 4.51 (t, J 8.1 Hz, 1H), 3.99 (dt, J 10.9, 4.8 Hz, 2H), 3.88-3.70 (m, 2H), 3.55-3.36 (m, 1H), 1.97-1.77 (m, 3H), 1.77-1.45 (m, 6H), 1.22 (dd, J 11.2, 6.9 Hz, 7H), 1.16-1.00 (m, 1H), 1.00-0.66 (m, 6H). |
| 323 | $\delta_H$ (400 MHz, DMSO-d$_6$) 10.89 (s, 1H), 10.58 (s, 1H), 8.50 (d, J 7.9 Hz, 1H), 8.41 (s, 1H), 7.70 (s, 1H), 7.50 (d, J 2.0 Hz, 1H), 6.98 (d, J 2.0 Hz, 1H), 4.48 (t, J 8.3 Hz, 1H), 4.39-4.16 (m, 2H), 3.99 (dt, J 10.3, 4.7 Hz, 2H), 3.89-3.72 (m, 2H), 1.91-1.42 (m, 8H), 1.38-1.14 (m, 3H), 1.07 (m, 1H), 0.86 (d, J 6.4 Hz, 6H), 0.44-0.20 (m, 4H). |
| 334 | $\delta_H$ (500 MHz, DMSO-d$_6$) 10.89-10.79 (m, 1H), 10.57-10.48 (m, 1H), 8.48-8.38 (m, 2H), 7.72 (s, 1H), 7.55-7.50 (m, 1H), 6.93-6.86 (m, 1H), 5.26-5.04 (m, 1H), 4.54-4.41 (m, 1H), 4.06-3.93 (m, 2H), 3.87-3.75 (m, 2H), 1.88-1.73 (m, 5H), 1.73-1.51 (m, 6H), 1.40-1.32 (m, 3H), 1.32-1.17 (m, 2H), 1.12-1.00 (m, 1H), 0.93-0.79 (m, 5H), 0.69-0.57 (m, 3H). |
| 336 | $\delta_H$ (400 MHz, DMSO-d$_6$) 10.86 (s, 1H), 10.58 (s, 1H), 9.43 (d, J 0.8 Hz, 1H), 8.44-8.35 (m, 2H), 7.72 (s, 1H), 4.53 (t, J 8.1 Hz, 1H), 4.03-3.95 (m, 2H), 3.80-3.70 (m, 2H), 2.36 (s, 3H), 1.90-1.45 (m, 8H), 1.40-1.16 (m, 2H), 1.10-0.96 (m, 1H), 0.90-0.70 (m, 6H). |

Examples 337 to 351

The title compounds were prepared by a two-step sequence:

Step 1: reaction of Intermediate 107 with the appropriate carbamoyl chloride in accordance with Procedure D.

Step 2: reaction of the material thereby obtained in accordance with Procedure C.

| Ex. | Structure | Product | LCMS Mass | LCMS RT (min) | LCMS Method No. |
|---|---|---|---|---|---|
| 337 | 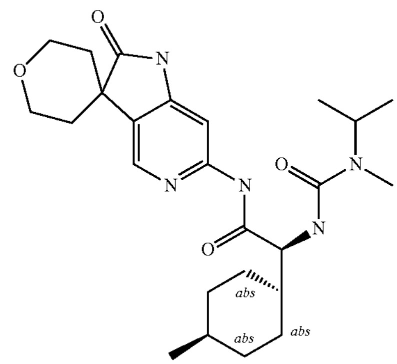 [SMILES: CC(C)N(C)C(=O)N[C@H](C(=O)Nc1cc2c(cn1)C1(CCOCC1)C(=O)N2)[C@H]1CC[C@@H](C)CC1] | (2S)-2-(4-Methylcyclohexyl)-2-{[methyl(propan-2-yl)-carbamoyl]amino}-N-(2-oxo-spiro[1H-pyrrolo[3,2-c]pyridine-3,4'-oxane]-6-yl)acetamide (trans isomer) | 472.4 | 1.39 | 27 |
| 338 | 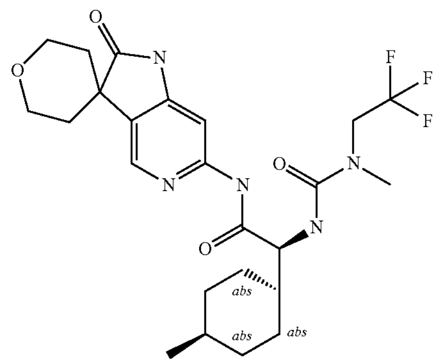 [SMILES: CN(CC(F)(F)F)C(=O)N[C@H](C(=O)Nc1cc2c(cn1)C1(CCOCC1)C(=O)N2)[C@H]1CC[C@@H](C)CC1] | (2S)-2-(4-Methylcyclohexyl)-2-{[methyl(2,2,2-trifluoroethyl)-carbamoyl]amino}-N-(2-oxo-spiro[1H-pyrrolo[3,2-c]pyridine-3,4'-oxane]-6-yl)acetamide (trans isomer) | 512.5 | 1.42 | 27 |
| 339 | 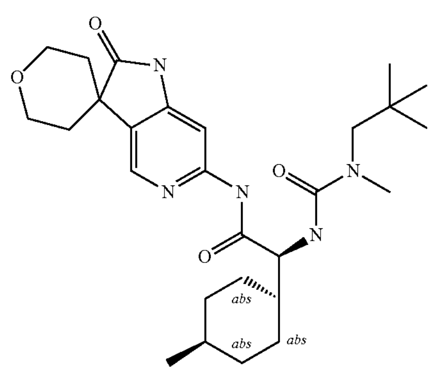 [SMILES: CN(CC(C)(C)C)C(=O)N[C@H](C(=O)Nc1cc2c(cn1)C1(CCOCC1)C(=O)N2)[C@H]1CC[C@@H](C)CC1] | (2S)-2-{[2,2-Dimethylpropyl-(methyl)carbamoyl]amino}-2-(4-methylcyclohexyl)-N-(2-oxo-spiro[1H-pyrrolo[3,2-c]pyridine-3,4'-oxane]-6-yl)acetamide (trans isomer) | 500.5 | 1.57 | 27 |
| 340 | 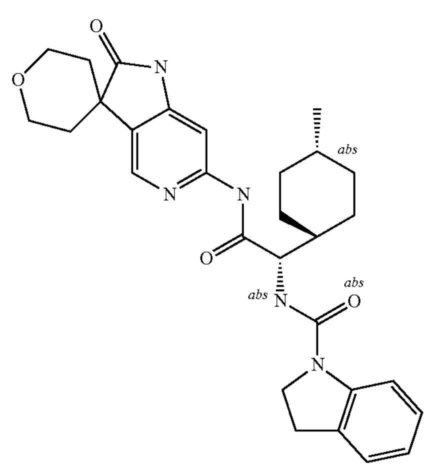 [SMILES: C[C@H]1CC[C@@H]([C@H](NC(=O)N2CCc3ccccc32)C(=O)Nc2cc3c(cn2)C2(CCOCC2)C(=O)N3)CC1] | N-{(1S)-1-(4-Methylcyclo-hexyl)-2-oxo-2-[(2-oxospiro-[1H-pyrrolo[3,2-c]pyridine-3,4'-oxane]-6-yl)amino]ethyl}-2,3-dihydroindole-1-carboxamide (trans isomer) | 518.5 | 1.55 | 27 |

-continued

| Ex. | Structure | Product | LCMS Mass | LCMS RT (min) | LCMS Method No. |
|---|---|---|---|---|---|
| 341 | 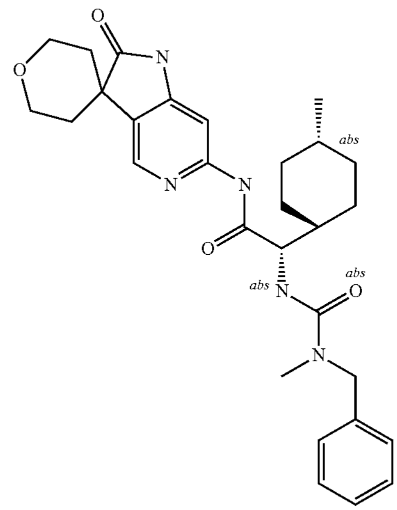 [SMILES: CN(Cc1ccccc1)C(=O)N[C@H](C(=O)Nc1cc2c(cn1)C1(CCOCC1)C(=O)N2)[C@H]1CC[C@@H](C)CC1] | (2S)-2-{[Benzyl(methyl)-carbamoyl]amino}-2-(4-methyl-cyclohexyl)-N-(2-oxospiro[1H-pyrrolo[3,2-c]pyridine-3,4'-oxane]-6-yl)acetamide (trans isomer) | 520.5 | 1.52 | 27 |
| 342 | 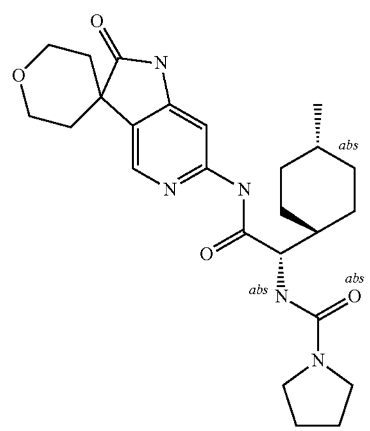 [SMILES: C[C@H]1CC[C@@H]([C@H](NC(=O)N2CCCC2)C(=O)Nc2cc3c(cn2)C2(CCOCC2)C(=O)N3)CC1] | N-{(1S)-1-(4-Methylcyclo-hexyl)-2-oxo-2-[(2-oxospiro-[1H-pyrrolo[3,2-c]pyridine-3,4'-oxane]-6-yl)amino]ethyl}-pyrrolidine-1-carboxamide (trans isomer) | 470.5 | 1.32 | 27 |
| 343 | 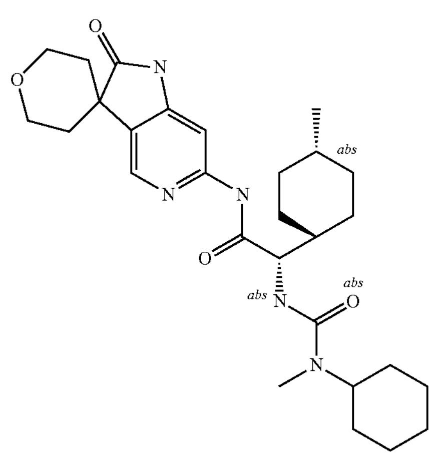 [SMILES: CN(C(=O)N[C@H](C(=O)Nc1cc2c(cn1)C1(CCOCC1)C(=O)N2)[C@H]1CC[C@@H](C)CC1)C1CCCCC1] | (2S)-2-{[Cyclohexyl(methyl)-carbamoyl]amino}-2-(4-methyl-cyclohexyl)-N-(2-oxospiro[1H-pyrrolo[3,2-c]pyridine-3,4'-oxane]-6-yl)acetamide (trans isomer) | 512.5 | 1.59 | 27 |

-continued

| Ex. | Structure | Product | LCMS Mass | LCMS RT (min) | LCMS Method No. |
|---|---|---|---|---|---|
| 344 | 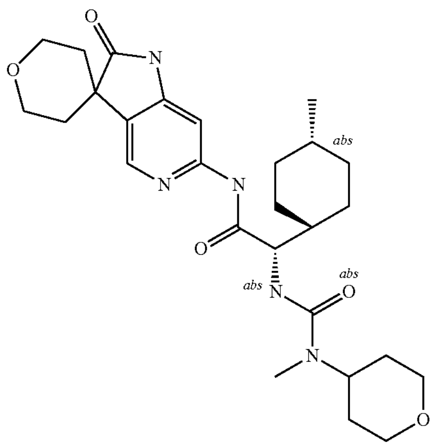 [SMILES: CN(C(=O)N[C@H](C(=O)Nc1cc2c(cn1)C1(CCOCC1)C(=O)N2)[C@H]1CC[C@@H](C)CC1)C1CCOCC1] | (2S)-2-(4-Methylcyclohexyl)-2-{[methyl(oxan-4-yl)carbamoyl]-amino}-N-(2-oxospiro[1H-pyrrolo[3,2-c]pyridine-3,4'-oxane]-6-yl)acetamide (trans isomer) | 514.5 | 1.26 | 27 |
| 345 | 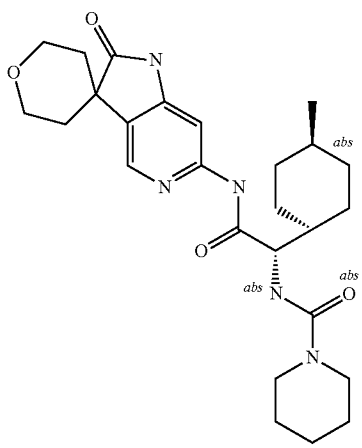 [SMILES: C[C@H]1CC[C@@H]([C@H](NC(=O)N2CCCCC2)C(=O)Nc2cc3c(cn2)C2(CCOCC2)C(=O)N3)CC1] | N-{(1S)-1-(4-Methylcyclohexyl)-2-oxo-2-[(2-oxospiro-[1H-pyrrolo[3,2-c]pyridine-3,4'-oxane]-6-yl)amino]ethyl}-piperidine-1-carboxamide (trans isomer) | 484.5 | 1.41 | 27 |
| 346 | 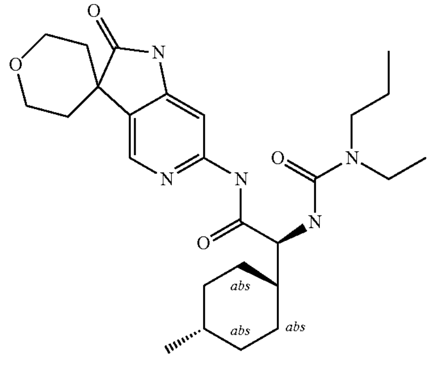 [SMILES: CCCN(CC)C(=O)N[C@H](C(=O)Nc1cc2c(cn1)C1(CCOCC1)C(=O)N2)[C@H]1CC[C@@H](C)CC1] | (2S)-2-{[Ethyl(propyl)-carbamoyl]amino}-2-(4-methyl-cyclohexyl)-N-(2-oxospiro[1H-pyrrolo[3,2-c]pyridine-3,4'-oxane]-6-yl)acetamide (trans isomer) | 486.4 | 1.47 | 27 |

| Ex. | Structure | Product | LCMS Mass | LCMS RT (min) | LCMS Method No. |
|---|---|---|---|---|---|
| 347 | 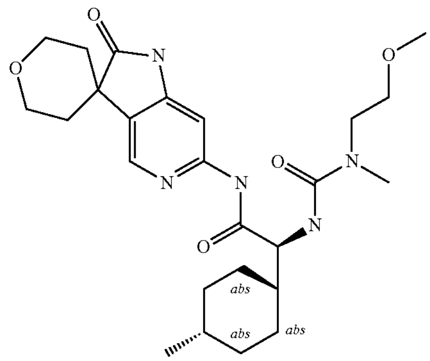 [SMILES: COCCN(C)C(=O)N[C@H](C(=O)Nc1cc2c(cn1)C1(CCOCC1)C(=O)N2)[C@H]1CC[C@@H](C)CC1] | (2S)-2-{[2-Methoxyethyl-(methyl)carbamoyl]amino}-2-(4-methylcyclohexyl)-N-(2-oxo-spiro[1H-pyrrolo[3,2-c]pyridine-3,4'-oxane]-6-yl)acetamide (trans isomer) | 488.5 | 1.3 | 27 |
| 348 | 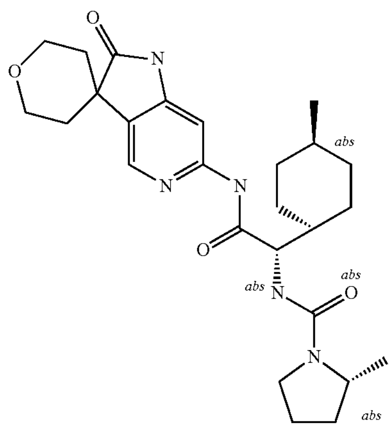 [SMILES: C[C@@H]1CCCN1C(=O)N[C@H](C(=O)Nc1cc2c(cn1)C1(CCOCC1)C(=O)N2)[C@H]1CC[C@@H](C)CC1] | (2R)-2-Methyl-N-{(1S)-1-(4-methylcyclohexyl)-2-oxo-2-[(2-oxospiro[1H-pyrrolo[3,2-c]-pyridine-3,4'-oxane]-6-yl)-amino]ethyl}pyrrolidine-1-carboxamide (trans isomer) | 484.4 | 1.44 | 27 |
| 349 | 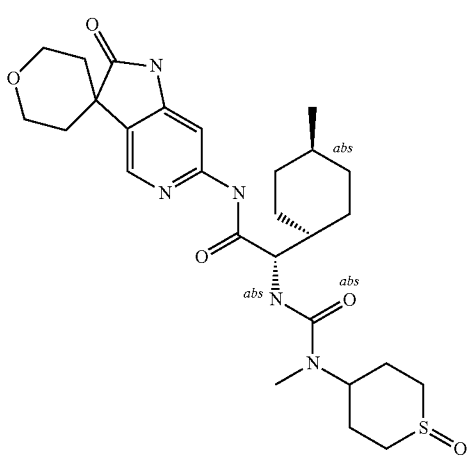 [SMILES: CN(C(=O)N[C@H](C(=O)Nc1cc2c(cn1)C1(CCOCC1)C(=O)N2)[C@H]1CC[C@@H](C)CC1)C1CCS(=O)CC1] | (2S)-2-(4-Methylcyclohexyl)-2-{[methyl-(1-oxothian-4-yl)-carbamoyl]amino}-N-(2-oxo-spiro[1H-pyrrolo[3,2-c]pyridine-3,4'-oxane]-6-yl)acetamide (trans isomer) | 546.5 | 1.13 | 27 |

-continued

| Ex. | Structure | Product | LCMS Mass | LCMS RT (min) | LCMS Method No. |
|---|---|---|---|---|---|
| 350 | 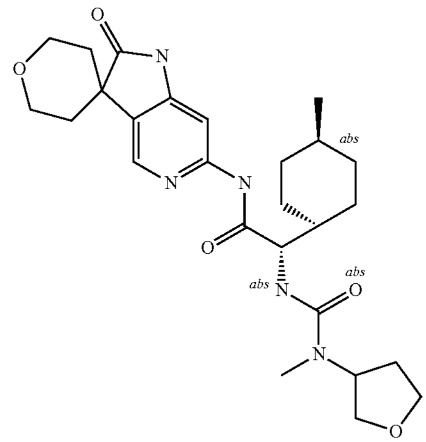 [SMILES: CN(C(=O)N[C@H](C(=O)Nc1cc2c(cn1)C1(CCOCC1)C(=O)N2)[C@H]1CC[C@@H](C)CC1)C1CCOC1] | (2S)-2-(4-Methylcyclohexyl)-2-{[methyl(oxolan-3-yl)-carbamoyl]amino}-N-(2-oxo-spiro[1H-pyrrolo[3,2-c]pyridine-3,4'-oxane]-6-yl)acetamide (trans isomer) | 500.5 | 1.25 | 27 |
| 351 | 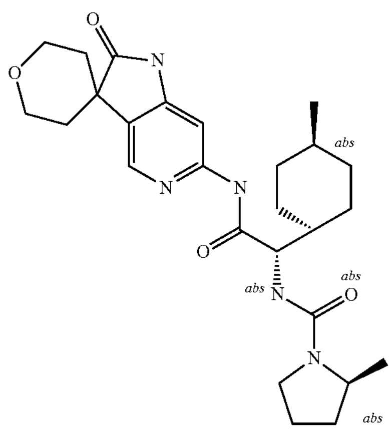 [SMILES: C[C@H]1CCCN1C(=O)N[C@H](C(=O)Nc1cc2c(cn1)C1(CCOCC1)C(=O)N2)[C@H]1CC[C@@H](C)CC1] | (2S)-2-Methyl-N-{(1S)-1-(4-methylcyclohexyl)-2-oxo-2-[(2-oxospiro[1H-pyrrolo[3,2-c]-pyridine-3,4'-oxane]-6-yl)-amino]ethyl}pyrrolidine-1-carboxamide (trans isomer) | 484.4 | 1.40 | 27 |

Example 352

The title compound was prepared by a two-step sequence:
Step 1: reaction of Intermediate 107 with tert-butyl chloroformate in accordance with Procedure E.
Step 2: reaction of the material thereby obtained in accordance with Procedure C.

| Ex. | Structure | Product | LCMS Mass | LCMS RT (min) | LCMS Method No. |
|---|---|---|---|---|---|
| 352 | 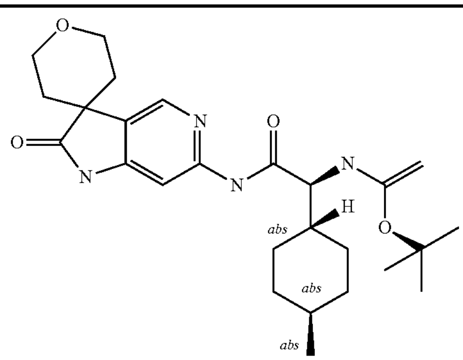 | tert-Butyl N-{(1S)-1-(4-methyl-cyclohexyl)-2-oxo-2-[(2-oxo-spiro[1H-pyrrolo[3,2-c]pyridine-3,4'-oxane]-6-yl)amino]ethyl}-carbamate (trans isomer) | 473.5 | 1.5 | 27 |

Examples 353 to 355

The title compounds were prepared by a two-step sequence:
Step 1: reaction of Intermediate 107 with the appropriate halogeno heterocycle in accordance with Procedure B.
Step 2: reaction of the material thereby obtained in accordance with Procedure C.

| Ex. | Structure | Product | LCMS Mass | LCMS RT (min) | LCMS Method No. |
|---|---|---|---|---|---|
| 353 | 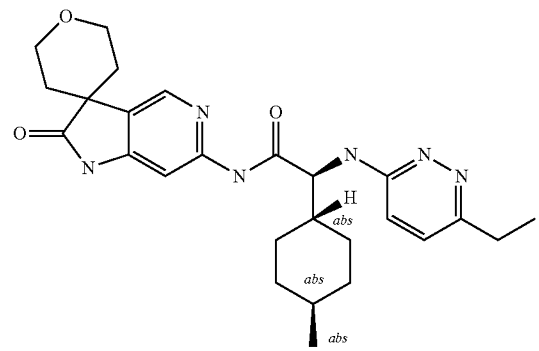 [SMILES: CCc1ccc(N[C@H](C(=O)Nc2cc3c(cn2)C2(CCOCC2)C(=O)N3)[C@H]2CC[C@H](C)CC2)nn1] | (2S)-2-[(6-Ethylpyridazin-3-yl)-amino]-2-(4-methylcyclohexyl)-N-(2-oxospiro[1H-pyrrolo[3,2-c]pyridine-3,4'-oxane]-6-yl)-acetamide (trans isomer) | 479.5 | 1.32 | 27 |
| 354 | 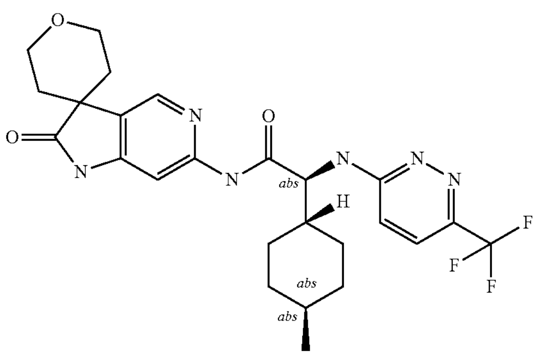 [SMILES: C[C@H]1CC[C@H]([C@H](Nc2ccc(C(F)(F)F)nn2)C(=O)Nc2cc3c(cn2)C2(CCOCC2)C(=O)N3)CC1] | (2S)-2-(4-Methylcyclohexyl)-N-(2-oxospiro[1H-pyrrolo[3,2-c]-pyridine-3,4'-oxane]-6-yl)-2-{[6-(trifluoromethyl)pyridazin-3-yl]amino}acetamide (trans isomer) | 519.4 | 1.47 | 27 |
| 355 | 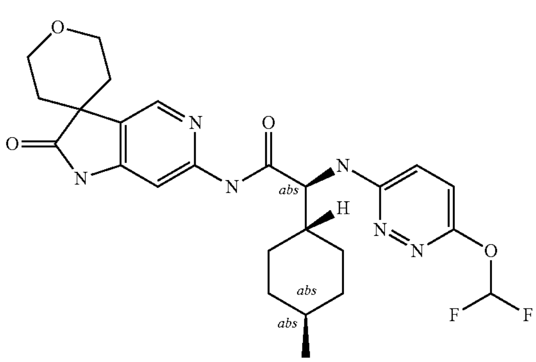 [SMILES: C[C@H]1CC[C@H]([C@H](Nc2ccc(OC(F)F)nn2)C(=O)Nc2cc3c(cn2)C2(CCOCC2)C(=O)N3)CC1] | (2S)-2-{[6-(Difluoromethoxy)-pyridazin-3-yl]amino}-2-(4-methylcyclohexyl)-N-(2-oxo-spiro[1H-pyrrolo[3,2-c]pyridine-3,4'-oxane]-6-yl)acetamide (trans isomer) | 517.5 | 1.49 | 27 |

Example 356

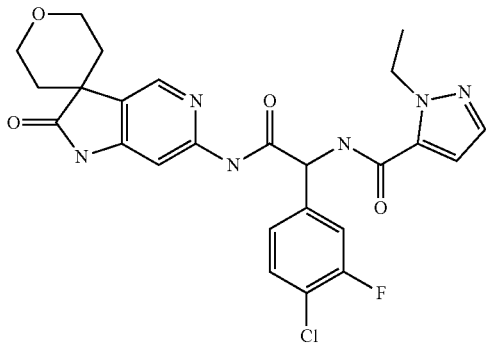

N-{1-(4-Chloro-3-fluorophenyl)-2-oxo-2-[(2-oxospiro[1H-pyrrolo[3,2-c]pyridine-3,4'-tetrahydropyran]-6-yl)amino]ethyl}-2-ethylpyrazole-3-carboxamide Trifluoroacetic acid (0.93 mL, 12.07 mmol) was added dropwise to a cooled solution of Intermediate 156 (115 mg, 0.18 mmol) in DCM (15 mL) under nitrogen at 0° C. The reaction mixture was allowed to warm to ambient temperature, then stirred for 18 h. The volatiles were concentrated in vacuo, and the residue was dissolved in acetonitrile (7.5 mL) and aqueous ammonium hydroxide solution (7.5 mL). The reaction mixture was stirred at 20° C. for 15 minutes, then the volatiles were concentrated in vacuo. The residue was diluted with water (20 mL), and the aqueous phase was extracted with DCM (3×20 mL). The combined organic layers were dried over anhydrous magnesium sulfate, filtered and concentrated in vacuo. The residue was purified by flash column chromatography, using a gradient of ethyl acetate in heptane (0-100%) followed by a gradient of MeOH-DCM (0-100%), to afford, after freeze-drying, the title compound (170 mg, 80%) as a white solid. $\delta_H$ (500 MHz, DMSO-$d_6$) 10.92 (br s, 1H), 10.88 (br s, 1H), 8.99 (d, J 7.0 Hz, 1H), 8.40 (s, 1H), 7.72-7.62 (m, 2H), 7.60 (dd, J 10.4, 1.9 Hz, 1H), 7.49 (d, J 2.0 Hz, 1H), 7.45 (dd, J 8.4, 1.8 Hz, 1H), 7.05 (d, J 2.0 Hz, 1H), 5.91 (d, J 6.8 Hz, 1H), 4.52-4.39 (m, 2H), 4.04-3.91 (m, 2H), 3.87-3.72 (m, 2H), 1.89-1.73 (m, 2H), 1.69-1.54 (m, 2H), 1.28 (t, J 7.1 Hz, 3H). uPLC-MS (method 1): MH+ m/z 527, RT 2.52 minutes.

Example 357

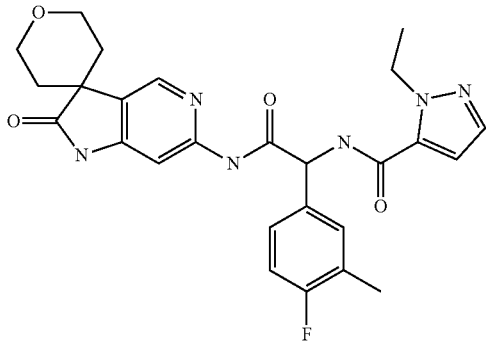 [SMILES: CCn1nccc1C(=O)NC(C(=O)Nc1cc2c(cn1)C1(CCOCC1)C(=O)N2)c1ccc(Cl)c(F)c1]

2-Ethyl-N-{1-(4-fluoro-3-methylphenyl)-2-oxo-2-[(2-oxospiro[1H-pyrrolo[3,2-c]-pyridine-3,4'-tetrahydropyran]-6-yl)amino]ethyl}pyrazole-3-carboxamide Trifluoroacetic acid (0.93 mL, 12.07 mmol) was added dropwise to a solution of Intermediate 160 (469 mg, 0.37 mmol) in DCM (20 mL) under a nitrogen atmosphere, and cooled to 0° C. The reaction mixture was stirred at 20° C. for 18 h. The volatiles were concentrated in vacuo, then the residue was dissolved in acetonitrile (9.5 mL) and aqueous ammonium hydroxide solution (9.5 mL). The reaction mixture was stirred at 20° C. for 15 minutes, and the volatiles were concentrated in vacuo. The residue was diluted with water (20 mL), and the aqueous phase was extracted with DCM (3×20 mL). The combined organic layers were dried over anhydrous magnesium sulfate, filtered and concentrated in vacuo. The residue was purified by flash column chromatography, using a gradient of ethyl acetate in heptane (0-100%) followed by a gradient of MeOH-DCM (0-100%), to give, after freeze drying, the title compound (160 mg, 84%) as a white solid. $\delta_H$ (500 MHz, DMSO-$d_6$) 10.86 (br s, 1H), 10.79 (br s, 1H), 8.87 (d, J 6.7 Hz, 1H), 8.38 (s, 1H), 7.67 (s, 1H), 7.55-7.45 (m, 2H), 7.43-7.36 (m, 1H), 7.19-7.11 (m, 1H), 7.04 (d, J 2.0 Hz, 1H), 5.82 (d, J 5.6 Hz, 1H), 4.52-4.39 (m, 2H), 4.03-3.93 (m, 2H), 3.86-3.72 (m, 2H), 2.24 (s, 3H), 1.88-1.75 (m, 2H), 1.68-1.54 (m, 2H), 1.28 (t, J 7.1 Hz, 3H). uPLC-MS (method 1): MH+ m/z 507, RT 2.34 minutes.

The invention claimed is:

1. A compound of formula (I), or a pharmaceutically acceptable salt thereof:

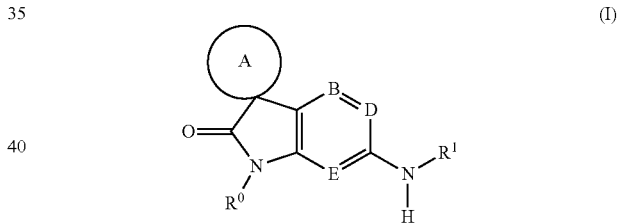

(I)

wherein
ring A represents $C_{3-9}$ cycloalkyl, $C_{3-7}$ heterocycloalkyl or $C_{4-9}$ heterobicycloalkyl, any of which groups may be optionally substituted by one or more substituents;
B represents C—$R^2$ or N;
D represents C—$R^3$ or N;
E represents C—$R^4$ or N;
$R^0$ represents hydrogen or $C_{1-6}$ alkyl;
$R^1$ represents —$COR^a$;
$R^a$ represents —$CH(R^5)N(H)C(O)R^6$, —$CH(R^5)N(H)S(O)_2R^6$, —$C(=CR^{5a}R^{5b})N(H)C(O)R^6$, —$CH(R^5)R^7$, —$CH(R^5)N(H)R^7$ or —$CH(R^5)C(O)N(H)R^7$;
$R^2$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;
$R^3$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;

R⁴ represents hydrogen, halogen, cyano, C₁₋₆ alkyl, fluoromethyl, difluoromethyl, trifluoromethyl, hydroxy, C₁₋₆ alkoxy, difluoromethoxy, trifluoromethoxy, C₁₋₆ alkyl-sulphinyl or C₁₋₆ alkylsulphonyl;

R⁵ represents hydrogen; or R⁵ represents C₁₋₅ alkyl, C₃₋₉ cycloalkyl, C₃₋₉ cyclo-alkyl(C₁₋₅)alkyl, C₄₋₉ bicycloalkyl, C₄₋₉ bicycloalkyl(C₁₋₅)alkyl, C₅₋₉ spirocycloalkyl, C₅₋₉ spirocycloalkyl(C₁₋₅)alkyl, C₉₋₁₁ tricycloalkyl, C₉₋₁₁ tricycloalkyl(C₁₋₅)alkyl, aryl, aryl-(C₁₋₅)alkyl, C₃₋₇ heterocycloalkyl, C₃₋₇ heterocycloalkyl(C₁₋₅)alkyl, heteroaryl or heteroaryl(C₁₋₅)alkyl, any of which groups may be optionally substituted by one or more substituents;

R⁵ᵃ represents C₃₋₇ cycloalkyl, C₄₋₉ bicycloalkyl, aryl, C₃₋₇ heterocycloalkyl or heteroaryl, any of which groups may be optionally substituted by one or more substituents; and R⁵ᵇ represents hydrogen or C₁₋₆ alkyl; or R⁵ᵃ and R⁵ᵇ, when taken together with the carbon atom to which they are both attached, represent C₃₋₇ cycloalkyl, C₄₋₉ bicycloalkyl or C₃₋₇ heterocycloalkyl, any of which groups may be optionally substituted by one or more substituents;

R⁶ represents —NR⁶ᵃR⁶ᵇ or —OR⁶ᶜ; or R⁶ represents C₁₋₉ alkyl, C₃₋₉ cycloalkyl, C₃₋₉ cycloalkyl(C₁₋₆)alkyl, aryl, aryl(C₁₋₆)alkyl, C₃₋₇ heterocycloalkyl, C₃₋₇ heterocycloalkyl-(C₁₋₆)alkyl, heteroaryl, heteroaryl(C₁₋₆)alkyl or spiro[(C₃₋₇)heterocycloalkyl][heteroaryl], any of which groups may be optionally substituted by one or more substituents;

R⁶ᵃ represents hydrogen; or R⁶ᵃ represents C₁₋₆ alkyl, C₃₋₇ cycloalkyl, C₃₋₇ cyclo-alkyl(C₁₋₆)alkyl, aryl, aryl(C₁₋₆)alkyl, C₃₋₇ heterocycloalkyl, C₃₋₇ heterocycloalkyl(C₁₋₆)-alkyl, heteroaryl, heteroaryl(C₁₋₆)alkyl or spiro[(C₃₋₇)heterocycloalkyl][heteroaryl], any of which groups may be optionally substituted by one or more substituents;

R⁶ᵇ represents hydrogen or C₁₋₆ alkyl;

R⁶ᶜ represents C₁₋₆ alkyl, C₃₋₇ cycloalkyl, C₃₋₇ cycloalkyl(C₁₋₆)alkyl, aryl, aryl(C₁₋₆)alkyl, C₃₋₇ heterocycloalkyl, C₃₋₇ heterocycloalkyl(C₁₋₆)alkyl, heteroaryl or heteroaryl(C₁₋₆)alkyl, any of which groups may be optionally substituted by one or more substituents; and R⁷ represents aryl, heteroaryl or spiro[(C₃₋₇)heterocycloalkyl][heteroaryl], any of which groups may be optionally substituted by one or more substituents.

2. A compound as claimed in claim 1 represented by formula (I-1), (I-2), (I-3), (I-4) or (I-5), or a pharmaceutically acceptable salt thereof:

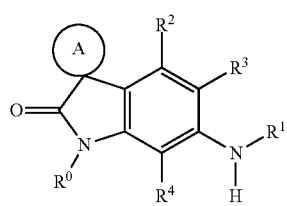
(I-1)

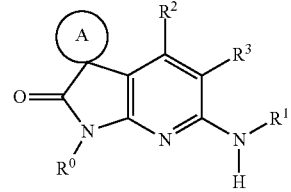
(I-2)

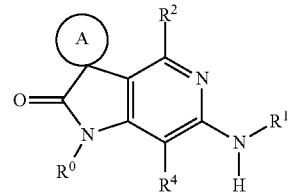
(I-3)

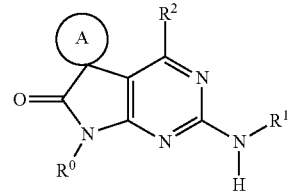
(I-4)

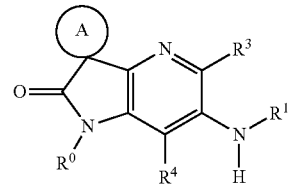
(I-5)

wherein A, R⁰, R¹, R², R³ and R⁴ are as defined in claim 1.

3. A compound as claimed in claim 1 represented by formula (IIA), or a pharmaceutically acceptable salt thereof:

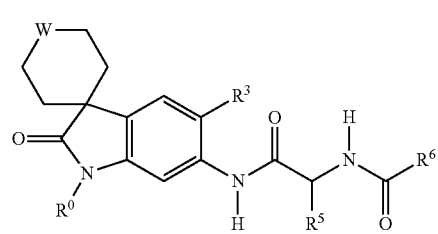
(IIA)

wherein
W represents O, S, S(O), S(O)₂, S(O)(NH) or N—R¹⁷;
R¹⁷ represents hydrogen or C₁₋₆ alkyl;
R⁰, R³,
R⁵ and R⁶ are as defined in claim 1.

4. A compound as claimed in claim 1 represented by formula (IIB), or a pharmaceutically acceptable salt thereof:

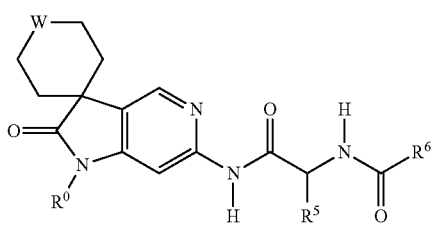

(IIB)

wherein
W represents O, S, S(O), S(O)$_2$, S(O)(NH) or N—R$^{17}$;
R$^{17}$ represents hydrogen or C$_{1-6}$ alkyl; and
R$^0$, R$^5$ and R$^6$ are as defined in claim 1.

5. A compound as claimed in claim 1 wherein R$^5$ represents C$_{1-5}$ alkyl, C$_{3-9}$ cycloalkyl, C$_{3-9}$ cycloalkyl(C$_{1-5}$)alkyl, C$_{4-9}$ bicycloalkyl, C$_{4-9}$ bicycloalkyl(C$_{1-5}$)-alkyl, C$_{5-9}$ spirocycloalkyl, C$_{9-11}$ tricycloalkyl, C$_{9-11}$ tricycloalkyl(C$_{1-5}$)alkyl, aryl, aryl-(C$_{1-5}$)alkyl, C$_{3-7}$ heterocycloalkyl, C$_{3-7}$ heterocycloalkyl(C$_{1-5}$)alkyl or heteroaryl(C$_{1-5}$)alkyl, any of which groups may be optionally substituted by one, two or three substituents independently selected from halogen, C$_{1-6}$ alkyl, trifluoromethyl, phenyl and C$_{1-6}$ alkoxy.

6. A compound as claimed in claim 1 wherein R$^6$ represents —NR$^{6a}$R$^{6b}$ or —OR$^{6c}$; or R$^6$ represents C$_{1-9}$ alkyl, aryl, C$_{3-7}$ heterocycloalkyl, heteroaryl, heteroaryl(C$_{1-6}$)alkyl or spiro[(C$_{3-7}$)heterocycloalkyl][heteroaryl], any of which groups may be optionally substituted by one, two or three substituents independently selected from halogen, C$_{1-6}$ alkyl, difluoromethyl, trifluoromethyl, difluoroethyl, trifluoroethyl, trifluoropropyl, cyclopropyl, cyclobutyl, cyclopropylmethyl, hydroxy, hydroxy(C$_{1-6}$)alkyl, oxo, C$_{1-6}$ alkoxy (C$_{1-6}$)alkyl, C$_{1-6}$ alkylsulfonyl, amino, amino(C$_{1-6}$)alkyl, di(C$_{1-6}$)alkyl-amino(C$_{1-6}$)alkyl and tetrahydropyranyl.

7. A pharmaceutical composition comprising a compound of formula (I) as defined in claim 1, or a pharmaceutically acceptable salt thereof, in association with a pharmaceutically acceptable carrier.

8. A method for the treatment of psoriasis, psoriatic arthritis, ankylosing spondylitis, chronic obstructive pulmonary disease, atopic dermatitis, arthritis, rheumatoid arthritis, systemic onset juvenile idiopathic arthritis, systemic lupus erythematosus, asthma, scleroderma, systemic sclerosis, lung fibrosis, Crohn's disease, ulcerative colitis and pain, which comprises administering to a patient in need of such treatment an effective amount of a compound of formula (I) as defined in claim 1, or a pharmaceutically acceptable salt thereof.

9. A compound as claimed in claim 1 represented by formula (IA), or a pharmaceutically acceptable salt thereof:

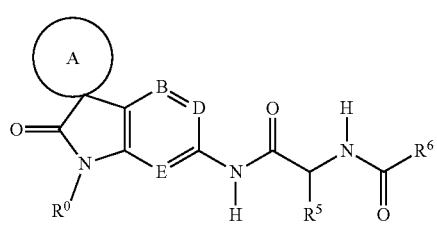

(IA)

wherein A, B, D, E, R$^0$, R$^5$ and R$^6$ are as defined in claim 1.

10. A compound as claimed in claim 1 represented by formula (IB), or a pharmaceutically acceptable salt thereof:

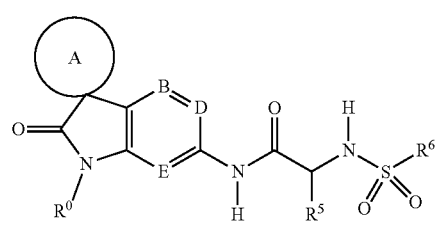

(IB)

wherein A, B, D, E, R$^0$, R$^5$ and R$^6$ are as defined in claim 1.

11. A compound as claimed in claim 1 represented by formula (IC), or a pharmaceutically acceptable salt thereof:

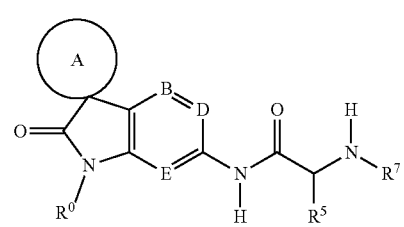

(IC)

wherein A, B, D, E, R$^0$, R$^5$ and R$^7$ are as defined in claim 1.

12. A compound as claimed in claim 1 represented by formula (ID), or a pharmaceutically acceptable salt thereof:

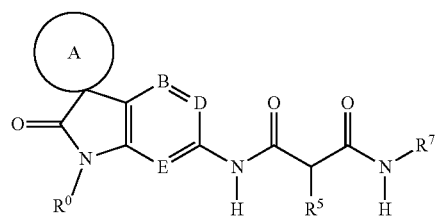

(ID)

wherein A, B, D, E, R$^0$, R$^5$ and R$^7$ are as defined in claim 1.

13. A compound as claimed in claim 1 represented by formula (IE), or a pharmaceutically acceptable salt thereof:

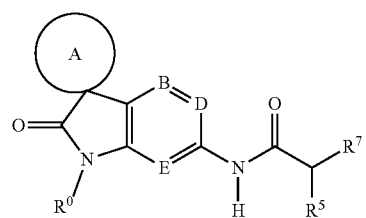

(IE)

wherein A, B, D, E, R$^0$, R$^5$ and R$^7$ are as defined in claim 1.

14. A compound as claimed in claim 1 represented by formula (IF), or a pharmaceutically acceptable salt thereof:

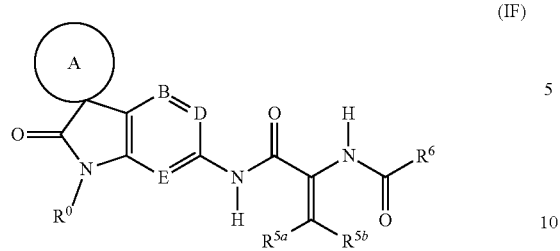
(IF)
wherein A, B, D, E, $R^0$, $R^{5a}$, $R^{5b}$ and $R^6$ are as defined in claim 1.
* * * * *